United States Patent [19]
Harpold et al.

[11] Patent Number: 6,090,623
[45] Date of Patent: *Jul. 18, 2000

[54] RECOMBINANT HUMAN CALCIUM CHANNEL $\beta_4$ SUBUNITS

[75] Inventors: Michael M. Harpold, El Cajon; Steven B. Ellis, San Diego; Mark E. Williams, Carlsbad; Ann F. McCue, La Mesa, all of Calif.

[73] Assignee: Merck & Co., Inc., Rahway, N.J.

[ * ] Notice: This patent is subject to a terminal disclaimer.

[21] Appl. No.: 08/949,386

[22] Filed: Oct. 14, 1997

Related U.S. Application Data

[63] Continuation of application No. 08/290,012, Aug. 11, 1994, abandoned, which is a continuation-in-part of application No. 08/149,097, Nov. 5, 1993, Pat. No. 5,874,236, and a continuation-in-part of application No. 08/105,536, Aug. 11, 1993, abandoned.

[51] Int. Cl.[7] ........................... C12N 15/12; C07K 14/435

[52] U.S. Cl. ............................ 435/369; 536/23.5; 435/6; 435/325; 435/254.2; 435/354; 435/356; 435/358; 435/364; 435/365

[58] Field of Search .......................... 536/23.5; 435/325, 435/254.2, 354, 356, 358, 364, 365, 369, 6

[56] References Cited

U.S. PATENT DOCUMENTS

| | | |
|---|---|---|
| 4,788,135 | 11/1988 | Davis et al. . |
| 4,906,564 | 3/1990 | Lyon et al. .................. 435/7 |
| 4,912,202 | 3/1990 | Campbell et al. . |
| 4,954,436 | 9/1990 | Froehner et al. . |
| 5,024,939 | 6/1991 | Gorman . |
| 5,051,403 | 9/1991 | Miljanich et al. . |
| 5,189,020 | 2/1993 | Miljanich et al. . |
| 5,264,371 | 11/1993 | Miljanich et al. . |
| 5,386,025 | 1/1995 | Jay et al. . |
| 5,401,629 | 3/1995 | Harpold et al. . |
| 5,407,820 | 4/1995 | Ellis et al. . |
| 5,424,218 | 6/1995 | Miljanich et al. . |
| 5,429,921 | 7/1995 | Harpold et al. . |
| 5,436,128 | 7/1995 | Harpold et al. . |
| 5,643,750 | 7/1997 | Spreyer et al. . |
| 5,686,241 | 11/1997 | Ellis et al. . |
| 5,710,250 | 1/1998 | Ellis et al. . |

FOREIGN PATENT DOCUMENTS

| | | |
|---|---|---|
| 2085502 | of 0000 | Canada . |
| 0507170 | 3/1992 | European Pat. Off. . |
| 0556651 | 4/1993 | European Pat. Off. . |
| 8907608 | 8/1989 | WIPO . |
| 8909834 | 10/1989 | WIPO . |
| 9113077 | 9/1991 | WIPO . |
| 9202639 | 2/1992 | WIPO . |
| 9213092 | 8/1992 | WIPO . |
| 9308469 | 4/1993 | WIPO . |
| 9402511 | 2/1994 | WIPO . |
| WO95/04144 | 2/1995 | WIPO . |

OTHER PUBLICATIONS

Castellano, A., et al. (1993) "Cloning and Expression of a Neuronal Calcium Channel β Subunit", *J. Biol. Chem.* 268: 12359–12366.

Scharf, S. J. (1990) "Cloning with PCR", in *PCR Protocols: a guide to methods and applications*, Innis, M. A., et al, eds., New York: Academic Press; Chapter 11, pp. 84–91.

Castellano, A., et al. (1993) "*Rattus norvegicus* cDNA sequence, complete 5' and 3' UTR's", GenBank database record, acc. No. L02315.

Powers, et al., "Assignment of the human gene for the $\alpha_1$ subunit of the cardiac DHP–sensitive $Ca^{2+}$ channel (CCHL1A1) to Chromosome 12p12–pter," *Genomics*, 10: 835–839 (1991).

Kim, et al., "IgG from patients with Lambert–Eaton syndrome blocks voltage–dependent calcium channels," *Science*, 239: 405–408 (1988).

Claudio, et al., "Genetic reconstitution of functional acetylcholine receptor channels in mouse fibroblasts," *Science*, 238: 1688–1694 (1987).

Tanabe, et al., "Primary structure of the receptor for calcium channel blockers from skeletal muscle," *Nature*, 328: 313–318 (1987).

Nakayama, et al., "Purification of a putative $Ca^{2+}$ channel protein from rabbit skeletal muscle," *J.Biol.Chem.*, 262: 6572–6576 (1987).

Vaghy, et al., "Identification of a novel 1,4–dihydropyridine– and phenylalkylamine–binding polypeptide in calcium channel preparations," *J.Biol.Chem.*, 262(29): 14337–14342 (1987).

Leung, et al., "Structural characterization of the 1,4–dihydropyridine receptor of the voltage–dependent $Ca^{2+}$ channel from rabbit skeletal muscle," *J.Biol.Chem.*, 262(17): 7943–7946 (1987).

Sharp, et al., "Identification and characterization of the dihydropyridine–binding subunit of the skeletal muscle dihydropyridine receptor," *J.Biol.Chem.*, 62(25): 12309–12315 (1987).

Takahashi, et al., "Subunit structure of dihydropyridine–sensitive calcium channels from skeletal muscle," *Proc.Nat-l.Acad.Sci. (USA)*, 84: 5478–5482 (1987).

Morton et al. "Monoclonal antibody identifies a 200–kDA subunit of the dihydropyridine–sensitive calcium channel," *J.Biol.Chem.*, 262(25): 11904–11907 (1987).

Barhanin, et al., "The calcium channel antagonists receptor from rabbit skeletal muscle: reconstitution after purification and subunit characterization," *Eur.J.Biochem.*, 164: 525–531 (1987).

(List continued on next page.)

*Primary Examiner*—David L. Fitzgerald
*Attorney, Agent, or Firm*—Joseph A. Coppola; Jack L. Tribble

[57] ABSTRACT

Isolated DNA encoding each of human calcium channel $\alpha_1$-, $\alpha_2$-, β- and γ-subunits, including subunits that arise as splice variants of primary transcripts, is provided. In particular DNA clones encoding each of the $\alpha_{1A-1}$, $\alpha_{1A-2}$, $\alpha_{1E-1}$, $\alpha_{1C-2}$, $\alpha_{1E-3}$, $\beta_{3-1}$, $\beta_{2C}$, $\beta_{2D}$, $\beta_{2E}$ and $\beta_4$ subunits of human calcium channels are provided. Cells and vectors containing the DNA, subunit specific antibodies and nucleic acid probes and methods for identifying compounds that modulate the activity of human calcium channels are also provided.

14 Claims, No Drawings

OTHER PUBLICATIONS

Sieber, et al., "The 165–kDa peptide of the purified skeletal muscle dihydropyridine receptor contains the known regulatory sites of the calcium channel," *Eur.J.Biochem.*, 167: 117–122 (1987).

Lang, et al., "The effect of myasthenic syndrome antibody on presynaptic calcium channels in the mouse," *J.Physiol.*, 390: 257–270 (1987).

Curran and Morgan, "Barium modules c–fos expression and post–translational modification," *Proc.Natl.Acad.Sci.*, 83: 3521–8524 (1986).

Fisch, et al., "c–fos sequences necessary for basal expression and induction by epidermal growth factor, 12–O–tetradecanoyl phorbol–13–acetate, and the calcium inophore," *Mol.Cell.Biol.*, 7(10): 3490–3502 (1987).

Noda, et al., "Existence of distinct sodium channel messenger RNAs in rat brain," *Nature*, 320: 188–192 (1986).

Noda, et al., "Expression of functional sodium channels from cloned cDNA," *Nature*, 322: 826–828 (1986).

Mierendorf et al., "Gene isolation by screening kgt11 libraries with antibodies," *Methods in Enz.*, 152: 458–469 (1986).

Gustin, et al., "Ion channels in yeast," *Science*, 233: 1195–1197 (1986).

Striessnig, et al., "Photoaffinity labelling of the phenylalkylamine receptor of the skeletal muscle transverse–tubule calcium channel," *FEBS Letters*, 212(2):247–253 (1987).

Froehner, "New insights into the molecular structure of the dihydropyridine–sensitive calcium channel," *TINS*, 11(3): 90–92 (1988).

Catterall, et al., "Molecular properties of dihydropyridine––sensitive calcium channels in skeletal muscle," *J.Biol.Chem.*, 263(8): 3535–3538 (1988).

Curtis, et al., "Purification of the calcium antagonist receptor of the voltage–sensitive calcium channel from skeletal muscle transverse tubules," *Biochemistry*, 23(10): 2113–2118 (1984).

Borsotto, et al., "The 1,4–dihydropyridine receptor associated with the skeletal muscle voltage–dependent $Ca^{2+}$ channel," *J.Biol.Chem.*, 260(26): 14255–14263 (1985).

Cooper, et al., "Purification and characterization of the dihydropyridine–sensitive voltage–dependent calcium channel from cardiac tissue," *J.Biol.Chem.*, 262(2): 509–512 (1987).

Wood, "Gene cloning based on long oligonucleotide probes," *Methods in Enzymology*, 152: 443–447 (1987).

Schmidt, et al., "Immunochemical analysis of subunit structure of 1,4–dihydropyridine receptors associated with voltage–dependent $Ca^{2+}$ channels in skeletal, cardiac, and smooth muscles," *Biochemistry*, 25: 3492–3495 (1986).

Mishina, et al., "Location of functional regions of acetylcholine receptor α–subunit by site–directed mutagenesis," *Nature*, 313: 364–369 (1985).

Hamill, et al., "Improved patch–clamp techniques for high––resolution current recording from cells and cell–free membrane patches," *Pfluger Archiv.European Journal of Physiology*, 391: 85–100 (1981).

Hess, et al., "Different modes of Ca channel gating behavior favored by dihydropyridine Ca agonist and antagonists," *Nature*, 311: 538–544 (1984).

Leung, et al., "Biochemical and ultrastructural characterization of the 1,4–dihydropyridine receptor from rabbit skeletal muscle," *J. of Biol.Chem.*, 263(2): 994–1001 (1988).

Imagawa, et al., "Phosphorylation of the 1,4–dihydropyridine receptor of the voltage–dependent $Ca^{2+}$ channel by an intrinsic protein kinase in isolated triads from rabbit skeletal muscle," *J. of Biol.Chem.*, 262(17): 8333–8339 (1987).

Miller, "Multiple calcium channels and neuronal function," *Science*, 235: 46–52 (1987).

Kozak, "An analysis of 5'–noncoding sequences from 699 vertebrate messenger RNAs," *Nucleic Acids Research*, 15(20): 8125–8148 (1987).

von Heijne, "Signal sequences: the limits of variation," *Journ. of Mol.Biol.*, 184: 99–105 (1985).

Hubbard, et al., "Synthesis and processing of asparagine–linked oligosaccharides[1,2]," *Ann.Rev.Biochem.*, 50: 555–583 (1981).

Feramisco, et al., "Optimal spatial requirements for the location of basic residues in peptide substrates for the cyclic AMP–dependent protein kinase," *Journal of Biological Chemistry*, 255(9): 4240–4245 (1980).

Takahashi, et al., "Identification of an α subunit of dihydropyridine–sensitive brain calcium channels," *Science*, 236: 88–91 (1987).

Hofmann, et al., "Regulation of the L–type calcium channel," *TINS*, 8: 393–398 (1987).

Curtis, et al., "Reconstitution of the voltage–sensitive calcium channel purified from skeletal muscle transverse tubules," *Biochemistry*, 25: 3077–3083 (1986).

Smith, et al., "Calcium channel activity in a purified dihydropyridine–receptor preparation of skeletal muscle," *Biochemistry*, 26: 7182–7188 (1987).

Meshi, et al., "Nucleotide sequence of the 30K protein cistron of cowpea strain of tobacco mosaic virus," *Nucleic Acids Research*, 10(19): 6111–6117 (1982).

Nikaido, et al., "Molecular cloning of a cDNA encoding human interleukin–2 receptor," *Nature*, 311: 631–636 (1984).

Roberts, et al., "Paraneoplastic myasthenic syndrome IgG inhibits $^{45}Ca^{2+}$ flux in a human small cell carcinoma line," *Nature*, 317: 737–739 (1985).

Starr, et al., "Primary structure of a calcium channel that is highly expressed in rat cerebellum," *Proc.Natl.Acad.Sci. USA*, 88: 5621–5625 (1991).

Snutch, et al., "Distinct calcium channels are generated by alternative splicing and are differently expressed in the mammalian CNS," *Neuron*, 7: 45–57 (1991).

Hui, et al., "Molecular cloning of multiple sybtypes of a novel rat brain isoform of the $a_1$ subunit of the voltage–dependent calcium channel," *Neuron*, 7: 35–44 (1991).

Bean et al., "Classes of calcium channels in vertebrate cells," *Annu.Rev. Physiol.*, 51: 367–384 (1989).

Swandulla, et al., "Do calcium channel classifications account for neuronal calcium channel diversity?" *TINS*, 14(2): 46–51 (1991).

Ruth et al., "Primary structure of the α subunit of the DHP–sensitive calcium channel from skeletal muscle," *Science*, 245: 1115–1118 (1989).

Mikami, et al., "Primary structure and functional expression of the cardiac dihydropyridine–sensitive calcium channel," *Nature*, 340: 230–233 (1989).

Biel, et al., "Primary structure and functional expression of a high voltage activated calcium channel from rabbit lung," *FEBS Letters*, 269(2): 409–412 (1990).

Mori, et al., "Primary structure and functional expression from complementary DNA of a brain calcium channel," *Nature*, 350: 398–402 (1991).

Snutch, et al., "Rat brain expresses a heterogeneous family of calcium channels," *Proc.Natl.Acad.Sci. USA,* 87: 3391–3395 (1990).

Perez–Reyes, et al., "Molecular diversity of L–type calcium channels," *J. of Biol. Chem.,* 265(33): 20430–20436 (1990).

Perez–Reyes, et al., "Induction of calcium currents by the expression of the $\alpha_1$–subunit of the dihydropyridine receptor from skeletal muscle," *Nature,* 340: 233–236 (1989).

Koch, et al., "Characterization of cDNA clones encoding two putative isoforms of the $\alpha_1$–subunit of the dihydropyridine–sensitive voltage–dependent calcium channel isolated from rat brain and rat aorta," *FEBS Letters,* 250(2): 386–388 (1989).

Slish, et al., "Evidence for the existence of a cardiac specific isoform of the $\alpha_1$–subunit of the voltage dependent calcium channel," *FEBS Letters,* 250(2): 509–514 (1989).

Varadi, et al., "Development regulation of expression of the $\alpha_1$ and $\alpha_2$ subunits mRNAs of the voltage–dependent calcium channel in a differentiating myogenic cell line," *FEBS Letters,* 250(2)CE: 515–518 (1989).

Ruth, et al., "Primary structure of the $\alpha$–subunit of the DHP–sensitive calcium channel from skeletal muscle," *Science,* 245: 1115–1118 (1989).

Jongh, et al., "Subunits of purified calcium channels: a 212–kDa form of $\alpha_1$ and partial amino acid sequence of a phosphorylation site of an independent $\beta$–subunit," *Proc.Natl.Acad.Sci. USA,* 86: 8585–8589 (1989).

Hamilton, et al., "Subunit composition of the purified dihydropyridine binding protein from skeletal muscle," *Biochemistry,* 28: 7820–7828 (1989).

Nunoki, et al., "Activation of purified calcium channels by stoichiometric protein phosphorylation," *Proc.Natl.Acad.Sci. USA,* 86: 6816–6820 (1989).

Ichida, et al., "Photoaffinity labeling with dihydropyridine derivatives of crude membranes from rat skeletal, cardiac, ileal, and uterine muscles and whole brain," *J.Biochem.,* 105: 767–774 (1989).

Sharp and Campbell, "Characterization of the 1,4–dihydropyridine receptor using subunit–specific polyclonal antibodies," *J.Biol.Chem.,* 264(5): 2816–2825 (1989).

Campbell, et al., "The biochemistry and molecular biology of the dihydropyridine–sensitive calcium channel," *TINS,* 11(10): 425–430 (1988).

Pelzer, et al., "Properties and regulation of calcium channels in muscle cells," *Rev.Physiol.Biochem.Pharmacol.,* 114: 107–207 (1990).

Kim, et al., "Studies on the structural requirements for the activity of the skeletal muscle dihydropyridine receptor/slow $Ca^{2+}$ channel," *J.Biol.Chem.,* 11858–11863 (1990).

Lotan, et al., "Specific block of calcium channel expression by a fragment of dihydropyridine receptor cDNA," *Science,* 243: 666–669 (1989).

Rampe, et al., "$[^3H]$Pn200–110 binding in a fibroblast cell line transformed with the $\alpha_1$ subunit of the skeletal muscle L–type $Ca^{2+}$ channel," *Biochem. and Biophys.Research Communications,* 169(3): 825–831 (1990).

Adams, et al., "Intramembrane charge movement restored in dysgenic skeletal muscle by injection of dihydropyridine receptor cDNAs," *Nature,* 346: 569–572 (1990).

Tanabe, et al., "Cardiac–type excitation–contraction coupling in a dysgenic skeletal muscle injected with cardiac dihydropyridine receptor cDNA," *Nature,* 344: 451–453 (1990).

Tanabe, et al., "Regions of the skeletal muscle dihydropyridine receptor critical for excitation–contraction coupling," *Nature,* 346: 567–569 (1991).

Regulla, et al., "Identification of the site of interaction of the dihydropyridine channel blockers nitrendipine and azidopine with the calcium–channel $\alpha_1$ subunit," *EMBO Journal,* 10(1): 45–49 (1991).

Williams, et al., "Structure and functional expression of $\alpha_1$, $\alpha_2$ and $\beta$ subunits of a novel human neuronal calcium channel subtype," *Neuron,* 8:71–84 (1992).

Olivera, et al., "Conotoxins," *J. of Biol.Chem.,* 266(33): 22067–22070 (1991).

Seino, et al., "Cloning of $\alpha_1$ subunit of a voltage–dependent calcium channel expressed in pancreatic $\beta$ cells," *Proc.Natl.Acad.Sci. USA,* 89: 584–588 (1992).

Perez–Reyes, et al., "Cloning and expression of a cardiac/brain $\beta$ subunit of the L–type calcium channel," *J. of Biol.Chem.,* 267(3): 1792–1797 (1992).

Miller, R., "Voltage–sensitive $Ca^{2+}$ channels," *J. of Biol.Chem.,* 267(3): 1403–1406 (1992).

Artalejo, et al., "$\omega$–Conotoxin GVIA blocks a $Ca^{2+}$ current in bovine chromaffin cells that is not of the 'classic' N type," *Neuron,* 8: 85–95 (1992).

Kasai, H., "Tonic inhibition and rebound facilitation of a neuronal calcium channel by a GTP–binding protein," *Proc.Natl.Acad.Sci. USA,* 88: 8855–8859 (1991).

Sher, et al., "Voltage–operated calcium channels in small cell lung carcinoma cell lines: pharmacological, functional, and immunological properties," *Cancer Research,* 5: 3892–3896 (1990).

Sher, et al., "$\omega$–Conotoxin binding and effects on calcium channel function in human neuroblastoma and rat pheochromocytoma cell lines," *FEBS Letters,* 235: (1,2): 178–182 (1988).

Koch, et al., "cDNA cloning of dihydropyridine–sensitive calcium channel from rat aorta," *J. of Biol.Chem.,* 265(29): 17786–17791 (1990).

Cohen, et al., "Distribution of $Ca^{2+}$ channels on frog motor nerve terminals revealed by fluorescent $\omega$–conotoxin," *J. of Neuroscience,* 11(4): 1032–1039 (1991).

Bosse, et al., "The cDNA and deduced amino acid sequence of the $\gamma$ subunit of the L–type calcium channel from rabbit skeletal muscle," *FEBS,* 267(1): 153–156 (1990).

Burns, et al., "Calcium channel activity of purified human synexin and structure of the human synexin gene," *Proc.Natl.Acad.Sci.,* 86: 3798–3802 (1989).

Campbell, et al., "32,000–Dalton subunit of the 1,4–dihydropyridine receptor," *Ann.N.Y.Acad.Sci.,* 560: 251–257 (1989).

Dascal, N., "The use of Xenopus oocytes for the study of ion channels," *CRC Critical Rev.Biochem.,* 22(4): 317–387 (1987).

DeJongh, et al., "Subunits of purified calcium channels," *J.Biol.Chem.,* 265(25): 14738–14741 (1990) (best available copy submitted).

Jay, et al., "Primary Structure of the $\gamma$ subunit of the DHP–sensitive calcium channel from skeletal muscle," *Science,* 248: 490–492 (1990).

Jay, et al., "Structural characterization of the dihydropyridine–sensitive calcium channel $\alpha_2$–subunit and the associated $\delta$ peptides," *J.Biol.Chem.,* 266(5): 3287–3293 (1991).

Leung, et al., "Monoclonal antibody characterization of the 1,4–dihydropyridine receptor of rabbit skeletal muscle," *Ann.N.Y.Acad.Sci.,* 522: 43–46 (1988).

Vaghy, et al., "Mechanism of action of calcium channel modulator drugs," *Ann.N.Y.Acad.Sci.,* 522: 176–186 (1988).

Ahlijanian, et al., "Subunit structure and localization of dihydropyridine–sensitive calcium channels in mammalian brain, spinal cord, and retina," *Neuron,* 4:819–832 (1990).

Blount, et al., "Assembly intermediates of the mouse muscle nicotinic Acetylcholine receptor in stably transfected fibroblasts," *J.Cell.Biol.,* 111: 2601 (1990).

Carbone, et al., "Ca currents in human neuroblastoma IMR32 cells: kinetics, permeability and pharmacology," *Pfluegers Arch.* 416: 170–179 (1990) (best available copy submitted).

Dascal, et al., "Expression of modulation of voltage–gated calcium channels after RNA injection in Xenopus oocytes," *Science,* 231: 1147–1150 (1986).

Hess, et al., "Calcium channels in vertebrate cells," *Ann.Rev.Neurosci.,* 13: 337–356 (1990).

Stanley, et al., "Characterization of a calcium current in a vertebrate cholinergic presynaptic nerve terminal," *J. Neurosci.,* 11: 985 (1991).

Wei, et al., "Heterologous regulation of the cardiac $Ca^{2+}$ channel $\alpha_1$ subunit by skeletal muscle $\beta$ and $\gamma$ subunits," *J.Biol.Chem.,* 266: 21943–21947 (1991).

Ahlijanian, et al., "Phosphorylation of an $\alpha1$–like subunit of an $\omega$–conotoxin–sensitive brain calcium channel by cAMP––dependent protein kinase and protein kinase C," *J.Biol.Chem.,* 266: 20192 (1991).

Claudio, T., "Stable expression of transfected Torpedo acetylcholine receptor $\alpha$ subunits in mouse fibroblast L cells," *Proc.Natl.Acad.Sci.,* 84: 5967–5971 (1987).

Hullin, et al., "Calcium channel $\beta$ subunit heterogeneity: functional expression of cloned cDNA from heart, aorta and brain," *EMBO J.,* 11: 885 (1992).

Kim, et al., "Rat brain expresses an alternatively spliced form of the dihydropyridine–sensitive L–type calcium channel $\alpha2$ subunit," *Proc.Natl.Acad.Sci.,* 89:3251 (1992).

Pragnell, et al., "Cloning and tissue–specific expression of the brain calcium channel $\beta$–subunit," *FEBS Letters,* 291: 253 (1991).

Sakamoto, et al., "A monoclonal antibody to the $\beta$ subunit of the skeletal muscle dihydropyridine receptor immunoprecipitates the brain $\omega$–conotoxin GVIA receptor," *J.Biol.Chem.,* 266: 18914 (1991).

Seagar, et al., "Molecular properties of dihydropyridine––sensitive calcium channels," *Ann.N.Y.Acad.Sci.,* 552: 162–175 (1988).

Tsien, et al., "Molecular diversity of voltage–dependent $Ca^{2+}$ channels," *Trends in Pharmacol.Sci.,* 12: 349 (1991).

Takahashi and Catterall, "Dihydropyridine–sensitive calcium channels in cardiac and skeletal muscle membranes: studies with antibodies against the $\alpha$–subunits," *Biochemistry,* 26(17): 1518–1526 (1987).

Cruz et al., "Characterization of $\omega$–Conotoxin Target. Evidence for Tissue–Specific Heterogeneity ion Calcium Channel Types", *Biochem. J.* 26:820 (1987).

Breitbart et al., "Alternative Splicing: A Ubiquitous Mechanism for the Generation of Multiple Protein Isoforms From Single Genes", *Ann. Rev. Biochem.* 56:467–495.

Williams et al., "Structure and Functional Expression of an $\omega$–Conotoxin–Sensitive Human N–Type Calcium Channel", *Science* 257:389–395 (1992).

Rosenfield et al., "Cloning and Characterization of a Lambert–Eaton Myasthenic Syndrome Antigen", *Annals of Neurology* 33:113–120 (1993).

Powers et al., "Skeletal Muscle and Brain Isoforms of a $\beta$–Subunit of Human Voltage–dependent Calcium Channels Are Encoded by a Single Gene", *J. Biol. Chem.* 267:22967–22972 (1992).

Wah et al., "Structure and Functional Expression of a Member of the Low–Voltage–Activated Calcium channel Family", *Science 260*:1133–1136.

Horne et al., "Molecular diversity of $Ca^{2+}$ channel $\alpha_1$ subunits from the marine ray *Discopyge ommata*", *Proc.Natl.Acad.Sci. 90*:3787–3791 (1993).

Yu et al., "Molecular characterization and nephron distribution of a family of transcripts encoding the pore–forming subunit of $Ca^{2+}$ channels in the kidney", *Proc.Natl.Acad.Sci.* 89:10494–10498 (1992).

Dubel et al., "Molecular cloning of the $\alpha$–1 subunit of an $\omega$–conotoxin–sensitive calcium channel", *Proc.Natl.Acad.Sci. 89*:5058–5062 (1992).

Soldatov, "Molecular diversity of L–type $Ca^{2+}$ channel transcripts in human fibroblasts", *Proc.Natl.Acad.Sci.* 89:4628–4632 (1992).

Leveque et al., "The synaptic vesicle protein synaptotagmim associates with calcium channels and is a putative Lambert–Eaton myasthenic syndrome antigen", *Proc.Natl.Acad.Sci. 89*:3625–3629 (1992).

Niidome et al., "Molecular cloning and characterization of a novel calcium channel from rabbit brain", *FEBS LTTRS 308*:7–13 (1992).

Elinor et al., "Functional expression of a rapidly inactivating neuronal calcium channel", *Nature 363*:455–458 (1993).

Ellis et al. (1988) "Sequence and Expression of mRNAs Encoding the $\alpha_1$ and $\alpha_2$ Subunits of DHP–Sensitive Calcium Channel", *Science 241*:1661–1664.

Spedding et al., 'Calcium Antgonists': A Class of Drugs with a Bright Future. Part II. Determination of Basic Pharmacological Properties, *Life Sciences 35*:575–587 (1984).

Brust et al., "Human neuronal voltage–dependent calcium channels: Studies on subunit structure and role in channel assembly," *Neuropharmacology* 32(11);1089–1102 (1993).

Collin, et al., "Cloning, chromosomal location and functional expression of the human voltage–dependent calcium––channel $\beta3$ subunit," *Eur. J. Biochem.* 220:257–262 (1994).

Williams, et al., "Structure and functional characterization of neuronal $\alpha_{1E}$ calcium channel subtypes," *J. Biol. Chem.* 269(35):22347–22357 (1994).

Stauderman et al., "Effect of $\beta_{1b}$, $\beta_{2e}$, $\beta_{3a}$, or $\beta_{4a}$ Subunits on the Pharmacological Sensitivity of HEK293 Cells Stably Transfected with $\alpha_{1A}$ Subunits of Human Voltage–Gated $Ca^{2+}$ Channels," Abstract from Society for Neuroscience Meeting, Washington, DC, Nov. 1996.

Urrutia et al, "Influence of Different $\beta$ Subunits on the Biophysical Properties of the Human $\alpha_{1A-2}$ Containing Calcium Channels Stably Expressed in HEK293 Cells," Abstract from Society for Neuroscience Meeting, Washington, DC, Nov. 1996.

Volsen et al., "Expression of Voltage–Dependent Calcium Channel $\beta$ Subunits in Human Cerebellar Purkinje Cells," Abstract from Society for Neuroscience Meeting, Washington, DC, Nov. 1996.

Volsen et al, "The Expression of Voltage–Dependent Calcium Channel Beta Subunits in the Human Cerebellum," *Neuroscience* 80(1):161–174 (1997).

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
        (A) LENGTH: 7635 base pairs
        (B) TYPE: nucleic acid
        (C) STRANDEDNESS: double

```
        (D) TOPOLOGY: linear (ii) MOLECULE TYPE: DNA (genomic)

(ix) FEATURE:
         (A) NAME/KEY: CDS
         (B) LOCATION: 511..6996

(ix) FEATURE:
         (A) NAME/KEY: 5'UTR
         (B) LOCATION: 1..510

(ix) FEATURE:
         (A) NAME/KEY: 3'UTR
         (B) LOCATION: 6994..7635

(xi) SEQUENCE DESCRIPTION: SEQ ID NO:1:

GGGCGAGCGC CTCCGTCCCC GGATGTGAGC TCCGGCTGCC CGCGGTCCCG AGCCAGCGGC          60

GCGCGGGCGG CGGCGGCGGG CACCGGGCAC CGCGGCGGGC GGGCAGACGG GCGGGCATGG         120

GGGGAGCGCC GAGCGGCCCC GGCGGCCGGG CCGGCATCAC CGCGGCGTCT CTCCGCTAGA         180

GGAGGGGACA AGCCAGTTCT CCTTTGCAGC AAAAAATTAC ATGTATATAT TATTAAGATA         240

ATATATACAT TGGATTTTAT TTTTTTAAAA AGTTTATTTT GCTCCATTTT TGAAAAAGAG         300

AGAGCTTGGG TGGCGAGCGG TTTTTTTTTA AAATCAATTA TCCTTATTTT CTGTTATTTG         360

TCCCCGTCCC TCCCCACCCC CCTGCTGAAG CGAGAATAAG GGCAGGGACC GCGGCTCCTA         420

CCTCTTGGTG ATCCCCTTCC CCATTCCGCC CCCGCCCCAA CGCCCAGCAC AGTGCCCTGC         480

ACACAGTAGT CGCTCAATAA ATGTTCGTGG ATG ATG ATG ATG ATG ATG ATG AAA          534
                                 Met Met Met Met Met Met Met Lys
                                   1               5

AAA ATG CAG CAT CAA CGG CAG CAG CAA GCG GAC CAC GCG AAC GAG GCA           582
Lys Met Gln His Gln Arg Gln Gln Gln Ala Asp His Ala Asn Glu Ala
 10                  15                  20

AAC TAT GCA AGA GGC ACC AGA CTT CCT CTT TCT GGT GAA GGA CCA ACT           630
Asn Tyr Ala Arg Gly Thr Arg Leu Pro Leu Ser Gly Glu Gly Pro Thr
 25                  30                  35                  40

TCT CAG CCG AAT AGC TCC AAG CAA ACT GTC CTG TCT TGG CAA GCT GCA           678
Ser Gln Pro Asn Ser Ser Lys Gln Thr Val Leu Ser Trp Gln Ala Ala
                 45                  50                  55

ATC GAT GCT GCT AGA CAG GCC AAG GCT GCC CAA ACT ATG AGC ACC TCT           726
Ile Asp Ala Ala Arg Gln Ala Lys Ala Ala Gln Thr Met Ser Thr Ser
             60                  65                  70

GCA CCC CCA CCT GTA GGA TCT CTC TCC CAA AGA AAA CGT CAG CAA TAC           774
Ala Pro Pro Pro Val Gly Ser Leu Ser Gln Arg Lys Arg Gln Gln Tyr
         75                  80                  85

GCC AAG AGC AAA AAA CAG GGT AAC TCG TCC AAC AGC CGA CCT GCC CGC           822
Ala Lys Ser Lys Lys Gln Gly Asn Ser Ser Asn Ser Arg Pro Ala Arg
     90                  95                 100

GCC CTT TTC TGT TTA TCA CTC AAT AAC CCC ATC CGA AGA GCC TGC ATT           870
Ala Leu Phe Cys Leu Ser Leu Asn Asn Pro Ile Arg Arg Ala Cys Ile
105                 110                 115                 120

AGT ATA GTG GAA TGG AAA CCA TTT GAC ATA TTT ATA TTA TTG GCT ATT           918
Ser Ile Val Glu Trp Lys Pro Phe Asp Ile Phe Ile Leu Leu Ala Ile
                125                 130                 135

TTT GCC AAT TGT GTG GCC TTA GCT ATT TAC ATC CCA TTC CCT GAA GAT           966
Phe Ala Asn Cys Val Ala Leu Ala Ile Tyr Ile Pro Phe Pro Glu Asp
            140                 145                 150

GAT TCT AAT TCA ACA AAT CAT AAC TTG GAA AAA GTA GAA TAT GCC TTC          1014
Asp Ser Asn Ser Thr Asn His Asn Leu Glu Lys Val Glu Tyr Ala Phe
        155                 160                 165

CTG ATT ATT TTT ACA GTC GAG ACA TTT TTG AAG ATT ATA GCG TAT GGA          1062
```

-continued

```
Leu Ile Ile Phe Thr Val Glu Thr Phe Leu Lys Ile Ile Ala Tyr Gly
        170                 175                 180

TTA TTG CTA CAT CCT AAT GCT TAT GTT AGG AAT GGA TGG AAT TTA CTG      1110
Leu Leu Leu His Pro Asn Ala Tyr Val Arg Asn Gly Trp Asn Leu Leu
185                 190                 195                 200

GAT TTT GTT ATA GTA ATA GTA GGA TTG TTT AGT GTA ATT TTG GAA CAA      1158
Asp Phe Val Ile Val Ile Val Gly Leu Phe Ser Val Ile Leu Glu Gln
                205                 210                 215

TTA ACC AAA GAA ACA GAA GGC GGG AAC CAC TCA AGC GGC AAA TCT GGA      1206
Leu Thr Lys Glu Thr Glu Gly Gly Asn His Ser Ser Gly Lys Ser Gly
            220                 225                 230

GGC TTT GAT GTC AAA GCC CTC CGT GCC TTT CGA GTG TTG CGA CCA CTT      1254
Gly Phe Asp Val Lys Ala Leu Arg Ala Phe Arg Val Leu Arg Pro Leu
        235                 240                 245

CGA CTA GTG TCA GGA GTG CCC AGT TTA CAA GTT GTC CTG AAC TCC ATT      1302
Arg Leu Val Ser Gly Val Pro Ser Leu Gln Val Val Leu Asn Ser Ile
250                 255                 260

ATA AAA GCC ATG GTT CCC CTC CTT CAC ATA GCC CTT TTG GTA TTA TTT      1350
Ile Lys Ala Met Val Pro Leu Leu His Ile Ala Leu Leu Val Leu Phe
265                 270                 275                 280

GTA ATC ATA ATC TAT GCT ATT ATA GGA TTG GAA CTT TTT ATT GGA AAA      1398
Val Ile Ile Ile Tyr Ala Ile Ile Gly Leu Glu Leu Phe Ile Gly Lys
                285                 290                 295

ATG CAC AAA ACA TGT TTT TTT GCT GAC TCA GAT ATC GTA GCT GAA GAG      1446
Met His Lys Thr Cys Phe Phe Ala Asp Ser Asp Ile Val Ala Glu Glu
            300                 305                 310

GAC CCA GCT CCA TGT GCG TTC TCA GGG AAT GGA CGC CAG TGT ACT GCC      1494
Asp Pro Ala Pro Cys Ala Phe Ser Gly Asn Gly Arg Gln Cys Thr Ala
        315                 320                 325

AAT GGC ACG GAA TGT AGG AGT GGC TGG GTT GGC CCG AAC GGA GGC ATC      1542
Asn Gly Thr Glu Cys Arg Ser Gly Trp Val Gly Pro Asn Gly Gly Ile
330                 335                 340

ACC AAC TTT GAT AAC TTT GCC TTT GCC ATG CTT ACT GTG TTT CAG TGC      1590
Thr Asn Phe Asp Asn Phe Ala Phe Ala Met Leu Thr Val Phe Gln Cys
345                 350                 355                 360

ATC ACC ATG GAG GGC TGG ACA GAC GTG CTC TAC TGG ATG AAT GAT GCT      1638
Ile Thr Met Glu Gly Trp Thr Asp Val Leu Tyr Trp Met Asn Asp Ala
                365                 370                 375

ATG GGA TTT GAA TTG CCC TGG GTG TAT TTT GTC AGT CTC GTC ATC TTT      1686
Met Gly Phe Glu Leu Pro Trp Val Tyr Phe Val Ser Leu Val Ile Phe
            380                 385                 390

GGG TCA TTT TTC GTA CTA AAT CTT GTA CTT GGT GTA TTG AGC GGA GAA      1734
Gly Ser Phe Phe Val Leu Asn Leu Val Leu Gly Val Leu Ser Gly Glu
        395                 400                 405

TTC TCA AAG GAA AGA GAG AAG GCA AAA GCA CGG GGA GAT TTC CAG AAG      1782
Phe Ser Lys Glu Arg Glu Lys Ala Lys Ala Arg Gly Asp Phe Gln Lys
410                 415                 420

CTC CGG GAG AAG CAG CAG CTG GAG GAG GAT CTA AAG GGC TAC TTG GAT      1830
Leu Arg Glu Lys Gln Gln Leu Glu Glu Asp Leu Lys Gly Tyr Leu Asp
425                 430                 435                 440

TGG ATC ACC CAA GCT GAG GAC ATC GAT CCG GAG AAT GAG GAA GAA GGA      1878
Trp Ile Thr Gln Ala Glu Asp Ile Asp Pro Glu Asn Glu Glu Glu Gly
                445                 450                 455

GGA GAG GAA GGC AAA CGA AAT ACT AGC ATG CCC ACC AGC GAG ACT GAG      1926
Gly Glu Glu Gly Lys Arg Asn Thr Ser Met Pro Thr Ser Glu Thr Glu
            460                 465                 470

TCT GTG AAC ACA GAG AAC GTC AGC GGT GAA GGC GAG AAC CGA GGC TGC      1974
Ser Val Asn Thr Glu Asn Val Ser Gly Glu Gly Glu Asn Arg Gly Cys
        475                 480                 485
```

```
TGT GGA AGT CTC TGT CAA GCC ATC TCA AAA TCC AAA CTC AGC CGA CGC        2022
Cys Gly Ser Leu Cys Gln Ala Ile Ser Lys Ser Lys Leu Ser Arg Arg
        490                 495                 500

TGG CGT CGC TGG AAC CGA TTC AAT CGC AGA AGA TGT AGG GCC GCC GTG        2070
Trp Arg Arg Trp Asn Arg Phe Asn Arg Arg Arg Cys Arg Ala Ala Val
505                 510                 515                 520

AAG TCT GTC ACG TTT TAC TGG CTG GTT ATC GTC CTG GTG TTT CTG AAC        2118
Lys Ser Val Thr Phe Tyr Trp Leu Val Ile Val Leu Val Phe Leu Asn
                525                 530                 535

ACC TTA ACC ATT TCC TCT GAG CAC TAC AAT CAG CCA GAT TGG TTG ACA        2166
Thr Leu Thr Ile Ser Ser Glu His Tyr Asn Gln Pro Asp Trp Leu Thr
        540                 545                 550

CAG ATT CAA GAT ATT GCC AAC AAA GTC CTC TTG GCT CTG TTC ACC TGC        2214
Gln Ile Gln Asp Ile Ala Asn Lys Val Leu Leu Ala Leu Phe Thr Cys
                555                 560                 565

GAG ATG CTG GTA AAA ATG TAC AGC TTG GGC CTC CAA GCA TAT TTC GTC        2262
Glu Met Leu Val Lys Met Tyr Ser Leu Gly Leu Gln Ala Tyr Phe Val
        570                 575                 580

TCT CTT TTC AAC CGG TTT GAT TGC TTC GTG GTG TGT GGT GGA ATC ACT        2310
Ser Leu Phe Asn Arg Phe Asp Cys Phe Val Val Cys Gly Gly Ile Thr
585                 590                 595                 600

GAG ACG ATC TTG GTG GAA CTG GAA ATC ATG TCT CCC CTG GGG ATC TCT        2358
Glu Thr Ile Leu Val Glu Leu Glu Ile Met Ser Pro Leu Gly Ile Ser
                605                 610                 615

GTG TTT CGG TGT GTG CGC CTC TTA AGA ATC TTC AAA GTG ACC AGG CAC        2406
Val Phe Arg Cys Val Arg Leu Leu Arg Ile Phe Lys Val Thr Arg His
        620                 625                 630

TGG ACT TCC CTG AGC AAC TTA GTG GCA TCC TTA TTA AAC TCC ATG AAG        2454
Trp Thr Ser Leu Ser Asn Leu Val Ala Ser Leu Leu Asn Ser Met Lys
                635                 640                 645

TCC ATC GCT TCG CTG TTG CTT CTG CTT TTT CTC TTC ATT ATC ATC TTT        2502
Ser Ile Ala Ser Leu Leu Leu Leu Phe Leu Phe Ile Ile Ile Phe
650                 655                 660

TCC TTG CTT GGG ATG CAG CTG TTT GGC GGC AAG TTT AAT TTT GAT GAA        2550
Ser Leu Leu Gly Met Gln Leu Phe Gly Gly Lys Phe Asn Phe Asp Glu
665                 670                 675                 680

ACG CAA ACC AAG CGG AGC ACC TTT GAC AAT TTC CCT CAA GCA CTT CTC        2598
Thr Gln Thr Lys Arg Ser Thr Phe Asp Asn Phe Pro Gln Ala Leu Leu
                685                 690                 695

ACA GTG TTC CAG ATC CTG ACA GGC GAA GAC TGG AAT GCT GTG ATG TAC        2646
Thr Val Phe Gln Ile Leu Thr Gly Glu Asp Trp Asn Ala Val Met Tyr
        700                 705                 710

GAT GGC ATC ATG GCT TAC GGG GGC CCA TCC TCT TCA GGA ATG ATC GTC        2694
Asp Gly Ile Met Ala Tyr Gly Gly Pro Ser Ser Ser Gly Met Ile Val
                715                 720                 725

TGC ATC TAC TTC ATC ATC CTC TTC ATT TGT GGT AAC TAT ATT CTA CTG        2742
Cys Ile Tyr Phe Ile Ile Leu Phe Ile Cys Gly Asn Tyr Ile Leu Leu
        730                 735                 740

AAT GTC TTC TTG GCC ATC GCT GTA GAC AAT TTG GCT GAT GCT GAA AGT        2790
Asn Val Phe Leu Ala Ile Ala Val Asp Asn Leu Ala Asp Ala Glu Ser
745                 750                 755                 760

CTG AAC ACT GCT CAG AAA GAA GAA GCG GAA GAA AAG GAG AGG AAA AAG        2838
Leu Asn Thr Ala Gln Lys Glu Glu Ala Glu Glu Lys Glu Arg Lys Lys
                765                 770                 775

ATT GCC AGA AAA GAG AGC CTA GAA AAT AAA AAG AAC AAC AAA CCA GAA        2886
Ile Ala Arg Lys Glu Ser Leu Glu Asn Lys Lys Asn Asn Lys Pro Glu
        780                 785                 790

GTC AAC CAG ATA GCC AAC AGT GAC AAC AAG GTT ACA ATT GAT GAC TAT        2934
Val Asn Gln Ile Ala Asn Ser Asp Asn Lys Val Thr Ile Asp Asp Tyr
                795                 800                 805
```

```
AGA GAA GAG GAT GAA GAC AAG GAC CCC TAT CCG CCT TGC GAT GTG CCA    2982
Arg Glu Asp Glu Asp Lys Asp Pro Tyr Pro Pro Cys Asp Val Pro
    810             815                 820

GTA GGG GAA GAG GAA GAG GAA GAG GAG GAG GAT GAA CCT GAG GTT CCT    3030
Val Gly Glu Glu Glu Glu Glu Glu Glu Glu Asp Glu Pro Glu Val Pro
825             830                 835                 840

GCC GGA CCC CGT CCT CGA AGG ATC TCG GAG TTG AAC ATG AAG GAA AAA    3078
Ala Gly Pro Arg Pro Arg Arg Ile Ser Glu Leu Asn Met Lys Glu Lys
            845                 850                 855

ATT GCC CCC ATC CCT GAA GGG AGC GCT TTC TTC ATT CTT AGC AAG ACC    3126
Ile Ala Pro Ile Pro Glu Gly Ser Ala Phe Phe Ile Leu Ser Lys Thr
            860                 865                 870

AAC CCG ATC CGC GTA GGC TGC CAC AAG CTC ATC AAC CAC CAC ATC TTC    3174
Asn Pro Ile Arg Val Gly Cys His Lys Leu Ile Asn His His Ile Phe
            875                 880                 885

ACC AAC CTC ATC CTT GTC TTC ATC ATG CTG AGC AGT GCT GCC CTG GCC    3222
Thr Asn Leu Ile Leu Val Phe Ile Met Leu Ser Ser Ala Ala Leu Ala
890                 895                 900

GCA GAG GAC CCC ATC CGC AGC CAC TCC TTC CGG AAC ACG ATA CTG GGT    3270
Ala Glu Asp Pro Ile Arg Ser His Ser Phe Arg Asn Thr Ile Leu Gly
905             910                 915                 920

TAC TTT GAC TAT GCC TTC ACA GCC ATC TTT ACT GTT GAG ATC CTG TTG    3318
Tyr Phe Asp Tyr Ala Phe Thr Ala Ile Phe Thr Val Glu Ile Leu Leu
            925                 930                 935

AAG ATG ACA ACT TTT GGA GCT TTC CTC CAC AAA GGG GCC TTC TGC AGG    3366
Lys Met Thr Thr Phe Gly Ala Phe Leu His Lys Gly Ala Phe Cys Arg
            940                 945                 950

AAC TAC TTC AAT TTG CTG GAT ATG CTG GTG GTT GGG GTG TCT CTG GTG    3414
Asn Tyr Phe Asn Leu Leu Asp Met Leu Val Val Gly Val Ser Leu Val
            955                 960                 965

TCA TTT GGG ATT CAA TCC AGT GCC ATC TCC GTT GTG AAG ATT CTG AGG    3462
Ser Phe Gly Ile Gln Ser Ser Ala Ile Ser Val Val Lys Ile Leu Arg
            970                 975                 980

GTC TTA AGG GTC CTG CGT CCC CTC AGG GCC ATC AAC AGA GCA AAA GGA    3510
Val Leu Arg Val Leu Arg Pro Leu Arg Ala Ile Asn Arg Ala Lys Gly
985                 990                 995                 1000

CTT AAG CAC GTG GTC CAG TGC GTC TTC GTG GCC ATC CGG ACC ATC GGC    3558
Leu Lys His Val Val Gln Cys Val Phe Val Ala Ile Arg Thr Ile Gly
            1005                1010                1015

AAC ATC ATG ATC GTC ACC ACC CTC CTG CAG TTC ATG TTT GCC TGT ATC    3606
Asn Ile Met Ile Val Thr Thr Leu Leu Gln Phe Met Phe Ala Cys Ile
            1020                1025                1030

GGG GTC CAG TTG TTC AAG GGG AAG TTC TAT CGC TGT ACG GAT GAA GCC    3654
Gly Val Gln Leu Phe Lys Gly Lys Phe Tyr Arg Cys Thr Asp Glu Ala
            1035                1040                1045

AAA AGT AAC CCT GAA GAA TGC AGG GGA CTT TTC ATC CTC TAC AAG GAT    3702
Lys Ser Asn Pro Glu Glu Cys Arg Gly Leu Phe Ile Leu Tyr Lys Asp
            1050                1055                1060

GGG GAT GTT GAC AGT CCT GTG GTC CGT GAA CGG ATC TGG CAA AAC AGT    3750
Gly Asp Val Asp Ser Pro Val Val Arg Glu Arg Ile Trp Gln Asn Ser
1065                1070                1075                1080

GAT TTC AAC TTC GAC AAC GTC CTC TCT GCT ATG ATG GCG CTC TTC ACA    3798
Asp Phe Asn Phe Asp Asn Val Leu Ser Ala Met Met Ala Leu Phe Thr
            1085                1090                1095

GTC TCC ACG TTT GAG GGC TGG CCT GCG TTG CTG TAT AAA GCC ATC GAC    3846
Val Ser Thr Phe Glu Gly Trp Pro Ala Leu Leu Tyr Lys Ala Ile Asp
            1100                1105                1110

TCG AAT GGA GAG AAC ATC GGC CCA ATC TAC AAC CAC CGC GTG GAG ATC    3894
Ser Asn Gly Glu Asn Ile Gly Pro Ile Tyr Asn His Arg Val Glu Ile
```

-continued

```
              1115                1120                1125
TCC ATC TTC TTC ATC ATC TAC ATC ATC ATT GTA GCT TTC TTC ATG ATG           3942
Ser Ile Phe Phe Ile Ile Tyr Ile Ile Ile Val Ala Phe Phe Met Met
        1130                1135                1140

AAC ATC TTT GTG GGC TTT GTC ATC GTT ACA TTT CAG GAA CAA GGA GAA           3990
Asn Ile Phe Val Gly Phe Val Ile Val Thr Phe Gln Glu Gln Gly Glu
1145                1150                1155                1160

AAA GAG TAT AAG AAC TGT GAG CTG GAC AAA AAT CAG CGT CAG TGT GTT          4038
Lys Glu Tyr Lys Asn Cys Glu Leu Asp Lys Asn Gln Arg Gln Cys Val
            1165                1170                1175

GAA TAC GCC TTG AAA GCA CGT CCC TTG CGG AGA TAC ATC CCC AAA AAC           4086
Glu Tyr Ala Leu Lys Ala Arg Pro Leu Arg Arg Tyr Ile Pro Lys Asn
        1180                1185                1190

CCC TAC CAG TAC AAG TTC TGG TAC GTG GTG AAC TCT TCG CCT TTC GAA           4134
Pro Tyr Gln Tyr Lys Phe Trp Tyr Val Val Asn Ser Ser Pro Phe Glu
    1195                1200                1205

TAC ATG ATG TTT GTC CTC ATC ATG CTC AAC ACA CTC TGC TTG GCC ATG           4182
Tyr Met Met Phe Val Leu Ile Met Leu Asn Thr Leu Cys Leu Ala Met
1210                1215                1220

CAG CAC TAC GAG CAG TCC AAG ATG TTC AAT GAT GCC ATG GAC ATT CTG           4230
Gln His Tyr Glu Gln Ser Lys Met Phe Asn Asp Ala Met Asp Ile Leu
1225                1230                1235                1240

AAC ATG GTC TTC ACC GGG GTG TTC ACC GTC GAG ATG GTT TTG AAA GTC           4278
Asn Met Val Phe Thr Gly Val Phe Thr Val Glu Met Val Leu Lys Val
            1245                1250                1255

ATC GCA TTT AAG CCT AAG GGG TAT TTT AGT GAC GCC TGG AAC ACG TTT           4326
Ile Ala Phe Lys Pro Lys Gly Tyr Phe Ser Asp Ala Trp Asn Thr Phe
        1260                1265                1270

GAC TCC CTC ATC GTA ATC GGC AGC ATT ATA GAC GTG GCC CTC AGC GAA          4374
Asp Ser Leu Ile Val Ile Gly Ser Ile Ile Asp Val Ala Leu Ser Glu
    1275                1280                1285

GCA GAC CCA ACT GAA AGT GAA AAT GTC CCT GTC CCA ACT GCT ACA CCT           4422
Ala Asp Pro Thr Glu Ser Glu Asn Val Pro Val Pro Thr Ala Thr Pro
1290                1295                1300

GGG AAC TCT GAA GAG AGC AAT AGA ATC TCC ATC ACC TTT TTC CGT CTT           4470
Gly Asn Ser Glu Glu Ser Asn Arg Ile Ser Ile Thr Phe Phe Arg Leu
1305                1310                1315                1320

TTC CGA GTG ATG CGA TTG GTG AAG CTT CTC AGC AGG GGG GAA GGC ATC          4518
Phe Arg Val Met Arg Leu Val Lys Leu Leu Ser Arg Gly Glu Gly Ile
            1325                1330                1335

CGG ACA TTG CTG TGG ACT TTT ATT AAG TTC TTT CAG GCG CTC CCG TAT           4566
Arg Thr Leu Leu Trp Thr Phe Ile Lys Phe Phe Gln Ala Leu Pro Tyr
        1340                1345                1350

GTG GCC CTC CTC ATA GCC ATG CTG TTC TTC ATC TAT GCG GTC ATT GGC           4614
Val Ala Leu Leu Ile Ala Met Leu Phe Phe Ile Tyr Ala Val Ile Gly
    1355                1360                1365

ATG CAG ATG TTT GGG AAA GTT GCC ATG AGA GAT AAC AAC CAG ATC AAT           4662
Met Gln Met Phe Gly Lys Val Ala Met Arg Asp Asn Asn Gln Ile Asn
1370                1375                1380

AGG AAC AAT AAC TTC CAG ACG TTT CCC CAG GCG GTG CTG CTG CTC TTC           4710
Arg Asn Asn Asn Phe Gln Thr Phe Pro Gln Ala Val Leu Leu Leu Phe
1385                1390                1395                1400

AGG TGT GCA ACA GGT GAG GCC TGG CAG GAG ATC ATG CTG GCC TGT CTC           4758
Arg Cys Ala Thr Gly Glu Ala Trp Gln Glu Ile Met Leu Ala Cys Leu
            1405                1410                1415

CCA GGG AAG CTC TGT GAC CCT GAG TCA GAT TAC AAC CCC GGG GAG GAG           4806
Pro Gly Lys Leu Cys Asp Pro Glu Ser Asp Tyr Asn Pro Gly Glu Glu
        1420                1425                1430

CAT ACA TGT GGG AGC AAC TTT GCC ATT GTC TAT TTC ATC AGT TTT TAC           4854
```

```
                          -continued

His Thr Cys Gly Ser Asn Phe Ala Ile Val Tyr Phe Ile Ser Phe Tyr
    1435                1440                1445

ATG CTC TGT GCA TTT CTG ATC ATC AAT CTG TTT GTG GCT GTC ATC ATG    4902
Met Leu Cys Ala Phe Leu Ile Ile Asn Leu Phe Val Ala Val Ile Met
    1450                1455                1460

GAT AAT TTC GAC TAT CTG ACC CGG GAC TGG TCT ATT TTG GGG CCT CAC    4950
Asp Asn Phe Asp Tyr Leu Thr Arg Asp Trp Ser Ile Leu Gly Pro His
1465                1470                1475                1480

CAT TTA GAT GAA TTC AAA AGA ATA TGG TCA GAA TAT GAC CCT GAG GCA    4998
His Leu Asp Glu Phe Lys Arg Ile Trp Ser Glu Tyr Asp Pro Glu Ala
                    1485                1490                1495

AAG GGA AGG ATA AAA CAC CTT GAT GTG GTC ACT CTG CTT CGA CGC ATC    5046
Lys Gly Arg Ile Lys His Leu Asp Val Val Thr Leu Leu Arg Arg Ile
                1500                1505                1510

CAG CCT CCC CTG GGG TTT GGG AAG TTA TGT CCA CAC AGG GTA GCG TGC    5094
Gln Pro Pro Leu Gly Phe Gly Lys Leu Cys Pro His Arg Val Ala Cys
            1515                1520                1525

AAG AGA TTA GTT GCC ATG AAC ATG CCT CTC AAC AGT GAC GGG ACA GTC    5142
Lys Arg Leu Val Ala Met Asn Met Pro Leu Asn Ser Asp Gly Thr Val
        1530                1535                1540

ATG TTT AAT GCA ACC CTG TTT GCT TTG GTT CGA ACG GCT CTT AAG ATC    5190
Met Phe Asn Ala Thr Leu Phe Ala Leu Val Arg Thr Ala Leu Lys Ile
1545                1550                1555                1560

AAG ACC GAA GGG AAC CTG GAG CAA GCT AAT GAA GAA CTT CGG GCT GTG    5238
Lys Thr Glu Gly Asn Leu Glu Gln Ala Asn Glu Glu Leu Arg Ala Val
                    1565                1570                1575

ATA AAG AAA ATT TGG AAG AAA ACC AGC ATG AAA TTA CTT GAC CAA GTT    5286
Ile Lys Lys Ile Trp Lys Lys Thr Ser Met Lys Leu Leu Asp Gln Val
                1580                1585                1590

GTC CCT CCA GCT GGT GAT GAT GAG GTA ACC GTG GGG AAG TTC TAT GCC    5334
Val Pro Pro Ala Gly Asp Asp Glu Val Thr Val Gly Lys Phe Tyr Ala
            1595                1600                1605

ACT TTC CTG ATA CAG GAC TAC TTT AGG AAA TTC AAG AAA CGG AAA GAA    5382
Thr Phe Leu Ile Gln Asp Tyr Phe Arg Lys Phe Lys Lys Arg Lys Glu
        1610                1615                1620

CAA GGA CTG GTG GGA AAG TAC CCT GCG AAG AAC ACC ACA ATT GCC CTA    5430
Gln Gly Leu Val Gly Lys Tyr Pro Ala Lys Asn Thr Thr Ile Ala Leu
1625                1630                1635                1640

CAG GCG GGA TTA AGG ACA CTG CAT GAC ATT GGG CCA GAA ATC CGG CGT    5478
Gln Ala Gly Leu Arg Thr Leu His Asp Ile Gly Pro Glu Ile Arg Arg
                    1645                1650                1655

GCT ATA TCG TGT GAT TTG CAA GAT GAC GAG CCT GAG GAA ACA AAA CGA    5526
Ala Ile Ser Cys Asp Leu Gln Asp Asp Glu Pro Glu Glu Thr Lys Arg
                1660                1665                1670

GAA GAA GAA GAT GAT GTG TTC AAA AGA AAT GGT GCC CTG CTT GGA AAC    5574
Glu Glu Glu Asp Asp Val Phe Lys Arg Asn Gly Ala Leu Leu Gly Asn
            1675                1680                1685

CAT GTC AAT CAT GTT AAT AGT GAT AGG AGA GAT TCC CTT CAG CAG ACC    5622
His Val Asn His Val Asn Ser Asp Arg Arg Asp Ser Leu Gln Gln Thr
        1690                1695                1700

AAT ACC ACC CAC CGT CCC CTG CAT GTC CAA AGG CCT TCA ATT CCA CCT    5670
Asn Thr Thr His Arg Pro Leu His Val Gln Arg Pro Ser Ile Pro Pro
1705                1710                1715                1720

GCA AGT GAT ACT GAG AAA CCG CTG TTT CCT CCA GCA GGA AAT TCG GTG    5718
Ala Ser Asp Thr Glu Lys Pro Leu Phe Pro Pro Ala Gly Asn Ser Val
                    1725                1730                1735

TGT CAT AAC CAT CAT AAC CAT AAT TCC ATA GGA AAG CAA GTT CCC ACC    5766
Cys His Asn His His Asn His Asn Ser Ile Gly Lys Gln Val Pro Thr
                1740                1745                1750
```

```
TCA ACA AAT GCC AAT CTC AAT AAT GCC AAT ATG TCC AAA GCT GCC CAT      5814
Ser Thr Asn Ala Asn Leu Asn Asn Ala Asn Met Ser Lys Ala Ala His
        1755                1760                1765

GGA AAG CGG CCC AGC ATT GGG AAC CTT GAG CAT GTG TCT GAA AAT GGG      5862
Gly Lys Arg Pro Ser Ile Gly Asn Leu Glu His Val Ser Glu Asn Gly
    1770                1775                1780

CAT CAT TCT TCC CAC AAG CAT GAC CGG GAG CCT CAG AGA AGG TCC AGT      5910
His His Ser Ser His Lys His Asp Arg Glu Pro Gln Arg Arg Ser Ser
1785                1790                1795                1800

GTG AAA AGA ACC CGC TAT TAT GAA ACT TAC ATT AGG TCC GAC TCA GGA      5958
Val Lys Arg Thr Arg Tyr Tyr Glu Thr Tyr Ile Arg Ser Asp Ser Gly
            1805                1810                1815

GAT GAA CAG CTC CCA ACT ATT TGC CGG GAA GAC CCA GAG ATA CAT GGC      6006
Asp Glu Gln Leu Pro Thr Ile Cys Arg Glu Asp Pro Glu Ile His Gly
        1820                1825                1830

TAT TTC AGG GAC CCC CAC TGC TTG GGG GAG CAG GAG TAT TTC AGT AGT      6054
Tyr Phe Arg Asp Pro His Cys Leu Gly Glu Gln Glu Tyr Phe Ser Ser
        1835                1840                1845

GAG GAA TGC TAC GAG GAT GAC AGC TCG CCC ACC TGG AGC AGG CAA AAC      6102
Glu Glu Cys Tyr Glu Asp Asp Ser Ser Pro Thr Trp Ser Arg Gln Asn
    1850                1855                1860

TAT GGC TAC TAC AGC AGA TAC CCA GGC AGA AAC ATC GAC TCT GAG AGG      6150
Tyr Gly Tyr Tyr Ser Arg Tyr Pro Gly Arg Asn Ile Asp Ser Glu Arg
1865                1870                1875                1880

CCC CGA GGC TAC CAT CAT CCC CAA GGA TTC TTG GAG GAC GAT GAC TCG      6198
Pro Arg Gly Tyr His His Pro Gln Gly Phe Leu Glu Asp Asp Asp Ser
            1885                1890                1895

CCC GTT TGC TAT GAT TCA CGG AGA TCT CCA AGG AGA CGC CTA CTA CCT      6246
Pro Val Cys Tyr Asp Ser Arg Arg Ser Pro Arg Arg Arg Leu Leu Pro
        1900                1905                1910

CCC ACC CCA GCA TCC CAC CGG AGA TCC TCC TTC AAC TTT GAG TGC CTG      6294
Pro Thr Pro Ala Ser His Arg Arg Ser Ser Phe Asn Phe Glu Cys Leu
        1915                1920                1925

CGC CGG CAG AGC AGC CAG GAA GAG GTC CCG TCG TCT CCC ATC TTC CCC      6342
Arg Arg Gln Ser Ser Gln Glu Glu Val Pro Ser Ser Pro Ile Phe Pro
    1930                1935                1940

CAT CGC ACG GCC CTG CCT CTG CAT CTA ATG CAG CAA CAG ATC ATG GCA      6390
His Arg Thr Ala Leu Pro Leu His Leu Met Gln Gln Gln Ile Met Ala
1945                1950                1955                1960

GTT GCC GGC CTA GAT TCA AGT AAA GCC CAG AAG TAC TCA CCG AGT CAC      6438
Val Ala Gly Leu Asp Ser Ser Lys Ala Gln Lys Tyr Ser Pro Ser His
            1965                1970                1975

TCG ACC CGG TCG TGG GCC ACC CCT CCA GCA ACC CCT CCC TAC CGG GAC      6486
Ser Thr Arg Ser Trp Ala Thr Pro Pro Ala Thr Pro Pro Tyr Arg Asp
        1980                1985                1990

TGG ACA CCG TGC TAC ACC CCC CTG ATC CAA GTG GAG CAG TCA GAG GCC      6534
Trp Thr Pro Cys Tyr Thr Pro Leu Ile Gln Val Glu Gln Ser Glu Ala
        1995                2000                2005

CTG GAC CAG GTG AAC GGC AGC CTG CCG TCC CTG CAC CGC AGC TCC TGG      6582
Leu Asp Gln Val Asn Gly Ser Leu Pro Ser Leu His Arg Ser Ser Trp
    2010                2015                2020

TAC ACA GAC GAG CCC GAC ATC TCC TAC CGG ACT TTC ACA CCA GCC AGC      6630
Tyr Thr Asp Glu Pro Asp Ile Ser Tyr Arg Thr Phe Thr Pro Ala Ser
2025                2030                2035                2040

CTG ACT GTC CCC AGC AGC TTC CGG AAC AAA AAC AGC GAC AAG CAG AGG      6678
Leu Thr Val Pro Ser Ser Phe Arg Asn Lys Asn Ser Asp Lys Gln Arg
            2045                2050                2055

AGT GCG GAC AGC TTG GTG GAG GCA GTC CTG ATA TCC GAA GGC TTG GGA      6726
Ser Ala Asp Ser Leu Val Glu Ala Val Leu Ile Ser Glu Gly Leu Gly
        2060                2065                2070
```

```
CGC TAT GCA AGG GAC CCA AAA TTT GTG TCA GCA ACA AAA CAC GAA ATC    6774
Arg Tyr Ala Arg Asp Pro Lys Phe Val Ser Ala Thr Lys His Glu Ile
        2075                2080                2085

GCT GAT GCC TGT GAC CTC ACC ATC GAC GAG ATG GAG AGT GCA GCC AGC    6822
Ala Asp Ala Cys Asp Leu Thr Ile Asp Glu Met Glu Ser Ala Ala Ser
        2090                2095                2100

ACC CTG CTT AAT GGG AAC GTG CGT CCC CGA GCC AAC GGG GAT GTG GGC    6870
Thr Leu Leu Asn Gly Asn Val Arg Pro Arg Ala Asn Gly Asp Val Gly
2105                2110                2115                2120

CCC CTC TCA CAC CGG CAG GAC TAT GAG CTA CAG GAC TTT GGT CCT GGC    6918
Pro Leu Ser His Arg Gln Asp Tyr Glu Leu Gln Asp Phe Gly Pro Gly
            2125                2130                2135

TAC AGC GAC GAA GAG CCA GAC CCT GGG AGG GAT GAG GAG GAC CTG GCG    6966
Tyr Ser Asp Glu Glu Pro Asp Pro Gly Arg Asp Glu Glu Asp Leu Ala
        2140                2145                2150

GAT GAA ATG ATA TGC ATC ACC ACC TTG TAGCCCCCAG CGAGGGGCAG          7013
Asp Glu Met Ile Cys Ile Thr Thr Leu
        2155                2160

ACTGGCTCTG GCCTCAGGTG GGGCGCAGGA GAGCCAGGGG AAAAGTGCCT CATAGTTAGG  7073

AAAGTTTAGG CACTAGTTGG GAGTAATATT CAATTAATTA GACTTTTGTA TAAGAGATGT  7133

CATGCCTCAA GAAAGCCATA AACCTGGTAG GAACAGGTCC CAAGCGGTTG AGCCTGGCAG  7193

AGTACCATGC GCTCGGCCCC AGCTGCAGGA AACAGCAGGC CCCGCCCTCT CACAGAGGAT  7253

GGGTGAGGAG GCCAGACCTG CCCTGCCCCA TTGTCCAGAT GGGCACTGCT GTGGAGTCTG  7313

CTTCTCCCAT GTACCAGGGC ACCAGGCCCA CCCAACTGAA GGCATGGCGG CGGGGTGCAG  7373

GGGAAAGTTA AAGGTGATGA CGATCATCAC ACCTGTGTCG TTACCTCAGC CATCGGTCTA  7433

GCATATCAGT CACTGGGCCC AACATATCCA TTTTTAAACC CTTTCCCCCA AATACACTGC  7493

GTCCTGGTTC CTGTTTAGCT GTTCTGAAAT ACGGTGTGTA AGTAAGTCAG AACCCAGCTA  7553

CCAGTGATTA TTGCGAGGGC AATGGGACCT CATAAATAAG GTTTTCTGTG ATGTGACGCC  7613

AGTTTACATA AGAGAATATC AC                                          7635

(2) INFORMATION FOR SEQ ID NO:2:

(i) SEQUENCE CHARACTERISTICS:
        (A) LENGTH: 104 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..102

(ix) FEATURE:
        (A) NAME/KEY: misc_feature
        (B) LOCATION: 1..104
        (D) OTHER INFORMATION: /note= "A 104-nucleotide
            alternative exon of alpha-1D."

(xi) SEQUENCE DESCRIPTION: SEQ ID NO:2:

GTA AAT GAT GCG ATA GGA TGG GAA TGG CCA TGG GTG TAT TTT GTT AGT   48
Val Asn Asp Ala Ile Gly Trp Glu Trp Pro Trp Val Tyr Phe Val Ser
1               5                   10                  15

CTG ATC ATC CTT GGC TCA TTT TTC GTC CTT AAC CTG GTT CTT GGT GTC   96
Leu Ile Ile Leu Gly Ser Phe Phe Val Leu Asn Leu Val Leu Gly Val
            20                  25                  30

CTT AGT GG                                                        104
```

Leu Ser (2) INFORMATION FOR SEQ ID NO:3:

(i) SEQUENCE CHARACTERISTICS:
        (A) LENGTH: 6575 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..6492

(xi) SEQUENCE DESCRIPTION: SEQ ID NO:3:

```
ATG GTC AAT GAG AAT ACG AGG ATG TAC ATT CCA GAG GAA AAC CAC CAA        48
Met Val Asn Glu Asn Thr Arg Met Tyr Ile Pro Glu Glu Asn His Gln
 1               5                  10                  15

GGT TCC AAC TAT GGG AGC CCA CGC CCC GCC CAT GCC AAC ATG AAT GCC        96
Gly Ser Asn Tyr Gly Ser Pro Arg Pro Ala His Ala Asn Met Asn Ala
                20                  25                  30

AAT GCC GCA GCG GGG CTG GCC CCT GAG CAC ATC CCC ACC CCG GGG GCT       144
Asn Ala Ala Ala Gly Leu Ala Pro Glu His Ile Pro Thr Pro Gly Ala
            35                  40                  45

GCC CTG TCG TGG CAG GCG GCC ATC GAC GCA GCC CGG CAG GCT AAG CTG       192
Ala Leu Ser Trp Gln Ala Ala Ile Asp Ala Ala Arg Gln Ala Lys Leu
        50                  55                  60

ATG GGC AGC GCT GGC AAT GCG ACC ATC TCC ACA GTC AGC TCC ACG CAG       240
Met Gly Ser Ala Gly Asn Ala Thr Ile Ser Thr Val Ser Ser Thr Gln
 65                 70                  75                  80

CGG AAG CGC CAG CAA TAT GGG AAA CCC AAG AAG CAG GGC AGC ACC ACG       288
Arg Lys Arg Gln Gln Tyr Gly Lys Pro Lys Lys Gln Gly Ser Thr Thr
                85                  90                  95

GCC ACA CGC CCG CCC CGA GCC CTG CTC TGC CTG ACC CTG AAG AAC CCC       336
Ala Thr Arg Pro Pro Arg Ala Leu Leu Cys Leu Thr Leu Lys Asn Pro
            100                 105                 110

ATC CGG AGG GCC TGC ATC AGC ATT GTC GAA TGG AAA CCA TTT GAA ATA       384
Ile Arg Arg Ala Cys Ile Ser Ile Val Glu Trp Lys Pro Phe Glu Ile
        115                 120                 125

ATT ATT TTA CTG ACT ATT TTT GCC AAT TGT GTG GCC TTA GCG ATC TAT       432
Ile Ile Leu Leu Thr Ile Phe Ala Asn Cys Val Ala Leu Ala Ile Tyr
    130                 135                 140

ATT CCC TTT CCA GAA GAT GAT TCC AAC GCC ACC AAT TCC AAC CTG GAA       480
Ile Pro Phe Pro Glu Asp Asp Ser Asn Ala Thr Asn Ser Asn Leu Glu
145                 150                 155                 160

CGA GTG GAA TAT CTC TTT CTC ATA ATT TTT ACG GTG GAA GCG TTT TTA       528
Arg Val Glu Tyr Leu Phe Leu Ile Ile Phe Thr Val Glu Ala Phe Leu
                165                 170                 175

AAA GTA ATC GCC TAT GGA CTC CTC TTT CAC CCC AAT GCC TAC CTC CGC       576
Lys Val Ile Ala Tyr Gly Leu Leu Phe His Pro Asn Ala Tyr Leu Arg
            180                 185                 190

AAC GGC TGG AAC CTA CTA GAT TTT ATA ATT GTG GTT GTG GGG CTT TTT       624
Asn Gly Trp Asn Leu Leu Asp Phe Ile Ile Val Val Val Gly Leu Phe
        195                 200                 205

AGT GCA ATT TTA GAA CAA GCA ACC AAA GCA GAT GGG GCA AAC GCT CTC       672
Ser Ala Ile Leu Glu Gln Ala Thr Lys Ala Asp Gly Ala Asn Ala Leu
    210                 215                 220

GGA GGG AAA GGG GCC GGA TTT GAT GTG AAG GCG CTG AGG GCC TTC CGC       720
Gly Gly Lys Gly Ala Gly Phe Asp Val Lys Ala Leu Arg Ala Phe Arg
225                 230                 235                 240
```

```
GTG CTG CGC CCC CTG CGG CTG GTG TCC GGA GTC CCA AGT CTC CAG GTG         768
Val Leu Arg Pro Leu Arg Leu Val Ser Gly Val Pro Ser Leu Gln Val
            245                 250                 255

GTC CTG AAT TCC ATC ATC AAG GCC ATG GTC CCC CTG CTG CAC ATC GCC         816
Val Leu Asn Ser Ile Ile Lys Ala Met Val Pro Leu Leu His Ile Ala
        260                 265                 270

CTG CTT GTG CTG TTT GTC ATC ATC ATC TAC GCC ATC ATC GGC TTG GAG         864
Leu Leu Val Leu Phe Val Ile Ile Ile Tyr Ala Ile Ile Gly Leu Glu
            275                 280                 285

CTC TTC ATG GGG AAG ATG CAC AAG ACC TGC TAC AAC CAG GAG GGC ATA         912
Leu Phe Met Gly Lys Met His Lys Thr Cys Tyr Asn Gln Glu Gly Ile
        290                 295                 300

GCA GAT GTT CCA GCA GAA GAT GAC CCT TCC CCT TGT GCG CTG GAA ACG         960
Ala Asp Val Pro Ala Glu Asp Asp Pro Ser Pro Cys Ala Leu Glu Thr
305                 310                 315                 320

GGC CAC GGG CGG CAG TGC CAG AAC GGC ACG GTG TGC AAG CCC GGC TGG        1008
Gly His Gly Arg Gln Cys Gln Asn Gly Thr Val Cys Lys Pro Gly Trp
            325                 330                 335

GAT GGT CCC AAG CAC GGC ATC ACC AAC TTT GAC AAC TTT GCC TTC GCC        1056
Asp Gly Pro Lys His Gly Ile Thr Asn Phe Asp Asn Phe Ala Phe Ala
        340                 345                 350

ATG CTC ACG GTG TTC CAG TGC ATC ACC ATG GAG GGC TGG ACG GAC GTG        1104
Met Leu Thr Val Phe Gln Cys Ile Thr Met Glu Gly Trp Thr Asp Val
            355                 360                 365

CTG TAC TGG GTC AAT GAT GCC GTA GGA AGG GAC TGG CCC TGG ATC TAT        1152
Leu Tyr Trp Val Asn Asp Ala Val Gly Arg Asp Trp Pro Trp Ile Tyr
        370                 375                 380

TTT GTT ACA CTA ATC ATC ATA GGG TCA TTT TTT GTA CTT AAC TTG GTT        1200
Phe Val Thr Leu Ile Ile Ile Gly Ser Phe Phe Val Leu Asn Leu Val
385                 390                 395                 400

CTC GGT GTG CTT AGC GGA GAG TTT TCC AAA GAG AGG GAG AAG GCC AAG        1248
Leu Gly Val Leu Ser Gly Glu Phe Ser Lys Glu Arg Glu Lys Ala Lys
            405                 410                 415

GCC CGG GGA GAT TTC CAG AAG CTG CGG GAG AAG CAG CAG CTA GAA GAG        1296
Ala Arg Gly Asp Phe Gln Lys Leu Arg Glu Lys Gln Gln Leu Glu Glu
        420                 425                 430

GAT CTC AAA GGC TAC CTG GAT TGG ATC ACT CAG GCC GAA GAC ATC GAT        1344
Asp Leu Lys Gly Tyr Leu Asp Trp Ile Thr Gln Ala Glu Asp Ile Asp
            435                 440                 445

CCT GAG AAT GAG GAC GAA GGC ATG GAT GAG GAG AAG CCC CGA AAC AGA        1392
Pro Glu Asn Glu Asp Glu Gly Met Asp Glu Glu Lys Pro Arg Asn Arg
        450                 455                 460

GGC ACT CCG GCG GGC ATG CTT GAT CAG AAG AAA GGG AAG TTT GCT TGG        1440
Gly Thr Pro Ala Gly Met Leu Asp Gln Lys Lys Gly Lys Phe Ala Trp
465                 470                 475                 480

TTT AGT CAC TCC ACA GAA ACC CAT GTG AGC ATG CCC ACC AGT GAG ACC        1488
Phe Ser His Ser Thr Glu Thr His Val Ser Met Pro Thr Ser Glu Thr
            485                 490                 495

GAG TCC GTC AAC ACC GAA AAC GTG GCT GGA GGT GAC ATC GAG GGA GAA        1536
Glu Ser Val Asn Thr Glu Asn Val Ala Gly Gly Asp Ile Glu Gly Glu
        500                 505                 510

AAC TGC GGG GCC AGG CTG GCC CAC CGG ATC TCC AAG TCA AAG TTC AGC        1584
Asn Cys Gly Ala Arg Leu Ala His Arg Ile Ser Lys Ser Lys Phe Ser
            515                 520                 525

CGC TAC TGG CGC CGG TGG AAT CGG TTC TGC AGA AGG AAG TGC CGC GCC        1632
Arg Tyr Trp Arg Arg Trp Asn Arg Phe Cys Arg Arg Lys Cys Arg Ala
        530                 535                 540

GCA GTC AAG TCT AAT GTC TTC TAC TGG CTG GTG ATT TTC CTG GTG TTC        1680
Ala Val Lys Ser Asn Val Phe Tyr Trp Leu Val Ile Phe Leu Val Phe
545                 550                 555                 560
```

```
CTC AAC ACG CTC ACC ATT GCC TCT GAG CAC TAC AAC CAG CCC AAC TGG    1728
Leu Asn Thr Leu Thr Ile Ala Ser Glu His Tyr Asn Gln Pro Asn Trp
            565                 570                 575

CTC ACA GAA GTC CAA GAC ACG GCA AAC AAG GCC CTG CTG GCC CTG TTC    1776
Leu Thr Glu Val Gln Asp Thr Ala Asn Lys Ala Leu Leu Ala Leu Phe
        580                 585                 590

ACG GCA GAG ATG CTC CTG AAG ATG TAC AGC CTG GGC CTG CAG GCC TAC    1824
Thr Ala Glu Met Leu Leu Lys Met Tyr Ser Leu Gly Leu Gln Ala Tyr
    595                 600                 605

TTC GTG TCC CTC TTC AAC CGC TTT GAC TGC TTC GTC GTG TGT GGC GGC    1872
Phe Val Ser Leu Phe Asn Arg Phe Asp Cys Phe Val Val Cys Gly Gly
610                 615                 620

ATC CTG GAG ACC ATC CTG GTG GAG ACC AAG ATC ATG TCC CCA CTG GGC    1920
Ile Leu Glu Thr Ile Leu Val Glu Thr Lys Ile Met Ser Pro Leu Gly
625                 630                 635                 640

ATC TCC GTG CTC AGA TGC GTC CGG CTG CTG AGG ATT TTC AAG ATC ACG    1968
Ile Ser Val Leu Arg Cys Val Arg Leu Leu Arg Ile Phe Lys Ile Thr
                645                 650                 655

AGG TAC TGG AAC TCC TTG AGC AAC CTG GTG GCA TCC TTG CTG AAC TCT    2016
Arg Tyr Trp Asn Ser Leu Ser Asn Leu Val Ala Ser Leu Leu Asn Ser
            660                 665                 670

GTG CGC TCC ATC GCC TCC CTG CTC CTT CTC CTC TTC CTC TTC ATC ATC    2064
Val Arg Ser Ile Ala Ser Leu Leu Leu Leu Leu Phe Leu Phe Ile Ile
        675                 680                 685

ATC TTC TCC CTC CTG GGG ATG CAG CTC TTT GGA GGA AAG TTC AAC TTT    2112
Ile Phe Ser Leu Leu Gly Met Gln Leu Phe Gly Gly Lys Phe Asn Phe
    690                 695                 700

GAT GAG ATG CAG ACC CGG AGG AGC ACA TTC GAT AAC TTC CCC CAG TCC    2160
Asp Glu Met Gln Thr Arg Arg Ser Thr Phe Asp Asn Phe Pro Gln Ser
705                 710                 715                 720

CTC CTC ACT GTG TTT CAG ATC CTG ACC GGG GAG GAC TGG AAT TCG GTG    2208
Leu Leu Thr Val Phe Gln Ile Leu Thr Gly Glu Asp Trp Asn Ser Val
                725                 730                 735

ATG TAT GAT GGG ATC ATG GCT TAT GGG GGC CCC TCT TTT CCA GGG ATG    2256
Met Tyr Asp Gly Ile Met Ala Tyr Gly Gly Pro Ser Phe Pro Gly Met
            740                 745                 750

TTA GTC TGT ATT TAC TTC ATC ATC CTC TTC ATC TGT GGA AAC TAT ATC    2304
Leu Val Cys Ile Tyr Phe Ile Ile Leu Phe Ile Cys Gly Asn Tyr Ile
        755                 760                 765

CTA CTG AAT GTG TTC TTG GCC ATT GCT GTG GAC AAC CTG GCT GAT GCT    2352
Leu Leu Asn Val Phe Leu Ala Ile Ala Val Asp Asn Leu Ala Asp Ala
    770                 775                 780

GAG AGC CTC ACA TCT GCC CAA AAG GAG GAG GAA GAG GAG AAG GAG AGA    2400
Glu Ser Leu Thr Ser Ala Gln Lys Glu Glu Glu Glu Glu Lys Glu Arg
785                 790                 795                 800

AAG AAG CTG GCC AGG ACT GCC AGC CCA GAG AAG AAA CAA GAG TTG GTG    2448
Lys Lys Leu Ala Arg Thr Ala Ser Pro Glu Lys Lys Gln Glu Leu Val
                805                 810                 815

GAG AAG CCG GCA GTG GGG GAA TCC AAG GAG GAG AAG ATT GAG CTG AAA    2496
Glu Lys Pro Ala Val Gly Glu Ser Lys Glu Glu Lys Ile Glu Leu Lys
            820                 825                 830

TCC ATC ACG GCT GAC GGA GAG TCT CCA CCC GCC ACC AAG ATC AAC ATG    2544
Ser Ile Thr Ala Asp Gly Glu Ser Pro Pro Ala Thr Lys Ile Asn Met
        835                 840                 845

GAT GAC CTC CAG CCC AAT GAA AAT GAG GAT AAG AGC CCC TAC CCC AAC    2592
Asp Asp Leu Gln Pro Asn Glu Asn Glu Asp Lys Ser Pro Tyr Pro Asn
    850                 855                 860

CCA GAA ACT ACA GGA GAA GAG GAT GAG GAG GAG CCA GAG ATG CCT GTC    2640
Pro Glu Thr Thr Gly Glu Glu Asp Glu Glu Glu Pro Glu Met Pro Val
```

```
              865                 870                 875                 880
GGC CCT CGC CCA CGA CCA CTC TCT GAG CTT CAC CTT AAG GAA AAG GCA            2688
Gly Pro Arg Pro Arg Pro Leu Ser Glu Leu His Leu Lys Glu Lys Ala
                    885                 890                 895

GTG CCC ATG CCA GAA GCC AGC GCG TTT TTC ATC TTC AGC TCT AAC AAC            2736
Val Pro Met Pro Glu Ala Ser Ala Phe Phe Ile Phe Ser Ser Asn Asn
                900                 905                 910

AGG TTT CGC CTC CAG TGC CAC CGC ATT GTC AAT GAC ACG ATC TTC ACC            2784
Arg Phe Arg Leu Gln Cys His Arg Ile Val Asn Asp Thr Ile Phe Thr
            915                 920                 925

AAC CTG ATC CTC TTC TTC ATT CTG CTC AGC AGC ATT TCC CTG GCT GCT            2832
Asn Leu Ile Leu Phe Phe Ile Leu Leu Ser Ser Ile Ser Leu Ala Ala
        930                 935                 940

GAG GAC CCG GTC CAG CAC ACC TCC TTC AGG AAC CAT ATT CTG TTT TAT            2880
Glu Asp Pro Val Gln His Thr Ser Phe Arg Asn His Ile Leu Phe Tyr
945                 950                 955                 960

TTT GAT ATT GTT TTT ACC ACC ATT TTC ACC ATT GAA ATT GCT CTG AAG            2928
Phe Asp Ile Val Phe Thr Thr Ile Phe Thr Ile Glu Ile Ala Leu Lys
                965                 970                 975

ATG ACT GCT TAT GGG GCT TTC TTG CAC AAG GGT TCT TTC TGC CGG AAC            2976
Met Thr Ala Tyr Gly Ala Phe Leu His Lys Gly Ser Phe Cys Arg Asn
            980                 985                 990

TAC TTC AAC ATC CTG GAC CTG CTG GTG GTC AGC GTG TCC CTC ATC TCC            3024
Tyr Phe Asn Ile Leu Asp Leu Leu Val Val Ser Val Ser Leu Ile Ser
        995                 1000                1005

TTT GGC ATC CAG TCC AGT GCA ATC AAT GTC GTG AAG ATC TTG CGA GTC            3072
Phe Gly Ile Gln Ser Ser Ala Ile Asn Val Val Lys Ile Leu Arg Val
        1010                1015                1020

CTG CGA GTA CTC AGG CCC CTG AGG GCC ATC AAC AGG GCC AAG GGG CTA            3120
Leu Arg Val Leu Arg Pro Leu Arg Ala Ile Asn Arg Ala Lys Gly Leu
1025                1030                1035                1040

AAG CAT GTG GTT CAG TGT GTG TTT GTC GCC ATC CGG ACC ATC GGG AAC            3168
Lys His Val Val Gln Cys Val Phe Val Ala Ile Arg Thr Ile Gly Asn
                1045                1050                1055

ATC GTG ATT GTC ACC ACC CTG CTG CAG TTC ATG TTT GCC TGC ATC GGG            3216
Ile Val Ile Val Thr Thr Leu Leu Gln Phe Met Phe Ala Cys Ile Gly
            1060                1065                1070

GTC CAG CTC TTC AAG GGA AAG CTG TAC ACC TGT TCA GAC AGT TCC AAG            3264
Val Gln Leu Phe Lys Gly Lys Leu Tyr Thr Cys Ser Asp Ser Ser Lys
        1075                1080                1085

CAG ACA GAG GCG GAA TGC AAG GGC AAC TAC ATC ACG TAC AAA GAC GGG            3312
Gln Thr Glu Ala Glu Cys Lys Gly Asn Tyr Ile Thr Tyr Lys Asp Gly
        1090                1095                1100

GAG GTT GAC CAC CCC ATC ATC CAA CCC CGC AGC TGG GAG AAC AGC AAG            3360
Glu Val Asp His Pro Ile Ile Gln Pro Arg Ser Trp Glu Asn Ser Lys
1105                1110                1115                1120

TTT GAC TTT GAC AAT GTT CTG GCA GCC ATG ATG GCC CTC TTC ACC GTC            3408
Phe Asp Phe Asp Asn Val Leu Ala Ala Met Met Ala Leu Phe Thr Val
                1125                1130                1135

TCC ACC TTC GAA GGG TGG CCA GAG CTG CTG TAC CGC TCC ATC GAC TCC            3456
Ser Thr Phe Glu Gly Trp Pro Glu Leu Leu Tyr Arg Ser Ile Asp Ser
            1140                1145                1150

CAC ACG GAA GAC AAG GGC CCC ATC TAC AAC TAC CGT GTG GAG ATC TCC            3504
His Thr Glu Asp Lys Gly Pro Ile Tyr Asn Tyr Arg Val Glu Ile Ser
        1155                1160                1165

ATC TTC TTC ATC ATC TAC ATC ATC ATC GCC TTC TTC ATG ATG AAC            3552
Ile Phe Phe Ile Ile Tyr Ile Ile Ile Ala Phe Phe Met Met Asn
        1170                1175                1180

ATC TTC GTG GGC TTC GTC ATC GTC ACC TTT CAG GAG CAG GGG GAG CAG            3600
```

```
Ile Phe Val Gly Phe Val Ile Val Thr Phe Gln Glu Gln Gly Glu Gln
1185                1190                1195                1200

GAG TAC AAG AAC TGT GAG CTG GAC AAG AAC CAG CGA CAG TGC GTG GAA      3648
Glu Tyr Lys Asn Cys Glu Leu Asp Lys Asn Gln Arg Gln Cys Val Glu
                1205                1210                1215

TAC GCC CTC AAG GCC CGG CCC CTG CGG AGG TAC ATC CCC AAG AAC CAG      3696
Tyr Ala Leu Lys Ala Arg Pro Leu Arg Arg Tyr Ile Pro Lys Asn Gln
            1220                1225                1230

CAC CAG TAC AAA GTG TGG TAC GTG GTC AAC TCC ACC TAC TTC GAG TAC      3744
His Gln Tyr Lys Val Trp Tyr Val Val Asn Ser Thr Tyr Phe Glu Tyr
        1235                1240                1245

CTG ATG TTC GTC CTC ATC CTC CTC AAC ACC ATC TGC CTG GCC ATG CAG      3792
Leu Met Phe Val Leu Ile Leu Leu Asn Thr Ile Cys Leu Ala Met Gln
    1250                1255                1260

CAC TAC GGC CAG AGC TGC CTG TTC AAA ATC GCC ATG AAC ATC CTC AAC      3840
His Tyr Gly Gln Ser Cys Leu Phe Lys Ile Ala Met Asn Ile Leu Asn
1265                1270                1275                1280

ATG CTC TTC ACT GGC CTC TTC ACC GTG GAG ATG ATC CTG AAG CTC ATT      3888
Met Leu Phe Thr Gly Leu Phe Thr Val Glu Met Ile Leu Lys Leu Ile
                1285                1290                1295

GCC TTC AAA CCC AAG GGT TAC TTT AGT GAT CCC TGG AAT GTT TTT GAC      3936
Ala Phe Lys Pro Lys Gly Tyr Phe Ser Asp Pro Trp Asn Val Phe Asp
            1300                1305                1310

TTC CTC ATC GTA ATT GGC AGC ATA ATT GAC GTC ATT CTC AGT GAG ACT      3984
Phe Leu Ile Val Ile Gly Ser Ile Ile Asp Val Ile Leu Ser Glu Thr
        1315                1320                1325

AAT CCA GCT GAA CAT ACC CAA TGC TCT CCC TCT ATG AAC GCA GAG GAA      4032
Asn Pro Ala Glu His Thr Gln Cys Ser Pro Ser Met Asn Ala Glu Glu
    1330                1335                1340

AAC TCC CGC ATC TCC ATC ACC TTC TTC CGC CTG TTC CGG GTC ATG CGT      4080
Asn Ser Arg Ile Ser Ile Thr Phe Phe Arg Leu Phe Arg Val Met Arg
1345                1350                1355                1360

CTG GTG AAG CTG CTG AGC CGT GGG GAG GGC ATC CGG ACG CTG CTG TGG      4128
Leu Val Lys Leu Leu Ser Arg Gly Glu Gly Ile Arg Thr Leu Leu Trp
                1365                1370                1375

ACC TTC ATC AAG TCC TTC CAG GCC CTG CCC TAT GTG GCC CTC CTG ATC      4176
Thr Phe Ile Lys Ser Phe Gln Ala Leu Pro Tyr Val Ala Leu Leu Ile
            1380                1385                1390

GTG ATG CTG TTC TTC ATC TAC GCG GTG ATC GGG ATG CAG GTG TTT GGG      4224
Val Met Leu Phe Phe Ile Tyr Ala Val Ile Gly Met Gln Val Phe Gly
        1395                1400                1405

AAA ATT GCC CTG AAT GAT ACC ACA GAG ATC AAC CGG AAC AAC AAC TTT      4272
Lys Ile Ala Leu Asn Asp Thr Thr Glu Ile Asn Arg Asn Asn Asn Phe
    1410                1415                1420

CAG ACC TTC CCC CAG GCC GTG CTG CTC CTC TTC AGG TGT GCC ACC GGG      4320
Gln Thr Phe Pro Gln Ala Val Leu Leu Leu Phe Arg Cys Ala Thr Gly
1425                1430                1435                1440

GAG GCC TGG CAG GAC ATC ATG CTG GCC TGC ATG CCA GGC AAG AAG TGT      4368
Glu Ala Trp Gln Asp Ile Met Leu Ala Cys Met Pro Gly Lys Lys Cys
                1445                1450                1455

GCC CCA GAG TCC GAG CCC AGC AAC AGC ACG GAG GGT GAA ACA CCC TGT      4416
Ala Pro Glu Ser Glu Pro Ser Asn Ser Thr Glu Gly Glu Thr Pro Cys
            1460                1465                1470

GGT AGC AGC TTT GCT GTC TTC TAC TTC ATC AGC TTC TAC ATG CTC TGT      4464
Gly Ser Ser Phe Ala Val Phe Tyr Phe Ile Ser Phe Tyr Met Leu Cys
        1475                1480                1485

GCC TTC CTG ATC ATC AAC CTC TTT GTA GCT GTC ATC ATG GAC AAC TTT      4512
Ala Phe Leu Ile Ile Asn Leu Phe Val Ala Val Ile Met Asp Asn Phe
    1490                1495                1500
```

```
GAC TAC CTG ACA AGG GAC TGG TCC ATC CTT GGT CCC CAC CAC CTG GAT      4560
Asp Tyr Leu Thr Arg Asp Trp Ser Ile Leu Gly Pro His His Leu Asp
1505                1510                1515                1520

GAG TTT AAA AGA ATC TGG GCA GAG TAT GAC CCT GAA GCC AAG GGT CGT      4608
Glu Phe Lys Arg Ile Trp Ala Glu Tyr Asp Pro Glu Ala Lys Gly Arg
                1525                1530                1535

ATC AAA CAC CTG GAT GTG GTG ACC CTC CTC CGG CGG ATT CAG CCG CCA      4656
Ile Lys His Leu Asp Val Val Thr Leu Leu Arg Arg Ile Gln Pro Pro
            1540                1545                1550

CTA GGT TTT GGG AAG CTG TGC CCT CAC CGC GTG GCT TGC AAA CGC CTG      4704
Leu Gly Phe Gly Lys Leu Cys Pro His Arg Val Ala Cys Lys Arg Leu
        1555                1560                1565

GTC TCC ATG AAC ATG CCT CTG AAC AGC GAC GGG ACA GTC ATG TTC AAT      4752
Val Ser Met Asn Met Pro Leu Asn Ser Asp Gly Thr Val Met Phe Asn
    1570                1575                1580

GCC ACC CTG TTT GCC CTG GTC AGG ACG GCC CTG AGG ATC AAA ACA GAA      4800
Ala Thr Leu Phe Ala Leu Val Arg Thr Ala Leu Arg Ile Lys Thr Glu
1585                1590                1595                1600

GGG AAC CTA GAA CAA GCC AAT GAG GAG CTG CGG GCG ATC ATC AAG AAG      4848
Gly Asn Leu Glu Gln Ala Asn Glu Glu Leu Arg Ala Ile Ile Lys Lys
                1605                1610                1615

ATC TGG AAG CGG ACC AGC ATG AAG CTG CTG GAC CAG GTG GTG CCC CCT      4896
Ile Trp Lys Arg Thr Ser Met Lys Leu Leu Asp Gln Val Val Pro Pro
            1620                1625                1630

GCA GGT GAT GAT GAG GTC ACC GTT GGC AAG TTC TAC GCC ACG TTC CTG      4944
Ala Gly Asp Asp Glu Val Thr Val Gly Lys Phe Tyr Ala Thr Phe Leu
        1635                1640                1645

ATC CAG GAG TAC TTC CGG AAG TTC AAG AAG CGC AAA GAG CAG GGC CTT      4992
Ile Gln Glu Tyr Phe Arg Lys Phe Lys Lys Arg Lys Glu Gln Gly Leu
    1650                1655                1660

GTG GGC AAG CCC TCC CAG AGG AAC GCG CTG TCT CTG CAG GCT GGC TTG      5040
Val Gly Lys Pro Ser Gln Arg Asn Ala Leu Ser Leu Gln Ala Gly Leu
1665                1670                1675                1680

CGC ACA CTG CAT GAC ATC GGG CCT GAG ATC CGA CGG GCC ATC TCT GGA      5088
Arg Thr Leu His Asp Ile Gly Pro Glu Ile Arg Arg Ala Ile Ser Gly
                1685                1690                1695

GAT CTC ACC GCT GAG GAG GAG CTG GAC AAG GCC ATG AAG GAG GCT GTG      5136
Asp Leu Thr Ala Glu Glu Glu Leu Asp Lys Ala Met Lys Glu Ala Val
            1700                1705                1710

TCC GCT GCT TCT GAA GAT GAC ATC TTC AGG AGG GCC GGT GGC CTG TTC      5184
Ser Ala Ala Ser Glu Asp Asp Ile Phe Arg Arg Ala Gly Gly Leu Phe
        1715                1720                1725

GGC AAC CAC GTC AGC TAC TAC CAA AGC GAC GGC CGG AGC GCC TTC CCC      5232
Gly Asn His Val Ser Tyr Tyr Gln Ser Asp Gly Arg Ser Ala Phe Pro
    1730                1735                1740

CAG ACC TTC ACC ACT CAG CGC CCG CTG CAC ATC AAC AAG GCG GGC AGC      5280
Gln Thr Phe Thr Thr Gln Arg Pro Leu His Ile Asn Lys Ala Gly Ser
1745                1750                1755                1760

AGC CAG GGC GAC ACT GAG TCG CCA TCC CAC GAG AAG CTG GTG GAC TCC      5328
Ser Gln Gly Asp Thr Glu Ser Pro Ser His Glu Lys Leu Val Asp Ser
                1765                1770                1775

ACC TTC ACC CCG AGC AGC TAC TCG TCC ACC GGC TCC AAC GCC AAC ATC      5376
Thr Phe Thr Pro Ser Ser Tyr Ser Ser Thr Gly Ser Asn Ala Asn Ile
            1780                1785                1790

AAC AAC GCC AAC AAC ACC GCC CTG GGT CGC CTC CCT CGC CCC GCC GGC      5424
Asn Asn Ala Asn Asn Thr Ala Leu Gly Arg Leu Pro Arg Pro Ala Gly
        1795                1800                1805

TAC CCC AGC ACA GTC AGC ACT GTG GAG GGC CAC GGG CCC CCC TTG TCC      5472
Tyr Pro Ser Thr Val Ser Thr Val Glu Gly His Gly Pro Pro Leu Ser
    1810                1815                1820
```

-continued

```
CCT GCC ATC CGG GTG CAG GAG GTG GCG TGG AAG CTC AGC TCC AAC AGG        5520
Pro Ala Ile Arg Val Gln Glu Val Ala Trp Lys Leu Ser Ser Asn Arg
1825                1830                1835                1840

TGC CAC TCC CGG GAG AGC CAG GCA GCC ATG GCG CGT CAG GAG GAG ACG        5568
Cys His Ser Arg Glu Ser Gln Ala Ala Met Ala Arg Gln Glu Glu Thr
                1845                1850                1855

TCT CAG GAT GAG ACC TAT GAA GTG AAG ATG AAC CAT GAC ACG GAG GCC        5616
Ser Gln Asp Glu Thr Tyr Glu Val Lys Met Asn His Asp Thr Glu Ala
1860                1865                1870

TGC AGT GAG CCC AGC CTG CTC TCC ACA GAG ATG CTC TCC TAC CAG GAT        5664
Cys Ser Glu Pro Ser Leu Leu Ser Thr Glu Met Leu Ser Tyr Gln Asp
        1875                1880                1885

GAC GAA AAT CGG CAA CTG ACG CTC CCA GAG GAG GAC AAG AGG GAC ATC        5712
Asp Glu Asn Arg Gln Leu Thr Leu Pro Glu Glu Asp Lys Arg Asp Ile
1890                1895                1900

CGG CAA TCT CCG AAG AGG GGT TTC CTC CGC TCT GCC TCA CTA GGT CGA        5760
Arg Gln Ser Pro Lys Arg Gly Phe Leu Arg Ser Ala Ser Leu Gly Arg
1905                1910                1915                1920

AGG GCC TCC TTC CAC CTG GAA TGT CTG AAG CGA CAG AAG GAC CGA GGG        5808
Arg Ala Ser Phe His Leu Glu Cys Leu Lys Arg Gln Lys Asp Arg Gly
                1925                1930                1935

GGA GAC ATC TCT CAG AAG ACA GTC CTG CCC TTG CAT CTG GTT CAT CAT        5856
Gly Asp Ile Ser Gln Lys Thr Val Leu Pro Leu His Leu Val His His
                1940                1945                1950

CAG GCA TTG GCA GTG GCA GGC CTG AGC CCC CTC CTC CAG AGA AGC CAT        5904
Gln Ala Leu Ala Val Ala Gly Leu Ser Pro Leu Leu Gln Arg Ser His
        1955                1960                1965

TCC CCT GCC TCA TTC CCT AGG CCT TTT GCC ACC CCA CCA GCC ACA CCT        5952
Ser Pro Ala Ser Phe Pro Arg Pro Phe Ala Thr Pro Pro Ala Thr Pro
    1970                1975                1980

GGC AGC CGA GGC TGG CCC CCA CAG CCC GTC CCC ACC CTG CGG CTT GAG        6000
Gly Ser Arg Gly Trp Pro Pro Gln Pro Val Pro Thr Leu Arg Leu Glu
1985                1990                1995                2000

GGG GTC GAG TCC AGT GAG AAA CTC AAC AGC AGC TTC CCA TCC ATC CAC        6048
Gly Val Glu Ser Ser Glu Lys Leu Asn Ser Ser Phe Pro Ser Ile His
                2005                2010                2015

TGC GGC TCC TGG GCT GAG ACC ACC CCC GGT GGC GGG GGC AGC AGC GCC        6096
Cys Gly Ser Trp Ala Glu Thr Thr Pro Gly Gly Gly Gly Ser Ser Ala
        2020                2025                2030

GCC CGG AGA GTC CGG CCC GTC TCC CTC ATG GTG CCC AGC CAG GCT GGG        6144
Ala Arg Arg Val Arg Pro Val Ser Leu Met Val Pro Ser Gln Ala Gly
            2035                2040                2045

GCC CCA GGG AGG CAG TTC CAC GGC AGT GCC AGC AGC CTG GTG GAA GCG        6192
Ala Pro Gly Arg Gln Phe His Gly Ser Ala Ser Ser Leu Val Glu Ala
    2050                2055                2060

GTC TTG ATT TCA GAA GGA CTG GGG CAG TTT GCT CAA GAT CCC AAG TTC        6240
Val Leu Ile Ser Glu Gly Leu Gly Gln Phe Ala Gln Asp Pro Lys Phe
2070                2075                2080                2085

ATC GAG GTC ACC ACC CAG GAG CTG GCC GAC GCC TGC GAC ATG ACC ATA        6288
Ile Glu Val Thr Thr Gln Glu Leu Ala Asp Ala Cys Asp Met Thr Ile
                2090                2095                2100

GAG GAG ATG GAG AGC GCG GCC GAC AAC ATC CTC AGC GGG GGC GCC CCA        6336
Glu Glu Met Glu Ser Ala Ala Asp Asn Ile Leu Ser Gly Gly Ala Pro
        2105                2110                2115

CAG AGC CCC AAT GGC GCC CTC TTA CCC TTT GTG AAC TGC AGG GAC GCG        6384
Gln Ser Pro Asn Gly Ala Leu Leu Pro Phe Val Asn Cys Arg Asp Ala
            2120                2125                2130

GGG CAG GAC CGA GCC GGG GGC GAA GAG GAC GCG GGC TGT GTG CGC GCG        6432
Gly Gln Asp Arg Ala Gly Gly Glu Glu Asp Ala Gly Cys Val Arg Ala
```

```
                    2135                2135                2140
CGG GGT CGA CCG AGT GAG GAG GAG CTC CAG GAC AGC AGG GTC TAC GTC    6480
Arg Gly Arg Pro Ser Glu Glu Glu Leu Gln Asp Ser Arg Val Tyr Val
2145                2150                2155                2160

AGC AGC CTG TAGTGGGCGC TGCCAGATGC GGGCTTTTTT TTATTTGTTT CAATGTTCCT    6539
Ser Ser Leu

AATGGGTTCG TTTCAGAAGT GCCTCACTGT TCTCGT    6575

(2) INFORMATION FOR SEQ ID NO:4:

(i) SEQUENCE CHARACTERISTICS:
        (A) LENGTH: 133 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

AGACCACGGC TTCCTCGAAT CTTGCGCGAA GCCGCCGGCCA TCGGAGGAG GGATTAATCC    60

AGACCCGCCG GGGGGTGTTT TCACATTTCT TCCTCTTCGTG GCTGCTCCT CCTATTAAAA    120

CCATTTTTGG TCC    133

(2) INFORMATION FOR SEQ ID NO:5:

(i) SEQUENCE CHARACTERISTICS:
        (A) LENGTH: 89 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

CGCTGAGGGC CTTCCGCGTG CTGCGCCCCC TGCGGCTGGT GTCCGGAGTC CCAAGTCTCC    60

AGGTGGTCCT GAATTCCATC ATCAAGGCC    89

(2) INFORMATION FOR SEQ ID NO:6:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..84
        (D) OTHER INFORMATION: /note= "An alternative exon of
            alpha-1C."

(xi) SEQUENCE DESCRIPTION: SEQ ID NO:6:

CAC TAT TTC TGT GAT GCA TGG AAT ACA TTT GAC GCC TTG ATT GTT GTG    48
His Tyr Phe Cys Asp Ala Trp Asn Thr Phe Asp Ala Leu Ile Val Val
  1               5                  10                  15

GGT AGC ATT GTT GAT ATA GCA ATC ACC GAG GTA AAC    84
Gly Ser Ile Val Asp Ile Ala Ile Thr Glu Val Asn
              20                  25

(2) INFORMATION FOR SEQ ID NO:7:

(i) SEQUENCE CHARACTERISTICS:
        (A) LENGTH: 7362 base pairs
```

```
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 144..7163

(ix) FEATURE:
            (A) NAME/KEY: 5'UTR
            (B) LOCATION: 1..143

(ix) FEATURE:
            (A) NAME/KEY: 3'UTR
            (B) LOCATION: 7161..7362

(xi) SEQUENCE DESCRIPTION: SEQ ID NO:7:

GCGGCGGCGG CTGCGGCGGT GGGGCCGGGC GAGGTCCGTG CGGTCCCGGC GGCTCCGTGG        60

CTGCTCCGCT CTGAGCGCCT GCGCGCCCCG CGCCCTCCCT GCCGGGGCCG CTGGGCCGGG       120

GATGCACGCG GGGCCCGGGA GCC ATG GTC CGC TTC GGG GAC GAG CTG GGC          170
                         Met Val Arg Phe Gly Asp Glu Leu Gly
                          1               5

GGC CGC TAT GGA GGC CCC GGC GGC GGA GAG CGG GCC CGG GGC GGC GGG        218
Gly Arg Tyr Gly Gly Pro Gly Gly Gly Glu Arg Ala Arg Gly Gly Gly
 10              15                  20                  25

GCC GGC GGG GCG GGG GGC CCG GGT CCC GGG GGG CTG CAG CCC GGC CAG        266
Ala Gly Gly Ala Gly Gly Pro Gly Pro Gly Gly Leu Gln Pro Gly Gln
             30                  35                  40

CGG GTC CTC TAC AAG CAA TCG ATC GCG CAG CGC GCG CGG ACC ATG GCG        314
Arg Val Leu Tyr Lys Gln Ser Ile Ala Gln Arg Ala Arg Thr Met Ala
                 45                  50                  55

CTG TAC AAC CCC ATC CCG GTC AAG CAG AAC TGC TTC ACC GTC AAC CGC        362
Leu Tyr Asn Pro Ile Pro Val Lys Gln Asn Cys Phe Thr Val Asn Arg
             60                  65                  70

TCG CTC TTC GTC TTC AGC GAG GAC AAC GTC GTC CGC AAA TAC GCG AAG        410
Ser Leu Phe Val Phe Ser Glu Asp Asn Val Val Arg Lys Tyr Ala Lys
 75                  80                  85

CGC ATC ACC GAG TGG CCT CCA TTC GAG AAT ATG ATC CTG GCC ACC ATC        458
Arg Ile Thr Glu Trp Pro Pro Phe Glu Asn Met Ile Leu Ala Thr Ile
 90                  95                 100                 105

ATC GCC AAC TGC ATC GTG CTG GCC CTG GAG CAG CAC CTC CCT GAT GGG        506
Ile Ala Asn Cys Ile Val Leu Ala Leu Glu Gln His Leu Pro Asp Gly
                110                 115                 120

GAC AAA ACG CCC ATG TCC GAG CGG CTG GAC GAC ACG GAG CCC TAT TTC        554
Asp Lys Thr Pro Met Ser Glu Arg Leu Asp Asp Thr Glu Pro Tyr Phe
                125                 130                 135

ATC GGG ATC TTT TGC TTC GAG GCA GGG ATC AAA ATC ATC GCT CTG GGC        602
Ile Gly Ile Phe Cys Phe Glu Ala Gly Ile Lys Ile Ile Ala Leu Gly
                140                 145                 150

TTT GTC TTC CAC AAG GGC TCT TAC CTG CGG AAC GGC TGG AAC GTC ATG        650
Phe Val Phe His Lys Gly Ser Tyr Leu Arg Asn Gly Trp Asn Val Met
            155                 160                 165

GAC TTC GTG GTC GTC CTC ACA GGG ATC CTT GCC ACG GCT GGA ACT GAC        698
Asp Phe Val Val Val Leu Thr Gly Ile Leu Ala Thr Ala Gly Thr Asp
170                 175                 180                 185

TTC GAC CTG CGA ACA CTG AGG GCT GTG CGT GTG CTG AGG CCC CTG AAG        746
Phe Asp Leu Arg Thr Leu Arg Ala Val Arg Val Leu Arg Pro Leu Lys
                190                 195                 200

CTG GTG TCT GGG ATT CCA AGT TTG CAG GTG GTG CTC AAG TCC ATC ATG        794
Leu Val Ser Gly Ile Pro Ser Leu Gln Val Val Leu Lys Ser Ile Met
                205                 210                 215
```

-continued

```
AAG GCC ATG GTT CCA CTC CTG CAG ATT GGG CTG CTT CTC TTC TTT GCC      842
Lys Ala Met Val Pro Leu Leu Gln Ile Gly Leu Leu Leu Phe Phe Ala
        220                 225                 230

ATC CTC ATG TTT GCC ATC ATT GGC CTG GAG TTC TAC ATG GGC AAG TTC      890
Ile Leu Met Phe Ala Ile Ile Gly Leu Glu Phe Tyr Met Gly Lys Phe
        235                 240                 245

CAC AAG GCC TGT TTC CCC AAC AGC ACA GAT GCG GAG CCC GTG GGT GAC      938
His Lys Ala Cys Phe Pro Asn Ser Thr Asp Ala Glu Pro Val Gly Asp
250                 255                 260                 265

TTC CCC TGT GGC AAG GAG GCC CCA GCC CGG CTG TGC GAG GGC GAC ACT      986
Phe Pro Cys Gly Lys Glu Ala Pro Ala Arg Leu Cys Glu Gly Asp Thr
                270                 275                 280

GAG TGC CGG GAG TAC TGG CCA GGA CCC AAC TTT GGC ATC ACC AAC TTT     1034
Glu Cys Arg Glu Tyr Trp Pro Gly Pro Asn Phe Gly Ile Thr Asn Phe
            285                 290                 295

GAC AAT ATC CTG TTT GCC ATC TTG ACG GTG TTC CAG TGC ATC ACC ATG     1082
Asp Asn Ile Leu Phe Ala Ile Leu Thr Val Phe Gln Cys Ile Thr Met
        300                 305                 310

GAG GGC TGG ACT GAC ATC CTC TAT AAT ACA AAC GAT GCG GCC GGC AAC     1130
Glu Gly Trp Thr Asp Ile Leu Tyr Asn Thr Asn Asp Ala Ala Gly Asn
        315                 320                 325

ACC TGG AAC TGG CTC TAC TTC ATC CCT CTC ATC ATC ATC GGC TCC TTC     1178
Thr Trp Asn Trp Leu Tyr Phe Ile Pro Leu Ile Ile Ile Gly Ser Phe
330                 335                 340                 345

TTC ATG CTC AAC CTG GTG CTG GGC GTG CTC TCG GGG GAG TTT GCC AAG     1226
Phe Met Leu Asn Leu Val Leu Gly Val Leu Ser Gly Glu Phe Ala Lys
                350                 355                 360

GAG CGA GAG AGG GTG GAG AAC CGC CGC GCC TTC CTG AAG CTG CGC CGG     1274
Glu Arg Glu Arg Val Glu Asn Arg Arg Ala Phe Leu Lys Leu Arg Arg
            365                 370                 375

CAG CAG CAG ATC GAG CGA GAG CTC AAC GGG TAC CTG GAG TGG ATC TTC     1322
Gln Gln Gln Ile Glu Arg Glu Leu Asn Gly Tyr Leu Glu Trp Ile Phe
        380                 385                 390

AAG GCG GAG GAA GTC ATG CTG GCC GAG GAG GAC AGG AAT GCA GAG GAG     1370
Lys Ala Glu Glu Val Met Leu Ala Glu Glu Asp Arg Asn Ala Glu Glu
        395                 400                 405

AAG TCC CCT TTG GAC GTG CTG AAG AGA GCG GCC ACC AAG AAG AGC AGA     1418
Lys Ser Pro Leu Asp Val Leu Lys Arg Ala Ala Thr Lys Lys Ser Arg
410                 415                 420                 425

AAT GAC CTG ATC CAC GCA GAG GAG GGA GAG GAC CGG TTT GCA GAT CTC     1466
Asn Asp Leu Ile His Ala Glu Glu Gly Glu Asp Arg Phe Ala Asp Leu
                430                 435                 440

TGT GCT GTT GGA TCC CCC TTC GCC CGC GCC AGC CTC AAG AGC GGG AAG     1514
Cys Ala Val Gly Ser Pro Phe Ala Arg Ala Ser Leu Lys Ser Gly Lys
            445                 450                 455

ACA GAG AGC TCG TCA TAC TTC CGG AGG AAG GAG AAG ATG TTC CGG TTT     1562
Thr Glu Ser Ser Ser Tyr Phe Arg Arg Lys Glu Lys Met Phe Arg Phe
        460                 465                 470

TTT ATC CGG CGC ATG GTG AAG GCT CAG AGC TTC TAC TGG GTG GTG CTG     1610
Phe Ile Arg Arg Met Val Lys Ala Gln Ser Phe Tyr Trp Val Val Leu
        475                 480                 485

TGC GTG GTG GCC CTG AAC ACA CTG TGT GTG GCC ATG GTG CAT TAC AAC     1658
Cys Val Val Ala Leu Asn Thr Leu Cys Val Ala Met Val His Tyr Asn
490                 495                 500                 505

CAG CCG CGG CGG CTT ACC ACG ACC CTG TAT TTT GCA GAG TTT GTT TTC     1706
Gln Pro Arg Arg Leu Thr Thr Thr Leu Tyr Phe Ala Glu Phe Val Phe
                510                 515                 520

CTG GGT CTC TTC CTC ACA GAG ATG TCC CTG AAG ATG TAT GGC CTG GGG     1754
Leu Gly Leu Phe Leu Thr Glu Met Ser Leu Lys Met Tyr Gly Leu Gly
```

-continued

```
              525                 530                 535
CCC AGA AGC TAC TTC CGG TCC TCC TTC AAC TGC TTC GAC TTT GGG GTC     1802
Pro Arg Ser Tyr Phe Arg Ser Ser Phe Asn Cys Phe Asp Phe Gly Val
        540                 545                 550

ATC GTG GGG AGC GTC TTT GAA GTG GTC TGG GCG GCC ATC AAG CCG GGA     1850
Ile Val Gly Ser Val Phe Glu Val Val Trp Ala Ala Ile Lys Pro Gly
555                 560                 565

AGC TCC TTT GGG ATC AGT GTG CTG CGG GCC CTC CGC CTG CTG AGG ATC     1898
Ser Ser Phe Gly Ile Ser Val Leu Arg Ala Leu Arg Leu Leu Arg Ile
570                 575                 580                 585

TTC AAA GTC ACG AAG TAC TGG AGC TCC CTG CGG AAC CTG GTG GTG TCC     1946
Phe Lys Val Thr Lys Tyr Trp Ser Ser Leu Arg Asn Leu Val Val Ser
        590                 595                 600

CTG CTG AAC TCC ATG AAG TCC ATC ATC AGC CTG CTC TTC TTG CTC TTC     1994
Leu Leu Asn Ser Met Lys Ser Ile Ile Ser Leu Leu Phe Leu Leu Phe
        605                 610                 615

CTG TTC ATT GTG GTC TTC GCC CTG CTG GGG ATG CAG CTG TTT GGG GGA     2042
Leu Phe Ile Val Val Phe Ala Leu Leu Gly Met Gln Leu Phe Gly Gly
        620                 625                 630

CAG TTC AAC TTC CAG GAT GAG ACT CCC ACA ACC AAC TTC GAC ACC TTC     2090
Gln Phe Asn Phe Gln Asp Glu Thr Pro Thr Thr Asn Phe Asp Thr Phe
        635                 640                 645

CCT GCC GCC ATC CTC ACT GTC TTC CAG ATC CTG ACG GGA GAG GAC TGG     2138
Pro Ala Ala Ile Leu Thr Val Phe Gln Ile Leu Thr Gly Glu Asp Trp
650                 655                 660                 665

AAT GCA GTG ATG TAT CAC GGG ATC GAA TCG CAA GGC GGC GTC AGC AAA     2186
Asn Ala Val Met Tyr His Gly Ile Glu Ser Gln Gly Gly Val Ser Lys
                670                 675                 680

GGC ATG TTC TCG TCC TTT TAC TTC ATT GTC CTG ACA CTG TTC GGA AAC     2234
Gly Met Phe Ser Ser Phe Tyr Phe Ile Val Leu Thr Leu Phe Gly Asn
                685                 690                 695

TAC ACT CTG CTG AAT GTC TTT CTG GCC ATC GCT GTG GAC AAC CTG GCC     2282
Tyr Thr Leu Leu Asn Val Phe Leu Ala Ile Ala Val Asp Asn Leu Ala
        700                 705                 710

AAC GCC CAA GAG CTG ACC AAG GAT GAA GAG GAG ATG GAA GAA GCA GCC     2330
Asn Ala Gln Glu Leu Thr Lys Asp Glu Glu Glu Met Glu Glu Ala Ala
        715                 720                 725

AAT CAG AAG CTT GCT CTG CAA AAG GCC AAA GAA GTG GCT GAA GTC AGC     2378
Asn Gln Lys Leu Ala Leu Gln Lys Ala Lys Glu Val Ala Glu Val Ser
730                 735                 740                 745

CCC ATG TCT GCC GCG AAC ATC TCC ATC GCC GCC AGG CAG CAG AAC TCG     2426
Pro Met Ser Ala Ala Asn Ile Ser Ile Ala Ala Arg Gln Gln Asn Ser
                750                 755                 760

GCC AAG GCG CGC TCG GTG TGG GAG CAG CGG GCC AGC CAG CTA CGG CTG     2474
Ala Lys Ala Arg Ser Val Trp Glu Gln Arg Ala Ser Gln Leu Arg Leu
                765                 770                 775

CAG AAC CTG CGG GCC AGC TGC GAG GCG CTG TAC AGC GAG ATG GAC CCC     2522
Gln Asn Leu Arg Ala Ser Cys Glu Ala Leu Tyr Ser Glu Met Asp Pro
        780                 785                 790

GAG GAG CGG CTG CGC TTC GCC ACT ACG CGC CAC CTG CGG CCC GAC ATG     2570
Glu Glu Arg Leu Arg Phe Ala Thr Thr Arg His Leu Arg Pro Asp Met
        795                 800                 805

AAG ACG CAC CTG GAC CGG CCG CTG GTG GTG GAG CTG GGC CGC GAC GGC     2618
Lys Thr His Leu Asp Arg Pro Leu Val Val Glu Leu Gly Arg Asp Gly
810                 815                 820                 825

GCG CGG GGG CCC GTG GGA GGC AAA GCC CGA CCT GAG GCT GCG GAG GCC     2666
Ala Arg Gly Pro Val Gly Gly Lys Ala Arg Pro Glu Ala Ala Glu Ala
                830                 835                 840

CCC GAG GGC GTC GAC CCT CCG CGC AGG CAC CAC CGG CAC CGC GAC AAG     2714
```

```
                                              -continued

Pro Glu Gly Val Asp Pro Pro Arg Arg His His Arg His Arg Asp Lys
            845                 850                 855

GAC AAG ACC CCC GCG GCG GGG GAC CAG GAC CGA GCA GAG GCC CCG AAG      2762
Asp Lys Thr Pro Ala Ala Gly Asp Gln Asp Arg Ala Glu Ala Pro Lys
        860                 865                 870

GCG GAG AGC GGG GAG CCC GGT GCC CGG GAG GAG CGG CCG CGG CCG CAC      2810
Ala Glu Ser Gly Glu Pro Gly Ala Arg Glu Glu Arg Pro Arg Pro His
    875                 880                 885

CGC AGC CAC AGC AAG GAG GCC GCG GGG CCC CCG GAG GCG CGG AGC GAG      2858
Arg Ser His Ser Lys Glu Ala Ala Gly Pro Pro Glu Ala Arg Ser Glu
890                 895                 900                 905

CGC GGC CGA GGC CCA GGC CCC GAG GGC GGC CGG CGG CAC CAC CGG CGC      2906
Arg Gly Arg Gly Pro Gly Pro Glu Gly Gly Arg Arg His His Arg Arg
                910                 915                 920

GGC TCC CCG GAG GAG GCG GCC GAG CGG GAG CCC CGA CGC CAC CGC GCG      2954
Gly Ser Pro Glu Glu Ala Ala Glu Arg Glu Pro Arg Arg His Arg Ala
            925                 930                 935

CAC CGG CAC CAG GAT CCG AGC AAG GAG TGC GCC GGC GCC AAG GGC GAG      3002
His Arg His Gln Asp Pro Ser Lys Glu Cys Ala Gly Ala Lys Gly Glu
        940                 945                 950

CGG CGC GCG CGG CAC CGC GGC GGC CCC CGA GCG GGG CCC CGG GAG GCG      3050
Arg Arg Ala Arg His Arg Gly Gly Pro Arg Ala Gly Pro Arg Glu Ala
    955                 960                 965

GAG AGC GGG GAG GAG CCG GCG CGG CGG CAC CGG GCC CGG CAC AAG GCG      3098
Glu Ser Gly Glu Glu Pro Ala Arg Arg His Arg Ala Arg His Lys Ala
970                 975                 980                 985

CAG CCT GCT CAC GAG GCT GTG GAG AAG GAG ACC ACG GAG AAG GAG GCC      3146
Gln Pro Ala His Glu Ala Val Glu Lys Glu Thr Thr Glu Lys Glu Ala
                990                 995                 1000

ACG GAG AAG GAG GCT GAG ATA GTG GAA GCC GAC AAG GAA AAG GAG CTC      3194
Thr Glu Lys Glu Ala Glu Ile Val Glu Ala Asp Lys Glu Lys Glu Leu
            1005                1010                1015

CGG AAC CAC CAG CCC CGG GAG CCA CAC TGT GAC CTG GAG ACC AGT GGG      3242
Arg Asn His Gln Pro Arg Glu Pro His Cys Asp Leu Glu Thr Ser Gly
        1020                1025                1030

ACT GTG ACT GTG GGT CCC ATG CAC ACA CTG CCC AGC ACC TGT CTC CAG      3290
Thr Val Thr Val Gly Pro Met His Thr Leu Pro Ser Thr Cys Leu Gln
    1035                1040                1045

AAG GTG GAG GAA CAG CCA GAG GAT GCA GAC AAT CAG CGG AAC GTC ACT      3338
Lys Val Glu Glu Gln Pro Glu Asp Ala Asp Asn Gln Arg Asn Val Thr
1050                1055                1060                1065

CGC ATG GGC AGT CAG CCC CCA GAC CCG AAC ACT ATT GTA CAT ATC CCA      3386
Arg Met Gly Ser Gln Pro Pro Asp Pro Asn Thr Ile Val His Ile Pro
                1070                1075                1080

GTG ATG CTG ACG GGC CCT CTT GGG GAA GCC ACG GTC GTT CCC AGT GGT      3434
Val Met Leu Thr Gly Pro Leu Gly Glu Ala Thr Val Val Pro Ser Gly
            1085                1090                1095

AAC GTG GAC CTG GAA AGC CAA GCA GAG GGG AAG AAG GAG GTG GAA GCG      3482
Asn Val Asp Leu Glu Ser Gln Ala Glu Gly Lys Lys Glu Val Glu Ala
        1100                1105                1110

GAT GAC GTG ATG AGG AGC GGC CCC CGG CCT ATC GTC CCA TAC AGC TCC      3530
Asp Asp Val Met Arg Ser Gly Pro Arg Pro Ile Val Pro Tyr Ser Ser
    1115                1120                1125

ATG TTC TGT TTA AGC CCC ACC AAC CTG CTC CGC CGC TTC TGC CAC TAC      3578
Met Phe Cys Leu Ser Pro Thr Asn Leu Leu Arg Arg Phe Cys His Tyr
1130                1135                1140                1145

ATC GTG ACC ATG AGG TAC TTC GAG GTG GTC ATT CTC GTG GTC ATC GCC      3626
Ile Val Thr Met Arg Tyr Phe Glu Val Val Ile Leu Val Val Ile Ala
                1150                1155                1160
```

```
TTG AGC AGC ATC GCC CTG GCT GCT GAG GAC CCA GTG CGC ACA GAC TCG    3674
Leu Ser Ser Ile Ala Leu Ala Ala Glu Asp Pro Val Arg Thr Asp Ser
        1165                1170                1175

CCC AGG AAC AAC GCT CTG AAA TAC CTG GAT TAC ATT TTC ACT GGT GTC    3722
Pro Arg Asn Asn Ala Leu Lys Tyr Leu Asp Tyr Ile Phe Thr Gly Val
            1180                1185                1190

TTT ACC TTT GAG ATG GTG ATA AAG ATG ATC GAC TTG GGA CTG CTG CTT    3770
Phe Thr Phe Glu Met Val Ile Lys Met Ile Asp Leu Gly Leu Leu Leu
        1195                1200                1205

CAC CCT GGA GCC TAT TTC CGG GAC TTG TGG AAC ATT CTG GAC TTC ATT    3818
His Pro Gly Ala Tyr Phe Arg Asp Leu Trp Asn Ile Leu Asp Phe Ile
1210                1215                1220                1225

GTG GTC AGT GGC GCC CTG GTG GCG TTT GCT TTC TCA GGA TCC AAA GGG    3866
Val Val Ser Gly Ala Leu Val Ala Phe Ala Phe Ser Gly Ser Lys Gly
                1230                1235                1240

AAA GAC ATC AAT ACC ATC AAG TCT CTG AGA GTC CTT CGT GTC CTG CGG    3914
Lys Asp Ile Asn Thr Ile Lys Ser Leu Arg Val Leu Arg Val Leu Arg
        1245                1250                1255

CCC CTC AAG ACC ATC AAA CGG CTG CCC AAG CTC AAG GCT GTG TTT GAC    3962
Pro Leu Lys Thr Ile Lys Arg Leu Pro Lys Leu Lys Ala Val Phe Asp
            1260                1265                1270

TGT GTG GTG AAC TCC CTG AAG AAT GTC CTC AAC ATC TTG ATT GTC TAC    4010
Cys Val Val Asn Ser Leu Lys Asn Val Leu Asn Ile Leu Ile Val Tyr
        1275                1280                1285

ATG CTC TTC ATG TTC ATA TTT GCC GTC ATT GCG GTG CAG CTC TTC AAA    4058
Met Leu Phe Met Phe Ile Phe Ala Val Ile Ala Val Gln Leu Phe Lys
1290                1295                1300                1305

GGG AAG TTT TTC TAC TGC ACA GAT GAA TCC AAG GAG CTG GAG AGG GAC    4106
Gly Lys Phe Phe Tyr Cys Thr Asp Glu Ser Lys Glu Leu Glu Arg Asp
                1310                1315                1320

TGC AGG GGT CAG TAT TTG GAT TAT GAG AAG GAG GAA GTG GAA GCT CAG    4154
Cys Arg Gly Gln Tyr Leu Asp Tyr Glu Lys Glu Glu Val Glu Ala Gln
        1325                1330                1335

CCC AGG CAG TGG AAG AAA TAC GAC TTT CAC TAC GAC AAT GTG CTC TGG    4202
Pro Arg Gln Trp Lys Lys Tyr Asp Phe His Tyr Asp Asn Val Leu Trp
            1340                1345                1350

GCT CTG CTG ACG CTG TTC ACA GTG TCC ACG GGA GAA GGC TGG CCC ATG    4250
Ala Leu Leu Thr Leu Phe Thr Val Ser Thr Gly Glu Gly Trp Pro Met
        1355                1360                1365

GTG CTG AAA CAC TCC GTG GAT GCC ACC TAT GAG GAG CAG GGT CCA AGC    4298
Val Leu Lys His Ser Val Asp Ala Thr Tyr Glu Glu Gln Gly Pro Ser
1370                1375                1380                1385

CCT GGG TAC CGC ATG GAG CTG TCC ATC TTC TAC GTG GTC TAC TTT GTG    4346
Pro Gly Tyr Arg Met Glu Leu Ser Ile Phe Tyr Val Val Tyr Phe Val
            1390                1395                1400

GTC TTT CCC TTC TTC TTC GTC AAC ATC TTT GTG GCT TTG ATC ATC ATC    4394
Val Phe Pro Phe Phe Phe Val Asn Ile Phe Val Ala Leu Ile Ile Ile
            1405                1410                1415

ACC TTC CAG GAG CAG GGG GAC AAG GTG ATG TCT GAA TGC AGC CTG GAG    4442
Thr Phe Gln Glu Gln Gly Asp Lys Val Met Ser Glu Cys Ser Leu Glu
        1420                1425                1430

AAG AAC GAG AGG GCT TGC ATT GAC TTC GCC ATC AGC GCC AAA CCC CTG    4490
Lys Asn Glu Arg Ala Cys Ile Asp Phe Ala Ile Ser Ala Lys Pro Leu
            1435                1440                1445

ACA CGG TAC ATG CCC CAA AAC CGG CAG TCG TTC CAG TAT AAG ACG TGG    4538
Thr Arg Tyr Met Pro Gln Asn Arg Gln Ser Phe Gln Tyr Lys Thr Trp
        1450                1455                1460                1465

ACA TTT GTG GTC TCC CCG CCC TTT GAA TAC TTC ATC ATG GCC ATG ATA    4586
Thr Phe Val Val Ser Pro Pro Phe Glu Tyr Phe Ile Met Ala Met Ile
                1470                1475                1480
```

-continued

```
GCC CTC AAC ACT GTG GTG CTG ATG ATG AAG TTC TAT GAT GCA CCC TAT        4634
Ala Leu Asn Thr Val Val Leu Met Met Lys Phe Tyr Asp Ala Pro Tyr
            1485                1490                1495

GAG TAC GAG CTG ATG CTG AAA TGC CTG AAC ATC GTG TTC ACA TCC ATG        4682
Glu Tyr Glu Leu Met Leu Lys Cys Leu Asn Ile Val Phe Thr Ser Met
        1500                1505                1510

TTC TCC ATG GAA TGC GTG CTG AAG ATC ATC GCC TTT GGG GTG CTG AAC        4730
Phe Ser Met Glu Cys Val Leu Lys Ile Ile Ala Phe Gly Val Leu Asn
        1515                1520                1525

TAT TTC AGA GAT GCC TGG AAT GTC TTT GAC TTT GTC ACT GTG TTG GGA        4778
Tyr Phe Arg Asp Ala Trp Asn Val Phe Asp Phe Val Thr Val Leu Gly
1530                1535                1540                1545

AGT ATT ACT GAT ATT TTA GTA ACA GAG ATT GCG GAA ACG AAC AAT TTC        4826
Ser Ile Thr Asp Ile Leu Val Thr Glu Ile Ala Glu Thr Asn Asn Phe
            1550                1555                1560

ATC AAC CTC AGC TTC CTC CGC CTC TTT CGA GCT GCG CGG CTG ATC AAG        4874
Ile Asn Leu Ser Phe Leu Arg Leu Phe Arg Ala Ala Arg Leu Ile Lys
        1565                1570                1575

CTG CTC CGC CAG GGC TAC ACC ATC CGC ATC CTG CTG TGG ACC TTT GTC        4922
Leu Leu Arg Gln Gly Tyr Thr Ile Arg Ile Leu Leu Trp Thr Phe Val
        1580                1585                1590

CAG TCC TTC AAG GCC CTG CCC TAC GTG TGT CTG CTC ATT GCC ATG CTG        4970
Gln Ser Phe Lys Ala Leu Pro Tyr Val Cys Leu Leu Ile Ala Met Leu
        1595                1600                1605

TTC TTC ATC TAC GCC ATC ATC GGC ATG CAG GTG TTT GGG AAT ATT GCC        5018
Phe Phe Ile Tyr Ala Ile Ile Gly Met Gln Val Phe Gly Asn Ile Ala
1610                1615                1620                1625

CTG GAT GAT GAC ACC AGC ATC AAC CGC CAC AAC AAC TTC CGG ACG TTT        5066
Leu Asp Asp Asp Thr Ser Ile Asn Arg His Asn Asn Phe Arg Thr Phe
            1630                1635                1640

TTG CAA GCC CTG ATG CTG CTG TTC AGG AGC GCC ACG GGG GAG GCC TGG        5114
Leu Gln Ala Leu Met Leu Leu Phe Arg Ser Ala Thr Gly Glu Ala Trp
        1645                1650                1655

CAC GAG ATC ATG CTG TCC TGC CTG AGC AAC CAG GCC TGT GAT GAG CAG        5162
His Glu Ile Met Leu Ser Cys Leu Ser Asn Gln Ala Cys Asp Glu Gln
        1660                1665                1670

GCC AAT GCC ACC GAG TGT GGA AGT GAC TTT GCC TAC TTC TAC TTC GTC        5210
Ala Asn Ala Thr Glu Cys Gly Ser Asp Phe Ala Tyr Phe Tyr Phe Val
1675                1680                1685

TCC TTC ATC TTC CTG TGC TCC TTT CTG ATG TTG AAC CTC TTT GTG GCT        5258
Ser Phe Ile Phe Leu Cys Ser Phe Leu Met Leu Asn Leu Phe Val Ala
1690                1695                1700                1705

GTG ATC ATG GAC AAT TTT GAG TAC CTC ACG CGG GAC TCT TCC ATC CTA        5306
Val Ile Met Asp Asn Phe Glu Tyr Leu Thr Arg Asp Ser Ser Ile Leu
            1710                1715                1720

GGT CCT CAC CAC TTG GAT GAG TTC ATC CGG GTC TGG GCT GAA TAC GAC        5354
Gly Pro His His Leu Asp Glu Phe Ile Arg Val Trp Ala Glu Tyr Asp
        1725                1730                1735

CCG GCT GCG TGT GGG CGC ATC AGT TAC AAT GAC ATG TTT GAG ATG CTG        5402
Pro Ala Ala Cys Gly Arg Ile Ser Tyr Asn Asp Met Phe Glu Met Leu
        1740                1745                1750

AAA CAC ATG TCC CCG CCT CTG GGG CTG GGG AAG AAA TGC CCT GCT CGA        5450
Lys His Met Ser Pro Pro Leu Gly Leu Gly Lys Lys Cys Pro Ala Arg
1755                1760                1765

GTT GCT TAC AAG CGC CTG GTT CGC ATG AAC ATG CCC ATC TCC AAC GAG        5498
Val Ala Tyr Lys Arg Leu Val Arg Met Asn Met Pro Ile Ser Asn Glu
1770                1775                1780                1785

GAC ATG ACT GTT CAC TTC ACG TCC ACG CTG ATG GCC CTC ATC CGG ACG        5546
Asp Met Thr Val His Phe Thr Ser Thr Leu Met Ala Leu Ile Arg Thr
```

```
                    1790                1795                1800
GCA CTG GAG ATC AAG CTG GCC CCA GCT GGG ACA AAG CAG CAT CAG TGT         5594
Ala Leu Glu Ile Lys Leu Ala Pro Ala Gly Thr Lys Gln His Gln Cys
            1805                1810                1815

GAC GCG GAG TTG AGG AAG GAG ATT TCC GTT GTG TGG GCC AAT CTG CCC         5642
Asp Ala Glu Leu Arg Lys Glu Ile Ser Val Val Trp Ala Asn Leu Pro
            1820                1825            1830

CAG AAG ACT TTG GAC TTG CTG GTA CCA CCC CAT AAG CCT GAT GAG ATG         5690
Gln Lys Thr Leu Asp Leu Leu Val Pro Pro His Lys Pro Asp Glu Met
        1835                1840                1845

ACA GTG GGG AAG GTT TAT GCA GCT CTG ATG ATA TTT GAC TTC TAC AAG         5738
Thr Val Gly Lys Val Tyr Ala Ala Leu Met Ile Phe Asp Phe Tyr Lys
1850                1855                1860                1865

CAG AAC AAA ACC ACC AGA GAC CAG ATG CAG CAG GCT CCT GGA GGC CTC         5786
Gln Asn Lys Thr Thr Arg Asp Gln Met Gln Gln Ala Pro Gly Gly Leu
                1870                1875                1880

TCC CAG ATG GGT CCT GTG TCC CTG TTC CAC CCT CTG AAG GCC ACC CTG         5834
Ser Gln Met Gly Pro Val Ser Leu Phe His Pro Leu Lys Ala Thr Leu
            1885                1890                1895

GAG CAG ACA CAG CCG GCT GTG CTC CGA GGA GCC CGG GTT TTC CTT CGA         5882
Glu Gln Thr Gln Pro Ala Val Leu Arg Gly Ala Arg Val Phe Leu Arg
        1900                1905                1910

CAG AAG AGT TCC ACC TCC CTC AGC AAT GGC GGG GCC ATA CAA AAC CAA         5930
Gln Lys Ser Ser Thr Ser Leu Ser Asn Gly Gly Ala Ile Gln Asn Gln
    1915                1920                1925

GAG AGT GGC ATC AAA GAG TCT GTC TCC TGG GGC ACT CAA AGG ACC CAG         5978
Glu Ser Gly Ile Lys Glu Ser Val Ser Trp Gly Thr Gln Arg Thr Gln
1930                1935                1940                1945

GAT GCA CCC CAT GAG GCC AGG CCA CCC CTG GAG CGT GGC CAC TCC ACA         6026
Asp Ala Pro His Glu Ala Arg Pro Pro Leu Glu Arg Gly His Ser Thr
                1950                1955                1960

GAG ATC CCT GTG GGG CGG TCA GGA GCA CTG GCT GTG GAC GTT CAG ATG         6074
Glu Ile Pro Val Gly Arg Ser Gly Ala Leu Ala Val Asp Val Gln Met
            1965                1970                1975

CAG AGC ATA ACC CGG AGG GGC CCT GAT GGG GAG CCC CAG CCT GGG CTG         6122
Gln Ser Ile Thr Arg Arg Gly Pro Asp Gly Glu Pro Gln Pro Gly Leu
        1980                1985                1990

GAG AGC CAG GGT CGA GCG GCC TCC ATG CCC CGC CTT GCG GCC GAG ACT         6170
Glu Ser Gln Gly Arg Ala Ala Ser Met Pro Arg Leu Ala Ala Glu Thr
    1995                2000                2005

CAG CCC GTC ACA GAT GCC AGC CCC ATG AAG CGC TCC ATC TCC ACG CTG         6218
Gln Pro Val Thr Asp Ala Ser Pro Met Lys Arg Ser Ile Ser Thr Leu
2010                2015                2020                2025

GCC CAG CGG CCC CGT GGG ACT CAT CTT TGC AGC ACC ACC CCG GAC CGC         6266
Ala Gln Arg Pro Arg Gly Thr His Leu Cys Ser Thr Thr Pro Asp Arg
                2030                2035                2040

CCA CCC CCT AGC CAG GCG TCG TCG CAC CAC CAC CAC CAC CGC TGC CAC         6314
Pro Pro Pro Ser Gln Ala Ser Ser His His His His His Arg Cys His
            2045                2050                2055

CGC CGC AGG GAC AGG AAG CAG AGG TCC CTG GAG AAG GGG CCC AGC CTG         6362
Arg Arg Arg Asp Arg Lys Gln Arg Ser Leu Glu Lys Gly Pro Ser Leu
        2060                2065                2070

TCT GCC GAT ATG GAT GGC GCA CCA AGC AGT GCT GTG GGG CCG GGG CTG         6410
Ser Ala Asp Met Asp Gly Ala Pro Ser Ser Ala Val Gly Pro Gly Leu
    2075                2080                2085

CCC CCG GGA GAG GGG CCT ACA GGC TGC CGG CGG GAA CGA GAG CGC CGG         6458
Pro Pro Gly Glu Gly Pro Thr Gly Cys Arg Arg Glu Arg Glu Arg Arg
2090                2095                2100                2105

CAG GAG CGG GGC CGG TCC CAG GAG CGG AGG CAG CCC TCA TCC TCC TCC         6506
```

```
Gln Glu Arg Gly Arg Ser Gln Glu Arg Gln Pro Ser Ser Ser Ser
            2110                2115                2120

TCG GAG AAG CAG CGC TTC TAC TCC TGC GAC CGC TTT GGG GGC CGT GAG      6554
Ser Glu Lys Gln Arg Phe Tyr Ser Cys Asp Arg Phe Gly Gly Arg Glu
        2125                2130                2135

CCC CCG AAG CCC AAG CCC TCC CTC AGC AGC CAC CCA ACG TCG CCA ACA      6602
Pro Pro Lys Pro Lys Pro Ser Leu Ser Ser His Pro Thr Ser Pro Thr
            2140                2145                2150

GCT GGC CAG GAG CCG GGA CCC CAC CCA CAG GGC AGT GGT TCC GTG AAT      6650
Ala Gly Gln Glu Pro Gly Pro His Pro Gln Gly Ser Gly Ser Val Asn
        2155                2160                2165

GGG AGC CCC TTG CTG TCA ACA TCT GGT GCT AGC ACC CCC GGC CGC GGT      6698
Gly Ser Pro Leu Leu Ser Thr Ser Gly Ala Ser Thr Pro Gly Arg Gly
2170                2175                2180                2185

GGG CGG AGG CAG CTC CCC CAG ACG CCC CTG ACT CCC CGC CCC AGC ATC      6746
Gly Arg Arg Gln Leu Pro Gln Thr Pro Leu Thr Pro Arg Pro Ser Ile
        2190                2195                2200

ACC TAC AAG ACG GCC AAC TCC TCA CCC ATC CAC TTC GCC GGG GCT CAG      6794
Thr Tyr Lys Thr Ala Asn Ser Ser Pro Ile His Phe Ala Gly Ala Gln
            2205                2210                2215

ACC AGC CTC CCT GCC TTC TCC CCA GGC CGG CTC AGC CGT GGG CTT TCC      6842
Thr Ser Leu Pro Ala Phe Ser Pro Gly Arg Leu Ser Arg Gly Leu Ser
        2220                2225                2230

GAA CAC AAC GCC CTG CTG CAG AGA GAC CCC CTC AGC CAG CCC CTG GCC      6890
Glu His Asn Ala Leu Leu Gln Arg Asp Pro Leu Ser Gln Pro Leu Ala
        2235                2240                2245

CCT GGC TCT CGA ATT GGC TCT GAC CCT TAC CTG GGG CAG CGT CTG GAC      6938
Pro Gly Ser Arg Ile Gly Ser Asp Pro Tyr Leu Gly Gln Arg Leu Asp
2250                2255                2260                2265

AGT GAG GCC TCT GTC CAC GCC CTG CCT GAG GAC ACG CTC ACT TTC GAG      6986
Ser Glu Ala Ser Val His Ala Leu Pro Glu Asp Thr Leu Thr Phe Glu
        2270                2275                2280

GAG GCT GTG GCC ACC AAC TCG GGC CGC TCC TCC AGG ACT TCC TAC GTG      7034
Glu Ala Val Ala Thr Asn Ser Gly Arg Ser Ser Arg Thr Ser Tyr Val
            2285                2290                2295

TCC TCC CTG ACC TCC CAG TCT CAC CCT CTC CGC CGC GTG CCC AAC GGT      7082
Ser Ser Leu Thr Ser Gln Ser His Pro Leu Arg Arg Val Pro Asn Gly
        2300                2305                2310

TAC CAC TGC ACC CTG GGA CTC AGC TCG GGT GGC CGA GCA CGG CAC AGC      7130
Tyr His Cys Thr Leu Gly Leu Ser Ser Gly Gly Arg Ala Arg His Ser
        2315                2320                2325

TAC CAC CAC CCT GAC CAA GAC CAC TGG TGC TAGCTGCACC GTGACCGCTC        7180
Tyr His His Pro Asp Gln Asp His Trp Cys
2330                2335                234

AGACGCCTGC ATGCAGCAGG CGTGTGTTCC AGTGGATGAG TTTTATCATC CACACGGGGC    7240

AGTCGGCCCT CGGGGGAGGC CTTGCCCACC TTGGTGAGGC TCCTGTGGCC CCTCCCTCCC    7300

CCTCCTCCCC TCTTTTACTC TAGACGACGA ATAAAGCCCT GTTGCTTGAG TGTACGTACC    7360

GC                                                                   7362

(2) INFORMATION FOR SEQ ID NO:8:

(i) SEQUENCE CHARACTERISTICS:
        (A) LENGTH: 7175 base pairs
        (B) TYPE: nucleic acid
        (C) STRANDEDNESS: double
        (D) TOPOLOGY: linear (ii) MOLECULE TYPE: DNA (genomic)

(ix) FEATURE:
```

```
        (A) NAME/KEY: CDS
        (B) LOCATION: 144..6857

(ix) FEATURE:
        (A) NAME/KEY: 5'UTR
        (B) LOCATION: 1..143

(ix) FEATURE:
        (A) NAME/KEY: 3'UTR
        (B) LOCATION: 6855..7175

(xi) SEQUENCE DESCRIPTION: SEQ ID NO:8:

GCGGCGGCGG CTGCGGCGGT GGGGCCGGGC GAGGTCCGTG CGGTCCCGGC GGCTCCGTGG       60

CTGCTCCGCT CTGAGCGCCT GCGCGCCCCG CGCCCTCCCT GCCGGGGCCG CTGGGCCGGG      120

GATGCACGCG GGGCCCGGGA GCC ATG GTC CGC TTC GGG GAC GAG CTG GGC          170
                         Met Val Arg Phe Gly Asp Glu Leu Gly
                           1               5

GGC CGC TAT GGA GGC CCC GGC GGC GGA GAG CGG GCC CGG GGC GGC GGG        218
Gly Arg Tyr Gly Gly Pro Gly Gly Gly Glu Arg Ala Arg Gly Gly Gly
 10                  15                  20                  25

GCC GGC GGG GCG GGG GGC CCG GGT CCC GGG GGG CTG CAG CCC GGC CAG        266
Ala Gly Gly Ala Gly Gly Pro Gly Pro Gly Gly Leu Gln Pro Gly Gln
                 30                  35                  40

CGG GTC CTC TAC AAG CAA TCG ATC GCG CAG CGC GCG CGG ACC ATG GCG        314
Arg Val Leu Tyr Lys Gln Ser Ile Ala Gln Arg Ala Arg Thr Met Ala
             45                  50                  55

CTG TAC AAC CCC ATC CCG GTC AAG CAG AAC TGC TTC ACC GTC AAC CGC        362
Leu Tyr Asn Pro Ile Pro Val Lys Gln Asn Cys Phe Thr Val Asn Arg
         60                  65                  70

TCG CTC TTC GTC TTC AGC GAG GAC AAC GTC GTC CGC AAA TAC GCG AAG        410
Ser Leu Phe Val Phe Ser Glu Asp Asn Val Val Arg Lys Tyr Ala Lys
 75                  80                  85

CGC ATC ACC GAG TGG CCT CCA TTC GAG AAT ATG ATC CTG GCC ACC ATC        458
Arg Ile Thr Glu Trp Pro Pro Phe Glu Asn Met Ile Leu Ala Thr Ile
 90                  95                 100                 105

ATC GCC AAC TGC ATC GTG CTG GCC CTG GAG CAG CAC CTC CCT GAT GGG        506
Ile Ala Asn Cys Ile Val Leu Ala Leu Glu Gln His Leu Pro Asp Gly
                110                 115                 120

GAC AAA ACG CCC ATG TCC GAG CGG CTG GAC GAC ACG GAG CCC TAT TTC        554
Asp Lys Thr Pro Met Ser Glu Arg Leu Asp Asp Thr Glu Pro Tyr Phe
            125                 130                 135

ATC GGG ATC TTT TGC TTC GAG GCA GGG ATC AAA ATC ATC GCT CTG GGC        602
Ile Gly Ile Phe Cys Phe Glu Ala Gly Ile Lys Ile Ile Ala Leu Gly
        140                 145                 150

TTT GTC TTC CAC AAG GGC TCT TAC CTG CGG AAC GGC TGG AAC GTC ATG        650
Phe Val Phe His Lys Gly Ser Tyr Leu Arg Asn Gly Trp Asn Val Met
155                 160                 165

GAC TTC GTG GTC GTC CTC ACA GGG ATC CTT GCC ACG GCT GGA ACT GAC        698
Asp Phe Val Val Val Leu Thr Gly Ile Leu Ala Thr Ala Gly Thr Asp
170                 175                 180                 185

TTC GAC CTG CGA ACA CTG AGG GCT GTG CGT GTG CTG AGG CCC CTG AAG        746
Phe Asp Leu Arg Thr Leu Arg Ala Val Arg Val Leu Arg Pro Leu Lys
                190                 195                 200

CTG GTG TCT GGG ATT CCA AGT TTG CAG GTG GTG CTC AAG TCC ATC ATG        794
Leu Val Ser Gly Ile Pro Ser Leu Gln Val Val Leu Lys Ser Ile Met
            205                 210                 215

AAG GCC ATG GTT CCA CTC CTG CAG ATT GGG CTG CTT CTC TTC TTT GCC        842
Lys Ala Met Val Pro Leu Leu Gln Ile Gly Leu Leu Leu Phe Phe Ala
        220                 225                 230

ATC CTC ATG TTT GCC ATC ATT GGC CTG GAG TTC TAC ATG GGC AAG TTC        890
Ile Leu Met Phe Ala Ile Ile Gly Leu Glu Phe Tyr Met Gly Lys Phe
```

```
                    235                 240                 245
CAC AAG GCC TGT TTC CCC AAC AGC ACA GAT GCG GAG CCC GTG GGT GAC    938
His Lys Ala Cys Phe Pro Asn Ser Thr Asp Ala Glu Pro Val Gly Asp
250             255                 260                 265

TTC CCC TGT GGC AAG GAG GCC CCA GCC CGG CTG TGC GAG GGC GAC ACT    986
Phe Pro Cys Gly Lys Glu Ala Pro Ala Arg Leu Cys Glu Gly Asp Thr
                270                 275                 280

GAG TGC CGG GAG TAC TGG CCA GGA CCC AAC TTT GGC ATC ACC AAC TTT   1034
Glu Cys Arg Glu Tyr Trp Pro Gly Pro Asn Phe Gly Ile Thr Asn Phe
            285                 290                 295

GAC AAT ATC CTG TTT GCC ATC TTG ACG GTG TTC CAG TGC ATC ACC ATG   1082
Asp Asn Ile Leu Phe Ala Ile Leu Thr Val Phe Gln Cys Ile Thr Met
        300                 305                 310

GAG GGC TGG ACT GAC ATC CTC TAT AAT ACA AAC GAT GCG GCC GGC AAC   1130
Glu Gly Trp Thr Asp Ile Leu Tyr Asn Thr Asn Asp Ala Ala Gly Asn
    315                 320                 325

ACC TGG AAC TGG CTC TAC TTC ATC CCT CTC ATC ATC ATC GGC TCC TTC   1178
Thr Trp Asn Trp Leu Tyr Phe Ile Pro Leu Ile Ile Ile Gly Ser Phe
330                 335                 340                 345

TTC ATG CTC AAC CTG GTG CTG GGC GTG CTC TCG GGG GAG TTT GCC AAG   1226
Phe Met Leu Asn Leu Val Leu Gly Val Leu Ser Gly Glu Phe Ala Lys
                350                 355                 360

GAG CGA GAG AGG GTG GAG AAC CGC CGC GCC TTC CTG AAG CTG CGC CGG   1274
Glu Arg Glu Arg Val Glu Asn Arg Arg Ala Phe Leu Lys Leu Arg Arg
            365                 370                 375

CAG CAG CAG ATC GAG CGA GAG CTC AAC GGG TAC CTG GAG TGG ATC TTC   1322
Gln Gln Gln Ile Glu Arg Glu Leu Asn Gly Tyr Leu Glu Trp Ile Phe
        380                 385                 390

AAG GCG GAG GAA GTC ATG CTG GCC GAG GAG GAC AGG AAT GCA GAG GAG   1370
Lys Ala Glu Glu Val Met Leu Ala Glu Glu Asp Arg Asn Ala Glu Glu
    395                 400                 405

AAG TCC CCT TTG GAC GTG CTG AAG AGA GCG GCC ACC AAG AAG AGC AGA   1418
Lys Ser Pro Leu Asp Val Leu Lys Arg Ala Ala Thr Lys Lys Ser Arg
410                 415                 420                 425

AAT GAC CTG ATC CAC GCA GAG GAG GGA GAG GAC CGG TTT GCA GAT CTC   1466
Asn Asp Leu Ile His Ala Glu Glu Gly Glu Asp Arg Phe Ala Asp Leu
                430                 435                 440

TGT GCT GTT GGA TCC CCC TTC GCC CGC GCC AGC CTC AAG AGC GGG AAG   1514
Cys Ala Val Gly Ser Pro Phe Ala Arg Ala Ser Leu Lys Ser Gly Lys
            445                 450                 455

ACA GAG AGC TCG TCA TAC TTC CGG AGG AAG GAG AAG ATG TTC CGG TTT   1562
Thr Glu Ser Ser Ser Tyr Phe Arg Arg Lys Glu Lys Met Phe Arg Phe
        460                 465                 470

TTT ATC CGG CGC ATG GTG AAG GCT CAG AGC TTC TAC TGG GTG GTG CTG   1610
Phe Ile Arg Arg Met Val Lys Ala Gln Ser Phe Tyr Trp Val Val Leu
    475                 480                 485

TGC GTG GTG GCC CTG AAC ACA CTG TGT GTG GCC ATG GTG CAT TAC AAC   1658
Cys Val Val Ala Leu Asn Thr Leu Cys Val Ala Met Val His Tyr Asn
490                 495                 500                 505

CAG CCG CGG CGG CTT ACC ACG ACC CTG TAT TTT GCA GAG TTT GTT TTC   1706
Gln Pro Arg Arg Leu Thr Thr Thr Leu Tyr Phe Ala Glu Phe Val Phe
                510                 515                 520

CTG GGT CTC TTC CTC ACA GAG ATG TCC CTG AAG ATG TAT GGC CTG GGG   1754
Leu Gly Leu Phe Leu Thr Glu Met Ser Leu Lys Met Tyr Gly Leu Gly
            525                 530                 535

CCC AGA AGC TAC TTC CGG TCC TCC TTC AAC TGC TTC GAC TTT GGG GTC   1802
Pro Arg Ser Tyr Phe Arg Ser Ser Phe Asn Cys Phe Asp Phe Gly Val
        540                 545                 550

ATC GTG GGG AGC GTC TTT GAA GTG GTC TGG GCG GCC ATC AAG CCG GGA   1850
```

```
                                                        -continued

Ile Val Gly Ser Val Phe Glu Val Val Trp Ala Ala Ile Lys Pro Gly
    555                 560                 565

AGC TCC TTT GGG ATC AGT GTG CTG CGG GCC CTC CGC CTG CTG AGG ATC      1898
Ser Ser Phe Gly Ile Ser Val Leu Arg Ala Leu Arg Leu Leu Arg Ile
570                 575                 580                 585

TTC AAA GTC ACG AAG TAC TGG AGC TCC CTG CGG AAC CTG GTG GTG TCC      1946
Phe Lys Val Thr Lys Tyr Trp Ser Ser Leu Arg Asn Leu Val Val Ser
                590                 595                 600

CTG CTG AAC TCC ATG AAG TCC ATC ATC AGC CTG CTC TTC TTG CTC TTC      1994
Leu Leu Asn Ser Met Lys Ser Ile Ile Ser Leu Leu Phe Leu Leu Phe
                605                 610                 615

CTG TTC ATT GTG GTC TTC GCC CTG CTG GGG ATG CAG CTG TTT GGG GGA      2042
Leu Phe Ile Val Val Phe Ala Leu Leu Gly Met Gln Leu Phe Gly Gly
                620                 625                 630

CAG TTC AAC TTC CAG GAT GAG ACT CCC ACA ACC AAC TTC GAC ACC TTC      2090
Gln Phe Asn Phe Gln Asp Glu Thr Pro Thr Thr Asn Phe Asp Thr Phe
635                 640                 645

CCT GCC GCC ATC CTC ACT GTC TTC CAG ATC CTG ACG GGA GAG GAC TGG      2138
Pro Ala Ala Ile Leu Thr Val Phe Gln Ile Leu Thr Gly Glu Asp Trp
650                 655                 660                 665

AAT GCA GTG ATG TAT CAC GGG ATC GAA TCG CAA GGC GGC GTC AGC AAA      2186
Asn Ala Val Met Tyr His Gly Ile Glu Ser Gln Gly Gly Val Ser Lys
                670                 675                 680

GGC ATG TTC TCG TCC TTT TAC TTC ATT GTC CTG ACA CTG TTC GGA AAC      2234
Gly Met Phe Ser Ser Phe Tyr Phe Ile Val Leu Thr Leu Phe Gly Asn
                685                 690                 695

TAC ACT CTG CTG AAT GTC TTT CTG GCC ATC GCT GTG GAC AAC CTG GCC      2282
Tyr Thr Leu Leu Asn Val Phe Leu Ala Ile Ala Val Asp Asn Leu Ala
                700                 705                 710

AAC GCC CAA GAG CTG ACC AAG GAT GAA GAG GAG ATG GAA GAA GCA GCC      2330
Asn Ala Gln Glu Leu Thr Lys Asp Glu Glu Glu Met Glu Glu Ala Ala
                715                 720                 725

AAT CAG AAG CTT GCT CTG CAA AAG GCC AAA GAA GTG GCT GAA GTC AGC      2378
Asn Gln Lys Leu Ala Leu Gln Lys Ala Lys Glu Val Ala Glu Val Ser
730                 735                 740                 745

CCC ATG TCT GCC GCG AAC ATC TCC ATC GCC GCC AGG CAG CAG AAC TCG      2426
Pro Met Ser Ala Ala Asn Ile Ser Ile Ala Ala Arg Gln Gln Asn Ser
                750                 755                 760

GCC AAG GCG CGC TCG GTG TGG GAG CAG CGG GCC AGC CAG CTA CGG CTG      2474
Ala Lys Ala Arg Ser Val Trp Glu Gln Arg Ala Ser Gln Leu Arg Leu
                765                 770                 775

CAG AAC CTG CGG GCC AGC TGC GAG GCG CTG TAC AGC GAG ATG GAC CCC      2522
Gln Asn Leu Arg Ala Ser Cys Glu Ala Leu Tyr Ser Glu Met Asp Pro
                780                 785                 790

GAG GAG CGG CTG CGC TTC GCC ACT ACG CGC CAC CTG CGG CCC GAC ATG      2570
Glu Glu Arg Leu Arg Phe Ala Thr Thr Arg His Leu Arg Pro Asp Met
795                 800                 805

AAG ACG CAC CTG GAC CGG CCG CTG GTG GTG GAG CTG GGC CGC GAC GGC      2618
Lys Thr His Leu Asp Arg Pro Leu Val Val Glu Leu Gly Arg Asp Gly
810                 815                 820                 825

GCG CGG GGG CCC GTG GGA GGC AAA GCC CGA CCT GAG GCT GCG GAG GCC      2666
Ala Arg Gly Pro Val Gly Gly Lys Ala Arg Pro Glu Ala Ala Glu Ala
                830                 835                 840

CCC GAG GGC GTC GAC CCT CCG CGC AGG CAC CAC CGG CAC CGC GAC AAG      2714
Pro Glu Gly Val Asp Pro Pro Arg Arg His His Arg His Arg Asp Lys
                845                 850                 855

GAC AAG ACC CCC GCG GCG GGG GAC CAG GAC CGA GCA GAG GCC CCG AAG      2762
Asp Lys Thr Pro Ala Ala Gly Asp Gln Asp Arg Ala Glu Ala Pro Lys
                860                 865                 870
```

```
GCG GAG AGC GGG GAG CCC GGT GCC CGG GAG GAG CGG CCG CGG CCG CAC      2810
Ala Glu Ser Gly Glu Pro Gly Ala Arg Glu Glu Arg Pro Arg Pro His
    875                 880                 885

CGC AGC CAC AGC AAG GAG GCC GCG GGG CCC CCG GAG GCG CGG AGC GAG      2858
Arg Ser His Ser Lys Glu Ala Ala Gly Pro Pro Glu Ala Arg Ser Glu
890                 895                 900                 905

CGC GGC CGA GGC CCA GGC CCC GAG GGC GGC CGG CGG CAC CAC CGG CGC      2906
Arg Gly Arg Gly Pro Gly Pro Glu Gly Gly Arg Arg His His Arg Arg
                910                 915                 920

GGC TCC CCG GAG GAG GCG GCC GAG CGG GAG CCC CGA CGC CAC CGC GCG      2954
Gly Ser Pro Glu Glu Ala Ala Glu Arg Glu Pro Arg Arg His Arg Ala
            925                 930                 935

CAC CGG CAC CAG GAT CCG AGC AAG GAG TGC GCC GGC GCC AAG GGC GAG      3002
His Arg His Gln Asp Pro Ser Lys Glu Cys Ala Gly Ala Lys Gly Glu
        940                 945                 950

CGG CGC GCG CGG CAC CGC GGC GGC CCC CGA GCG GGG CCC CGG GAG GCG      3050
Arg Arg Ala Arg His Arg Gly Gly Pro Arg Ala Gly Pro Arg Glu Ala
    955                 960                 965

GAG AGC GGG GAG GAG CCG GCG CGG CGG CAC CGG GCC CGG CAC AAG GCG      3098
Glu Ser Gly Glu Glu Pro Ala Arg Arg His Arg Ala Arg His Lys Ala
970                 975                 980                 985

CAG CCT GCT CAC GAG GCT GTG GAG AAG GAG ACC ACG GAG AAG GAG GCC      3146
Gln Pro Ala His Glu Ala Val Glu Lys Glu Thr Thr Glu Lys Glu Ala
                990                 995                 1000

ACG GAG AAG GAG GCT GAG ATA GTG GAA GCC GAC AAG GAA AAG GAG CTC      3194
Thr Glu Lys Glu Ala Glu Ile Val Glu Ala Asp Lys Glu Lys Glu Leu
            1005                1010                1015

CGG AAC CAC CAG CCC CGG GAG CCA CAC TGT GAC CTG GAG ACC AGT GGG      3242
Arg Asn His Gln Pro Arg Glu Pro His Cys Asp Leu Glu Thr Ser Gly
        1020                1025                1030

ACT GTG ACT GTG GGT CCC ATG CAC ACA CTG CCC AGC ACC TGT CTC CAG      3290
Thr Val Thr Val Gly Pro Met His Thr Leu Pro Ser Thr Cys Leu Gln
    1035                1040                1045

AAG GTG GAG GAA CAG CCA GAG GAT GCA GAC AAT CAG CGG AAC GTC ACT      3338
Lys Val Glu Glu Gln Pro Glu Asp Ala Asp Asn Gln Arg Asn Val Thr
1050                1055                1060                1065

CGC ATG GGC AGT CAG CCC CCA GAC CCG AAC ACT ATT GTA CAT ATC CCA      3386
Arg Met Gly Ser Gln Pro Pro Asp Pro Asn Thr Ile Val His Ile Pro
                1070                1075                1080

GTG ATG CTG ACG GGC CCT CTT GGG GAA GCC ACG GTC GTT CCC AGT GGT      3434
Val Met Leu Thr Gly Pro Leu Gly Glu Ala Thr Val Val Pro Ser Gly
            1085                1090                1095

AAC GTG GAC CTG GAA AGC CAA GCA GAG GGG AAG AAG GAG GTG GAA GCG      3482
Asn Val Asp Leu Glu Ser Gln Ala Glu Gly Lys Lys Glu Val Glu Ala
        1100                1105                1110

GAT GAC GTG ATG AGG AGC GGC CCC CGG CCT ATC GTC CCA TAC AGC TCC      3530
Asp Asp Val Met Arg Ser Gly Pro Arg Pro Ile Val Pro Tyr Ser Ser
    1115                1120                1125

ATG TTC TGT TTA AGC CCC ACC AAC CTG CTC CGC CGC TTC TGC CAC TAC      3578
Met Phe Cys Leu Ser Pro Thr Asn Leu Leu Arg Arg Phe Cys His Tyr
1130                1135                1140                1145

ATC GTG ACC ATG AGG TAC TTC GAG GTG GTC ATT CTC GTG GTC ATC GCC      3626
Ile Val Thr Met Arg Tyr Phe Glu Val Val Ile Leu Val Val Ile Ala
                1150                1155                1160

TTG AGC AGC ATC GCC CTG GCT GCT GAG GAC CCA GTG CGC ACA GAC TCG      3674
Leu Ser Ser Ile Ala Leu Ala Ala Glu Asp Pro Val Arg Thr Asp Ser
            1165                1170                1175

CCC AGG AAC AAC GCT CTG AAA TAC CTG GAT TAC ATT TTC ACT GGT GTC      3722
Pro Arg Asn Asn Ala Leu Lys Tyr Leu Asp Tyr Ile Phe Thr Gly Val
        1180                1185                1190
```

```
TTT ACC TTT GAG ATG GTG ATA AAG ATG ATC GAC TTG GGA CTG CTG CTT      3770
Phe Thr Phe Glu Met Val Ile Lys Met Ile Asp Leu Gly Leu Leu Leu
        1195                1200                1205

CAC CCT GGA GCC TAT TTC CGG GAC TTG TGG AAC ATT CTG GAC TTC ATT      3818
His Pro Gly Ala Tyr Phe Arg Asp Leu Trp Asn Ile Leu Asp Phe Ile
1210                1215                1220                1225

GTG GTC AGT GGC GCC CTG GTG GCG TTT GCT TTC TCA GGA TCC AAA GGG      3866
Val Val Ser Gly Ala Leu Val Ala Phe Ala Phe Ser Gly Ser Lys Gly
            1230                1235                1240

AAA GAC ATC AAT ACC ATC AAG TCT CTG AGA GTC CTT CGT GTC CTG CGG      3914
Lys Asp Ile Asn Thr Ile Lys Ser Leu Arg Val Leu Arg Val Leu Arg
                1245                1250                1255

CCC CTC AAG ACC ATC AAA CGG CTG CCC AAG CTC AAG GCT GTG TTT GAC      3962
Pro Leu Lys Thr Ile Lys Arg Leu Pro Lys Leu Lys Ala Val Phe Asp
            1260                1265                1270

TGT GTG GTG AAC TCC CTG AAG AAT GTC CTC AAC ATC TTG ATT GTC TAC      4010
Cys Val Val Asn Ser Leu Lys Asn Val Leu Asn Ile Leu Ile Val Tyr
        1275                1280                1285

ATG CTC TTC ATG TTC ATA TTT GCC GTC ATT GCG GTG CAG CTC TTC AAA      4058
Met Leu Phe Met Phe Ile Phe Ala Val Ile Ala Val Gln Leu Phe Lys
1290                1295                1300                1305

GGG AAG TTT TTC TAC TGC ACA GAT GAA TCC AAG GAG CTG GAG AGG GAC      4106
Gly Lys Phe Phe Tyr Cys Thr Asp Glu Ser Lys Glu Leu Glu Arg Asp
            1310                1315                1320

TGC AGG GGT CAG TAT TTG GAT TAT GAG AAG GAG GAA GTG GAA GCT CAG      4154
Cys Arg Gly Gln Tyr Leu Asp Tyr Glu Lys Glu Glu Val Glu Ala Gln
                1325                1330                1335

CCC AGG CAG TGG AAG AAA TAC GAC TTT CAC TAC GAC AAT GTG CTC TGG      4202
Pro Arg Gln Trp Lys Lys Tyr Asp Phe His Tyr Asp Asn Val Leu Trp
            1340                1345                1350

GCT CTG CTG ACG CTG TTC ACA GTG TCC ACG GGA GAA GGC TGG CCC ATG      4250
Ala Leu Leu Thr Leu Phe Thr Val Ser Thr Gly Glu Gly Trp Pro Met
        1355                1360                1365

GTG CTG AAA CAC TCC GTG GAT GCC ACC TAT GAG GAG CAG GGT CCA AGC      4298
Val Leu Lys His Ser Val Asp Ala Thr Tyr Glu Glu Gln Gly Pro Ser
1370                1375                1380                1385

CCT GGG TAC CGC ATG GAG CTG TCC ATC TTC TAC GTG GTC TAC TTT GTG      4346
Pro Gly Tyr Arg Met Glu Leu Ser Ile Phe Tyr Val Val Tyr Phe Val
            1390                1395                1400

GTC TTT CCC TTC TTC TTC GTC AAC ATC TTT GTG GCT TTG ATC ATC ATC      4394
Val Phe Pro Phe Phe Phe Val Asn Ile Phe Val Ala Leu Ile Ile Ile
            1405                1410                1415

ACC TTC CAG GAG CAG GGG GAC AAG GTG ATG TCT GAA TGC AGC CTG GAG      4442
Thr Phe Gln Glu Gln Gly Asp Lys Val Met Ser Glu Cys Ser Leu Glu
        1420                1425                1430

AAG AAC GAG AGG GCT TGC ATT GAC TTC GCC ATC AGC GCC AAA CCC CTG      4490
Lys Asn Glu Arg Ala Cys Ile Asp Phe Ala Ile Ser Ala Lys Pro Leu
    1435                1440                1445

ACA CGG TAC ATG CCC CAA AAC CGG CAG TCG TTC CAG TAT AAG ACG TGG      4538
Thr Arg Tyr Met Pro Gln Asn Arg Gln Ser Phe Gln Tyr Lys Thr Trp
1450                1455                1460                1465

ACA TTT GTG GTC TCC CCG CCC TTT GAA TAC TTC ATC ATG GCC ATG ATA      4586
Thr Phe Val Val Ser Pro Pro Phe Glu Tyr Phe Ile Met Ala Met Ile
            1470                1475                1480

GCC CTC AAC ACT GTG GTG CTG ATG ATG AAG TTC TAT GAT GCA CCC TAT      4634
Ala Leu Asn Thr Val Val Leu Met Met Lys Phe Tyr Asp Ala Pro Tyr
        1485                1490                1495

GAG TAC GAG CTG ATG CTG AAA TGC CTG AAC ATC GTG TTC ACA TCC ATG      4682
Glu Tyr Glu Leu Met Leu Lys Cys Leu Asn Ile Val Phe Thr Ser Met
```

-continued

```
          1500                1505               1510
TTC TCC ATG GAA TGC GTG CTG AAG ATC ATC GCC TTT GGG GTG CTG AAC    4730
Phe Ser Met Glu Cys Val Leu Lys Ile Ile Ala Phe Gly Val Leu Asn
        1515                1520               1525

TAT TTC AGA GAT GCC TGG AAT GTC TTT GAC TTT GTC ACT GTG TTG GGA    4778
Tyr Phe Arg Asp Ala Trp Asn Val Phe Asp Phe Val Thr Val Leu Gly
1530                1535               1540               1545

AGT ATT ACT GAT ATT TTA GTA ACA GAG ATT GCG GAA ACG AAC AAT TTC    4826
Ser Ile Thr Asp Ile Leu Val Thr Glu Ile Ala Glu Thr Asn Asn Phe
        1550                1555               1560

ATC AAC CTC AGC TTC CTC CGC CTC TTT CGA GCT GCG CGG CTG ATC AAG    4874
Ile Asn Leu Ser Phe Leu Arg Leu Phe Arg Ala Ala Arg Leu Ile Lys
        1565                1570               1575

CTG CTC CGC CAG GGC TAC ACC ATC CGC ATC CTG CTG TGG ACC TTT GTC    4922
Leu Leu Arg Gln Gly Tyr Thr Ile Arg Ile Leu Leu Trp Thr Phe Val
        1580                1585               1590

CAG TCC TTC AAG GCC CTG CCC TAC GTG TGT CTG CTC ATT GCC ATG CTG    4970
Gln Ser Phe Lys Ala Leu Pro Tyr Val Cys Leu Leu Ile Ala Met Leu
        1595                1600               1605

TTC TTC ATC TAC GCC ATC ATC GGC ATG CAG GTG TTT GGG AAT ATT GCC    5018
Phe Phe Ile Tyr Ala Ile Ile Gly Met Gln Val Phe Gly Asn Ile Ala
1610                1615               1620               1625

CTG GAT GAT GAC ACC AGC ATC AAC CGC CAC AAC AAC TTC CGG ACG TTT    5066
Leu Asp Asp Asp Thr Ser Ile Asn Arg His Asn Asn Phe Arg Thr Phe
        1630                1635               1640

TTG CAA GCC CTG ATG CTG CTG TTC AGG AGC GCC ACG GGG GAG GCC TGG    5114
Leu Gln Ala Leu Met Leu Leu Phe Arg Ser Ala Thr Gly Glu Ala Trp
        1645                1650               1655

CAC GAG ATC ATG CTG TCC TGC CTG AGC AAC CAG GCC TGT GAT GAG CAG    5162
His Glu Ile Met Leu Ser Cys Leu Ser Asn Gln Ala Cys Asp Glu Gln
        1660                1665               1670

GCC AAT GCC ACC GAG TGT GGA AGT GAC TTT GCC TAC TTC TAC TTC GTC    5210
Ala Asn Ala Thr Glu Cys Gly Ser Asp Phe Ala Tyr Phe Tyr Phe Val
        1675                1680               1685

TCC TTC ATC TTC CTG TGC TCC TTT CTG ATG TTG AAC CTC TTT GTG GCT    5258
Ser Phe Ile Phe Leu Cys Ser Phe Leu Met Leu Asn Leu Phe Val Ala
1690                1695               1700               1705

GTG ATC ATG GAC AAT TTT GAG TAC CTC ACG CGG GAC TCT TCC ATC CTA    5306
Val Ile Met Asp Asn Phe Glu Tyr Leu Thr Arg Asp Ser Ser Ile Leu
        1710                1715               1720

GGT CCT CAC CAC TTG GAT GAG TTC ATC CGG GTC TGG GCT GAA TAC GAC    5354
Gly Pro His His Leu Asp Glu Phe Ile Arg Val Trp Ala Glu Tyr Asp
        1725                1730               1735

CCG GCT GCG TGT GGG CGC ATC AGT TAC AAT GAC ATG TTT GAG ATG CTG    5402
Pro Ala Ala Cys Gly Arg Ile Ser Tyr Asn Asp Met Phe Glu Met Leu
        1740                1745               1750

AAA CAC ATG TCC CCG CCT CTG GGG CTG GGG AAG AAA TGC CCT GCT CGA    5450
Lys His Met Ser Pro Pro Leu Gly Leu Gly Lys Lys Cys Pro Ala Arg
        1755                1760               1765

GTT GCT TAC AAG CGC CTG GTT CGC ATG AAC ATG CCC ATC TCC AAC GAG    5498
Val Ala Tyr Lys Arg Leu Val Arg Met Asn Met Pro Ile Ser Asn Glu
1770                1775               1780               1785

GAC ATG ACT GTT CAC TTC ACG TCC ACG CTG ATG GCC CTC ATC CGG ACG    5546
Asp Met Thr Val His Phe Thr Ser Thr Leu Met Ala Leu Ile Arg Thr
        1790                1795               1800

GCA CTG GAG ATC AAG CTG GCC CCA GCT GGG ACA AAG CAG CAT CAG TGT    5594
Ala Leu Glu Ile Lys Leu Ala Pro Ala Gly Thr Lys Gln His Gln Cys
        1805                1810               1815

GAC GCG GAG TTG AGG AAG GAG ATT TCC GTT GTG TGG GCC AAT CTG CCC    5642
```

```
Asp Ala Glu Leu Arg Lys Glu Ile Ser Val Val Trp Ala Asn Leu Pro
    1820                1825                1830

CAG AAG ACT TTG GAC TTG CTG GTA CCA CCC CAT AAG CCT GAT GAG ATG      5690
Gln Lys Thr Leu Asp Leu Leu Val Pro Pro His Lys Pro Asp Glu Met
1835                1840                1845

ACA GTG GGG AAG GTT TAT GCA GCT CTG ATG ATA TTT GAC TTC TAC AAG      5738
Thr Val Gly Lys Val Tyr Ala Ala Leu Met Ile Phe Asp Phe Tyr Lys
1850                1855                1860                1865

CAG AAC AAA ACC ACC AGA GAC CAG ATG CAG CAG GCT CCT GGA GGC CTC      5786
Gln Asn Lys Thr Thr Arg Asp Gln Met Gln Gln Ala Pro Gly Gly Leu
                1870                1875                1880

TCC CAG ATG GGT CCT GTG TCC CTG TTC CAC CCT CTG AAG GCC ACC CTG      5834
Ser Gln Met Gly Pro Val Ser Leu Phe His Pro Leu Lys Ala Thr Leu
            1885                1890                1895

GAG CAG ACA CAG CCG GCT GTG CTC CGA GGA GCC CGG GTT TTC CTT CGA      5882
Glu Gln Thr Gln Pro Ala Val Leu Arg Gly Ala Arg Val Phe Leu Arg
        1900                1905                1910

CAG AAG AGT TCC ACC TCC CTC AGC AAT GGC GGG GCC ATA CAA AAC CAA      5930
Gln Lys Ser Ser Thr Ser Leu Ser Asn Gly Gly Ala Ile Gln Asn Gln
    1915                1920                1925

GAG AGT GGC ATC AAA GAG TCT GTC TCC TGG GGC ACT CAA AGG ACC CAG      5978
Glu Ser Gly Ile Lys Glu Ser Val Ser Trp Gly Thr Gln Arg Thr Gln
1930                1935                1940                1945

GAT GCA CCC CAT GAG GCC AGG CCA CCC CTG GAG CGT GGC CAC TCC ACA      6026
Asp Ala Pro His Glu Ala Arg Pro Pro Leu Glu Arg Gly His Ser Thr
                1950                1955                1960

GAG ATC CCT GTG GGG CGG TCA GGA GCA CTG GCT GTG GAC GTT CAG ATG      6074
Glu Ile Pro Val Gly Arg Ser Gly Ala Leu Ala Val Asp Val Gln Met
            1965                1970                1975

CAG AGC ATA ACC CGG AGG GGC CCT GAT GGG GAG CCC CAG CCT GGG CTG      6122
Gln Ser Ile Thr Arg Arg Gly Pro Asp Gly Glu Pro Gln Pro Gly Leu
        1980                1985                1990

GAG AGC CAG GGT CGA GCG GCC TCC ATG CCC CGC CTT GCG GCC GAG ACT      6170
Glu Ser Gln Gly Arg Ala Ala Ser Met Pro Arg Leu Ala Ala Glu Thr
    1995                2000                2005

CAG CCC GTC ACA GAT GCC AGC CCC ATG AAG CGC TCC ATC TCC ACG CTG      6218
Gln Pro Val Thr Asp Ala Ser Pro Met Lys Arg Ser Ile Ser Thr Leu
2010                2015                2020                2025

GCC CAG CGG CCC CGT GGG ACT CAT CTT TGC AGC ACC ACC CCG GAC CGC      6266
Ala Gln Arg Pro Arg Gly Thr His Leu Cys Ser Thr Thr Pro Asp Arg
                2030                2035                2040

CCA CCC CCT AGC CAG GCG TCG TCG CAC CAC CAC CAC CAC CGC TGC CAC      6314
Pro Pro Pro Ser Gln Ala Ser Ser His His His His His Arg Cys His
            2045                2050                2055

CGC CGC AGG GAC AGG AAG CAG AGG TCC CTG GAG AAG GGG CCC AGC CTG      6362
Arg Arg Arg Asp Arg Lys Gln Arg Ser Leu Glu Lys Gly Pro Ser Leu
        2060                2065                2070

TCT GCC GAT ATG GAT GGC GCA CCA AGC AGT GCT GTG GGG CCG GGG CTG      6410
Ser Ala Asp Met Asp Gly Ala Pro Ser Ser Ala Val Gly Pro Gly Leu
    2075                2080                2085

CCC CCG GGA GAG GGG CCT ACA GGC TGC CGG CGG GAA CGA GAG CGC CGG      6458
Pro Pro Gly Glu Gly Pro Thr Gly Cys Arg Arg Glu Arg Glu Arg Arg
2090                2095                2100                2105

CAG GAG CGG GGC CGG TCC CAG GAG CGG AGG CAG CCC TCA TCC TCC TCC      6506
Gln Glu Arg Gly Arg Ser Gln Glu Arg Arg Gln Pro Ser Ser Ser Ser
                2110                2115                2120

TCG GAG AAG CAG CGC TTC TAC TCC TGC GAC CGC TTT GGG GGC CGT GAG      6554
Ser Glu Lys Gln Arg Phe Tyr Ser Cys Asp Arg Phe Gly Gly Arg Glu
            2125                2130                2135
```

-continued

```
CCC CCG AAG CCC AAG CCC TCC CTC AGC AGC CAC CCA ACG TCG CCA ACA      6602
Pro Pro Lys Pro Lys Pro Ser Leu Ser Ser His Pro Thr Ser Pro Thr
        2140            2145                2150

GCT GGC CAG GAG CCG GGA CCC CAC CCA CAG GCC GGC TCA GCC GTG GGC      6650
Ala Gly Gln Glu Pro Gly Pro His Pro Gln Ala Gly Ser Ala Val Gly
            2155            2160                2165

TTT CCG AAC ACA ACG CCC TGC TGC AGA GAG ACC CCC TCA GCC AGC CCC      6698
Phe Pro Asn Thr Thr Pro Cys Cys Arg Glu Thr Pro Ser Ala Ser Pro
2170                2175                2180                2185

TGG CCC CTG GCT CTC GAA TTG GCT CTG ACC CTT ACC TGG GGC AGC GTC      6746
Trp Pro Leu Ala Leu Glu Leu Ala Leu Thr Leu Thr Trp Gly Ser Val
                2190            2195                2200

TGG ACA GTG AGG CCT CTG TCC ACG CCC TGC CTG AGG ACA CGC TCA CTT      6794
Trp Thr Val Arg Pro Leu Ser Thr Pro Cys Leu Arg Thr Arg Ser Leu
            2205            2210                2215

TCG AGG AGG CTG TGG CCA CCA ACT CGG GCC GCT CCT CCA GGA CTT CCT      6842
Ser Arg Arg Leu Trp Pro Pro Thr Arg Ala Ala Pro Pro Gly Leu Pro
            2220            2225                2230

ACG TGT CCT CCC TGACCTCCCA GTCTCACCCT CTCCGCCGCG TGCCCAACGG           6894
Thr Cys Pro Pro
        2235

TTACCACTGC ACCCTGGGAC TCAGCTCGGG TGGCCGAGCA CGGCACAGCT ACCACCACCC     6954

TGACCAAGAC CACTGGTGCT AGCTGCACCG TGACCGCTCA GACGCCTGCA TGCAGCAGGC     7014

GTGTGTTCCA GTGGATGAGT TTTATCATCC ACACGGGGCA GTCGGCCCTC GGGGGAGGCC     7074

TTGCCCACCT TGGTGAGGCT CCTGTGGCCC CTCCCTCCCC CTCCTCCCCT CTTTTACTCT     7134

AGACGACGAA TAAAGCCCTG TTGCTTGAGT GTACGTACCG C                         7175
```

(2) INFORMATION FOR SEQ ID NO:9:

(i) SEQUENCE CHARACTERISTICS:
        (A) LENGTH: 1546 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1437

(ix) FEATURE:
        (A) NAME/KEY: 3'UTR
        (B) LOCATION: 1435..1546

(xi) SEQUENCE DESCRIPTION: SEQ ID NO:9:

```
ATG GTC CAG AAG ACC AGC ATG TCC CGG GGC CCT TAC CCA CCC TCC CAG        48
Met Val Gln Lys Thr Ser Met Ser Arg Gly Pro Tyr Pro Pro Ser Gln
  1               5                  10                  15

GAG ATC CCC ATG GAG GTC TTC GAC CCC AGC CCG CAG GGC AAA TAC AGC        96
Glu Ile Pro Met Glu Val Phe Asp Pro Ser Pro Gln Gly Lys Tyr Ser
                20                  25                  30

AAG AGG AAA GGG CGA TTC AAA CGG TCA GAT GGG AGC ACG TCC TCG GAT       144
Lys Arg Lys Gly Arg Phe Lys Arg Ser Asp Gly Ser Thr Ser Ser Asp
            35                  40                  45

ACC ACA TCC AAC AGC TTT GTC CGC CAG GGC TCA GCG GAG TCC TAC ACC       192
Thr Thr Ser Asn Ser Phe Val Arg Gln Gly Ser Ala Glu Ser Tyr Thr
        50                  55                  60

AGC CGT CCA TCA GAC TCT GAT GTA TCT CTG GAG GAG GAC CGG GAA GCC       240
Ser Arg Pro Ser Asp Ser Asp Val Ser Leu Glu Glu Asp Arg Glu Ala
 65                  70                  75                  80
```

-continued

| | | | | | | | | | | | | | | | |
|---|---|---|---|---|---|---|---|---|---|---|---|---|---|---|---|
| TTA | AGG | AAG | GAA | GCA | GAG | CGC | CAG | GCA | TTA | GCG | CAG | CTC | GAG | AAG | GCC | 288 |
| Leu | Arg | Lys | Glu | Ala | Glu | Arg | Gln | Ala | Leu | Ala | Gln | Leu | Glu | Lys | Ala | |
| | | | | 85 | | | | | 90 | | | | | 95 | | |
| AAG | ACC | AAG | CCA | GTG | GCA | TTT | GCT | GTG | CGG | ACA | AAT | GTT | GGC | TAC | AAT | 336 |
| Lys | Thr | Lys | Pro | Val | Ala | Phe | Ala | Val | Arg | Thr | Asn | Val | Gly | Tyr | Asn | |
| | | | 100 | | | | | 105 | | | | | 110 | | | |
| CCG | TCT | CCA | GGG | GAT | GAG | GTG | CCT | GTG | CAG | GGA | GTG | GCC | ATC | ACC | TTC | 384 |
| Pro | Ser | Pro | Gly | Asp | Glu | Val | Pro | Val | Gln | Gly | Val | Ala | Ile | Thr | Phe | |
| | | 115 | | | | | 120 | | | | | 125 | | | | |
| GAG | CCC | AAA | GAC | TTC | CTG | CAC | ATC | AAG | GAG | AAA | TAC | AAT | AAT | GAC | TGG | 432 |
| Glu | Pro | Lys | Asp | Phe | Leu | His | Ile | Lys | Glu | Lys | Tyr | Asn | Asn | Asp | Trp | |
| | 130 | | | | | 135 | | | | | 140 | | | | | |
| TGG | ATC | GGG | CGG | CTG | GTG | AAG | GAG | GGC | TGT | GAG | GTT | GGC | TTC | ATT | CCC | 480 |
| Trp | Ile | Gly | Arg | Leu | Val | Lys | Glu | Gly | Cys | Glu | Val | Gly | Phe | Ile | Pro | |
| 145 | | | | | 150 | | | | | 155 | | | | | 160 | |
| AGC | CCC | GTC | AAA | CTG | GAC | AGC | CTT | CGC | CTG | CTG | CAG | GAA | CAG | AAG | CTG | 528 |
| Ser | Pro | Val | Lys | Leu | Asp | Ser | Leu | Arg | Leu | Leu | Gln | Glu | Gln | Lys | Leu | |
| | | | 165 | | | | | 170 | | | | | 175 | | | |
| CGC | CAG | AAC | CGC | CTC | GGC | TCC | AGC | AAA | TCA | GGC | GAT | AAC | TCC | AGT | TCC | 576 |
| Arg | Gln | Asn | Arg | Leu | Gly | Ser | Ser | Lys | Ser | Gly | Asp | Asn | Ser | Ser | Ser | |
| | | | 180 | | | | | 185 | | | | | 190 | | | |
| AGT | CTG | GGA | GAT | GTG | GTG | ACT | GGC | ACC | CGC | CGC | CCC | ACA | CCC | CCT | GCC | 624 |
| Ser | Leu | Gly | Asp | Val | Val | Thr | Gly | Thr | Arg | Arg | Pro | Thr | Pro | Pro | Ala | |
| | | 195 | | | | | 200 | | | | | 205 | | | | |
| AGT | GCC | AAA | CAG | AAG | CAG | AAG | TCG | ACA | GAG | CAT | GTG | CCC | CCC | TAT | GAC | 672 |
| Ser | Ala | Lys | Gln | Lys | Gln | Lys | Ser | Thr | Glu | His | Val | Pro | Pro | Tyr | Asp | |
| | 210 | | | | | 215 | | | | | 220 | | | | | |
| GTG | GTG | CCT | TCC | ATG | AGG | CCC | ATC | ATC | CTG | GTG | GGA | CCG | TCG | CTC | AAG | 720 |
| Val | Val | Pro | Ser | Met | Arg | Pro | Ile | Ile | Leu | Val | Gly | Pro | Ser | Leu | Lys | |
| 225 | | | | | 230 | | | | | 235 | | | | | 240 | |
| GGC | TAC | GAG | GTT | ACA | GAC | ATG | ATG | CAG | AAA | GCT | TTA | TTT | GAC | TTC | TTG | 768 |
| Gly | Tyr | Glu | Val | Thr | Asp | Met | Met | Gln | Lys | Ala | Leu | Phe | Asp | Phe | Leu | |
| | | | 245 | | | | | 250 | | | | | 255 | | | |
| AAG | CAT | CGG | TTT | GAT | GGC | AGG | ATC | TCC | ATC | ACT | CGT | GTG | ACG | GCA | GAT | 816 |
| Lys | His | Arg | Phe | Asp | Gly | Arg | Ile | Ser | Ile | Thr | Arg | Val | Thr | Ala | Asp | |
| | | 260 | | | | | 265 | | | | | 270 | | | | |
| ATT | TCC | CTG | GCT | AAG | CGC | TCA | GTT | CTC | AAC | AAC | CCC | AGC | AAA | CAC | ATC | 864 |
| Ile | Ser | Leu | Ala | Lys | Arg | Ser | Val | Leu | Asn | Asn | Pro | Ser | Lys | His | Ile | |
| | 275 | | | | | 280 | | | | | 285 | | | | | |
| ATC | ATT | GAG | CGC | TCC | AAC | ACA | CGC | TCC | AGC | CTG | GCT | GAG | GTG | CAG | AGT | 912 |
| Ile | Ile | Glu | Arg | Ser | Asn | Thr | Arg | Ser | Ser | Leu | Ala | Glu | Val | Gln | Ser | |
| 290 | | | | | 295 | | | | | 300 | | | | | | |
| GAA | ATC | GAG | CGA | ATC | TTC | GAG | CTG | GCC | CGG | ACC | CTT | CAG | TTG | GTC | GCT | 960 |
| Glu | Ile | Glu | Arg | Ile | Phe | Glu | Leu | Ala | Arg | Thr | Leu | Gln | Leu | Val | Ala | |
| 305 | | | | 310 | | | | | 315 | | | | | 320 | | |
| CTG | GAT | GCT | GAC | ACC | ATC | AAT | CAC | CCA | GCC | CAG | CTG | TCC | AAG | ACC | TCG | 1008 |
| Leu | Asp | Ala | Asp | Thr | Ile | Asn | His | Pro | Ala | Gln | Leu | Ser | Lys | Thr | Ser | |
| | | | | 325 | | | | | 330 | | | | | 335 | | |
| CTG | GCC | CCC | ATC | ATT | GTT | TAC | ATC | AAG | ATC | ACC | TCT | CCC | AAG | GTA | CTT | 1056 |
| Leu | Ala | Pro | Ile | Ile | Val | Tyr | Ile | Lys | Ile | Thr | Ser | Pro | Lys | Val | Leu | |
| | | | 340 | | | | | 345 | | | | | 350 | | | |
| CAA | AGG | CTC | ATC | AAG | TCC | CGA | GGA | AAG | TCT | CAG | TCC | AAA | CAC | CTC | AAT | 1104 |
| Gln | Arg | Leu | Ile | Lys | Ser | Arg | Gly | Lys | Ser | Gln | Ser | Lys | His | Leu | Asn | |
| | | 355 | | | | | 360 | | | | | 365 | | | | |
| GTC | CAA | ATA | GCG | GCC | TCG | GAA | AAG | CTG | GCA | CAG | TGC | CCC | CCT | GAA | ATG | 1152 |
| Val | Gln | Ile | Ala | Ala | Ser | Glu | Lys | Leu | Ala | Gln | Cys | Pro | Pro | Glu | Met | |
| | 370 | | | | | 375 | | | | | 380 | | | | | |
| TTT | GAC | ATC | ATC | CTG | GAT | GAG | AAC | CAA | TTG | GAG | GAT | GCC | TGC | GAG | CAT | 1200 |
| Phe | Asp | Ile | Ile | Leu | Asp | Glu | Asn | Gln | Leu | Glu | Asp | Ala | Cys | Glu | His | |
| 385 | | | | 390 | | | | | 395 | | | | | 400 | | |

```
CTG GCG GAG TAC TTG GAA GCC TAT TGG AAG GCC ACA CAC CCG CCC AGC    1248
Leu Ala Glu Tyr Leu Glu Ala Tyr Trp Lys Ala Thr His Pro Pro Ser
                405                 410                 415

AGC ACG CCA CCC AAT CCG CTG CTG AAC CGC ACC ATG GCT ACC GCA GCC    1296
Ser Thr Pro Pro Asn Pro Leu Leu Asn Arg Thr Met Ala Thr Ala Ala
                420                 425                 430

CTG GCT GCC AGC CCT GCC CCT GTC TCC AAC CTC CAG GTA CAG GTG CTC    1344
Leu Ala Ala Ser Pro Ala Pro Val Ser Asn Leu Gln Val Gln Val Leu
                435                 440                 445

ACC TCG CTC AGG AGA AAC CTC GGC TTC TGG GGC GGG CTG GAG TCC TCA    1392
Thr Ser Leu Arg Arg Asn Leu Gly Phe Trp Gly Gly Leu Glu Ser Ser
                450                 455                 460

CAG CGG GGC AGT GTG GTG CCC CAG GAG CAG GAA CAT GCC ATG TAGTGGGCGC  1444
Gln Arg Gly Ser Val Val Pro Gln Glu Gln Glu His Ala Met
465                 470                 475

CCTGCCCGTC TTCCCTCCTG CTCTGGGGTC GGAACTGGAG TGCAGGGAAC ATGGAGGAGG   1504

AAGGGAAGAG CTTTATTTTG TAAAAAAATA AGATGAGCGG CA                     1546

(2) INFORMATION FOR SEQ ID NO:10:

(i) SEQUENCE CHARACTERISTICS:
         (A) LENGTH: 1851 base pairs
         (B) TYPE: nucleic acid
         (C) STRANDEDNESS: double
         (D) TOPOLOGY: linear (ii) MOLECULE TYPE: DNA (genomic)

(ix) FEATURE:
         (A) NAME/KEY: CDS
         (B) LOCATION: 1..1797
         (D) OTHER INFORMATION: /standard_name= "Beta1-3"

(ix) FEATURE:
         (A) NAME/KEY: 3'UTR
         (B) LOCATION: 1795..1851

(xi) SEQUENCE DESCRIPTION: SEQ ID NO:10:

ATG GTC CAG AAG ACC AGC ATG TCC CGG GGC CCT TAC CCA CCC TCC CAG    48
Met Val Gln Lys Thr Ser Met Ser Arg Gly Pro Tyr Pro Pro Ser Gln
 1               5                  10                  15

GAG ATC CCC ATG GGA GTC TTC GAC CCC AGC CCG CAG GGC AAA TAC AGC    96
Glu Ile Pro Met Gly Val Phe Asp Pro Ser Pro Gln Gly Lys Tyr Ser
                20                  25                  30

AAG AGG AAA GGG CGA TTC AAA CGG TCA GAT GGG AGC ACG TCC TCG GAT    144
Lys Arg Lys Gly Arg Phe Lys Arg Ser Asp Gly Ser Thr Ser Ser Asp
            35                  40                  45

ACC ACA TCC AAC AGC TTT GTC CGC CAG GGC TCA GCG GAG TCC TAC ACC    192
Thr Thr Ser Asn Ser Phe Val Arg Gln Gly Ser Ala Glu Ser Tyr Thr
        50                  55                  60

AGC CGT CCA TCA GAC TCT GAT GTA TCT CTG GAG GAG GAC CGG GAA GCC    240
Ser Arg Pro Ser Asp Ser Asp Val Ser Leu Glu Glu Asp Arg Glu Ala
65                  70                  75                  80

TTA AGG AAG GAA GCA GAG CGC CAG GCA TTA GCG CAG CTC GAG AAG GCC    288
Leu Arg Lys Glu Ala Glu Arg Gln Ala Leu Ala Gln Leu Glu Lys Ala
                85                  90                  95

AAG ACC AAG CCA GTG GCA TTT GCT GTG CGG ACA AAT GTT GGC TAC AAT    336
Lys Thr Lys Pro Val Ala Phe Ala Val Arg Thr Asn Val Gly Tyr Asn
                100                 105                 110

CCG TCT CCA GGG GAT GAG GTG CCT GTG CAG GGA GTG GCC ATC ACC TTC    384
Pro Ser Pro Gly Asp Glu Val Pro Val Gln Gly Val Ala Ile Thr Phe
            115                 120                 125
```

```
GAG CCC AAA GAC TTC CTG CAC ATC AAG GAG AAA TAC AAT AAT GAC TGG       432
Glu Pro Lys Asp Phe Leu His Ile Lys Glu Lys Tyr Asn Asn Asp Trp
    130                 135                 140

TGG ATC GGG CGG CTG GTG AAG GAG GGC TGT GAG GTT GGC TTC ATT CCC       480
Trp Ile Gly Arg Leu Val Lys Glu Gly Cys Glu Val Gly Phe Ile Pro
145                 150                 155                 160

AGC CCC GTC AAA CTG GAC AGC CTT CGC CTG CTG CAG GAA CAG AAG CTG       528
Ser Pro Val Lys Leu Asp Ser Leu Arg Leu Leu Gln Glu Gln Lys Leu
                165                 170                 175

CGC CAG AAC CGC CTC GGC TCC AGC AAA TCA GGC GAT AAC TCC AGT TCC       576
Arg Gln Asn Arg Leu Gly Ser Ser Lys Ser Gly Asp Asn Ser Ser Ser
            180                 185                 190

AGT CTG GGA GAT GTG GTG ACT GGC ACC CGC CGC CCC ACA CCC CCT GCC       624
Ser Leu Gly Asp Val Val Thr Gly Thr Arg Arg Pro Thr Pro Pro Ala
        195                 200                 205

AGT GCC AAA CAG AAG CAG AAG TCG ACA GAG CAT GTG CCC CCC TAT GAC       672
Ser Ala Lys Gln Lys Gln Lys Ser Thr Glu His Val Pro Pro Tyr Asp
    210                 215                 220

GTG GTG CCT TCC ATG AGG CCC ATC ATC CTG GTG GGA CCG TCG CTC AAG       720
Val Val Pro Ser Met Arg Pro Ile Ile Leu Val Gly Pro Ser Leu Lys
225                 230                 235                 240

GGC TAC GAG GTT ACA GAC ATG ATG CAG AAA GCT TTA TTT GAC TTC TTG       768
Gly Tyr Glu Val Thr Asp Met Met Gln Lys Ala Leu Phe Asp Phe Leu
                245                 250                 255

AAG CAT CGG TTT GAT GGC AGG ATC TCC ATC ACT CGT GTG ACG GCA GAT       816
Lys His Arg Phe Asp Gly Arg Ile Ser Ile Thr Arg Val Thr Ala Asp
            260                 265                 270

ATT TCC CTG GCT AAG CGC TCA GTT CTC AAC AAC CCC AGC AAA CAC ATC       864
Ile Ser Leu Ala Lys Arg Ser Val Leu Asn Asn Pro Ser Lys His Ile
        275                 280                 285

ATC ATT GAG CGC TCC AAC ACA CGC TCC AGC CTG GCT GAG GTG CAG AGT       912
Ile Ile Glu Arg Ser Asn Thr Arg Ser Ser Leu Ala Glu Val Gln Ser
    290                 295                 300

GAA ATC GAG CGA ATC TTC GAG CTG GCC CGG ACC CTT CAG TTG GTC GCT       960
Glu Ile Glu Arg Ile Phe Glu Leu Ala Arg Thr Leu Gln Leu Val Ala
305                 310                 315                 320

CTG GAT GCT GAC ACC ATC AAT CAC CCA GCC CAG CTG TCC AAG ACC TCG      1008
Leu Asp Ala Asp Thr Ile Asn His Pro Ala Gln Leu Ser Lys Thr Ser
                325                 330                 335

CTG GCC CCC ATC ATT GTT TAC ATC AAG ATC ACC TCT CCC AAG GTA CTT      1056
Leu Ala Pro Ile Ile Val Tyr Ile Lys Ile Thr Ser Pro Lys Val Leu
            340                 345                 350

CAA AGG CTC ATC AAG TCC CGA GGA AAG TCT CAG TCC AAA CAC CTC AAT      1104
Gln Arg Leu Ile Lys Ser Arg Gly Lys Ser Gln Ser Lys His Leu Asn
        355                 360                 365

GTC CAA ATA GCG GCC TCG GAA AAG CTG GCA CAG TGC CCC CCT GAA ATG      1152
Val Gln Ile Ala Ala Ser Glu Lys Leu Ala Gln Cys Pro Pro Glu Met
    370                 375                 380

TTT GAC ATC ATC CTG GAT GAG AAC CAA TTG GAG GAT GCC TGC GAG CAT      1200
Phe Asp Ile Ile Leu Asp Glu Asn Gln Leu Glu Asp Ala Cys Glu His
385                 390                 395                 400

CTG GCG GAG TAC TTG GAA GCC TAT TGG AAG GCC ACA CAC CCG CCC AGC      1248
Leu Ala Glu Tyr Leu Glu Ala Tyr Trp Lys Ala Thr His Pro Pro Ser
                405                 410                 415

AGC ACG CCA CCC AAT CCG CTG CTG AAC CGC ACC ATG GCT ACC GCA GCC      1296
Ser Thr Pro Pro Asn Pro Leu Leu Asn Arg Thr Met Ala Thr Ala Ala
            420                 425                 430

CTG GCT GCC AGC CCT GCC CCT GTC TCC AAC CTC CAG GGA CCC TAC CTT      1344
Leu Ala Ala Ser Pro Ala Pro Val Ser Asn Leu Gln Gly Pro Tyr Leu
        435                 440                 445
```

-continued

```
GCT TCC GGG GAC CAG CCA CTG GAA CGG GCC ACC GGG GAG CAC GCC AGC      1392
Ala Ser Gly Asp Gln Pro Leu Glu Arg Ala Thr Gly Glu His Ala Ser
    450                 455                 460

ATG CAC GAG TAC CCA GGG GAG CTG GGC CAG CCC CCA GGC CTT TAC CCC      1440
Met His Glu Tyr Pro Gly Glu Leu Gly Gln Pro Pro Gly Leu Tyr Pro
465                 470                 475                 480

AGC AGC CAC CCA CCA GGC CGG GCA GGC ACG CTA CGG GCA CTG TCC CGC      1488
Ser Ser His Pro Pro Gly Arg Ala Gly Thr Leu Arg Ala Leu Ser Arg
                485                 490                 495

CAA GAC ACT TTT GAT GCC GAC ACC CCC GGC AGC CGA AAC TCT GCC TAC      1536
Gln Asp Thr Phe Asp Ala Asp Thr Pro Gly Ser Arg Asn Ser Ala Tyr
            500                 505                 510

ACG GAG CTG GGA GAC TCA TGT GTG GAC ATG GAG ACT GAC CCC TCA GAG      1584
Thr Glu Leu Gly Asp Ser Cys Val Asp Met Glu Thr Asp Pro Ser Glu
        515                 520                 525

GGG CCA GGG CTT GGA GAC CCT GCA GGG GGC ACG CCC CCA GCC CGA          1632
Gly Pro Gly Leu Gly Asp Pro Ala Gly Gly Thr Pro Pro Ala Arg
    530                 535                 540

CAG GGA TCC TGG GAG GAC GAG GAA GAA GAC TAT GAG GAA GAG CTG ACC      1680
Gln Gly Ser Trp Glu Asp Glu Glu Glu Asp Tyr Glu Glu Glu Leu Thr
545                 550                 555                 560

GAC AAC CGG AAC CGG GGC CGG AAT AAG GCC CGC TAC TGC GCT GAG GGT      1728
Asp Asn Arg Asn Arg Gly Arg Asn Lys Ala Arg Tyr Cys Ala Glu Gly
                565                 570                 575

GGG GGT CCA GTT TTG GGG CGC AAC AAG AAT GAG CTG GAG GGC TGG GGA      1776
Gly Gly Pro Val Leu Gly Arg Asn Lys Asn Glu Leu Glu Gly Trp Gly
            580                 585                 590

CGA GGC GTC TAC ATT CGC TGAGAGGCAG GGGCCACACG GCGGGAGGAA             1824
Arg Gly Val Tyr Ile Arg
        595

GGGCTCTGAG CCCAGGGGAG GGGAGGG                                        1851

(2) INFORMATION FOR SEQ ID NO:11:

(i) SEQUENCE CHARACTERISTICS:
        (A) LENGTH: 3600 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 35..3310
        (D) OTHER INFORMATION: /standard_name= "Alpha-2"

(ix) FEATURE:
        (A) NAME/KEY: 5'UTR
        (B) LOCATION: 1..34

(ix) FEATURE:
        (A) NAME/KEY: 3'UTR
        (B) LOCATION: 3308..3600

(xi) SEQUENCE DESCRIPTION: SEQ ID NO:11:

GCGGGGGAGG GGGCATTGAT CTTCGATCGC GAAG ATG GCT GCT GGC TGC CTG        52
                                     Met Ala Ala Gly Cys Leu
                                     1               5

CTG GCC TTG ACT CTG ACA CTT TTC CAA TCT TTG CTC ATC GGC CCC TCG      100
Leu Ala Leu Thr Leu Thr Leu Phe Gln Ser Leu Leu Ile Gly Pro Ser
        10                  15                  20

TCG GAG GAG CCG TTC CCT TCG GCC GTC ACT ATC AAA TCA TGG GTG GAT      148
Ser Glu Glu Pro Phe Pro Ser Ala Val Thr Ile Lys Ser Trp Val Asp
```

-continued

```
                    25                      30                      35
AAG ATG CAA GAA GAC CTT GTC ACA CTG GCA AAA ACA GCA AGT GGA GTC        196
Lys Met Gln Glu Asp Leu Val Thr Leu Ala Lys Thr Ala Ser Gly Val
        40                      45                      50

AAT CAG CTT GTT GAT ATT TAT GAG AAA TAT CAA GAT TTG TAT ACT GTG        244
Asn Gln Leu Val Asp Ile Tyr Glu Lys Tyr Gln Asp Leu Tyr Thr Val
55                      60                      65                  70

GAA CCA AAT AAT GCA CGC CAG CTG GTA GAA ATT GCA GCC AGG GAT ATT        292
Glu Pro Asn Asn Ala Arg Gln Leu Val Glu Ile Ala Ala Arg Asp Ile
                    75                      80                      85

GAG AAA CTT CTG AGC AAC AGA TCT AAA GCC CTG GTG AGC CTG GCA TTG        340
Glu Lys Leu Leu Ser Asn Arg Ser Lys Ala Leu Val Ser Leu Ala Leu
                90                      95                     100

GAA GCG GAG AAA GTT CAA GCA GCT CAC CAG TGG AGA GAA GAT TTT GCA        388
Glu Ala Glu Lys Val Gln Ala Ala His Gln Trp Arg Glu Asp Phe Ala
            105                     110                     115

AGC AAT GAA GTT GTC TAC TAC AAT GCA AAG GAT GAT CTC GAT CCT GAG        436
Ser Asn Glu Val Val Tyr Tyr Asn Ala Lys Asp Asp Leu Asp Pro Glu
        120                     125                     130

AAA AAT GAC AGT GAG CCA GGC AGC CAG AGG ATA AAA CCT GTT TTC ATT        484
Lys Asn Asp Ser Glu Pro Gly Ser Gln Arg Ile Lys Pro Val Phe Ile
135                     140                     145                 150

GAA GAT GCT AAT TTT GGA CGA CAA ATA TCT TAT CAG CAC GCA GCA GTC        532
Glu Asp Ala Asn Phe Gly Arg Gln Ile Ser Tyr Gln His Ala Ala Val
                    155                     160                     165

CAT ATT CCT ACT GAC ATC TAT GAG GGC TCA ACA ATT GTG TTA AAT GAA        580
His Ile Pro Thr Asp Ile Tyr Glu Gly Ser Thr Ile Val Leu Asn Glu
                170                     175                     180

CTC AAC TGG ACA AGT GCC TTA GAT GAA GTT TTC AAA AAG AAT CGC GAG        628
Leu Asn Trp Thr Ser Ala Leu Asp Glu Val Phe Lys Lys Asn Arg Glu
            185                     190                     195

GAA GAC CCT TCA TTA TTG TGG CAG GTT TTT GGC AGT GCC ACT GGC CTA        676
Glu Asp Pro Ser Leu Leu Trp Gln Val Phe Gly Ser Ala Thr Gly Leu
        200                     205                     210

GCT CGA TAT TAT CCA GCT TCA CCA TGG GTT GAT AAT AGT AGA ACT CCA        724
Ala Arg Tyr Tyr Pro Ala Ser Pro Trp Val Asp Asn Ser Arg Thr Pro
215                     220                     225                 230

AAT AAG ATT GAC CTT TAT GAT GTA CGC AGA AGA CCA TGG TAC ATC CAA        772
Asn Lys Ile Asp Leu Tyr Asp Val Arg Arg Arg Pro Trp Tyr Ile Gln
                    235                     240                     245

GGA GCT GCA TCT CCT AAA GAC ATG CTT ATT CTG GTG GAT GTG AGT GGA        820
Gly Ala Ala Ser Pro Lys Asp Met Leu Ile Leu Val Asp Val Ser Gly
                250                     255                     260

AGT GTT AGT GGA TTG ACA CTT AAA CTG ATC CGA ACA TCT GTC TCC GAA        868
Ser Val Ser Gly Leu Thr Leu Lys Leu Ile Arg Thr Ser Val Ser Glu
            265                     270                     275

ATG TTA GAA ACC CTC TCA GAT GAT GAT TTC GTG AAT GTA GCT TCA TTT        916
Met Leu Glu Thr Leu Ser Asp Asp Asp Phe Val Asn Val Ala Ser Phe
        280                     285                     290

AAC AGC AAT GCT CAG GAT GTA AGC TGT TTT CAG CAC CTT GTC CAA GCA        964
Asn Ser Asn Ala Gln Asp Val Ser Cys Phe Gln His Leu Val Gln Ala
295                     300                     305                 310

AAT GTA AGA AAT AAA AAA GTG TTG AAA GAC GCG GTG AAT AAT ATC ACA       1012
Asn Val Arg Asn Lys Lys Val Leu Lys Asp Ala Val Asn Asn Ile Thr
                    315                     320                     325

GCC AAA GGA ATT ACA GAT TAT AAG AAG GGC TTT AGT TTT GCT TTT GAA       1060
Ala Lys Gly Ile Thr Asp Tyr Lys Lys Gly Phe Ser Phe Ala Phe Glu
                330                     335                     340

CAG CTG CTT AAT TAT AAT GTT TCC AGA GCA AAC TGC AAT AAG ATT ATT       1108
```

```
        Gln Leu Leu Asn Tyr Asn Val Ser Arg Ala Asn Cys Asn Lys Ile Ile
                345                 350                 355

ATG CTA TTC ACG GAT GGA GGA GAA GAG AGA GCC CAG GAG ATA TTT AAC         1156
Met Leu Phe Thr Asp Gly Gly Glu Glu Arg Ala Gln Glu Ile Phe Asn
360                 365                 370

AAA TAC AAT AAA GAT AAA AAA GTA CGT GTA TTC AGG TTT TCA GTT GGT         1204
Lys Tyr Asn Lys Asp Lys Lys Val Arg Val Phe Arg Phe Ser Val Gly
375                 380                 385                 390

CAA CAC AAT TAT GAG AGA GGA CCT ATT CAG TGG ATG GCC TGT GAA AAC         1252
Gln His Asn Tyr Glu Arg Gly Pro Ile Gln Trp Met Ala Cys Glu Asn
                395                 400                 405

AAA GGT TAT TAT TAT GAA ATT CCT TCC ATT GGT GCA ATA AGA ATC AAT         1300
Lys Gly Tyr Tyr Tyr Glu Ile Pro Ser Ile Gly Ala Ile Arg Ile Asn
                    410                 415                 420

ACT CAG GAA TAT TTG GAT GTT TTG GGA AGA CCA ATG GTT TTA GCA GGA         1348
Thr Gln Glu Tyr Leu Asp Val Leu Gly Arg Pro Met Val Leu Ala Gly
                425                 430                 435

GAC AAA GCT AAG CAA GTC CAA TGG ACA AAT GTG TAC CTG GAT GCA TTG         1396
Asp Lys Ala Lys Gln Val Gln Trp Thr Asn Val Tyr Leu Asp Ala Leu
        440                 445                 450

GAA CTG GGA CTT GTC ATT ACT GGA ACT CTT CCG GTC TTC AAC ATA ACC         1444
Glu Leu Gly Leu Val Ile Thr Gly Thr Leu Pro Val Phe Asn Ile Thr
455                 460                 465                 470

GGC CAA TTT GAA AAT AAG ACA AAC TTA AAG AAC CAG CTG ATT CTT GGT         1492
Gly Gln Phe Glu Asn Lys Thr Asn Leu Lys Asn Gln Leu Ile Leu Gly
                475                 480                 485

GTG ATG GGA GTA GAT GTG TCT TTG GAA GAT ATT AAA AGA CTG ACA CCA         1540
Val Met Gly Val Asp Val Ser Leu Glu Asp Ile Lys Arg Leu Thr Pro
                490                 495                 500

CGT TTT ACA CTG TGC CCC AAT GGG TAT TAC TTT GCA ATC GAT CCT AAT         1588
Arg Phe Thr Leu Cys Pro Asn Gly Tyr Tyr Phe Ala Ile Asp Pro Asn
            505                 510                 515

GGT TAT GTT TTA TTA CAT CCA AAT CTT CAG CCA AAG AAC CCC AAA TCT         1636
Gly Tyr Val Leu Leu His Pro Asn Leu Gln Pro Lys Asn Pro Lys Ser
            520                 525                 530

CAG GAG CCA GTA ACA TTG GAT TTC CTT GAT GCA GAG TTA GAG AAT GAT         1684
Gln Glu Pro Val Thr Leu Asp Phe Leu Asp Ala Glu Leu Glu Asn Asp
535                 540                 545                 550

ATT AAA GTG GAG ATT CGA AAT AAG ATG ATT GAT GGG GAA AGT GGA GAA         1732
Ile Lys Val Glu Ile Arg Asn Lys Met Ile Asp Gly Glu Ser Gly Glu
                555                 560                 565

AAA ACA TTC AGA ACT CTG GTT AAA TCT CAA GAT GAG AGA TAT ATT GAC         1780
Lys Thr Phe Arg Thr Leu Val Lys Ser Gln Asp Glu Arg Tyr Ile Asp
                570                 575                 580

AAA GGA AAC AGG ACA TAC ACA TGG ACA CCT GTC AAT GGC ACA GAT TAC         1828
Lys Gly Asn Arg Thr Tyr Thr Trp Thr Pro Val Asn Gly Thr Asp Tyr
                585                 590                 595

AGT TTG GCC TTG GTA TTA CCA ACC TAC AGT TTT TAC TAT ATA AAA GCC         1876
Ser Leu Ala Leu Val Leu Pro Thr Tyr Ser Phe Tyr Tyr Ile Lys Ala
            600                 605                 610

AAA CTA GAA GAG ACA ATA ACT CAG GCC AGA TCA AAA AAG GGC AAA ATG         1924
Lys Leu Glu Glu Thr Ile Thr Gln Ala Arg Ser Lys Lys Gly Lys Met
615                 620                 625                 630

AAG GAT TCG GAA ACC CTG AAG CCA GAT AAT TTT GAA GAA TCT GGC TAT         1972
Lys Asp Ser Glu Thr Leu Lys Pro Asp Asn Phe Glu Glu Ser Gly Tyr
                635                 640                 645

ACA TTC ATA GCA CCA AGA GAT TAC TGC AAT GAC CTG AAA ATA TCG GAT         2020
Thr Phe Ile Ala Pro Arg Asp Tyr Cys Asn Asp Leu Lys Ile Ser Asp
            650                 655                 660
```

```
AAT AAC ACT GAA TTT CTT TTA AAT TTC AAC GAG TTT ATT GAT AGA AAA       2068
Asn Asn Thr Glu Phe Leu Leu Asn Phe Asn Glu Phe Ile Asp Arg Lys
            665                 670                 675

ACT CCA AAC AAC CCA TCA TGT AAC GCG GAT TTG ATT AAT AGA GTC TTG       2116
Thr Pro Asn Asn Pro Ser Cys Asn Ala Asp Leu Ile Asn Arg Val Leu
    680                 685                 690

CTT GAT GCA GGC TTT ACA AAT GAA CTT GTC CAA AAT TAC TGG AGT AAG       2164
Leu Asp Ala Gly Phe Thr Asn Glu Leu Val Gln Asn Tyr Trp Ser Lys
695                 700                 705                 710

CAG AAA AAT ATC AAG GGA GTG AAA GCA CGA TTT GTT GTG ACT GAT GGT       2212
Gln Lys Asn Ile Lys Gly Val Lys Ala Arg Phe Val Val Thr Asp Gly
            715                 720                 725

GGG ATT ACC AGA GTT TAT CCC AAA GAG GCT GGA GAA AAT TGG CAA GAA       2260
Gly Ile Thr Arg Val Tyr Pro Lys Glu Ala Gly Glu Asn Trp Gln Glu
    730                 735                 740

AAC CCA GAG ACA TAT GAG GAC AGC TTC TAT AAA AGG AGC CTA GAT AAT       2308
Asn Pro Glu Thr Tyr Glu Asp Ser Phe Tyr Lys Arg Ser Leu Asp Asn
745                 750                 755

GAT AAC TAT GTT TTC ACT GCT CCC TAC TTT AAC AAA AGT GGA CCT GGT       2356
Asp Asn Tyr Val Phe Thr Ala Pro Tyr Phe Asn Lys Ser Gly Pro Gly
            760                 765                 770

GCC TAT GAA TCG GGC ATT ATG GTA AGC AAA GCT GTA GAA ATA TAT ATT       2404
Ala Tyr Glu Ser Gly Ile Met Val Ser Lys Ala Val Glu Ile Tyr Ile
775                 780                 785                 790

CAA GGG AAA CTT CTT AAA CCT GCA GTT GTT GGA ATT AAA ATT GAT GTA       2452
Gln Gly Lys Leu Leu Lys Pro Ala Val Val Gly Ile Lys Ile Asp Val
                795                 800                 805

AAT TCC TGG ATA GAG AAT TTC ACC AAA ACC TCA ATC AGA GAT CCG TGT       2500
Asn Ser Trp Ile Glu Asn Phe Thr Lys Thr Ser Ile Arg Asp Pro Cys
            810                 815                 820

GCT GGT CCA GTT TGT GAC TGC AAA AGA AAC AGT GAC GTA ATG GAT TGT       2548
Ala Gly Pro Val Cys Asp Cys Lys Arg Asn Ser Asp Val Met Asp Cys
    825                 830                 835

GTG ATT CTG GAT GAT GGT GGG TTT CTT CTG ATG GCA AAT CAT GAT GAT       2596
Val Ile Leu Asp Asp Gly Gly Phe Leu Leu Met Ala Asn His Asp Asp
840                 845                 850

TAT ACT AAT CAG ATT GGA AGA TTT TTT GGA GAG ATT GAT CCC AGC TTG       2644
Tyr Thr Asn Gln Ile Gly Arg Phe Phe Gly Glu Ile Asp Pro Ser Leu
855                 860                 865                 870

ATG AGA CAC CTG GTT AAT ATA TCA GTT TAT GCT TTT AAC AAA TCT TAT       2692
Met Arg His Leu Val Asn Ile Ser Val Tyr Ala Phe Asn Lys Ser Tyr
            875                 880                 885

GAT TAT CAG TCA GTA TGT GAG CCC GGT GCT GCA CCA AAA CAA GGA GCA       2740
Asp Tyr Gln Ser Val Cys Glu Pro Gly Ala Ala Pro Lys Gln Gly Ala
    890                 895                 900

GGA CAT CGC TCA GCA TAT GTG CCA TCA GTA GCA GAC ATA TTA CAA ATT       2788
Gly His Arg Ser Ala Tyr Val Pro Ser Val Ala Asp Ile Leu Gln Ile
905                 910                 915

GGC TGG TGG GCC ACT GCT GCT GCC TGG TCT ATT CTA CAG CAG TTT CTC       2836
Gly Trp Trp Ala Thr Ala Ala Ala Trp Ser Ile Leu Gln Gln Phe Leu
920                 925                 930

TTG AGT TTG ACC TTT CCA CGA CTC CTT GAG GCA GTT GAG ATG GAG GAT       2884
Leu Ser Leu Thr Phe Pro Arg Leu Leu Glu Ala Val Glu Met Glu Asp
935                 940                 945                 950

GAT GAC TTC ACG GCC TCC CTG TCC AAG CAG AGC TGC ATT ACT GAA CAA       2932
Asp Asp Phe Thr Ala Ser Leu Ser Lys Gln Ser Cys Ile Thr Glu Gln
            955                 960                 965

ACC CAG TAT TTC TTC GAT AAC GAC AGT AAA TCA TTC AGT GGT GTA TTA       2980
Thr Gln Tyr Phe Phe Asp Asn Asp Ser Lys Ser Phe Ser Gly Val Leu
    970                 975                 980
```

```
GAC TGT GGA AAC TGT TCC AGA ATC TTT CAT GGA GAA AAG CTT ATG AAC      3028
Asp Cys Gly Asn Cys Ser Arg Ile Phe His Gly Glu Lys Leu Met Asn
            985                 990                 995

ACC AAC TTA ATA TTC ATA ATG GTT GAG AGC AAA GGG ACA TGT CCA TGT      3076
Thr Asn Leu Ile Phe Ile Met Val Glu Ser Lys Gly Thr Cys Pro Cys
           1000                1005                1010

GAC ACA CGA CTG CTC ATA CAA GCG GAG CAG ACT TCT GAC GGT CCA AAT      3124
Asp Thr Arg Leu Leu Ile Gln Ala Glu Gln Thr Ser Asp Gly Pro Asn
1015                1020                1025                1030

CCT TGT GAC ATG GTT AAG CAA CCT AGA TAC CGA AAA GGG CCT GAT GTC      3172
Pro Cys Asp Met Val Lys Gln Pro Arg Tyr Arg Lys Gly Pro Asp Val
                1035                1040                1045

TGC TTT GAT AAC AAT GTC TTG GAG GAT TAT ACT GAC TGT GGT GGT GTT      3220
Cys Phe Asp Asn Asn Val Leu Glu Asp Tyr Thr Asp Cys Gly Gly Val
            1050                1055                1060

TCT GGA TTA AAT CCC TCC CTG TGG TAT ATC ATT GGA ATC CAG TTT CTA      3268
Ser Gly Leu Asn Pro Ser Leu Trp Tyr Ile Ile Gly Ile Gln Phe Leu
           1065                1070                1075

CTA CTT TGG CTG GTA TCT GGC AGC ACA CAC CGG CTG TTA TGACCTTCTA       3317
Leu Leu Trp Leu Val Ser Gly Ser Thr His Arg Leu Leu
       1080                1085                1090

AAAACCAAAT CTGCATAGTT AAACTCCAGA CCCTGCCAAA ACATGAGCCC TGCCCTCAAT    3377

TACAGTAACG TAGGGTCAGC TATAAAATCA GACAAACATT AGCTGGGCCT GTTCCATGGC    3437

ATAACACTAA GGCGCAGACT CCTAAGGCAC CCACTGGCTG CATGTCAGGG TGTCAGATCC    3497

TTAAACGTGT GTGAATGCTG CATCATCTAT GTGTAACATC AAAGCAAAAT CCTATACGTG    3557

TCCTCTATTG GAAAATTTGG GCGTTTGTTG TTGCATTGTT GGT                      3600

(2) INFORMATION FOR SEQ ID NO:12:

(i) SEQUENCE CHARACTERISTICS:
        (A) LENGTH: 323 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:12:

CCCCCTGCCA GTGGCCAAAC AGAAGCAGAA GTCGGGTAAT GAAATGACTA ACTTAGCCTT     60

TGAACTAGAC CCCCTAGAGT TAGAGGAGGA AGAGGCTGAG CTTGGTGAGC AGAGTGGCTC    120

TGCCAAGACT AGTGTTAGCA GTGTCACCAC CCCGCCACCC CATGGCAAAC GCATCCCCTT    180

CTTTAAGAAG ACAGAGCATG TGCCCCCCTA TGACGTGGTG CCTTCCATGA GGCCCATCAT    240

CCTGGTGGGA CCGTCGCTCA AGGGCTACGA GGTTACAGAC ATGATGCAGA AAGCTTTATT    300

TGACTTCTTG AAGCATCGGT TTG                                           323

(2) INFORMATION FOR SEQ ID NO:13:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:13:

CCTATTGGTG TAGGTATACC AACAATTAAT TTAAGAAAAA GGAGACCCAA TATCCAG        57
```

(2) INFORMATION FOR SEQ ID NO:14:

(i) SEQUENCE CHARACTERISTICS:
        (A) LENGTH: 180 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..132

(xi) SEQUENCE DESCRIPTION: SEQ ID NO:14:

```
TGG TCC TTT GCC TGC GCC TGT GCC GCC TTC ATC CTC CTC TTT CTC GGC         48
Trp Ser Phe Ala Cys Ala Cys Ala Ala Phe Ile Leu Leu Phe Leu Gly
  1               5                  10                  15

GGT CTC GCC CTC CTG CTG TTC TCC CTG CCT CGA ATG CCC CGG AAC CCA         96
Gly Leu Ala Leu Leu Leu Phe Ser Leu Pro Arg Met Pro Arg Asn Pro
             20                  25                  30

TGG GAG TCC TGC ATG GAT GCT GAG CCC GAG CAC TAACCCTCCT GCGGCCCTAG      149
Trp Glu Ser Cys Met Asp Ala Glu Pro Glu His
         35                  40

CGACCCTCAG GCTTCTTCCC AGGAAGCGGG G                                      180
```

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO:15:

```
AATTCGGTAC GTACACTCGA GC                                                 22
```

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO:16:

```
GCTCGAGTGT ACGTACCG                                                      18
```

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO:17:

```
CCATGGTACC TTCGTTGACG                                                    20
```

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO:18:

```
AATTCGTCAA CGAAGGTACC ATGG                                              24
```

(2) INFORMATION FOR SEQ ID NO:19:

(i) SEQUENCE CHARACTERISTICS:
        (A) LENGTH: 2153 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 53..1504
        (D) OTHER INFORMATION: /standard_name= "Beta-3-1"

(xi) SEQUENCE DESCRIPTION: SEQ ID NO:19:

```
CCGCCTCGGA CCCCCTGTCC CGGGGGAGGG GGAGAGCCCG CTACCCTGGT CT ATG           55
                                                         Met
                                                          1

TCT TTT TCT GAC TCC AGT GCA ACC TTC CTG CTG AAC GAG GGT TCA GCC        103
Ser Phe Ser Asp Ser Ser Ala Thr Phe Leu Leu Asn Glu Gly Ser Ala
         5                  10                  15

GAC TCC TAC ACC AGC CGC CCA TCT CTG GAC TCA GAC GTC TCC CTG GAG        151
Asp Ser Tyr Thr Ser Arg Pro Ser Leu Asp Ser Asp Val Ser Leu Glu
             20                  25                  30

GAG GAC CGG GAG AGT GCC CGG CGT GAA GTA GAG AGC CAG GCT CAG CAG        199
Glu Asp Arg Glu Ser Ala Arg Arg Glu Val Glu Ser Gln Ala Gln Gln
 35                  40                  45

CAG CTC GAA AGG GCC AAG CAC AAA CCT GTG GCA TTT GCG GTG AGG ACC        247
Gln Leu Glu Arg Ala Lys His Lys Pro Val Ala Phe Ala Val Arg Thr
 50                  55                  60                  65

AAT GTC AGC TAC TGT GGC GTA CTG GAT GAG GAG TGC CCA GTC CAG GGC        295
Asn Val Ser Tyr Cys Gly Val Leu Asp Glu Glu Cys Pro Val Gln Gly
                 70                  75                  80

TCT GGA GTC AAC TTT GAG GCC AAA GAT TTT CTG CAC ATT AAA GAG AAG        343
Ser Gly Val Asn Phe Glu Ala Lys Asp Phe Leu His Ile Lys Glu Lys
             85                  90                  95

TAC AGC AAT GAC TGG TGG ATC GGG CGG CTA GTG AAA GAG GGC GGG GAC        391
Tyr Ser Asn Asp Trp Trp Ile Gly Arg Leu Val Lys Glu Gly Gly Asp
         100                 105                 110

ATC GCC TTC ATC CCC AGC CCC CAG CGC CTG GAG AGC ATC CGG CTC AAA        439
Ile Ala Phe Ile Pro Ser Pro Gln Arg Leu Glu Ser Ile Arg Leu Lys
     115                 120                 125

CAG GAG CAG AAG GCC AGG AGA TCT GGG AAC CCT TCC AGC CTG AGT GAC        487
Gln Glu Gln Lys Ala Arg Arg Ser Gly Asn Pro Ser Ser Leu Ser Asp
130                 135                 140                 145

ATT GGC AAC CGA CGC TCC CCT CCG CCA TCT CTA GCC AAG CAG AAG CAA        535
Ile Gly Asn Arg Arg Ser Pro Pro Pro Ser Leu Ala Lys Gln Lys Gln
                150                 155                 160

AAG CAG GCG GAA CAT GTT CCC CCG TAT GAC GTG GTG CCC TCC ATG CGG        583
```

```
                Lys Gln Ala Glu His Val Pro Pro Tyr Asp Val Pro Ser Met Arg
                                165                 170                 175

CCT GTG GTG CTG GTG GGA CCC TCT CTG AAA GGT TAT GAG GTC ACA GAC          631
Pro Val Val Leu Val Gly Pro Ser Leu Lys Gly Tyr Glu Val Thr Asp
            180                 185                 190

ATG ATG CAG AAG GCT CTC TTC GAC TTC CTC AAA CAC AGA TTT GAT GGC          679
Met Met Gln Lys Ala Leu Phe Asp Phe Leu Lys His Arg Phe Asp Gly
195                 200                 205

AGG ATC TCC ATC ACC CGA GTC ACA GCC GAC CTC TCC CTG GCA AAG CGA          727
Arg Ile Ser Ile Thr Arg Val Thr Ala Asp Leu Ser Leu Ala Lys Arg
210                 215                 220                 225

TCT GTG CTC AAC AAT CCG GGC AAG AGG ACC ATC ATT GAG CGC TCC TCT          775
Ser Val Leu Asn Asn Pro Gly Lys Arg Thr Ile Ile Glu Arg Ser Ser
            230                 235                 240

GCC CGC TCC AGC ATT GCG GAA GTG CAG AGT GAG ATC GAG CGC ATA TTT          823
Ala Arg Ser Ser Ile Ala Glu Val Gln Ser Glu Ile Glu Arg Ile Phe
            245                 250                 255

GAG CTG GCC AAA TCC CTG CAG CTA GTA GTG TTG GAC GCT GAC ACC ATC          871
Glu Leu Ala Lys Ser Leu Gln Leu Val Val Leu Asp Ala Asp Thr Ile
        260                 265                 270

AAC CAC CCA GCA CAG CTG GCC AAG ACC TCG CTG GCC CCC ATC ATC GTC          919
Asn His Pro Ala Gln Leu Ala Lys Thr Ser Leu Ala Pro Ile Ile Val
275                 280                 285

TTT GTC AAA GTG TCC TCA CCA AAG GTA CTC CAG CGT CTC ATT CGC TCC          967
Phe Val Lys Val Ser Ser Pro Lys Val Leu Gln Arg Leu Ile Arg Ser
290                 295                 300                 305

CGG GGG AAG TCA CAG ATG AAG CAC CTG ACC GTA CAG ATG ATG GCA TAT         1015
Arg Gly Lys Ser Gln Met Lys His Leu Thr Val Gln Met Met Ala Tyr
            310                 315                 320

GAT AAG CTG GTT CAG TGC CCA CCG GAG TCA TTT GAT GTG ATT CTG GAT         1063
Asp Lys Leu Val Gln Cys Pro Pro Glu Ser Phe Asp Val Ile Leu Asp
            325                 330                 335

GAG AAC CAG CTG GAG GAT GCC TGT GAG CAC CTG GCT GAG TAC CTG GAG         1111
Glu Asn Gln Leu Glu Asp Ala Cys Glu His Leu Ala Glu Tyr Leu Glu
        340                 345                 350

GTT TAC TGG CGG GCC ACG CAC CAC CCA GCC CCT GGC CCC GGA CTT CTG         1159
Val Tyr Trp Arg Ala Thr His His Pro Ala Pro Gly Pro Gly Leu Leu
355                 360                 365

GGT CCT CCC AGT GCC ATC CCC GGA CTT CAG AAC CAG CAG CTG CTG GGG         1207
Gly Pro Pro Ser Ala Ile Pro Gly Leu Gln Asn Gln Gln Leu Leu Gly
370                 375                 380                 385

GAG CGT GGC GAG GAG CAC TCC CCC CTT GAG CGG GAC AGC TTG ATG CCC         1255
Glu Arg Gly Glu Glu His Ser Pro Leu Glu Arg Asp Ser Leu Met Pro
            390                 395                 400

TCT GAT GAG GCC AGC GAG AGC TCC CGC CAA GCC TGG ACA GGA TCT TCA         1303
Ser Asp Glu Ala Ser Glu Ser Ser Arg Gln Ala Trp Thr Gly Ser Ser
            405                 410                 415

CAG CGT AGC TCC CGC CAC CTG GAG GAG GAC TAT GCA GAT GCC TAC CAG         1351
Gln Arg Ser Ser Arg His Leu Glu Glu Asp Tyr Ala Asp Ala Tyr Gln
        420                 425                 430

GAC CTG TAC CAG CCT CAC CGC CAA CAC ACC TCG GGG CTG CCT AGT GCT         1399
Asp Leu Tyr Gln Pro His Arg Gln His Thr Ser Gly Leu Pro Ser Ala
        435                 440                 445

AAC GGG CAT GAC CCC CAA GAC CGG CTT CTA GCC CAG GAC TCA GAA CAC         1447
Asn Gly His Asp Pro Gln Asp Arg Leu Leu Ala Gln Asp Ser Glu His
450                 455                 460                 465

AAC CAC AGT GAC CGG AAC TGG CAG CGC AAC CGG CCT TGG CCC AAG GAT         1495
Asn His Ser Asp Arg Asn Trp Gln Arg Asn Arg Pro Trp Pro Lys Asp
            470                 475                 480
```

-continued

| | |
|---|---|
| AGC TAC TGA CAG C CTCCTGCTGC CCTACCCTGG CAGGCACAGG<br>Ser Tyr * | 1538 |
| CGCAGCTGGC TGGGGGGCCC ACTCCAGGCA GGGTGGCGTT AGACTGGCAT | 1588 |
| CAGGCTGGCA CTAGGCTCAG CCCCCAAAAC CCCCTGCCCA GCCCCAGCTT CAGGGCTGCC | 1648 |
| TGTGGTCCCA AGGTTCTGGG AGAAACAGGG GACCCCCTCA CCTCCTGGGC AGTGACCCCT | 1708 |
| ACTAGGCTCC CATTCCAGGT ACTAGCTGTG TGTTCTGCAC CCCTGGCACC TTCCTCTCCT | 1768 |
| CCCACACAGG AAGCTGCCCC ACTGGGCAGT GCCCTCAGGC CAGGATCCCC TTAGCAGGGT | 1828 |
| CCTTCCCACC AGACTCAGGG AAGGGATGCC CCATTAAAGT GACAAAAGGG TGGGTGTGGG | 1888 |
| CACCATGGCA TGAGGAAGAA ACAAGGTCCC TGAGCAGGCA CAAGTCCTGA CAGTCAAGGG | 1948 |
| ACTGCTTTGG CATCCAGGGC CTCCAGTCAC CTCACTGCCA TACATTAGAA ATGAGACAAT | 2008 |
| TCAAAGCCCC CCCAGGGTGG CACACCCATC TGTTGCTGGG GTGTGGCAGC CACATCCAAG | 2068 |
| ACTGGAGCAG CAGGCTGGCC ACGCTTGGGC CAGAGAGAGC TCACAGCTGA AGCTCTTGGA | 2128 |
| GGGAAGGGCT CTCCTCACCC AATCG | 2153 |

(2) INFORMATION FOR SEQ ID NO:20:

(i) SEQUENCE CHARACTERISTICS:
        (A) LENGTH: 2144 base pairs
        (B) TYPE: nucleic acid
        (C) STRANDEDNESS: single
        (D) TOPOLOGY: unknown (ii) MOLECULE TYPE: DNA (genomic)

(ix) FEATURE:
        (A) NAME/KEY: CDS
        (B) LOCATION: 51..1492
        (D) OTHER INFORMATION: /product= "A Beta3 subunit of human
            calcium channel"

(ii) MOLECULE TYPE: cDNA (xi) SEQUENCE DESCRIPTION: SEQ ID NO:20:

| | |
|---|---|
| CGCCCCCGGC GCCGCTCGTT CCCCCGACCC GGACTCCCCC ATGTATGACG ACTCCTACGT | 60 |
| GCCCGGGTTT GAGGACTCGG AGGCGGTTTC AGCCGACTCC TACACCAGCC GCCCATCTCT | 120 |
| GGACTCAGAC GTCTCCCTGG AGGAGGACCG GGAGAGTGCC CGGCGTGAAG TAGAGAGCCA | 180 |
| GGCTCAGCAG CAGCTCGAAA GGGCCAAGCA CAAACCTGTG GCATTTGCGG TGAGGACCAA | 240 |
| TGTCAGCTAC TGTGGCGTAC TGGATGAGGA GTGCCCAGTC CAGGGCTCTG GAGTCAACTT | 300 |
| TGAGGCCAAA GATTTTCTGC ACATTAAAGA GAAGTACAGC AATGACTGGT GGATCGGGCG | 360 |
| GCTAGTGAAA GAGGGCGGGG ACATCGCCTT CATCCCCAGC CCCCAGCGCC TGGAGAGCAT | 420 |
| CCGGCTCAAA CAGGAGCAGA AGGCCAGGAG ATCTGGGAAC CCTTCCAGCC TGAGTGACAT | 480 |
| TGGCAACCGA CGCTCCCCTC CGCCATCTCT AGCCAAGCAG AAGCAAAAGC AGGCGGAACA | 540 |
| TGTTCCCCCG TATGACGTGG TGCCCTCCAT GCGGCCTGTG GTGCTGGTGG GACCCTCTCT | 600 |
| GAAAGGTTAT GAGGTCACAG ACATGATGCA GAAGGCTCTC TTCGACTTCC TCAAACACAG | 660 |
| ATTTGATGGC AGGATCTCCA TCACCCGAGT CACAGCCGAC CTCTCCCTGG CAAAGCGATC | 720 |
| TGTGCTCAAC AATCCGGGCA AGAGGACCAT CATTGAGCGC TCCTCTGCCC GCTCCAGCAT | 780 |
| TGCGGAAGTG CAGAGTGAGA TCGAGCGCAT ATTTGAGCTG GCCAAATCCC TGCAGCTAGT | 840 |
| AGTGTTGGAC GCTGACACCA TCAACCACCC AGCACAGCTG GCCAAGACCT CGCTGGCCCC | 900 |
| CATCATCGTC TTTGTCAAAG TGTCCTCACC AAAGGTACTC CAGCGTCTCA TTCGCTCCCG | 960 |
| GGGGAAGTCA CAGATGAAGC ACCTGACCGT ACAGATGATG GCATATGATA AGCTGGTTCA | 1020 |

```
GTGCCCACCG GAGTCATTTG ATGTGATTCT GGATGAGAAC CAGCTGGAGG ATGCCTGTGA    1080

GCACCTGGCT GAGTACCTGG AGGTTTACTG GCGGGCCACG CACCACCCAG CCCCTGGCCC    1140

CGGACTTCTG GGTCCTCCCA GTGCCATCCC CGGACTTCAG AACCAGCAGC TGCTGGGGGA    1200

GCGTGGCGAG GAGCACTCCC CCCTTGAGCG GGACAGCTTG ATGCCCTCTG ATGAGGCCAG    1260

CGAGAGCTCC CGCCAAGCCT GGACAGGATC TTCACAGCGT AGCTCCCGCC ACCTGGAGGA    1320

GGACTATGCA GATGCCTACC AGGACCTGTA CCAGCCTCAC CGCCAACACA CCTCGGGGCT    1380

GCCTAGTGCT AACGGGCATG ACCCCCAAGA CCGGCTTCTA GCCCAGGACT CAGAACACAA    1440

CCACAGTGAC CGGAACTGGC AGCGCAACCG GCCTTGGCCC AAGGATAGCT ACTGACAGCC    1500

TCCTGCTGCC CTACCCTGGC AGGCACAGGC GCAGCTGGCT GGGGGGCCCA CTCCAGGCAG    1560

GGTGGCGTTA GACTGGCATC AGGCTGGCAC TAGGCTCAGC CCCCAAAACC CCCTGCCCAG    1620

CCCCAGCTTC AGGGCTGCCT GTGGTCCCAA GGTTCTGGGA GAAACAGGGG ACCCCCTCAC    1680

CTCCTGGGCA GTGACCCCTA CTAGGCTCCC ATTCCAGGTA CTAGCTGTGT GTTCTGCACC    1740

CCTGGCACCT TCCTCTCCTC CCACACAGGA AGCTGCCCCA CTGGGCAGTG CCCTCAGGCC    1800

AGGATCCCCT TAGCAGGGTC CTTCCCACCA GACTCAGGGA AGGGATGCCC CATTAAAGTG    1860

ACAAAAGGGT GGGTGTGGGC ACCATGGCAT GAGGAAGAAA CAAGGTCCCT GAGCAGGCAC    1920

AAGTCCTGAC AGTCAAGGGA CTGCTTTGGC ATCCAGGGCC TCCAGTCACC TCACTGCCAT    1980

ACATTAGAAA TGAGACAATT CAAAGCCCCC CCAGGGTGGC ACACCCATCT GTTGCTGGGG    2040

TGTGGCAGCC ACATCCAAGA CTGGAGCAGC AGGCTGGCCA CGCTTGGGCC AGAGAGAGCT    2100

CACAGCTGAA GCTCTTGGAG GGAAGGGCTC TCCTCACCCA ATCG                    2144

(2) INFORMATION FOR SEQ ID NO:21:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO:21:

CTCAGTACCA TCTCTGATAC CAGCCCCA                                        28

(2) INFORMATION FOR SEQ ID NO:22:

(i) SEQUENCE CHARACTERISTICS:
        (A) LENGTH: 7808 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 237..7769
        (D) OTHER INFORMATION: /standard_name= "Alpha-1A-1"

(xi) SEQUENCE DESCRIPTION: SEQ ID NO:22:

GATGTCCCGA GCTGCTATCC CCGGCTCGGC CCGGGCAGCC GCCTTCTGAG CCCCCGACCC      60

GAGGCGCCGA GCCGCCGCCG CCCGATGGGC TGGGCCGTGG AGCGTCTCCG CAGTCGTAGC    120

TCCAGCCGCC GCGCTCCCAG CCCCGGCAGC CTCAGCATCA GCGGCGGCGG CGGCGGCGGC    180
```

```
GGCGTCTTCC GCATCGTTCG CCGCAGCGTA ACCCGGAGCC CTTTGCTCTT TGCAGA                              236

ATG GCC CGC TTC GGA GAC GAG ATG CCG GCC CGC TAC GGG GGA GGA GGC                            284
Met Ala Arg Phe Gly Asp Glu Met Pro Ala Arg Tyr Gly Gly Gly Gly
 1               5                   10                  15

TCC GGG GCA GCC GCC GGG GTG GTC GTG GGC AGC GGA GGC GGG CGA GGA                            332
Ser Gly Ala Ala Ala Gly Val Val Val Gly Ser Gly Gly Gly Arg Gly
                20                  25                  30

GCC GGG GGC AGC CGG CAG GGC GGG CAG CCC GGG GCG CAA AGG ATG TAC                            380
Ala Gly Gly Ser Arg Gln Gly Gly Gln Pro Gly Ala Gln Arg Met Tyr
            35                  40                  45

AAG CAG TCA ATG GCG CAG AGA GCG CGG ACC ATG GCA CTC TAC AAC CCC                            428
Lys Gln Ser Met Ala Gln Arg Ala Arg Thr Met Ala Leu Tyr Asn Pro
        50                  55                  60

ATC CCC GTC CGA CAG AAC TGC CTC ACG GTT AAC CGG TCT CTC TTC CTC                            476
Ile Pro Val Arg Gln Asn Cys Leu Thr Val Asn Arg Ser Leu Phe Leu
 65              70                  75                  80

TTC AGC GAA GAC AAC GTG GTG AGA AAA TAC GCC AAA AAG ATC ACC GAA                            524
Phe Ser Glu Asp Asn Val Val Arg Lys Tyr Ala Lys Lys Ile Thr Glu
                85                  90                  95

TGG CCT CCC TTT GAA TAT ATG ATT TTA GCC ACC ATC ATA GCG AAT TGC                            572
Trp Pro Pro Phe Glu Tyr Met Ile Leu Ala Thr Ile Ile Ala Asn Cys
               100                 105                 110

ATC GTC CTC GCA CTG GAG CAG CAT CTG CCT GAT GAT GAC AAG ACC CCG                            620
Ile Val Leu Ala Leu Glu Gln His Leu Pro Asp Asp Asp Lys Thr Pro
           115                 120                 125

ATG TCT GAA CGG CTG GAT GAC ACA GAA CCA TAC TTC ATT GGA ATT TTT                            668
Met Ser Glu Arg Leu Asp Asp Thr Glu Pro Tyr Phe Ile Gly Ile Phe
130                 135                 140

TGT TTC GAG GCT GGA ATT AAA ATC ATT GCC CTT GGG TTT GCC TTC CAC                            716
Cys Phe Glu Ala Gly Ile Lys Ile Ile Ala Leu Gly Phe Ala Phe His
145                 150                 155                 160

AAA GGC TCC TAC TTG AGG AAT GGC TGG AAT GTC ATG GAC TTT GTG GTG                            764
Lys Gly Ser Tyr Leu Arg Asn Gly Trp Asn Val Met Asp Phe Val Val
                165                 170                 175

GTG CTA ACG GGC ATC TTG GCG ACA GTT GGG ACG GAG TTT GAC CTA CGG                            812
Val Leu Thr Gly Ile Leu Ala Thr Val Gly Thr Glu Phe Asp Leu Arg
            180                 185                 190

ACG CTG AGG GCA GTT CGA GTG CTG CGG CCG CTC AAG CTG GTG TCT GGA                            860
Thr Leu Arg Ala Val Arg Val Leu Arg Pro Leu Lys Leu Val Ser Gly
        195                 200                 205

ATC CCA AGT TTA CAA GTC GTC CTG AAG TCG ATC ATG AAG GCG ATG ATC                            908
Ile Pro Ser Leu Gln Val Val Leu Lys Ser Ile Met Lys Ala Met Ile
        210                 215                 220

CCT TTG CTG CAG ATC GGC CTC CTC CTA TTT TTT GCA ATC CTT ATT TTT                            956
Pro Leu Leu Gln Ile Gly Leu Leu Leu Phe Phe Ala Ile Leu Ile Phe
225                 230                 235                 240

GCA ATC ATA GGG TTA GAA TTT TAT ATG GGA AAA TTT CAT ACC ACC TGC                           1004
Ala Ile Ile Gly Leu Glu Phe Tyr Met Gly Lys Phe His Thr Thr Cys
                245                 250                 255

TTT GAA GAG GGG ACA GAT GAC ATT CAG GGT GAG TCT CCG GCT CCA TGT                           1052
Phe Glu Glu Gly Thr Asp Asp Ile Gln Gly Glu Ser Pro Ala Pro Cys
            260                 265                 270

GGG ACA GAA GAG CCC GCC CGC ACC TGC CCC AAT GGG ACC AAA TGT CAG                           1100
Gly Thr Glu Glu Pro Ala Arg Thr Cys Pro Asn Gly Thr Lys Cys Gln
        275                 280                 285

CCC TAC TGG GAA GGG CCC AAC AAC GGG ATC ACT CAG TTC GAC AAC ATC                           1148
Pro Tyr Trp Glu Gly Pro Asn Asn Gly Ile Thr Gln Phe Asp Asn Ile
        290                 295                 300

CTG TTT GCA GTG CTG ACT GTT TTC CAG TGC ATA ACC ATG GAA GGG TGG                           1196
Leu Phe Ala Val Leu Thr Val Phe Gln Cys Ile Thr Met Glu Gly Trp
```

```
Leu Phe Ala Val Leu Thr Val Phe Gln Cys Ile Thr Met Glu Gly Trp
305                 310                 315                 320

ACT GAT CTC CTC TAC AAT AGC AAC GAT GCC TCA GGG AAC ACT TGG AAC      1244
Thr Asp Leu Leu Tyr Asn Ser Asn Asp Ala Ser Gly Asn Thr Trp Asn
                325                 330                 335

TGG TTG TAC TTC ATC CCC CTC ATC ATC ATC GGC TCC TTT TTT ATG CTG      1292
Trp Leu Tyr Phe Ile Pro Leu Ile Ile Ile Gly Ser Phe Phe Met Leu
                340                 345                 350

AAC CTT GTG CTG GGT GTG CTG TCA GGG GAG TTT GCC AAA GAA AGG GAA      1340
Asn Leu Val Leu Gly Val Leu Ser Gly Glu Phe Ala Lys Glu Arg Glu
                355                 360                 365

CGG GTG GAG AAC CGG CGG GCT TTT CTG AAG CTG AGG CGG CAA CAA CAG      1388
Arg Val Glu Asn Arg Arg Ala Phe Leu Lys Leu Arg Arg Gln Gln Gln
370                 375                 380

ATT GAA CGT GAG CTC AAT GGG TAC ATG GAA TGG ATC TCA AAA GCA GAA      1436
Ile Glu Arg Glu Leu Asn Gly Tyr Met Glu Trp Ile Ser Lys Ala Glu
385                 390                 395                 400

GAG GTG ATC CTC GCC GAG GAT GAA ACT GAC GGG GAG CAG AGG CAT CCC      1484
Glu Val Ile Leu Ala Glu Asp Glu Thr Asp Gly Glu Gln Arg His Pro
                405                 410                 415

TTT GAT GGA GCT CTG CGG AGA ACC ACC ATA AAG AAA AGC AAG ACA GAT      1532
Phe Asp Gly Ala Leu Arg Arg Thr Thr Ile Lys Lys Ser Lys Thr Asp
                420                 425                 430

TTG CTC AAC CCC GAA GAG GCT GAG GAT CAG CTG GCT GAT ATA GCC TCT      1580
Leu Leu Asn Pro Glu Glu Ala Glu Asp Gln Leu Ala Asp Ile Ala Ser
                435                 440                 445

GTG GGT TCT CCC TTC GCC CGA GCC AGC ATT AAA AGT GCC AAG CTG GAG      1628
Val Gly Ser Pro Phe Ala Arg Ala Ser Ile Lys Ser Ala Lys Leu Glu
        450                 455                 460

AAC TCG ACC TTT TTT CAC AAA AAG GAG AGG AGG ATG CGT TTC TAC ATC      1676
Asn Ser Thr Phe Phe His Lys Lys Glu Arg Arg Met Arg Phe Tyr Ile
465                 470                 475                 480

CGC CGC ATG GTC AAA ACT CAG GCC TTC TAC TGG ACT GTA CTC AGT TTG      1724
Arg Arg Met Val Lys Thr Gln Ala Phe Tyr Trp Thr Val Leu Ser Leu
                485                 490                 495

GTA GCT CTC AAC ACG CTG TGT GTT GCT ATT GTT CAC TAC AAC CAG CCC      1772
Val Ala Leu Asn Thr Leu Cys Val Ala Ile Val His Tyr Asn Gln Pro
            500                 505                 510

GAG TGG CTC TCC GAC TTC CTT TAC TAT GCA GAA TTC ATT TTC TTA GGA      1820
Glu Trp Leu Ser Asp Phe Leu Tyr Tyr Ala Glu Phe Ile Phe Leu Gly
            515                 520                 525

CTC TTT ATG TCC GAA ATG TTT ATA AAA ATG TAC GGG CTT GGG ACG CGG      1868
Leu Phe Met Ser Glu Met Phe Ile Lys Met Tyr Gly Leu Gly Thr Arg
        530                 535                 540

CCT TAC TTC CAC TCT TCC TTC AAC TGC TTT GAC TGT GGG GTT ATC ATT      1916
Pro Tyr Phe His Ser Ser Phe Asn Cys Phe Asp Cys Gly Val Ile Ile
545                 550                 555                 560

GGG AGC ATC TTC GAG GTC ATC TGG GCT GTC ATA AAA CCT GGC ACA TCC      1964
Gly Ser Ile Phe Glu Val Ile Trp Ala Val Ile Lys Pro Gly Thr Ser
                565                 570                 575

TTT GGA ATC AGC GTG TTA CGA GCC CTC AGG TTA TTG CGT ATT TTC AAA      2012
Phe Gly Ile Ser Val Leu Arg Ala Leu Arg Leu Leu Arg Ile Phe Lys
                580                 585                 590

GTC ACA AAG TAC TGG GCA TCT CTC AGA AAC CTG GTC GTC TCT CTC CTC      2060
Val Thr Lys Tyr Trp Ala Ser Leu Arg Asn Leu Val Val Ser Leu Leu
            595                 600                 605

AAC TCC ATG AAG TCC ATC ATC AGC CTG TTG TTT CTC CTT TTC CTG TTC      2108
Asn Ser Met Lys Ser Ile Ile Ser Leu Leu Phe Leu Leu Phe Leu Phe
            610                 615                 620
```

```
ATT GTC GTC TTC GCC CTT TTG GGA ATG CAA CTC TTC GGC GGC CAG TTT      2156
Ile Val Val Phe Ala Leu Leu Gly Met Gln Leu Phe Gly Gly Gln Phe
625                 630                 635                 640

AAT TTC GAT GAA GGG ACT CCT CCC ACC AAC TTC GAT ACT TTT CCA GCA      2204
Asn Phe Asp Glu Gly Thr Pro Pro Thr Asn Phe Asp Thr Phe Pro Ala
                645                 650                 655

GCA ATA ATG ACG GTG TTT CAG ATC CTG ACG GGC GAA GAC TGG AAC GAG      2252
Ala Ile Met Thr Val Phe Gln Ile Leu Thr Gly Glu Asp Trp Asn Glu
            660                 665                 670

GTC ATG TAC GAC GGG ATC AAG TCT CAG GGG GGC GTG CAG GGC GGC ATG      2300
Val Met Tyr Asp Gly Ile Lys Ser Gln Gly Gly Val Gln Gly Gly Met
        675                 680                 685

GTG TTC TCC ATC TAT TTC ATT GTA CTG ACG CTC TTT GGG AAC TAC ACC      2348
Val Phe Ser Ile Tyr Phe Ile Val Leu Thr Leu Phe Gly Asn Tyr Thr
690                 695                 700

CTC CTG AAT GTG TTC TTG GCC ATC GCT GTG GAC AAT CTG GCC AAC GCC      2396
Leu Leu Asn Val Phe Leu Ala Ile Ala Val Asp Asn Leu Ala Asn Ala
705                 710                 715                 720

CAG GAG CTC ACC AAG GTG GAG GCG GAC GAG CAA GAG GAA GAA GAA GCA      2444
Gln Glu Leu Thr Lys Val Glu Ala Asp Glu Gln Glu Glu Glu Glu Ala
                725                 730                 735

GCG AAC CAG AAA CTT GCC CTA CAG AAA GCC AAG GAG GTG GCA GAA GTG      2492
Ala Asn Gln Lys Leu Ala Leu Gln Lys Ala Lys Glu Val Ala Glu Val
            740                 745                 750

AGT CCT CTG TCC GCG GCC AAC ATG TCT ATA GCT GTG AAA GAG CAA CAG      2540
Ser Pro Leu Ser Ala Ala Asn Met Ser Ile Ala Val Lys Glu Gln Gln
        755                 760                 765

AAG AAT CAA AAG CCA GCC AAG TCC GTG TGG GAG CAG CGG ACC AGT GAG      2588
Lys Asn Gln Lys Pro Ala Lys Ser Val Trp Glu Gln Arg Thr Ser Glu
770                 775                 780

ATG CGA AAG CAG AAC TTG CTG GCC AGC CGG GAG GCC CTG TAT AAC GAA      2636
Met Arg Lys Gln Asn Leu Leu Ala Ser Arg Glu Ala Leu Tyr Asn Glu
785                 790                 795                 800

ATG GAC CCG GAC GAG CGC TGG AAG GCT GCC TAC ACG CGG CAC CTG CGG      2684
Met Asp Pro Asp Glu Arg Trp Lys Ala Ala Tyr Thr Arg His Leu Arg
                805                 810                 815

CCA GAC ATG AAG ACG CAC TTG GAC CGG CCG CTG GTG GTG GAC CCG CAG      2732
Pro Asp Met Lys Thr His Leu Asp Arg Pro Leu Val Val Asp Pro Gln
            820                 825                 830

GAG AAC CGC AAC AAC AAC ACC AAC AAG AGC CGG GCG GCC GAG CCC ACC      2780
Glu Asn Arg Asn Asn Asn Thr Asn Lys Ser Arg Ala Ala Glu Pro Thr
        835                 840                 845

GTG GAC CAG CGC CTC GGC CAG CAG CGC GCC GAG GAC TTC CTC AGG AAA      2828
Val Asp Gln Arg Leu Gly Gln Gln Arg Ala Glu Asp Phe Leu Arg Lys
850                 855                 860

CAG GCC CGC TAC CAC GAT CGG GCC CGG GAC CCC AGC GGC TCG GCG GGC      2876
Gln Ala Arg Tyr His Asp Arg Ala Arg Asp Pro Ser Gly Ser Ala Gly
865                 870                 875                 880

CTG GAC GCA CGG AGG CCC TGG GCG GGA AGC CAG GAG GCC GAG CTG AGC      2924
Leu Asp Ala Arg Arg Pro Trp Ala Gly Ser Gln Glu Ala Glu Leu Ser
                885                 890                 895

CGG GAG GGA CCC TAC GGC CGC GAG TCG GAC CAC CAC GCC CGG GAG GGC      2972
Arg Glu Gly Pro Tyr Gly Arg Glu Ser Asp His His Ala Arg Glu Gly
            900                 905                 910

AGC CTG GAG CAA CCC GGG TTC TGG GAG GGC GAG GCC GAG CGA GGC AAG      3020
Ser Leu Glu Gln Pro Gly Phe Trp Glu Gly Glu Ala Glu Arg Gly Lys
        915                 920                 925

GCC GGG GAC CCC CAC CGG AGG CAC GTG CAC CGG CAG GGG GGC AGC AGG      3068
Ala Gly Asp Pro His Arg Arg His Val His Arg Gln Gly Gly Ser Arg
930                 935                 940
```

```
GAG AGC CGC AGC GGG TCC CCG CGC ACG GGC GCG GAC GGG GAG CAT CGA       3116
Glu Ser Arg Ser Gly Ser Pro Arg Thr Gly Ala Asp Gly Glu His Arg
945                 950                 955                 960

CGT CAT CGC GCG CAC CGC AGG CCC GGG GAG GAG GGT CCG GAG GAC AAG       3164
Arg His Arg Ala His Arg Arg Pro Gly Glu Glu Gly Pro Glu Asp Lys
                965                 970                 975

GCG GAG CGG AGG GCG CGG CAC CGC GAG GGC AGC CGG CCG GCC CGG GGC       3212
Ala Glu Arg Arg Ala Arg His Arg Glu Gly Ser Arg Pro Ala Arg Gly
            980                 985                 990

GGC GAG GGC GAG GGC GAG GGC CCC GAC GGG GGC GAG CGC AGG AGA AGG       3260
Gly Glu Gly Glu Gly Glu Gly Pro Asp Gly Gly Glu Arg Arg Arg Arg
        995                 1000                1005

CAC CGG CAT GGC GCT CCA GCC ACG TAC GAG GGG GAC GCG CGG AGG GAG       3308
His Arg His Gly Ala Pro Ala Thr Tyr Glu Gly Asp Ala Arg Arg Glu
    1010                1015                1020

GAC AAG GAG CGG AGG CAT CGG AGG AGG AAA GAG AAC CAG GGC TCC GGG       3356
Asp Lys Glu Arg Arg His Arg Arg Arg Lys Glu Asn Gln Gly Ser Gly
1025                1030                1035                1040

GTC CCT GTG TCG GGC CCC AAC CTG TCA ACC ACC CGG CCA ATC CAG CAG       3404
Val Pro Val Ser Gly Pro Asn Leu Ser Thr Thr Arg Pro Ile Gln Gln
                1045                1050                1055

GAC CTG GGC CGC CAA GAC CCA CCC CTG GCA GAG GAT ATT GAC AAC ATG       3452
Asp Leu Gly Arg Gln Asp Pro Pro Leu Ala Glu Asp Ile Asp Asn Met
            1060                1065                1070

AAG AAC AAC AAG CTG GCC ACC GCG GAG TCG GCC GCT CCC CAC GGC AGC       3500
Lys Asn Asn Lys Leu Ala Thr Ala Glu Ser Ala Ala Pro His Gly Ser
        1075                1080                1085

CTT GGC CAC GCC GGC CTG CCC CAG AGC CCA GCC AAG ATG GGA AAC AGC       3548
Leu Gly His Ala Gly Leu Pro Gln Ser Pro Ala Lys Met Gly Asn Ser
    1090                1095                1100

ACC GAC CCC GGC CCC ATG CTG GCC ATC CCT GCC ATG GCC ACC AAC CCC       3596
Thr Asp Pro Gly Pro Met Leu Ala Ile Pro Ala Met Ala Thr Asn Pro
1105                1110                1115                1120

CAG AAC GCC GCC AGC CGC CGG ACG CCC AAC AAC CCG GGG AAC CCA TCC       3644
Gln Asn Ala Ala Ser Arg Arg Thr Pro Asn Asn Pro Gly Asn Pro Ser
                1125                1130                1135

AAT CCC GGC CCC CCC AAG ACC CCC GAG AAT AGC CTT ATC GTC ACC AAC       3692
Asn Pro Gly Pro Pro Lys Thr Pro Glu Asn Ser Leu Ile Val Thr Asn
            1140                1145                1150

CCC AGC GGC ACC CAG ACC AAT TCA GCT AAG ACT GCC AGG AAA CCC GAC       3740
Pro Ser Gly Thr Gln Thr Asn Ser Ala Lys Thr Ala Arg Lys Pro Asp
        1155                1160                1165

CAC ACC ACA GTG GAC ATC CCC CCA GCC TGC CCA CCC CCC CTC AAC CAC       3788
His Thr Thr Val Asp Ile Pro Pro Ala Cys Pro Pro Pro Leu Asn His
    1170                1175                1180

ACC GTC GTA CAA GTG AAC AAA AAC GCC AAC CCA GAC CCA CTG CCA AAA       3836
Thr Val Val Gln Val Asn Lys Asn Ala Asn Pro Asp Pro Leu Pro Lys
1185                1190                1195                1200

AAA GAG GAA GAG AAG AAG GAG GAG GAG GAA GAC GAC CGT GGG GAA GAC       3884
Lys Glu Glu Glu Lys Lys Glu Glu Glu Asp Asp Arg Gly Glu Asp
                1205                1210                1215

GGC CCT AAG CCA ATG CCT CCC TAT AGC TCC ATG TTC ATC CTG TCC ACG       3932
Gly Pro Lys Pro Met Pro Pro Tyr Ser Ser Met Phe Ile Leu Ser Thr
            1220                1225                1230

ACC AAC CCC CTT CGC CGC CTG TGC CAT TAC ATC CTG AAC CTG CGC TAC       3980
Thr Asn Pro Leu Arg Arg Leu Cys His Tyr Ile Leu Asn Leu Arg Tyr
        1235                1240                1245

TTT GAG ATG TGC ATC CTC ATG GTC ATT GCC ATG AGC AGC ATC GCC CTG       4028
Phe Glu Met Cys Ile Leu Met Val Ile Ala Met Ser Ser Ile Ala Leu
```

-continued

```
     1250                1255                1260
GCC GCC GAG GAC CCT GTG CAG CCC AAC GCA CCT CGG AAC AAC GTG CTG      4076
Ala Ala Glu Asp Pro Val Gln Pro Asn Ala Pro Arg Asn Asn Val Leu
1265                1270                1275                1280

CGA TAC TTT GAC TAC GTT TTT ACA GGC GTC TTC ACC TTT GAG ATG GTG      4124
Arg Tyr Phe Asp Tyr Val Phe Thr Gly Val Phe Thr Phe Glu Met Val
                1285                1290                1295

ATC AAG ATG ATT GAC CTG GGG CTC GTC CTG CAT CAG GGT GCC TAC TTC      4172
Ile Lys Met Ile Asp Leu Gly Leu Val Leu His Gln Gly Ala Tyr Phe
            1300                1305                1310

CGT GAC CTC TGG AAT ATT CTC GAC TTC ATA GTG GTC AGT GGG GCC CTG      4220
Arg Asp Leu Trp Asn Ile Leu Asp Phe Ile Val Val Ser Gly Ala Leu
        1315                1320                1325

GTA GCC TTT GCC TTC ACT GGC AAT AGC AAA GGA AAA GAC ATC AAC ACG      4268
Val Ala Phe Ala Phe Thr Gly Asn Ser Lys Gly Lys Asp Ile Asn Thr
    1330                1335                1340

ATT AAA TCC CTC CGA GTC CTC CGG GTG CTA CGA CCT CTT AAA ACC ATC      4316
Ile Lys Ser Leu Arg Val Leu Arg Val Leu Arg Pro Leu Lys Thr Ile
1345                1350                1355                1360

AAG CGG CTG CCA AAG CTC AAG GCT GTG TTT GAC TGT GTG GTG AAC TCA      4364
Lys Arg Leu Pro Lys Leu Lys Ala Val Phe Asp Cys Val Val Asn Ser
                1365                1370                1375

CTT AAA AAC GTC TTC AAC ATC CTC ATC GTC TAC ATG CTA TTC ATG TTC      4412
Leu Lys Asn Val Phe Asn Ile Leu Ile Val Tyr Met Leu Phe Met Phe
            1380                1385                1390

ATC TTC GCC GTG GTG GCT GTG CAG CTC TTC AAG GGG AAA TTC TTC CAC      4460
Ile Phe Ala Val Val Ala Val Gln Leu Phe Lys Gly Lys Phe Phe His
        1395                1400                1405

TGC ACT GAC GAG TCC AAA GAG TTT GAG AAA GAT TGT CGA GGC AAA TAC      4508
Cys Thr Asp Glu Ser Lys Glu Phe Glu Lys Asp Cys Arg Gly Lys Tyr
    1410                1415                1420

CTC CTC TAC GAG AAG AAT GAG GTG AAG GCG CGA GAC CGG GAG TGG AAG      4556
Leu Leu Tyr Glu Lys Asn Glu Val Lys Ala Arg Asp Arg Glu Trp Lys
1425                1430                1435                1440

AAG TAT GAA TTC CAT TAC GAC AAT GTG CTG TGG GCT CTG CTG ACC CTC      4604
Lys Tyr Glu Phe His Tyr Asp Asn Val Leu Trp Ala Leu Leu Thr Leu
                1445                1450                1455

TTC ACC GTG TCC ACG GGA GAA GGC TGG CCA CAG GTC CTC AAG CAT TCG      4652
Phe Thr Val Ser Thr Gly Glu Gly Trp Pro Gln Val Leu Lys His Ser
            1460                1465                1470

GTG GAC GCC ACC TTT GAG AAC CAG GGC CCC AGC CCC GGG TAC CGC ATG      4700
Val Asp Ala Thr Phe Glu Asn Gln Gly Pro Ser Pro Gly Tyr Arg Met
        1475                1480                1485

GAG ATG TCC ATT TTC TAC GTC GTC TAC TTT GTG GTG TTC CCC TTC TTC      4748
Glu Met Ser Ile Phe Tyr Val Val Tyr Phe Val Val Phe Pro Phe Phe
    1490                1495                1500

TTT GTC AAT ATC TTT GTG GCC TTG ATC ATC ATC ACC TTC CAG GAG CAA      4796
Phe Val Asn Ile Phe Val Ala Leu Ile Ile Ile Thr Phe Gln Glu Gln
1505                1510                1515                1520

GGG GAC AAG ATG ATG GAG GAA TAC AGC CTG GAG AAA AAT GAG AGG GCC      4844
Gly Asp Lys Met Met Glu Glu Tyr Ser Leu Glu Lys Asn Glu Arg Ala
                1525                1530                1535

TGC ATT GAT TTC GCC ATC AGC GCC AAG CCG CTG ACC CGA CAC ATG CCG      4892
Cys Ile Asp Phe Ala Ile Ser Ala Lys Pro Leu Thr Arg His Met Pro
            1540                1545                1550

CAG AAC AAG CAG AGC TTC CAG TAC CGC ATG TGG CAG TTC GTG GTG TCT      4940
Gln Asn Lys Gln Ser Phe Gln Tyr Arg Met Trp Gln Phe Val Val Ser
        1555                1560                1565

CCG CCT TTC GAG TAC ACG ATC ATG GCC ATG ATC GCC CTC AAC ACC ATC      4988
```

-continued

```
Pro Pro Phe Glu Tyr Thr Ile Met Ala Met Ile Ala Leu Asn Thr Ile
    1570                1575                1580

GTG CTT ATG ATG AAG TTC TAT GGG GCT TCT GTT GCT TAT GAA AAT GCC        5036
Val Leu Met Met Lys Phe Tyr Gly Ala Ser Val Ala Tyr Glu Asn Ala
1585                1590                1595                1600

CTG CGG GTG TTC AAC ATC GTC TTC ACC TCC CTC TTC TCT CTG GAA TGT        5084
Leu Arg Val Phe Asn Ile Val Phe Thr Ser Leu Phe Ser Leu Glu Cys
                1605                1610                1615

GTG CTG AAA GTC ATG GCT TTT GGG ATT CTG AAT TAT TTC CGC GAT GCC        5132
Val Leu Lys Val Met Ala Phe Gly Ile Leu Asn Tyr Phe Arg Asp Ala
            1620                1625                1630

TGG AAC ATC TTC GAC TTT GTG ACT GTT CTG GGC AGC ATC ACC GAT ATC        5180
Trp Asn Ile Phe Asp Phe Val Thr Val Leu Gly Ser Ile Thr Asp Ile
        1635                1640                1645

CTC GTG ACT GAG TTT GGG AAT CCG AAT AAC TTC ATC AAC CTG AGC TTT        5228
Leu Val Thr Glu Phe Gly Asn Pro Asn Asn Phe Ile Asn Leu Ser Phe
    1650                1655                1660

CTC CGC CTC TTC CGA GCT GCC CGG CTC ATC AAA CTT CTC CGT CAG GGT        5276
Leu Arg Leu Phe Arg Ala Ala Arg Leu Ile Lys Leu Leu Arg Gln Gly
1665                1670                1675                1680

TAC ACC ATC CGC ATT CTT CTC TGG ACC TTT GTG CAG TCC TTC AAG GCC        5324
Tyr Thr Ile Arg Ile Leu Leu Trp Thr Phe Val Gln Ser Phe Lys Ala
                1685                1690                1695

CTG CCT TAT GTC TGT CTG CTG ATC GCC ATG CTC TTC TTC ATC TAT GCC        5372
Leu Pro Tyr Val Cys Leu Leu Ile Ala Met Leu Phe Phe Ile Tyr Ala
            1700                1705                1710

ATC ATT GGG ATG CAG GTG TTT GGT AAC ATT GGC ATC GAC GTG GAG GAC        5420
Ile Ile Gly Met Gln Val Phe Gly Asn Ile Gly Ile Asp Val Glu Asp
        1715                1720                1725

GAG GAC AGT GAT GAA GAT GAG TTC CAA ATC ACT GAG CAC AAT AAC TTC        5468
Glu Asp Ser Asp Glu Asp Glu Phe Gln Ile Thr Glu His Asn Asn Phe
    1730                1735                1740

CGG ACC TTC TTC CAG GCC CTC ATG CTT CTC TTC CGG AGT GCC ACC GGG        5516
Arg Thr Phe Phe Gln Ala Leu Met Leu Leu Phe Arg Ser Ala Thr Gly
1745                1750                1755                1760

GAA GCT TGG CAC AAC ATC ATG CTT TCC TGC CTC AGC GGG AAA CCG TGT        5564
Glu Ala Trp His Asn Ile Met Leu Ser Cys Leu Ser Gly Lys Pro Cys
                1765                1770                1775

GAT AAG AAC TCT GGC ATC CTG ACT CGA GAG TGT GGC AAT GAA TTT GCT        5612
Asp Lys Asn Ser Gly Ile Leu Thr Arg Glu Cys Gly Asn Glu Phe Ala
            1780                1785                1790

TAT TTT TAC TTT GTT TCC TTC ATC TTC CTC TGC TCG TTT CTG ATG CTG        5660
Tyr Phe Tyr Phe Val Ser Phe Ile Phe Leu Cys Ser Phe Leu Met Leu
        1795                1800                1805

AAT CTC TTT GTC GCC GTC ATC ATG GAC AAC TTT GAG TAC CTC ACC CGA        5708
Asn Leu Phe Val Ala Val Ile Met Asp Asn Phe Glu Tyr Leu Thr Arg
    1810                1815                1820

GAC TCC TCC ATC CTG GGC CCC CAC CAC CTG GAT GAG TAC GTG CGT GTC        5756
Asp Ser Ser Ile Leu Gly Pro His His Leu Asp Glu Tyr Val Arg Val
1825                1830                1835                1840

TGG GCC GAG TAT GAC CCC GCA GCT TGG GGC CGC ATG CCT TAC CTG GAC        5804
Trp Ala Glu Tyr Asp Pro Ala Ala Trp Gly Arg Met Pro Tyr Leu Asp
                1845                1850                1855

ATG TAT CAG ATG CTG AGA CAC ATG TCT CCG CCC CTG GGT CTG GGG AAG        5852
Met Tyr Gln Met Leu Arg His Met Ser Pro Pro Leu Gly Leu Gly Lys
            1860                1865                1870

AAG TGT CCG GCC AGA GTG GCT TAC AAG CGG CTT CTG CGG ATG GAC CTG        5900
Lys Cys Pro Ala Arg Val Ala Tyr Lys Arg Leu Leu Arg Met Asp Leu
        1875                1880                1885
```

-continued

```
CCC GTC GCA GAT GAC AAC ACC GTC CAC TTC AAT TCC ACC CTC ATG GCT        5948
Pro Val Ala Asp Asp Asn Thr Val His Phe Asn Ser Thr Leu Met Ala
            1890                1895                1900

CTG ATC CGC ACA GCC CTG GAC ATC AAG ATT GCC AAG GGA GGA GCC GAC        5996
Leu Ile Arg Thr Ala Leu Asp Ile Lys Ile Ala Lys Gly Gly Ala Asp
1905                1910                1915                1920

AAA CAG CAG ATG GAC GCT GAG CTG CGG AAG GAG ATG ATG GCG ATT TGG        6044
Lys Gln Gln Met Asp Ala Glu Leu Arg Lys Glu Met Met Ala Ile Trp
                1925                1930                1935

CCC AAT CTG TCC CAG AAG ACG CTA GAC CTG CTG GTC ACA CCT CAC AAG        6092
Pro Asn Leu Ser Gln Lys Thr Leu Asp Leu Leu Val Thr Pro His Lys
            1940                1945                1950

TCC ACG GAC CTC ACC GTG GGG AAG ATC TAC GCA GCC ATG ATG ATC ATG        6140
Ser Thr Asp Leu Thr Val Gly Lys Ile Tyr Ala Ala Met Met Ile Met
        1955                1960                1965

GAG TAC TAC CGG CAG AGC AAG GCC AAG AAG CTG CAG GCC ATG CGC GAG        6188
Glu Tyr Tyr Arg Gln Ser Lys Ala Lys Lys Leu Gln Ala Met Arg Glu
    1970                1975                1980

GAG CAG GAC CGG ACA CCC CTC ATG TTC CAG CGC ATG GAG CCC CCG TCC        6236
Glu Gln Asp Arg Thr Pro Leu Met Phe Gln Arg Met Glu Pro Pro Ser
1985                1990                1995                2000

CCA ACG CAG GAA GGG GGA CCT GGC CAG AAC GCC CTC CCC TCC ACC CAG        6284
Pro Thr Gln Glu Gly Gly Pro Gly Gln Asn Ala Leu Pro Ser Thr Gln
                2005                2010                2015

CTG GAC CCA GGA GGA GCC CTG ATG GCT CAC GAA AGC GGC CTC AAG GAG        6332
Leu Asp Pro Gly Gly Ala Leu Met Ala His Glu Ser Gly Leu Lys Glu
            2020                2025                2030

AGC CCG TCC TGG GTG ACC CAG CGT GCC CAG GAG ATG TTC CAG AAG ACG        6380
Ser Pro Ser Trp Val Thr Gln Arg Ala Gln Glu Met Phe Gln Lys Thr
        2035                2040                2045

GGC ACA TGG AGT CCG GAA CAA GGC CCC CCT ACC GAC ATG CCC AAC AGC        6428
Gly Thr Trp Ser Pro Glu Gln Gly Pro Pro Thr Asp Met Pro Asn Ser
    2050                2055                2060

CAG CCT AAC TCT CAG TCC GTG GAG ATG CGA GAG ATG GGC AGA GAT GGC        6476
Gln Pro Asn Ser Gln Ser Val Glu Met Arg Glu Met Gly Arg Asp Gly
2065                2070                2075                2080

TAC TCC GAC AGC GAG CAC TAC CTC CCC ATG GAA GGC CAG GGC CGG GCT        6524
Tyr Ser Asp Ser Glu His Tyr Leu Pro Met Glu Gly Gln Gly Arg Ala
                2085                2090                2095

GCC TCC ATG CCC CGC CTC CCT GCA GAG AAC CAG AGG AGA AGG GGC CGG        6572
Ala Ser Met Pro Arg Leu Pro Ala Glu Asn Gln Arg Arg Arg Gly Arg
            2100                2105                2110

CCA CGT GGG AAT AAC CTC AGT ACC ATC TCA GAC ACC AGC CCC ATG AAG        6620
Pro Arg Gly Asn Asn Leu Ser Thr Ile Ser Asp Thr Ser Pro Met Lys
        2115                2120                2125

CGT TCA GCC TCC GTG CTG GGC CCC AAG GCC CGA CGC CTG GAC GAT TAC        6668
Arg Ser Ala Ser Val Leu Gly Pro Lys Ala Arg Arg Leu Asp Asp Tyr
    2130                2135                2140

TCG CTG GAG CGG GTC CCG CCC GAG GAG AAC CAG CGG CAC CAC CAG CGG        6716
Ser Leu Glu Arg Val Pro Pro Glu Glu Asn Gln Arg His His Gln Arg
2145                2150                2155                2160

CGC CGC GAC CGC AGC CAC CGC GCC TCT GAG CGC TCC CTG GGC CGC TAC        6764
Arg Arg Asp Arg Ser His Arg Ala Ser Glu Arg Ser Leu Gly Arg Tyr
                2165                2170                2175

ACC GAT GTG GAC ACA GGC TTG GGG ACA GAC CTG AGC ATG ACC ACC CAA        6812
Thr Asp Val Asp Thr Gly Leu Gly Thr Asp Leu Ser Met Thr Thr Gln
            2180                2185                2190

TCC GGG GAC CTG CCG TCG AAG GAG CGG GAC CAG GAG CGG GGC CGG CCC        6860
Ser Gly Asp Leu Pro Ser Lys Glu Arg Asp Gln Glu Arg Gly Arg Pro
        2195                2200                2205
```

-continued

```
AAG GAT CGG AAG CAT CGA CAG CAC CAC CAC CAC CAC CAC CAC CAC          6908
Lys Asp Arg Lys His Arg Gln His His His His His His His His
        2210            2215                2220

CAT CCC CCG CCC CCC GAC AAG GAC CGC TAT GCC CAG GAA CGG CCG GAC      6956
His Pro Pro Pro Pro Asp Lys Asp Arg Tyr Ala Gln Glu Arg Pro Asp
2225            2230            2235            2240

CAC GGC CGG GCA CGG GCT CGG GAC CAG CGC TGG TCC CGC TCG CCC AGC      7004
His Gly Arg Ala Arg Ala Arg Asp Gln Arg Trp Ser Arg Ser Pro Ser
                2245            2250            2255

GAG GGC CGA GAG CAC ATG GCG CAC CGG CAG GGC AGT AGT TCC GTA AGT      7052
Glu Gly Arg Glu His Met Ala His Arg Gln Gly Ser Ser Ser Val Ser
        2260            2265            2270

GGA AGC CCA GCC CCC TCA ACA TCT GGT ACC AGC ACT CCG CGG CGG GGC      7100
Gly Ser Pro Ala Pro Ser Thr Ser Gly Thr Ser Thr Pro Arg Arg Gly
        2275            2280            2285

CGC CGC CAG CTC CCC CAG ACC CCC TCC ACC CCC CGG CCA CAC GTG TCC      7148
Arg Arg Gln Leu Pro Gln Thr Pro Ser Thr Pro Arg Pro His Val Ser
        2290            2295            2300

TAT TCC CCT GTG ATC CGT AAG GCC GGC GGC TCG GGG CCC CCG CAG CAG      7196
Tyr Ser Pro Val Ile Arg Lys Ala Gly Gly Ser Gly Pro Pro Gln Gln
2305            2310            2315            2320

CAG CAG CAG CAG CAG CAG CAG CAG CAG GCG GTG GCC AGG CCG GGC CGG      7244
Gln Gln Gln Gln Gln Gln Gln Gln Gln Ala Val Ala Arg Pro Gly Arg
            2325            2330            2335

GCG GCC ACC AGC GGC CCT CGG AGG TAC CCA GGC CCC ACG GCC GAG CCT      7292
Ala Ala Thr Ser Gly Pro Arg Arg Tyr Pro Gly Pro Thr Ala Glu Pro
            2340            2345            2350

CTG GCC GGA GAT CGG CCG CCC ACG GGG GGC CAC AGC AGC GGC CGC TCG      7340
Leu Ala Gly Asp Arg Pro Pro Thr Gly Gly His Ser Ser Gly Arg Ser
        2355            2360            2365

CCC AGG ATG GAG AGG CGG GTC CCA GGC CCG GCC CGG AGC GAG TCC CCC      7388
Pro Arg Met Glu Arg Arg Val Pro Gly Pro Ala Arg Ser Glu Ser Pro
        2370            2375            2380

AGG GCC TGT CGA CAC GGC GGG GCC CGG TGG CCG GCA TCT GGC CCG CAC      7436
Arg Ala Cys Arg His Gly Gly Ala Arg Trp Pro Ala Ser Gly Pro His
2385            2390            2395            2400

GTG TCC GAG GGG CCC CCG GGT CCC CGG CAC CAT GGC TAC TAC CGG GGC      7484
Val Ser Glu Gly Pro Pro Gly Pro Arg His His Gly Tyr Tyr Arg Gly
            2405            2410            2415

TCC GAC TAC GAC GAG GCC GAT GGC CCG GGC AGC GGG GGC GGC GAG GAG      7532
Ser Asp Tyr Asp Glu Ala Asp Gly Pro Gly Ser Gly Gly Gly Glu Glu
            2420            2425            2430

GCC ATG GCC GGG GCC TAC GAC GCG CCA CCC CCC GTA CGA CAC GCG TCC      7580
Ala Met Ala Gly Ala Tyr Asp Ala Pro Pro Pro Val Arg His Ala Ser
        2435            2440            2445

TCG GGC GCC ACC GGG CGC TCG CCC AGG ACT CCC CGG GCC TCG GGC CCG      7628
Ser Gly Ala Thr Gly Arg Ser Pro Arg Thr Pro Arg Ala Ser Gly Pro
2450            2455            2460

GCC TGC GCC TCG CCT TCT CGG CAC GGC CGG CGA CTC CCC AAC GGC TAC      7676
Ala Cys Ala Ser Pro Ser Arg His Gly Arg Arg Leu Pro Asn Gly Tyr
2465            2470            2475            2480

TAC CCG GCG CAC GGA CTG GCC AGG CCC CGC GGG CCG GGC TCC AGG AAG      7724
Tyr Pro Ala His Gly Leu Ala Arg Pro Arg Gly Pro Gly Ser Arg Lys
            2485            2490            2495

GGC CTG CAC GAA CCC TAC AGC GAG AGT GAC GAT GAT TGG TGC TAAGCCCGGG  7776
Gly Leu His Glu Pro Tyr Ser Glu Ser Asp Asp Asp Trp Cys
            2500            2505            2510

CGAGGTGGCG CCCGCCCGGC CCCCCACGCA CC                                  7808
```

(2) INFORMATION FOR SEQ ID NO:23:

(i) SEQUENCE CHARACTERISTICS:
        (A) LENGTH: 7791 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 237..7037
        (D) OTHER INFORMATION: /standard_name= "Alpha-1A-2"

(xi) SEQUENCE DESCRIPTION: SEQ ID NO:23:

```
GATGTCCCGA GCTGCTATCC CCGGCTCGGC CCGGGCAGCC GCCTTCTGAG CCCCCGACCC      60

GAGGCGCCGA GCCGCCGCCG CCCGATGGGC TGGGCCGTGG AGCGTCTCCG CAGTCGTAGC     120

TCCAGCCGCC GCGCTCCCAG CCCCGGCAGC CTCAGCATCA GCGGCGGCGG CGGCGGCGGC     180

GGCGTCTTCC GCATCGTTCG CCGCAGCGTA ACCCGGAGCC CTTTGCTCTT TGCAGA        236

ATG GCC CGC TTC GGA GAC GAG ATG CCG GCC CGC TAC GGG GGA GGA GGC      284
Met Ala Arg Phe Gly Asp Glu Met Pro Ala Arg Tyr Gly Gly Gly Gly
 1               5                  10                  15

TCC GGG GCA GCC GCC GGG GTG GTC GTG GGC AGC GGA GGC GGG CGA GGA      332
Ser Gly Ala Ala Ala Gly Val Val Val Gly Ser Gly Gly Gly Arg Gly
             20                  25                  30

GCC GGG GGC AGC CGG CAG GGC GGG CAG CCC GGG GCG CAA AGG ATG TAC      380
Ala Gly Gly Ser Arg Gln Gly Gly Gln Pro Gly Ala Gln Arg Met Tyr
         35                  40                  45

AAG CAG TCA ATG GCG CAG AGA GCG CGG ACC ATG GCA CTC TAC AAC CCC      428
Lys Gln Ser Met Ala Gln Arg Ala Arg Thr Met Ala Leu Tyr Asn Pro
 50                  55                  60

ATC CCC GTC CGA CAG AAC TGC CTC ACG GTT AAC CGG TCT CTC TTC CTC      476
Ile Pro Val Arg Gln Asn Cys Leu Thr Val Asn Arg Ser Leu Phe Leu
 65                  70                  75                  80

TTC AGC GAA GAC AAC GTG GTG AGA AAA TAC GCC AAA AAG ATC ACC GAA      524
Phe Ser Glu Asp Asn Val Val Arg Lys Tyr Ala Lys Lys Ile Thr Glu
                 85                  90                  95

TGG CCT CCC TTT GAA TAT ATG ATT TTA GCC ACC ATC ATA GCG AAT TGC      572
Trp Pro Pro Phe Glu Tyr Met Ile Leu Ala Thr Ile Ile Ala Asn Cys
            100                 105                 110

ATC GTC CTC GCA CTG GAG CAG CAT CTG CCT GAT GAT GAC AAG ACC CCG      620
Ile Val Leu Ala Leu Glu Gln His Leu Pro Asp Asp Asp Lys Thr Pro
        115                 120                 125

ATG TCT GAA CGG CTG GAT GAC ACA GAA CCA TAC TTC ATT GGA ATT TTT      668
Met Ser Glu Arg Leu Asp Asp Thr Glu Pro Tyr Phe Ile Gly Ile Phe
    130                 135                 140

TGT TTC GAG GCT GGA ATT AAA ATC ATT GCC CTT GGG TTT GCC TTC CAC      716
Cys Phe Glu Ala Gly Ile Lys Ile Ile Ala Leu Gly Phe Ala Phe His
145                 150                 155                 160

AAA GGC TCC TAC TTG AGG AAT GGC TGG AAT GTC ATG GAC TTT GTG GTG      764
Lys Gly Ser Tyr Leu Arg Asn Gly Trp Asn Val Met Asp Phe Val Val
                165                 170                 175

GTG CTA ACG GGC ATC TTG GCG ACA GTT GGG ACG GAG TTT GAC CTA CGG      812
Val Leu Thr Gly Ile Leu Ala Thr Val Gly Thr Glu Phe Asp Leu Arg
            180                 185                 190

ACG CTG AGG GCA GTT CGA GTG CTG CGG CCG CTC AAG CTG GTG TCT GGA      860
Thr Leu Arg Ala Val Arg Val Leu Arg Pro Leu Lys Leu Val Ser Gly
        195                 200                 205

ATC CCA AGT TTA CAA GTC GTC CTG AAG TCG ATC ATG AAG GCG ATG ATC      908
```

```
Ile Pro Ser Leu Gln Val Val Leu Lys Ser Ile Met Lys Ala Met Ile
    210                 215                 220

CCT TTG CTG CAG ATC GGC CTC CTC CTA TTT TTT GCA ATC CTT ATT TTT      956
Pro Leu Leu Gln Ile Gly Leu Leu Leu Phe Phe Ala Ile Leu Ile Phe
225                 230                 235                 240

GCA ATC ATA GGG TTA GAA TTT TAT ATG GGA AAA TTT CAT ACC ACC TGC     1004
Ala Ile Ile Gly Leu Glu Phe Tyr Met Gly Lys Phe His Thr Thr Cys
                245                 250                 255

TTT GAA GAG GGG ACA GAT GAC ATT CAG GGT GAG TCT CCG GCT CCA TGT     1052
Phe Glu Glu Gly Thr Asp Asp Ile Gln Gly Glu Ser Pro Ala Pro Cys
                260                 265                 270

GGG ACA GAA GAG CCC GCC CGC ACC TGC CCC AAT GGG ACC AAA TGT CAG     1100
Gly Thr Glu Glu Pro Ala Arg Thr Cys Pro Asn Gly Thr Lys Cys Gln
            275                 280                 285

CCC TAC TGG GAA GGG CCC AAC AAC GGG ATC ACT CAG TTC GAC AAC ATC     1148
Pro Tyr Trp Glu Gly Pro Asn Asn Gly Ile Thr Gln Phe Asp Asn Ile
        290                 295                 300

CTG TTT GCA GTG CTG ACT GTT TTC CAG TGC ATA ACC ATG GAA GGG TGG     1196
Leu Phe Ala Val Leu Thr Val Phe Gln Cys Ile Thr Met Glu Gly Trp
305                 310                 315                 320

ACT GAT CTC CTC TAC AAT AGC AAC GAT GCC TCA GGG AAC ACT TGG AAC     1244
Thr Asp Leu Leu Tyr Asn Ser Asn Asp Ala Ser Gly Asn Thr Trp Asn
                325                 330                 335

TGG TTG TAC TTC ATC CCC CTC ATC ATC ATC GGC TCC TTT TTT ATG CTG     1292
Trp Leu Tyr Phe Ile Pro Leu Ile Ile Ile Gly Ser Phe Phe Met Leu
                340                 345                 350

AAC CTT GTG CTG GGT GTG CTG TCA GGG GAG TTT GCC AAA GAA AGG GAA     1340
Asn Leu Val Leu Gly Val Leu Ser Gly Glu Phe Ala Lys Glu Arg Glu
                355                 360                 365

CGG GTG GAG AAC CGG CGG GCT TTT CTG AAG CTG AGG CGG CAA CAA CAG     1388
Arg Val Glu Asn Arg Arg Ala Phe Leu Lys Leu Arg Arg Gln Gln Gln
370                 375                 380

ATT GAA CGT GAG CTC AAT GGG TAC ATG GAA TGG ATC TCA AAA GCA GAA     1436
Ile Glu Arg Glu Leu Asn Gly Tyr Met Glu Trp Ile Ser Lys Ala Glu
385                 390                 395                 400

GAG GTG ATC CTC GCC GAG GAT GAA ACT GAC GGG GAG CAG AGG CAT CCC     1484
Glu Val Ile Leu Ala Glu Asp Glu Thr Asp Gly Glu Gln Arg His Pro
                405                 410                 415

TTT GAT GGA GCT CTG CGG AGA ACC ACC ATA AAG AAA AGC AAG ACA GAT     1532
Phe Asp Gly Ala Leu Arg Arg Thr Thr Ile Lys Lys Ser Lys Thr Asp
            420                 425                 430

TTG CTC AAC CCC GAA GAG GCT GAG GAT CAG CTG GCT GAT ATA GCC TCT     1580
Leu Leu Asn Pro Glu Glu Ala Glu Asp Gln Leu Ala Asp Ile Ala Ser
        435                 440                 445

GTG GGT TCT CCC TTC GCC CGA GCC AGC ATT AAA AGT GCC AAG CTG GAG     1628
Val Gly Ser Pro Phe Ala Arg Ala Ser Ile Lys Ser Ala Lys Leu Glu
450                 455                 460

AAC TCG ACC TTT TTT CAC AAA AAG GAG AGG AGG ATG CGT TTC TAC ATC     1676
Asn Ser Thr Phe Phe His Lys Lys Glu Arg Arg Met Arg Phe Tyr Ile
465                 470                 475                 480

CGC CGC ATG GTC AAA ACT CAG GCC TTC TAC TGG ACT GTA CTC AGT TTG     1724
Arg Arg Met Val Lys Thr Gln Ala Phe Tyr Trp Thr Val Leu Ser Leu
                485                 490                 495

GTA GCT CTC AAC ACG CTG TGT GTT GCT ATT GTT CAC TAC AAC CAG CCC     1772
Val Ala Leu Asn Thr Leu Cys Val Ala Ile Val His Tyr Asn Gln Pro
                500                 505                 510

GAG TGG CTC TCC GAC TTC CTT TAC TAT GCA GAA TTC ATT TTC TTA GGA     1820
Glu Trp Leu Ser Asp Phe Leu Tyr Tyr Ala Glu Phe Ile Phe Leu Gly
            515                 520                 525
```

```
CTC TTT ATG TCC GAA ATG TTT ATA AAA ATG TAC GGG CTT GGG ACG CGG   1868
Leu Phe Met Ser Glu Met Phe Ile Lys Met Tyr Gly Leu Gly Thr Arg
    530             535             540

CCT TAC TTC CAC TCT TCC TTC AAC TGC TTT GAC TGT GGG GTT ATC ATT   1916
Pro Tyr Phe His Ser Ser Phe Asn Cys Phe Asp Cys Gly Val Ile Ile
545             550             555                 560

GGG AGC ATC TTC GAG GTC ATC TGG GCT GTC ATA AAA CCT GGC ACA TCC   1964
Gly Ser Ile Phe Glu Val Ile Trp Ala Val Ile Lys Pro Gly Thr Ser
            565             570             575

TTT GGA ATC AGC GTG TTA CGA GCC CTC AGG TTA TTG CGT ATT TTC AAA   2012
Phe Gly Ile Ser Val Leu Arg Ala Leu Arg Leu Leu Arg Ile Phe Lys
        580             585             590

GTC ACA AAG TAC TGG GCA TCT CTC AGA AAC CTG GTC GTC TCT CTC CTC   2060
Val Thr Lys Tyr Trp Ala Ser Leu Arg Asn Leu Val Val Ser Leu Leu
    595             600             605

AAC TCC ATG AAG TCC ATC ATC AGC CTG TTG TTT CTC CTT TTC CTG TTC   2108
Asn Ser Met Lys Ser Ile Ile Ser Leu Leu Phe Leu Leu Phe Leu Phe
610             615             620

ATT GTC GTC TTC GCC CTT TTG GGA ATG CAA CTC TTC GGC GGC CAG TTT   2156
Ile Val Val Phe Ala Leu Leu Gly Met Gln Leu Phe Gly Gly Gln Phe
625             630             635                 640

AAT TTC GAT GAA GGG ACT CCT CCC ACC AAC TTC GAT ACT TTT CCA GCA   2204
Asn Phe Asp Glu Gly Thr Pro Pro Thr Asn Phe Asp Thr Phe Pro Ala
            645             650             655

GCA ATA ATG ACG GTG TTT CAG ATC CTG ACG GGC GAA GAC TGG AAC GAG   2252
Ala Ile Met Thr Val Phe Gln Ile Leu Thr Gly Glu Asp Trp Asn Glu
        660             665             670

GTC ATG TAC GAC GGG ATC AAG TCT CAG GGG GGC GTG CAG GGC GGC ATG   2300
Val Met Tyr Asp Gly Ile Lys Ser Gln Gly Gly Val Gln Gly Gly Met
    675             680             685

GTG TTC TCC ATC TAT TTC ATT GTA CTG ACG CTC TTT GGG AAC TAC ACC   2348
Val Phe Ser Ile Tyr Phe Ile Val Leu Thr Leu Phe Gly Asn Tyr Thr
690             695             700

CTC CTG AAT GTG TTC TTG GCC ATC GCT GTG GAC AAT CTG GCC AAC GCC   2396
Leu Leu Asn Val Phe Leu Ala Ile Ala Val Asp Asn Leu Ala Asn Ala
705             710             715             720

CAG GAG CTC ACC AAG GTG GAG GCG GAC GAG CAA GAG GAA GAA GAA GCA   2444
Gln Glu Leu Thr Lys Val Glu Ala Asp Glu Gln Glu Glu Glu Glu Ala
            725             730             735

GCG AAC CAG AAA CTT GCC CTA CAG AAA GCC AAG GAG GTG GCA GAA GTG   2492
Ala Asn Gln Lys Leu Ala Leu Gln Lys Ala Lys Glu Val Ala Glu Val
        740             745             750

AGT CCT CTG TCC GCG GCC AAC ATG TCT ATA GCT GTG AAA GAG CAA CAG   2540
Ser Pro Leu Ser Ala Ala Asn Met Ser Ile Ala Val Lys Glu Gln Gln
    755             760             765

AAG AAT CAA AAG CCA GCC AAG TCC GTG TGG GAG CAG CGG ACC AGT GAG   2588
Lys Asn Gln Lys Pro Ala Lys Ser Val Trp Glu Gln Arg Thr Ser Glu
770             775             780

ATG CGA AAG CAG AAC TTG CTG GCC AGC CGG GAG GCC CTG TAT AAC GAA   2636
Met Arg Lys Gln Asn Leu Leu Ala Ser Arg Glu Ala Leu Tyr Asn Glu
785             790             795             800

ATG GAC CCG GAC GAG CGC TGG AAG GCT GCC TAC ACG CGG CAC CTG CGG   2684
Met Asp Pro Asp Glu Arg Trp Lys Ala Ala Tyr Thr Arg His Leu Arg
            805             810             815

CCA GAC ATG AAG ACG CAC TTG GAC CGG CCG CTG GTG GTG GAC CCG CAG   2732
Pro Asp Met Lys Thr His Leu Asp Arg Pro Leu Val Val Asp Pro Gln
        820             825             830

GAG AAC CGC AAC AAC AAC ACC AAC AAG AGC CGG GCG GCC GAG CCC ACC   2780
Glu Asn Arg Asn Asn Asn Thr Asn Lys Ser Arg Ala Ala Glu Pro Thr
    835             840             845
```

```
GTG GAC CAG CGC CTC GGC CAG CAG CGC GCC GAG GAC TTC CTC AGG AAA      2828
Val Asp Gln Arg Leu Gly Gln Gln Arg Ala Glu Asp Phe Leu Arg Lys
    850                 855                 860

CAG GCC CGC TAC CAC GAT CGG GCC CGG GAC CCC AGC GGC TCG GCG GGC      2876
Gln Ala Arg Tyr His Asp Arg Ala Arg Asp Pro Ser Gly Ser Ala Gly
865                 870                 875                 880

CTG GAC GCA CGG AGG CCC TGG GCG GGA AGC CAG GAG GCC GAG CTG AGC      2924
Leu Asp Ala Arg Arg Pro Trp Ala Gly Ser Gln Glu Ala Glu Leu Ser
                885                 890                 895

CGG GAG GGA CCC TAC GGC CGC GAG TCG GAC CAC CAC GCC CGG GAG GGC      2972
Arg Glu Gly Pro Tyr Gly Arg Glu Ser Asp His His Ala Arg Glu Gly
            900                 905                 910

AGC CTG GAG CAA CCC GGG TTC TGG GAG GGC GAG GCC GAG CGA GGC AAG      3020
Ser Leu Glu Gln Pro Gly Phe Trp Glu Gly Glu Ala Glu Arg Gly Lys
        915                 920                 925

GCC GGG GAC CCC CAC CGG AGG CAC GTG CAC CGG CAG GGG GGC AGC AGG      3068
Ala Gly Asp Pro His Arg Arg His Val His Arg Gln Gly Gly Ser Arg
    930                 935                 940

GAG AGC CGC AGC GGG TCC CCG CGC ACG GGC GCG GAC GGG GAG CAT CGA      3116
Glu Ser Arg Ser Gly Ser Pro Arg Thr Gly Ala Asp Gly Glu His Arg
945                 950                 955                 960

CGT CAT CGC GCG CAC CGC AGG CCC GGG GAG GAG GGT CCG GAG GAC AAG      3164
Arg His Arg Ala His Arg Arg Pro Gly Glu Glu Gly Pro Glu Asp Lys
                965                 970                 975

GCG GAG CGG AGG GCG CGG CAC CGC GAG GGC AGC CGG CCG GCC CGG GGC      3212
Ala Glu Arg Arg Ala Arg His Arg Glu Gly Ser Arg Pro Ala Arg Gly
            980                 985                 990

GGC GAG GGC GAG GGC GAG GGC CCC GAC GGG GGC GAG CGC AGG AGA AGG      3260
Gly Glu Gly Glu Gly Glu Gly Pro Asp Gly Gly Glu Arg Arg Arg Arg
        995                 1000                1005

CAC CGG CAT GGC GCT CCA GCC ACG TAC GAG GGG GAC GCG CGG AGG GAG      3308
His Arg His Gly Ala Pro Ala Thr Tyr Glu Gly Asp Ala Arg Arg Glu
    1010                1015                1020

GAC AAG GAG CGG AGG CAT CGG AGG AGG AAA GAG AAC CAG GGC TCC GGG      3356
Asp Lys Glu Arg Arg His Arg Arg Arg Lys Glu Asn Gln Gly Ser Gly
1025                1030                1035                1040

GTC CCT GTG TCG GGC CCC AAC CTG TCA ACC ACC CGG CCA ATC CAG CAG      3404
Val Pro Val Ser Gly Pro Asn Leu Ser Thr Thr Arg Pro Ile Gln Gln
                1045                1050                1055

GAC CTG GGC CGC CAA GAC CCA CCC CTG GCA GAG GAT ATT GAC AAC ATG      3452
Asp Leu Gly Arg Gln Asp Pro Pro Leu Ala Glu Asp Ile Asp Asn Met
            1060                1065                1070

AAG AAC AAC AAG CTG GCC ACC GCG GAG TCG GCC GCT CCC CAC GGC AGC      3500
Lys Asn Asn Lys Leu Ala Thr Ala Glu Ser Ala Ala Pro His Gly Ser
        1075                1080                1085

CTT GGC CAC GCC GGC CTG CCC CAG AGC CCA GCC AAG ATG GGA AAC AGC      3548
Leu Gly His Ala Gly Leu Pro Gln Ser Pro Ala Lys Met Gly Asn Ser
    1090                1095                1100

ACC GAC CCC GGC CCC ATG CTG GCC ATC CCT GCC ATG GCC ACC AAC CCC      3596
Thr Asp Pro Gly Pro Met Leu Ala Ile Pro Ala Met Ala Thr Asn Pro
1105                1110                1115                1120

CAG AAC GCC GCC AGC CGC CGG ACG CCC AAC AAC CCG GGG AAC CCA TCC      3644
Gln Asn Ala Ala Ser Arg Arg Thr Pro Asn Asn Pro Gly Asn Pro Ser
                1125                1130                1135

AAT CCC GGC CCC CCC AAG ACC CCC GAG AAT AGC CTT ATC GTC ACC AAC      3692
Asn Pro Gly Pro Pro Lys Thr Pro Glu Asn Ser Leu Ile Val Thr Asn
            1140                1145                1150

CCC AGC GGC ACC CAG ACC AAT TCA GCT AAG ACT GCC AGG AAA CCC GAC      3740
Pro Ser Gly Thr Gln Thr Asn Ser Ala Lys Thr Ala Arg Lys Pro Asp
```

-continued

|   |   |   |   |   |   |   |   |   |   |   |   |   |   |   |   |
|---|---|---|---|---|---|---|---|---|---|---|---|---|---|---|---|
| | | | | 1155 | | | | 1160 | | | | 1165 | | | |
| CAC | ACC | ACA | GTG | GAC | ATC | CCC | CCA | GCC | TGC | CCA | CCC | CCC | CTC | AAC | CAC | 3788 |
| His | Thr | Thr | Val | Asp | Ile | Pro | Pro | Ala | Cys | Pro | Pro | Pro | Leu | Asn | His | |
| | | | | 1170 | | | | | 1175 | | | | 1180 | | | |

ACC GTC GTA CAA GTG AAC AAA AAC GCC AAC CCA GAC CCA CTG CCA AAA  3836
Thr Val Val Gln Val Asn Lys Asn Ala Asn Pro Asp Pro Leu Pro Lys
1185                1190                1195                1200

AAA GAG GAA GAG AAG AAG GAG GAG GAG GAA GAC GAC CGT GGG GAA GAC  3884
Lys Glu Glu Glu Lys Lys Glu Glu Glu Asp Asp Arg Gly Glu Asp
              1205                1210                1215

GGC CCT AAG CCA ATG CCT CCC TAT AGC TCC ATG TTC ATC CTG TCC ACG  3932
Gly Pro Lys Pro Met Pro Pro Tyr Ser Ser Met Phe Ile Leu Ser Thr
              1220                1225                1230

ACC AAC CCC CTT CGC CGC CTG TGC CAT TAC ATC CTG AAC CTG CGC TAC  3980
Thr Asn Pro Leu Arg Arg Leu Cys His Tyr Ile Leu Asn Leu Arg Tyr
              1235                1240                1245

TTT GAG ATG TGC ATC CTC ATG GTC ATT GCC ATG AGC AGC ATC GCC CTG  4028
Phe Glu Met Cys Ile Leu Met Val Ile Ala Met Ser Ser Ile Ala Leu
          1250                1255                1260

GCC GCC GAG GAC CCT GTG CAG CCC AAC GCA CCT CGG AAC AAC GTG CTG  4076
Ala Ala Glu Asp Pro Val Gln Pro Asn Ala Pro Arg Asn Asn Val Leu
1265                1270                1275                1280

CGA TAC TTT GAC TAC GTT TTT ACA GGC GTC TTC ACC TTT GAG ATG GTG  4124
Arg Tyr Phe Asp Tyr Val Phe Thr Gly Val Phe Thr Phe Glu Met Val
              1285                1290                1295

ATC AAG ATG ATT GAC CTG GGG CTC GTC CTG CAT CAG GGT GCC TAC TTC  4172
Ile Lys Met Ile Asp Leu Gly Leu Val Leu His Gln Gly Ala Tyr Phe
          1300                1305                1310

CGT GAC CTC TGG AAT ATT CTC GAC TTC ATA GTG GTC AGT GGG GCC CTG  4220
Arg Asp Leu Trp Asn Ile Leu Asp Phe Ile Val Val Ser Gly Ala Leu
          1315                1320                1325

GTA GCC TTT GCC TTC ACT GGC AAT AGC AAA GGA AAA GAC ATC AAC ACG  4268
Val Ala Phe Ala Phe Thr Gly Asn Ser Lys Gly Lys Asp Ile Asn Thr
          1330                1335                1340

ATT AAA TCC CTC CGA GTC CTC CGG GTG CTA CGA CCT CTT AAA ACC ATC  4316
Ile Lys Ser Leu Arg Val Leu Arg Val Leu Arg Pro Leu Lys Thr Ile
1345                1350                1355                1360

AAG CGG CTG CCA AAG CTC AAG GCT GTG TTT GAC TGT GTG GTG AAC TCA  4364
Lys Arg Leu Pro Lys Leu Lys Ala Val Phe Asp Cys Val Val Asn Ser
              1365                1370                1375

CTT AAA AAC GTC TTC AAC ATC CTC ATC GTC TAC ATG CTA TTC ATG TTC  4412
Leu Lys Asn Val Phe Asn Ile Leu Ile Val Tyr Met Leu Phe Met Phe
              1380                1385                1390

ATC TTC GCC GTG GTG GCT GTG CAG CTC TTC AAG GGG AAA TTC TTC CAC  4460
Ile Phe Ala Val Val Ala Val Gln Leu Phe Lys Gly Lys Phe Phe His
          1395                1400                1405

TGC ACT GAC GAG TCC AAA GAG TTT GAG AAA GAT TGT CGA GGC AAA TAC  4508
Cys Thr Asp Glu Ser Lys Glu Phe Glu Lys Asp Cys Arg Gly Lys Tyr
          1410                1415                1420

CTC CTC TAC GAG AAG AAT GAG GTG AAG GCG CGA GAC CGG GAG TGG AAG  4556
Leu Leu Tyr Glu Lys Asn Glu Val Lys Ala Arg Asp Arg Glu Trp Lys
1425                1430                1435                1440

AAG TAT GAA TTC CAT TAC GAC AAT GTG CTG TGG GCT CTG CTG ACC CTC  4604
Lys Tyr Glu Phe His Tyr Asp Asn Val Leu Trp Ala Leu Leu Thr Leu
              1445                1450                1455

TTC ACC GTG TCC ACG GGA GAA GGC TGG CCA CAG GTC CTC AAG CAT TCG  4652
Phe Thr Val Ser Thr Gly Glu Gly Trp Pro Gln Val Leu Lys His Ser
              1460                1465                1470

GTG GAC GCC ACC TTT GAG AAC CAG GGC CCC AGC CCC GGG TAC CGC ATG  4700

```
Val Asp Ala Thr Phe Glu Asn Gln Gly Pro Ser Pro Gly Tyr Arg Met
        1475                1480                1485

GAG ATG TCC ATT TTC TAC GTC GTC TAC TTT GTG GTG TTC CCC TTC TTC      4748
Glu Met Ser Ile Phe Tyr Val Val Tyr Phe Val Val Phe Pro Phe Phe
    1490                1495                1500

TTT GTC AAT ATC TTT GTG GCC TTG ATC ATC ATC ACC TTC CAG GAG CAA      4796
Phe Val Asn Ile Phe Val Ala Leu Ile Ile Ile Thr Phe Gln Glu Gln
1505                1510                1515                1520

GGG GAC AAG ATG ATG GAG GAA TAC AGC CTG GAG AAA AAT GAG AGG GCC      4844
Gly Asp Lys Met Met Glu Glu Tyr Ser Leu Glu Lys Asn Glu Arg Ala
        1525                1530                1535

TGC ATT GAT TTC GCC ATC AGC GCC AAG CCG CTG ACC CGA CAC ATG CCG      4892
Cys Ile Asp Phe Ala Ile Ser Ala Lys Pro Leu Thr Arg His Met Pro
            1540                1545                1550

CAG AAC AAG CAG AGC TTC CAG TAC CGC ATG TGG CAG TTC GTG GTG TCT      4940
Gln Asn Lys Gln Ser Phe Gln Tyr Arg Met Trp Gln Phe Val Val Ser
            1555                1560                1565

CCG CCT TTC GAG TAC ACG ATC ATG GCC ATG ATC GCC CTC AAC ACC ATC      4988
Pro Pro Phe Glu Tyr Thr Ile Met Ala Met Ile Ala Leu Asn Thr Ile
    1570                1575                1580

GTG CTT ATG ATG AAG TTC TAT GGG GCT TCT GTT GCT TAT GAA AAT GCC      5036
Val Leu Met Met Lys Phe Tyr Gly Ala Ser Val Ala Tyr Glu Asn Ala
1585                1590                1595                1600

CTG CGG GTG TTC AAC ATC GTC TTC ACC TCC CTC TTC TCT CTG GAA TGT      5084
Leu Arg Val Phe Asn Ile Val Phe Thr Ser Leu Phe Ser Leu Glu Cys
            1605                1610                1615

GTG CTG AAA GTC ATG GCT TTT GGG ATT CTG AAT TAT TTC CGC GAT GCC      5132
Val Leu Lys Val Met Ala Phe Gly Ile Leu Asn Tyr Phe Arg Asp Ala
            1620                1625                1630

TGG AAC ATC TTC GAC TTT GTG ACT GTT CTG GGC AGC ATC ACC GAT ATC      5180
Trp Asn Ile Phe Asp Phe Val Thr Val Leu Gly Ser Ile Thr Asp Ile
        1635                1640                1645

CTC GTG ACT GAG TTT GGG AAT CCG AAT AAC TTC ATC AAC CTG AGC TTT      5228
Leu Val Thr Glu Phe Gly Asn Pro Asn Asn Phe Ile Asn Leu Ser Phe
    1650                1655                1660

CTC CGC CTC TTC CGA GCT GCC CGG CTC ATC AAA CTT CTC CGT CAG GGT      5276
Leu Arg Leu Phe Arg Ala Ala Arg Leu Ile Lys Leu Leu Arg Gln Gly
1665                1670                1675                1680

TAC ACC ATC CGC ATT CTT CTC TGG ACC TTT GTG CAG TCC TTC AAG GCC      5324
Tyr Thr Ile Arg Ile Leu Leu Trp Thr Phe Val Gln Ser Phe Lys Ala
            1685                1690                1695

CTG CCT TAT GTC TGT CTG CTG ATC GCC ATG CTC TTC TTC ATC TAT GCC      5372
Leu Pro Tyr Val Cys Leu Leu Ile Ala Met Leu Phe Phe Ile Tyr Ala
    1700                1705                1710

ATC ATT GGG ATG CAG GTG TTT GGT AAC ATT GGC ATC GAC GTG GAG GAC      5420
Ile Ile Gly Met Gln Val Phe Gly Asn Ile Gly Ile Asp Val Glu Asp
        1715                1720                1725

GAG GAC AGT GAT GAA GAT GAG TTC CAA ATC ACT GAG CAC AAT AAC TTC      5468
Glu Asp Ser Asp Glu Asp Glu Phe Gln Ile Thr Glu His Asn Asn Phe
    1730                1735                1740

CGG ACC TTC TTC CAG GCC CTC ATG CTT CTC TTC CGG AGT GCC ACC GGG      5516
Arg Thr Phe Phe Gln Ala Leu Met Leu Leu Phe Arg Ser Ala Thr Gly
1745                1750                1755                1760

GAA GCT TGG CAC AAC ATC ATG CTT TCC TGC CTC AGC GGG AAA CCG TGT      5564
Glu Ala Trp His Asn Ile Met Leu Ser Cys Leu Ser Gly Lys Pro Cys
            1765                1770                1775

GAT AAG AAC TCT GGC ATC CTG ACT CGA GAG TGT GGC AAT GAA TTT GCT      5612
Asp Lys Asn Ser Gly Ile Leu Thr Arg Glu Cys Gly Asn Glu Phe Ala
    1780                1785                1790
```

-continued

| | | |
|---|---|---|
| TAT TTT TAC TTT GTT TCC TTC ATC TTC CTC TGC TCG TTT CTG ATG CTG<br>Tyr Phe Tyr Phe Val Ser Phe Ile Phe Leu Cys Ser Phe Leu Met Leu<br>       1795                     1800                   1805 | 5660 |
| AAT CTC TTT GTC GCC GTC ATC ATG GAC AAC TTT GAG TAC CTC ACC CGA<br>Asn Leu Phe Val Ala Val Ile Met Asp Asn Phe Glu Tyr Leu Thr Arg<br>    1810                     1815                  1820 | 5708 |
| GAC TCC TCC ATC CTG GGC CCC CAC CAC CTG GAT GAG TAC GTG CGT GTC<br>Asp Ser Ser Ile Leu Gly Pro His His Leu Asp Glu Tyr Val Arg Val<br>1825                   1830                   1835                  1840 | 5756 |
| TGG GCC GAG TAT GAC CCC GCA GCT TGG GGC CGC ATG CCT TAC CTG GAC<br>Trp Ala Glu Tyr Asp Pro Ala Ala Trp Gly Arg Met Pro Tyr Leu Asp<br>               1845                   1850                  1855 | 5804 |
| ATG TAT CAG ATG CTG AGA CAC ATG TCT CCG CCC CTG GGT CTG GGG AAG<br>Met Tyr Gln Met Leu Arg His Met Ser Pro Pro Leu Gly Leu Gly Lys<br>               1860                   1865                  1870 | 5852 |
| AAG TGT CCG GCC AGA GTG GCT TAC AAG CGG CTT CTG CGG ATG GAC CTG<br>Lys Cys Pro Ala Arg Val Ala Tyr Lys Arg Leu Leu Arg Met Asp Leu<br>             1875                   1880                  1885 | 5900 |
| CCC GTC GCA GAT GAC AAC ACC GTC CAC TTC AAT TCC ACC CTC ATG GCT<br>Pro Val Ala Asp Asp Asn Thr Val His Phe Asn Ser Thr Leu Met Ala<br>    1890                     1895                  1900 | 5948 |
| CTG ATC CGC ACA GCC CTG GAC ATC AAG ATT GCC AAG GGA GGA GCC GAC<br>Leu Ile Arg Thr Ala Leu Asp Ile Lys Ile Ala Lys Gly Gly Ala Asp<br>1905                   1910                   1915                  1920 | 5996 |
| AAA CAG CAG ATG GAC GCT GAG CTG CGG AAG GAG ATG ATG GCG ATT TGG<br>Lys Gln Gln Met Asp Ala Glu Leu Arg Lys Glu Met Met Ala Ile Trp<br>               1925                   1930                  1935 | 6044 |
| CCC AAT CTG TCC CAG AAG ACG CTA GAC CTG CTG GTC ACA CCT CAC AAG<br>Pro Asn Leu Ser Gln Lys Thr Leu Asp Leu Leu Val Thr Pro His Lys<br>    1940                     1945                  1950 | 6092 |
| TCC ACG GAC CTC ACC GTG GGG AAG ATC TAC GCA GCC ATG ATG ATC ATG<br>Ser Thr Asp Leu Thr Val Gly Lys Ile Tyr Ala Ala Met Met Ile Met<br>             1955                   1960                  1965 | 6140 |
| GAG TAC TAC CGG CAG AGC AAG GCC AAG AAG CTG CAG GCC ATG CGC GAG<br>Glu Tyr Tyr Arg Gln Ser Lys Ala Lys Lys Leu Gln Ala Met Arg Glu<br>    1970                     1975                  1980 | 6188 |
| GAG CAG GAC CGG ACA CCC CTC ATG TTC CAG CGC ATG GAG CCC CCG TCC<br>Glu Gln Asp Arg Thr Pro Leu Met Phe Gln Arg Met Glu Pro Pro Ser<br>1985                   1990                   1995                  2000 | 6236 |
| CCA ACG CAG GAA GGG GGA CCT GGC CAG AAC GCC CTC CCC TCC ACC CAG<br>Pro Thr Gln Glu Gly Gly Pro Gly Gln Asn Ala Leu Pro Ser Thr Gln<br>             2005                   2010                  2015 | 6284 |
| CTG GAC CCA GGA GGA GCC CTG ATG GCT CAC GAA AGC GGC CTC AAG GAG<br>Leu Asp Pro Gly Gly Ala Leu Met Ala His Glu Ser Gly Leu Lys Glu<br>    2020                     2025                  2030 | 6332 |
| AGC CCG TCC TGG GTG ACC CAG CGT GCC CAG GAG ATG TTC CAG AAG ACG<br>Ser Pro Ser Trp Val Thr Gln Arg Ala Gln Glu Met Phe Gln Lys Thr<br>             2035                   2040                  2045 | 6380 |
| GGC ACA TGG AGT CCG GAA CAA GGC CCC CCT ACC GAC ATG CCC AAC AGC<br>Gly Thr Trp Ser Pro Glu Gln Gly Pro Pro Thr Asp Met Pro Asn Ser<br>    2050                     2055                  2060 | 6428 |
| CAG CCT AAC TCT CAG TCC GTG GAG ATG CGA GAG ATG GGC AGA GAT GGC<br>Gln Pro Asn Ser Gln Ser Val Glu Met Arg Glu Met Gly Arg Asp Gly<br>2065                   2070                   2075                  2080 | 6476 |
| TAC TCC GAC AGC GAG CAC TAC CTC CCC ATG GAA GGC CAG GGC CGG GCT<br>Tyr Ser Asp Ser Glu His Tyr Leu Pro Met Glu Gly Gln Gly Arg Ala<br>               2085                   2090                  2095 | 6524 |
| GCC TCC ATG CCC CGC CTC CCT GCA GAG AAC CAG AGG AGA AGG GGC CGG<br>Ala Ser Met Pro Arg Leu Pro Ala Glu Asn Gln Arg Arg Arg Gly Arg<br>    2100                     2105                  2110 | 6572 |

```
CCA CGT GGG AAT AAC CTC AGT ACC ATC TCA GAC ACC AGC CCC ATG AAG      6620
Pro Arg Gly Asn Asn Leu Ser Thr Ile Ser Asp Thr Ser Pro Met Lys
            2115                2120                2125

CGT TCA GCC TCC GTG CTG GGC CCC AAG GCC CGA CGC CTG GAC GAT TAC      6668
Arg Ser Ala Ser Val Leu Gly Pro Lys Ala Arg Arg Leu Asp Asp Tyr
    2130                2135                2140

TCG CTG GAG CGG GTC CCG CCC GAG GAG AAC CAG CGG CAC CAC CAG CGG      6716
Ser Leu Glu Arg Val Pro Pro Glu Glu Asn Gln Arg His His Gln Arg
2145                2150                2155                2160

CGC CGC GAC CGC AGC CAC CGC GCC TCT GAG CGC TCC CTG GGC CGC TAC      6764
Arg Arg Asp Arg Ser His Arg Ala Ser Glu Arg Ser Leu Gly Arg Tyr
                2165                2170                2175

ACC GAT GTG GAC ACA GGC TTG GGG ACA GAC CTG AGC ATG ACC ACC CAA      6812
Thr Asp Val Asp Thr Gly Leu Gly Thr Asp Leu Ser Met Thr Thr Gln
            2180                2185                2190

TCC GGG GAC CTG CCG TCG AAG GAG CGG GAC CAG GAG CGG GGC CGG CCC      6860
Ser Gly Asp Leu Pro Ser Lys Glu Arg Asp Gln Glu Arg Gly Arg Pro
        2195                2200                2205

AAG GAT CGG AAG CAT CGA CAG CAC CAC CAC CAC CAC CAC CAC CAC CAC      6908
Lys Asp Arg Lys His Arg Gln His His His His His His His His His
    2210                2215                2220

CAT CCC CCG CCC CCC GAC AAG GAC CGC TAT GCC CAG GAA CGG CCG GAC      6956
His Pro Pro Pro Pro Asp Lys Asp Arg Tyr Ala Gln Glu Arg Pro Asp
2225                2230                2235                2240

CAC GGC CGG GCA CGG GCT CGG GAC CAG CGC TGG TCC CGC TCG CCC AGC      7004
His Gly Arg Ala Arg Ala Arg Asp Gln Arg Trp Ser Arg Ser Pro Ser
                2245                2250                2255

GAG GGC CGA GAG CAC ATG GCG CAC CGG CAG TAGTTCCGTA AGTGGAAGCC        7054
Glu Gly Arg Glu His Met Ala His Arg Gln
            2260                2265

CAGCCCCCTC AACATCTGGT ACCAGCACTC CGCGGCGGGG CCGCCGCCAG CTCCCCCAGA    7114

CCCCCTCCAC CCCCCGGCCA CACGTGTCCT ATTCCCCTGT GATCCGTAAG GCCGGCGGCT    7174

CGGGGCCCCC GCAGCAGCAG CAGCAGCAGC AGGCGGTGGC CAGGCCGGGC CGGGCGGCCA    7234

CCAGCGGCCC TCGGAGGTAC CCAGGCCCCA CGGCCGAGCC TCTGGCCGGA GATCGGCCGC    7294

CCACGGGGGG CCACAGCAGC GGCCGCTCGC CCAGGATGGA GAGGCGGGTC CCAGGCCCGG    7354

CCCGGAGCGA GTCCCCCAGG GCCTGTCGAC ACGGCGGGGC CCGGTGGCCG GCATCTGGCC    7414

CGCACGTGTC CGAGGGGCCC CCGGGTCCCC GGCACCATGG CTACTACCGG GGCTCCGACT    7474

ACGACGAGGC CGATGGCCCG GGCAGCGGGG GCGGCGAGGA GGCCATGGCC GGGGCCTACG    7534

ACGCGCCACC CCCCGTACGA CACGCGTCCT CGGGCGCCAC CGGGCGCTCG CCCAGGACTC    7594

CCCGGGCCTC GGGCCCGGCC TGCGCCTCGC CTTCTCGGCA CGGCCGGCGA CTCCCCAACG    7654

GCTACTACCC GGCGCACGGA CTGGCCAGGC CCCGCGGGCC GGGCTCCAGG AAGGGCCTGC    7714

ACGAACCCTA CAGCGAGAGT GACGATGATT GGTGCTAAGC CCGGGCGAGG TGGCGCCCGC    7774

CCGGCCCCCC ACGCACC                                                   7791

(2) INFORMATION FOR SEQ ID NO:24:

(i) SEQUENCE CHARACTERISTICS:
            (A) LENGTH: 7032 base pairs
            (B) TYPE: nucleic acid
            (C) STRANDEDNESS: double
            (D) TOPOLOGY: linear (ii) MOLECULE TYPE: DNA (genomic)

(ix) FEATURE:
```

```
         (A) NAME/KEY: CDS
         (B) LOCATION: 166..6921
         (D) OTHER INFORMATION: /standard_name= "Alpha-1E-1"

(xi) SEQUENCE DESCRIPTION: SEQ ID NO:24:

GCTGCTGCTG CCTCTCCGAA GAGCTCGCGG AGCTCCCCAG AGGCGGTGGT CCCCGTGCTT        60

GTCTGGATGC GGCTCTGAGT CTCCGTGTGT CTTTCTGCTT GTTGCTGTGT GCGGGTGTTC       120

GGCCGCGATC ACCTTTGTGT GTCTTCTGTC TGTTTAAACC TCAGG ATG GCT CGC          174
                                              Met Ala Arg
                                                1

TTC GGG GAG GCG GTG GTC GCC AGG CCA GGG TCC GGC GAT GGA GAC TCG         222
Phe Gly Glu Ala Val Val Ala Arg Pro Gly Ser Gly Asp Gly Asp Ser
      5              10                  15

GAC CAG AGC AGG AAC CGG CAA GGA ACC CCC GTG CCG GCC TCG GGG CAG         270
Asp Gln Ser Arg Asn Arg Gln Gly Thr Pro Val Pro Ala Ser Gly Gln
 20              25                  30                  35

GCG GCC GCC TAC AAG CAG ACG AAA GCA CAG AGG GCG CGG ACT ATG GCT         318
Ala Ala Ala Tyr Lys Gln Thr Lys Ala Gln Arg Ala Arg Thr Met Ala
             40                  45                  50

TTG TAC AAC CCC ATT CCC GTC CGG CAG AAC TGT TTC ACC GTC AAC AGA         366
Leu Tyr Asn Pro Ile Pro Val Arg Gln Asn Cys Phe Thr Val Asn Arg
                 55                  60                  65

TCC CTG TTC ATC TTC GGA GAA GAT AAC ATT GTC AGG AAA TAT GCC AAG         414
Ser Leu Phe Ile Phe Gly Glu Asp Asn Ile Val Arg Lys Tyr Ala Lys
         70                  75                  80

AAG CTC ATC GAT TGG CCG CCA TTT GAG TAC ATG ATC CTG GCC ACC ATC         462
Lys Leu Ile Asp Trp Pro Pro Phe Glu Tyr Met Ile Leu Ala Thr Ile
 85                  90                  95

ATT GCC AAC TGC ATC GTC CTG GCC CTG GAG CAG CAT CTT CCT GAG GAT         510
Ile Ala Asn Cys Ile Val Leu Ala Leu Glu Gln His Leu Pro Glu Asp
100                 105                 110                 115

GAC AAG ACC CCC ATG TCC CGA AGA CTG GAG AAG ACA GAA CCT TAT TTC         558
Asp Lys Thr Pro Met Ser Arg Arg Leu Glu Lys Thr Glu Pro Tyr Phe
                120                 125                 130

ATT GGG ATC TTT TGC TTT GAA GCT GGG ATC AAA ATT GTG GCC CTG GGG         606
Ile Gly Ile Phe Cys Phe Glu Ala Gly Ile Lys Ile Val Ala Leu Gly
            135                 140                 145

TTC ATC TTC CAT AAG GGC TCT TAC CTC CGC AAT GGC TGG AAT GTC ATG         654
Phe Ile Phe His Lys Gly Ser Tyr Leu Arg Asn Gly Trp Asn Val Met
        150                 155                 160

GAC TTC ATC GTG GTC CTC AGT GGC ATC CTG GCC ACT GCA GGA ACC CAC         702
Asp Phe Ile Val Val Leu Ser Gly Ile Leu Ala Thr Ala Gly Thr His
    165                 170                 175

TTC AAT ACT CAC GTG GAC CTG AGG ACC CTC CGG GCT GTG CGT GTC CTG         750
Phe Asn Thr His Val Asp Leu Arg Thr Leu Arg Ala Val Arg Val Leu
180                 185                 190                 195

CGG CCT TTG AAG CTC GTG TCA GGG ATA CCT AGC CTG CAG ATT GTG TTG         798
Arg Pro Leu Lys Leu Val Ser Gly Ile Pro Ser Leu Gln Ile Val Leu
                200                 205                 210

AAG TCC ATC ATG AAG GCC ATG GTA CCT CTT CTG CAG ATT GGC CTT CTG         846
Lys Ser Ile Met Lys Ala Met Val Pro Leu Leu Gln Ile Gly Leu Leu
            215                 220                 225

CTC TTC TTT GCC ATC CTG ATG TTT GCT ATC ATT GGT TTG GAG TTC TAC         894
Leu Phe Phe Ala Ile Leu Met Phe Ala Ile Ile Gly Leu Glu Phe Tyr
        230                 235                 240

AGT GGC AAG TTA CAT CGA GCG TGC TTC ATG AAC AAT TCA GGT ATT CTA         942
Ser Gly Lys Leu His Arg Ala Cys Phe Met Asn Asn Ser Gly Ile Leu
    245                 250                 255

GAA GGA TTT GAC CCC CCT CAC CCA TGT GGT GTG CAG GGC TGC CCA GCT         990
Glu Gly Phe Asp Pro Pro His Pro Cys Gly Val Gln Gly Cys Pro Ala
```

```
                Glu Gly Phe Asp Pro Pro His Pro Cys Gly Val Gln Gly Cys Pro Ala
                260                 265                 270                 275

GGT TAT GAA TGC AAG GAC TGG ATC GGC CCC AAT GAT GGG ATC ACC CAG         1038
Gly Tyr Glu Cys Lys Asp Trp Ile Gly Pro Asn Asp Gly Ile Thr Gln
                280                 285                 290

TTT GAT AAC ATC CTT TTT GCT GTG CTG ACT GTC TTC CAG TGC ATC ACC         1086
Phe Asp Asn Ile Leu Phe Ala Val Leu Thr Val Phe Gln Cys Ile Thr
                295                 300                 305

ATG GAA GGG TGG ACC ACT GTG CTG TAC AAT ACC AAT GAT GCC TTA GGA         1134
Met Glu Gly Trp Thr Thr Val Leu Tyr Asn Thr Asn Asp Ala Leu Gly
                310                 315                 320

GCC ACC TGG AAT TGG CTG TAC TTC ATC CCC CTC ATC ATC ATT GGA TCC         1182
Ala Thr Trp Asn Trp Leu Tyr Phe Ile Pro Leu Ile Ile Ile Gly Ser
                325                 330                 335

TTC TTT GTT CTC AAC CTA GTC CTG GGA GTG CTT TCC GGG GAA TTT GCC         1230
Phe Phe Val Leu Asn Leu Val Leu Gly Val Leu Ser Gly Glu Phe Ala
340                 345                 350                 355

AAA GAG AGA GAG AGA GTG GAG AAC CGA AGG GCT TTC ATG AAG CTG CGG         1278
Lys Glu Arg Glu Arg Val Glu Asn Arg Arg Ala Phe Met Lys Leu Arg
                360                 365                 370

CGC CAG CAG CAG ATT GAG CGT GAG CTG AAT GGC TAC CGT GCC TGG ATA         1326
Arg Gln Gln Gln Ile Glu Arg Glu Leu Asn Gly Tyr Arg Ala Trp Ile
                375                 380                 385

GAC AAA GCA GAG GAA GTC ATG CTC GCT GAA GAA AAT AAA AAT GCT GGA         1374
Asp Lys Ala Glu Glu Val Met Leu Ala Glu Glu Asn Lys Asn Ala Gly
                390                 395                 400

ACA TCC GCC TTA GAA GTG CTT CGA AGG GCA ACC ATC AAG AGG AGC CGG         1422
Thr Ser Ala Leu Glu Val Leu Arg Arg Ala Thr Ile Lys Arg Ser Arg
                405                 410                 415

ACA GAG GCC ATG ACT CGA GAC TCC AGT GAT GAG CAC TGT GTT GAT ATC         1470
Thr Glu Ala Met Thr Arg Asp Ser Ser Asp Glu His Cys Val Asp Ile
420                 425                 430                 435

TCC TCT GTG GGC ACA CCT CTG GCC CGA GCC AGT ATC AAA AGT GCA AAG         1518
Ser Ser Val Gly Thr Pro Leu Ala Arg Ala Ser Ile Lys Ser Ala Lys
                440                 445                 450

GTA GAC GGG GTC TCT TAT TTC CGG CAC AAG GAA AGG CTT CTG CGC ATC         1566
Val Asp Gly Val Ser Tyr Phe Arg His Lys Glu Arg Leu Leu Arg Ile
                455                 460                 465

TCC ATT CGC CAC ATG GTT AAA TCC CAG GTG TTT TAC TGG ATT GTG CTG         1614
Ser Ile Arg His Met Val Lys Ser Gln Val Phe Tyr Trp Ile Val Leu
                470                 475                 480

AGC CTT GTG GCA CTC AAC ACT GCC TGT GTG GCC ATT GTC CAT CAC AAC         1662
Ser Leu Val Ala Leu Asn Thr Ala Cys Val Ala Ile Val His His Asn
485                 490                 495

CAG CCC CAG TGG CTC ACC CAC CTC CTC TAC TAT GCA GAA TTT CTG TTT         1710
Gln Pro Gln Trp Leu Thr His Leu Leu Tyr Tyr Ala Glu Phe Leu Phe
500                 505                 510                 515

CTG GGA CTC TTC CTC TTG GAG ATG TCC CTG AAG ATG TAT GGC ATG GGG         1758
Leu Gly Leu Phe Leu Leu Glu Met Ser Leu Lys Met Tyr Gly Met Gly
                520                 525                 530

CCT CGC CTT TAT TTT CAC TCT TCA TTC AAC TGC TTT GAT TTT GGG GTC         1806
Pro Arg Leu Tyr Phe His Ser Ser Phe Asn Cys Phe Asp Phe Gly Val
                535                 540                 545

ACA GTG GGC AGT ATC TTT GAA GTG GTC TGG GCA ATC TTC AGA CCT GGT         1854
Thr Val Gly Ser Ile Phe Glu Val Val Trp Ala Ile Phe Arg Pro Gly
                550                 555                 560

ACG TCT TTT GGA ATC AGT GTC TTG CGA GCC CTC CGG CTT CTA AGA ATA         1902
Thr Ser Phe Gly Ile Ser Val Leu Arg Ala Leu Arg Leu Leu Arg Ile
                565                 570                 575
```

```
TTT AAA ATA ACC AAG TAT TGG GCT TCC CTA CGG AAT TTG GTG GTC TCC    1950
Phe Lys Ile Thr Lys Tyr Trp Ala Ser Leu Arg Asn Leu Val Val Ser
580                 585                 590                 595

TTG ATG AGC TCA ATG AAG TCT ATC ATC AGT TTG CTT TTC CTC CTC TTC    1998
Leu Met Ser Ser Met Lys Ser Ile Ile Ser Leu Leu Phe Leu Leu Phe
                    600                 605                 610

CTC TTC ATC GTT GTC TTT GCT CTC CTA GGA ATG CAG TTA TTT GGA GGC    2046
Leu Phe Ile Val Val Phe Ala Leu Leu Gly Met Gln Leu Phe Gly Gly
                615                 620                 625

AGG TTT AAC TTT AAT GAT GGG ACT CCT TCG GCA AAT TTT GAT ACC TTC    2094
Arg Phe Asn Phe Asn Asp Gly Thr Pro Ser Ala Asn Phe Asp Thr Phe
            630                 635                 640

CCT GCA GCC ATC ATG ACT GTG TTC CAG ATC CTG ACG GGT GAG GAC TGG    2142
Pro Ala Ala Ile Met Thr Val Phe Gln Ile Leu Thr Gly Glu Asp Trp
        645                 650                 655

AAT GAG GTG ATG TAC AAT GGG ATC CGC TCC CAG GGT GGG GTC AGC TCA    2190
Asn Glu Val Met Tyr Asn Gly Ile Arg Ser Gln Gly Gly Val Ser Ser
660                 665                 670                 675

GGC ATG TGG TCT GCC ATC TAC TTC ATT GTG CTC ACC TTG TTT GGC AAC    2238
Gly Met Trp Ser Ala Ile Tyr Phe Ile Val Leu Thr Leu Phe Gly Asn
                680                 685                 690

TAC ACG CTA CTG AAT GTG TTC TTG GCT ATC GCT GTG GAT AAT CTC GCC    2286
Tyr Thr Leu Leu Asn Val Phe Leu Ala Ile Ala Val Asp Asn Leu Ala
            695                 700                 705

AAC GCC CAG GAA CTG ACC AAG GAT GAA CAG GAG GAA GAA GAG GCC TTC    2334
Asn Ala Gln Glu Leu Thr Lys Asp Glu Gln Glu Glu Glu Glu Ala Phe
        710                 715                 720

AAC CAG AAA CAT GCA CTG CAG AAG GCC AAG GAG GTC AGC CCG ATG TCT    2382
Asn Gln Lys His Ala Leu Gln Lys Ala Lys Glu Val Ser Pro Met Ser
725                 730                 735

GCA CCC AAC ATG CCT TCG ATC GAG AGG GAG CGG AGG CGC GGC CAC CAC    2430
Ala Pro Asn Met Pro Ser Ile Glu Arg Glu Arg Arg Arg His His
740                 745                 750                 755

ATG TCC GTG TGG GAG CAG CGT ACC AGC CAG CTG AGG AAG CAC ATG CAG    2478
Met Ser Val Trp Glu Gln Arg Thr Ser Gln Leu Arg Lys His Met Gln
                760                 765                 770

ATG TCC AGC CAG GAG GCC CTC AAC AGA GAG GAG GCG CCG ACC ATG AAC    2526
Met Ser Ser Gln Glu Ala Leu Asn Arg Glu Glu Ala Pro Thr Met Asn
            775                 780                 785

CCG CTC AAC CCC CTC AAC CCG CTC AGC TCC CTC AAC CCG CTC AAT GCC    2574
Pro Leu Asn Pro Leu Asn Pro Leu Ser Ser Leu Asn Pro Leu Asn Ala
        790                 795                 800

CAC CCC AGC CTT TAT CGG CGA CCC AGG GCC ATT GAG GGC CTG GCC CTG    2622
His Pro Ser Leu Tyr Arg Arg Pro Arg Ala Ile Glu Gly Leu Ala Leu
    805                 810                 815

GGC CTG GCC CTG GAG AAG TTC GAG GAG GAG CGC ATC AGC CGT GGG GGG    2670
Gly Leu Ala Leu Glu Lys Phe Glu Glu Glu Arg Ile Ser Arg Gly Gly
820                 825                 830                 835

TCC CTC AAG GGG GAT GGA GGG GAC CGA TCC AGT GCC CTG GAC AAC CAG    2718
Ser Leu Lys Gly Asp Gly Gly Asp Arg Ser Ser Ala Leu Asp Asn Gln
                840                 845                 850

AGG ACC CCT TTG TCC CTG GGC CAG CGG GAG CCA CCA TGG CTG GCC AGG    2766
Arg Thr Pro Leu Ser Leu Gly Gln Arg Glu Pro Pro Trp Leu Ala Arg
            855                 860                 865

CCC TGT CAT GGA AAC TGT GAC CCG ACT CAG CAG GAG GCA GGG GGA GGA    2814
Pro Cys His Gly Asn Cys Asp Pro Thr Gln Gln Glu Ala Gly Gly Gly
        870                 875                 880

GAG GCT GTG GTG ACC TTT GAG GAC CGG GCC AGG CAC AGG CAG AGC CAA    2862
Glu Ala Val Val Thr Phe Glu Asp Arg Ala Arg His Arg Gln Ser Gln
    885                 890                 895
```

-continued

| | |
|---|---|
| CGG CGC AGC CGG CAT CGC CGC GTC AGG ACA GAA GGC AAG GAG TCC TCT<br>Arg Arg Ser Arg His Arg Arg Val Arg Thr Glu Gly Lys Glu Ser Ser<br>900     905     910     915 | 2910 |
| TCA GCC TCC CGG AGC AGG TCT GCC AGC CAG GAA CGC AGT CTG GAT GAA<br>Ser Ala Ser Arg Ser Arg Ser Ala Ser Gln Glu Arg Ser Leu Asp Glu<br>    920     925     930 | 2958 |
| GCC ATG CCC ACT GAA GGG GAG AAG GAC CAT GAG CTC AGG GGC AAC CAT<br>Ala Met Pro Thr Glu Gly Glu Lys Asp His Glu Leu Arg Gly Asn His<br>     935     940     945 | 3006 |
| GGT GCC AAG GAG CCA ACG ATC CAA GAA GAG AGA GCC CAG GAT TTA AGG<br>Gly Ala Lys Glu Pro Thr Ile Gln Glu Glu Arg Ala Gln Asp Leu Arg<br>950     955     960 | 3054 |
| AGG ACC AAC AGT CTG ATG GTG TCC AGA GGC TCC GGG CTG GCA GGA GGC<br>Arg Thr Asn Ser Leu Met Val Ser Arg Gly Ser Gly Leu Ala Gly Gly<br>  965     970     975 | 3102 |
| CTT GAT GAG GCT GAC ACC CCC CTA GTC CTG CCC CAT CCT GAG CTG GAA<br>Leu Asp Glu Ala Asp Thr Pro Leu Val Leu Pro His Pro Glu Leu Glu<br>980     985     990     995 | 3150 |
| GTG GGG AAG CAC GTG GTG CTG ACG GAG CAG GAG CCA GAA GGC AGC AGT<br>Val Gly Lys His Val Val Leu Thr Glu Gln Glu Pro Glu Gly Ser Ser<br>    1000     1005     1010 | 3198 |
| GAG CAG GCC CTG CTG GGG AAT GTG CAG CTA GAC ATG GGC CGG GTC ATC<br>Glu Gln Ala Leu Leu Gly Asn Val Gln Leu Asp Met Gly Arg Val Ile<br>    1015     1020     1025 | 3246 |
| AGC CAG AGC GAG CCT GAC CTC TCC TGC ATC ACG GCC AAC ACG GAC AAG<br>Ser Gln Ser Glu Pro Asp Leu Ser Cys Ile Thr Ala Asn Thr Asp Lys<br>    1030     1035     1040 | 3294 |
| GCC ACC ACC GAG AGC ACC AGC GTC ACC GTC GCC ATC CCC GAC GTG GAC<br>Ala Thr Thr Glu Ser Thr Ser Val Thr Val Ala Ile Pro Asp Val Asp<br>1045     1050     1055 | 3342 |
| CCC TTG GTG GAC TCA ACC GTG GTG CAC ATT AGC AAC AAG ACG GAT GGG<br>Pro Leu Val Asp Ser Thr Val Val His Ile Ser Asn Lys Thr Asp Gly<br>1060     1065     1070     1075 | 3390 |
| GAA GCC AGT CCC TTG AAG GAG GCA GAG ATC AGA GAG GAT GAG GAG GAG<br>Glu Ala Ser Pro Leu Lys Glu Ala Glu Ile Arg Glu Asp Glu Glu Glu<br>    1080     1085     1090 | 3438 |
| GTG GAG AAG AAG AAG CAG AAG AAG GAG AAG CGT GAG ACA GGC AAA GCC<br>Val Glu Lys Lys Lys Gln Lys Lys Glu Lys Arg Glu Thr Gly Lys Ala<br>    1095     1100     1105 | 3486 |
| ATG GTG CCC CAC AGC TCA ATG TTC ATC TTC AGC ACC ACC AAC CCG ATC<br>Met Val Pro His Ser Ser Met Phe Ile Phe Ser Thr Thr Asn Pro Ile<br>    1110     1115     1120 | 3534 |
| CGG AGG GCC TGC CAC TAC ATC GTG AAC CTG CGC TAC TTT GAG ATG TGC<br>Arg Arg Ala Cys His Tyr Ile Val Asn Leu Arg Tyr Phe Glu Met Cys<br>1125     1130     1135 | 3582 |
| ATC CTC CTG GTG ATT GCA GCC AGC AGC ATC GCC CTG GCG GCA GAG GAC<br>Ile Leu Leu Val Ile Ala Ala Ser Ser Ile Ala Leu Ala Ala Glu Asp<br>1140     1145     1150     1155 | 3630 |
| CCC GTC CTG ACC AAC TCG GAG CGC AAC AAA GTC CTG AGG TAT TTT GAC<br>Pro Val Leu Thr Asn Ser Glu Arg Asn Lys Val Leu Arg Tyr Phe Asp<br>    1160     1165     1170 | 3678 |
| TAT GTG TTC ACG GGC GTG TTC ACC TTT GAG ATG GTT ATA AAG ATG ATA<br>Tyr Val Phe Thr Gly Val Phe Thr Phe Glu Met Val Ile Lys Met Ile<br>    1175     1180     1185 | 3726 |
| GAC CAA GGC TTG ATC CTG CAG GAT GGG TCC TAC TTC CGA GAC TTG TGG<br>Asp Gln Gly Leu Ile Leu Gln Asp Gly Ser Tyr Phe Arg Asp Leu Trp<br>1190     1195     1200 | 3774 |
| AAC ATC CTG GAC TTT GTG GTG GTC GTT GGC GCA TTG GTG GCC TTT GCT<br>Asn Ile Leu Asp Phe Val Val Val Val Gly Ala Leu Val Ala Phe Ala | 3822 |

```
                  1205                    1210                    1215
CTG GCG AAC GCT TTG GGA ACC AAC AAA GGA CGG GAC ATC AAG ACC ATC       3870
Leu Ala Asn Ala Leu Gly Thr Asn Lys Gly Arg Asp Ile Lys Thr Ile
1220                1225                    1230                    1235

AAG TCT CTG CGG GTG CTC CGA GTT CTA AGG CCA CTG AAA ACC ATC AAG       3918
Lys Ser Leu Arg Val Leu Arg Val Leu Arg Pro Leu Lys Thr Ile Lys
                1240                    1245                    1250

CGC TTG CCC AAG CTC AAG GCC GTC TTC GAC TGC GTA GTG ACC TCC TTG       3966
Arg Leu Pro Lys Leu Lys Ala Val Phe Asp Cys Val Val Thr Ser Leu
            1255                    1260                    1265

AAG AAT GTC TTC AAC ATA CTC ATT GTG TAC AAG CTC TTC ATG TTC ATC       4014
Lys Asn Val Phe Asn Ile Leu Ile Val Tyr Lys Leu Phe Met Phe Ile
        1270                    1275                    1280

TTT GCT GTC ATC GCA GTT CAG CTC TTC AAG GGA AAG TTC TTT TAT TGC       4062
Phe Ala Val Ile Ala Val Gln Leu Phe Lys Gly Lys Phe Phe Tyr Cys
    1285                    1290                    1295

ACG GAC AGT TCC AAG GAC ACA GAG AAG GAG TGC ATA GGC AAC TAT GTA       4110
Thr Asp Ser Ser Lys Asp Thr Glu Lys Glu Cys Ile Gly Asn Tyr Val
1300                1305                    1310                    1315

GAT CAC GAG AAA AAC AAG ATG GAG GTG AAG GGC CGG GAA TGG AAG CGC       4158
Asp His Glu Lys Asn Lys Met Glu Val Lys Gly Arg Glu Trp Lys Arg
                1320                    1325                    1330

CAT GAA TTC CAC TAC GAC AAC ATT ATC TGG GCC CTG CTG ACC CTC TTC       4206
His Glu Phe His Tyr Asp Asn Ile Ile Trp Ala Leu Leu Thr Leu Phe
            1335                    1340                    1345

ACC GTC TCC ACA GGG GAA GGA TGG CCT CAA GTT CTG CAG CAC TCT GTA       4254
Thr Val Ser Thr Gly Glu Gly Trp Pro Gln Val Leu Gln His Ser Val
        1350                    1355                    1360

GAT GTG ACA GAG GAA GAC CGA GGC CCA AGC CGC AGC AAC CGC ATG GAG       4302
Asp Val Thr Glu Glu Asp Arg Gly Pro Ser Arg Ser Asn Arg Met Glu
    1365                    1370                    1375

ATG TCT ATC TTT TAT GTA GTC TAC TTT GTG GTC TTC CCC TTC TTC TTT       4350
Met Ser Ile Phe Tyr Val Val Tyr Phe Val Val Phe Pro Phe Phe Phe
1380                1385                    1390                    1395

GTC AAT ATC TTT GTG GCT CTC ATC ATC ATC ACC TTC CAG GAG CAA GGG       4398
Val Asn Ile Phe Val Ala Leu Ile Ile Ile Thr Phe Gln Glu Gln Gly
                1400                    1405                    1410

GAT AAG ATG ATG GAG GAG TGC AGC CTG GAG AAG AAT GAG AGG GCG TGC       4446
Asp Lys Met Met Glu Glu Cys Ser Leu Glu Lys Asn Glu Arg Ala Cys
            1415                    1420                    1425

ATC GAC TTC GCC ATC AGC GCC AAA CCT CTC ACC CGC TAC ATG CCG CAG       4494
Ile Asp Phe Ala Ile Ser Ala Lys Pro Leu Thr Arg Tyr Met Pro Gln
        1430                    1435                    1440

AAC AGA CAC ACC TTC CAG TAC CGC GTG TGG CAC TTT GTG GTG TCT CCG       4542
Asn Arg His Thr Phe Gln Tyr Arg Val Trp His Phe Val Val Ser Pro
    1445                    1450                    1455

TCC TTT GAG TAC ACC ATT ATG GCC ATG ATC GCC TTG AAT ACT GTT GTG       4590
Ser Phe Glu Tyr Thr Ile Met Ala Met Ile Ala Leu Asn Thr Val Val
1460                1465                    1470                    1475

CTG ATG ATG AAG TAT TAT TCT GCT CCC TGT ACC TAT GAG CTG GCC CTG       4638
Leu Met Met Lys Tyr Tyr Ser Ala Pro Cys Thr Tyr Glu Leu Ala Leu
                1480                    1485                    1490

AAG TAC CTG AAT ATC GCC TTC ACC ATG GTG TTT TCC CTG GAA TGT GTC       4686
Lys Tyr Leu Asn Ile Ala Phe Thr Met Val Phe Ser Leu Glu Cys Val
            1495                    1500                    1505

CTG AAG GTC ATC GCT TTT GGC TTT TTG AAC TAT TTC CGA GAC ACC TGG       4734
Leu Lys Val Ile Ala Phe Gly Phe Leu Asn Tyr Phe Arg Asp Thr Trp
        1510                    1515                    1520

AAT ATC TTT GAC TTC ATC ACC GTG ATT GGC AGT ATC ACA GAA ATT ATC       4782
```

```
Asn Ile Phe Asp Phe Ile Thr Val Ile Gly Ser Ile Thr Glu Ile Ile
    1525            1530                1535

CTG ACA GAC AGC AAG CTG GTG AAC ACC AGT GGC TTC AAT ATG AGC TTT    4830
Leu Thr Asp Ser Lys Leu Val Asn Thr Ser Gly Phe Asn Met Ser Phe
1540            1545                1550                1555

CTG AAG CTC TTC CGA GCT GCC CGC CTC ATA AAG CTC CTG CGT CAG GGC    4878
Leu Lys Leu Phe Arg Ala Ala Arg Leu Ile Lys Leu Leu Arg Gln Gly
                1560                1565                1570

TAT ACC ATA CGC ATT TTG CTG TGG ACC TTT GTG CAG TCC TTT AAG GCC    4926
Tyr Thr Ile Arg Ile Leu Leu Trp Thr Phe Val Gln Ser Phe Lys Ala
            1575                1580                1585

CTC CCT TAT GTC TGC CTT TTA ATT GCC ATG CTT TTC TTC ATT TAT GCC    4974
Leu Pro Tyr Val Cys Leu Leu Ile Ala Met Leu Phe Phe Ile Tyr Ala
        1590                1595                1600

ATC ATT GGG ATG CAG GTA TTT GGA AAC ATA AAA TTA GAC GAG GAG AGT    5022
Ile Ile Gly Met Gln Val Phe Gly Asn Ile Lys Leu Asp Glu Glu Ser
    1605                1610                1615

CAC ATC AAC CGG CAC AAC AAC TTC CGG AGT TTC TTT GGG TCC CTA ATG    5070
His Ile Asn Arg His Asn Asn Phe Arg Ser Phe Phe Gly Ser Leu Met
1620            1625                1630                1635

CTA CTC TTC AGG AGT GCC ACA GGT GAG GCC TGG CAG GAG ATT ATG CTG    5118
Leu Leu Phe Arg Ser Ala Thr Gly Glu Ala Trp Gln Glu Ile Met Leu
                1640                1645                1650

TCA TGC CTT GGG GAG AAG GGC TGT GAG CCT GAC ACC ACC GCA CCA TCA    5166
Ser Cys Leu Gly Glu Lys Gly Cys Glu Pro Asp Thr Thr Ala Pro Ser
            1655                1660                1665

GGG CAG AAC GAG AAT GAA CGC TGC GGC ACC GAT CTG GCC TAC GTG TAC    5214
Gly Gln Asn Glu Asn Glu Arg Cys Gly Thr Asp Leu Ala Tyr Val Tyr
        1670                1675                1680

TTT GTC TCC TTC ATC TTC TTC TGC TCC TTC TTG ATG CTC AAC CTG TTT    5262
Phe Val Ser Phe Ile Phe Phe Cys Ser Phe Leu Met Leu Asn Leu Phe
    1685                1690                1695

GTG GCC GTC ATC ATG GAC AAC TTT GAG TAC CTG ACT CGG GAC TCC TCC    5310
Val Ala Val Ile Met Asp Asn Phe Glu Tyr Leu Thr Arg Asp Ser Ser
1700            1705                1710                1715

ATC CTG GGG CCT CAC CAC TTG GAC GAG TTT GTC CGC GTC TGG GCA GAA    5358
Ile Leu Gly Pro His His Leu Asp Glu Phe Val Arg Val Trp Ala Glu
                1720                1725                1730

TAT GAC CGA GCA GCA TGT GGC CGC ATC CAT TAC ACT GAG ATG TAT GAA    5406
Tyr Asp Arg Ala Ala Cys Gly Arg Ile His Tyr Thr Glu Met Tyr Glu
            1735                1740                1745

ATG CTG ACT CTC ATG TCA CCT CCG CTA GGC CTC GGC AAG AGA TGT CCC    5454
Met Leu Thr Leu Met Ser Pro Pro Leu Gly Leu Gly Lys Arg Cys Pro
        1750                1755                1760

TCC AAA GTG GCA TAT AAG AGG TTG GTC CTG ATG AAC ATG CCA GTA GCT    5502
Ser Lys Val Ala Tyr Lys Arg Leu Val Leu Met Asn Met Pro Val Ala
    1765                1770                1775

GAG GAC ATG ACG GTC CAC TTC ACC TCC ACA CTT ATG GCT CTG ATC CGG    5550
Glu Asp Met Thr Val His Phe Thr Ser Thr Leu Met Ala Leu Ile Arg
1780            1785                1790                1795

ACA GCT CTG GAC ATT AAA ATT GCC AAA GGT GGT GCA GAC AGG CAG CAG    5598
Thr Ala Leu Asp Ile Lys Ile Ala Lys Gly Gly Ala Asp Arg Gln Gln
                1800                1805                1810

CTA GAC TCA GAG CTA CAA AAG GAG ACC CTA GCC ATC TGG CCT CAC CTA    5646
Leu Asp Ser Glu Leu Gln Lys Glu Thr Leu Ala Ile Trp Pro His Leu
            1815                1820                1825

TCC CAG AAG ATG CTG GAT CTG CTT GTG CCC ATG CCC AAA GCC TCT GAC    5694
Ser Gln Lys Met Leu Asp Leu Leu Val Pro Met Pro Lys Ala Ser Asp
        1830                1835                1840
```

-continued

```
CTG ACT GTG GGC AAA ATC TAT GCA GCA ATG ATG ATC ATG GAC TAC TAT          5742
Leu Thr Val Gly Lys Ile Tyr Ala Ala Met Met Ile Met Asp Tyr Tyr
        1845                1850                1855

AAG CAG AGT AAG GTG AAG AAG CAG AGG CAG CAG CTG GAG GAA CAG AAA          5790
Lys Gln Ser Lys Val Lys Lys Gln Arg Gln Gln Leu Glu Glu Gln Lys
1860                1865                1870                1875

AAT GCC CCC ATG TTC CAG CGC ATG GAG CCT TCA TCT CTG CCT CAG GAG          5838
Asn Ala Pro Met Phe Gln Arg Met Glu Pro Ser Ser Leu Pro Gln Glu
                1880                1885                1890

ATC ATT GCT AAT GCC AAA GCC CTG CCT TAC CTC CAG CAG GAC CCC GTT          5886
Ile Ile Ala Asn Ala Lys Ala Leu Pro Tyr Leu Gln Gln Asp Pro Val
        1895                1900                1905

TCA GGC CTG AGT GGC CGG AGT GGA TAC CCT TCG ATG AGT CCA CTC TCT          5934
Ser Gly Leu Ser Gly Arg Ser Gly Tyr Pro Ser Met Ser Pro Leu Ser
            1910                1915                1920

CCC CAG GAT ATA TTC CAG TTG GCT TGT ATG GAC CCC GCC GAT GAC GGA          5982
Pro Gln Asp Ile Phe Gln Leu Ala Cys Met Asp Pro Ala Asp Asp Gly
        1925                1930                1935

CAG TTC CAA GAA CGG CAG TCT CTG GTG GTG ACA GAC CCT AGC TCC ATG          6030
Gln Phe Gln Glu Arg Gln Ser Leu Val Val Thr Asp Pro Ser Ser Met
1940                1945                1950                1955

AGA CGT TCA TTT TCC ACT ATT CGG GAT AAG CGT TCA AAT TCC TCG TGG          6078
Arg Arg Ser Phe Ser Thr Ile Arg Asp Lys Arg Ser Asn Ser Ser Trp
                1960                1965                1970

TTG GAG GAA TTC TCC ATG GAG CGA AGC AGT GAA AAT ACC TAC AAG TCC          6126
Leu Glu Glu Phe Ser Met Glu Arg Ser Ser Glu Asn Thr Tyr Lys Ser
        1975                1980                1985

CGT CGC CGG AGT TAC CAC TCC TCC TTG CGG CTG TCA GCC CAC CGC CTG          6174
Arg Arg Arg Ser Tyr His Ser Ser Leu Arg Leu Ser Ala His Arg Leu
            1990                1995                2000

AAC TCT GAT TCA GGC CAC AAG TCT GAC ACT CAC CCC TCA GGG GGC AGG          6222
Asn Ser Asp Ser Gly His Lys Ser Asp Thr His Pro Ser Gly Gly Arg
        2005                2010                2015

GAG CGG CGA CGA TCA AAA GAG CGA AAG CAT CTT CTC TCT CCT GAT GTC          6270
Glu Arg Arg Arg Ser Lys Glu Arg Lys His Leu Leu Ser Pro Asp Val
2020                2025                2030                2035

TCC CGC TGC AAT TCA GAA GAG CGA GGG ACC CAG GCT GAC TGG GAG TCC          6318
Ser Arg Cys Asn Ser Glu Glu Arg Gly Thr Gln Ala Asp Trp Glu Ser
                2040                2045                2050

CCA GAG CGC CGT CAA TCC AGG TCA CCC AGT GAG GGC AGG TCA CAG ACG          6366
Pro Glu Arg Arg Gln Ser Arg Ser Pro Ser Glu Gly Arg Ser Gln Thr
        2055                2060                2065

CCC AAC AGA CAG GGC ACA GGT TCC CTA AGT GAG AGC TCC ATC CCC TCT          6414
Pro Asn Arg Gln Gly Thr Gly Ser Leu Ser Glu Ser Ser Ile Pro Ser
        2070                2075                2080

GTC TCT GAC ACC AGC ACC CCA AGA AGA AGT CGT CGG CAG CTC CCA CCC          6462
Val Ser Asp Thr Ser Thr Pro Arg Arg Ser Arg Arg Gln Leu Pro Pro
    2085                2090                2095

GTC CCG CCA AAG CCC CGG CCC CTC CTT TCC TAC AGC TCC CTG ATT CGA          6510
Val Pro Pro Lys Pro Arg Pro Leu Leu Ser Tyr Ser Ser Leu Ile Arg
2100                2105                2110                2115

CAC GCG GGC AGC ATC TCT CCA CCT GCT GAT GGA AGC GAG GAG GGC TCC          6558
His Ala Gly Ser Ile Ser Pro Pro Ala Asp Gly Ser Glu Glu Gly Ser
                2120                2125                2130

CCG CTG ACC TCC CAA GCT CTG GAG AGC AAC AAT GCT TGG CTG ACC GAG          6606
Pro Leu Thr Ser Gln Ala Leu Glu Ser Asn Asn Ala Trp Leu Thr Glu
        2135                2140                2145

TCT TCC AAC TCT CCG CAC CCC CAG CAG AGG CAA CAT GCC TCC CCA CAG          6654
Ser Ser Asn Ser Pro His Pro Gln Gln Arg Gln His Ala Ser Pro Gln
        2150                2155                2160
```

```
CGC TAC ATC TCC GAG CCC TAC TTG GCC CTG CAC GAA GAC TCC CAC GCC         6702
Arg Tyr Ile Ser Glu Pro Tyr Leu Ala Leu His Glu Asp Ser His Ala
    2165                2170                2175

TCA GAC TGT GTT GAG GAG GAG ACG CTC ACT TTC GAA GCA GCC GTG GCT         6750
Ser Asp Cys Val Glu Glu Glu Thr Leu Thr Phe Glu Ala Ala Val Ala
2180                2185                2190                2195

ACT AGC CTG GGC CGT TCC AAC ACC ATC GGC TCA GCC CCA CCC CTG CGG         6798
Thr Ser Leu Gly Arg Ser Asn Thr Ile Gly Ser Ala Pro Pro Leu Arg
                2200                2205                2210

CAT AGC TGG CAG ATG CCC AAC GGG CAC TAT CGG CGG CGG AGG CGC GGG         6846
His Ser Trp Gln Met Pro Asn Gly His Tyr Arg Arg Arg Arg Arg Gly
        2215                2220                2225

GGG CCT GGG CCA GGC ATG ATG TGT GGG GCT GTC AAC AAC CTG CTA AGT         6894
Gly Pro Gly Pro Gly Met Met Cys Gly Ala Val Asn Asn Leu Leu Ser
            2230                2235                2240

GAC ACG GAA GAA GAT GAC AAA TGC TAGAGGCTGC TCCCCCCTCC GATGCATGCT        6948
Asp Thr Glu Glu Asp Asp Lys Cys
        2245                2250

CTTCTCTCAC ATGGAGAAAA CCAAGACAGA ATTGGGAAGC CAGTGCGGCC CCGCGGGGAG       7008

GAAGAGGGAA AAGGAAGATG GAAG                                              7032

(2) INFORMATION FOR SEQ ID NO:25:

(i) SEQUENCE CHARACTERISTICS:
        (A) LENGTH: 7089 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 166..6978
        (D) OTHER INFORMATION: /standard_name= "Alpha-1E-3"

(xi) SEQUENCE DESCRIPTION: SEQ ID NO:25:

GCTGCTGCTG CCTCTCCGAA GAGCTCGCGG AGCTCCCCAG AGGCGGTGGT CCCCGTGCTT         60

GTCTGGATGC GGCTCTGAGT CTCCGTGTGT CTTTCTGCTT GTTGCTGTGT GCGGGTGTTC        120

GGCCGCGATC ACCTTTGTGT GTCTTCTGTC TGTTTAAACC TCAGG ATG GCT CGC           174
                                              Met Ala Arg
                                                1

TTC GGG GAG GCG GTG GTC GCC AGG CCA GGG TCC GGC GAT GGA GAC TCG         222
Phe Gly Glu Ala Val Val Ala Arg Pro Gly Ser Gly Asp Gly Asp Ser
    5                   10                  15

GAC CAG AGC AGG AAC CGG CAA GGA ACC CCC GTG CCG GCC TCG GGG CAG         270
Asp Gln Ser Arg Asn Arg Gln Gly Thr Pro Val Pro Ala Ser Gly Gln
 20                  25                  30                  35

GCG GCC GCC TAC AAG CAG ACG AAA GCA CAG AGG GCG CGG ACT ATG GCT         318
Ala Ala Ala Tyr Lys Gln Thr Lys Ala Gln Arg Ala Arg Thr Met Ala
                40                  45                  50

TTG TAC AAC CCC ATT CCC GTC CGG CAG AAC TGT TTC ACC GTC AAC AGA         366
Leu Tyr Asn Pro Ile Pro Val Arg Gln Asn Cys Phe Thr Val Asn Arg
            55                  60                  65

TCC CTG TTC ATC TTC GGA GAA GAT AAC ATT GTC AGG AAA TAT GCC AAG         414
Ser Leu Phe Ile Phe Gly Glu Asp Asn Ile Val Arg Lys Tyr Ala Lys
        70                  75                  80

AAG CTC ATC GAT TGG CCG CCA TTT GAG TAC ATG ATC CTG GCC ACC ATC         462
Lys Leu Ile Asp Trp Pro Pro Phe Glu Tyr Met Ile Leu Ala Thr Ile
    85                  90                  95
```

| | |
|---|---|
| ATT GCC AAC TGC ATC GTC CTG GCC CTG GAG CAG CAT CTT CCT GAG GAT<br>Ile Ala Asn Cys Ile Val Leu Ala Leu Glu Gln His Leu Pro Glu Asp<br>100                         105                  110                     115 | 510 |
| GAC AAG ACC CCC ATG TCC CGA AGA CTG GAG AAG ACA GAA CCT TAT TTC<br>Asp Lys Thr Pro Met Ser Arg Arg Leu Glu Lys Thr Glu Pro Tyr Phe<br>                    120                        125                     130 | 558 |
| ATT GGG ATC TTT TGC TTT GAA GCT GGG ATC AAA ATT GTG GCC CTG GGG<br>Ile Gly Ile Phe Cys Phe Glu Ala Gly Ile Lys Ile Val Ala Leu Gly<br>                135                      140                     145 | 606 |
| TTC ATC TTC CAT AAG GGC TCT TAC CTC CGC AAT GGC TGG AAT GTC ATG<br>Phe Ile Phe His Lys Gly Ser Tyr Leu Arg Asn Gly Trp Asn Val Met<br>     150                        155                     160 | 654 |
| GAC TTC ATC GTG GTC CTC AGT GGC ATC CTG GCC ACT GCA GGA ACC CAC<br>Asp Phe Ile Val Val Leu Ser Gly Ile Leu Ala Thr Ala Gly Thr His<br>165                         170                  175 | 702 |
| TTC AAT ACT CAC GTG GAC CTG AGG ACC CTC CGG GCT GTG CGT GTC CTG<br>Phe Asn Thr His Val Asp Leu Arg Thr Leu Arg Ala Val Arg Val Leu<br>180                         185                  190               195 | 750 |
| CGG CCT TTG AAG CTC GTG TCA GGG ATA CCT AGC CTG CAG ATT GTG TTG<br>Arg Pro Leu Lys Leu Val Ser Gly Ile Pro Ser Leu Gln Ile Val Leu<br>                    200                     205                 210 | 798 |
| AAG TCC ATC ATG AAG GCC ATG GTA CCT CTT CTG CAG ATT GGC CTT CTG<br>Lys Ser Ile Met Lys Ala Met Val Pro Leu Leu Gln Ile Gly Leu Leu<br>             215                     220                   225 | 846 |
| CTC TTC TTT GCC ATC CTG ATG TTT GCT ATC ATT GGT TTG GAG TTC TAC<br>Leu Phe Phe Ala Ile Leu Met Phe Ala Ile Ile Gly Leu Glu Phe Tyr<br>         230                     235                     240 | 894 |
| AGT GGC AAG TTA CAT CGA GCG TGC TTC ATG AAC AAT TCA GGT ATT CTA<br>Ser Gly Lys Leu His Arg Ala Cys Phe Met Asn Asn Ser Gly Ile Leu<br>         245                     250                     255 | 942 |
| GAA GGA TTT GAC CCC CCT CAC CCA TGT GGT GTG CAG GGC TGC CCA GCT<br>Glu Gly Phe Asp Pro Pro His Pro Cys Gly Val Gln Gly Cys Pro Ala<br>260                         265                  270               275 | 990 |
| GGT TAT GAA TGC AAG GAC TGG ATC GGC CCC AAT GAT GGG ATC ACC CAG<br>Gly Tyr Glu Cys Lys Asp Trp Ile Gly Pro Asn Asp Gly Ile Thr Gln<br>                    280                     285                 290 | 1038 |
| TTT GAT AAC ATC CTT TTT GCT GTG CTG ACT GTC TTC CAG TGC ATC ACC<br>Phe Asp Asn Ile Leu Phe Ala Val Leu Thr Val Phe Gln Cys Ile Thr<br>             295                     300                   305 | 1086 |
| ATG GAA GGG TGG ACC ACT GTG CTG TAC AAT ACC AAT GAT GCC TTA GGA<br>Met Glu Gly Trp Thr Thr Val Leu Tyr Asn Thr Asn Asp Ala Leu Gly<br>         310                     315                  320 | 1134 |
| GCC ACC TGG AAT TGG CTG TAC TTC ATC CCC CTC ATC ATC ATT GGA TCC<br>Ala Thr Trp Asn Trp Leu Tyr Phe Ile Pro Leu Ile Ile Ile Gly Ser<br>325                         330                  335 | 1182 |
| TTC TTT GTT CTC AAC CTA GTC CTG GGA GTG CTT TCC GGG GAA TTT GCC<br>Phe Phe Val Leu Asn Leu Val Leu Gly Val Leu Ser Gly Glu Phe Ala<br>340                       345                  350               355 | 1230 |
| AAA GAG AGA GAG AGA GTG GAG AAC CGA AGG GCT TTC ATG AAG CTG CGG<br>Lys Glu Arg Glu Arg Val Glu Asn Arg Arg Ala Phe Met Lys Leu Arg<br>                    360                     365                 370 | 1278 |
| CGC CAG CAG CAG ATT GAG CGT GAG CTG AAT GGC TAC CGT GCC TGG ATA<br>Arg Gln Gln Gln Ile Glu Arg Glu Leu Asn Gly Tyr Arg Ala Trp Ile<br>             375                     380                 385 | 1326 |
| GAC AAA GCA GAG GAA GTC ATG CTC GCT GAA GAA AAT AAA AAT GCT GGA<br>Asp Lys Ala Glu Glu Val Met Leu Ala Glu Glu Asn Lys Asn Ala Gly<br>         390                     395                  400 | 1374 |
| ACA TCC GCC TTA GAA GTG CTT CGA AGG GCA ACC ATC AAG AGG AGC CGG<br>Thr Ser Ala Leu Glu Val Leu Arg Arg Ala Thr Ile Lys Arg Ser Arg<br>405                         410                  415 | 1422 |

```
ACA GAG GCC ATG ACT CGA GAC TCC AGT GAT GAG CAC TGT GTT GAT ATC    1470
Thr Glu Ala Met Thr Arg Asp Ser Ser Asp Glu His Cys Val Asp Ile
420                 425                 430                 435

TCC TCT GTG GGC ACA CCT CTG GCC CGA GCC AGT ATC AAA AGT GCA AAG    1518
Ser Ser Val Gly Thr Pro Leu Ala Arg Ala Ser Ile Lys Ser Ala Lys
                440                 445                 450

GTA GAC GGG GTC TCT TAT TTC CGG CAC AAG GAA AGG CTT CTG CGC ATC    1566
Val Asp Gly Val Ser Tyr Phe Arg His Lys Glu Arg Leu Leu Arg Ile
            455                 460                 465

TCC ATT CGC CAC ATG GTT AAA TCC CAG GTG TTT TAC TGG ATT GTG CTG    1614
Ser Ile Arg His Met Val Lys Ser Gln Val Phe Tyr Trp Ile Val Leu
        470                 475                 480

AGC CTT GTG GCA CTC AAC ACT GCC TGT GTG GCC ATT GTC CAT CAC AAC    1662
Ser Leu Val Ala Leu Asn Thr Ala Cys Val Ala Ile Val His His Asn
485                 490                 495

CAG CCC CAG TGG CTC ACC CAC CTC CTC TAC TAT GCA GAA TTT CTG TTT    1710
Gln Pro Gln Trp Leu Thr His Leu Leu Tyr Tyr Ala Glu Phe Leu Phe
500                 505                 510                 515

CTG GGA CTC TTC CTC TTG GAG ATG TCC CTG AAG ATG TAT GGC ATG GGG    1758
Leu Gly Leu Phe Leu Leu Glu Met Ser Leu Lys Met Tyr Gly Met Gly
                520                 525                 530

CCT CGC CTT TAT TTT CAC TCT TCA TTC AAC TGC TTT GAT TTT GGG GTC    1806
Pro Arg Leu Tyr Phe His Ser Ser Phe Asn Cys Phe Asp Phe Gly Val
            535                 540                 545

ACA GTG GGC AGT ATC TTT GAA GTG GTC TGG GCA ATC TTC AGA CCT GGT    1854
Thr Val Gly Ser Ile Phe Glu Val Val Trp Ala Ile Phe Arg Pro Gly
        550                 555                 560

ACG TCT TTT GGA ATC AGT GTC TTG CGA GCC CTC CGG CTT CTA AGA ATA    1902
Thr Ser Phe Gly Ile Ser Val Leu Arg Ala Leu Arg Leu Leu Arg Ile
565                 570                 575

TTT AAA ATA ACC AAG TAT TGG GCT TCC CTA CGG AAT TTG GTG GTC TCC    1950
Phe Lys Ile Thr Lys Tyr Trp Ala Ser Leu Arg Asn Leu Val Val Ser
580                 585                 590                 595

TTG ATG AGC TCA ATG AAG TCT ATC ATC AGT TTG CTT TTC CTC CTC TTC    1998
Leu Met Ser Ser Met Lys Ser Ile Ile Ser Leu Leu Phe Leu Leu Phe
                600                 605                 610

CTC TTC ATC GTT GTC TTT GCT CTC CTA GGA ATG CAG TTA TTT GGA GGC    2046
Leu Phe Ile Val Val Phe Ala Leu Leu Gly Met Gln Leu Phe Gly Gly
            615                 620                 625

AGG TTT AAC TTT AAT GAT GGG ACT CCT TCG GCA AAT TTT GAT ACC TTC    2094
Arg Phe Asn Phe Asn Asp Gly Thr Pro Ser Ala Asn Phe Asp Thr Phe
        630                 635                 640

CCT GCA GCC ATC ATG ACT GTG TTC CAG ATC CTG ACG GGT GAG GAC TGG    2142
Pro Ala Ala Ile Met Thr Val Phe Gln Ile Leu Thr Gly Glu Asp Trp
645                 650                 655

AAT GAG GTG ATG TAC AAT GGG ATC CGC TCC CAG GGT GGG GTC AGC TCA    2190
Asn Glu Val Met Tyr Asn Gly Ile Arg Ser Gln Gly Gly Val Ser Ser
660                 665                 670                 675

GGC ATG TGG TCT GCC ATC TAC TTC ATT GTG CTC ACC TTG TTT GGC AAC    2238
Gly Met Trp Ser Ala Ile Tyr Phe Ile Val Leu Thr Leu Phe Gly Asn
                680                 685                 690

TAC ACG CTA CTG AAT GTG TTC TTG GCT ATC GCT GTG GAT AAT CTC GCC    2286
Tyr Thr Leu Leu Asn Val Phe Leu Ala Ile Ala Val Asp Asn Leu Ala
            695                 700                 705

AAC GCC CAG GAA CTG ACC AAG GAT GAA CAG GAG GAA GAG GCC TTC        2334
Asn Ala Gln Glu Leu Thr Lys Asp Glu Gln Glu Glu Glu Ala Phe
        710                 715                 720

AAC CAG AAA CAT GCA CTG CAG AAG GCC AAG GAG GTC AGC CCG ATG TCT    2382
Asn Gln Lys His Ala Leu Gln Lys Ala Lys Glu Val Ser Pro Met Ser
```

```
                    725                     730                     735
GCA CCC AAC ATG CCT TCG ATC GAA AGA GAC AGA AGG AGA AGA CAC CAC       2430
Ala Pro Asn Met Pro Ser Ile Glu Arg Asp Arg Arg Arg Arg His His
740                     745                     750                     755

ATG TCG ATG TGG GAG CCA CGC AGC AGC CAC CTG AGG GAG CGG AGG CGC       2478
Met Ser Met Trp Glu Pro Arg Ser Ser His Leu Arg Glu Arg Arg Arg
                        760                     765                     770

CGG CAC CAC ATG TCC GTG TGG GAG CAG CGT ACC AGC CAG CTG AGG AAG       2526
Arg His His Met Ser Val Trp Glu Gln Arg Thr Ser Gln Leu Arg Lys
                775                     780                     785

CAC ATG CAG ATG TCC AGC CAG GAG GCC CTC AAC AGA GAG GAG GCG CCG       2574
His Met Gln Met Ser Ser Gln Glu Ala Leu Asn Arg Glu Glu Ala Pro
        790                     795                     800

ACC ATG AAC CCG CTC AAC CCC CTC AAC CCG CTC AGC TCC CTC AAC CCG       2622
Thr Met Asn Pro Leu Asn Pro Leu Asn Pro Leu Ser Ser Leu Asn Pro
805                     810                     815

CTC AAT GCC CAC CCC AGC CTT TAT CGG CGA CCC AGG GCC ATT GAG GGC       2670
Leu Asn Ala His Pro Ser Leu Tyr Arg Arg Pro Arg Ala Ile Glu Gly
820                     825                     830                     835

CTG GCC CTG GGC CTG GCC CTG GAG AAG TTC GAG GAG GAG CGC ATC AGC       2718
Leu Ala Leu Gly Leu Ala Leu Glu Lys Phe Glu Glu Glu Arg Ile Ser
                        840                     845                     850

CGT GGG GGG TCC CTC AAG GGG GAT GGA GGG GAC CGA TCC AGT GCC CTG       2766
Arg Gly Gly Ser Leu Lys Gly Asp Gly Gly Asp Arg Ser Ser Ala Leu
                855                     860                     865

GAC AAC CAG AGG ACC CCT TTG TCC CTG GGC CAG CGG GAG CCA CCA TGG       2814
Asp Asn Gln Arg Thr Pro Leu Ser Leu Gly Gln Arg Glu Pro Pro Trp
        870                     875                     880

CTG GCC AGG CCC TGT CAT GGA AAC TGT GAC CCG ACT CAG CAG GAG GCA       2862
Leu Ala Arg Pro Cys His Gly Asn Cys Asp Pro Thr Gln Gln Glu Ala
885                     890                     895

GGG GGA GGA GAG GCT GTG GTG ACC TTT GAG GAC CGG GCC AGG CAC AGG       2910
Gly Gly Gly Glu Ala Val Val Thr Phe Glu Asp Arg Ala Arg His Arg
900                     905                     910                     915

CAG AGC CAA CGG CGC AGC CGG CAT CGC CGC GTC AGG ACA GAA GGC AAG       2958
Gln Ser Gln Arg Arg Ser Arg His Arg Arg Val Arg Thr Glu Gly Lys
                        920                     925                     930

GAG TCC TCT TCA GCC TCC CGG AGC AGG TCT GCC AGC CAG GAA CGC AGT       3006
Glu Ser Ser Ser Ala Ser Arg Ser Arg Ser Ala Ser Gln Glu Arg Ser
                935                     940                     945

CTG GAT GAA GCC ATG CCC ACT GAA GGG GAG AAG GAC CAT GAG CTC AGG       3054
Leu Asp Glu Ala Met Pro Thr Glu Gly Glu Lys Asp His Glu Leu Arg
        950                     955                     960

GGC AAC CAT GGT GCC AAG GAG CCA ACG ATC CAA GAA GAG AGA GCC CAG       3102
Gly Asn His Gly Ala Lys Glu Pro Thr Ile Gln Glu Glu Arg Ala Gln
965                     970                     975

GAT TTA AGG AGG ACC AAC AGT CTG ATG GTG TCC AGA GGC TCC GGG CTG       3150
Asp Leu Arg Arg Thr Asn Ser Leu Met Val Ser Arg Gly Ser Gly Leu
980                     985                     990                     995

GCA GGA GGC CTT GAT GAG GCT GAC ACC CCC CTA GTC CTG CCC CAT CCT       3198
Ala Gly Gly Leu Asp Glu Ala Asp Thr Pro Leu Val Leu Pro His Pro
                        1000                    1005                    1010

GAG CTG GAA GTG GGG AAG CAC GTG GTG CTG ACG GAG CAG GAG CCA GAA       3246
Glu Leu Glu Val Gly Lys His Val Val Leu Thr Glu Gln Glu Pro Glu
                1015                    1020                    1025

GGC AGC AGT GAG CAG GCC CTG CTG GGG AAT GTG CAG CTA GAC ATG GGC       3294
Gly Ser Ser Glu Gln Ala Leu Leu Gly Asn Val Gln Leu Asp Met Gly
        1030                    1035                    1040

CGG GTC ATC AGC CAG AGC GAG CCT GAC CTC TCC TGC ATC ACG GCC AAC       3342
```

```
Arg Val Ile Ser Gln Ser Glu Pro Asp Leu Ser Cys Ile Thr Ala Asn
    1045                1050                1055

ACG GAC AAG GCC ACC ACC GAG AGC ACC AGC GTC ACC GTC GCC ATC CCC      3390
Thr Asp Lys Ala Thr Thr Glu Ser Thr Ser Val Thr Val Ala Ile Pro
1060                1065                1070                1075

GAC GTG GAC CCC TTG GTG GAC TCA ACC GTG GTG CAC ATT AGC AAC AAG      3438
Asp Val Asp Pro Leu Val Asp Ser Thr Val Val His Ile Ser Asn Lys
                1080                1085                1090

ACG GAT GGG GAA GCC AGT CCC TTG AAG GAG GCA GAG ATC AGA GAG GAT      3486
Thr Asp Gly Glu Ala Ser Pro Leu Lys Glu Ala Glu Ile Arg Glu Asp
            1095                1100                1105

GAG GAG GAG GTG GAG AAG AAG AAG CAG AAG AAG GAG AAG CGT GAG ACA      3534
Glu Glu Glu Val Glu Lys Lys Lys Gln Lys Lys Glu Lys Arg Glu Thr
            1110                1115                1120

GGC AAA GCC ATG GTG CCC CAC AGC TCA ATG TTC ATC TTC AGC ACC ACC      3582
Gly Lys Ala Met Val Pro His Ser Ser Met Phe Ile Phe Ser Thr Thr
1125                1130                1135

AAC CCG ATC CGG AGG GCC TGC CAC TAC ATC GTG AAC CTG CGC TAC TTT      3630
Asn Pro Ile Arg Arg Ala Cys His Tyr Ile Val Asn Leu Arg Tyr Phe
1140                1145                1150                1155

GAG ATG TGC ATC CTC CTG GTG ATT GCA GCC AGC AGC ATC GCC CTG GCG      3678
Glu Met Cys Ile Leu Leu Val Ile Ala Ala Ser Ser Ile Ala Leu Ala
                1160                1165                1170

GCA GAG GAC CCC GTC CTG ACC AAC TCG GAG CGC AAC AAA GTC CTG AGG      3726
Ala Glu Asp Pro Val Leu Thr Asn Ser Glu Arg Asn Lys Val Leu Arg
            1175                1180                1185

TAT TTT GAC TAT GTG TTC ACG GGC GTG TTC ACC TTT GAG ATG GTT ATA      3774
Tyr Phe Asp Tyr Val Phe Thr Gly Val Phe Thr Phe Glu Met Val Ile
            1190                1195                1200

AAG ATG ATA GAC CAA GGC TTG ATC CTG CAG GAT GGG TCC TAC TTC CGA      3822
Lys Met Ile Asp Gln Gly Leu Ile Leu Gln Asp Gly Ser Tyr Phe Arg
1205                1210                1215

GAC TTG TGG AAC ATC CTG GAC TTT GTG GTG GTC GTT GGC GCA TTG GTG      3870
Asp Leu Trp Asn Ile Leu Asp Phe Val Val Val Val Gly Ala Leu Val
1220                1225                1230                1235

GCC TTT GCT CTG GCG AAC GCT TTG GGA ACC AAC AAA GGA CGG GAC ATC      3918
Ala Phe Ala Leu Ala Asn Ala Leu Gly Thr Asn Lys Gly Arg Asp Ile
                1240                1245                1250

AAG ACC ATC AAG TCT CTG CGG GTG CTC CGA GTT CTA AGG CCA CTG AAA      3966
Lys Thr Ile Lys Ser Leu Arg Val Leu Arg Val Leu Arg Pro Leu Lys
            1255                1260                1265

ACC ATC AAG CGC TTG CCC AAG CTC AAG GCC GTC TTC GAC TGC GTA GTG      4014
Thr Ile Lys Arg Leu Pro Lys Leu Lys Ala Val Phe Asp Cys Val Val
            1270                1275                1280

ACC TCC TTG AAG AAT GTC TTC AAC ATA CTC ATT GTG TAC AAG CTC TTC      4062
Thr Ser Leu Lys Asn Val Phe Asn Ile Leu Ile Val Tyr Lys Leu Phe
1285                1290                1295

ATG TTC ATC TTT GCT GTC ATC GCA GTT CAG CTC TTC AAG GGA AAG TTC      4110
Met Phe Ile Phe Ala Val Ile Ala Val Gln Leu Phe Lys Gly Lys Phe
1300                1305                1310                1315

TTT TAT TGC ACG GAC AGT TCC AAG GAC ACA GAG AAG GAG TGC ATA GGC      4158
Phe Tyr Cys Thr Asp Ser Ser Lys Asp Thr Glu Lys Glu Cys Ile Gly
                1320                1325                1330

AAC TAT GTA GAT CAC GAG AAA AAC AAG ATG GAG GTG AAG GGC CGG GAA      4206
Asn Tyr Val Asp His Glu Lys Asn Lys Met Glu Val Lys Gly Arg Glu
            1335                1340                1345

TGG AAG CGC CAT GAA TTC CAC TAC GAC AAC ATT ATC TGG GCC CTG CTG      4254
Trp Lys Arg His Glu Phe His Tyr Asp Asn Ile Ile Trp Ala Leu Leu
            1350                1355                1360
```

```
ACC CTC TTC ACC GTC TCC ACA GGG GAA GGA TGG CCT CAA GTT CTG CAG       4302
Thr Leu Phe Thr Val Ser Thr Gly Glu Gly Trp Pro Gln Val Leu Gln
        1365                1370                1375

CAC TCT GTA GAT GTG ACA GAG GAA GAC CGA GGC CCA AGC CGC AGC AAC       4350
His Ser Val Asp Val Thr Glu Glu Asp Arg Gly Pro Ser Arg Ser Asn
1380                1385                1390                1395

CGC ATG GAG ATG TCT ATC TTT TAT GTA GTC TAC TTT GTG GTC TTC CCC       4398
Arg Met Glu Met Ser Ile Phe Tyr Val Val Tyr Phe Val Val Phe Pro
                1400                1405                1410

TTC TTC TTT GTC AAT ATC TTT GTG GCT CTC ATC ATC ATC ACC TTC CAG       4446
Phe Phe Phe Val Asn Ile Phe Val Ala Leu Ile Ile Ile Thr Phe Gln
        1415                1420                1425

GAG CAA GGG GAT AAG ATG ATG GAG GAG TGC AGC CTG GAG AAG AAT GAG       4494
Glu Gln Gly Asp Lys Met Met Glu Glu Cys Ser Leu Glu Lys Asn Glu
        1430                1435                1440

AGG GCG TGC ATC GAC TTC GCC ATC AGC GCC AAA CCT CTC ACC CGC TAC       4542
Arg Ala Cys Ile Asp Phe Ala Ile Ser Ala Lys Pro Leu Thr Arg Tyr
        1445                1450                1455

ATG CCG CAG AAC AGA CAC ACC TTC CAG TAC CGC GTG TGG CAC TTT GTG       4590
Met Pro Gln Asn Arg His Thr Phe Gln Tyr Arg Val Trp His Phe Val
1460                1465                1470                1475

GTG TCT CCG TCC TTT GAG TAC ACC ATT ATG GCC ATG ATC GCC TTG AAT       4638
Val Ser Pro Ser Phe Glu Tyr Thr Ile Met Ala Met Ile Ala Leu Asn
                1480                1485                1490

ACT GTT GTG CTG ATG ATG AAG TAT TAT TCT GCT CCC TGT ACC TAT GAG       4686
Thr Val Val Leu Met Met Lys Tyr Tyr Ser Ala Pro Cys Thr Tyr Glu
        1495                1500                1505

CTG GCC CTG AAG TAC CTG AAT ATC GCC TTC ACC ATG GTG TTT TCC CTG       4734
Leu Ala Leu Lys Tyr Leu Asn Ile Ala Phe Thr Met Val Phe Ser Leu
        1510                1515                1520

GAA TGT GTC CTG AAG GTC ATC GCT TTT GGC TTT TTG AAC TAT TTC CGA       4782
Glu Cys Val Leu Lys Val Ile Ala Phe Gly Phe Leu Asn Tyr Phe Arg
        1525                1530                1535

GAC ACC TGG AAT ATC TTT GAC TTC ATC ACC GTG ATT GGC AGT ATC ACA       4830
Asp Thr Trp Asn Ile Phe Asp Phe Ile Thr Val Ile Gly Ser Ile Thr
1540                1545                1550                1555

GAA ATT ATC CTG ACA GAC AGC AAG CTG GTG AAC ACC AGT GGC TTC AAT       4878
Glu Ile Ile Leu Thr Asp Ser Lys Leu Val Asn Thr Ser Gly Phe Asn
                1560                1565                1570

ATG AGC TTT CTG AAG CTC TTC CGA GCT GCC CGC CTC ATA AAG CTC CTG       4926
Met Ser Phe Leu Lys Leu Phe Arg Ala Ala Arg Leu Ile Lys Leu Leu
        1575                1580                1585

CGT CAG GGC TAT ACC ATA CGC ATT TTG CTG TGG ACC TTT GTG CAG TCC       4974
Arg Gln Gly Tyr Thr Ile Arg Ile Leu Leu Trp Thr Phe Val Gln Ser
        1590                1595                1600

TTT AAG GCC CTC CCT TAT GTC TGC CTT TTA ATT GCC ATG CTT TTC TTC       5022
Phe Lys Ala Leu Pro Tyr Val Cys Leu Leu Ile Ala Met Leu Phe Phe
        1605                1610                1615

ATT TAT GCC ATC ATT GGG ATG CAG GTA TTT GGA AAC ATA AAA TTA GAC       5070
Ile Tyr Ala Ile Ile Gly Met Gln Val Phe Gly Asn Ile Lys Leu Asp
1620                1625                1630                1635

GAG GAG AGT CAC ATC AAC CGG CAC AAC AAC TTC CGG AGT TTC TTT GGG       5118
Glu Glu Ser His Ile Asn Arg His Asn Asn Phe Arg Ser Phe Phe Gly
                1640                1645                1650

TCC CTA ATG CTA CTC TTC AGG AGT GCC ACA GGT GAG GCC TGG CAG GAG       5166
Ser Leu Met Leu Leu Phe Arg Ser Ala Thr Gly Glu Ala Trp Gln Glu
        1655                1660                1665

ATT ATG CTG TCA TGC CTT GGG GAG AAG GGC TGT GAG CCT GAC ACC ACC       5214
Ile Met Leu Ser Cys Leu Gly Glu Lys Gly Cys Glu Pro Asp Thr Thr
1670                1675                1680
```

```
GCA CCA TCA GGG CAG AAC GAG AAT GAA CGC TGC GGC ACC GAT CTG GCC        5262
Ala Pro Ser Gly Gln Asn Glu Asn Glu Arg Cys Gly Thr Asp Leu Ala
        1685                1690                1695

TAC GTG TAC TTT GTC TCC TTC ATC TTC TTC TGC TCC TTC TTG ATG CTC        5310
Tyr Val Tyr Phe Val Ser Phe Ile Phe Phe Cys Ser Phe Leu Met Leu
1700                1705                1710                1715

AAC CTG TTT GTG GCC GTC ATC ATG GAC AAC TTT GAG TAC CTG ACT CGG        5358
Asn Leu Phe Val Ala Val Ile Met Asp Asn Phe Glu Tyr Leu Thr Arg
                1720                1725                1730

GAC TCC TCC ATC CTG GGG CCT CAC CAC TTG GAC GAG TTT GTC CGC GTC        5406
Asp Ser Ser Ile Leu Gly Pro His His Leu Asp Glu Phe Val Arg Val
        1735                1740                1745

TGG GCA GAA TAT GAC CGA GCA GCA TGT GGC CGC ATC CAT TAC ACT GAG        5454
Trp Ala Glu Tyr Asp Arg Ala Ala Cys Gly Arg Ile His Tyr Thr Glu
            1750                1755                1760

ATG TAT GAA ATG CTG ACT CTC ATG TCA CCT CCG CTA GGC CTC GGC AAG        5502
Met Tyr Glu Met Leu Thr Leu Met Ser Pro Pro Leu Gly Leu Gly Lys
        1765                1770                1775

AGA TGT CCC TCC AAA GTG GCA TAT AAG AGG TTG GTC CTG ATG AAC ATG        5550
Arg Cys Pro Ser Lys Val Ala Tyr Lys Arg Leu Val Leu Met Asn Met
1780                1785                1790                1795

CCA GTA GCT GAG GAC ATG ACG GTC CAC TTC ACC TCC ACA CTT ATG GCT        5598
Pro Val Ala Glu Asp Met Thr Val His Phe Thr Ser Thr Leu Met Ala
                1800                1805                1810

CTG ATC CGG ACA GCT CTG GAC ATT AAA ATT GCC AAA GGT GGT GCA GAC        5646
Leu Ile Arg Thr Ala Leu Asp Ile Lys Ile Ala Lys Gly Gly Ala Asp
        1815                1820                1825

AGG CAG CAG CTA GAC TCA GAG CTA CAA AAG GAG ACC CTA GCC ATC TGG        5694
Arg Gln Gln Leu Asp Ser Glu Leu Gln Lys Glu Thr Leu Ala Ile Trp
            1830                1835                1840

CCT CAC CTA TCC CAG AAG ATG CTG GAT CTG CTT GTG CCC ATG CCC AAA        5742
Pro His Leu Ser Gln Lys Met Leu Asp Leu Leu Val Pro Met Pro Lys
        1845                1850                1855

GCC TCT GAC CTG ACT GTG GGC AAA ATC TAT GCA GCA ATG ATG ATC ATG        5790
Ala Ser Asp Leu Thr Val Gly Lys Ile Tyr Ala Ala Met Met Ile Met
1860                1865                1870                1875

GAC TAC TAT AAG CAG AGT AAG GTG AAG AAG CAG AGG CAG CAG CTG GAG        5838
Asp Tyr Tyr Lys Gln Ser Lys Val Lys Lys Gln Arg Gln Gln Leu Glu
                1880                1885                1890

GAA CAG AAA AAT GCC CCC ATG TTC CAG CGC ATG GAG CCT TCA TCT CTG        5886
Glu Gln Lys Asn Ala Pro Met Phe Gln Arg Met Glu Pro Ser Ser Leu
        1895                1900                1905

CCT CAG GAG ATC ATT GCT AAT GCC AAA GCC CTG CCT TAC CTC CAG CAG        5934
Pro Gln Glu Ile Ile Ala Asn Ala Lys Ala Leu Pro Tyr Leu Gln Gln
            1910                1915                1920

GAC CCC GTT TCA GGC CTG AGT GGC CGG AGT GGA TAC CCT TCG ATG AGT        5982
Asp Pro Val Ser Gly Leu Ser Gly Arg Ser Gly Tyr Pro Ser Met Ser
        1925                1930                1935

CCA CTC TCT CCC CAG GAT ATA TTC CAG TTG GCT TGT ATG GAC CCC GCC        6030
Pro Leu Ser Pro Gln Asp Ile Phe Gln Leu Ala Cys Met Asp Pro Ala
1940                1945                1950                1955

GAT GAC GGA CAG TTC CAA GAA CGG CAG TCT CTG GTG GTG ACA GAC CCT        6078
Asp Asp Gly Gln Phe Gln Glu Arg Gln Ser Leu Val Val Thr Asp Pro
                1960                1965                1970

AGC TCC ATG AGA CGT TCA TTT TCC ACT ATT CGG GAT AAG CGT TCA AAT        6126
Ser Ser Met Arg Arg Ser Phe Ser Thr Ile Arg Asp Lys Arg Ser Asn
        1975                1980                1985

TCC TCG TGG TTG GAG GAA TTC TCC ATG GAG CGA AGC AGT GAA AAT ACC        6174
Ser Ser Trp Leu Glu Glu Phe Ser Met Glu Arg Ser Ser Glu Asn Thr
```

```
                1990                1995                2000
TAC AAG TCC CGT CGC CGG AGT TAC CAC TCC TCC TTG CGG CTG TCA GCC    6222
Tyr Lys Ser Arg Arg Arg Ser Tyr His Ser Ser Leu Arg Leu Ser Ala
    2005                2010                2015

CAC CGC CTG AAC TCT GAT TCA GGC CAC AAG TCT GAC ACT CAC CCC TCA    6270
His Arg Leu Asn Ser Asp Ser Gly His Lys Ser Asp Thr His Pro Ser
2020                2025                2030                2035

GGG GGC AGG GAG CGG CGA CGA TCA AAA GAG CGA AAG CAT CTT CTC TCT    6318
Gly Gly Arg Glu Arg Arg Arg Ser Lys Glu Arg Lys His Leu Leu Ser
            2040                2045                2050

CCT GAT GTC TCC CGC TGC AAT TCA GAA GAG CGA GGG ACC CAG GCT GAC    6366
Pro Asp Val Ser Arg Cys Asn Ser Glu Glu Arg Gly Thr Gln Ala Asp
                2055                2060                2065

TGG GAG TCC CCA GAG CGC CGT CAA TCC AGG TCA CCC AGT GAG GGC AGG    6414
Trp Glu Ser Pro Glu Arg Arg Gln Ser Arg Ser Pro Ser Glu Gly Arg
            2070                2075                2080

TCA CAG ACG CCC AAC AGA CAG GGC ACA GGT TCC CTA AGT GAG AGC TCC    6462
Ser Gln Thr Pro Asn Arg Gln Gly Thr Gly Ser Leu Ser Glu Ser Ser
    2085                2090                2095

ATC CCC TCT GTC TCT GAC ACC AGC ACC CCA AGA AGA AGT CGT CGG CAG    6510
Ile Pro Ser Val Ser Asp Thr Ser Thr Pro Arg Arg Ser Arg Arg Gln
2100                2105                2110                2115

CTC CCA CCC GTC CCG CCA AAG CCC CGG CCC CTC CTT TCC TAC AGC TCC    6558
Leu Pro Pro Val Pro Pro Lys Pro Arg Pro Leu Leu Ser Tyr Ser Ser
                2120                2125                2130

CTG ATT CGA CAC GCG GGC AGC ATC TCT CCA CCT GCT GAT GGA AGC GAG    6606
Leu Ile Arg His Ala Gly Ser Ile Ser Pro Pro Ala Asp Gly Ser Glu
            2135                2140                2145

GAG GGC TCC CCG CTG ACC TCC CAA GCT CTG GAG AGC AAC AAT GCT TGG    6654
Glu Gly Ser Pro Leu Thr Ser Gln Ala Leu Glu Ser Asn Asn Ala Trp
        2150                2155                2160

CTG ACC GAG TCT TCC AAC TCT CCG CAC CCC CAG CAG AGG CAA CAT GCC    6702
Leu Thr Glu Ser Ser Asn Ser Pro His Pro Gln Gln Arg Gln His Ala
    2165                2170                2175

TCC CCA CAG CGC TAC ATC TCC GAG CCC TAC TTG GCC CTG CAC GAA GAC    6750
Ser Pro Gln Arg Tyr Ile Ser Glu Pro Tyr Leu Ala Leu His Glu Asp
2180                2185                2190                2195

TCC CAC GCC TCA GAC TGT GTT GAG GAG GAG ACG CTC ACT TTC GAA GCA    6798
Ser His Ala Ser Asp Cys Val Glu Glu Glu Thr Leu Thr Phe Glu Ala
                2200                2205                2210

GCC GTG GCT ACT AGC CTG GGC CGT TCC AAC ACC ATC GGC TCA GCC CCA    6846
Ala Val Ala Thr Ser Leu Gly Arg Ser Asn Thr Ile Gly Ser Ala Pro
            2215                2220                2225

CCC CTG CGG CAT AGC TGG CAG ATG CCC AAC GGG CAC TAT CGG CGG CGG    6894
Pro Leu Arg His Ser Trp Gln Met Pro Asn Gly His Tyr Arg Arg Arg
        2230                2235                2240

AGG CGC GGG GGG CCT GGG CCA GGC ATG ATG TGT GGG GCT GTC AAC AAC    6942
Arg Arg Gly Gly Pro Gly Pro Gly Met Met Cys Gly Ala Val Asn Asn
    2245                2250                2255

CTG CTA AGT GAC ACG GAA GAA GAT GAC AAA TGC TAGAGGCTGC TCCCCCCTCC  6995
Leu Leu Ser Asp Thr Glu Glu Asp Asp Lys Cys
2260                2265                2270

GATGCATGCT CTTCTCTCAC ATGGAGAAAA CCAAGACAGA ATTGGGAAGC CAGTGCGGCC  7055

CCGCGGGGAG GAAGAGGGAA AAGGAAGATG GAAG                              7089

(2) INFORMATION FOR SEQ ID NO:26:

(i) SEQUENCE CHARACTERISTICS:
        (A) LENGTH: 2634 base pairs
```

(B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 1..1983
      (D) OTHER INFORMATION: /standard_name= "Beta-2d"

(xi) SEQUENCE DESCRIPTION: SEQ ID NO:26:

```
ATG GTC CAA AGG GAC ATG TCC AAG TCT CCT CCC ACA CCG GCG GCG GCG      48
Met Val Gln Arg Asp Met Ser Lys Ser Pro Pro Thr Pro Ala Ala Ala
 1               5                  10                  15

GTG GCG CAG GAG ATC CAG ATG GAA CTG CTA GAG AAC GTG GCT CCC GCG      96
Val Ala Gln Glu Ile Gln Met Glu Leu Leu Glu Asn Val Ala Pro Ala
                 20                  25                  30

GGG GCG CTC GGA GCC GCC GCA CAG TCA TAT GGA AAA GGA GCC AGA AGG     144
Gly Ala Leu Gly Ala Ala Ala Gln Ser Tyr Gly Lys Gly Ala Arg Arg
             35                  40                  45

AAA AAC AGA TTT AAA GGA TCT GAT GGA AGC ACG TCA TCT GAT ACT ACC     192
Lys Asn Arg Phe Lys Gly Ser Asp Gly Ser Thr Ser Ser Asp Thr Thr
 50                  55                  60

TCA AAT AGT TTT GTT CGC CAG GGT TCG GCA GAC TCC TAC ACT AGC CGT     240
Ser Asn Ser Phe Val Arg Gln Gly Ser Ala Asp Ser Tyr Thr Ser Arg
 65                  70                  75                  80

CCA TCC GAT TCC GAT GTA TCT CTG GAG GAG GAC CGG GAG GCA GTG CGC     288
Pro Ser Asp Ser Asp Val Ser Leu Glu Glu Asp Arg Glu Ala Val Arg
                 85                  90                  95

AGA GAA GCG GAG CGG CAG GCC CAG GCA CAG TTG GAA AAA GCA AAG ACA     336
Arg Glu Ala Glu Arg Gln Ala Gln Ala Gln Leu Glu Lys Ala Lys Thr
            100                 105                 110

AAG CCC GTT GCA TTT GCG GTT CGG ACA AAT GTC AGC TAC AGT GCG GCC     384
Lys Pro Val Ala Phe Ala Val Arg Thr Asn Val Ser Tyr Ser Ala Ala
            115                 120                 125

CAT GAA GAT GAT GTT CCA GTG CCT GGC ATG GCC ATC TCA TTC GAA GCA     432
His Glu Asp Asp Val Pro Val Pro Gly Met Ala Ile Ser Phe Glu Ala
130                 135                 140

AAA GAT TTT CTG CAT GTT AAG GAA AAA TTT AAC AAT GAC TGG TGG ATA     480
Lys Asp Phe Leu His Val Lys Glu Lys Phe Asn Asn Asp Trp Trp Ile
145                 150                 155                 160

GGG CGA TTG GTA AAA GAA GGC TGT GAA ATC GGA TTC ATT CCA AGC CCA     528
Gly Arg Leu Val Lys Glu Gly Cys Glu Ile Gly Phe Ile Pro Ser Pro
                165                 170                 175

GTC AAA CTA GAA AAC ATG AGG CTG CAG CAT GAA CAG AGA GCC AAG CAA     576
Val Lys Leu Glu Asn Met Arg Leu Gln His Glu Gln Arg Ala Lys Gln
            180                 185                 190

GGG AAA TTC TAC TCC AGT AAA TCA GGA GGA AAT TCA TCA TCC AGT TTG     624
Gly Lys Phe Tyr Ser Ser Lys Ser Gly Gly Asn Ser Ser Ser Ser Leu
            195                 200                 205

GGT GAC ATA GTA CCT AGT TCC AGA AAA TCA ACA CCT CCA TCA TCT GCT     672
Gly Asp Ile Val Pro Ser Ser Arg Lys Ser Thr Pro Pro Ser Ser Ala
            210                 215                 220

ATA GAC ATA GAT GCT ACT GGC TTA GAT GCA GAA GAA AAT GAT ATT CCA     720
Ile Asp Ile Asp Ala Thr Gly Leu Asp Ala Glu Glu Asn Asp Ile Pro
225                 230                 235                 240

GCA AAC CAC CGC TCC CCT AAA CCC AGT GCA AAC AGT GTA ACG TCA CCC     768
Ala Asn His Arg Ser Pro Lys Pro Ser Ala Asn Ser Val Thr Ser Pro
                245                 250                 255

CAC TCC AAA GAG AAA AGA ATG CCC TTC TTT AAG AAG ACA GAG CAC ACT     816
His Ser Lys Glu Lys Arg Met Pro Phe Phe Lys Lys Thr Glu His Thr
```

-continued

|     |     |     |     |     |     |     |     |     |     |     |     |     |     |      |
|-----|-----|-----|-----|-----|-----|-----|-----|-----|-----|-----|-----|-----|-----|------|
|     |     | 260 |     |     |     | 265 |     |     |     | 270 |     |     |     |      |
| CCT | CCG | TAT | GAT | GTG | GTA | CCT | TCC | ATG | CGA | CCA | GTG | GTC | CTA | GTG GGC | 864 |
| Pro | Pro | Tyr | Asp | Val | Val | Pro | Ser | Met | Arg | Pro | Val | Val | Leu | Val Gly |
|     |     | 275 |     |     |     | 280 |     |     |     | 285 |     |     |     |      |
| CCT | TCT | CTG | AAG | GGC | TAC | GAG | GTC | ACA | GAT | ATG | ATG | CAA | AAA | GCG CTG | 912 |
| Pro | Ser | Leu | Lys | Gly | Tyr | Glu | Val | Thr | Asp | Met | Met | Gln | Lys | Ala Leu |
|     |     | 290 |     |     |     | 295 |     |     |     | 300 |     |     |     |      |
| TTT | GAT | TTT | TTA | AAA | CAC | AGA | TTT | GAA | GGG | CGG | ATA | TCC | ATC | ACA AGG | 960 |
| Phe | Asp | Phe | Leu | Lys | His | Arg | Phe | Glu | Gly | Arg | Ile | Ser | Ile | Thr Arg |
| 305 |     |     |     | 310 |     |     |     | 315 |     |     |     | 320 |     |      |
| GTC | ACC | GCT | GAC | ATC | TCG | CTT | GCC | AAA | CGC | TCG | GTA | TTA | AAC | AAT CCC | 1008 |
| Val | Thr | Ala | Asp | Ile | Ser | Leu | Ala | Lys | Arg | Ser | Val | Leu | Asn | Asn Pro |
|     |     |     |     | 325 |     |     |     | 330 |     |     |     | 335 |     |      |
| AGT | AAG | CAC | GCA | ATA | ATA | GAA | AGA | TCC | AAC | ACA | AGG | TCA | AGC | TTA GCG | 1056 |
| Ser | Lys | His | Ala | Ile | Ile | Glu | Arg | Ser | Asn | Thr | Arg | Ser | Ser | Leu Ala |
|     |     |     | 340 |     |     |     | 345 |     |     |     | 350 |     |     |      |
| GAA | GTT | CAG | AGT | GAA | ATC | GAA | AGG | ATT | TTT | GAA | CTT | GCA | AGA | ACA TTG | 1104 |
| Glu | Val | Gln | Ser | Glu | Ile | Glu | Arg | Ile | Phe | Glu | Leu | Ala | Arg | Thr Leu |
|     |     | 355 |     |     |     | 360 |     |     |     | 365 |     |     |     |      |
| CAG | TTG | GTG | GTC | CTT | GAC | GCG | GAT | ACA | ATT | AAT | CAT | CCA | GCT | CAA CTC | 1152 |
| Gln | Leu | Val | Val | Leu | Asp | Ala | Asp | Thr | Ile | Asn | His | Pro | Ala | Gln Leu |
|     | 370 |     |     |     | 375 |     |     |     | 380 |     |     |     |     |      |
| AGT | AAA | ACC | TCC | TTG | GCC | CCT | ATT | ATA | GTA | TAT | GTA | AAG | ATT | TCT TCT | 1200 |
| Ser | Lys | Thr | Ser | Leu | Ala | Pro | Ile | Ile | Val | Tyr | Val | Lys | Ile | Ser Ser |
| 385 |     |     |     | 390 |     |     |     | 395 |     |     |     |     |     | 400  |
| CCT | AAG | GTT | TTA | CAA | AGG | TTA | ATA | AAA | TCT | CGA | GGG | AAA | TCT | CAA GCT | 1248 |
| Pro | Lys | Val | Leu | Gln | Arg | Leu | Ile | Lys | Ser | Arg | Gly | Lys | Ser | Gln Ala |
|     |     |     | 405 |     |     |     | 410 |     |     |     | 415 |     |     |      |
| AAA | CAC | CTC | AAC | GTC | CAG | ATG | GTA | GCA | GCT | GAT | AAA | CTG | GCT | CAG TGT | 1296 |
| Lys | His | Leu | Asn | Val | Gln | Met | Val | Ala | Ala | Asp | Lys | Leu | Ala | Gln Cys |
|     |     | 420 |     |     |     | 425 |     |     |     | 430 |     |     |     |      |
| CCT | CCA | GAG | CTG | TTC | GAT | GTG | ATC | TTG | GAT | GAG | AAC | CAG | CTT | GAG GAT | 1344 |
| Pro | Pro | Glu | Leu | Phe | Asp | Val | Ile | Leu | Asp | Glu | Asn | Gln | Leu | Glu Asp |
|     |     | 435 |     |     |     | 440 |     |     |     | 445 |     |     |     |      |
| GCC | TGT | GAG | CAC | CTT | GCC | GAC | TAT | CTG | GAG | GCC | TAC | TGG | AAG | GCC ACC | 1392 |
| Ala | Cys | Glu | His | Leu | Ala | Asp | Tyr | Leu | Glu | Ala | Tyr | Trp | Lys | Ala Thr |
|     | 450 |     |     |     | 455 |     |     |     | 460 |     |     |     |     |      |
| CAT | CCT | CCC | AGC | AGT | AGC | CTC | CCC | AAC | CCT | CTC | CTT | AGC | CGT | ACA TTA | 1440 |
| His | Pro | Pro | Ser | Ser | Ser | Leu | Pro | Asn | Pro | Leu | Leu | Ser | Arg | Thr Leu |
| 465 |     |     |     | 470 |     |     |     | 475 |     |     |     |     |     | 480  |
| GCC | ACT | TCA | AGT | CTG | CCT | CTT | AGC | CCC | ACC | CTA | GCC | TCT | AAT | TCA CAG | 1488 |
| Ala | Thr | Ser | Ser | Leu | Pro | Leu | Ser | Pro | Thr | Leu | Ala | Ser | Asn | Ser Gln |
|     |     |     | 485 |     |     |     | 490 |     |     |     | 495 |     |     |      |
| GGT | TCT | CAA | GGT | GAT | CAG | AGG | ACT | GAT | CGC | TCC | GCT | CCT | ATC | CGT TCT | 1536 |
| Gly | Ser | Gln | Gly | Asp | Gln | Arg | Thr | Asp | Arg | Ser | Ala | Pro | Ile | Arg Ser |
|     |     | 500 |     |     |     | 505 |     |     |     | 510 |     |     |     |      |
| GCT | TCC | CAA | GCT | GAA | GAA | GAA | CCT | AGT | GTG | GAA | CCA | GTC | AAG | AAA TCC | 1584 |
| Ala | Ser | Gln | Ala | Glu | Glu | Glu | Pro | Ser | Val | Glu | Pro | Val | Lys | Lys Ser |
|     |     | 515 |     |     |     | 520 |     |     |     | 525 |     |     |     |      |
| CAG | CAC | CGC | TCT | TCC | TCC | TCA | GCC | CCA | CAC | CAC | AAC | CAT | CGC | AGT GGG | 1632 |
| Gln | His | Arg | Ser | Ser | Ser | Ser | Ala | Pro | His | His | Asn | His | Arg | Ser Gly |
|     | 530 |     |     |     | 535 |     |     |     | 540 |     |     |     |     |      |
| ACA | AGT | CGC | GGC | CTC | TCC | AGG | CAA | GAG | ACA | TTT | GAC | TCG | GAA | ACC CAG | 1680 |
| Thr | Ser | Arg | Gly | Leu | Ser | Arg | Gln | Glu | Thr | Phe | Asp | Ser | Glu | Thr Gln |
| 545 |     |     |     | 550 |     |     |     | 555 |     |     |     |     |     | 560  |
| GAG | AGT | CGA | GAC | TCT | GCC | TAC | GTA | GAG | CCA | AAG | GAA | GAT | TAT | TCC CAT | 1728 |
| Glu | Ser | Arg | Asp | Ser | Ala | Tyr | Val | Glu | Pro | Lys | Glu | Asp | Tyr | Ser His |
|     |     |     | 565 |     |     |     | 570 |     |     |     | 575 |     |     |      |
| GAC | CAC | GTG | GAC | CAC | TAT | GCC | TCA | CAC | CGT | GAC | CAC | AAC | CAC | AGA GAC | 1776 |

```
Asp His Val Asp His Tyr Ala Ser His Arg Asp His Asn His Arg Asp
            580                 585                 590

GAG ACC CAC GGG AGC AGT GAC CAC AGA CAC AGG GAG TCC CGG CAC CGT    1824
Glu Thr His Gly Ser Ser Asp His Arg His Arg Glu Ser Arg His Arg
        595                 600                 605

TCC CGG GAC GTG GAT CGA GAG CAG GAC CAC AAC GAG TGC AAC AAG CAG    1872
Ser Arg Asp Val Asp Arg Glu Gln Asp His Asn Glu Cys Asn Lys Gln
610                 615                 620

CGC AGC CGT CAT AAA TCC AAG GAT CGC TAC TGT GAA AAG GAT GGA GAA    1920
Arg Ser Arg His Lys Ser Lys Asp Arg Tyr Cys Glu Lys Asp Gly Glu
625                 630                 635                 640

GTG ATA TCA AAA AAA CGG AAT GAG GCT GGG GAG TGG AAC AGG GAT GTT    1968
Val Ile Ser Lys Lys Arg Asn Glu Ala Gly Glu Trp Asn Arg Asp Val
                645                 650                 655

TAC ATC CCC CAA TGAGTTTTGC CCTTTTGTGT TTTTTTTTTT TTTTTTTTGA        2020
Tyr Ile Pro Gln
            660

AGTCTTGTAT AACTAACAGC ATCCCCAAAA CAAAAAGTCT TGGGGTCTA CACTGCAATC   2080

ATATGTGATC TGTCTTGTAA TATTTTGTAT TATTGCTGTT GCTTGAATAG CAATAGCATG  2140

GATAGAGTAT TGAGATACTT TTTCTTTTGT AAGTGCTACA TAAATTGGCC TGGTATGGCT  2200

GCAGTCCTCC GGTTGCATAC TGGACTCTTC AAAAACTGTT TTGGGTAGCT GCCACTTGAA  2260

CAAAATCTGT TGCCACCCAG GTGATGTTAG TGTTTTAAGA AATGTAGTTG ATGTATCCAA  2320

CAAGCCAGAA TCAGCACAGA TAAAAAGTGG AATTTCTTGT TTCTCCAGAT TTTTAATACG  2380

TTAATACGCA GGCATCTGAT TTGCATATTC ATTCATGGAC CACTGTTTCT TGCTTGTACC  2440

TCTGGCTGAC TAAATTTGGG GACAGATTCA GTCTTGCCTT ACACAAAGGG GATCATAAAG  2500

TTAGAATCTA TTTTCTATGT ACTAGTACTG TGTACTGTAT AGACAGTTTG TAAATGTTAT  2560

TTCTGCAAAC AAACACCTCC TTATTATATA TAATATATAT ATATATATCA GTTTGATCAC  2620

ACTATTTTAG AGTC                                                   2634

(2) INFORMATION FOR SEQ ID NO:27:

(i) SEQUENCE CHARACTERISTICS:
        (A) LENGTH: 1823 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 69..1631
        (D) OTHER INFORMATION: /standard_name= "Beta-4"

(xi) SEQUENCE DESCRIPTION: SEQ ID NO:27:

AGCCCAGCCT CGGGGGCCAG CCCCCTCCGC CACCGCACA CGGGCTGGCC ATGCGGCGGC    60

TCTGAACG ATG TCC TCC TCC TCC TAC GCC AAG AAC GGG ACC GCG GAC GGG   110
         Met Ser Ser Ser Ser Tyr Ala Lys Asn Gly Thr Ala Asp Gly
             1               5                   10

CCG CAC TCC CCC ACC TCG CAG GTG GCC CGA GGC ACC ACA ACC CGG AGG    158
Pro His Ser Pro Thr Ser Gln Val Ala Arg Gly Thr Thr Thr Arg Arg
 15                  20                  25                  30

AGC AGG TTG AAA AGA TCC GAT GGC AGC ACC ACT TCG ACC AGC TTC ATC    206
Ser Arg Leu Lys Arg Ser Asp Gly Ser Thr Thr Ser Thr Ser Phe Ile
                 35                  40                  45

CTC AGA CAG GGT TCA GCG GAT TCC TAC ACA AGC AGG CCG TCT GAC TCC    254
Leu Arg Gln Gly Ser Ala Asp Ser Tyr Thr Ser Arg Pro Ser Asp Ser
```

```
            50                      55                      60
GAT GTC TCT TTG GAA GAG GAC CGG GAA GCA ATT CGA CAG GAG AGA GAA    302
Asp Val Ser Leu Glu Glu Asp Arg Glu Ala Ile Arg Gln Glu Arg Glu
            65                      70                      75

CAG CAA GCA GCT ATC CAG CTT GAG AGA GCA AAG TCC AAA CCT GTA GCA    350
Gln Gln Ala Ala Ile Gln Leu Glu Arg Ala Lys Ser Lys Pro Val Ala
            80                      85                      90

TTT GCC GTG AAG ACA AAT GTG AGC TAC TGC GGC GCC CTG GAC GAG GAT    398
Phe Ala Val Lys Thr Asn Val Ser Tyr Cys Gly Ala Leu Asp Glu Asp
95                      100                     105                     110

GTG CCT GTT CCA AGC ACA GCT ATC TCC TTT GAT GCT AAA GAC TTT CTA    446
Val Pro Val Pro Ser Thr Ala Ile Ser Phe Asp Ala Lys Asp Phe Leu
                    115                     120                     125

CAT ATT AAA GAG AAA TAT AAC AAT GAT TGG TGG ATA GGA AGG CTG GTG    494
His Ile Lys Glu Lys Tyr Asn Asn Asp Trp Trp Ile Gly Arg Leu Val
                    130                     135                     140

AAA GAG GGC TGT GAA ATT GGC TTC ATT CCA AGT CCA CTC AGA TTG GAG    542
Lys Glu Gly Cys Glu Ile Gly Phe Ile Pro Ser Pro Leu Arg Leu Glu
                    145                     150                     155

AAC ATA CGG ATC CAG CAA GAA CAA AAA AGA GGA CGT TTT CAC GGA GGG    590
Asn Ile Arg Ile Gln Gln Glu Gln Lys Arg Gly Arg Phe His Gly Gly
            160                     165                     170

AAA TCA AGT GGA AAT TCT TCT TCA AGT CTT GGA GAA ATG GTA TCT GGG    638
Lys Ser Ser Gly Asn Ser Ser Ser Ser Leu Gly Glu Met Val Ser Gly
175                     180                     185                     190

ACA TTC CGA GCA ACT CCC ACA TCA ACA GCA AAA CAG AAG CAA AAA GTG    686
Thr Phe Arg Ala Thr Pro Thr Ser Thr Ala Lys Gln Lys Gln Lys Val
                    195                     200                     205

ACG GAG CAC ATT CCT CCT TAC GAT GTT GTA CCG TCA ATG CGT CCG GTG    734
Thr Glu His Ile Pro Pro Tyr Asp Val Val Pro Ser Met Arg Pro Val
                    210                     215                     220

GTG TTA GTG GGG CCG TCA CTG AAA GGT TAC GAG GTA ACA GAC ATG ATG    782
Val Leu Val Gly Pro Ser Leu Lys Gly Tyr Glu Val Thr Asp Met Met
                    225                     230                     235

CAG AAA GCC CTC TTT GAT TCC CTG AAG CAC AGG TTT GAT GGG AGG ATT    830
Gln Lys Ala Leu Phe Asp Ser Leu Lys His Arg Phe Asp Gly Arg Ile
            240                     245                     250

TCA ATA ACG AGA GTG ACA GCT GAC ATT TCT CTT GCT AAG AGG TCT GTC    878
Ser Ile Thr Arg Val Thr Ala Asp Ile Ser Leu Ala Lys Arg Ser Val
255                     260                     265                     270

CTA AAT AAT CCC AGC AAG AGA GCA ATA ATT GAA CGT TCG AAC ACC CGG    926
Leu Asn Asn Pro Ser Lys Arg Ala Ile Ile Glu Arg Ser Asn Thr Arg
                    275                     280                     285

TCC AGC TTA GCG GAA GTA CAA AGT GAA ATT GAA AGA ATC TTT GAG TTG    974
Ser Ser Leu Ala Glu Val Gln Ser Glu Ile Glu Arg Ile Phe Glu Leu
                    290                     295                     300

GCA AGA TCT TTG CAA CTG GTT GTT CTT GAT GCA GAC ACC ATC AAT CAC    1022
Ala Arg Ser Leu Gln Leu Val Val Leu Asp Ala Asp Thr Ile Asn His
            305                     310                     315

CCA GCA CAA CTT ATA AAG ACT TCC TTA GCA CCA ATT ATT GTT CAT GTA    1070
Pro Ala Gln Leu Ile Lys Thr Ser Leu Ala Pro Ile Ile Val His Val
            320                     325                     330

AAA GTC TCA TCT CCA AAG GTT TTA CAG CGG TTG ATT AAA TCT AGA GGA    1118
Lys Val Ser Ser Pro Lys Val Leu Gln Arg Leu Ile Lys Ser Arg Gly
335                     340                     345                     350

AAG TCA CAA AGT AAA CAC TTG AAT GTT CAA CTG GTG GCA GCT GAT AAA    1166
Lys Ser Gln Ser Lys His Leu Asn Val Gln Leu Val Ala Ala Asp Lys
                    355                     360                     365

CTT GCA CAA TGC CCC CCA GAA ATG TTT GAT GTT ATA TTG GAT GAA AAT    1214
```

-continued

```
            Leu Ala Gln Cys Pro Glu Met Phe Asp Val Ile Leu Asp Glu Asn
                    370                 375                 380

CAG CTT GAG GAT GCA TGT GAA CAT CTA GGG GAG TAC CTG GAG GCG TAC        1262
Gln Leu Glu Asp Ala Cys Glu His Leu Gly Glu Tyr Leu Glu Ala Tyr
            385                 390                 395

TGG CGT GCC ACC CAC ACA ACC AGT AGC ACA CCC ATG ACC CCG CTG CTG        1310
Trp Arg Ala Thr His Thr Thr Ser Ser Thr Pro Met Thr Pro Leu Leu
400                 405                 410

GGA AGG AAT TTG GGC TCC ACG GCA CTC TCA CCA TAT CCC ACA GCA ATT        1358
Gly Arg Asn Leu Gly Ser Thr Ala Leu Ser Pro Tyr Pro Thr Ala Ile
415                 420                 425                 430

TCT GGG TTA CAG AGT CAG CGA ATG AGG CAC AGC AAC CAC TCC ACA GAG        1406
Ser Gly Leu Gln Ser Gln Arg Met Arg His Ser Asn His Ser Thr Glu
                435                 440                 445

AAC TCT CCA ATT GAA AGA CGA AGT CTA ATG ACC TCT GAT GAA AAT TAT        1454
Asn Ser Pro Ile Glu Arg Arg Ser Leu Met Thr Ser Asp Glu Asn Tyr
            450                 455                 460

CAC AAT GAA AGG GCT CGG AAG AGT AGG AAC CGC TTG TCT TCC AGT TCT        1502
His Asn Glu Arg Ala Arg Lys Ser Arg Asn Arg Leu Ser Ser Ser Ser
        465                 470                 475

CAG CAT AGC CGA GAT CAT TAC CCT CTT GTG GAA GAA GAT TAC CCT GAC        1550
Gln His Ser Arg Asp His Tyr Pro Leu Val Glu Glu Asp Tyr Pro Asp
480                 485                 490

TCA TAC CAG GAC ACT TAC AAA CCC CAT AGG AAC CGA GGA TCA CCT GGG        1598
Ser Tyr Gln Asp Thr Tyr Lys Pro His Arg Asn Arg Gly Ser Pro Gly
495                 500                 505                 510

GGA TAT AGC CAT GAC TCC CGA CAT AGG CTT TGAGTCTAAT GAAACAAAAA         1648
Gly Tyr Ser His Asp Ser Arg His Arg Leu
                515                 520

ATATTCATCT GTTGACAATT TGCCATAGCA GTGCTAGGAT AAACCAATCA TCTTAACTTG      1708

GCTAACATAG CACAGTATTT ACTGTGCTAA TGGGCTGCTG TCATTTTATG CTAAGTAAGG      1768

GGCAAAAAAA AAAATTACAT TATGCCCTTG AGTCTAGATG GATATTAGAT GCCCG          1823

(2) INFORMATION FOR SEQ ID NO:28:

(i) SEQUENCE CHARACTERISTICS:
            (A) LENGTH: 520 amino acids
            (B) TYPE: amino acid
            (D) TOPOLOGY: linear (ii) MOLECULE TYPE: protein (xi) SEQUENCE DESCRIPTION: SEQ ID NO:28:

Met Ser Ser Ser Tyr Ala Lys Asn Gly Thr Ala Asp Gly Pro His
1               5                   10                  15

Ser Pro Thr Ser Gln Val Ala Arg Gly Thr Thr Arg Arg Ser Arg
            20                  25                  30

Leu Lys Arg Ser Asp Gly Ser Thr Thr Ser Thr Ser Phe Ile Leu Arg
        35                  40                  45

Gln Gly Ser Ala Asp Ser Tyr Thr Ser Arg Pro Ser Asp Ser Asp Val
    50                  55                  60

Ser Leu Glu Glu Asp Arg Glu Ala Ile Arg Gln Glu Arg Glu Gln Gln
65                  70                  75                  80

Ala Ala Ile Gln Leu Glu Arg Ala Lys Ser Lys Pro Val Ala Phe Ala
                85                  90                  95

Val Lys Thr Asn Val Ser Tyr Cys Gly Ala Leu Asp Glu Asp Val Pro
            100                 105                 110

Val Pro Ser Thr Ala Ile Ser Phe Asp Ala Lys Asp Phe Leu His Ile
```

```
            115                 120                 125
Lys Glu Lys Tyr Asn Asn Asp Trp Trp Ile Gly Arg Leu Val Lys Glu
    130                 135                 140

Gly Cys Glu Ile Gly Phe Ile Pro Ser Pro Leu Arg Leu Glu Asn Ile
145                 150                 155                 160

Arg Ile Gln Gln Glu Gln Lys Arg Gly Arg Phe His Gly Gly Lys Ser
                165                 170                 175

Ser Gly Asn Ser Ser Ser Ser Leu Gly Glu Met Val Ser Gly Thr Phe
            180                 185                 190

Arg Ala Thr Pro Thr Ser Thr Ala Lys Gln Lys Gln Lys Val Thr Glu
        195                 200                 205

His Ile Pro Pro Tyr Asp Val Val Pro Ser Met Arg Pro Val Val Leu
    210                 215                 220

Val Gly Pro Ser Leu Lys Gly Tyr Glu Val Thr Asp Met Met Gln Lys
225                 230                 235                 240

Ala Leu Phe Asp Ser Leu Lys His Arg Phe Asp Gly Arg Ile Ser Ile
                245                 250                 255

Thr Arg Val Thr Ala Asp Ile Ser Leu Ala Lys Arg Ser Val Leu Asn
            260                 265                 270

Asn Pro Ser Lys Arg Ala Ile Ile Glu Arg Ser Asn Thr Arg Ser Ser
        275                 280                 285

Leu Ala Glu Val Gln Ser Glu Ile Glu Arg Ile Phe Glu Leu Ala Arg
    290                 295                 300

Ser Leu Gln Leu Val Val Leu Asp Ala Asp Thr Ile Asn His Pro Ala
305                 310                 315                 320

Gln Leu Ile Lys Thr Ser Leu Ala Pro Ile Ile Val His Val Lys Val
                325                 330                 335

Ser Ser Pro Lys Val Leu Gln Arg Leu Ile Lys Ser Arg Gly Lys Ser
            340                 345                 350

Gln Ser Lys His Leu Asn Val Gln Leu Val Ala Ala Asp Lys Leu Ala
        355                 360                 365

Gln Cys Pro Pro Glu Met Phe Asp Val Ile Leu Asp Glu Asn Gln Leu
    370                 375                 380

Glu Asp Ala Cys Glu His Leu Gly Glu Tyr Leu Glu Ala Tyr Trp Arg
385                 390                 395                 400

Ala Thr His Thr Thr Ser Ser Thr Pro Met Thr Pro Leu Leu Gly Arg
                405                 410                 415

Asn Leu Gly Ser Thr Ala Leu Ser Pro Tyr Pro Thr Ala Ile Ser Gly
            420                 425                 430

Leu Gln Ser Gln Arg Met Arg His Ser Asn His Ser Thr Glu Asn Ser
        435                 440                 445

Pro Ile Glu Arg Arg Ser Leu Met Thr Ser Asp Glu Asn Tyr His Asn
    450                 455                 460

Glu Arg Ala Arg Lys Ser Arg Asn Arg Leu Ser Ser Ser Ser Gln His
465                 470                 475                 480

Ser Arg Asp His Tyr Pro Leu Val Glu Glu Asp Tyr Pro Asp Ser Tyr
                485                 490                 495

Gln Asp Thr Tyr Lys Pro His Arg Asn Arg Gly Ser Pro Gly Gly Tyr
            500                 505                 510

Ser His Asp Ser Arg His Arg Leu
        515                 520

(2) INFORMATION FOR SEQ ID NO:29:
```

```
    (i) SEQUENCE CHARACTERISTICS:
        (A) LENGTH: 3636 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 35..3346
        (D) OTHER INFORMATION: /standard_name= "Alpha-2a"

(ix) FEATURE:
        (A) NAME/KEY: 5'UTR
        (B) LOCATION: 1..34

(ix) FEATURE:
        (A) NAME/KEY: 3'UTR
        (B) LOCATION: 3347..3636

(xi) SEQUENCE DESCRIPTION: SEQ ID NO:29:

GCGGGGGAGG GGGCATTGAT CTTCGATCGC GAAG ATG GCT GCT GGC TGC CTG              52
                                     Met Ala Ala Gly Cys Leu
                                       1               5

CTG GCC TTG ACT CTG ACA CTT TTC CAA TCT TTG CTC ATC GGC CCC TCG           100
Leu Ala Leu Thr Leu Thr Leu Phe Gln Ser Leu Leu Ile Gly Pro Ser
             10                  15                  20

TCG GAG GAG CCG TTC CCT TCG GCC GTC ACT ATC AAA TCA TGG GTG GAT           148
Ser Glu Glu Pro Phe Pro Ser Ala Val Thr Ile Lys Ser Trp Val Asp
         25                  30                  35

AAG ATG CAA GAA GAC CTT GTC ACA CTG GCA AAA ACA GCA AGT GGA GTC           196
Lys Met Gln Glu Asp Leu Val Thr Leu Ala Lys Thr Ala Ser Gly Val
     40                  45                  50

AAT CAG CTT GTT GAT ATT TAT GAG AAA TAT CAA GAT TTG TAT ACT GTG           244
Asn Gln Leu Val Asp Ile Tyr Glu Lys Tyr Gln Asp Leu Tyr Thr Val
 55                  60                  65                  70

GAA CCA AAT AAT GCA CGC CAG CTG GTA GAA ATT GCA GCC AGG GAT ATT           292
Glu Pro Asn Asn Ala Arg Gln Leu Val Glu Ile Ala Ala Arg Asp Ile
                 75                  80                  85

GAG AAA CTT CTG AGC AAC AGA TCT AAA GCC CTG GTG AGC CTG GCA TTG           340
Glu Lys Leu Leu Ser Asn Arg Ser Lys Ala Leu Val Ser Leu Ala Leu
             90                  95                 100

GAA GCG GAG AAA GTT CAA GCA GCT CAC CAG TGG AGA GAA GAT TTT GCA           388
Glu Ala Glu Lys Val Gln Ala Ala His Gln Trp Arg Glu Asp Phe Ala
        105                 110                 115

AGC AAT GAA GTT GTC TAC TAC AAT GCA AAG GAT GAT CTC GAT CCT GAG           436
Ser Asn Glu Val Val Tyr Tyr Asn Ala Lys Asp Asp Leu Asp Pro Glu
    120                 125                 130

AAA AAT GAC AGT GAG CCA GGC AGC CAG AGG ATA AAA CCT GTT TTC ATT           484
Lys Asn Asp Ser Glu Pro Gly Ser Gln Arg Ile Lys Pro Val Phe Ile
135                 140                 145                 150

GAA GAT GCT AAT TTT GGA CGA CAA ATA TCT TAT CAG CAC GCA GCA GTC           532
Glu Asp Ala Asn Phe Gly Arg Gln Ile Ser Tyr Gln His Ala Ala Val
                155                 160                 165

CAT ATT CCT ACT GAC ATC TAT GAG GGC TCA ACA ATT GTG TTA AAT GAA           580
His Ile Pro Thr Asp Ile Tyr Glu Gly Ser Thr Ile Val Leu Asn Glu
            170                 175                 180

CTC AAC TGG ACA AGT GCC TTA GAT GAA GTT TTC AAA AAG AAT CGC GAG           628
Leu Asn Trp Thr Ser Ala Leu Asp Glu Val Phe Lys Lys Asn Arg Glu
        185                 190                 195

GAA GAC CCT TCA TTA TTG TGG CAG GTT TTT GGC AGT GCC ACT GGC CTA           676
Glu Asp Pro Ser Leu Leu Trp Gln Val Phe Gly Ser Ala Thr Gly Leu
    200                 205                 210
```

```
GCT CGA TAT TAT CCA GCT TCA CCA TGG GTT GAT AAT AGT AGA ACT CCA        724
Ala Arg Tyr Tyr Pro Ala Ser Pro Trp Val Asp Asn Ser Arg Thr Pro
215             220                 225                 230

AAT AAG ATT GAC CTT TAT GAT GTA CGC AGA AGA CCA TGG TAC ATC CAA        772
Asn Lys Ile Asp Leu Tyr Asp Val Arg Arg Arg Pro Trp Tyr Ile Gln
                235                 240                 245

GGA GCT GCA TCT CCT AAA GAC ATG CTT ATT CTG GTG GAT GTG AGT GGA        820
Gly Ala Ala Ser Pro Lys Asp Met Leu Ile Leu Val Asp Val Ser Gly
                250                 255                 260

AGT GTT AGT GGA TTG ACA CTT AAA CTG ATC CGA ACA TCT GTC TCC GAA        868
Ser Val Ser Gly Leu Thr Leu Lys Leu Ile Arg Thr Ser Val Ser Glu
            265                 270                 275

ATG TTA GAA ACC CTC TCA GAT GAT GAT TTC GTG AAT GTA GCT TCA TTT        916
Met Leu Glu Thr Leu Ser Asp Asp Asp Phe Val Asn Val Ala Ser Phe
280                 285                 290

AAC AGC AAT GCT CAG GAT GTA AGC TGT TTT CAG CAC CTT GTC CAA GCA        964
Asn Ser Asn Ala Gln Asp Val Ser Cys Phe Gln His Leu Val Gln Ala
295                 300                 305                 310

AAT GTA AGA AAT AAA AAA GTG TTG AAA GAC GCG GTG AAT AAT ATC ACA       1012
Asn Val Arg Asn Lys Lys Val Leu Lys Asp Ala Val Asn Asn Ile Thr
                315                 320                 325

GCC AAA GGA ATT ACA GAT TAT AAG AAG GGC TTT AGT TTT GCT TTT GAA       1060
Ala Lys Gly Ile Thr Asp Tyr Lys Lys Gly Phe Ser Phe Ala Phe Glu
                330                 335                 340

CAG CTG CTT AAT TAT AAT GTT TCC AGA GCA AAC TGC AAT AAG ATT ATT       1108
Gln Leu Leu Asn Tyr Asn Val Ser Arg Ala Asn Cys Asn Lys Ile Ile
            345                 350                 355

ATG CTA TTC ACG GAT GGA GGA GAA GAG AGA GCC CAG GAG ATA TTT AAC       1156
Met Leu Phe Thr Asp Gly Gly Glu Glu Arg Ala Gln Glu Ile Phe Asn
360                 365                 370

AAA TAC AAT AAA GAT AAA AAA GTA CGT GTA TTC AGG TTT TCA GTT GGT       1204
Lys Tyr Asn Lys Asp Lys Lys Val Arg Val Phe Arg Phe Ser Val Gly
375                 380                 385                 390

CAA CAC AAT TAT GAG AGA GGA CCT ATT CAG TGG ATG GCC TGT GAA AAC       1252
Gln His Asn Tyr Glu Arg Gly Pro Ile Gln Trp Met Ala Cys Glu Asn
                395                 400                 405

AAA GGT TAT TAT TAT GAA ATT CCT TCC ATT GGT GCA ATA AGA ATC AAT       1300
Lys Gly Tyr Tyr Tyr Glu Ile Pro Ser Ile Gly Ala Ile Arg Ile Asn
                410                 415                 420

ACT CAG GAA TAT TTG GAT GTT TTG GGA AGA CCA ATG GTT TTA GCA GGA       1348
Thr Gln Glu Tyr Leu Asp Val Leu Gly Arg Pro Met Val Leu Ala Gly
                425                 430                 435

GAC AAA GCT AAG CAA GTC CAA TGG ACA AAT GTG TAC CTG GAT GCA TTG       1396
Asp Lys Ala Lys Gln Val Gln Trp Thr Asn Val Tyr Leu Asp Ala Leu
            440                 445                 450

GAA CTG GGA CTT GTC ATT ACT GGA ACT CTT CCG GTC TTC AAC ATA ACC       1444
Glu Leu Gly Leu Val Ile Thr Gly Thr Leu Pro Val Phe Asn Ile Thr
455                 460                 465                 470

GGC CAA TTT GAA AAT AAG ACA AAC TTA AAG AAC CAG CTG ATT CTT GGT       1492
Gly Gln Phe Glu Asn Lys Thr Asn Leu Lys Asn Gln Leu Ile Leu Gly
                475                 480                 485

GTG ATG GGA GTA GAT GTG TCT TTG GAA GAT ATT AAA AGA CTG ACA CCA       1540
Val Met Gly Val Asp Val Ser Leu Glu Asp Ile Lys Arg Leu Thr Pro
                490                 495                 500

CGT TTT ACA CTG TGC CCC AAT GGG TAT TAC TTT GCA ATC GAT CCT AAT       1588
Arg Phe Thr Leu Cys Pro Asn Gly Tyr Tyr Phe Ala Ile Asp Pro Asn
            505                 510                 515

GGT TAT GTT TTA TTA CAT CCA AAT CTT CAG CCA AAG CCT ATT GGT GTA       1636
Gly Tyr Val Leu Leu His Pro Asn Leu Gln Pro Lys Pro Ile Gly Val
```

```
              520                 525                 530
GGT ATA CCA ACA ATT AAT TTA AGA AAA AGG AGA CCC AAT ATC CAG AAC       1684
Gly Ile Pro Thr Ile Asn Leu Arg Lys Arg Arg Pro Asn Ile Gln Asn
535                 540                 545                 550

CCC AAA TCT CAG GAG CCA GTA ACA TTG GAT TTC CTT GAT GCA GAG TTA       1732
Pro Lys Ser Gln Glu Pro Val Thr Leu Asp Phe Leu Asp Ala Glu Leu
                555                 560                 565

GAG AAT GAT ATT AAA GTG GAG ATT CGA AAT AAG ATG ATT GAT GGG GAA       1780
Glu Asn Asp Ile Lys Val Glu Ile Arg Asn Lys Met Ile Asp Gly Glu
            570                 575                 580

AGT GGA GAA AAA ACA TTC AGA ACT CTG GTT AAA TCT CAA GAT GAG AGA       1828
Ser Gly Glu Lys Thr Phe Arg Thr Leu Val Lys Ser Gln Asp Glu Arg
        585                 590                 595

TAT ATT GAC AAA GGA AAC AGG ACA TAC ACA TGG ACA CCT GTC AAT GGC       1876
Tyr Ile Asp Lys Gly Asn Arg Thr Tyr Thr Trp Thr Pro Val Asn Gly
    600                 605                 610

ACA GAT TAC AGT TTG GCC TTG GTA TTA CCA ACC TAC AGT TTT TAC TAT       1924
Thr Asp Tyr Ser Leu Ala Leu Val Leu Pro Thr Tyr Ser Phe Tyr Tyr
615                 620                 625                 630

ATA AAA GCC AAA CTA GAA GAG ACA ATA ACT CAG GCC AGA TAT TCG GAA       1972
Ile Lys Ala Lys Leu Glu Glu Thr Ile Thr Gln Ala Arg Tyr Ser Glu
                635                 640                 645

ACC CTG AAG CCA GAT AAT TTT GAA GAA TCT GGC TAT ACA TTC ATA GCA       2020
Thr Leu Lys Pro Asp Asn Phe Glu Glu Ser Gly Tyr Thr Phe Ile Ala
            650                 655                 660

CCA AGA GAT TAC TGC AAT GAC CTG AAA ATA TCG GAT AAT AAC ACT GAA       2068
Pro Arg Asp Tyr Cys Asn Asp Leu Lys Ile Ser Asp Asn Asn Thr Glu
        665                 670                 675

TTT CTT TTA AAT TTC AAC GAG TTT ATT GAT AGA AAA ACT CCA AAC AAC       2116
Phe Leu Leu Asn Phe Asn Glu Phe Ile Asp Arg Lys Thr Pro Asn Asn
    680                 685                 690

CCA TCA TGT AAC GCG GAT TTG ATT AAT AGA GTC TTG CTT GAT GCA GGC       2164
Pro Ser Cys Asn Ala Asp Leu Ile Asn Arg Val Leu Leu Asp Ala Gly
695                 700                 705                 710

TTT ACA AAT GAA CTT GTC CAA AAT TAC TGG AGT AAG CAG AAA AAT ATC       2212
Phe Thr Asn Glu Leu Val Gln Asn Tyr Trp Ser Lys Gln Lys Asn Ile
                715                 720                 725

AAG GGA GTG AAA GCA CGA TTT GTT GTG ACT GAT GGT GGG ATT ACC AGA       2260
Lys Gly Val Lys Ala Arg Phe Val Val Thr Asp Gly Gly Ile Thr Arg
            730                 735                 740

GTT TAT CCC AAA GAG GCT GGA GAA AAT TGG CAA GAA AAC CCA GAG ACA       2308
Val Tyr Pro Lys Glu Ala Gly Glu Asn Trp Gln Glu Asn Pro Glu Thr
        745                 750                 755

TAT GAG GAC AGC TTC TAT AAA AGG AGC CTA GAT AAT GAT AAC TAT GTT       2356
Tyr Glu Asp Ser Phe Tyr Lys Arg Ser Leu Asp Asn Asp Asn Tyr Val
    760                 765                 770

TTC ACT GCT CCC TAC TTT AAC AAA AGT GGA CCT GGT GCC TAT GAA TCG       2404
Phe Thr Ala Pro Tyr Phe Asn Lys Ser Gly Pro Gly Ala Tyr Glu Ser
775                 780                 785                 790

GGC ATT ATG GTA AGC AAA GCT GTA GAA ATA TAT ATT CAA GGG AAA CTT       2452
Gly Ile Met Val Ser Lys Ala Val Glu Ile Tyr Ile Gln Gly Lys Leu
                795                 800                 805

CTT AAA CCT GCA GTT GTT GGA ATT AAA ATT GAT GTA AAT TCC TGG ATA       2500
Leu Lys Pro Ala Val Val Gly Ile Lys Ile Asp Val Asn Ser Trp Ile
            810                 815                 820

GAG AAT TTC ACC AAA ACC TCA ATC AGA GAT CCG TGT GCT GGT CCA GTT       2548
Glu Asn Phe Thr Lys Thr Ser Ile Arg Asp Pro Cys Ala Gly Pro Val
        825                 830                 835

TGT GAC TGC AAA AGA AAC AGT GAC GTA ATG GAT TGT GTG ATT CTG GAT       2596
```

```
Cys Asp Cys Lys Arg Asn Ser Asp Val Met Asp Cys Val Ile Leu Asp
    840                 845                 850

GAT GGT GGG TTT CTT CTG ATG GCA AAT CAT GAT GAT TAT ACT AAT CAG      2644
Asp Gly Gly Phe Leu Leu Met Ala Asn His Asp Asp Tyr Thr Asn Gln
855                 860                 865                 870

ATT GGA AGA TTT TTT GGA GAG ATT GAT CCC AGC TTG ATG AGA CAC CTG      2692
Ile Gly Arg Phe Phe Gly Glu Ile Asp Pro Ser Leu Met Arg His Leu
                875                 880                 885

GTT AAT ATA TCA GTT TAT GCT TTT AAC AAA TCT TAT GAT TAT CAG TCA      2740
Val Asn Ile Ser Val Tyr Ala Phe Asn Lys Ser Tyr Asp Tyr Gln Ser
            890                 895                 900

GTA TGT GAG CCC GGT GCT GCA CCA AAA CAA GGA GCA GGA CAT CGC TCA      2788
Val Cys Glu Pro Gly Ala Ala Pro Lys Gln Gly Ala Gly His Arg Ser
                905                 910                 915

GCA TAT GTG CCA TCA GTA GCA GAC ATA TTA CAA ATT GGC TGG TGG GCC      2836
Ala Tyr Val Pro Ser Val Ala Asp Ile Leu Gln Ile Gly Trp Trp Ala
    920                 925                 930

ACT GCT GCT GCC TGG TCT ATT CTA CAG CAG TTT CTC TTG AGT TTG ACC      2884
Thr Ala Ala Ala Trp Ser Ile Leu Gln Gln Phe Leu Leu Ser Leu Thr
935                 940                 945                 950

TTT CCA CGA CTC CTT GAG GCA GTT GAG ATG GAG GAT GAT GAC TTC ACG      2932
Phe Pro Arg Leu Leu Glu Ala Val Glu Met Glu Asp Asp Asp Phe Thr
                955                 960                 965

GCC TCC CTG TCC AAG CAG AGC TGC ATT ACT GAA CAA ACC CAG TAT TTC      2980
Ala Ser Leu Ser Lys Gln Ser Cys Ile Thr Glu Gln Thr Gln Tyr Phe
            970                 975                 980

TTC GAT AAC GAC AGT AAA TCA TTC AGT GGT GTA TTA GAC TGT GGA AAC      3028
Phe Asp Asn Asp Ser Lys Ser Phe Ser Gly Val Leu Asp Cys Gly Asn
                985                 990                 995

TGT TCC AGA ATC TTT CAT GGA GAA AAG CTT ATG AAC ACC AAC TTA ATA      3076
Cys Ser Arg Ile Phe His Gly Glu Lys Leu Met Asn Thr Asn Leu Ile
    1000                1005                1010

TTC ATA ATG GTT GAG AGC AAA GGG ACA TGT CCA TGT GAC ACA CGA CTG      3124
Phe Ile Met Val Glu Ser Lys Gly Thr Cys Pro Cys Asp Thr Arg Leu
1015                1020                1025                1030

CTC ATA CAA GCG GAG CAG ACT TCT GAC GGT CCA AAT CCT TGT GAC ATG      3172
Leu Ile Gln Ala Glu Gln Thr Ser Asp Gly Pro Asn Pro Cys Asp Met
                1035                1040                1045

GTT AAG CAA CCT AGA TAC CGA AAA GGG CCT GAT GTC TGC TTT GAT AAC      3220
Val Lys Gln Pro Arg Tyr Arg Lys Gly Pro Asp Val Cys Phe Asp Asn
            1050                1055                1060

AAT GTC TTG GAG GAT TAT ACT GAC TGT GGT GGT GTT TCT GGA TTA AAT      3268
Asn Val Leu Glu Asp Tyr Thr Asp Cys Gly Gly Val Ser Gly Leu Asn
                1065                1070                1075

CCC TCC CTG TGG TAT ATC ATT GGA ATC CAG TTT CTA CTA CTT TGG CTG      3316
Pro Ser Leu Trp Tyr Ile Ile Gly Ile Gln Phe Leu Leu Leu Trp Leu
    1080                1085                1090

GTA TCT GGC AGC ACA CAC CGG CTG TTA TGACCTTCTA AAAACCAAAT            3363
Val Ser Gly Ser Thr His Arg Leu Leu
1095                1100

CTGCATAGTT AAACTCCAGA CCCTGCCAAA ACATGAGCCC TGCCCTCAAT TACAGTAACG    3423

TAGGGTCAGC TATAAAATCA GACAAACATT AGCTGGGCCT GTTCCATGGC ATAACACTAA    3483

GGCGCAGACT CCTAAGGCAC CCACTGGCTG CATGTCAGGG TGTCAGATCC TTAAACGTGT    3543

GTGAATGCTG CATCATCTAT GTGTAACATC AAAGCAAAAT CCTATACGTG TCCTCTATTG    3603

GAAAATTTGG GCGTTTGTTG TTGCATTGTT GGT                                 3636
```

(2) INFORMATION FOR SEQ ID NO:30:

(i) SEQUENCE CHARACTERISTICS:
    (A) LENGTH: 3585 base pairs
    (B) TYPE: nucleic acid
    (C) STRANDEDNESS: double
    (D) TOPOLOGY: linear (ii) MOLECULE TYPE: DNA (genomic)

(ix) FEATURE:
    (A) NAME/KEY: CDS
    (B) LOCATION: 35..3295
    (D) OTHER INFORMATION: /standard_name= "Alpha-2c"

(ix) FEATURE:
    (A) NAME/KEY: 5'UTR
    (B) LOCATION: 1..34

(ix) FEATURE:
    (A) NAME/KEY: 3'UTR
    (B) LOCATION: 3296..3585

(xi) SEQUENCE DESCRIPTION: SEQ ID NO:30:

```
GCGGGGGAGG GGGCATTGAT CTTCGATCGC GAAG ATG GCT GCT GGC TGC CTG           52
                                     Met Ala Ala Gly Cys Leu
                                      1               5

CTG GCC TTG ACT CTG ACA CTT TTC CAA TCT TTG CTC ATC GGC CCC TCG        100
Leu Ala Leu Thr Leu Thr Leu Phe Gln Ser Leu Leu Ile Gly Pro Ser
        10                  15                  20

TCG GAG GAG CCG TTC CCT TCG GCC GTC ACT ATC AAA TCA TGG GTG GAT        148
Ser Glu Glu Pro Phe Pro Ser Ala Val Thr Ile Lys Ser Trp Val Asp
            25                  30                  35

AAG ATG CAA GAA GAC CTT GTC ACA CTG GCA AAA ACA GCA AGT GGA GTC        196
Lys Met Gln Glu Asp Leu Val Thr Leu Ala Lys Thr Ala Ser Gly Val
 40                  45                  50

AAT CAG CTT GTT GAT ATT TAT GAG AAA TAT CAA GAT TTG TAT ACT GTG        244
Asn Gln Leu Val Asp Ile Tyr Glu Lys Tyr Gln Asp Leu Tyr Thr Val
 55                  60                  65                  70

GAA CCA AAT AAT GCA CGC CAG CTG GTA GAA ATT GCA GCC AGG GAT ATT        292
Glu Pro Asn Asn Ala Arg Gln Leu Val Glu Ile Ala Ala Arg Asp Ile
            75                  80                  85

GAG AAA CTT CTG AGC AAC AGA TCT AAA GCC CTG GTG AGC CTG GCA TTG        340
Glu Lys Leu Leu Ser Asn Arg Ser Lys Ala Leu Val Ser Leu Ala Leu
        90                  95                 100

GAA GCG GAG AAA GTT CAA GCA GCT CAC CAG TGG AGA GAA GAT TTT GCA        388
Glu Ala Glu Lys Val Gln Ala Ala His Gln Trp Arg Glu Asp Phe Ala
           105                 110                 115

AGC AAT GAA GTT GTC TAC TAC AAT GCA AAG GAT GAT CTC GAT CCT GAG        436
Ser Asn Glu Val Val Tyr Tyr Asn Ala Lys Asp Asp Leu Asp Pro Glu
    120                 125                 130

AAA AAT GAC AGT GAG CCA GGC AGC CAG AGG ATA AAA CCT GTT TTC ATT        484
Lys Asn Asp Ser Glu Pro Gly Ser Gln Arg Ile Lys Pro Val Phe Ile
135                 140                 145                 150

GAA GAT GCT AAT TTT GGA CGA CAA ATA TCT TAT CAG CAC GCA GCA GTC        532
Glu Asp Ala Asn Phe Gly Arg Gln Ile Ser Tyr Gln His Ala Ala Val
                155                 160                 165

CAT ATT CCT ACT GAC ATC TAT GAG GGC TCA ACA ATT GTG TTA AAT GAA        580
His Ile Pro Thr Asp Ile Tyr Glu Gly Ser Thr Ile Val Leu Asn Glu
            170                 175                 180

CTC AAC TGG ACA AGT GCC TTA GAT GAA GTT TTC AAA AAG AAT CGC GAG        628
Leu Asn Trp Thr Ser Ala Leu Asp Glu Val Phe Lys Lys Asn Arg Glu
        185                 190                 195

GAA GAC CCT TCA TTA TTG TGG CAG GTT TTT GGC AGT GCC ACT GGC CTA        676
Glu Asp Pro Ser Leu Leu Trp Gln Val Phe Gly Ser Ala Thr Gly Leu
    200                 205                 210
```

```
GCT CGA TAT TAT CCA GCT TCA CCA TGG GTT GAT AAT AGT AGA ACT CCA      724
Ala Arg Tyr Tyr Pro Ala Ser Pro Trp Val Asp Asn Ser Arg Thr Pro
215             220                 225                 230

AAT AAG ATT GAC CTT TAT GAT GTA CGC AGA AGA CCA TGG TAC ATC CAA      772
Asn Lys Ile Asp Leu Tyr Asp Val Arg Arg Arg Pro Trp Tyr Ile Gln
                235                 240                 245

GGA GCT GCA TCT CCT AAA GAC ATG CTT ATT CTG GTG GAT GTG AGT GGA      820
Gly Ala Ala Ser Pro Lys Asp Met Leu Ile Leu Val Asp Val Ser Gly
            250                 255                 260

AGT GTT AGT GGA TTG ACA CTT AAA CTG ATC CGA ACA TCT GTC TCC GAA      868
Ser Val Ser Gly Leu Thr Leu Lys Leu Ile Arg Thr Ser Val Ser Glu
        265                 270                 275

ATG TTA GAA ACC CTC TCA GAT GAT GAT TTC GTG AAT GTA GCT TCA TTT      916
Met Leu Glu Thr Leu Ser Asp Asp Asp Phe Val Asn Val Ala Ser Phe
280                 285                 290

AAC AGC AAT GCT CAG GAT GTA AGC TGT TTT CAG CAC CTT GTC CAA GCA      964
Asn Ser Asn Ala Gln Asp Val Ser Cys Phe Gln His Leu Val Gln Ala
295                 300                 305                 310

AAT GTA AGA AAT AAA AAA GTG TTG AAA GAC GCG GTG AAT AAT ATC ACA     1012
Asn Val Arg Asn Lys Lys Val Leu Lys Asp Ala Val Asn Asn Ile Thr
                315                 320                 325

GCC AAA GGA ATT ACA GAT TAT AAG AAG GGC TTT AGT TTT GCT TTT GAA     1060
Ala Lys Gly Ile Thr Asp Tyr Lys Lys Gly Phe Ser Phe Ala Phe Glu
            330                 335                 340

CAG CTG CTT AAT TAT AAT GTT TCC AGA GCA AAC TGC AAT AAG ATT ATT     1108
Gln Leu Leu Asn Tyr Asn Val Ser Arg Ala Asn Cys Asn Lys Ile Ile
        345                 350                 355

ATG CTA TTC ACG GAT GGA GGA GAA GAG AGA GCC CAG GAG ATA TTT AAC     1156
Met Leu Phe Thr Asp Gly Gly Glu Glu Arg Ala Gln Glu Ile Phe Asn
360                 365                 370

AAA TAC AAT AAA GAT AAA AAA GTA CGT GTA TTC AGG TTT TCA GTT GGT     1204
Lys Tyr Asn Lys Asp Lys Lys Val Arg Val Phe Arg Phe Ser Val Gly
375                 380                 385                 390

CAA CAC AAT TAT GAG AGA GGA CCT ATT CAG TGG ATG GCC TGT GAA AAC     1252
Gln His Asn Tyr Glu Arg Gly Pro Ile Gln Trp Met Ala Cys Glu Asn
                395                 400                 405

AAA GGT TAT TAT TAT GAA ATT CCT TCC ATT GGT GCA ATA AGA ATC AAT     1300
Lys Gly Tyr Tyr Tyr Glu Ile Pro Ser Ile Gly Ala Ile Arg Ile Asn
            410                 415                 420

ACT CAG GAA TAT TTG GAT GTT TTG GGA AGA CCA ATG GTT TTA GCA GGA     1348
Thr Gln Glu Tyr Leu Asp Val Leu Gly Arg Pro Met Val Leu Ala Gly
        425                 430                 435

GAC AAA GCT AAG CAA GTC CAA TGG ACA AAT GTG TAC CTG GAT GCA TTG     1396
Asp Lys Ala Lys Gln Val Gln Trp Thr Asn Val Tyr Leu Asp Ala Leu
440                 445                 450

GAA CTG GGA CTT GTC ATT ACT GGA ACT CTT CCG GTC TTC AAC ATA ACC     1444
Glu Leu Gly Leu Val Ile Thr Gly Thr Leu Pro Val Phe Asn Ile Thr
455                 460                 465                 470

GGC CAA TTT GAA AAT AAG ACA AAC TTA AAG AAC CAG CTG ATT CTT GGT     1492
Gly Gln Phe Glu Asn Lys Thr Asn Leu Lys Asn Gln Leu Ile Leu Gly
                475                 480                 485

GTG ATG GGA GTA GAT GTG TCT TTG GAA GAT ATT AAA AGA CTG ACA CCA     1540
Val Met Gly Val Asp Val Ser Leu Glu Asp Ile Lys Arg Leu Thr Pro
            490                 495                 500

CGT TTT ACA CTG TGC CCC AAT GGG TAT TAC TTT GCA ATC GAT CCT AAT     1588
Arg Phe Thr Leu Cys Pro Asn Gly Tyr Tyr Phe Ala Ile Asp Pro Asn
        505                 510                 515

GGT TAT GTT TTA TTA CAT CCA AAT CTT CAG CCA AAG GAG CCA GTA ACA     1636
Gly Tyr Val Leu Leu His Pro Asn Leu Gln Pro Lys Glu Pro Val Thr
```

-continued

```
                520                      525                      530
TTG GAT TTC CTT GAT GCA GAG TTA GAG AAT GAT ATT AAA GTG GAG ATT      1684
Leu Asp Phe Leu Asp Ala Glu Leu Glu Asn Asp Ile Lys Val Glu Ile
535                     540                     545                 550

CGA AAT AAG ATG ATT GAT GGG GAA AGT GGA GAA AAA ACA TTC AGA ACT      1732
Arg Asn Lys Met Ile Asp Gly Glu Ser Gly Glu Lys Thr Phe Arg Thr
                        555                     560                     565

CTG GTT AAA TCT CAA GAT GAG AGA TAT ATT GAC AAA GGA AAC AGG ACA      1780
Leu Val Lys Ser Gln Asp Glu Arg Tyr Ile Asp Lys Gly Asn Arg Thr
                570                     575                     580

TAC ACA TGG ACA CCT GTC AAT GGC ACA GAT TAC AGT TTG GCC TTG GTA      1828
Tyr Thr Trp Thr Pro Val Asn Gly Thr Asp Tyr Ser Leu Ala Leu Val
            585                     590                     595

TTA CCA ACC TAC AGT TTT TAC TAT ATA AAA GCC AAA CTA GAA GAG ACA      1876
Leu Pro Thr Tyr Ser Phe Tyr Tyr Ile Lys Ala Lys Leu Glu Glu Thr
        600                     605                     610

ATA ACT CAG GCC AGA TCA AAA AAG GGC AAA ATG AAG GAT TCG GAA ACC      1924
Ile Thr Gln Ala Arg Ser Lys Lys Gly Lys Met Lys Asp Ser Glu Thr
615                     620                     625                     630

CTG AAG CCA GAT AAT TTT GAA GAA TCT GGC TAT ACA TTC ATA GCA CCA      1972
Leu Lys Pro Asp Asn Phe Glu Glu Ser Gly Tyr Thr Phe Ile Ala Pro
                        635                     640                     645

AGA GAT TAC TGC AAT GAC CTG AAA ATA TCG GAT AAT AAC ACT GAA TTT      2020
Arg Asp Tyr Cys Asn Asp Leu Lys Ile Ser Asp Asn Asn Thr Glu Phe
                650                     655                     660

CTT TTA AAT TTC AAC GAG TTT ATT GAT AGA AAA ACT CCA AAC AAC CCA      2068
Leu Leu Asn Phe Asn Glu Phe Ile Asp Arg Lys Thr Pro Asn Asn Pro
            665                     670                     675

TCA TGT AAC GCG GAT TTG ATT AAT AGA GTC TTG CTT GAT GCA GGC TTT      2116
Ser Cys Asn Ala Asp Leu Ile Asn Arg Val Leu Leu Asp Ala Gly Phe
        680                     685                     690

ACA AAT GAA CTT GTC CAA AAT TAC TGG AGT AAG CAG AAA AAT ATC AAG      2164
Thr Asn Glu Leu Val Gln Asn Tyr Trp Ser Lys Gln Lys Asn Ile Lys
695                     700                     705                     710

GGA GTG AAA GCA CGA TTT GTT GTG ACT GAT GGT GGG ATT ACC AGA GTT      2212
Gly Val Lys Ala Arg Phe Val Val Thr Asp Gly Gly Ile Thr Arg Val
                        715                     720                     725

TAT CCC AAA GAG GCT GGA GAA AAT TGG CAA GAA AAC CCA GAG ACA TAT      2260
Tyr Pro Lys Glu Ala Gly Glu Asn Trp Gln Glu Asn Pro Glu Thr Tyr
                730                     735                     740

GAG GAC AGC TTC TAT AAA AGG AGC CTA GAT AAT GAT AAC TAT GTT TTC      2308
Glu Asp Ser Phe Tyr Lys Arg Ser Leu Asp Asn Asp Asn Tyr Val Phe
            745                     750                     755

ACT GCT CCC TAC TTT AAC AAA AGT GGA CCT GGT GCC TAT GAA TCG GGC      2356
Thr Ala Pro Tyr Phe Asn Lys Ser Gly Pro Gly Ala Tyr Glu Ser Gly
        760                     765                     770

ATT ATG GTA AGC AAA GCT GTA GAA ATA TAT ATT CAA GGG AAA CTT CTT      2404
Ile Met Val Ser Lys Ala Val Glu Ile Tyr Ile Gln Gly Lys Leu Leu
775                     780                     785                     790

AAA CCT GCA GTT GTT GGA ATT AAA ATT GAT GTA AAT TCC TGG ATA GAG      2452
Lys Pro Ala Val Val Gly Ile Lys Ile Asp Val Asn Ser Trp Ile Glu
                        795                     800                     805

AAT TTC ACC AAA ACC TCA ATC AGA GAT CCG TGT GCT GGT CCA GTT TGT      2500
Asn Phe Thr Lys Thr Ser Ile Arg Asp Pro Cys Ala Gly Pro Val Cys
                810                     815                     820

GAC TGC AAA AGA AAC AGT GAC GTA ATG GAT TGT GTG ATT CTG GAT GAT      2548
Asp Cys Lys Arg Asn Ser Asp Val Met Asp Cys Val Ile Leu Asp Asp
            825                     830                     835

GGT GGG TTT CTT CTG ATG GCA AAT CAT GAT GAT TAT ACT AAT CAG ATT      2596
```

```
Gly Gly Phe Leu Leu Met Ala Asn His Asp Asp Tyr Thr Asn Gln Ile
    840                 845                 850

GGA AGA TTT TTT GGA GAG ATT GAT CCC AGC TTG ATG AGA CAC CTG GTT        2644
Gly Arg Phe Phe Gly Glu Ile Asp Pro Ser Leu Met Arg His Leu Val
855                 860                 865                 870

AAT ATA TCA GTT TAT GCT TTT AAC AAA TCT TAT GAT TAT CAG TCA GTA        2692
Asn Ile Ser Val Tyr Ala Phe Asn Lys Ser Tyr Asp Tyr Gln Ser Val
                875                 880                 885

TGT GAG CCC GGT GCT GCA CCA AAA CAA GGA GCA GGA CAT CGC TCA GCA        2740
Cys Glu Pro Gly Ala Ala Pro Lys Gln Gly Ala Gly His Arg Ser Ala
            890                 895                 900

TAT GTG CCA TCA GTA GCA GAC ATA TTA CAA ATT GGC TGG TGG GCC ACT        2788
Tyr Val Pro Ser Val Ala Asp Ile Leu Gln Ile Gly Trp Trp Ala Thr
        905                 910                 915

GCT GCT GCC TGG TCT ATT CTA CAG CAG TTT CTC TTG AGT TTG ACC TTT        2836
Ala Ala Ala Trp Ser Ile Leu Gln Gln Phe Leu Leu Ser Leu Thr Phe
    920                 925                 930

CCA CGA CTC CTT GAG GCA GTT GAG ATG GAG GAT GAT GAC TTC ACG GCC        2884
Pro Arg Leu Leu Glu Ala Val Glu Met Glu Asp Asp Asp Phe Thr Ala
935                 940                 945                 950

TCC CTG TCC AAG CAG AGC TGC ATT ACT GAA CAA ACC CAG TAT TTC TTC        2932
Ser Leu Ser Lys Gln Ser Cys Ile Thr Glu Gln Thr Gln Tyr Phe Phe
                955                 960                 965

GAT AAC GAC AGT AAA TCA TTC AGT GGT GTA TTA GAC TGT GGA AAC TGT        2980
Asp Asn Asp Ser Lys Ser Phe Ser Gly Val Leu Asp Cys Gly Asn Cys
            970                 975                 980

TCC AGA ATC TTT CAT GGA GAA AAG CTT ATG AAC ACC AAC TTA ATA TTC        3028
Ser Arg Ile Phe His Gly Glu Lys Leu Met Asn Thr Asn Leu Ile Phe
        985                 990                 995

ATA ATG GTT GAG AGC AAA GGG ACA TGT CCA TGT GAC ACA CGA CTG CTC        3076
Ile Met Val Glu Ser Lys Gly Thr Cys Pro Cys Asp Thr Arg Leu Leu
    1000                1005                1010

ATA CAA GCG GAG CAG ACT TCT GAC GGT CCA AAT CCT TGT GAC ATG GTT        3124
Ile Gln Ala Glu Gln Thr Ser Asp Gly Pro Asn Pro Cys Asp Met Val
1015                1020                1025                1030

AAG CAA CCT AGA TAC CGA AAA GGG CCT GAT GTC TGC TTT GAT AAC AAT        3172
Lys Gln Pro Arg Tyr Arg Lys Gly Pro Asp Val Cys Phe Asp Asn Asn
                1035                1040                1045

GTC TTG GAG GAT TAT ACT GAC TGT GGT GGT GTT TCT GGA TTA AAT CCC        3220
Val Leu Glu Asp Tyr Thr Asp Cys Gly Gly Val Ser Gly Leu Asn Pro
            1050                1055                1060

TCC CTG TGG TAT ATC ATT GGA ATC CAG TTT CTA CTA CTT TGG CTG GTA        3268
Ser Leu Trp Tyr Ile Ile Gly Ile Gln Phe Leu Leu Leu Trp Leu Val
        1065                1070                1075

TCT GGC AGC ACA CAC CGG CTG TTA TGACCTTCTA AAACCAAAT CTGCATAGTT        3322
Ser Gly Ser Thr His Arg Leu Leu
    1080                1085

AAACTCCAGA CCCTGCCAAA ACATGAGCCC TGCCCTCAAT TACAGTAACG TAGGGTCAGC      3382

TATAAAATCA GACAAACATT AGCTGGGCCT GTTCCATGGC ATAACACTAA GGCGCAGACT      3442

CCTAAGGCAC CCACTGGCTG CATGTCAGGG TGTCAGATCC TTAAACGTGT GTGAATGCTG      3502

CATCATCTAT GTGTAACATC AAAGCAAAAT CCTATACGTG TCCTCTATTG GAAAATTTGG      3562

GCGTTTGTTG TTGCATTGTT GGT                                              3585
```

(2) INFORMATION FOR SEQ ID NO:31:

(i) SEQUENCE CHARACTERISTICS:
        (A) LENGTH: 3564 base pairs
        (B) TYPE: nucleic acid (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 35..3374 ([0081]1625 to 1639 & [0081]1908 to 1928)
        (D) OTHER INFORMATION: /standard_name= "Alpha-2d"

(ix) FEATURE:
        (A) NAME/KEY: 5'UTR
        (B) LOCATION: 1..34

(ix) FEATURE:
        (A) NAME/KEY: 3'UTR
        (B) LOCATION: 3375..3565

(xi) SEQUENCE DESCRIPTION: SEQ ID NO:31:

```
GCGGGGGAGG GGGCATTGAT CTTCGATCGC GAAG ATG GCT GCT GGC TGC CTG        52
                                     Met Ala Ala Gly Cys Leu
                                      1               5

CTG GCC TTG ACT CTG ACA CTT TTC CAA TCT TTG CTC ATC GGC CCC TCG     100
Leu Ala Leu Thr Leu Thr Leu Phe Gln Ser Leu Leu Ile Gly Pro Ser
            10                  15                  20

TCG GAG GAG CCG TTC CCT TCG GCC GTC ACT ATC AAA TCA TGG GTG GAT     148
Ser Glu Glu Pro Phe Pro Ser Ala Val Thr Ile Lys Ser Trp Val Asp
        25                  30                  35

AAG ATG CAA GAA GAC CTT GTC ACA CTG GCA AAA ACA GCA AGT GGA GTC     196
Lys Met Gln Glu Asp Leu Val Thr Leu Ala Lys Thr Ala Ser Gly Val
    40                  45                  50

AAT CAG CTT GTT GAT ATT TAT GAG AAA TAT CAA GAT TTG TAT ACT GTG     244
Asn Gln Leu Val Asp Ile Tyr Glu Lys Tyr Gln Asp Leu Tyr Thr Val
 55                  60                  65                  70

GAA CCA AAT AAT GCA CGC CAG CTG GTA GAA ATT GCA GCC AGG GAT ATT     292
Glu Pro Asn Asn Ala Arg Gln Leu Val Glu Ile Ala Ala Arg Asp Ile
                75                  80                  85

GAG AAA CTT CTG AGC AAC AGA TCT AAA GCC CTG GTG AGC CTG GCA TTG     340
Glu Lys Leu Leu Ser Asn Arg Ser Lys Ala Leu Val Ser Leu Ala Leu
            90                  95                 100

GAA GCG GAG AAA GTT CAA GCA GCT CAC CAG TGG AGA GAA GAT TTT GCA     388
Glu Ala Glu Lys Val Gln Ala Ala His Gln Trp Arg Glu Asp Phe Ala
        105                 110                 115

AGC AAT GAA GTT GTC TAC TAC AAT GCA AAG GAT GAT CTC GAT CCT GAG     436
Ser Asn Glu Val Val Tyr Tyr Asn Ala Lys Asp Asp Leu Asp Pro Glu
    120                 125                 130

AAA AAT GAC AGT GAG CCA GGC AGC CAG AGG ATA AAA CCT GTT TTC ATT     484
Lys Asn Asp Ser Glu Pro Gly Ser Gln Arg Ile Lys Pro Val Phe Ile
135                 140                 145                 150

GAA GAT GCT AAT TTT GGA CGA CAA ATA TCT TAT CAG CAC GCA GCA GTC     532
Glu Asp Ala Asn Phe Gly Arg Gln Ile Ser Tyr Gln His Ala Ala Val
                155                 160                 165

CAT ATT CCT ACT GAC ATC TAT GAG GGC TCA ACA ATT GTG TTA AAT GAA     580
His Ile Pro Thr Asp Ile Tyr Glu Gly Ser Thr Ile Val Leu Asn Glu
            170                 175                 180

CTC AAC TGG ACA AGT GCC TTA GAT GAA GTT TTC AAA AAG AAT CGC GAG     628
Leu Asn Trp Thr Ser Ala Leu Asp Glu Val Phe Lys Lys Asn Arg Glu
        185                 190                 195

GAA GAC CCT TCA TTA TTG TGG CAG GTT TTT GGC AGT GCC ACT GGC CTA     676
Glu Asp Pro Ser Leu Leu Trp Gln Val Phe Gly Ser Ala Thr Gly Leu
    200                 205                 210

GCT CGA TAT TAT CCA GCT TCA CCA TGG GTT GAT AAT AGT AGA ACT CCA     724
Ala Arg Tyr Tyr Pro Ala Ser Pro Trp Val Asp Asn Ser Arg Thr Pro
215                 220                 225                 230
```

-continued

| | | |
|---|---|---|
| AAT AAG ATT GAC CTT TAT GAT GTA CGC AGA AGA CCA TGG TAC ATC CAA<br>Asn Lys Ile Asp Leu Tyr Asp Val Arg Arg Pro Trp Tyr Ile Gln<br>235                              240                          245 | 772 |
| GGA GCT GCA TCT CCT AAA GAC ATG CTT ATT CTG GTG GAT GTG AGT GGA<br>Gly Ala Ala Ser Pro Lys Asp Met Leu Ile Leu Val Asp Val Ser Gly<br>               250                          255                          260 | 820 |
| AGT GTT AGT GGA TTG ACA CTT AAA CTG ATC CGA ACA TCT GTC TCC GAA<br>Ser Val Ser Gly Leu Thr Leu Lys Leu Ile Arg Thr Ser Val Ser Glu<br>        265                          270                          275 | 868 |
| ATG TTA GAA ACC CTC TCA GAT GAT GAT TTC GTG AAT GTA GCT TCA TTT<br>Met Leu Glu Thr Leu Ser Asp Asp Asp Phe Val Asn Val Ala Ser Phe<br>280                              285                          290 | 916 |
| AAC AGC AAT GCT CAG GAT GTA AGC TGT TTT CAG CAC CTT GTC CAA GCA<br>Asn Ser Asn Ala Gln Asp Val Ser Cys Phe Gln His Leu Val Gln Ala<br>295                              300                          305                          310 | 964 |
| AAT GTA AGA AAT AAA AAA GTG TTG AAA GAC GCG GTG AAT AAT ATC ACA<br>Asn Val Arg Asn Lys Lys Val Leu Lys Asp Ala Val Asn Asn Ile Thr<br>               315                          320                          325 | 1012 |
| GCC AAA GGA ATT ACA GAT TAT AAG AAG GGC TTT AGT TTT GCT TTT GAA<br>Ala Lys Gly Ile Thr Asp Tyr Lys Lys Gly Phe Ser Phe Ala Phe Glu<br>        330                          335                          340 | 1060 |
| CAG CTG CTT AAT TAT AAT GTT TCC AGA GCA AAC TGC AAT AAG ATT ATT<br>Gln Leu Leu Asn Tyr Asn Val Ser Arg Ala Asn Cys Asn Lys Ile Ile<br>345                              350                          355 | 1108 |
| ATG CTA TTC ACG GAT GGA GGA GAA GAG AGA GCC CAG GAG ATA TTT AAC<br>Met Leu Phe Thr Asp Gly Gly Glu Glu Arg Ala Gln Glu Ile Phe Asn<br>        360                          365                          370 | 1156 |
| AAA TAC AAT AAA GAT AAA AAA GTA CGT GTA TTC AGG TTT TCA GTT GGT<br>Lys Tyr Asn Lys Asp Lys Lys Val Arg Val Phe Arg Phe Ser Val Gly<br>375                              380                          385                          390 | 1204 |
| CAA CAC AAT TAT GAG AGA GGA CCT ATT CAG TGG ATG GCC TGT GAA AAC<br>Gln His Asn Tyr Glu Arg Gly Pro Ile Gln Trp Met Ala Cys Glu Asn<br>               395                          400                          405 | 1252 |
| AAA GGT TAT TAT TAT GAA ATT CCT TCC ATT GGT GCA ATA AGA ATC AAT<br>Lys Gly Tyr Tyr Tyr Glu Ile Pro Ser Ile Gly Ala Ile Arg Ile Asn<br>        410                          415                          420 | 1300 |
| ACT CAG GAA TAT TTG GAT GTT TTG GGA AGA CCA ATG GTT TTA GCA GGA<br>Thr Gln Glu Tyr Leu Asp Val Leu Gly Arg Pro Met Val Leu Ala Gly<br>425                              430                          435 | 1348 |
| GAC AAA GCT AAG CAA GTC CAA TGG ACA AAT GTG TAC CTG GAT GCA TTG<br>Asp Lys Ala Lys Gln Val Gln Trp Thr Asn Val Tyr Leu Asp Ala Leu<br>440                              445                          450 | 1396 |
| GAA CTG GGA CTT GTC ATT ACT GGA ACT CTT CCG GTC TTC AAC ATA ACC<br>Glu Leu Gly Leu Val Ile Thr Gly Thr Leu Pro Val Phe Asn Ile Thr<br>455                              460                          465                          470 | 1444 |
| GGC CAA TTT GAA AAT AAG ACA AAC TTA AAG AAC CAG CTG ATT CTT GGT<br>Gly Gln Phe Glu Asn Lys Thr Asn Leu Lys Asn Gln Leu Ile Leu Gly<br>               475                          480                          485 | 1492 |
| GTG ATG GGA GTA GAT GTG TCT TTG GAA GAT ATT AAA AGA CTG ACA CCA<br>Val Met Gly Val Asp Val Ser Leu Glu Asp Ile Lys Arg Leu Thr Pro<br>        490                          495                          500 | 1540 |
| CGT TTT ACA CTG TGC CCC AAT GGG TAT TAC TTT GCA ATC GAT CCT AAT<br>Arg Phe Thr Leu Cys Pro Asn Gly Tyr Tyr Phe Ala Ile Asp Pro Asn<br>505                              510                          515 | 1588 |
| GGT TAT GTT TTA TTA CAT CCA AAT CTT CAG CCA AAG GAG CCA GTA ACA<br>Gly Tyr Val Leu Leu His Pro Asn Leu Gln Pro Lys Glu Pro Val Thr<br>        520                          525                          530 | 1636 |
| TTG GAT TTC CTT GAT GCA GAG TTA GAG AAT GAT ATT AAA GTG GAG ATT<br>Leu Asp Phe Leu Asp Ala Glu Leu Glu Asn Asp Ile Lys Val Glu Ile | 1684 |

-continued

```
535                 540                 545                 550
CGA AAT AAG ATG ATT GAT GGG GAA AGT GGA GAA AAA ACA TTC AGA ACT      1732
Arg Asn Lys Met Ile Asp Gly Glu Ser Gly Glu Lys Thr Phe Arg Thr
            555                 560                 565

CTG GTT AAA TCT CAA GAT GAG AGA TAT ATT GAC AAA GGA AAC AGG ACA      1780
Leu Val Lys Ser Gln Asp Glu Arg Tyr Ile Asp Lys Gly Asn Arg Thr
        570                 575                 580

TAC ACA TGG ACA CCT GTC AAT GGC ACA GAT TAC AGT TTG GCC TTG GTA      1828
Tyr Thr Trp Thr Pro Val Asn Gly Thr Asp Tyr Ser Leu Ala Leu Val
            585                 590                 595

TTA CCA ACC TAC AGT TTT TAC TAT ATA AAA GCC AAA CTA GAA GAG ACA      1876
Leu Pro Thr Tyr Ser Phe Tyr Tyr Ile Lys Ala Lys Leu Glu Glu Thr
        600                 605                 610

ATA ACT CAG GCC AGA TAT TCG GAA ACC CTG AAG CCA GAT AAT TTT GAA      1924
Ile Thr Gln Ala Arg Tyr Ser Glu Thr Leu Lys Pro Asp Asn Phe Glu
615                 620                 625                 630

GAA TCT GGC TAT ACA TTC ATA GCA CCA AGA GAT TAC TGC AAT GAC CTG      1972
Glu Ser Gly Tyr Thr Phe Ile Ala Pro Arg Asp Tyr Cys Asn Asp Leu
            635                 640                 645

AAA ATA TCG GAT AAT AAC ACT GAA TTT CTT TTA AAT TTC AAC GAG TTT      2020
Lys Ile Ser Asp Asn Asn Thr Glu Phe Leu Leu Asn Phe Asn Glu Phe
        650                 655                 660

ATT GAT AGA AAA ACT CCA AAC AAC CCA TCA TGT AAC GCG GAT TTG ATT      2068
Ile Asp Arg Lys Thr Pro Asn Asn Pro Ser Cys Asn Ala Asp Leu Ile
            665                 670                 675

AAT AGA GTC TTG CTT GAT GCA GGC TTT ACA AAT GAA CTT GTC CAA AAT      2116
Asn Arg Val Leu Leu Asp Ala Gly Phe Thr Asn Glu Leu Val Gln Asn
        680                 685                 690

TAC TGG AGT AAG CAG AAA AAT ATC AAG GGA GTG AAA GCA CGA TTT GTT      2164
Tyr Trp Ser Lys Gln Lys Asn Ile Lys Gly Val Lys Ala Arg Phe Val
695                 700                 705                 710

GTG ACT GAT GGT GGG ATT ACC AGA GTT TAT CCC AAA GAG GCT GGA GAA      2212
Val Thr Asp Gly Gly Ile Thr Arg Val Tyr Pro Lys Glu Ala Gly Glu
            715                 720                 725

AAT TGG CAA GAA AAC CCA GAG ACA TAT GAG GAC AGC TTC TAT AAA AGG      2260
Asn Trp Gln Glu Asn Pro Glu Thr Tyr Glu Asp Ser Phe Tyr Lys Arg
        730                 735                 740

AGC CTA GAT AAT GAT AAC TAT GTT TTC ACT GCT CCC TAC TTT AAC AAA      2308
Ser Leu Asp Asn Asp Asn Tyr Val Phe Thr Ala Pro Tyr Phe Asn Lys
            745                 750                 755

AGT GGA CCT GGT GCC TAT GAA TCG GGC ATT ATG GTA AGC AAA GCT GTA      2356
Ser Gly Pro Gly Ala Tyr Glu Ser Gly Ile Met Val Ser Lys Ala Val
        760                 765                 770

GAA ATA TAT ATT CAA GGG AAA CTT CTT AAA CCT GCA GTT GTT GGA ATT      2404
Glu Ile Tyr Ile Gln Gly Lys Leu Leu Lys Pro Ala Val Val Gly Ile
775                 780                 785                 790

AAA ATT GAT GTA AAT TCC TGG ATA GAG AAT TTC ACC AAA ACC TCA ATC      2452
Lys Ile Asp Val Asn Ser Trp Ile Glu Asn Phe Thr Lys Thr Ser Ile
            795                 800                 805

AGA GAT CCG TGT GCT GGT CCA GTT TGT GAC TGC AAA AGA AAC AGT GAC      2500
Arg Asp Pro Cys Ala Gly Pro Val Cys Asp Cys Lys Arg Asn Ser Asp
        810                 815                 820

GTA ATG GAT TGT GTG ATT CTG GAT GAT GGT GGG TTT CTT CTG ATG GCA      2548
Val Met Asp Cys Val Ile Leu Asp Asp Gly Gly Phe Leu Leu Met Ala
            825                 830                 835

AAT CAT GAT GAT TAT ACT AAT CAG ATT GGA AGA TTT TTT GGA GAG ATT      2596
Asn His Asp Asp Tyr Thr Asn Gln Ile Gly Arg Phe Phe Gly Glu Ile
        840                 845                 850

GAT CCC AGC TTG ATG AGA CAC CTG GTT AAT ATA TCA GTT TAT GCT TTT      2644
```

```
Asp Pro Ser Leu Met Arg His Leu Val Asn Ile Ser Val Tyr Ala Phe
855                 860                 865                 870

AAC AAA TCT TAT GAT TAT CAG TCA GTA TGT GAG CCC GGT GCT GCA CCA      2692
Asn Lys Ser Tyr Asp Tyr Gln Ser Val Cys Glu Pro Gly Ala Ala Pro
                875                 880                 885

AAA CAA GGA GCA GGA CAT CGC TCA GCA TAT GTG CCA TCA GTA GCA GAC      2740
Lys Gln Gly Ala Gly His Arg Ser Ala Tyr Val Pro Ser Val Ala Asp
            890                 895                 900

ATA TTA CAA ATT GGC TGG TGG GCC ACT GCT GCT GCC TGG TCT ATT CTA      2788
Ile Leu Gln Ile Gly Trp Trp Ala Thr Ala Ala Ala Trp Ser Ile Leu
        905                 910                 915

CAG CAG TTT CTC TTG AGT TTG ACC TTT CCA CGA CTC CTT GAG GCA GTT      2836
Gln Gln Phe Leu Leu Ser Leu Thr Phe Pro Arg Leu Leu Glu Ala Val
    920                 925                 930

GAG ATG GAG GAT GAT GAC TTC ACG GCC TCC CTG TCC AAG CAG AGC TGC      2884
Glu Met Glu Asp Asp Asp Phe Thr Ala Ser Leu Ser Lys Gln Ser Cys
935                 940                 945                 950

ATT ACT GAA CAA ACC CAG TAT TTC TTC GAT AAC GAC AGT AAA TCA TTC      2932
Ile Thr Glu Gln Thr Gln Tyr Phe Phe Asp Asn Asp Ser Lys Ser Phe
                955                 960                 965

AGT GGT GTA TTA GAC TGT GGA AAC TGT TCC AGA ATC TTT CAT GGA GAA      2980
Ser Gly Val Leu Asp Cys Gly Asn Cys Ser Arg Ile Phe His Gly Glu
            970                 975                 980

AAG CTT ATG AAC ACC AAC TTA ATA TTC ATA ATG GTT GAG AGC AAA GGG      3028
Lys Leu Met Asn Thr Asn Leu Ile Phe Ile Met Val Glu Ser Lys Gly
        985                 990                 995

ACA TGT CCA TGT GAC ACA CGA CTG CTC ATA CAA GCG GAG CAG ACT TCT      3076
Thr Cys Pro Cys Asp Thr Arg Leu Leu Ile Gln Ala Glu Gln Thr Ser
    1000                1005                1010

GAC GGT CCA AAT CCT TGT GAC ATG GTT AAG CAA CCT AGA TAC CGA AAA      3124
Asp Gly Pro Asn Pro Cys Asp Met Val Lys Gln Pro Arg Tyr Arg Lys
1015                1020                1025                1030

GGG CCT GAT GTC TGC TTT GAT AAC AAT GTC TTG GAG GAT TAT ACT GAC      3172
Gly Pro Asp Val Cys Phe Asp Asn Asn Val Leu Glu Asp Tyr Thr Asp
                1035                1040                1045

TGT GGT GGT GTT TCT GGA TTA AAT CCC TCC CTG TGG TAT ATC ATT GGA      3220
Cys Gly Gly Val Ser Gly Leu Asn Pro Ser Leu Trp Tyr Ile Ile Gly
            1050                1055                1060

ATC CAG TTT CTA CTA CTT TGG CTG GTA TCT GGC AGC ACA CAC CGG CTG      3268
Ile Gln Phe Leu Leu Leu Trp Leu Val Ser Gly Ser Thr His Arg Leu
        1065                1070                1075

TTA TGACCTTCTA AAAACCAAAT CTGCATAGTT AAACTCCAGA CCCTGCCAAA           3321
Leu

ACATGAGCCC TGCCCTCAAT TACAGTAACG TAGGGTCAGC TATAAAATCA GACAAACATT    3381

AGCTGGGCCT GTTCCATGGC ATAACACTAA GGCGCAGACT CCTAAGGCAC CCACTGGCTG    3441

CATGTCAGGG TGTCAGATCC TTAAACGTGT GTGAATGCTG CATCATCTAT GTGTAACATC    3501

AAAGCAAAAT CCTATACGTG TCCTCTATTG GAAAATTTGG GCGTTTGTTG TTGCATTGTT    3561

GGT                                                                  3564
```

(2) INFORMATION FOR SEQ ID NO:32:

(i) SEQUENCE CHARACTERISTICS:
        (A) LENGTH: 3579 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 35..3289
        (D) OTHER INFORMATION: /standard_name= "Alpha-2e"

(ix) FEATURE:
        (A) NAME/KEY: 5'UTR
        (B) LOCATION: 1..34

(ix) FEATURE:
        (A) NAME/KEY: 3'UTR
        (B) LOCATION: 3289..3579

(xi) SEQUENCE DESCRIPTION: SEQ ID NO:32:

```
GCGGGGGAGG GGGCATTGAT CTTCGATCGC GAAG ATG GCT GCT GGC TGC CTG         52
                                     Met Ala Ala Gly Cys Leu
                                      1               5

CTG GCC TTG ACT CTG ACA CTT TTC CAA TCT TTG CTC ATC GGC CCC TCG      100
Leu Ala Leu Thr Leu Thr Leu Phe Gln Ser Leu Leu Ile Gly Pro Ser
             10                  15                  20

TCG GAG GAG CCG TTC CCT TCG GCC GTC ACT ATC AAA TCA TGG GTG GAT      148
Ser Glu Glu Pro Phe Pro Ser Ala Val Thr Ile Lys Ser Trp Val Asp
         25                  30                  35

AAG ATG CAA GAA GAC CTT GTC ACA CTG GCA AAA ACA GCA AGT GGA GTC      196
Lys Met Gln Glu Asp Leu Val Thr Leu Ala Lys Thr Ala Ser Gly Val
     40                  45                  50

AAT CAG CTT GTT GAT ATT TAT GAG AAA TAT CAA GAT TTG TAT ACT GTG      244
Asn Gln Leu Val Asp Ile Tyr Glu Lys Tyr Gln Asp Leu Tyr Thr Val
 55                  60                  65                  70

GAA CCA AAT AAT GCA CGC CAG CTG GTA GAA ATT GCA GCC AGG GAT ATT      292
Glu Pro Asn Asn Ala Arg Gln Leu Val Glu Ile Ala Ala Arg Asp Ile
                 75                  80                  85

GAG AAA CTT CTG AGC AAC AGA TCT AAA GCC CTG GTG AGC CTG GCA TTG      340
Glu Lys Leu Leu Ser Asn Arg Ser Lys Ala Leu Val Ser Leu Ala Leu
             90                  95                 100

GAA GCG GAG AAA GTT CAA GCA GCT CAC CAG TGG AGA GAA GAT TTT GCA      388
Glu Ala Glu Lys Val Gln Ala Ala His Gln Trp Arg Glu Asp Phe Ala
        105                 110                 115

AGC AAT GAA GTT GTC TAC TAC AAT GCA AAG GAT GAT CTC GAT CCT GAG      436
Ser Asn Glu Val Val Tyr Tyr Asn Ala Lys Asp Asp Leu Asp Pro Glu
    120                 125                 130

AAA AAT GAC AGT GAG CCA GGC AGC CAG AGG ATA AAA CCT GTT TTC ATT      484
Lys Asn Asp Ser Glu Pro Gly Ser Gln Arg Ile Lys Pro Val Phe Ile
135                 140                 145                 150

GAA GAT GCT AAT TTT GGA CGA CAA ATA TCT TAT CAG CAC GCA GCA GTC      532
Glu Asp Ala Asn Phe Gly Arg Gln Ile Ser Tyr Gln His Ala Ala Val
                155                 160                 165

CAT ATT CCT ACT GAC ATC TAT GAG GGC TCA ACA ATT GTG TTA AAT GAA      580
His Ile Pro Thr Asp Ile Tyr Glu Gly Ser Thr Ile Val Leu Asn Glu
            170                 175                 180

CTC AAC TGG ACA AGT GCC TTA GAT GAA GTT TTC AAA AAG AAT CGC GAG      628
Leu Asn Trp Thr Ser Ala Leu Asp Glu Val Phe Lys Lys Asn Arg Glu
        185                 190                 195

GAA GAC CCT TCA TTA TTG TGG CAG GTT TTT GGC AGT GCC ACT GGC CTA      676
Glu Asp Pro Ser Leu Leu Trp Gln Val Phe Gly Ser Ala Thr Gly Leu
    200                 205                 210

GCT CGA TAT TAT CCA GCT TCA CCA TGG GTT GAT AAT AGT AGA ACT CCA      724
Ala Arg Tyr Tyr Pro Ala Ser Pro Trp Val Asp Asn Ser Arg Thr Pro
215                 220                 225                 230

AAT AAG ATT GAC CTT TAT GAT GTA CGC AGA AGA CCA TGG TAC ATC CAA      772
Asn Lys Ile Asp Leu Tyr Asp Val Arg Arg Arg Pro Trp Tyr Ile Gln
                235                 240                 245
```

```
GGA GCT GCA TCT CCT AAA GAC ATG CTT ATT CTG GTG GAT GTG AGT GGA       820
Gly Ala Ala Ser Pro Lys Asp Met Leu Ile Leu Val Asp Val Ser Gly
        250                 255                 260

AGT GTT AGT GGA TTG ACA CTT AAA CTG ATC CGA ACA TCT GTC TCC GAA       868
Ser Val Ser Gly Leu Thr Leu Lys Leu Ile Arg Thr Ser Val Ser Glu
            265                 270                 275

ATG TTA GAA ACC CTC TCA GAT GAT GAT TTC GTG AAT GTA GCT TCA TTT       916
Met Leu Glu Thr Leu Ser Asp Asp Asp Phe Val Asn Val Ala Ser Phe
280                 285                 290

AAC AGC AAT GCT CAG GAT GTA AGC TGT TTT CAG CAC CTT GTC CAA GCA       964
Asn Ser Asn Ala Gln Asp Val Ser Cys Phe Gln His Leu Val Gln Ala
295                 300                 305                 310

AAT GTA AGA AAT AAA AAA GTG TTG AAA GAC GCG GTG AAT AAT ATC ACA      1012
Asn Val Arg Asn Lys Lys Val Leu Lys Asp Ala Val Asn Asn Ile Thr
                315                 320                 325

GCC AAA GGA ATT ACA GAT TAT AAG AAG GGC TTT AGT TTT GCT TTT GAA      1060
Ala Lys Gly Ile Thr Asp Tyr Lys Lys Gly Phe Ser Phe Ala Phe Glu
            330                 335                 340

CAG CTG CTT AAT TAT AAT GTT TCC AGA GCA AAC TGC AAT AAG ATT ATT      1108
Gln Leu Leu Asn Tyr Asn Val Ser Arg Ala Asn Cys Asn Lys Ile Ile
        345                 350                 355

ATG CTA TTC ACG GAT GGA GGA GAA GAG AGA GCC CAG GAG ATA TTT AAC      1156
Met Leu Phe Thr Asp Gly Gly Glu Glu Arg Ala Gln Glu Ile Phe Asn
360                 365                 370

AAA TAC AAT AAA GAT AAA AAA GTA CGT GTA TTC AGG TTT TCA GTT GGT      1204
Lys Tyr Asn Lys Asp Lys Lys Val Arg Val Phe Arg Phe Ser Val Gly
375                 380                 385                 390

CAA CAC AAT TAT GAG AGA GGA CCT ATT CAG TGG ATG GCC TGT GAA AAC      1252
Gln His Asn Tyr Glu Arg Gly Pro Ile Gln Trp Met Ala Cys Glu Asn
                395                 400                 405

AAA GGT TAT TAT TAT GAA ATT CCT TCC ATT GGT GCA ATA AGA ATC AAT      1300
Lys Gly Tyr Tyr Tyr Glu Ile Pro Ser Ile Gly Ala Ile Arg Ile Asn
            410                 415                 420

ACT CAG GAA TAT TTG GAT GTT TTG GGA AGA CCA ATG GTT TTA GCA GGA      1348
Thr Gln Glu Tyr Leu Asp Val Leu Gly Arg Pro Met Val Leu Ala Gly
        425                 430                 435

GAC AAA GCT AAG CAA GTC CAA TGG ACA AAT GTG TAC CTG GAT GCA TTG      1396
Asp Lys Ala Lys Gln Val Gln Trp Thr Asn Val Tyr Leu Asp Ala Leu
440                 445                 450

GAA CTG GGA CTT GTC ATT ACT GGA ACT CTT CCG GTC TTC AAC ATA ACC      1444
Glu Leu Gly Leu Val Ile Thr Gly Thr Leu Pro Val Phe Asn Ile Thr
455                 460                 465                 470

GGC CAA TTT GAA AAT AAG ACA AAC TTA AAG AAC CAG CTG ATT CTT GGT      1492
Gly Gln Phe Glu Asn Lys Thr Asn Leu Lys Asn Gln Leu Ile Leu Gly
                475                 480                 485

GTG ATG GGA GTA GAT GTG TCT TTG GAA GAT ATT AAA AGA CTG ACA CCA      1540
Val Met Gly Val Asp Val Ser Leu Glu Asp Ile Lys Arg Leu Thr Pro
            490                 495                 500

CGT TTT ACA CTG TGC CCC AAT GGG TAT TAC TTT GCA ATC GAT CCT AAT      1588
Arg Phe Thr Leu Cys Pro Asn Gly Tyr Tyr Phe Ala Ile Asp Pro Asn
        505                 510                 515

GGT TAT GTT TTA TTA CAT CCA AAT CTT CAG CCA AAG AAC CCC AAA TCT      1636
Gly Tyr Val Leu Leu His Pro Asn Leu Gln Pro Lys Asn Pro Lys Ser
520                 525                 530

CAG GAG CCA GTA ACA TTG GAT TTC CTT GAT GCA GAG TTA GAG AAT GAT      1684
Gln Glu Pro Val Thr Leu Asp Phe Leu Asp Ala Glu Leu Glu Asn Asp
535                 540                 545                 550

ATT AAA GTG GAG ATT CGA AAT AAG ATG ATT GAT GGG GAA AGT GGA GAA      1732
Ile Lys Val Glu Ile Arg Asn Lys Met Ile Asp Gly Glu Ser Gly Glu
                555                 560                 565
```

```
AAA ACA TTC AGA ACT CTG GTT AAA TCT CAA GAT GAG AGA TAT ATT GAC    1780
Lys Thr Phe Arg Thr Leu Val Lys Ser Gln Asp Glu Arg Tyr Ile Asp
            570                 575                 580

AAA GGA AAC AGG ACA TAC ACA TGG ACA CCT GTC AAT GGC ACA GAT TAC    1828
Lys Gly Asn Arg Thr Tyr Thr Trp Thr Pro Val Asn Gly Thr Asp Tyr
            585                 590                 595

AGT TTG GCC TTG GTA TTA CCA ACC TAC AGT TTT TAC TAT ATA AAA GCC    1876
Ser Leu Ala Leu Val Leu Pro Thr Tyr Ser Phe Tyr Tyr Ile Lys Ala
            600                 605                 610

AAA CTA GAA GAG ACA ATA ACT CAG GCC AGA TAT TCG GAA ACC CTG AAG    1924
Lys Leu Glu Glu Thr Ile Thr Gln Ala Arg Tyr Ser Glu Thr Leu Lys
615                 620                 625                 630

CCA GAT AAT TTT GAA GAA TCT GGC TAT ACA TTC ATA GCA CCA AGA GAT    1972
Pro Asp Asn Phe Glu Glu Ser Gly Tyr Thr Phe Ile Ala Pro Arg Asp
            635                 640                 645

TAC TGC AAT GAC CTG AAA ATA TCG GAT AAT AAC ACT GAA TTT CTT TTA    2020
Tyr Cys Asn Asp Leu Lys Ile Ser Asp Asn Asn Thr Glu Phe Leu Leu
            650                 655                 660

AAT TTC AAC GAG TTT ATT GAT AGA AAA ACT CCA AAC AAC CCA TCA TGT    2068
Asn Phe Asn Glu Phe Ile Asp Arg Lys Thr Pro Asn Asn Pro Ser Cys
            665                 670                 675

AAC GCG GAT TTG ATT AAT AGA GTC TTG CTT GAT GCA GGC TTT ACA AAT    2116
Asn Ala Asp Leu Ile Asn Arg Val Leu Leu Asp Ala Gly Phe Thr Asn
            680                 685                 690

GAA CTT GTC CAA AAT TAC TGG AGT AAG CAG AAA AAT ATC AAG GGA GTG    2164
Glu Leu Val Gln Asn Tyr Trp Ser Lys Gln Lys Asn Ile Lys Gly Val
695                 700                 705                 710

AAA GCA CGA TTT GTT GTG ACT GAT GGT GGG ATT ACC AGA GTT TAT CCC    2212
Lys Ala Arg Phe Val Val Thr Asp Gly Gly Ile Thr Arg Val Tyr Pro
            715                 720                 725

AAA GAG GCT GGA GAA AAT TGG CAA GAA AAC CCA GAG ACA TAT GAG GAC    2260
Lys Glu Ala Gly Glu Asn Trp Gln Glu Asn Pro Glu Thr Tyr Glu Asp
            730                 735                 740

AGC TTC TAT AAA AGG AGC CTA GAT AAT GAT AAC TAT GTT TTC ACT GCT    2308
Ser Phe Tyr Lys Arg Ser Leu Asp Asn Asp Asn Tyr Val Phe Thr Ala
            745                 750                 755

CCC TAC TTT AAC AAA AGT GGA CCT GGT GCC TAT GAA TCG GGC ATT ATG    2356
Pro Tyr Phe Asn Lys Ser Gly Pro Gly Ala Tyr Glu Ser Gly Ile Met
760                 765                 770

GTA AGC AAA GCT GTA GAA ATA TAT ATT CAA GGG AAA CTT CTT AAA CCT    2404
Val Ser Lys Ala Val Glu Ile Tyr Ile Gln Gly Lys Leu Leu Lys Pro
775                 780                 785                 790

GCA GTT GTT GGA ATT AAA ATT GAT GTA AAT TCC TGG ATA GAG AAT TTC    2452
Ala Val Val Gly Ile Lys Ile Asp Val Asn Ser Trp Ile Glu Asn Phe
            795                 800                 805

ACC AAA ACC TCA ATC AGA GAT CCG TGT GCT GGT CCA GTT TGT GAC TGC    2500
Thr Lys Thr Ser Ile Arg Asp Pro Cys Ala Gly Pro Val Cys Asp Cys
            810                 815                 820

AAA AGA AAC AGT GAC GTA ATG GAT TGT GTG ATT CTG GAT GAT GGT GGG    2548
Lys Arg Asn Ser Asp Val Met Asp Cys Val Ile Leu Asp Asp Gly Gly
            825                 830                 835

TTT CTT CTG ATG GCA AAT CAT GAT GAT TAT ACT AAT CAG ATT GGA AGA    2596
Phe Leu Leu Met Ala Asn His Asp Asp Tyr Thr Asn Gln Ile Gly Arg
            840                 845                 850

TTT TTT GGA GAG ATT GAT CCC AGC TTG ATG AGA CAC CTG GTT AAT ATA    2644
Phe Phe Gly Glu Ile Asp Pro Ser Leu Met Arg His Leu Val Asn Ile
855                 860                 865                 870

TCA GTT TAT GCT TTT AAC AAA TCT TAT GAT TAT CAG TCA GTA TGT GAG    2692
Ser Val Tyr Ala Phe Asn Lys Ser Tyr Asp Tyr Gln Ser Val Cys Glu
```

```
                      875                 880                 885
CCC GGT GCT GCA CCA AAA CAA GGA GCA GGA CAT CGC TCA GCA TAT GTG    2740
Pro Gly Ala Ala Pro Lys Gln Gly Ala Gly His Arg Ser Ala Tyr Val
            890                 895                 900

CCA TCA GTA GCA GAC ATA TTA CAA ATT GGC TGG TGG GCC ACT GCT GCT    2788
Pro Ser Val Ala Asp Ile Leu Gln Ile Gly Trp Trp Ala Thr Ala Ala
            905                 910                 915

GCC TGG TCT ATT CTA CAG CAG TTT CTC TTG AGT TTG ACC TTT CCA CGA    2836
Ala Trp Ser Ile Leu Gln Gln Phe Leu Leu Ser Leu Thr Phe Pro Arg
    920                 925                 930

CTC CTT GAG GCA GTT GAG ATG GAG GAT GAT GAC TTC ACG GCC TCC CTG    2884
Leu Leu Glu Ala Val Glu Met Glu Asp Asp Asp Phe Thr Ala Ser Leu
935                 940                 945                 950

TCC AAG CAG AGC TGC ATT ACT GAA CAA ACC CAG TAT TTC TTC GAT AAC    2932
Ser Lys Gln Ser Cys Ile Thr Glu Gln Thr Gln Tyr Phe Phe Asp Asn
            955                 960                 965

GAC AGT AAA TCA TTC AGT GGT GTA TTA GAC TGT GGA AAC TGT TCC AGA    2980
Asp Ser Lys Ser Phe Ser Gly Val Leu Asp Cys Gly Asn Cys Ser Arg
            970                 975                 980

ATC TTT CAT GGA GAA AAG CTT ATG AAC ACC AAC TTA ATA TTC ATA ATG    3028
Ile Phe His Gly Glu Lys Leu Met Asn Thr Asn Leu Ile Phe Ile Met
            985                 990                 995

GTT GAG AGC AAA GGG ACA TGT CCA TGT GAC ACA CGA CTG CTC ATA CAA    3076
Val Glu Ser Lys Gly Thr Cys Pro Cys Asp Thr Arg Leu Leu Ile Gln
    1000                1005                1010

GCG GAG CAG ACT TCT GAC GGT CCA AAT CCT TGT GAC ATG GTT AAG CAA    3124
Ala Glu Gln Thr Ser Asp Gly Pro Asn Pro Cys Asp Met Val Lys Gln
1015                1020                1025                1030

CCT AGA TAC CGA AAA GGG CCT GAT GTC TGC TTT GAT AAC AAT GTC TTG    3172
Pro Arg Tyr Arg Lys Gly Pro Asp Val Cys Phe Asp Asn Asn Val Leu
                1035                1040                1045

GAG GAT TAT ACT GAC TGT GGT GGT GTT TCT GGA TTA AAT CCC TCC CTG    3220
Glu Asp Tyr Thr Asp Cys Gly Gly Val Ser Gly Leu Asn Pro Ser Leu
            1050                1055                1060

TGG TAT ATC ATT GGA ATC CAG TTT CTA CTA CTT TGG CTG GTA TCT GGC    3268
Trp Tyr Ile Ile Gly Ile Gln Phe Leu Leu Leu Trp Leu Val Ser Gly
            1065                1070                1075

AGC ACA CAC CGG CTG TTA TGACCTTCTA AAAACCAAAT CTGCATAGTT           3316
Ser Thr His Arg Leu Leu
    1080                108

AAACTCCAGA CCCTGCCAAA ACATGAGCCC TGCCCTCAAT TACAGTAACG TAGGGTCAGC  3376

TATAAAATCA GACAAACATT AGCTGGGCCT GTTCCATGGC ATAACACTAA GGCGCAGACT  3436

CCTAAGGCAC CCACTGGCTG CATGTCAGGG TGTCAGATCC TTAAACGTGT GTGAATGCTG  3496

CATCATCTAT GTGTAACATC AAAGCAAAAT CCTATACGTG TCCTCTATTG GAAAATTTGG  3556

GCGTTTGTTG TTGCATTGTT GGT                                         3579

(2) INFORMATION FOR SEQ ID NO:33:

(i) SEQUENCE CHARACTERISTICS:
        (A) LENGTH: 1681 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1437
        (D) OTHER INFORMATION: /standard_name= "Beta-1-1"
```

(ix) FEATURE:
        (A) NAME/KEY: 3'UTR
        (B) LOCATION: 1435..1681

(xi) SEQUENCE DESCRIPTION: SEQ ID NO:33:

| | | | | | | | | | | | | | | | | |
|---|---|---|---|---|---|---|---|---|---|---|---|---|---|---|---|---|
| ATG | GTC | CAG | AAG | ACC | AGC | ATG | TCC | CGG | GGC | CCT | TAC | CCA | CCC | TCC | CAG | 48 |
| Met | Val | Gln | Lys | Thr | Ser | Met | Ser | Arg | Gly | Pro | Tyr | Pro | Pro | Ser | Gln | |
| 1 | | | | 5 | | | | | 10 | | | | | 15 | | |
| GAG | ATC | CCC | ATG | GAG | GTC | TTC | GAC | CCC | AGC | CCG | CAG | GGC | AAA | TAC | AGC | 96 |
| Glu | Ile | Pro | Met | Glu | Val | Phe | Asp | Pro | Ser | Pro | Gln | Gly | Lys | Tyr | Ser | |
| | | | 20 | | | | | 25 | | | | | 30 | | | |
| AAG | AGG | AAA | GGG | CGA | TTC | AAA | CGG | TCA | GAT | GGG | AGC | ACG | TCC | TCG | GAT | 144 |
| Lys | Arg | Lys | Gly | Arg | Phe | Lys | Arg | Ser | Asp | Gly | Ser | Thr | Ser | Ser | Asp | |
| | | 35 | | | | | 40 | | | | | 45 | | | | |
| ACC | ACA | TCC | AAC | AGC | TTT | GTC | CGC | CAG | GGC | TCA | GCG | GAG | TCC | TAC | ACC | 192 |
| Thr | Thr | Ser | Asn | Ser | Phe | Val | Arg | Gln | Gly | Ser | Ala | Glu | Ser | Tyr | Thr | |
| | 50 | | | | | 55 | | | | | 60 | | | | | |
| AGC | CGT | CCA | TCA | GAC | TCT | GAT | GTA | TCT | CTG | GAG | GAG | GAC | CGG | GAA | GCC | 240 |
| Ser | Arg | Pro | Ser | Asp | Ser | Asp | Val | Ser | Leu | Glu | Glu | Asp | Arg | Glu | Ala | |
| 65 | | | | 70 | | | | | 75 | | | | | 80 | | |
| TTA | AGG | AAG | GAA | GCA | GAG | CGC | CAG | GCA | TTA | GCG | CAG | CTC | GAG | AAG | GCC | 288 |
| Leu | Arg | Lys | Glu | Ala | Glu | Arg | Gln | Ala | Leu | Ala | Gln | Leu | Glu | Lys | Ala | |
| | | | | 85 | | | | | 90 | | | | | 95 | | |
| AAG | ACC | AAG | CCA | GTG | GCA | TTT | GCT | GTG | CGG | ACA | AAT | GTT | GGC | TAC | AAT | 336 |
| Lys | Thr | Lys | Pro | Val | Ala | Phe | Ala | Val | Arg | Thr | Asn | Val | Gly | Tyr | Asn | |
| | | | 100 | | | | | 105 | | | | | 110 | | | |
| CCG | TCT | CCA | GGG | GAT | GAG | GTG | CCT | GTG | CAG | GGA | GTG | GCC | ATC | ACC | TTC | 384 |
| Pro | Ser | Pro | Gly | Asp | Glu | Val | Pro | Val | Gln | Gly | Val | Ala | Ile | Thr | Phe | |
| | | 115 | | | | | 120 | | | | | 125 | | | | |
| GAG | CCC | AAA | GAC | TTC | CTG | CAC | ATC | AAG | GAG | AAA | TAC | AAT | AAT | GAC | TGG | 432 |
| Glu | Pro | Lys | Asp | Phe | Leu | His | Ile | Lys | Glu | Lys | Tyr | Asn | Asn | Asp | Trp | |
| | 130 | | | | | 135 | | | | | 140 | | | | | |
| TGG | ATC | GGG | CGG | CTG | GTG | AAG | GAG | GGC | TGT | GAG | GTT | GGC | TTC | ATT | CCC | 480 |
| Trp | Ile | Gly | Arg | Leu | Val | Lys | Glu | Gly | Cys | Glu | Val | Gly | Phe | Ile | Pro | |
| 145 | | | | 150 | | | | | 155 | | | | | 160 | | |
| AGC | CCC | GTC | AAA | CTG | GAC | AGC | CTT | CGC | CTG | CTG | CAG | GAA | CAG | AAG | CTG | 528 |
| Ser | Pro | Val | Lys | Leu | Asp | Ser | Leu | Arg | Leu | Leu | Gln | Glu | Gln | Lys | Leu | |
| | | | | 165 | | | | | 170 | | | | | 175 | | |
| CGC | CAG | AAC | CGC | CTC | GGC | TCC | AGC | AAA | TCA | GGC | GAT | AAC | TCC | AGT | TCC | 576 |
| Arg | Gln | Asn | Arg | Leu | Gly | Ser | Ser | Lys | Ser | Gly | Asp | Asn | Ser | Ser | Ser | |
| | | | 180 | | | | | 185 | | | | | 190 | | | |
| AGT | CTG | GGA | GAT | GTG | GTG | ACT | GGC | ACC | CGC | CGC | CCC | ACA | CCC | CCT | GCC | 624 |
| Ser | Leu | Gly | Asp | Val | Val | Thr | Gly | Thr | Arg | Arg | Pro | Thr | Pro | Pro | Ala | |
| | | 195 | | | | | 200 | | | | | 205 | | | | |
| AGT | GGT | AAT | GAA | ATG | ACT | AAC | TTA | GCC | TTT | GAA | CTA | GAC | CCC | CTA | GAG | 672 |
| Ser | Gly | Asn | Glu | Met | Thr | Asn | Leu | Ala | Phe | Glu | Leu | Asp | Pro | Leu | Glu | |
| | 210 | | | | | 215 | | | | | 220 | | | | | |
| TTA | GAG | GAG | GAA | GAG | GCT | GAG | CTT | GGT | GAG | CAG | AGT | GGC | TCT | GCC | AAG | 720 |
| Leu | Glu | Glu | Glu | Glu | Ala | Glu | Leu | Gly | Glu | Gln | Ser | Gly | Ser | Ala | Lys | |
| 225 | | | | 230 | | | | | 235 | | | | | 240 | | |
| ACT | AGT | GTT | AGC | AGT | GTC | ACC | ACC | CCG | CCA | CCC | CAT | GGC | AAA | CGC | ATC | 768 |
| Thr | Ser | Val | Ser | Ser | Val | Thr | Thr | Pro | Pro | Pro | His | Gly | Lys | Arg | Ile | |
| | | | | 245 | | | | | 250 | | | | | 255 | | |
| CCC | TTC | TTT | AAG | AAG | ACA | GAG | CAT | GTG | CCC | CCC | TAT | GAC | GTG | GTG | CCT | 816 |
| Pro | Phe | Phe | Lys | Lys | Thr | Glu | His | Val | Pro | Pro | Tyr | Asp | Val | Val | Pro | |
| | | | 260 | | | | | 265 | | | | | 270 | | | |
| TCC | ATG | AGG | CCC | ATC | ATC | CTG | GTG | GGA | CCG | TCG | CTC | AAG | GGC | TAC | GAG | 864 |
| Ser | Met | Arg | Pro | Ile | Ile | Leu | Val | Gly | Pro | Ser | Leu | Lys | Gly | Tyr | Glu | |
| | | 275 | | | | | 280 | | | | | 285 | | | | |

```
GTT ACA GAC ATG ATG CAG AAA GCT TTA TTT GAC TTC TTG AAG CAT CGG      912
Val Thr Asp Met Met Gln Lys Ala Leu Phe Asp Phe Leu Lys His Arg
    290                 295                 300

TTT GAT GGC AGG ATC TCC ATC ACT CGT GTG ACG GCA GAT ATT TCC CTG      960
Phe Asp Gly Arg Ile Ser Ile Thr Arg Val Thr Ala Asp Ile Ser Leu
305                 310                 315                 320

GCT AAG CGC TCA GTT CTC AAC AAC CCC AGC AAA CAC ATC ATC ATT GAG     1008
Ala Lys Arg Ser Val Leu Asn Asn Pro Ser Lys His Ile Ile Ile Glu
                325                 330                 335

CGC TCC AAC ACA CGC TCC AGC CTG GCT GAG GTG CAG AGT GAA ATC GAG     1056
Arg Ser Asn Thr Arg Ser Ser Leu Ala Glu Val Gln Ser Glu Ile Glu
                340                 345                 350

CGA ATC TTC GAG CTG GCC CGG ACC CTT CAG TTG GTC GCT CTG GAT GCT     1104
Arg Ile Phe Glu Leu Ala Arg Thr Leu Gln Leu Val Ala Leu Asp Ala
            355                 360                 365

GAC ACC ATC AAT CAC CCA GCC CAG CTG TCC AAG ACC TCG CTG GCC CCC     1152
Asp Thr Ile Asn His Pro Ala Gln Leu Ser Lys Thr Ser Leu Ala Pro
370                 375                 380

ATC ATT GTT TAC ATC AAG ATC ACC TCT CCC AAG GTA CTT CAA AGG CTC     1200
Ile Ile Val Tyr Ile Lys Ile Thr Ser Pro Lys Val Leu Gln Arg Leu
385                 390                 395                 400

ATC AAG TCC CGA GGA AAG TCT CAG TCC AAA CAC CTC AAT GTC CAA ATA     1248
Ile Lys Ser Arg Gly Lys Ser Gln Ser Lys His Leu Asn Val Gln Ile
                405                 410                 415

GCG GCC TCG GAA AAG CTG GCA CAG TGC CCC CCT GAA ATG TTT GAC ATC     1296
Ala Ala Ser Glu Lys Leu Ala Gln Cys Pro Pro Glu Met Phe Asp Ile
                420                 425                 430

ATC CTG GAT GAG AAC CAA TTG GAG GAT GCC TGC GAG CAT CTG GCG GAG     1344
Ile Leu Asp Glu Asn Gln Leu Glu Asp Ala Cys Glu His Leu Ala Glu
            435                 440                 445

TAC TTG GAA GCC TAT TGG AAG GCC ACA CAC CCG CCC AGC AGC ACG CCA     1392
Tyr Leu Glu Ala Tyr Trp Lys Ala Thr His Pro Pro Ser Ser Thr Pro
450                 455                 460

CCC AAT CCG CTG CTG AAC CGC ACC ATG GCT ACC GCA GCC CTG GCT         1437
Pro Asn Pro Leu Leu Asn Arg Thr Met Ala Thr Ala Ala Leu Ala
465                 470                 475

GCCAGCCCTG CCCCTGTCTC AACCTCCAG GTACAGGTGC TCACCTCGCT CAGGAGAAAC    1497

CTCGGCTTCT GGGGCGGGCT GGAGTCCTCA CAGCGGGGCA GTGTGGTGCC CCAGGAGCAG   1557

GAACATGCCA TGTAGTGGGC GCCCTGCCCG TCTTCCCTCC TGCTCTGGGG TCGGAACTGG   1617

AGTGCAGGGA ACATGGAGGA GGAAGGGAAG AGCTTTATTT TGTAAAAAAA TAAGATGAGC   1677

GGCA                                                                1681

(2) INFORMATION FOR SEQ ID NO:34:

(i) SEQUENCE CHARACTERISTICS:
        (A) LENGTH: 1526 base pairs
        (B) TYPE: nucleic acid
        (C) STRANDEDNESS: double
        (D) TOPOLOGY: linear (ii) MOLECULE TYPE: DNA (genomic)

(ix) FEATURE:
         (A) NAME/KEY: CDS
         (B) LOCATION: 1..651
         (D) OTHER INFORMATION: /standard_name= "Beta-1-4"

(xi) SEQUENCE DESCRIPTION: SEQ ID NO:34:

ATG GTC CAG AAG ACC AGC ATG TCC CGG GGC CCT TAC CCA CCC TCC CAG      48
Met Val Gln Lys Thr Ser Met Ser Arg Gly Pro Tyr Pro Pro Ser Gln
1               5                   10                  15
```

```
GAG ATC CCC ATG GAG GTC TTC GAC CCC AGC CCG CAG GGC AAA TAC AGC        96
Glu Ile Pro Met Glu Val Phe Asp Pro Ser Pro Gln Gly Lys Tyr Ser
             20                  25                  30

AAG AGG AAA GGG CGA TTC AAA CGG TCA GAT GGG AGC ACG TCC TCG GAT       144
Lys Arg Lys Gly Arg Phe Lys Arg Ser Asp Gly Ser Thr Ser Ser Asp
         35                  40                  45

ACC ACA TCC AAC AGC TTT GTC CGC CAG GGC TCA GCG GAG TCC TAC ACC       192
Thr Thr Ser Asn Ser Phe Val Arg Gln Gly Ser Ala Glu Ser Tyr Thr
     50                  55                  60

AGC CGT CCA TCA GAC TCT GAT GTA TCT CTG GAG GAG GAC CGG GAA GCC       240
Ser Arg Pro Ser Asp Ser Asp Val Ser Leu Glu Glu Asp Arg Glu Ala
 65                  70                  75                  80

TTA AGG AAG GAA GCA GAG CGC CAG GCA TTA GCG CAG CTC GAG AAG GCC       288
Leu Arg Lys Glu Ala Glu Arg Gln Ala Leu Ala Gln Leu Glu Lys Ala
                 85                  90                  95

AAG ACC AAG CCA GTG GCA TTT GCT GTG CGG ACA AAT GTT GGC TAC AAT       336
Lys Thr Lys Pro Val Ala Phe Ala Val Arg Thr Asn Val Gly Tyr Asn
             100                 105                 110

CCG TCT CCA GGG GAT GAG GTG CCT GTG CAG GGA GTG GCC ATC ACC TTC       384
Pro Ser Pro Gly Asp Glu Val Pro Val Gln Gly Val Ala Ile Thr Phe
         115                 120                 125

GAG CCC AAA GAC TTC CTG CAC ATC AAG GAG AAA TAC AAT AAT GAC TGG       432
Glu Pro Lys Asp Phe Leu His Ile Lys Glu Lys Tyr Asn Asn Asp Trp
     130                 135                 140

TGG ATC GGG CGG CTG GTG AAG GAG GGC TGT GAG GTT GGC TTC ATT CCC       480
Trp Ile Gly Arg Leu Val Lys Glu Gly Cys Glu Val Gly Phe Ile Pro
145                 150                 155                 160

AGC CCC GTC AAA CTG GAC AGC CTT CGC CTG CTG CAG GAA CAG AAG CTG       528
Ser Pro Val Lys Leu Asp Ser Leu Arg Leu Leu Gln Glu Gln Lys Leu
                 165                 170                 175

CGC CAG AAC CGC CTC GGC TCC AGC AAA TCA GGC GAT AAC TCC AGT TCC       576
Arg Gln Asn Arg Leu Gly Ser Ser Lys Ser Gly Asp Asn Ser Ser Ser
             180                 185                 190

AGT CTG GGA GAT GTG GTG ACT GGC ACC CGC CGC CCC ACA CCC CCT GCC       624
Ser Leu Gly Asp Val Val Thr Gly Thr Arg Arg Pro Thr Pro Pro Ala
         195                 200                 205

AGT GAC AGA GCA TGT GCC CCC CTA TGACGTGGTG CCTTCCATGA GGCCCATCAT      678
Ser Asp Arg Ala Cys Ala Pro Leu
     210                 215

CCTGGTGGGA CCGTCGCTCA AGGGCTACGA GGTTACAGAC ATGATGCAGA AAGCTTTATT     738

TGACTTCTTG AAGCATCGGT TTGATGGCAG GATCTCCATC ACTCGTGTGA CGGCAGATAT     798

TTCCCTGGCT AAGCGCTCAG TTCTCAACAA CCCCAGCAAA CACATCATCA TTGAGCGCTC     858

CAACACACGC TCCAGCCTGG CTGAGGTGCA GAGTGAAATC GAGCGAATCT TCGAGCTGGC     918

CCGGACCCTT CAGTTGGTCG CTCTGGATGC TGACACCATC AATCACCCAG CCCAGCTGTC     978

CAAGACCTCG CTGGCCCCCA TCATTGTTTA CATCAAGATC ACCTCTCCCA AGGTACTTCA    1038

AAGGCTCATC AAGTCCCGAG GAAAGTCTCA GTCCAAACAC CTCAATGTCC AAATAGCGGC    1098

CTCGGAAAAG CTGGCACAGT GCCCCCCTGA AATGTTTGAC ATCATCCTGG ATGAGAACCA    1158

ATTGGAGGAT GCCTGCGAGC ATCTGGCGGA GTACTTGGAA GCCTATTGGA AGGCCACACA    1218

CCCGCCCAGC AGCACGCCAC CCAATCCGCT GCTGAACCGC ACCATGGCTA CCGCAGCCCT    1278

GGCTGCCAGC CCTGCCCCTG TCTCCAACCT CCAGGTACAG GTGCTCACCT CGCTCAGGAG    1338

AAACCTCGGC TTCTGGGGCG GGCTGGAGTC CTCACAGCGG GGCAGTGTGG TGCCCCAGGA    1398

GCAGGAACAT GCCATGTAGT GGGCGCCCTG CCCGTCTTCC CTCCTGCTCT GGGGTCGGAA    1458
```

```
CTGGAGTGCA GGGAACATGG AGGAGGAAGG GAAGAGCTTT ATTTTGTAAA AAAATAAGAT    1518

GAGCGGCA                                                             1526
```

(2) INFORMATION FOR SEQ ID NO:35:

(i) SEQUENCE CHARACTERISTICS:
        (A) LENGTH: 1393 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..660
        (D) OTHER INFORMATION: /standard_name= "Beta-1-5"

(xi) SEQUENCE DESCRIPTION: SEQ ID NO:35:

```
ATG GTC CAG AAG ACC AGC ATG TCC CGG GGC CCT TAC CCA CCC TCC CAG      48
Met Val Gln Lys Thr Ser Met Ser Arg Gly Pro Tyr Pro Pro Ser Gln
 1               5                  10                  15

GAG ATC CCC ATG GAG GTC TTC GAC CCC AGC CCG CAG GGC AAA TAC AGC      96
Glu Ile Pro Met Glu Val Phe Asp Pro Ser Pro Gln Gly Lys Tyr Ser
                20                  25                  30

AAG AGG AAA GGG CGA TTC AAA CGG TCA GAT GGG AGC ACG TCC TCG GAT     144
Lys Arg Lys Gly Arg Phe Lys Arg Ser Asp Gly Ser Thr Ser Ser Asp
            35                  40                  45

ACC ACA TCC AAC AGC TTT GTC CGC CAG GGC TCA GCG GAG TCC TAC ACC     192
Thr Thr Ser Asn Ser Phe Val Arg Gln Gly Ser Ala Glu Ser Tyr Thr
50                  55                  60

AGC CGT CCA TCA GAC TCT GAT GTA TCT CTG GAG GAG GAC CGG GAA GCC     240
Ser Arg Pro Ser Asp Ser Asp Val Ser Leu Glu Glu Asp Arg Glu Ala
65                  70                  75                  80

TTA AGG AAG GAA GCA GAG CGC CAG GCA TTA GCG CAG CTC GAG AAG GCC     288
Leu Arg Lys Glu Ala Glu Arg Gln Ala Leu Ala Gln Leu Glu Lys Ala
                85                  90                  95

AAG ACC AAG CCA GTG GCA TTT GCT GTG CGG ACA AAT GTT GGC TAC AAT     336
Lys Thr Lys Pro Val Ala Phe Ala Val Arg Thr Asn Val Gly Tyr Asn
            100                 105                 110

CCG TCT CCA GGG GAT GAG GTG CCT GTG CAG GGA GTG GCC ATC ACC TTC     384
Pro Ser Pro Gly Asp Glu Val Pro Val Gln Gly Val Ala Ile Thr Phe
        115                 120                 125

GAG CCC AAA GAC TTC CTG CAC ATC AAG GAG AAA TAC AAT AAT GAC TGG     432
Glu Pro Lys Asp Phe Leu His Ile Lys Glu Lys Tyr Asn Asn Asp Trp
    130                 135                 140

TGG ATC GGG CGG CTG GTG AAG GAG GGC TGT GAG GTT GGC TTC ATT CCC     480
Trp Ile Gly Arg Leu Val Lys Glu Gly Cys Glu Val Gly Phe Ile Pro
145                 150                 155                 160

AGC CCC GTC AAA CTG GAC AGC CTT CGC CTG CTG CAG GAA CAG AAG CTG     528
Ser Pro Val Lys Leu Asp Ser Leu Arg Leu Leu Gln Glu Gln Lys Leu
                165                 170                 175

CGC CAG AAC CGC CTC GGC TCC AGC AAA TCA GGC GAT AAC TCC AGT TCC     576
Arg Gln Asn Arg Leu Gly Ser Ser Lys Ser Gly Asp Asn Ser Ser Ser
            180                 185                 190

AGT CTG GGA GAT GTG GTG ACT GGC ACC CGC CGC CCC ACA CCC CCT GCC     624
Ser Leu Gly Asp Val Val Thr Gly Thr Arg Arg Pro Thr Pro Pro Ala
        195                 200                 205

AGT GGT TAC AGA CAT GAT GCA GAA AGC TTT ATT TGACTTCTTG AAGCATCGGT   677
Ser Gly Tyr Arg His Asp Ala Glu Ser Phe Ile
    210                 215                 220

TTGATGGCAG GATCTCCATC ACTCGTGTGA CGGCAGATAT TTCCCTGGCT AAGCGCTCAG   737
```

```
TTCTCAACAA CCCCAGCAAA CACATCATCA TTGAGCGCTC CAACACACGC TCCAGCCTGG      797

CTGAGGTGCA GAGTGAAATC GAGCGAATCT TCGAGCTGGC CCGGACCCTT CAGTTGGTCG      857

CTCTGGATGC TGACACCATC AATCACCCAG CCCAGCTGTC CAAGACCTCG CTGGCCCCCA      917

TCATTGTTTA CATCAAGATC ACCTCTCCCA AGGTACTTCA AAGGCTCATC AAGTCCCGAG      977

GAAAGTCTCA GTCCAAACAC CTCAATGTCC AAATAGCGGC CTCGGAAAAG CTGGCACAGT     1037

GCCCCCCTGA AATGTTTGAC ATCATCCTGG ATGAGAACCA ATTGGAGGAT GCCTGCGAGC     1097

ATCTGGCGGA GTACTTGGAA GCCTATTGGA AGGCCACACA CCCGCCCAGC AGCACGCCAC     1157

CCAATCCGCT GCTGAACCGC ACCATGGCTA CCGCAGCCCT GGCTGCCAGC CCTGCCCCTG     1217

TCTCCAACCT CCAGGTACAG GTGCTCACCT CGCTCAGGAG AAACCTCGGC TTCTGGGGCG     1277

GGCTGGAGTC CTCACAGCGG GGCAGTGTGG TGCCCCAGGA GCAGGAACAT GCCATGTAGT     1337

GGGCGCCCTG CCCGTCTTCC CTCCTGCTCT GGGGTCGGAA CTGGAGTGCA GGGAAC        1393
```

(2) INFORMATION FOR SEQ ID NO:36:

(i) SEQUENCE CHARACTERISTICS:
        (A) LENGTH: 6725 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 226..6642
        (D) OTHER INFORMATION: /standard_name= "Alpha-1C-2"

(xi) SEQUENCE DESCRIPTION: SEQ ID NO:36:

```
CTCGAGGAGG CAGTAGTGGA AAGGAGCAGT TTTTGGGGTT TGATGCCATA ATGGGAATCA       60

GGTAATCGTC GGCGGGGAAG AAGAAACGCT GCAGACCACG GCTTCCTCGA ATCTTGCGCG      120

AAAGCCGCCG GCCTCGGAGG AGGGATTAAT CCAGACCCGC CGGGGGGTGT TTTCACATTT      180

CTTCCTCTTC GTGGCTGCTC CTCCTATTAA AACCATTTTT GGTCC ATG GTC AAT          234
                                                   Met Val Asn
                                                     1

GAG AAT ACG AGG ATG TAC ATT CCA GAG GAA AAC CAC CAA GGT TCC AAC        282
Glu Asn Thr Arg Met Tyr Ile Pro Glu Glu Asn His Gln Gly Ser Asn
        5                   10                  15

TAT GGG AGC CCA CGC CCC GCC CAT GCC AAC ATG AAT GCC AAT GCG GCA        330
Tyr Gly Ser Pro Arg Pro Ala His Ala Asn Met Asn Ala Asn Ala Ala
 20                  25                  30                  35

GCG GGG CTG GCC CCT GAG CAC ATC CCC ACC CCG GGG GCT GCC CTG TCG        378
Ala Gly Leu Ala Pro Glu His Ile Pro Thr Pro Gly Ala Ala Leu Ser
                 40                  45                  50

TGG CAG GCG GCC ATC GAC GCA GCC CGG CAG GCT AAG CTG ATG GGC AGC        426
Trp Gln Ala Ala Ile Asp Ala Ala Arg Gln Ala Lys Leu Met Gly Ser
             55                  60                  65

GCT GGC AAT GCG ACC ATC TCC ACA GTC AGC TCC ACG CAG CGG AAG CGG        474
Ala Gly Asn Ala Thr Ile Ser Thr Val Ser Ser Thr Gln Arg Lys Arg
         70                  75                  80

CAG CAA TAT GGG AAA CCC AAG AAG CAG GGC AGC ACC ACG GCC ACA CGC        522
Gln Gln Tyr Gly Lys Pro Lys Lys Gln Gly Ser Thr Thr Ala Thr Arg
     85                  90                  95

CCG CCC CGA GCC CTG CTC TGC CTG ACC CTG AAG AAC CCC ATC CGG AGG        570
Pro Pro Arg Ala Leu Leu Cys Leu Thr Leu Lys Asn Pro Ile Arg Arg
100                 105                 110                 115
```

```
GCC TGC ATC AGC ATT GTC GAA TGG AAA CCA TTT GAA ATA ATT ATT TTA        618
Ala Cys Ile Ser Ile Val Glu Trp Lys Pro Phe Glu Ile Ile Ile Leu
            120                 125                 130

CTG ACT ATT TTT GCC AAT TGT GTG GCC TTA GCG ATC TAT ATT CCC TTT        666
Leu Thr Ile Phe Ala Asn Cys Val Ala Leu Ala Ile Tyr Ile Pro Phe
            135                 140                 145

CCA GAA GAT GAT TCC AAC GCC ACC AAT TCC AAC CTG GAA CGA GTG GAA        714
Pro Glu Asp Asp Ser Asn Ala Thr Asn Ser Asn Leu Glu Arg Val Glu
        150                 155                 160

TAT CTC TTT CTC ATA ATT TTT ACG GTG GAA GCG TTT TTA AAA GTA ATC        762
Tyr Leu Phe Leu Ile Ile Phe Thr Val Glu Ala Phe Leu Lys Val Ile
        165                 170                 175

GCC TAT GGA CTC CTC TTT CAC CCC AAT GCC TAC CTC CGC AAC GGC TGG        810
Ala Tyr Gly Leu Leu Phe His Pro Asn Ala Tyr Leu Arg Asn Gly Trp
180                 185                 190                 195

AAC CTA CTA GAT TTT ATA ATT GTG GTT GTG GGG CTT TTT AGT GCA ATT        858
Asn Leu Leu Asp Phe Ile Ile Val Val Val Gly Leu Phe Ser Ala Ile
                200                 205                 210

TTA GAA CAA GCA ACC AAA GCA GAT GGG GCA AAC GCT CTC GGA GGG AAA        906
Leu Glu Gln Ala Thr Lys Ala Asp Gly Ala Asn Ala Leu Gly Gly Lys
            215                 220                 225

GGG GCC GGA TTT GAT GTG AAG GCG CTG AGG GCC TTC CGC GTG CTG CGC        954
Gly Ala Gly Phe Asp Val Lys Ala Leu Arg Ala Phe Arg Val Leu Arg
            230                 235                 240

CCC CTG CGG CTG GTG TCC GGA GTC CCA AGT CTC CAG GTG GTC CTG AAT       1002
Pro Leu Arg Leu Val Ser Gly Val Pro Ser Leu Gln Val Val Leu Asn
            245                 250                 255

TCC ATC ATC AAG GCC ATG GTC CCC CTG CTG CAC ATC GCC CTG CTT GTG       1050
Ser Ile Ile Lys Ala Met Val Pro Leu Leu His Ile Ala Leu Leu Val
260                 265                 270                 275

CTG TTT GTC ATC ATC ATC TAC GCC ATC ATC GGC TTG GAG CTC TTC ATG       1098
Leu Phe Val Ile Ile Ile Tyr Ala Ile Ile Gly Leu Glu Leu Phe Met
                280                 285                 290

GGG AAG ATG CAC AAG ACC TGC TAC AAC CAG GAG GGC ATA GCA GAT GTT       1146
Gly Lys Met His Lys Thr Cys Tyr Asn Gln Glu Gly Ile Ala Asp Val
            295                 300                 305

CCA GCA GAA GAT GAC CCT TCC CCT TGT GCG CTG GAA ACG GGC CAC GGG       1194
Pro Ala Glu Asp Asp Pro Ser Pro Cys Ala Leu Glu Thr Gly His Gly
        310                 315                 320

CGG CAG TGC CAG AAC GGC ACG GTG TGC AAG CCC GGC TGG GAT GGT CCC       1242
Arg Gln Cys Gln Asn Gly Thr Val Cys Lys Pro Gly Trp Asp Gly Pro
        325                 330                 335

AAG CAC GGC ATC ACC AAC TTT GAC AAC TTT GCC TTC GCC ATG CTC ACG       1290
Lys His Gly Ile Thr Asn Phe Asp Asn Phe Ala Phe Ala Met Leu Thr
340                 345                 350                 355

GTG TTC CAG TGC ATC ACC ATG GAG GGC TGG ACG GAC GTG CTG TAC TGG       1338
Val Phe Gln Cys Ile Thr Met Glu Gly Trp Thr Asp Val Leu Tyr Trp
                360                 365                 370

GTC AAT GAT GCC GTA GGA AGG GAC TGG CCC TGG ATC TAT TTT GTT ACA       1386
Val Asn Asp Ala Val Gly Arg Asp Trp Pro Trp Ile Tyr Phe Val Thr
            375                 380                 385

CTA ATC ATC ATA GGG TCA TTT TTT GTA CTT AAC TTG GTT CTC GGT GTG       1434
Leu Ile Ile Ile Gly Ser Phe Phe Val Leu Asn Leu Val Leu Gly Val
            390                 395                 400

CTT AGC GGA GAG TTT TCC AAA GAG AGG GAG AAG GCC AAG GCC CGG GGA       1482
Leu Ser Gly Glu Phe Ser Lys Glu Arg Glu Lys Ala Lys Ala Arg Gly
        405                 410                 415

GAT TTC CAG AAG CTG CGG GAG AAG CAG CAG CTA GAA GAG GAT CTC AAA       1530
Asp Phe Gln Lys Leu Arg Glu Lys Gln Gln Leu Glu Glu Asp Leu Lys
420                 425                 430                 435
```

-continued

```
GGC TAC CTG GAT TGG ATC ACT CAG GCC GAA GAC ATC GAT CCT GAG AAT      1578
Gly Tyr Leu Asp Trp Ile Thr Gln Ala Glu Asp Ile Asp Pro Glu Asn
                440                 445                 450

GAG GAC GAA GGC ATG GAT GAG GAG AAG CCC CGA AAC ATG AGC ATG CCC      1626
Glu Asp Glu Gly Met Asp Glu Glu Lys Pro Arg Asn Met Ser Met Pro
                    455                 460                 465

ACC AGT GAG ACC GAG TCC GTC AAC ACC GAA AAC GTG GCT GGA GGT GAC      1674
Thr Ser Glu Thr Glu Ser Val Asn Thr Glu Asn Val Ala Gly Gly Asp
                470                 475                 480

ATC GAG GGA GAA AAC TGC GGG GCC AGG CTG GCC CAC CGG ATC TCC AAG      1722
Ile Glu Gly Glu Asn Cys Gly Ala Arg Leu Ala His Arg Ile Ser Lys
            485                 490                 495

TCA AAG TTC AGC CGC TAC TGG CGC CGG TGG AAT CGG TTC TGC AGA AGG      1770
Ser Lys Phe Ser Arg Tyr Trp Arg Arg Trp Asn Arg Phe Cys Arg Arg
500                 505                 510                 515

AAG TGC CGC GCC GCA GTC AAG TCT AAT GTC TTC TAC TGG CTG GTG ATT      1818
Lys Cys Arg Ala Ala Val Lys Ser Asn Val Phe Tyr Trp Leu Val Ile
                    520                 525                 530

TTC CTG GTG TTC CTC AAC ACG CTC ACC ATT GCC TCT GAG CAC TAC AAC      1866
Phe Leu Val Phe Leu Asn Thr Leu Thr Ile Ala Ser Glu His Tyr Asn
                535                 540                 545

CAG CCC AAC TGG CTC ACA GAA GTC CAA GAC ACG GCA AAC AAG GCC CTG      1914
Gln Pro Asn Trp Leu Thr Glu Val Gln Asp Thr Ala Asn Lys Ala Leu
            550                 555                 560

CTG GCC CTG TTC ACG GCA GAG ATG CTC CTG AAG ATG TAC AGC CTG GGC      1962
Leu Ala Leu Phe Thr Ala Glu Met Leu Leu Lys Met Tyr Ser Leu Gly
        565                 570                 575

CTG CAG GCC TAC TTC GTG TCC CTC TTC AAC CGC TTT GAC TGC TTC GTC      2010
Leu Gln Ala Tyr Phe Val Ser Leu Phe Asn Arg Phe Asp Cys Phe Val
580                 585                 590                 595

GTG TGT GGC GGC ATC CTG GAG ACC ATC CTG GTG GAG ACC AAG ATC ATG      2058
Val Cys Gly Gly Ile Leu Glu Thr Ile Leu Val Glu Thr Lys Ile Met
                    600                 605                 610

TCC CCA CTG GGC ATC TCC GTG CTC AGA TGC GTC CGG CTG CTG AGG ATT      2106
Ser Pro Leu Gly Ile Ser Val Leu Arg Cys Val Arg Leu Leu Arg Ile
                615                 620                 625

TTC AAG ATC ACG AGG TAC TGG AAC TCC TTG AGC AAC CTG GTG GCA TCC      2154
Phe Lys Ile Thr Arg Tyr Trp Asn Ser Leu Ser Asn Leu Val Ala Ser
            630                 635                 640

TTG CTG AAC TCT GTG CGC TCC ATC GCC TCC CTG CTC CTT CTC CTC TTC      2202
Leu Leu Asn Ser Val Arg Ser Ile Ala Ser Leu Leu Leu Leu Leu Phe
        645                 650                 655

CTC TTC ATC ATC ATC TTC TCC CTC CTG GGG ATG CAG CTC TTT GGA GGA      2250
Leu Phe Ile Ile Ile Phe Ser Leu Leu Gly Met Gln Leu Phe Gly Gly
660                 665                 670                 675

AAG TTC AAC TTT GAT GAG ATG CAG ACC CGG AGG AGC ACA TTC GAT AAC      2298
Lys Phe Asn Phe Asp Glu Met Gln Thr Arg Arg Ser Thr Phe Asp Asn
                    680                 685                 690

TTC CCC CAG TCC CTC CTC ACT GTG TTT CAG ATC CTG ACC GGG GAG GAC      2346
Phe Pro Gln Ser Leu Leu Thr Val Phe Gln Ile Leu Thr Gly Glu Asp
                695                 700                 705

TGG AAT TCG GTG ATG TAT GAT GGG ATC ATG GCT TAT GGC GGC CCC TCT      2394
Trp Asn Ser Val Met Tyr Asp Gly Ile Met Ala Tyr Gly Gly Pro Ser
            710                 715                 720

TTT CCA GGG ATG TTA GTC TGT ATT TAC TTC ATC ATC CTC TTC ATC TGT      2442
Phe Pro Gly Met Leu Val Cys Ile Tyr Phe Ile Ile Leu Phe Ile Cys
        725                 730                 735

GGA AAC TAT ATC CTA CTG AAT GTG TTC TTG GCC ATT GCT GTG GAC AAC      2490
Gly Asn Tyr Ile Leu Leu Asn Val Phe Leu Ala Ile Ala Val Asp Asn
```

```
            740                 745                 750                 755

CTG GCT GAT GCT GAG AGC CTC ACA TCT GCC CAA AAG GAG GAG GAA GAG                2538
Leu Ala Asp Ala Glu Ser Leu Thr Ser Ala Gln Lys Glu Glu Glu Glu
                    760                 765                 770

GAG AAG GAG AGA AAG AAG CTG GCC AGG ACT GCC AGC CCA GAG AAG AAA                2586
Glu Lys Glu Arg Lys Lys Leu Ala Arg Thr Ala Ser Pro Glu Lys Lys
                775                 780                 785

CAA GAG TTG GTG GAG AAG CCG GCA GTG GGG GAA TCC AAG GAG GAG AAG                2634
Gln Glu Leu Val Glu Lys Pro Ala Val Gly Glu Ser Lys Glu Glu Lys
            790                 795                 800

ATT GAG CTG AAA TCC ATC ACG GCT GAC GGA GAG TCT CCA CCC GCC ACC                2682
Ile Glu Leu Lys Ser Ile Thr Ala Asp Gly Glu Ser Pro Pro Ala Thr
            805                 810                 815

AAG ATC AAC ATG GAT GAC CTC CAG CCC AAT GAA AAT GAG GAT AAG AGC                2730
Lys Ile Asn Met Asp Asp Leu Gln Pro Asn Glu Asn Glu Asp Lys Ser
820                 825                 830                 835

CCC TAC CCC AAC CCA GAA ACT ACA GGA GAA GAG GAT GAG GAG GAG CCA                2778
Pro Tyr Pro Asn Pro Glu Thr Thr Gly Glu Glu Asp Glu Glu Glu Pro
                    840                 845                 850

GAG ATG CCT GTC GGC CCT CGC CCA CGA CCA CTC TCT GAG CTT CAC CTT                2826
Glu Met Pro Val Gly Pro Arg Pro Arg Pro Leu Ser Glu Leu His Leu
                855                 860                 865

AAG GAA AAG GCA GTG CCC ATG CCA GAA GCC AGC GCG TTT TTC ATC TTC                2874
Lys Glu Lys Ala Val Pro Met Pro Glu Ala Ser Ala Phe Phe Ile Phe
            870                 875                 880

AGC TCT AAC AAC AGG TTT CGC CTC CAG TGC CAC CGC ATT GTC AAT GAC                2922
Ser Ser Asn Asn Arg Phe Arg Leu Gln Cys His Arg Ile Val Asn Asp
            885                 890                 895

ACG ATC TTC ACC AAC CTG ATC CTC TTC TTC ATT CTG CTC AGC AGC ATT                2970
Thr Ile Phe Thr Asn Leu Ile Leu Phe Phe Ile Leu Leu Ser Ser Ile
900                 905                 910                 915

TCC CTG GCT GCT GAG GAC CCG GTC CAG CAC ACC TCC TTC AGG AAC CAT                3018
Ser Leu Ala Ala Glu Asp Pro Val Gln His Thr Ser Phe Arg Asn His
                    920                 925                 930

ATT CTG TTT TAT TTT GAT ATT GTT TTT ACC ACC ATT TTC ACC ATT GAA                3066
Ile Leu Phe Tyr Phe Asp Ile Val Phe Thr Thr Ile Phe Thr Ile Glu
                935                 940                 945

ATT GCT CTG AAG ATG ACT GCT TAT GGG GCT TTC TTG CAC AAG GGT TCT                3114
Ile Ala Leu Lys Met Thr Ala Tyr Gly Ala Phe Leu His Lys Gly Ser
            950                 955                 960

TTC TGC CGG AAC TAC TTC AAC ATC CTG GAC CTG CTG GTG GTC AGC GTG                3162
Phe Cys Arg Asn Tyr Phe Asn Ile Leu Asp Leu Leu Val Val Ser Val
            965                 970                 975

TCC CTC ATC TCC TTT GGC ATC CAG TCC AGT GCA ATC AAT GTC GTG AAG                3210
Ser Leu Ile Ser Phe Gly Ile Gln Ser Ser Ala Ile Asn Val Val Lys
980                 985                 990                 995

ATC TTG CGA GTC CTG CGA GTA CTC AGG CCC CTG AGG GCC ATC AAC AGG                3258
Ile Leu Arg Val Leu Arg Val Leu Arg Pro Leu Arg Ala Ile Asn Arg
                    1000                1005                1010

GCC AAG GGG CTA AAG CAT GTG GTT CAG TGT GTG TTT GTC GCC ATC CGG                3306
Ala Lys Gly Leu Lys His Val Val Gln Cys Val Phe Val Ala Ile Arg
                1015                1020                1025

ACC ATC GGG AAC ATC GTG ATT GTC ACC ACC CTG CTG CAG TTC ATG TTT                3354
Thr Ile Gly Asn Ile Val Ile Val Thr Thr Leu Leu Gln Phe Met Phe
            1030                1035                1040

GCC TGC ATC GGG GTC CAG CTC TTC AAG GGA AAG CTG TAC ACC TGT TCA                3402
Ala Cys Ile Gly Val Gln Leu Phe Lys Gly Lys Leu Tyr Thr Cys Ser
            1045                1050                1055

GAC AGT TCC AAG CAG ACA GAG GCG GAA TGC AAG GGC AAC TAC ATC ACG                3450
```

-continued

```
Asp Ser Ser Lys Gln Thr Glu Ala Glu Cys Lys Gly Asn Tyr Ile Thr
1060                1065                1070                1075

TAC AAA GAC GGG GAG GTT GAC CAC CCC ATC ATC CAA CCC CGC AGC TGG      3498
Tyr Lys Asp Gly Glu Val Asp His Pro Ile Ile Gln Pro Arg Ser Trp
                1080                1085                1090

GAG AAC AGC AAG TTT GAC TTT GAC AAT GTT CTG GCA GCC ATG ATG GCC      3546
Glu Asn Ser Lys Phe Asp Phe Asp Asn Val Leu Ala Ala Met Met Ala
                    1095                1100                1105

CTC TTC ACC GTC TCC ACC TTC GAA GGG TGG CCA GAG CTG CTG TAC CGC      3594
Leu Phe Thr Val Ser Thr Phe Glu Gly Trp Pro Glu Leu Leu Tyr Arg
                        1110                1115                1120

TCC ATC GAC TCC CAC ACG GAA GAC AAG GGC CCC ATC TAC AAC TAC CGT      3642
Ser Ile Asp Ser His Thr Glu Asp Lys Gly Pro Ile Tyr Asn Tyr Arg
                1125                1130                1135

GTG GAG ATC TCC ATC TTC TTC ATC ATC TAC ATC ATC ATC GCC TTC          3690
Val Glu Ile Ser Ile Phe Phe Ile Ile Tyr Ile Ile Ile Ala Phe
1140                1145                1150                1155

TTC ATG ATG AAC ATC TTC GTG GGC TTC GTC ATC GTC ACC TTT CAG GAG      3738
Phe Met Met Asn Ile Phe Val Gly Phe Val Ile Val Thr Phe Gln Glu
                1160                1165                1170

CAG GGG GAG CAG GAG TAC AAG AAC TGT GAG CTG GAC AAG AAC CAG CGA      3786
Gln Gly Glu Gln Glu Tyr Lys Asn Cys Glu Leu Asp Lys Asn Gln Arg
                    1175                1180                1185

CAG TGC GTG GAA TAC GCC CTC AAG GCC CGG CCC CTG CGG AGG TAC ATC      3834
Gln Cys Val Glu Tyr Ala Leu Lys Ala Arg Pro Leu Arg Arg Tyr Ile
                1190                1195                1200

CCC AAG AAC CAG CAC CAG TAC AAA GTG TGG TAC GTG GTC AAC TCC ACC      3882
Pro Lys Asn Gln His Gln Tyr Lys Val Trp Tyr Val Val Asn Ser Thr
                1205                1210                1215

TAC TTC GAG TAC CTG ATG TTC GTC CTC ATC CTG CTC AAC ACC ATC TGC      3930
Tyr Phe Glu Tyr Leu Met Phe Val Leu Ile Leu Leu Asn Thr Ile Cys
1220                1225                1230                1235

CTG GCC ATG CAG CAC TAC GGC CAG AGC TGC CTG TTC AAA ATC GCC ATG      3978
Leu Ala Met Gln His Tyr Gly Gln Ser Cys Leu Phe Lys Ile Ala Met
                    1240                1245                1250

AAC ATC CTC AAC ATG CTC TTC ACT GGC CTC TTT ACC GTG GAG ATG ATC      4026
Asn Ile Leu Asn Met Leu Phe Thr Gly Leu Phe Thr Val Glu Met Ile
                1255                1260                1265

CTG AAG CTC ATT GCC TTC AAA CCC AAG CAC TAT TTC TGT GAT GCA TGG      4074
Leu Lys Leu Ile Ala Phe Lys Pro Lys His Tyr Phe Cys Asp Ala Trp
                1270                1275                1280

AAT ACA TTT GAC GCC TTG ATT GTT GTG GGT AGC ATT GTT GAT ATA GCA      4122
Asn Thr Phe Asp Ala Leu Ile Val Val Gly Ser Ile Val Asp Ile Ala
                    1285                1290                1295

ATC ACC GAG GTA AAC CCA GCT GAA CAT ACC CAA TGC TCT CCC TCT ATG      4170
Ile Thr Glu Val Asn Pro Ala Glu His Thr Gln Cys Ser Pro Ser Met
1300                1305                1310                1315

AAC GCA GAG GAA AAC TCC CGC ATC TCC ATC ACC TTC TTC CGC CTG TTC      4218
Asn Ala Glu Glu Asn Ser Arg Ile Ser Ile Thr Phe Phe Arg Leu Phe
                    1320                1325                1330

CGG GTC ATG CGT CTG GTG AAG CTG CTG AGC CGT GGG GAG GGC ATC CGG      4266
Arg Val Met Arg Leu Val Lys Leu Leu Ser Arg Gly Glu Gly Ile Arg
                1335                1340                1345

ACG CTG CTG TGG ACC TTC ATC AAG TCC TTC CAG GCC CTG CCC TAT GTG      4314
Thr Leu Leu Trp Thr Phe Ile Lys Ser Phe Gln Ala Leu Pro Tyr Val
                    1350                1355                1360

GCC CTC CTG ATC GTG ATG CTG TTC TTC ATC TAC GCG GTG ATC GGG ATG      4362
Ala Leu Leu Ile Val Met Leu Phe Phe Ile Tyr Ala Val Ile Gly Met
                1365                1370                1375
```

-continued

```
CAG GTG TTT GGG AAA ATT GCC CTG AAT GAT ACC ACA GAG ATC AAC CGG    4410
Gln Val Phe Gly Lys Ile Ala Leu Asn Asp Thr Thr Glu Ile Asn Arg
1380            1385                1390                1395

AAC AAC AAC TTT CAG ACC TTC CCC CAG GCC GTG CTG CTC CTC TTC AGG    4458
Asn Asn Asn Phe Gln Thr Phe Pro Gln Ala Val Leu Leu Leu Phe Arg
            1400                1405                1410

TGT GCC ACC GGG GAG GCC TGG CAG GAC ATC ATG CTG GCC TGC ATG CCA    4506
Cys Ala Thr Gly Glu Ala Trp Gln Asp Ile Met Leu Ala Cys Met Pro
        1415                1420                1425

GGC AAG AAG TGT GCC CCA GAG TCC GAG CCC AGC AAC AGC ACG GAG GGT    4554
Gly Lys Lys Cys Ala Pro Glu Ser Glu Pro Ser Asn Ser Thr Glu Gly
    1430                1435                1440

GAA ACA CCC TGT GGT AGC AGC TTT GCT GTC TTC TAC TTC ATC AGC TTC    4602
Glu Thr Pro Cys Gly Ser Ser Phe Ala Val Phe Tyr Phe Ile Ser Phe
1445                1450                1455

TAC ATG CTC TGT GCC TTC CTG ATC ATC AAC CTC TTT GTA GCT GTC ATC    4650
Tyr Met Leu Cys Ala Phe Leu Ile Ile Asn Leu Phe Val Ala Val Ile
1460            1465                1470                1475

ATG GAC AAC TTT GAC TAC CTG ACA AGG GAC TGG TCC ATC CTT GGT CCC    4698
Met Asp Asn Phe Asp Tyr Leu Thr Arg Asp Trp Ser Ile Leu Gly Pro
            1480                1485                1490

CAC CAC CTG GAT GAG TTT AAA AGA ATC TGG GCA GAG TAT GAC CCT GAA    4746
His His Leu Asp Glu Phe Lys Arg Ile Trp Ala Glu Tyr Asp Pro Glu
        1495                1500                1505

GCC AAG GGT CGT ATC AAA CAC CTG GAT GTG GTG ACC CTC CTC CGG CGG    4794
Ala Lys Gly Arg Ile Lys His Leu Asp Val Val Thr Leu Leu Arg Arg
    1510                1515                1520

ATT CAG CCG CCA CTA GGT TTT GGG AAG CTG TGC CCT CAC CGC GTG GCT    4842
Ile Gln Pro Pro Leu Gly Phe Gly Lys Leu Cys Pro His Arg Val Ala
1525                1530                1535

TGC AAA CGC CTG GTC TCC ATG AAC ATG CCT CTG AAC AGC GAC GGG ACA    4890
Cys Lys Arg Leu Val Ser Met Asn Met Pro Leu Asn Ser Asp Gly Thr
1540            1545                1550                1555

GTC ATG TTC AAT GCC ACC CTG TTT GCC CTG GTC AGG ACG GCC CTG AGG    4938
Val Met Phe Asn Ala Thr Leu Phe Ala Leu Val Arg Thr Ala Leu Arg
            1560                1565                1570

ATC AAA ACA GAA GGG AAC CTA GAA CAA GCC AAT GAG GAG CTG CGG GCG    4986
Ile Lys Thr Glu Gly Asn Leu Glu Gln Ala Asn Glu Glu Leu Arg Ala
        1575                1580                1585

ATC ATC AAG AAG ATC TGG AAG CGG ACC AGC ATG AAG CTG CTG GAC CAG    5034
Ile Ile Lys Lys Ile Trp Lys Arg Thr Ser Met Lys Leu Leu Asp Gln
    1590                1595                1600

GTG GTG CCC CCT GCA GGT GAT GAT GAG GTC ACC GTT GGC AAG TTC TAC    5082
Val Val Pro Pro Ala Gly Asp Asp Glu Val Thr Val Gly Lys Phe Tyr
1605                1610                1615

GCC ACG TTC CTG ATC CAG GAG TAC TTC CGG AAG TTC AAG AAG CGC AAA    5130
Ala Thr Phe Leu Ile Gln Glu Tyr Phe Arg Lys Phe Lys Lys Arg Lys
1620            1625                1630                1635

GAG CAG GGC CTT GTG GGC AAG CCC TCC CAG AGG AAC GCG CTG TCT CTG    5178
Glu Gln Gly Leu Val Gly Lys Pro Ser Gln Arg Asn Ala Leu Ser Leu
            1640                1645                1650

CAG GCT GGC TTG CGC ACA CTG CAT GAC ATC GGG CCT GAG ATC CGA CGG    5226
Gln Ala Gly Leu Arg Thr Leu His Asp Ile Gly Pro Glu Ile Arg Arg
        1655                1660                1665

GCC ATC TCT GGA GAT CTC ACC GCT GAG GAG GAG CTG GAC AAG GCC ATG    5274
Ala Ile Ser Gly Asp Leu Thr Ala Glu Glu Glu Leu Asp Lys Ala Met
    1670                1675                1680

AAG GAG GCT GTG TCC GCT GCT TCT GAA GAT GAC ATC TTC AGG AGG GCC    5322
Lys Glu Ala Val Ser Ala Ala Ser Glu Asp Asp Ile Phe Arg Arg Ala
1685                1690                1695
```

```
GGT GGC CTG TTC GGC AAC CAC GTC AGC TAC TAC CAA AGC GAC GGC CGG           5370
Gly Gly Leu Phe Gly Asn His Val Ser Tyr Tyr Gln Ser Asp Gly Arg
1700                1705                1710                1715

AGC GCC TTC CCC CAG ACC TTC ACC ACT CAG CGC CCG CTG CAC ATC AAC           5418
Ser Ala Phe Pro Gln Thr Phe Thr Thr Gln Arg Pro Leu His Ile Asn
                1720                1725                1730

AAG GCG GGC AGC AGC CAG GGC GAC ACT GAG TCG CCA TCC CAC GAG AAG           5466
Lys Ala Gly Ser Ser Gln Gly Asp Thr Glu Ser Pro Ser His Glu Lys
            1735                1740                1745

CTG GTG GAC TCC ACC TTC ACC CCG AGC AGC TAC TCG TCC ACC GGC TCC           5514
Leu Val Asp Ser Thr Phe Thr Pro Ser Ser Tyr Ser Ser Thr Gly Ser
        1750                1755                1760

AAC GCC AAC ATC AAC AAC GCC AAC AAC ACC GCC CTG GGT CGC CTC CCT           5562
Asn Ala Asn Ile Asn Asn Ala Asn Asn Thr Ala Leu Gly Arg Leu Pro
    1765                1770                1775

CGC CCC GCC GGC TAC CCC AGC ACG GTC AGC ACT GTG GAG GGC CAC GGG           5610
Arg Pro Ala Gly Tyr Pro Ser Thr Val Ser Thr Val Glu Gly His Gly
1780                1785                1790                1795

CCC CCC TTG TCC CCT GCC ATC CGG GTG CAG GAG GTG GCG TGG AAG CTC           5658
Pro Pro Leu Ser Pro Ala Ile Arg Val Gln Glu Val Ala Trp Lys Leu
                1800                1805                1810

AGC TCC AAC AGG TGC CAC TCC CGG GAG AGC CAG GCA GCC ATG GCG GGT           5706
Ser Ser Asn Arg Cys His Ser Arg Glu Ser Gln Ala Ala Met Ala Gly
            1815                1820                1825

CAG GAG GAG ACG TCT CAG GAT GAG ACC TAT GAA GTG AAG ATG AAC CAT           5754
Gln Glu Glu Thr Ser Gln Asp Glu Thr Tyr Glu Val Lys Met Asn His
        1830                1835                1840

GAC ACG GAG GCC TGC AGT GAG CCC AGC CTG CTC TCC ACA GAG ATG CTC           5802
Asp Thr Glu Ala Cys Ser Glu Pro Ser Leu Leu Ser Thr Glu Met Leu
    1845                1850                1855

TCC TAC CAG GAT GAC GAA AAT CGG CAA CTG ACG CTC CCA GAG GAG GAC           5850
Ser Tyr Gln Asp Asp Glu Asn Arg Gln Leu Thr Leu Pro Glu Glu Asp
1860                1865                1870                1875

AAG AGG GAC ATC CGG CAA TCT CCG AAG AGG GGT TTC CTC CGC TCT GCC           5898
Lys Arg Asp Ile Arg Gln Ser Pro Lys Arg Gly Phe Leu Arg Ser Ala
                1880                1885                1890

TCA CTA GGT CGA AGG GCC TCC TTC CAC CTG GAA TGT CTG AAG CGA CAG           5946
Ser Leu Gly Arg Arg Ala Ser Phe His Leu Glu Cys Leu Lys Arg Gln
            1895                1900                1905

AAG GAC CGA GGG GGA GAC ATC TCT CAG AAG ACA GTC CTG CCC TTG CAT           5994
Lys Asp Arg Gly Gly Asp Ile Ser Gln Lys Thr Val Leu Pro Leu His
        1910                1915                1920

CTG GTT CAT CAT CAG GCA TTG GCA GTG GCA GGC CTG AGC CCC CTC CTC           6042
Leu Val His His Gln Ala Leu Ala Val Ala Gly Leu Ser Pro Leu Leu
    1925                1930                1935

CAG AGA AGC CAT TCC CCT GCC TCA TTC CCT AGG CCT TTT GCC ACC CCA           6090
Gln Arg Ser His Ser Pro Ala Ser Phe Pro Arg Pro Phe Ala Thr Pro
1940                1945                1950                1955

CCA GCC ACA CCT GGC AGC CGA GGC TGG CCC CCA CAG CCC GTC CCC ACC           6138
Pro Ala Thr Pro Gly Ser Arg Gly Trp Pro Pro Gln Pro Val Pro Thr
                1960                1965                1970

CTG CGG CTT GAG GGG GTC GAG TCC AGT GAG AAA CTC AAC AGC AGC TTC           6186
Leu Arg Leu Glu Gly Val Glu Ser Ser Glu Lys Leu Asn Ser Ser Phe
            1975                1980                1985

CCA TCC ATC CAC TGC GGC TCC TGG GCT GAG ACC ACC CCC GGT GGC GGG           6234
Pro Ser Ile His Cys Gly Ser Trp Ala Glu Thr Thr Pro Gly Gly Gly
        1990                1995                2000

GGC AGC AGC GCC GCC CGG AGA GTC CGG CCC GTC TCC CTC ATG GTG CCC           6282
Gly Ser Ser Ala Ala Arg Arg Val Arg Pro Val Ser Leu Met Val Pro
```

```
          2005                2010                2015
AGC CAG GCT GGG GCC CCA GGG AGG CAG TTC CAC GGC AGT GCC AGC AGC      6330
Ser Gln Ala Gly Ala Pro Gly Arg Gln Phe His Gly Ser Ala Ser Ser
2020            2025                2030                2035

CTG GTG GAA GCG GTC TTG ATT TCA GAA GGA CTG GGG CAG TTT GCT CAA      6378
Leu Val Glu Ala Val Leu Ile Ser Glu Gly Leu Gly Gln Phe Ala Gln
            2040                2045                2050

GAT CCC AAG TTC ATC GAG GTC ACC ACC CAG GAG CTG GCC GAC GCC TGC      6426
Asp Pro Lys Phe Ile Glu Val Thr Thr Gln Glu Leu Ala Asp Ala Cys
                2055                2060                2065

GAC ATG ACC ATA GAG GAG ATG GAG AGC GCG GCC GAC AAC ATC CTC AGC      6474
Asp Met Thr Ile Glu Glu Met Glu Ser Ala Ala Asp Asn Ile Leu Ser
            2070                2075                2080

GGG GGC GCC CCA CAG AGC CCC AAT GGC GCC CTC TTA CCC TTT GTG AAC      6522
Gly Gly Ala Pro Gln Ser Pro Asn Gly Ala Leu Leu Pro Phe Val Asn
2085                2090                2095

TGC AGG GAC GCG GGG CAG GAC CGA GCC GGG GGC GAA GAG GAC GCG GGC      6570
Cys Arg Asp Ala Gly Gln Asp Arg Ala Gly Gly Glu Glu Asp Ala Gly
            2100                2105                2110                2115

TGT GTG CGC GCG CGG GGT CGA CCG AGT GAG GAG GAG CTC CAG GAC AGC      6618
Cys Val Arg Ala Arg Gly Arg Pro Ser Glu Glu Glu Leu Gln Asp Ser
                2120                2125                2130

AGG GTC TAC GTC AGC AGC CTG TAGTGGGCGC TGCCAGATGC GGGCTTTTTT         6669
Arg Val Tyr Val Ser Ser Leu
            2135

TTATTTGTTT CAATGTTCCT AATGGGTTCG TTTCAGAAGT GCCTCACTGT TCTCGT        6725

(2) INFORMATION FOR SEQ ID NO:37:

(i) SEQUENCE CHARACTERISTICS:
        (A) LENGTH: 2970 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 502..2316
        (D) OTHER INFORMATION: /standard_name= "Beta-2C"

(xi) SEQUENCE DESCRIPTION: SEQ ID NO:37:

CAGCAGCGTG CTAAGAAGCA GTCACATAAA CAGCAGCAGG AGTAGGCCTC CTGCTTTTCA      60

AAAGCAGAGT ACTGCAGGGT CGCGAAATGC AAGACACTCA GATGTTTGAA AATCTCCCGA     120

GTTGAGAATG GCTACTGTAA AAGCGTCACC AAGAAACTCT GACGATCTGG ACAGTCCTAA     180

CTCTGTGTTA GCAATACTTA CTTCCGGAAA ATTAATGCTA CTTCTTGTAG ATTTTTGCAA     240

ATAGGAAACC CCCTTGAAGA AGATCTCAAA TTACGCCCCC CACCCCCAAA AAAAGACAAA     300

CAGGGGAGAA CAAAGTTTTG GCATGCCTGC AGGAACGGTG GCTTTTTTAG AAACTACCTA     360

GGAGGCAGAA GCTAAGTGAT TTGCTCATGC CTCTTACCTG GGAGTAGAAG GTGGGAAGAA     420

ATGGACCGAG GCTGTGACGA GAAGACAAGG CACAGTGCAG CTTGGTGAAG CCACACGCTG     480

ACTGCGTTCT GCCCCCTCTT C ATG CAG TGC TGC GGG CTG GTG CAT CGC CGG      531
                       Met Gln Cys Cys Gly Leu Val His Arg Arg
                        1               5                   10

CGA GTA CGG GTG TCC TAT GGT TCG GCA GAC TCC TAC ACT AGC CGT CCA      579
Arg Val Arg Val Ser Tyr Gly Ser Ala Asp Ser Tyr Thr Ser Arg Pro
            15                  20                  25

TCC GAT TCC GAT GTA TCT CTG GAG GAG GAC CGG GAG GCA GTG CGC AGA      627
```

```
Ser Asp Ser Asp Val Ser Leu Glu Glu Asp Arg Glu Ala Val Arg Arg
            30                  35                  40

GAA GCG GAG CGG CAG GCC CAG GCA CAG TTG GAA AAA GCA AAG ACA AAG        675
Glu Ala Glu Arg Gln Ala Gln Ala Gln Leu Glu Lys Ala Lys Thr Lys
            45                  50                  55

CCC GTT GCA TTT GCG GTT CGG ACA AAT GTC AGC TAC AGT GCG GCC CAT        723
Pro Val Ala Phe Ala Val Arg Thr Asn Val Ser Tyr Ser Ala Ala His
    60                  65                  70

GAA GAT GAT GTT CCA GTG CCT GGC ATG GCC ATC TCA TTC GAA GCA AAA        771
Glu Asp Asp Val Pro Val Pro Gly Met Ala Ile Ser Phe Glu Ala Lys
75                  80                  85                  90

GAT TTT CTG CAT GTT AAG GAA AAA TTT AAC AAT GAC TGG TGG ATA GGG        819
Asp Phe Leu His Val Lys Glu Lys Phe Asn Asn Asp Trp Trp Ile Gly
                95                  100                 105

CGA TTG GTA AAA GAA GGC TGT GAA ATC GGA TTC ATT CCA AGC CCA GTC        867
Arg Leu Val Lys Glu Gly Cys Glu Ile Gly Phe Ile Pro Ser Pro Val
            110                 115                 120

AAA CTA GAA AAC ATG AGG CTG CAG CAT GAA CAG AGA GCC AAG CAA GGG        915
Lys Leu Glu Asn Met Arg Leu Gln His Glu Gln Arg Ala Lys Gln Gly
                125                 130                 135

AAA TTC TAC TCC AGT AAA TCA GGA GGA AAT TCA TCA TCC AGT TTG GGT        963
Lys Phe Tyr Ser Ser Lys Ser Gly Gly Asn Ser Ser Ser Ser Leu Gly
    140                 145                 150

GAC ATA GTA CCT AGT TCC AGA AAA TCA ACA CCT CCA TCA TCT GCT ATA       1011
Asp Ile Val Pro Ser Ser Arg Lys Ser Thr Pro Pro Ser Ser Ala Ile
155                 160                 165                 170

GAC ATA GAT GCT ACT GGC TTA GAT GCA GAA GAA AAT GAT ATT CCA GCA       1059
Asp Ile Asp Ala Thr Gly Leu Asp Ala Glu Glu Asn Asp Ile Pro Ala
                175                 180                 185

AAC CAC CGC TCC CCT AAA CCC AGT GCA AAC AGT GTA ACG TCA CCC CAC       1107
Asn His Arg Ser Pro Lys Pro Ser Ala Asn Ser Val Thr Ser Pro His
            190                 195                 200

TCC AAA GAG AAA AGA ATG CCC TTC TTT AAG AAG ACA GAG CAC ACT CCT       1155
Ser Lys Glu Lys Arg Met Pro Phe Phe Lys Lys Thr Glu His Thr Pro
            205                 210                 215

CCG TAT GAT GTG GTA CCT TCC ATG CGA CCA GTG GTC CTA GTG GGC CCT       1203
Pro Tyr Asp Val Val Pro Ser Met Arg Pro Val Val Leu Val Gly Pro
        220                 225                 230

TCT CTG AAG GGC TAC GAG GTC ACA GAT ATG ATG CAA AAA GCG CTG TTT       1251
Ser Leu Lys Gly Tyr Glu Val Thr Asp Met Met Gln Lys Ala Leu Phe
235                 240                 245                 250

GAT TTT TTA AAA CAC AGA TTT GAA GGG CGG ATA TCC ATC ACA AGG GTC       1299
Asp Phe Leu Lys His Arg Phe Glu Gly Arg Ile Ser Ile Thr Arg Val
                255                 260                 265

ACC GCT GAC ATC TCG CTT GCC AAA CGC TCG GTA TTA AAC AAT CCC AGT       1347
Thr Ala Asp Ile Ser Leu Ala Lys Arg Ser Val Leu Asn Asn Pro Ser
                270                 275                 280

AAG CAC GCA ATA ATA GAA AGA TCC AAC ACA AGG TCA AGC TTA GCG GAA       1395
Lys His Ala Ile Ile Glu Arg Ser Asn Thr Arg Ser Ser Leu Ala Glu
            285                 290                 295

GTT CAG AGT GAA ATC GAA AGG ATT TTT GAA CTT GCA AGA ACA TTG CAG       1443
Val Gln Ser Glu Ile Glu Arg Ile Phe Glu Leu Ala Arg Thr Leu Gln
        300                 305                 310

TTG GTG GTC CTT GAC GCG GAT ACA ATT AAT CAT CCA GCT CAA CTC AGT       1491
Leu Val Val Leu Asp Ala Asp Thr Ile Asn His Pro Ala Gln Leu Ser
315                 320                 325                 330

AAA ACC TCC TTG GCC CCT ATT ATA GTA TAT GTA AAG ATT TCT TCT CCT       1539
Lys Thr Ser Leu Ala Pro Ile Ile Val Tyr Val Lys Ile Ser Ser Pro
                335                 340                 345
```

```
AAG GTT TTA CAA AGG TTA ATA AAA TCT CGA GGG AAA TCT CAA GCT AAA        1587
Lys Val Leu Gln Arg Leu Ile Lys Ser Arg Gly Lys Ser Gln Ala Lys
            350                 355                 360

CAC CTC AAC GTC CAG ATG GTA GCA GCT GAT AAA CTG GCT CAG TGT CCT        1635
His Leu Asn Val Gln Met Val Ala Ala Asp Lys Leu Ala Gln Cys Pro
                365                 370                 375

CCA GAG CTG TTC GAT GTG ATC TTG GAT GAG AAC CAG CTT GAG GAT GCC        1683
Pro Glu Leu Phe Asp Val Ile Leu Asp Glu Asn Gln Leu Glu Asp Ala
        380                 385                 390

TGT GAG CAC CTT GCC GAC TAT CTG GAG GCC TAC TGG AAG GCC ACC CAT        1731
Cys Glu His Leu Ala Asp Tyr Leu Glu Ala Tyr Trp Lys Ala Thr His
395                 400                 405                 410

CCT CCC AGC AGT AGC CTC CCC AAC CCT CTC CTT AGC CGT ACA TTA GCC        1779
Pro Pro Ser Ser Ser Leu Pro Asn Pro Leu Leu Ser Arg Thr Leu Ala
                415                 420                 425

ACT TCA AGT CTG CCT CTT AGC CCC ACC CTA GCC TCT AAT TCA CAG GGT        1827
Thr Ser Ser Leu Pro Leu Ser Pro Thr Leu Ala Ser Asn Ser Gln Gly
            430                 435                 440

TCT CAA GGT GAT CAG AGG ACT GAT CGC TCC GCT CCT ATC CGT TCT GCT        1875
Ser Gln Gly Asp Gln Arg Thr Asp Arg Ser Ala Pro Ile Arg Ser Ala
        445                 450                 455

TCC CAA GCT GAA GAA GAA CCT AGT GTG GAA CCA GTC AAG AAA TCC CAG        1923
Ser Gln Ala Glu Glu Glu Pro Ser Val Glu Pro Val Lys Lys Ser Gln
460                 465                 470

CAC CGC TCT TCC TCC TCA GCC CCA CAC CAC AAC CAT CGC AGT GGG ACA        1971
His Arg Ser Ser Ser Ser Ala Pro His His Asn His Arg Ser Gly Thr
475                 480                 485                 490

AGT CGC GGC CTC TCC AGG CAA GAG ACA TTT GAC TCG GAA ACC CAG GAG        2019
Ser Arg Gly Leu Ser Arg Gln Glu Thr Phe Asp Ser Glu Thr Gln Glu
                495                 500                 505

AGT CGA GAC TCT GCC TAC GTA GAG CCA AAG GAA GAT TAT TCC CAT GAC        2067
Ser Arg Asp Ser Ala Tyr Val Glu Pro Lys Glu Asp Tyr Ser His Asp
            510                 515                 520

CAC GTG GAC CAC TAT GCC TCA CAC CGT GAC CAC AAC CAC AGA GAC GAG        2115
His Val Asp His Tyr Ala Ser His Arg Asp His Asn His Arg Asp Glu
        525                 530                 535

ACC CAC GGG AGC AGT GAC CAC AGA CAC AGG GAG TCC CGG CAC CGT TCC        2163
Thr His Gly Ser Ser Asp His Arg His Arg Glu Ser Arg His Arg Ser
    540                 545                 550

CGG GAC GTG GAT CGA GAG CAG GAC CAC AAC GAG TGC AAC AAG CAG CGC        2211
Arg Asp Val Asp Arg Glu Gln Asp His Asn Glu Cys Asn Lys Gln Arg
555                 560                 565                 570

AGC CGT CAT AAA TCC AAG GAT CGC TAC TGT GAA AAG GAT GGA GAA GTG        2259
Ser Arg His Lys Ser Lys Asp Arg Tyr Cys Glu Lys Asp Gly Glu Val
                575                 580                 585

ATA TCA AAA AAA CGG AAT GAG GCT GGG GAG TGG AAC AGG GAT GTT TAC        2307
Ile Ser Lys Lys Arg Asn Glu Ala Gly Glu Trp Asn Arg Asp Val Tyr
            590                 595                 600

ATC CCC CAA TGAGTTTTGC CCTTTTGTGT TTTTTTTTTT TTTTTTTGA                 2356
Ile Pro Gln
        605

AGTCTTGTAT AACTAACAGC ATCCCCAAAA CAAAAAGTCT TTGGGGTCTA CACTGCAATC      2416

ATATGTGATC TGTCTTGTAA TATTTTGTAT TATTGCTGTT GCTTGAATAG CAATAGCATG      2476

GATAGAGTAT TGAGATACTT TTTCTTTTGT AAGTGCTACA TAAATTGGCC TGGTATGGCT      2536

GCAGTCCTCC GGTTGCATAC TGGACTCTTC AAAAACTGTT TTGGGTAGCT GCCCACTTGAA     2596

CAAAATCTGT TGCCACCCAG GTGATGTTAG TGTTTTAAGA AATGTAGTTG ATGTATCCAA      2656

CAAGCCAGAA TCAGCACAGA TAAAAAGTGG AATTTCTTGT TTCTCCAGAT TTTTAATACG      2716
```

```
TTAATACGCA GGCATCTGAT TTGCATATTC ATTCATGGAC CACTGTTTCT TGCTTGTACC     2776

TCTGGCTGAC TAAATTTGGG GACAGATTCA GTCTTGCCTT ACACAAAGGG GATCATAAAG     2836

TTAGAATCTA TTTTCTATGT ACTAGTACTG TGTACTGTAT AGACAGTTTG TAAATGTTAT     2896

TTCTGCAAAC AAACACCTCC TTATTATATA TAATATATAT ATATATATCA GTTTGATCAC     2956

ACTATTTTAG AGTC                                                      2970

(2) INFORMATION FOR SEQ ID NO:38:

(i) SEQUENCE CHARACTERISTICS:
        (A) LENGTH: 2712 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 223..2061
        (D) OTHER INFORMATION: /standard_name= "Beta-2E"

(xi) SEQUENCE DESCRIPTION: SEQ ID NO:38:

AGTGTGTGTT TTCAGCCCCT CCTGGAATGG GAAAATAAGA ATCTCCCTGG ATGGGAGTCC       60

TCTGGGGCAG GGAGTGAAAG CCCCGGAGGC AGAAAGGGAC GGAGAACAGG GGCTTGCCCA      120

GAGCATGGAT AGGAAAGGAG CTGGGGTTCT CCGGGGCTCA GCGCGCACTG AGAACCTGTG      180

CCCGGGGCTG CAGCTGCGGA CGATAAAGGC GCTGTCTGGC TC ATG AAG GCC ACC         234
                                              Met Lys Ala Thr
                                                1

TGG ATC AGG CTT CTG AAA AGA GCC AAG GGA GGA AGG CTG AAG AAT TCT        282
Trp Ile Arg Leu Leu Lys Arg Ala Lys Gly Gly Arg Leu Lys Asn Ser
  5              10                  15                  20

GAT ATC TGT GGT TCG GCA GAC TCC TAC ACT AGC CGT CCA TCC GAT TCC        330
Asp Ile Cys Gly Ser Ala Asp Ser Tyr Thr Ser Arg Pro Ser Asp Ser
                 25                  30                  35

GAT GTA TCT CTG GAG GAG GAC CGG GAG GCA GTG CGC AGA GAA GCG GAG        378
Asp Val Ser Leu Glu Glu Asp Arg Glu Ala Val Arg Arg Glu Ala Glu
             40                  45                  50

CGG CAG GCC CAG GCA CAG TTG GAA AAA GCA AAG ACA AAG CCC GTT GCA        426
Arg Gln Ala Gln Ala Gln Leu Glu Lys Ala Lys Thr Lys Pro Val Ala
         55                  60                  65

TTT GCG GTT CGG ACA AAT GTC AGC TAC AGT GCG GCC CAT GAA GAT GAT        474
Phe Ala Val Arg Thr Asn Val Ser Tyr Ser Ala Ala His Glu Asp Asp
     70                  75                  80

GTT CCA GTG CCT GGC ATG GCC ATC TCA TTC GAA GCA AAA GAT TTT CTG        522
Val Pro Val Pro Gly Met Ala Ile Ser Phe Glu Ala Lys Asp Phe Leu
 85                  90                  95                 100

CAT GTT AAG GAA AAA TTT AAC AAT GAC TGG TGG ATA GGG CGA TTG GTA        570
His Val Lys Glu Lys Phe Asn Asn Asp Trp Trp Ile Gly Arg Leu Val
                105                 110                 115

AAA GAA GGC TGT GAA ATC GGA TTC ATT CCA AGC CCA GTC AAA CTA GAA        618
Lys Glu Gly Cys Glu Ile Gly Phe Ile Pro Ser Pro Val Lys Leu Glu
            120                 125                 130

AAC ATG AGG CTG CAG CAT GAA CAG AGA GCC AAG CAA GGG AAA TTC TAC        666
Asn Met Arg Leu Gln His Glu Gln Arg Ala Lys Gln Gly Lys Phe Tyr
        135                 140                 145

TCC AGT AAA TCA GGA GGA AAT TCA TCA TCC AGT TTG GGT GAC ATA GTA        714
Ser Ser Lys Ser Gly Gly Asn Ser Ser Ser Ser Leu Gly Asp Ile Val
    150                 155                 160
```

-continued

| | | | | | | | | | | | | | | | | |
|---|---|---|---|---|---|---|---|---|---|---|---|---|---|---|---|---|
| CCT | AGT | TCC | AGA | AAA | TCA | ACA | CCT | CCA | TCA | TCT | GCT | ATA | GAC | ATA | GAT | 762 |
| Pro | Ser | Ser | Arg | Lys | Ser | Thr | Pro | Pro | Ser | Ser | Ala | Ile | Asp | Ile | Asp | |
| 165 | | | | 170 | | | | | 175 | | | | | | 180 | |
| GCT | ACT | GGC | TTA | GAT | GCA | GAA | GAA | AAT | GAT | ATT | CCA | GCA | AAC | CAC | CGC | 810 |
| Ala | Thr | Gly | Leu | Asp | Ala | Glu | Glu | Asn | Asp | Ile | Pro | Ala | Asn | His | Arg | |
| | | | | 185 | | | | | 190 | | | | | 195 | | |
| TCC | CCT | AAA | CCC | AGT | GCA | AAC | AGT | GTA | ACG | TCA | CCC | CAC | TCC | AAA | GAG | 858 |
| Ser | Pro | Lys | Pro | Ser | Ala | Asn | Ser | Val | Thr | Ser | Pro | His | Ser | Lys | Glu | |
| | | | 200 | | | | | 205 | | | | | 210 | | | |
| AAA | AGA | ATG | CCC | TTC | TTT | AAG | AAG | ACA | GAG | CAC | ACT | CCT | CCG | TAT | GAT | 906 |
| Lys | Arg | Met | Pro | Phe | Phe | Lys | Lys | Thr | Glu | His | Thr | Pro | Pro | Tyr | Asp | |
| | | | 215 | | | | | 220 | | | | | 225 | | | |
| GTG | GTA | CCT | TCC | ATG | CGA | CCA | GTG | GTC | CTA | GTG | GGC | CCT | TCT | CTG | AAG | 954 |
| Val | Val | Pro | Ser | Met | Arg | Pro | Val | Val | Leu | Val | Gly | Pro | Ser | Leu | Lys | |
| | 230 | | | | | 235 | | | | | 240 | | | | | |
| GGC | TAC | GAG | GTC | ACA | GAT | ATG | ATG | CAA | AAA | GCG | CTG | TTT | GAT | TTT | TTA | 1002 |
| Gly | Tyr | Glu | Val | Thr | Asp | Met | Met | Gln | Lys | Ala | Leu | Phe | Asp | Phe | Leu | |
| 245 | | | | 250 | | | | | 255 | | | | | | 260 | |
| AAA | CAC | AGA | TTT | GAA | GGG | CGG | ATA | TCC | ATC | ACA | AGG | GTC | ACC | GCT | GAC | 1050 |
| Lys | His | Arg | Phe | Glu | Gly | Arg | Ile | Ser | Ile | Thr | Arg | Val | Thr | Ala | Asp | |
| | | | | 265 | | | | | 270 | | | | | 275 | | |
| ATC | TCG | CTT | GCC | AAA | CGC | TCG | GTA | TTA | AAC | AAT | CCC | AGT | AAG | CAC | GCA | 1098 |
| Ile | Ser | Leu | Ala | Lys | Arg | Ser | Val | Leu | Asn | Asn | Pro | Ser | Lys | His | Ala | |
| | | | 280 | | | | | 285 | | | | | 290 | | | |
| ATA | ATA | GAA | AGA | TCC | AAC | ACA | AGG | TCA | AGC | TTA | GCG | GAA | GTT | CAG | AGT | 1146 |
| Ile | Ile | Glu | Arg | Ser | Asn | Thr | Arg | Ser | Ser | Leu | Ala | Glu | Val | Gln | Ser | |
| | | | 295 | | | | | 300 | | | | | 305 | | | |
| GAA | ATC | GAA | AGG | ATT | TTT | GAA | CTT | GCA | AGA | ACA | TTG | CAG | TTG | GTG | GTC | 1194 |
| Glu | Ile | Glu | Arg | Ile | Phe | Glu | Leu | Ala | Arg | Thr | Leu | Gln | Leu | Val | Val | |
| | 310 | | | | | 315 | | | | | 320 | | | | | |
| CTT | GAC | GCG | GAT | ACA | ATT | AAT | CAT | CCA | GCT | CAA | CTC | AGT | AAA | ACC | TCC | 1242 |
| Leu | Asp | Ala | Asp | Thr | Ile | Asn | His | Pro | Ala | Gln | Leu | Ser | Lys | Thr | Ser | |
| 325 | | | | 330 | | | | | 335 | | | | | | 340 | |
| TTG | GCC | CCT | ATT | ATA | GTA | TAT | GTA | AAG | ATT | TCT | TCT | CCT | AAG | GTT | TTA | 1290 |
| Leu | Ala | Pro | Ile | Ile | Val | Tyr | Val | Lys | Ile | Ser | Ser | Pro | Lys | Val | Leu | |
| | | | | 345 | | | | | 350 | | | | | 355 | | |
| CAA | AGG | TTA | ATA | AAA | TCT | CGA | GGG | AAA | TCT | CAA | GCT | AAA | CAC | CTC | AAC | 1338 |
| Gln | Arg | Leu | Ile | Lys | Ser | Arg | Gly | Lys | Ser | Gln | Ala | Lys | His | Leu | Asn | |
| | | | 360 | | | | | 365 | | | | | 370 | | | |
| GTC | CAG | ATG | GTA | GCA | GCT | GAT | AAA | CTG | GCT | CAG | TGT | CCT | CCA | GAG | CTG | 1386 |
| Val | Gln | Met | Val | Ala | Ala | Asp | Lys | Leu | Ala | Gln | Cys | Pro | Pro | Glu | Leu | |
| | | 375 | | | | | 380 | | | | | 385 | | | | |
| TTC | GAT | GTG | ATC | TTG | GAT | GAG | AAC | CAG | CTT | GAG | GAT | GCC | TGT | GAG | CAC | 1434 |
| Phe | Asp | Val | Ile | Leu | Asp | Glu | Asn | Gln | Leu | Glu | Asp | Ala | Cys | Glu | His | |
| | | 390 | | | | | 395 | | | | | 400 | | | | |
| CTT | GCC | GAC | TAT | CTG | GAG | GCC | TAC | TGG | AAG | GCC | ACC | CAT | CCT | CCC | AGC | 1482 |
| Leu | Ala | Asp | Tyr | Leu | Glu | Ala | Tyr | Trp | Lys | Ala | Thr | His | Pro | Pro | Ser | |
| 405 | | | | 410 | | | | | 415 | | | | | | 420 | |
| AGT | AGC | CTC | CCC | AAC | CCT | CTC | CTT | AGC | CGT | ACA | TTA | GCC | ACT | TCA | AGT | 1530 |
| Ser | Ser | Leu | Pro | Asn | Pro | Leu | Leu | Ser | Arg | Thr | Leu | Ala | Thr | Ser | Ser | |
| | | | | 425 | | | | | 430 | | | | | 435 | | |
| CTG | CCT | CTT | AGC | CCC | ACC | CTA | GCC | TCT | AAT | TCA | CAG | GGT | TCT | CAA | GGT | 1578 |
| Leu | Pro | Leu | Ser | Pro | Thr | Leu | Ala | Ser | Asn | Ser | Gln | Gly | Ser | Gln | Gly | |
| | | | 440 | | | | | 445 | | | | | 450 | | | |
| GAT | CAG | AGG | ACT | GAT | CGC | TCC | GCT | CCT | ATC | CGT | TCT | GCT | TCC | CAA | GCT | 1626 |
| Asp | Gln | Arg | Thr | Asp | Arg | Ser | Ala | Pro | Ile | Arg | Ser | Ala | Ser | Gln | Ala | |
| | | 455 | | | | | 460 | | | | | 465 | | | | |
| GAA | GAA | GAA | CCT | AGT | GTG | GAA | CCA | GTC | AAG | AAA | TCC | CAG | CAC | CGC | TCT | 1674 |
| Glu | Glu | Glu | Pro | Ser | Val | Glu | Pro | Val | Lys | Lys | Ser | Gln | His | Arg | Ser | |
| | | 470 | | | | | 475 | | | | | 480 | | | | |

-continued

```
TCC TCC TCA GCC CCA CAC CAC AAC CAT CGC AGT GGG ACA AGT CGC GGC       1722
Ser Ser Ser Ala Pro His His Asn His Arg Ser Gly Thr Ser Arg Gly
485                 490                 495                 500

CTC TCC AGG CAA GAG ACA TTT GAC TCG GAA ACC CAG GAG AGT CGA GAC       1770
Leu Ser Arg Gln Glu Thr Phe Asp Ser Glu Thr Gln Glu Ser Arg Asp
                505                 510                 515

TCT GCC TAC GTA GAG CCA AAG GAA GAT TAT TCC CAT GAC CAC GTG GAC       1818
Ser Ala Tyr Val Glu Pro Lys Glu Asp Tyr Ser His Asp His Val Asp
            520                 525                 530

CAC TAT GCC TCA CAC CGT GAC CAC AAC CAC AGA GAC GAG ACC CAC GGG       1866
His Tyr Ala Ser His Arg Asp His Asn His Arg Asp Glu Thr His Gly
        535                 540                 545

AGC AGT GAC CAC AGA CAC AGG GAG TCC CGG CAC CGT TCC CGG GAC GTG       1914
Ser Ser Asp His Arg His Arg Glu Ser Arg His Arg Ser Arg Asp Val
    550                 555                 560

GAT CGA GAG CAG GAC CAC AAC GAG TGC AAC AAG CAG CGC AGC CGT CAT       1962
Asp Arg Glu Gln Asp His Asn Glu Cys Asn Lys Gln Arg Ser Arg His
565                 570                 575                 580

AAA TCC AAG GAT CGC TAC TGT GAA AAG GAT GGA GAA GTG ATA TCA AAA       2010
Lys Ser Lys Asp Arg Tyr Cys Glu Lys Asp Gly Glu Val Ile Ser Lys
                585                 590                 595

AAA CGG AAT GAG GCT GGG GAG TGG AAC AGG GAT GTT TAC ATC CCC CAA       2058
Lys Arg Asn Glu Ala Gly Glu Trp Asn Arg Asp Val Tyr Ile Pro Gln
            600                 605                 610

TGAGTTTTGC CCTTTTGTGT TTTTTTTTTT TTTTTTTTGA AGTCTTGTAT AACTAACAGC     2118

ATCCCCAAAA CAAAAAGTCT TTGGGGTCTA CACTGCAATC ATATGTGATC TGTCTTGTAA     2178

TATTTTGTAT TATTGCTGTT GCTTGAATAG CAATAGCATG GATAGAGTAT TGAGATACTT     2238

TTTCTTTTGT AAGTGCTACA TAAATTGGCC TGGTATGGCT GCAGTCCTCC GGTTGCATAC     2298

TGGACTCTTC AAAAACTGTT TTGGGTAGCT GCCACTTGAA CAAAATCTGT TGCCACCCAG     2358

GTGATGTTAG TGTTTTAAGA AATGTAGTTG ATGTATCCAA CAAGCCAGAA TCAGCACAGA     2418

TAAAAAGTGG AATTTCTTGT TTCTCCAGAT TTTTAATACG TTAATACGCA GGCATCTGAT     2478

TTGCATATTC ATTCATGGAC CACTGTTTCT TGCTTGTACC TCTGGCTGAC TAAATTTGGG     2538

GACAGATTCA GTCTTGCCTT ACACAAAGGG GATCATAAAG TTAGAATCTA TTTTCTATGT     2598

ACTAGTACTG TGTACTGTAT AGACAGTTTG TAAATGTTAT TTCTGCAAAC AAACACCTCC     2658

TTATTATATA TAATATATAT ATATATATCA GTTTGATCAC ACTATTTTAG AGTC           2712
```

RECOMBINANT HUMAN CALCIUM CHANNEL $\beta_4$ SUBUNITS

This is a continuation of application Ser. No. 08/290,012, filed Aug. 11, 1994, now abandoned, which is a continuation-in-part of U.S. application Ser. No. 08/149,097, filed Nov. 5, 1993, now U.S. Pat. No. 5,874,236 and a continuation-in-part of U.S. application Ser. No. 08/105,536, filed Aug. 11, 1993 and now abandoned. U.S. application Ser. No. 08/149,097 is a continuation-in-part of U.S. application Ser. No. 08/105,536.

This application is also related to U.S. application Ser No. 08/193,078, now U.S. Pat. No. 5,846,757, which is the U.S. National Stage of International PCT Application Serial No. PCT/US92/06903, filed Aug. 14, 1992. That application is a continuation-in-part of U.S. application Ser. No. 07/868,354, filed Apr. 10, 1992, now abandoned, and is a continuation-in-part of U.S. application Ser. No. 07/745,206, filed Aug. 15, 1991, now U.S. Pat. No. 5,429,921. U.S. application Ser. No. 07/868,354 is also a continuation-in-part of U.S. application Ser. No. 07/745,206, which is a continuation-in-part of U.S. application Ser. No. 07/620,250, filed Nov. 30, 1990, now abandoned, which is a continuation-in-part of U.S. application Ser. No. 07/176,899, filed Apr. 4, 1988, now abandoned, and is also a continuation-in-part of U.S. application Ser. No. 07/482,384, filed Feb. 20, 1990, now U.S. Pat. No. 5,386,025. This application is also related to U.S. application Ser. No. 07/914,231, filed Jul. 13, 1992, now U.S. Pat. No. 5,407,820 which in turn is a continuation of U.S. application Ser. No. 07/603,751, filed Nov. 8, 1990, now abandoned, which is the U.S. National Stage of International Application Serial No. PCT/US89/01408, which is a continuation-in-part of U.S. application Ser. No. 07/176,899.

The subject matter of each of U.S. Pat. Nos. 5,846,757, 5,874,236, 5,407,820, 5,429,921, and 5,386,025, and U.S. application Ser. Nos. 08/105,536, 07/868,354, 07/620,250, 07/603,751, and 07/176,899 is, to the extent permitted, incorporated herein in its entirety.

TECHNICAL FIELD

The present invention relates to molecular biology and pharmacology. More particularly, the invention relates to calcium channel compositions and methods of making and using the same.

BACKGROUND OF THE INVENTION

Calcium channels are membrane-spanning, multi-subunit proteins that allow controlled entry of $Ca^{2+}$ ions into cells from the extracellular fluid. Cells throughout the animal kingdom, and at least some bacterial, fungal and plant cells, possess one or more types of calcium channel.

The most common type of calcium channel is voltage dependent. "Opening" of a voltage-dependent channel to allow an influx of $Ca^{2+}$ ions into the cells requires a depolarization to a certain level of the potential difference between the inside of the cell bearing the channel and the extracellular medium bathing the cell. The rate of influx of $Ca^{2+}$ into the cell depends on this potential difference. All "excitable" cells in animals, such as neurons of the central nervous system (CNS), peripheral nerve cells and muscle cells, including those of skeletal muscles, cardiac muscles, and venous and arterial smooth muscles, have voltage-dependent calcium channels.

Multiple types of calcium channels have been identified in mammalian cells from various tissues, including skeletal muscle, cardiac muscle, lung, smooth muscle and brain, [see, e.g., Bean, B. P. (1989) *Ann. Rev. Physiol.* 51:367–384 and Hess, P. (1990) *Ann. Rev. Neurosci.* 56:337]. The different types of calcium channels have been broadly categorized into four classes, L-, T-, N-, and P-type, distinguished by current kinetics, holding potential sensitivity and sensitivity to calcium channel agonists and antagonists.

Calcium channels are multisubunit proteins that contain two large subunits, designated $a_1$ and $\alpha_2$ which have molecular weights between about 130 and about 200 kilodaltons ("kD"), and one to three different smaller subunits of less than about 60 kD in molecular weight. At least one of the larger subunits and possibly some of the smaller subunits are glycosylated. Some of the subunits are capable of being phosphorylated. The $\alpha_1$ subunit has a molecular weight of about 150 to about 170 kD when analyzed by sodium dodecylsulfate (SDS)-polyacrylamide gel electrophoresis (PAGE) after isolation from mammalian muscle tissue and has specific binding sites for various 1,4-dihydropyridines (DHPs) and phenylalkylamines. Under non-reducing conditions (in the presence of N-ethylmaleimide), the $\alpha_2$ subunit migrates in SDS-PAGE as a band corresponding to a molecular weight of about 160–190 kD. Upon reduction, a large fragment and smaller fragments are released. The $\beta$ subunit of the rabbit skeletal muscle calcium channel is a phosphorylated protein that has a molecular weight of 52–65 kD as determined by SDS-PAGE analysis. This subunit is insensitive to reducing conditions. The $\gamma$ subunit of the calcium channel, which is not observed in all purified preparations, appears to be a glycoprotein with an apparent molecular weight of 30–33 kD, as determined by SDS-PAGE analysis.

In order to study calcium channel structure and function, large amounts of pure channel protein are needed. Because of the complex nature of these multisubunit proteins, the varying concentrations of calcium channels in tissue sources of the protein, the presence of mixed populations of calcium channels in tissues, difficulties in obtaining tissues of interest, and the modifications of the native protein that can occur during the isolation procedure, it is extremely difficult to obtain large amounts of highly purified, completely intact calcium channel protein.

Characterization of a particular type of calcium channel by analysis of whole cells is severely restricted by the presence of mixed populations of different types of calcium channels in the majority of cells. Single-channel recording methods that are used to examine individual calcium channels do not reveal any information regarding the molecular structure or biochemical composition of the channel. Furthermore, in performing this type of analysis, the channel is isolated from other cellular constituents that might be important for natural functions and pharmacological interactions.

Characterization of the gene or genes encoding calcium channels provides another means of characterization of different types of calcium channels. The amino acid sequence determined from a complete nucleotide sequence of the coding region of a gene encoding a calcium channel protein represents the primary structure of the protein. Furthermore, secondary structure of the calcium channel protein and the relationship of the protein to the membrane may be predicted based on analysis of the primary structure. For instance, hydropathy plots of the $\alpha_1$ subunit protein of the rabbit skeletal muscle calcium channel indicate that it contains four internal repeats, each containing six putative transmembrane regions [Tanabe, T. et al. (1987) *Nature* 328:313].

Because calcium channels are present in various tissues and have a central role in regulating intracellular calcium ion concentrations, they are implicated in a number of vital processes in animals, including neurotransmitter release, muscle contraction, pacemaker activity, and secretion of hormones and other substances. These processes appear to be involved in numerous human disorders, such as CNS and cardiovascular diseases. Calcium channels, thus, are also implicated in numerous disorders. A number of compounds useful for treating various cardiovascular diseases in animals, including humans, are thought to exert their beneficial effects by modulating functions of voltage-dependent calcium channels present in cardiac and/or vascular smooth muscle. Many of these compounds bind to calcium channels and block, or reduce the rate of, influx of $Ca^{2+}$ into the cells in response to depolarization of the cell membrane.

The results of studies of recombinant expression of rabbit calcium channel $\alpha_1$ subunit-encoding cDNA clones and transcripts of the cDNA clones indicate that the $\alpha_1$ subunit forms the pore through which calcium enters cells. The relevance of the barium currents generated in these recombinant cells to the actual current generated by calcium channels containing as one component the respective $\alpha_1$ subunits in vivo is unclear. In order to completely and accurately characterize and evaluate different calcium channel types, however, it is essential to examine the functional properties of recombinant channels containing all of the subunits as found in vivo.

In order to conduct this examination and to fully understand calcium channel structure and function, it is critical to identify and characterize as many calcium channel subunits as possible. Also in order to prepare recombinant cells for use in identifying compounds that interact with calcium channels, it is necessary to be able to produce cells that express uniform populations of calcium channels containing defined subunits.

An understanding of the pharmacology of compounds that interact with calcium channels in other organ systems, such as the CNS, may aid in the rational design of compounds that specifically interact with subtypes of human calcium channels to have desired therapeutic effects, such as in the treatment of neurodegenerative and cardiovascular disorders. Such understanding and the ability to rationally design therapeutically effective compounds, however, have been hampered by an inability to independently determine the types of human calcium channels and the molecular nature of individual subtypes, particularly in the CNS, and by the unavailability of pure preparations of specific channel subtypes to use for evaluation of the specificity of calcium channel-effecting compounds. Thus, identification of DNA encoding human calcium channel subunits and the use of such DNA for expression of calcium channel subunits and functional calcium channels would aid in screening and designing therapeutically effective compounds.

Therefore, it is an object herein, to provide DNA encoding specific calcium channel subunits and to provide eukaryotic cells bearing recombinant tissue-specific or subtype- specific calcium channels. It is also an object to provide assays for identification of potentially therapeutic compounds that act as calcium channel antagonists and agonists.

SUMMARY OF THE INVENTION

Isolated and purified nucleic acid fragments that encode human calcium channel subunits are provided. DNA encoding $\alpha_1$ subunits of a human calcium channel, and RNA, encoding such subunits, made upon transcription of such DNA are provided. In particular, DNA fragments encoding $\alpha_1$ subunits of voltage-dependent human calcium channels (VDCCs) type A, type B (also referred to as VDCC IV), type C (also referred to as VDCC II) type D (also referred to as VDCC III) and type E are provided.

DNA encoding $\alpha_{1A}$, $\alpha_{1B}$, $\alpha_{1C}$, $\alpha_{1D}$ and $\alpha_{1E}$ subunits is provided. DNA encoding an $\alpha_{1D}$ subunit that includes the amino acids substantially as set forth as residues 10–2161 of SEQ ID No. 1 is provided. DNA encoding an $\alpha_{1D}$ subunit that includes substantially the amino acids set forth as amino acids 1–34 in SEQ ID No. 2 in place of amino acids 373–406 of SEQ ID No. 1 is also provided. DNA encoding an $\alpha_{1C}$ subunit that includes the amino acids substantially as set forth in SEQ ID No. 3 or SEQ ID No. 6 and DNA encoding an $\alpha_{1B}$ subunit that includes an amino acid sequence substantially as set forth in SEQ ID No. 7 or in SEQ ID No. 8 is also provided.

DNA encoding $\alpha_{1A}$ subunits is also provided. Such DNA includes DNA encoding an $\alpha_{1A}$ subunit that has substantially the same sequence of amino acids as encoded by the DNA set forth in SEQ ID No. 22 or No. 23 or other splice variants of $\alpha_{1A}$ that include all or part of the sequence set forth in SEQ ID No. 22 or 23. The sequence set forth in SEQ ID NO. 22 is a splice variant designated $\alpha_{1A-1}$; and the sequence set forth in SEQ ID NO. 23 is a splice variant designated $\alpha_{1A-2}$. DNA encoding $\alpha_{1A}$ subunits also include DNA encoding subunits that can be isolated using all or a portion of the DNA having SEQ ID NO. 21, 22 or 23 or DNA obtained from the phage lysate of an *E. coli* host containing DNA encoding an $\alpha_{1A}$ subunit that has been deposited in the American Type Culture Collection, 12301 Parklawn Drive, Rockville, Md. 20852 U.S.A. under Accession No. 75293 in accord with the Budapest Treaty. The DNA in such phage includes a DNA fragment having the sequence set forth in SEQ ID No. 21. This fragment selectively hybridizes under conditions of high stringency to DNA encoding $\alpha_{1A}$ but not to DNA encoding $\alpha_{1B}$ and, thus, can be used to isolate DNA that encodes $\alpha_{1A}$ subunits.

DNA encoding $\alpha_{1E}$ subunits of a human calcium channel is also provided. This DNA includes DNA that encodes an $\alpha_{1E}$ splice variant designated $\alpha_{1E-1}$ encoded by the DNA set forth in SEQ ID No. 24, and a variant designated $\alpha_{1E-3}$ encoded by SEQ ID No. 25. This DNA also includes other splice variants thereof that encodes sequences of amino acids encoded by all or a portion of the sequences of nucleotides set forth in SEQ ID Nos. 24 and 25 and DNA that hybridizes under conditions of high stringency to the DNA of SEQ ID. No. 24 or 25 and that encodes an $\alpha_{1E}$ splice variant.

DNA encoding $\alpha_2$ subunits of a human calcium channel, and RNA encoding such subunits, made upon transcription of such a DNA are provided. DNA encoding splice variants of the $\alpha_2$ subunit, including tissue-specific splice variants, are also provided. In particular, DNA encoding the $\alpha_{2a}$–$\alpha_{2e}$ subunit subtypes is provided. In particularly preferred embodiments, the DNA encoding the $\alpha_2$ subunit that is produced by alternative processing of a primary transcript that includes DNA encoding the amino acids set forth in SEQ ID 11 and the DNA of SEQ ID No. 13 inserted between nucleotides 1624 and 1625 of SEQ ID No. 11 is provided. The DNA and amino acid sequences of $\alpha_{2a}$–$\alpha_{2e}$ are set forth in SEQ. ID Nos. 11($\alpha_{2b}$), 29($\alpha_{2a}$) and 30–32 ($\alpha_{2c}$–$\alpha_{2e}$), respectively.

Isolated and purified DNA fragments encoding human calcium channel $\beta$ subunits, including DNA encoding $\beta_1$, $\beta_2$, $\beta_3$ and $\beta_4$ subunits, and splice variants of the $\beta$ subunits are provided. RNA encoding β subunits, made upon transcription of the DNA is also provided.

DNA encoding a $\beta_1$ subunit that is produced by alternative processing of a primary transcript that includes DNA encoding the amino acids set forth in SEQ ID No. 9, but including the DNA set forth in SEQ ID No. 12 inserted in place of nucleotides 615–781 of SEQ ID No. 9 is also provided. DNA encoding $\beta_1$ subunits that are encoded by transcripts that have the sequence set forth in SEQ ID No. 9 including the DNA set forth in SEQ ID No. 12 inserted in place of nucleotides 615–781 of SEQ ID No. 9, but that lack one or more of the following sequences of nucleotides: nucleotides 14–34 of SEQ ID No. 12, nucleotides 13–34 of SEQ ID No. 12, nucleotides 35–55 of SEQ ID No 12, nucleotides 56–190 of SEQ ID No. 12 and nucleotides 191–271 of SEQ ID No. 12 are also provided. In particular, $\beta_1$ subunit splice variants $\beta_{1-1}$–$\beta_{1-5}$ (see, SEQ ID Nos. 9, 10 and 33–35) described below, are provided.

$\beta_2$ subunit splice variants $\beta_{2c}$–$\beta_{2e}$, that include all or a portion of SEQ ID Nos. 26, 37 and 38 are provided; $\beta_3$ subunit splice variants, including $\beta_3$ subunit splice variants that have the sequences set forth in SEQ ID Nos 19 and 20, and DNA encoding the $\beta_4$ subunit that includes DNA having the sequence set forth in SEQ ID No. 27 and the amino acid sequence set forth in SEQ ID No. 28 are provided.

Also *Escherichia coli* (*E. coli*) host cells harboring plasmids containing DNA encoding $\beta_3$ have been deposited in accord with the Budapest Treaty under Accession No. 69048 at the American Type Culture Collection. The deposited clone encompasses nucleotides 122–457 in SEQ ID No. 19 and 107–443 in SEQ ID No. 20.

DNA encoding β subunits that are produced by alternative processing of a primary transcript encoding a β subunit, including a transcript that includes DNA including a primary transcript that encodes $\beta_3$ as deposited including a primary transcript that encodes $\beta_3$ as deposited alternative exons are provided or may be constructed from the DNA provided herein.

DNA encoding γ subunits of human calcium channels is DNA encoding γ subunits of human calcium channels is also provided. RNA, encoding γ subunits, made upon DNA containing the sequence of nucleotides set forth in SEQ ID No. 14 is provided.

Full-length DNA clones and corresponding RNA transcripts, encoding $\alpha_1$, including splice variants of $\alpha_{1D}$, transcripts, encoding $\alpha_1$, including splice variants of $\alpha_{1A}$, $\alpha_{1D}$, $\alpha_{1B}$, $\alpha_{1C}$, and $\alpha_{1E}$, $\alpha_2$ and β subunits, including $\beta_{1-1}$–$\beta_{1-5}$, $\beta_{2C}$, $\beta_{2D}$, $\beta_{2E}$, $\beta_{3-1}$ and $\beta_4$ of human calcium channels are provided. Also provided are DNA clones encoding substantial portions of the certain $\alpha_{1C}$ subtype subunits and γ subunits of voltage-dependent human calcium channels for the preparation of full-length DNA clones encoding the corresponding full-length subunits. Full-length clones may be readily obtained using the disclosed DNA as a probe as described herein.

The $\alpha_{1A}$ subunit, $\alpha_{1C}$ subunit, $\alpha_{1E}$ subunit and splice variants thereof, the $\beta_{2D}$, $\beta_{2C}$ and $\beta_{2E}$ subunits and $\beta_4$ subunits and nucleic acids encoding these subunits are of particular interest herein.

Eukaryotic cells containing heterologous DNA encoding one or more calcium channel subunits, particularly human calcium channel subunits, or containing RNA transcripts of DNA clones encoding one or more of the subunits are provided. A single $\alpha_1$ subunit can form a channel. The requisite combination of subunits for formation of active channels in selected cells, however, can be determined empirically using the methods herein. For example, if a selected $\alpha_1$ subtype or variant does not form an active channel in a selected cell line, an additional subunit or subunits can be added until an active channel is formed.

In preferred embodiments, the cells contain DNA or RNA encoding a human $\alpha_1$ subunit, preferably at least an $\alpha_{1D}$, $\alpha_{1B}$, $\alpha_{1A}$ or $\alpha_{1E}$ subunit. In more preferred embodiments, the cells contain DNA or RNA encoding additional heterologous subunits, including at least one β, $\alpha_2$ or γ subunit. In such embodiments, eukaryotic cells stably or transiently transfected with any combination of one, two, three or four of the subunit-encoding DNA clones, such as DNA encoding any of $\alpha_1$, $\alpha_1$+β, $\alpha_1$+β+$\alpha_2$, are provided.

The eukaryotic cells provided herein contain heterologous DNA that encodes an $\alpha_1$ subunit or heterologous DNA that encodes an $\alpha_1$ subunit and heterologous DNA that encodes a β subunit. At least one subunit selected is $\alpha_{1A-1}$, $\alpha_{1A-2}$, $\alpha_{1c-2}$, $\alpha_{1E-1}$, $\alpha_{1E-3}$, $\beta_{2C}$, $\beta_{2D}$, $\beta_{2F}$, a $\beta_{3-1}$, $\beta_{3-2}$ subunit or a $\beta_4$ subunit. In preferred embodiments, the cells express such heterologous calcium channel subunits and include one or more of the subunits in membrane-spanning heterologous calcium channels. In more preferred embodiments, the eukaryotic cells express functional, heterologous calcium channels that are capable of gating the passage of calcium channel-selective ions and/or binding compounds that, at physiological concentrations, modulate the activity of the heterologous calcium channel. In certain embodiments, the heterologous calcium channels include at least one heterologous calcium channel subunit. In most preferred embodiments, the calcium channels that are expressed on the surface of the eukaryotic cells are composed substantially or entirely of subunits encoded by the heterologous DNA or RNA. In preferred embodiments, the heterologous calcium channels of such cells are distinguishable from any endogenous calcium channels of the host cell. Such cells provide a means to obtain homogeneous populations of calcium channels. Typically, the cells contain the selected calcium channel as the only heterologous ion channel expressed by the cell.

In certain embodiments the recombinant eukaryotic cells that contain the heterologous DNA encoding the calcium channel subunits are produced by transfection with DNA encoding one or more of the subunits or are injected with RNA transcripts of DNA encoding one or more of the calcium channel subunits. The DNA may be introduced as a linear DNA fragment or may be included in an expression vector for stable or transient expression of the subunit-encoding DNA. Vectors containing DNA encoding human calcium channel subunits are also provided.

The eukaryotic cells that express heterologous calcium channels may be used in assays for calcium channel function or, in the case of cells transformed with fewer subunit-encoding nucleic acids than necessary to constitute a functional recombinant human calcium channel, such cells may be used to assess the effects of additional subunits on calcium channel activity. The additional subunits can be provided by subsequently transfecting such a cell with one or more DNA clones or RNA transcripts encoding human calcium channel subunits.

The recombinant eukaryotic cells that express membrane spanning heterologous calcium channels may be used in methods for identifying compounds that modulate calcium channel activity. In particular, the cells are used in assays that identify agonists and antagonists of calcium channel activity in humans and/or assessing the contribution of the various calcium channel subunits to the transport and regulation of transport of calcium ions. Because the cells constitute homogeneous populations of calcium channels, they provide a means to identify agonists or antagonists of calcium channel activity that are specific for each such population.

The assays that use the eukaryotic cells for identifying compounds that modulate calcium channel activity are also provided. In practicing these assays the eukaryotic cell that expresses a heterologous calcium channel, containing at least one subunit encoded by the DNA provided herein, is in a solution containing a test compound and a calcium channel selective ion, the cell membrane is depolarized, and current flowing into the cell is detected. If the test compound is one that modulates calcium channel activity, the current that is detected is different from that produced by depolarizing the same or a substantially identical cell in the presence of the same calcium channel-selective ion but in the absence of the compound. In preferred embodiments, prior to the depolarization step, the cell is maintained at a holding potential which substantially inactivates calcium channels which are endogenous to the cell. Also in preferred embodiments, the cells are mammalian cells, most preferably HEK cells, or amphibian oöcytes.

Nucleic acid probes, typically labeled for detection, containing at least about 14, preferably 16, or, if desired, 20 or 30 or more, contiguous nucleotides of $\alpha_{1D}$, $\alpha_{1C}$, $\alpha_{1B}$, $\alpha_{1A}$ and $\alpha_{1E}$, $\alpha_2$, $\beta$, including $\beta_1$, $\beta_2$, $\beta_3$ and $\beta_4$ splice variants and $\gamma$ subunit-encoding DNA are provided. Methods using the probes for the isolation and cloning of calcium channel subunit-encoding DNA, including splice variants within tissues and inter-tissue variants are also provided.

Purified human calcium channel subunits and purified human calcium channels are provided. The subunits and channels can be isolated from a eukaryotic cell transfected with DNA that encodes the subunit.

In another embodiment, immunoglobulins or antibodies obtained from the serum of an animal immunized with a substantially pure preparation of a human calcium channel, human calcium channel subunit or epitope-containing fragment of a human calcium subunit are provided. Monoclonal antibodies produced using a human calcium channel, human calcium channel subunit or epitope-containing fragment thereof as an immunogen are also provided. E. coli fusion proteins including a fragment of a human calcium channel subunit may also be used as immunogen. Such fusion proteins may contain a bacterial protein or portion thereof, such as the E. coli TrpE protein, fused to a calcium channel subunit peptide. The immunoglobulins that are produced using the calcium channel subunits or purified calcium channels as immunogens have, among other properties, the ability to specifically and preferentially bind to and/or cause the immunoprecipitation of a human calcium channel or a subunit thereof which may be present in a biological sample or a solution derived from such a biological sample. Such antibodies may also be used to selectively isolate cells that express calcium channels that contain the subunit for which the antibodies are specific.

Methods for modulating the activity of ion channels by contacting the calcium channels with an effective amount of the above-described antibodies are also provided.

A diagnostic method for determining the presence of Lambert Eaton Syndrome (LES) in a human based on immunological reactivity of LES immunoglobulin G (IgG) with a human calcium channel subunit or a eukaryotic cell which expresses a recombinant human calcium channel or a subunit thereof is also provided. In particular, an immunoassay method for diagnosing Lambert-Eaton Syndrome in a person by combining serum or an IgG fraction from the person (test serum) with calcium channel proteins, including the $\alpha$ and $\beta$ subunits, and ascertaining whether antibodies in the test serum react with one or more of the subunits, or a recombinant cell which expresses one or more of the subunits to a greater extent than antibodies in control serum, obtained from a person or group of persons known to be free of the Syndrome, is provided. Any immunoassay procedure known in the art for detecting antibodies against a given antigen in serum can be employed in the method.

DETAILED DESCRIPTION OF THE INVENTION

Definitions

Unless defined otherwise, all technical and scientific terms used herein have the same meaning as is commonly understood by one of skill in the art to which this invention belongs. All patents and publications referred to herein are incorporated by reference herein.

Reference to each of the calcium channel subunits includes the subunits that are specifically disclosed herein and human calcium channel subunits encoded by DNA that can be isolated by using the DNA disclosed as probes and screening an appropriate human cDNA or genomic library under at least low stringency. Such DNA also includes DNA that encodes proteins that have about 40% homology to any of the subunits proteins described herein or DNA that hybridizes under conditions of at least low stringency to the DNA provided herein and the protein encoded by such DNA exhibits additional identifying characteristics, such as function or molecular weight.

It is understood that subunits that are encoded by transcripts that represent splice variants of the disclosed subunits or other such subunits may exhibit less than 40% overall homology to any single subunit, but will include regions of such homology to one or more such subunits. It is also understood that 40% homology refers to proteins that share approximately 40% of their amino acids in common or that share somewhat less, but include conservative amino acid substitutions, whereby the activity of the protein is not substantially altered.

As used herein, the $\alpha_1$ subunits types, encoded by different genes, are designated as type $\alpha_{1A}$, $\alpha_{1B}$, $\alpha_{1C}$, $\alpha_{1D}$ and $\alpha_{1E}$. These types have also been referred to as VDCC IV for $\alpha_{1B}$, VDCC II for $\alpha_{1C}$ and VDCC III for $\alpha_{1D}$. Subunit subtypes, which are splice variants, are referred to, for example as $\alpha_{1B-1}$, $\alpha_{1B-2}$, $\alpha_{1C-1}$ etc.

Thus, as used herein, DNA encoding the $\alpha_1$ subunit refers to DNA that hybridizes to the DNA provided herein under conditions of at least low stringency or encodes a subunit that has at least about 40% homology to protein encoded by DNA disclosed herein that encodes an $\alpha_1$ subunit of a human calcium channel. An $\alpha_1$ subunit may be identified by its ability to form a calcium channel. Typically, $\alpha_1$ subunits have molecular masses greater than at least about 120 kD. Also, hydropathy plots of deduced $\alpha_1$ subunit amino acid sequences indicate that the $\alpha_1$ subunits contain four internal repeats, each containing six putative transmembrane domains.

The activity of a calcium channel may be assessed in vitro by methods known to those of skill in the art, including the electrophysiological and other methods described herein. Typically, $\alpha_1$ subunits include regions to which one or more modulators of calcium channel activity, such as a 1,4-DHP or $\omega$-CgTx, interact directly or indirectly. Types of $\alpha_1$ subunits may be distinguished by any method known to those of skill in the art, including on the basis of binding specificity. For example, it has been found herein that $\alpha_{1B}$ subunits participate in the formation of channels that have previously been referred to as N-type channels, $\alpha_{1D}$ subunits participate in the formation of channels that had previously been referred to as L-type channels, and $\alpha_{1A}$ subunits appear to participate in the formation of channels that exhibit characteristics typical of channels that had previously been designated P-type channels. Thus, for example, the activity of channels that contain the $\alpha_{1B}$ subunit are insensitive to 1,4-DHPs; whereas the activity of channels that contain the $\alpha_{1D}$ subunit are modulated or altered by a 1,4-DHP. It is presently preferable to refer to calcium channels based on pharmacological characteristics and current kinetics and to avoid historical designations. Types and subtypes of $\alpha_1$ subunits may be characterized on the basis of the effects of such modulators on the subunit or a channel containing the subunit as well as differences in currents and current kinetics produced by calcium channels containing the subunit.

As used herein, an $\alpha_2$ subunit is encoded by DNA that hybridizes to the DNA provided herein under conditions of low stringency or encodes a protein that has at least about 40% homology with that disclosed herein. Such DNA encodes a protein that typically has a molecular mass greater than about 120 kD, but does not form a calcium channel in the absence of an $\alpha_1$ subunit, and may alter the activity of a calcium channel that contains an $\alpha_1$ subunit. Subtypes of the $\alpha_2$ subunit that arise as splice variants are designated by lower case letter, such as $\alpha_{2a}, \ldots \alpha_{2e}$. In addition, the $\alpha_2$ subunit and the large fragment produced when the protein is subjected to reducing conditions appear to be glycosylated with at least N-linked sugars and do not specifically bind to the 1,4-DHPs and phenylalkylamines that specifically bind to the $\alpha_1$ subunit. The smaller fragment, the C-terminal fragment, is referred to as the δ subunit and includes amino acids from about 946 (SEQ ID No. 11) through about the C-terminus. This fragment may dissociate from the remaining portion of $\alpha_2$ when the $\alpha_2$ subunit is exposed to reducing conditions.

As used herein, a β subunit is encoded by DNA that hybridizes to the DNA provided herein under conditions of low stringency or encodes a protein that has at least about 40% homology with that disclosed herein and is a protein that typically has a molecular mass lower than the α subunits and on the order of about 50–80 kD, does not form a detectable calcium channel in the absence of an $\alpha_1$ subunit, but may alter the activity of a calcium channel that contains an $\alpha_1$ subunit or that contains an $\alpha_1$ and $\alpha_2$ subunit.

Types of the β subunit that are encoded by different genes are designated with subscripts, such as $\beta_1, \beta_2, \beta_3$ and $\beta_4$. Subtypes of β subunits that arise as splice variants of a particular type are designated with a numerical subscript referring to the type and to the variant. Such subtypes include, but are not limited to the $\beta_1$ splice variants, including $\beta_{1-1}$–$\beta_{1-5}$ and $\beta_2$ variants, including $\beta_{2C}$–$\beta_{2E}$.

As used herein, a γ subunit is a subunit encoded by DNA disclosed herein as encoding the γ subunit and may be isolated and identified using the DNA disclosed herein as a probe by hybridization or other such method known to those of skill in the art, whereby full-length clones encoding a γ subunit may be isolated or constructed. A γ subunit will be encoded by DNA that hybridizes to the DNA provided herein under conditions of low stringency or exhibits sufficient sequence homology to encode a protein that has at least about 40% homology with the γ subunit described herein.

Thus, one of skill in the art, in light of the disclosure herein, can identify DNA encoding $\alpha_1, \alpha_2, \beta, \delta$ and γ calcium channel subunits, including types encoded by different genes and subtypes that represent splice variants. For example, DNA probes based on the DNA disclosed herein may be used to screen an appropriate library, including a genomic or cDNA library, for hybridization to the probe and obtain DNA in one or more clones that includes an open reading fragment that encodes an entire protein. Subsequent to screening an appropriate library with the DNA disclosed herein, the isolated DNA can be examined for the presence of an open reading frame from which the sequence of the encoded protein may be deduced. Determination of the molecular weight and comparison with the sequences herein should reveal the identity of the subunit as an $\alpha_1, \alpha_2$ etc. subunit. Functional assays may, if necessary, be used to determine whether the subunit is an $\alpha_1, \alpha_2$ subunit or β subunit.

For example, DNA encoding an $\alpha_{1A}$ subunit may be isolated by screening an appropriate library with DNA, encoding all or a portion of the human $\alpha_{1A}$ subunit. Such DNA includes the DNA in the phage deposited under ATCC Accession No. 75293 that encodes a portion of an $\alpha_1$ subunit. DNA encoding an $\alpha_{1A}$ subunit may be obtained from an appropriate library by screening with an oligonucleotide having all or a portion of the sequence set forth in SEQ ID No. 21, 22 and/or 23 or with the DNA in the deposited phage. Alternatively, such DNA may have a sequence that encodes an $\alpha_{1A}$ subunit that is encoded by SEQ ID NO. 22 or 23.

Similarly, DNA encoding $\beta_3$ may be isolated by screening a human cDNA library with DNA probes prepared from the plasmid β1.42 deposited under ATCC Accession No. 69048 or may be obtained from an appropriate library using probes having sequences prepared according to the sequences set forth in SEQ ID Nos. 19 and/or 20. Also, DNA encoding $\beta_4$ may be isolated by screening a human cDNA library with DNA probes prepared according to DNA set forth in SEQ ID No. 27, which sets forth the DNA sequence of a clone encoding a $\beta_4$ subunit. The amino acid sequence is set forth in SEQ ID No. 28. Any method known to those of skill in the art for isolation and identification of DNA and preparation of full-length genomic or cDNA clones, including methods exemplified herein, may be used.

The subunit encoded by isolated DNA may be identified by comparison with the DNA and amino acid sequences of the subunits provided herein. Splice variants share extensive regions of homology, but include non-homologous regions, subunits encoded by different genes share a uniform distribution of non-homologous sequences.

As used herein, a splice variant refers to a variant produced by differential processing of a primary transcript of genomic DNA that results in more than one type of mRNA. Splice variants may occur within a single tissue type or among tissues (tissue-specific variants). Thus, cDNA clones that encode calcium channel subunit subtypes that have regions of identical amino acids and regions of different amino acid sequences are referred to herein as "splice variants".

As used herein, a "calcium channel-selective ion" is an ion that is capable of flowing through, or being blocked from flowing through, a calcium channel which spans a cellular membrane under conditions which would substantially similarly permit or block the flow of $Ca^{2+}$. $Ba^{2+}$ is an example of an ion which is a calcium channel-selective ion.

As used herein, a compound that modulates calcium channel activity is one that affects the ability of the calcium channel to pass calcium channel-selective ions or affects other detectable calcium channel features, such as current kinetics. Such compounds include calcium channel antagonists and agonists and compounds that exert their effect on the activity of the calcium channel directly or indirectly.

As used herein, a "substantially pure" subunit or protein is a subunit or protein that is sufficiently free of other polypeptide contaminants to appear homogeneous by SDS-PAGE or to be unambiguously sequenced.

As used herein, selectively hybridize means that a DNA fragment hybridizes to a second fragment with sufficient specificity to permit the second fragment to be identified or isolated from among a plurality of fragments. In general, selective hybridization occurs at conditions of high stringency.

As used herein, heterologous or foreign DNA and RNA are used interchangeably and refer to DNA or RNA that does not occur naturally as part of the genome in which it is present or which is found in a location or locations in the genome that differ from that in which it occurs in nature. It is DNA or RNA that is not endogenous to the cell and has been artificially introduced into the cell. Examples of heterologous DNA include, but are not limited to, DNA that encodes a calcium channel subunit and DNA that encodes RNA or proteins that mediate or alter expression of endogenous DNA by affecting transcription, translation, or other regulatable biochemical processes. The cell that expresses the heterologous DNA, such as DNA encoding a calcium channel subunit, may contain DNA encoding the same or different calcium channel subunits. The heterologous DNA need not be expressed and may be introduced in a manner such that it is integrated into the host cell genome or is maintained episomally.

As used herein, operative linkage of heterologous DNA to regulatory and effector sequences of nucleotides, such as promoters, enhancers, transcriptional and translational stop sites, and other signal sequences, refers to the functional relationship between such DNA and such sequences of nucleotides. For example, operative linkage of heterologous DNA to a promoter refers to the physical and functional relationship between the DNA and the promoter such that the transcription of such DNA is initiated from the promoter by an RNA polymerase that specifically recognizes, binds to and transcribes the DNA in reading frame.

As used herein, isolated, substantially pure DNA refers to DNA fragments purified according to standard techniques employed by those skilled in the art [see, e.g., Maniatis et al. (1982) *Molecular Cloning: A Laboratory Manual*, Cold Spring Harbor Laboratory Press, Cold Spring Harbor, N.Y.].

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, vector or plasmid refers to discrete elements that are used to introduce heterologous DNA into cells for either expression of the heterologous DNA or for replication of the cloned heterologous DNA. Selection and use of such vectors and plasmids are well within the level of skill of the art.

As used herein, expression vector includes vectors capable of expressing DNA fragments that are in operative linkage with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or may integrate into the host cell genome.

As used herein, a promoter region refers to the portion of DNA of a gene that controls transcription of the DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated.

As used herein, a recombinant eukaryotic cell is a eukaryotic cell that contains heterologous DNA or RNA.

As used herein, a recombinant or heterologous calcium channel refers to a calcium channel that contains one or more subunits that are encoded by heterologous DNA that has been introduced into and expressed in a eukaryotic cell that expresses the recombinant calcium channel. A recombinant calcium channel may also include subunits that are produced by DNA endogenous to the cell. In certain embodiments, the recombinant or heterologous calcium channel may contain only subunits that are encoded by heterologous DNA.

As used herein, "functional" with respect to a recombinant or heterologous calcium channel means that the channel is able to provide for and regulate entry of calcium channel-selective ions, including, but not limited to, $Ca^{2+}$ or $Ba^{2+}$, in response to a stimulus and/or bind ligands with affinity for the channel. Preferably such calcium channel activity is distinguishable, such as by electrophysiological, pharmacological and other means known to those of skill in the art, from any endogenous calcium channel activity that is in the host cell.

As used herein, a peptide having an amino acid sequence substantially as set forth in a particular SEQ ID No. includes peptides that have the same function but may include minor variations in sequence, such as conservative amino acid changes or minor deletions or insertions that do not alter the activity of the peptide. The activity of a calcium channel receptor subunit peptide refers to its ability to form functional calcium channels with other such subunits.

As used herein, a physiological concentration of a compound is that which is necessary and sufficient for a biological process to occur. For example, a physiological concentration of a calcium channel-selective ion is a concentration of the calcium channel-selective ion necessary and sufficient to provide an inward current when the channel is open.

As used herein, activity of a calcium channel refers to the movement of a calcium channel-selective ion through a calcium channel. Such activity may be measured by any method known to those of skill in the art, including, but not limited to, measurement of the amount of current which flows through the recombinant channel in response to a stimulus.

As used herein, a "functional assay" refers to an assay that identifies functional calcium channels. A functional assay, thus, is an assay to assess function.

As understood by those skilled in the art, assay methods for identifying compounds, such as antagonists and agonists, that modulate calcium channel activity, generally require comparison to a control. One type of a "control" cell or "control" culture is a cell or culture that is treated substantially the same as the cell or culture exposed to the test compound except that the control culture is not exposed to the test compound. Another type of a "control" cell or "control" culture may be a cell or a culture of cells which are identical to the transfected cells except the cells employed for the control culture do not express functional calcium channels. In this situation, the response of the test cell to the test compound is compared to the response (or lack of response) of the calcium channel-negative cell to the test compound, when cells or cultures of each type of cell are exposed to substantially the same reaction conditions in the presence of the compound being assayed. For example, in methods that use patch clamp electrophysiological procedures, the same cell can be tested in the presence and absence of the test compound, by changing the external solution bathing the cell as known in the art.

It is also understood that each of the subunits disclosed herein may be modified by making conservative amino acid substitutions and the resulting modified subunits are contemplated herein. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Bejacmin/Cummings Pub. co., p.224). Such substitutions are preferably, although not exclusively, made in accordance with those set forth in TABLE 1 as follows:

TABLE 1

| Original residue | Conservative substitution |
| --- | --- |
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions. Any such modification of the polypeptide may be effected by any means known to those of skill in this art. Mutation may be effected by any method known to those of skill in the art, including site-specific or site-directed mutagenesis of DNA encoding the protein and the use of DNA amplification methods using primers to introduce and amplify alterations in the DNA template.

Identification and Isolation of DNA Encoding Human Calcium Channel Subunits

Methods for identifying and isolating DNA encoding $\alpha_1$, $\alpha_2$, $\beta$ and $\gamma$ subunits of human calcium channels are provided.

Identification and isolation of such DNA may be accomplished by hybridizing, under appropriate conditions, at least low stringency whereby DNA that encodes the desired subunit is isolated, restriction enzyme-digested human DNA with a labeled probe having at least 14, preferably 16 or more nucleotides and derived from any contiguous portion of DNA having a sequence of nucleotides set forth herein by sequence identification number. Once a hybridizing fragment is identified in the hybridization reaction, it can be cloned employing standard cloning techniques known to those of skill in the art. Full-length clones may be identified by the presence of a complete open reading frame and the identity of the encoded protein verified by sequence comparison with the subunits provided herein and by functional assays to assess calcium channel-forming ability or other function. This method can be used to identify genomic DNA encoding the subunit or cDNA encoding splice variants of human calcium channel subunits generated by alternative splicing of the primary transcript of genomic subunit DNA. For instance, DNA, cDNA or genomic DNA, encoding a calcium channel subunit may be identified by hybridization to a DNA probe and characterized by methods known to those of skill in the art, such as restriction mapping and DNA sequencing, and compared to the DNA provided herein in order to identify heterogeneity or divergence in the sequences of the DNA. Such sequence differences may indicate that the transcripts from which the cDNA was produced result from alternative splicing of a primary transcript, if the non-homologous and homologous regions are clustered, or from a different gene if the non-homologous regions are distributed throughout the cloned DNA.

Any suitable method for isolating genes using the DNA provided herein may be used. For example, oligonucleotides corresponding to regions of sequence differences have been used to isolate, by hybridization, DNA encoding the full-length splice variant and can be used to isolate genomic clones. A probe, based on a nucleotide sequence disclosed herein, which encodes at least a portion of a subunit of a human calcium channel, such as a tissue-specific exon, may be used as a probe to clone related DNA, to clone a full-length cDNA clone or genomic clone encoding the human calcium channel subunit.

Labeled, including, but not limited to, radioactively or enzymatically labeled, RNA or single-stranded DNA of at least 14 substantially contiguous bases, preferably 16 or more, generally at least 30 contiguous bases of a nucleic acid which encodes at least a portion of a human calcium channel subunit, the sequence of which nucleic acid corresponds to a segment of a nucleic acid sequence disclosed herein by reference to a SEQ ID No. are provided. Such nucleic acid segments may be used as probes in the methods provided herein for cloning DNA encoding calcium channel subunits. See, generally, Sambrook et al. (1989) *Molecular Cloning: A Laboratory Manual,* 2nd Edition, Cold Spring Harbor Laboratory Press.

In addition, nucleic acid amplification techniques, which are well known in the art, can be used to locate splice variants of calcium channel subunits by employing oligonucleotides based on DNA sequences surrounding the divergent sequence primers for amplifying human RNA or genomic DNA. Size and sequence determinations of the amplification products can reveal splice variants. Furthermore, isolation of human genomic DNA sequences by hybridization can yield DNA containing multiple exons, separated by introns, that correspond to different splice variants of transcripts encoding human calcium channel subunits.

DNA encoding types and subtypes of each of the $\alpha_1$, $\alpha_2$, $\beta$ and $\gamma$ subunits of voltage-dependent human calcium channels has been cloned herein by nucleic acid amplification of cDNA from selected tissues or by screening human cDNA libraries prepared from isolated poly A+ mRNA from cell lines or tissue of human origin having such calcium channels. Among the sources of such cells or tissue for obtaining mRNA are human brain tissue or a human cell line of neural origin, such as a neuroblastoma cell line, human skeletal muscle or smooth muscle cells, and the like. Methods of preparing cDNA libraries are well known in the art [see generally Ausubel et al. (1987) *Current Protocols in Molecular Biology*, Wiley-Interscience, New York; and Davis et al. (1986) *Basic Methods in Molecular Biology*, Elsevier Science Publishing Co., New York].

Preferred regions from which to construct probes include 5' and/or 3' coding sequences, sequences predicted to encode transmembrane domains, sequences predicted to encode cytoplasmic loops, signal sequences, ligand-binding sites, and other functionally significant sequences (see Table, below). Either the full-length subunit-encoding DNA or fragments thereof can be used as probes, preferably labeled with suitable label means for ready detection. When fragments are used as probes, preferably the DNA sequences will be typically from the carboxyl-end-encoding portion of the DNA, and most preferably will include predicted transmembrane domain-encoding portions based on hydropathy analysis of the deduced amino acid sequence [see, e.g., Kyte and Doolittle [(1982) *J. Mol. Biol.* 167:105].

Riboprobes that are specific for human calcium channel subunit types or subtypes have been prepared. These probes are useful for identifying expression of particular subunits in selected tissues and cells. The regions from which the probes were prepared were identified by comparing the DNA and amino acid sequences of all known α or β subunit subtypes. Regions of least homology, preferably human-derived sequences, and generally about 250 to about 600 nucleotides were selected. Numerous riboprobes for α and β subunits have been prepared; some of these are listed in the following Table.

TABLE 2

SUMMARY OF RNA PROBES

| SUBUNIT SPECIFIC- ITY | NUCLEO- TIDE POSITION | PROBE NAME | PROBE TYPE | ORIENTA- TION |
|---|---|---|---|---|
| α1A generic | 3357–3840 | pGEM7Zα1A* | riboprobe | n/a |
|  | 761–790 | SE700 | oligo | antisense |
|  | 3440–3464 | SE718 | oligo | antisense |
|  | 3542–3565 | SE724 | oligo | sense |
| α1B generic | 3091–3463 | pGEM7Zα1B$_{cyt}$ | riboprobe | n/a |
|  | 6635–6858 | pGEM7Zα1B$_{cooh}$ | riboprobe | n/a |
| α1B-1 specific | 6490–6676 | pCRII α1B-1/187 | riboprobe | n/a |
| α1E generic | 3114–3462 | pGEM7Zα1E | riboprobe | n/a |
| α2b | 1321–1603 | pCRIIα2b | riboprobe | n/a |
| β generic(?) | 212–236 | SE300 | oligo | antisense |
| β1 generic | 1267–1291 | SE301 | oligo | antisense |
| β1-2 specific | 1333–1362 | SE17 | oligo | antisense |
|  | 1682–1706 | SE23 | oligo | sense |
|  | 2742–2766 | SE43 | oligo | antisense |
|  | 27–56 | SE208 | oligo | antisense |
|  | 340–364 | SE274 | oligo | antisense |
|  | 340–364 | SE275 | oligo | sense |
| β3 specific | 1309–1509 |  | riboprobe | n/a |
| β4 specific | 1228–1560 |  | riboprobe | n/a |

*The pGEM series are available from Promega, Madison WI; see also, U.S. Pat. No. 4,766,072.

The above-noted nucleotide regions are also useful in selecting regions of the protein for preparation of subunit-specific antibodies, discussed below.

The DNA clones and fragments thereof provided herein thus can be used to isolate genomic clones encoding each subunit and to isolate any splice variants by hybridization screening of libraries prepared from different human tissues. Nucleic acid amplification techniques, which are well known in the art, can also be used to locate DNA encoding splice variants of human calcium channel subunits. This is accomplished by employing oligonucleotides based on DNA sequences surrounding divergent sequence(s) as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns, that correspond to different splice variants of transcripts encoding human calcium channel subunits.

Once DNA encoding a calcium channel subunit is isolated, ribonuclease (RNase) protection assays can be employed to determine which tissues express mRNA encoding a particular calcium channel subunit or variant. These assays provide a sensitive means for detecting and quantitating an RNA species in a complex mixture of total cellular RNA. The subunit DNA is labeled and hybridized with cellular RNA. If complementary mRNA is present in the cellular RNA, a DNA-RNA hybrid results. The RNA sample is then treated with RNase, which degrades single-stranded RNA. Any RNA-DNA hybrids are protected from RNase degradation and can be visualized by gel electrophoresis and autoradiography. In situ hybridization techniques can also be used to determine which tissues express mRNA encoding a particular calcium channel subunit. The labeled subunit DNAs are hybridized to different tissue slices to visualize subunit mRNA expression.

With respect to each of the respective subunits ($\alpha_1$, $\alpha_2$, β or γ) of human calcium channels, once the DNA encoding the channel subunit was identified by a nucleic acid screening method, the isolated clone was used for further screening to identify overlapping clones. Some of the cloned DNA fragments can and have been subcloned into an appropriate vector such as pIBI24/25 (IBI, New Haven, Conn.), M13mp18/19, pGEM4, pGEM3, pGEM7Z, pSP72 and other such vectors known to those of skill in this art, and characterized by DNA sequencing and restriction enzyme mapping. A sequential series of overlapping clones may thus be generated for each of the subunits until a full-length clone can be prepared by methods, known to those of skill in the art, that include identification of translation initiation (start) and translation termination (stop) codons. For expression of the cloned DNA, the 5' noncoding region and other transcriptional and translational control regions of such a clone may be replaced with an efficient ribosome binding site and other regulatory regions as known in the art. Other modifications of the 5' end, known to those of skill in the art, that may be required to optimize translation and/or transcription efficiency may also be effected, if deemed necessary.

Examples II–VIII, below, describe in detail the cloning of each of the various subunits of a human calcium channel as well as subtypes and splice variants, including tissue-specific variants thereof. In the few instances in which partial sequences of a subunit are disclosed, it is well within the skill of the art, in view of the teaching herein, to obtain the corresponding full-length clones and sequence thereof encoding the subunit, subtype or splice variant thereof using the methods described above and exemplified below.

Identification and Isolation of DNA Encoding $\alpha_1$ Subunits

A number of voltage-dependent calcium channel $\alpha_1$ subunit genes, which are expressed in the human CNS and in other tissues, have been identified and have been designated as $\alpha_{1A}$, $\alpha_{1B}$ (or VDCC IV), $\alpha_{1C}$ (or VDCC II), $\alpha_{1D}$ (or VDCC III) and $\alpha_{1E}$. DNA, isolated from a human neural cDNA library, that encodes each of the subunit types has been isolated. DNA encoding subtypes of each of the types, which arise as splice variants are also provided. Subtypes are herein designated, for example, as $\alpha_{1B-1}$, $\alpha_{1B-2}$.

The $\alpha_1$ subunit types A B, C, D and E of voltage-dependent calcium channels, and subtypes thereof, differ with respect to sensitivity to known classes of calcium channel agonists and antagonists, such as DHPs, phenylalkylamines, omega conotoxin ($\omega$-CgTx), the funnel web spider toxin $\omega$-Aga-IV, and pyrazonoylguanidines. These subunit types also appear to differ in the holding potential and in the kinetics of currents produced upon depolarization of cell membranes containing calcium channels that include different types of $\alpha_1$ subunits.

DNA that encodes an $\alpha_1$ subunit that binds to at least one compound selected from among dihydropyridines, phenylalkylamines, $\omega$-CgTx, components of funnel web spider toxin, and pyrazonoylguanidines is provided. For example, the $\alpha_{1B}$ subunit provided herein appears to specifically interact with $\omega$-CgTx in N-type channels, and the $\alpha_{1D}$ subunit provided herein specifically interacts with DHPs in L-type channels.

Identification and Isolation of DNA Encoding the $\alpha_{1D}$ Human Calcium Channel Subunit The $\alpha_{1D}$ subunit cDNA has been isolated using fragments of the rabbit skeletal muscle calcium channel $\alpha_1$ subunit cDNA as a probe to screen a cDNA library of a human neuroblastoma cell line, IMR32, to obtain clone $\alpha$1.36. This clone was used as a probe to screen additional IMR32 cell cDNA libraries to obtain overlapping clones, which were then employed for screening until a sufficient series of clones to span the length of the nucleotide sequence encoding the human $\alpha_{1D}$ subunit was obtained. Full-length clones encoding $\alpha_{1D}$ were constructed by ligating portions of partial $\alpha_{1D}$ clones as described in Example II. SEQ ID No. 1 shows the 7,635 nucleotide sequence of the cDNA encoding the $\alpha_{1D}$ subunit. There is a 6,483 nucleotide sequence reading frame which encodes a sequence of 2,161 amino acids (as set forth in SEQ ID No. 1).

SEQ ID No. 2 provides the sequence of an alternative exon encoding the IS6 transmembrane domain [see Tanabe, T., et al. (1987) *Nature* 328:313–318 for a description of transmembrane domain terminology] of the $\alpha_{1D}$ subunit.

SEQ ID No. 1 also shows the 2,161 amino acid sequence deduced from the human neuronal calcium channel $\alpha_{1D}$ subunit DNA. Based on the amino acid sequence, the $\alpha_{1D}$ protein has a calculated Mr of 245,163. The $\alpha_{1D}$ subunit of the calcium channel contains four putative internal repeated sequence regions. Four internally repeated regions represent 24 putative transmembrane segments, and the amino- and carboxyl-termini extend intracellularly.

The $\alpha_{1D}$ subunit has been shown to mediate DHP-sensitive, high-voltage-activated, long-lasting calcium channel activity. This calcium channel activity was detected when oöcytes were co-injected with RNA transcripts encoding an $\alpha_{1D}$ and $\beta_{1-2}$ or $\alpha_{1D}$, $\alpha_{2b}$ and $\beta_{1-2}$ subunits. This activity was distinguished from $Ba^{2+}$ currents detected when oöcytes were injected with RNA transcripts encoding the $\beta_{1-2} \pm \alpha_{2b}$ subunits. These currents pharmacologically and biophysically resembled $Ca^{2+}$ currents reported for uninjected oöcytes.

Identification and Isolation of DNA Encoding the $\alpha_{1A}$ Human Calcium Channel Subunit Biological material containing DNA encoding a portion of the $\alpha_{1A}$ subunit had been deposited in the American Type Culture Collection, 12301 Parklawn Drive, Rockville, Md. 20852 U.S.A. under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted.

A portion of an $\alpha_{1A}$ subunit is encoded by an approximately 3 kb insert in $\lambda$gt10 phage designated $\alpha$1.254 in *E. coli* host strain NM514. A phage lysate of this material has been deposited as at the American Type Culture Collection under ATCC Accession No. 75293, as described above. DNA encoding $\alpha_{1A}$ may also be identified by screening with a probe prepared from DNA that has SEQ ID No. 21:
5' CTCAGTACCATCTCTGATACCAGCCCCA 3'.

$\alpha_{1A}$ splice variants have been obtained. The sequences of two $\alpha_{1A}$ splice variants, $\alpha_{1a-1}$ and $\alpha_{1a-2}$ are set forth in SEQ. ID Nos. 22 and 23. Other splice variants may be obtained by screening a human library as described above or using all or a portion of the sequences set forth in SEQ ID Nos. 22 and 23.

Identification and Isolation of DNA Encoding the $\alpha_{1B}$ Human Calcium Channel Subunit DNA encoding the $\alpha_{1B}$ subunit was isolated by screening a human basal ganglia cDNA library with fragments of the rabbit skeletal muscle calcium channel $\alpha_1$ subunit-encoding cDNA. A portion of one of the positive clones was used to screen an IMR32 cell cDNA library. Clones that hybridized to the basal ganglia DNA probe were used to further screen an IMR32 cell cDNA library to identify overlapping clones that in turn were used to screen a human hippocampus cDNA library. In this way, a sufficient series of clones to span nearly the entire length of the nucleotide sequence encoding the human $\alpha_{1B}$ subunit was obtained. Nucleic acid amplification of specific regions of the IMR32 cell $\alpha_{1B}$ mRNA yielded additional segments of the $\alpha_{1B}$ coding sequence.

A full-length $\alpha_{1B}$ DNA clone was constructed by ligating portions of the partial cDNA clones as described in Example II.C. SEQ ID Nos. 7 and 8 show the nucleotide sequences of DNA clones encoding the $\alpha_{1B}$ subunit as well as the deduced amino acid sequences. The $\alpha_{1B}$ subunit encoded by SEQ ID No. 7 is referred to as the $\alpha_{1B-1}$ subunit to distinguish it from another $\alpha_{1B}$ subunit, $\alpha_{1B-2}$, encoded by the nucleotide sequence shown as SEQ ID No. 8, which is derived from alternative splicing of the $\alpha_{1B}$ subunit transcript.

Nucleic acid amplification of IMR32 cell mRNA using oligonucleotide primers designed according to nucleotide sequences within the $\alpha_{1B-1}$-encoding DNA has identified variants of the $\alpha_{1B}$ transcript that appear to be splice variants because they contain divergent coding sequences.

Identification and Isolation of DNA Encoding the $\alpha_{1C}$ Human Calcium Channel Subunit Numerous $\alpha_{1C}$-specific DNA clones were isolated. Characterization of the sequence revealed the $\alpha_{1C}$ coding sequence, the $\alpha_{1C}$ initiation of translation sequence, and an alternatively spliced region of $\alpha_{1C}$. Alternatively spliced variants of the $\alpha_{1C}$ subunit have been identified. SEQ ID No. 3 sets forth DNA encoding a substantial protion of an $\alpha_{1C}$ subunit. The DNA sequences set forth in SEQ ID No. 4 and No. 5 encode two possible amino terminal ends of the $\alpha_{1C}$ protein. SEQ ID No. 6 encodes an alternative exon for the IV S3 transmembrane domain. The sequences of substantial portions of two $\alpha_{1C}$ splice variants, designated $\alpha_{1C-1}$ and $\alpha_{1C-2}$, are set forth in SEQ ID NOs. 3 and 36, respectively.

The isolation and identification of DNA clones encoding portions of the $\alpha_{1C}$ subunit is described in detail in Example II.

Identification and Isolation of DNA Encoding the $\alpha_{1E}$ Human Calcium Channel Subunit DNA encoding $\alpha_{1E}$ human calcium channel subunits have been isolated from an oligo dT-primed human hippocampus library. The resulting clones, which are splice variants, were designated $\alpha_{1E-1}$ and $\alpha_{1E-3}$. The subunit designated $\alpha_{1E-1}$ has the amino acid sequence set forth in SEQ ID No. 24, and a subunit designated $\alpha_{1E-3}$ has the amino acid sequence set forth in SEQ ID No. 25. These splice variants differ by virtue of a 57 base pair insert between nucleotides 2405 and 2406 of SEQ. ID No. 24.

The $\alpha_{1E}$ subunits provided herein appear to participate in the formation of calcium channels that have properties of high-voltage activated calcium channels and low-voltage activated channels. These channels are rapidly inactivating compared to other high voltage-activated calcium channels. In addition these channels exhibit pharmacological profiles that are similar to voltage-activated channels, but are also sensitive to DHPs and ω-Aga-IVA, which block certain high voltage activated channels. Additional details regarding the electrophysiology and pharmacology of channels containing $\alpha_{1E}$ subunits is provided in Example VII. F.

Identification and Isolation of DNA Encoding Encoding Additional $\alpha_1$ Human Calcium Channel Subunit Types and Subtypes DNA encoding additional $\alpha_1$ subunits can be isolated and identified using the DNA provided herein as described for the $\alpha_{1A}$, $\alpha_{1B}$, $\alpha_{1C}$, $\alpha_{1D}$ and $\alpha_{1E}$ subunits or using other methods known to those of skill in the art. In particular, the DNA provided herein may be used to screen appropriate libraries to isolate related DNA. Full-length clones can be constructed using methods, such as those described herein, and the resulting subunits characterized by comparison of their sequences and electrophysiological and pharmacological properties with the subunits exemplified herein.

Identification and Isolation of DNA Encoding β Human Calcium Channel Subunits

DNA Encoding $\beta_1$

To isolate DNA encoding the $\beta_1$ subunit, a human hippocampus cDNA library was screened by hybridization to a DNA fragment encoding a rabbit skeletal muscle calcium channel β subunit. A hybridizing clone was selected and was in turn used to isolate overlapping clones until the overlapping clones encompassing DNA encoding the entire human calcium channel β subunit were isolated and sequenced.

Five alternatively spliced forms of the human calcium channel $\beta_1$ subunit have been identified and DNA encoding a number of forms have been isolated. These forms are designated $\beta_{1-1}$, expressed in skeletal muscle, $\beta_{1-2}$, expressed in the CNS, $\beta_{1-3}$, also expressed in the CNS, $\beta_{1-4}$, expressed in aorta tissue and HEK 293 cells, and $\beta_{1-5}$, expressed in HEK 293 cells. Full-length DNA clones encoding the $\beta_{1-2}$ and $\beta_{1-3}$ subunits have been constructed. The subunits $\beta_{1-1}$, $\beta_{1-2}$, $\beta_{1-4}$ and $\beta_{1-5}$ have been identified by nucleic acid amplification analysis as alternatively spliced forms of the β subunit. Sequences of the $\beta_1$ splice variants are set forth in SEQ ID Nos. 9, 10 and 33–35.

DNA Encoding $\beta_2$

DNA encoding the $\beta_2$ splice variants has been obtained. These splice variants include $\beta_{2C}$–$\beta_{2E}$. Splice variants $\beta_{2C}$–$\beta_{2E}$ include all of sequence set forth in SEQ ID No. 26, except for the portion at the 5' end (up to nucleotide 182), which differs among splice variants. The sequence set forth in SEQ ID No. 26 encodes $\beta_{2D}$. Additional splice variants may be isolated using the methods described herein and oligonucleotides including all or portions of the DNA set forth in SEQ ID. No. 26 or may be prepared or obtained as described in the Examples. The sequences of $\beta_2$ splice variants $\beta_{2C}$ and $\beta_{2E}$ are set forth in SEQ ID Nos. 37 and 38, respectively.

DNA Encoding $\beta_3$

DNA encoding the $\beta_1$ subunit and any splice variants thereof may be isolated by screening a library, as described above for the $\beta_1$ subunit, using DNA probes prepared according to SEQ ID Nos. 19, 20 or using all or a portion of the deposited $\beta_3$ clone plasmid β1.42 (ATCC Accession No. 69048).

The *E. coli* host containing plasmid β1.42 that includes DNA encoding a $\beta_3$ subunit has been deposited as ATCC Accession No. 69048 in the American Type Culture Collection, 12301 Parklawn Drive, Rockville, Md. 20852 U.S.A. under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted.

The $\beta_3$ encoding plasmid is designated β1.42. The plasmid contains a 2.5 kb EcoRI fragment encoding $\beta_3$ inserted into vector pGem®7 zF(+) and has been deposited in *E. coli* host strain DH5α. The sequences of $\beta_3$ splice variants, designated $\beta_{3-1}$ and $\beta_{3-2}$ are set forth in SEQ ID Nos. 19 and 20, respectively.

Identification and Isolation of DNA Encoding the α2 Human Calcium Channel Subunit DNA encoding a human neuronal calcium channel $\alpha_2$ subunit was isolated in a manner substantially similar to that used for isolating DNA encoding an $\alpha_1$ subunit, except that a human genomic DNA library was probed under low and high stringency conditions with a fragment of DNA encoding the rabbit skeletal muscle calcium channel $\alpha_2$ subunit. The fragment included nucleotides having a sequence corresponding to the nucleotide sequence between nucleotides 43 and 272 inclusive of rabbit back skeletal muscle calcium channel $\alpha_2$ subunit cDNA as disclosed in PCT International Patent Application Publication No. WO 89/09834, which corresponds to U.S. application Ser. No. 07/620,520 (now allowed U.S. application Ser. No. 07/914,231), which is a continuation-in-part of U.S. Ser. No. 176,899, filed Apr. 4, 1988, which applications have been incorporated herein by reference.

Example IV describes the isolation of DNA clones encoding $\alpha_2$ subunits of a human calcium channel from a human DNA library using genomic DNA and cDNA clones, identified by hybridization to the genomic DNA, as probes.

SEQ ID Nos. 11 and 29–32 show the sequence of DNA encoding $\alpha_2$ subunits. As described in Example V, nucleic acid amplification analysis of RNA from human skeletal muscle, brain tissue and aorta using oligonucleotide primers specific for a region of the human neuronal $\alpha_2$ subunit cDNA that diverges from the rabbit skeletal muscle calcium channel $\alpha_2$ subunit cDNA identified splice variants of the human calcium channel $\alpha_2$ subunit transcript.

Identification and Isolation of DNA Encoding γ Human Calcium Channel Subunits

DNA encoding a portion of a human neuronal calcium channel γ subunit has been isolated as described in detail in Example VI. SEQ ID No. 14 shows the nucleotide sequence at the 3'-end of this DNA which includes a reading frame encoding a sequence of 43 amino acid residues. Since the portion that has been obtained is homologous to the rabbit clone, described in allowed co-owned U.S. application Ser. No. 07/482,384, the remainder of the clone can be obtained using routine methods.

Antibodies

Antibodies, monoclonal or polyclonal, specific for calcium channel subunit subtypes or for calcium channel types can be prepared employing standard techniques, known to those of skill in the art, using the subunit proteins or portions thereof as antigens. Anti-peptide and anti-fusion protein antibodies can be used [see, for example, Bahouth et al. (1991) *Trends Pharmacol. Sci.* 12:338–343; Current *Protocols in Molecular Biology* (Ausubel et al., eds.) John Wiley and Sons, New York (1984)]. Factors to consider in selecting portions of the calcium channel subunits for use as immunogens (as either a synthetic peptide or a recombinantly produced bacterial fusion protein) include antigenicity accessibility (i.e., extracellular and cytoplasmic domains), uniqueness to the particular subunit, and other factors known to those of skill in this art.

The availability of subunit-specific antibodies makes possible the application of the technique of immunohistochemistry to monitor the distribution and expression density of various subunits (e.g., in normal vs diseased brain tissue). Such antibodies could also be employed in diagnostic, such as LES diagnosis, and therapeutic applications, such as using antibodies that modulate activities of calcium channels.

The antibodies can be administered to a subject employing standard methods, such as, for example, by intraperitoneal, intramuscular, intravenous, or subcutaneous injection, implant or transdermal modes of administration, and the like. One of skill in the art can empirically determine dose forms, treatment regiments, etc., depending on the mode of administration employed.

Subunit-specific monoclonal antibodies and polyclonal antisera have been prepared. The regions from which the antigens came were identified by comparing the DNA and amino acid sequences of all known α or β subunit subtypes. Regions of least homology, preferably human-derived sequences were selected. The selected regions or fusion proteins containing the selected regions are used as immunogens. Hydrophobicity analyses of residues in selected protein regions and fusion proteins are also performed; regions of high hydrophobicity are avoided. Also, and more importantly, when preparing fusion proteins in bacterial hosts, rare codons are avoided. In particular, inclusion of 3 or more successive rare codons in a selected host is avoided. Numerous antibodies, polyclonal and monoclonal, specific for α or β subunit types or subtypes have been prepared; some of these are listed in the following Table. Exemplary antibodies and peptide antigens used to prepare the antibodies are set forth in the following Table:

TABLE 3

| SPECIFICITY | AMINO ACID NUMBER | ANTIGEN NAME | ANTIBODY TYPE |
|---|---|---|---|
| α1 generic | 112–140 | peptide 1A#1 | polyclonal |
| α1 generic | 1420–1447 | peptide 1A#2 | polyclonal |
| α1A generic | 1048–1208 | α1A#2(b)GST fusion* | polyclonal monoclonal |
| α1B generic | 983–1106 | α1B#2(b) GST fusion | polyclonal monoclonal |
| α1B-1 | 2164–2339 | α1B-1#3 GST fusion | polyclonal |
| α1B-2 | 2164–2237 | α1B-2#4 GST fusion | polyclonal |
| α1E generic | 985–1004 (α1E-3) | α1E#2(a) GST fusion | polyclonal |

*GST gene fusion system is available from Pharmacia; see also, Smith et al. (1988) Gene 67:31. The system provides pGEX plasmids that are designed for inducible, high-level expression of genes or gene fragments as fusions with *Schistosoma japonicum* GST. Upon expression in a bacterial host, the resulting fusion proteins are purified from bacterial lysates by affinity chromatography.

The GST fusion proteins are each specific for the cytoplasmic loop region IIS6-IIS1, which is a region of low subtype homology for all subtypes, including $\alpha_{1C}$ and $\alpha_{1D}$, for which similar fusions and antisera can be prepared.

Preparation of Recombinant Eukaryotic Cells Containing DNA Encoding Heterologous Calcium Channel Subunits DNA encoding one or more of the calcium channel subunits or a portion of a calcium channel subunit may be introduced into a host cell for expression or replication of the DNA. Such DNA may be introduced using methods described in the following examples or using other procedures well known to those skilled in the art. Incorporation of cloned DNA into a suitable expression vector, transfection of eukaryotic cells with a plasmid vector or a combination of plasmid vectors, each encoding one or more distinct genes or with linear DNA, and selection of transfected cells are also well known in the art [see, e.g., Sambrook et al. (1989) *Molecular Cloning: A Laboratory Manual, Second Edition*, Cold Spring Harbor Laboratory Press]. Cloned full-length DNA encoding any of the subunits of a human calcium channel may be introduced into a plasmid vector for expression in a eukaryotic cell. Such DNA may be genomic DNA or cDNA. Host cells may be transfected with one or a combination of the plasmids, each of which encodes at least one calcium channel subunit. Alternatively, host cells may be transfected with linear DNA using methods well known to those of skill in the art.

While the DNA provided herein may be expressed in any eukaryotic cell, including yeast cells such as P. pastoris [see, e.g., Cregg et al. (1987) *Bio/Technology* 5:479], mammalian expression systems for expression of the DNA encoding the human calcium channel subunits provided herein are preferred.

The heterologous DNA may be introduced by any method known to those of skill in the art, such as transfection with a vector encoding the heterologous DNA. Particularly preferred vectors for transfection of mammalian cells are the pSV2dhfr expression vectors, which contain the SV40 early promoter, mouse dhfr gene, SV40 polyadenylation and splice sites and sequences necessary for maintaining the vector in bacteria, cytomegalovirus (CMV) promoter-based vectors such as pCDNA1, or pcDNA-amp and MMTV promoter-based vectors. DNA encoding the human calcium channel subunits has been inserted in the vector pCDNA1 at a position immediately following the CMV promoter. The vector pCDNA1 is presently preferred.

Stably or transiently transfected mammalian cells may be prepared by methods known in the art by transfecting cells with an expression vector having a selectable marker gene such as the gene for thymidine kinase, dihydrofolate reductase, neomycin resistance or the like, and, for transient transfection, growing the transfected cells under conditions selective for cells expressing the marker gene. Functional voltage-dependent calcium channels have been produced in HEK 293 cells transfected with a derivative of the vector pCDNA1 that contains DNA encoding a human calcium channel subunit.

The heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Eukaryotic cells in which DNA or RNA may be introduced, include any cells that are transfectable by such DNA or RNA or into which such DNA may be injected. Virtually any eukaryotic cell can serve as a vehicle for heterologous DNA. Preferred cells are those that can also express the DNA and RNA and most preferred cells are those that can form recombinant or heterologous calcium channels that include one or more subunits encoded by the heterologous DNA. Such cells may be identified empirically or selected from among those known to be readily transfected or injected. Preferred cells for introducing DNA include those that can be transiently or stably transfected and include, but are not limited to, cells of mammalian origin, such as COS cells, mouse L cells, CHO cells, human embryonic kidney cells, African green monkey cells and other such cells known to those of skill in the art, amphibian cells, such as *Xenopus laevis* oöcytes, or those of yeast such as *Saccharomyces cerevisiae* or *Pichia pastoris*. Preferred cells for expressing injected RNA transcripts or cDNA include *Xenopus laevis* oöcytes. Cells that are preferred for transfection of DNA are those that can be readily and efficiently transfected. Such cells are known to those of skill in the art or may be empirically identified. Preferred cells include DG44 cells and HEK 293 cells, particularly HEK 293 cells that can be frozen in liquid nitrogen and then thawed and regrown. Such HEK 293 cells are described, for example in U.S. Pat. No. 5,024,939 to Gorman [see, also Stillman et al. (1985) *Mol. Cell.Biol.* 5:2051–2060].

The cells may be used as vehicles for replicating heterologous DNA introduced therein or for expressing the heterologous DNA introduced therein. In certain embodiments, the cells are used as vehicles for expressing the heterologous DNA as a means to produce substantially pure human calcium channel subunits or heterologous calcium channels. Host cells containing the heterologous DNA may be cultured under conditions whereby the calcium channels are expressed. The calcium channel subunits may be purified using protein purification methods known to those of skill in the art. For example, antibodies, such as those provided herein, that specifically bind to one or more of the subunits may be used for affinity purification of the subunit or calcium channels containing the subunits.

Substantially pure subunits of a human calcium channel $\alpha_1$ subunits of a human calcium channel, $\alpha_2$ subunits of a human calcium channel, $\beta$ subunits of a human calcium channel and $\gamma$ subunits of a human calcium channel are provided. Substantially pure isolated calcium channels that contain at least one of the human calcium channel subunits are also provided. Substantially pure calcium channels that contain a mixture of one or more subunits encoded by the host cell and one or more subunits encoded by heterologous DNA or RNA that has been introduced into the cell are also provided. Substantially pure subtype- or tissue-type specific calcium channels are also provided.

In other embodiments, eukaryotic cells that contain heterologous DNA encoding at least one of an $\alpha_1$ subunit of a human calcium channel, an $\alpha_2$ subunit of a human calcium channel, a $\beta$ subunit of a human calcium channel and a $\gamma$ subunit of a human calcium channel are provided. In accordance with one preferred embodiment, the heterologous DNA is expressed in the eukaryotic cell and preferably encodes a human calcium channel $\alpha_1$ subunit.

Expression of Heterologous Calcium Channels
Electrophysiology and Pharmacology

Electrophysiological methods for measuring calcium channel activity are known to those of skill in the art and are exemplified herein. Any such methods may be used in order to detect the formation of functional calcium channels and to characterize the kinetics and other characteristics of the resulting currents. Pharmacological studies may be combined with the electrophysiological measurements in order to further characterize the calcium channels.

With respect to measurement of the activity of functional heterologous calcium channels, preferably, endogenous ion channel activity and, if desired, heterologous channel activity of channels that do not contain the desired subunits, of a host cell can be inhibited to a significant extent by chemical, pharmacological and electrophysiological means, including the use of differential holding potential, to increase the S/N ratio of the measured heterologous calcium channel activity.

Thus, various combinations of subunits encoded by the DNA provided herein are introduced into eukaryotic cells. The resulting cells can be examined to ascertain whether functional channels are expressed and to determine the properties of the channels. In particularly preferred aspects, the eukaryotic cell which contains the heterologous DNA expresses it and forms a recombinant functional calcium channel activity. In more preferred aspects, the recombinant calcium channel activity is readily detectable because it is a type that is absent from the untransfected host cell or is of a magnitude and/or pharmacological properties or exhibits biophysical properties not exhibited in the untransfected cell.

The eukaryotic cells can be transfected with various combinations of the subunit subtypes provided herein. The resulting cells will provide a uniform population of calcium channels for study of calcium channel activity and for use in the drug screening assays provided herein. Experiments that have been performed have demonstrated the inadequacy of prior classification schemes.

Preferred among transfected cells is a recombinant eukaryotic cell with a functional heterologous calcium channel. The recombinant cell can be produced by introduction of and expression of heterologous DNA or RNA transcripts encoding an $\alpha_1$ subunit of a human calcium channel, more preferably also expressing, a heterologous DNA encoding a $\beta$ subunit of a human calcium channel and/or heterologous DNA encoding an $\alpha_2$ subunit of a human calcium channel. Especially preferred is the expression in such a recombinant cell of each of the $\alpha_1$, $\beta$ and $\alpha_2$ subunits encoded by such heterologous DNA or RNA transcripts, and optionally expression of heterologous DNA or an RNA transcript encoding a $\gamma$ subunit of a human calcium channel.

The functional calcium channels may preferably include at least an $\alpha_1$ subunit and a $\beta$ subunit of a human calcium channel. Eukaryotic cells expressing these two subunits and also cells expressing additional subunits, have been prepared by transfection of DNA and by injection of RNA transcripts. Such cells have exhibited voltage-dependent calcium channel activity attributable to calcium channels that contain one or more of the heterologous human calcium channel subunits. For example, eukaryotic cells expressing heterologous calcium channels containing an $\alpha_2$ subunit in addition to the $\alpha_1$ subunit and a $\beta$ subunit have been shown to exhibit increased calcium selective ion flow across the cellular membrane in response to depolarization, indicating that the $\alpha_2$ subunit may potentiate calcium channel function. Cells that have been co-transfected with increasing ratios of $\alpha_2$ to $\alpha_1$ and the activity of the resulting calcium channels has been measured. The results indicate that increasing the amount of $\alpha_2$-encoding DNA relative to the other transfected subunits increases calcium channel activity.

Eukaryotic cells which express heterologous calcium channels containing at least a human $\alpha_1$ subunit, a human $\beta$ subunit and a human $\alpha_2$ subunit are preferred. Eukaryotic cells transformed with a composition containing cDNA or an RNA transcript that encodes an $\alpha_1$ subunit alone or in combination with a $\beta$ and/or an $\alpha_2$ subunit may be used to produce cells that express functional calcium channels. Since recombinant cells expressing human calcium channels containing all of the human subunits encoded by the heterologous cDNA or RNA are especially preferred, it is desirable to inject or transfect such host cells with a sufficient concentration of the subunit-encoding nucleic acids to form calcium channels that contain the human subunits encoded by heterologous DNA or RNA. The precise amounts and ratios of DNA or RNA encoding the subunits may be empirically determined and optimized for a particular combination of subunits, cells and assay conditions.

In particular, mammalian cells have been transiently and stably tranfected with DNA encoding one or more human calcium channel subunits. Such cells express heterologous calcium channels that exhibit pharmacological and electrophysiological properties that can be ascribed to human calcium channels. Such cells, however, represent homogeneous populations and the pharmacological and electrophysiological data provides insights into human calcium channel activity heretofore unattainable. For example, HEK cells that have been transiently transfected with DNA encoding the $\alpha_{1E-1}$, $\alpha_{2b}$, and $\beta_{1-3}$ subunits. The resulting cells transiently express these subunits, which form calcium channels that have properties that appear to be a pharmacologically distinct class of voltage-activated calcium channels distinct from those of L-, N-, T- and P-type channels. The observed $\alpha_{1E}$ currents were insensitive to drugs and toxins previously used to define other classes of voltage-activated calcium channels.

HEK cells that have been transiently transfected with DNA encoding $\alpha_{1B-1}$, $\alpha_{2b}$, and $\beta_{1-2}$ express heterologous calcium channels that exhibt sensitivity to $\omega$-conotoxin and currents typical of N-type channels. It has been found that alteration of the molar ratios of $\alpha_{1B-1}$, $\alpha_{2b}$ and $\beta_{1-2}$ introduced the cells into to achieve equivalent mRNA levels significantly increased the number of receptors per cell, the current density, and affected the $K_d$ for $\omega$-conotoxin.

The electrophysiological properties of these channels produced from $\alpha_{1B-1}$, $\alpha_{2b}$, and $\beta_{1-2}$ was compared with those of channels produced by transiently transfecting HEK cells with DNA encoding $\alpha_{1B-1}$, $\alpha_{2b}$ and $\beta_{1-3}$. The channels exhibited similar voltage dependence of activation, substantially identical voltage dependence, similar kinetics of activation and tail currents that could be fit by a single exponential. The voltage dependence of the kinetics of inactivation was significantly different at all voltages examined.

In certain embodiments, the eukaryotic cell with a heterologous calcium channel is produced by introducing into the cell a first composition, which contains at least one RNA transcript that is translated in the cell into a subunit of a human calcium channel. In preferred embodiments, the subunits that are translated include an $\alpha_1$ subunit of a human calcium channel. More preferably, the composition that is introduced contains an RNA transcript which encodes an $\alpha_1$ subunit of a human calcium channel and also contains (1) an RNA transcript which encodes a $\beta$ subunit of a human calcium channel and/or (2) an RNA transcript which encodes an $\alpha_2$ subunit of a human calcium channel. Especially preferred is the introduction of RNA encoding an $\alpha_1$, a $\beta$ and an $\alpha_2$ human calcium channel subunit, and, optionally, a $\gamma$ subunit of a human calcium channel.

Methods for in vitro transcription of a cloned DNA and injection of the resulting RNA into eukaryotic cells are well known in the art. Transcripts of any of the full-length DNA encoding any of the subunits of a human calcium channel may be injected alone or in combination with other transcripts into eukaryotic cells for expression in the cells. Amphibian oocytes are particularly preferred for expression of in vitro transcripts of the human calcium channel subunit cDNA clones provided herein. Amphibian oocytes that express functional heterologous calcium channels have been produced by this method.

Assays and Clinical Uses of the Cells and Calcium Channels

Assays

Assays for Identifying Compounds that Modulate Calcium Channel Activity

Among the uses for eukaryotic cells which recombinantly express one or more subunits are assays for determining whether a test compound has calcium channel agonist or antagonist activity. These eukaryotic cells may also be used to select from among known calcium channel agonists and antagonists those exhibiting a particular calcium channel subtype specificity and to thereby select compounds that have potential as disease- or tissue-specific therapeutic agents.

In vitro methods for identifying compounds, such as calcium channel agonist and antagonists, that modulate the activity of calcium channels using eukaryotic cells that express heterologous human calcium channels are provided.

In particular, the assays use eukaryotic cells that express heterologous human calcium channel subunits encoded by heterologous DNA provided herein, for screening potential calcium channel agonists and antagonists which are specific for human calcium channels and particularly for screening for compounds that are specific for particular human calcium channel subtypes. Such assays may be used in conjunction with methods of rational drug design to select among agonists and antagonists, which differ slightly in structure, those particularly useful for modulating the activity of human calcium channels, and to design or select compounds that exhibit subtype- or tissue-specific calcium channel antagonist and agonist activities.

These assays should accurately predict the relative therapeutic efficacy of a compound for the treatment of certain disorders in humans. In addition, since subtype- and tissue-specific calcium channel subunits are provided, cells with tissue-specific or subtype-specific recombinant calcium channels may be prepared and used in assays for identification of human calcium channel tissue- or subtype-specific drugs.

Desirably, the host cell for the expression of calcium channel subunits does not produce endogenous calcium channel subunits of the type or in an amount that substantially interferes with the detection of heterologous calcium channel subunits in ligand binding assays or detection of heterologous calcium channel function, such as generation of calcium current, in functional assays. Also, the host cells preferably should not produce endogenous calcium channels which detectably interact with compounds having, at physiological concentrations (generally nanomolar or picomolar concentrations), affinity for calcium channels that contain one or all of the human calcium channel subunits provided herein.

With respect to ligand binding assays for identifying a compound which has affinity for calcium channels, cells are employed which express, preferably, at least a heterologous $\alpha_1$ subunit. Transfected eukaryotic cells which express at least an $\alpha_1$ subunit may be used to determine the ability of a test compound to specifically bind to heterologous calcium channels by, for example, evaluating the ability of the test compound to inhibit the interaction of a labeled compound known to specifically interact with calcium channels. Such ligand binding assays may be performed on intact transfected cells or membranes prepared therefrom.

The capacity of a test compound to bind to or otherwise interact with membranes that contain heterologous calcium channels or subunits thereof may be determined by using any appropriate method, such as competitive binding analysis, such as Scatchard plots, in which the binding capacity of such membranes is determined in the presence and absence of one or more concentrations of a compound having known affinity for the calcium channel. Where necessary, the results may be compared to a control experiment designed in accordance with methods known to those of skill in the art. For example, as a negative control, the results may be compared to those of assays of an identically treated membrane preparation from host cells which have not been transfected with one or more subunit-encoding nucleic acids.

The assays involve contacting the cell membrane of a recombinant eukaryotic cell which expresses at least one subunit of a human calcium channel, preferably at least an $\alpha_1$ subunit of a human calcium channel, with a test compound and measuring the ability of the test compound to specifically bind to the membrane or alter or modulate the activity of a heterologous calcium channel on the membrane.

In preferred embodiments, the assay uses a recombinant cell that has a calcium channel containing an $\alpha_1$ subunit of a human calcium channel in combination with a $\beta$ subunit of a human calcium channel and/or an $\alpha_2$ subunit of a human calcium channel. Recombinant cells expressing heterologous calcium channels containing each of the $\alpha_1$, $\beta$ and $\alpha_2$ human subunits, and, optionally, a $\gamma$ subunit of a human calcium channel are especially preferred for use in such assays.

In certain embodiments, the assays for identifying compounds that modulate calcium channel activity are practiced by measuring the calcium channel activity of a eukaryotic cell having a heterologous, functional calcium channel when such cell is exposed to a solution containing the test compound and a calcium channel-selective ion and comparing the measured calcium channel activity to the calcium channel activity of the same cell or a substantially identical control cell in a solution not containing the test compound. The cell is maintained in a solution having a concentration of calcium channel-selective ions sufficient to provide an inward current when the channel is open. Rcombinant cells expressing calcium channels that include each of the $\alpha_1$, $\beta$ and $\alpha_2$ human subunits, and, optionally, a $\gamma$ subunit of a human calcium channel, are especially preferred for use in such assays. Methods for practicing such assays are known to those of skill in the art. For example, for similar methods applied with *Xenopus laevis* oöcytes and acetylcholine receptors, see, Mishina et al. [(1985) *Nature* 313:364] and, with such oöcytes and sodium channels [see, Noda et al. (1986) *Nature* 322:826–828]. For similar studies which have been carried out with the acetylcholine receptor, see, e.g., Claudio et al. [(1987) *Science* 238:1688–1694].

Functional recombinant or heterologous calcium channels may be identified by any method known to those of skill in the art. For example, electrophysiological procedures for measuring the current across an ion-selective membrane of a cell, which are well known, may be used. The amount and duration of the flow of calcium-selective ions through heterologous calcium channels of a recombinant cell containing DNA encoding one or more of the subunits provided herein has been measured using electrophysiological recordings using a two electrode and the whole-cell patch clamp techniques. In order to improve the sensitivity of the assays, known methods can be used to eliminate or reduce non-calcium currents and calcium currents resulting from endogenous calcium channels, when measuring calcium currents through recombinant channels. For example, the DHP Bay K 8644 specifically enhances L-type calcium channel function by increasing the duration of the open state of the channels [see, e.g., Hess, J. B., et al. (1984) *Nature* 311:538–544]. Prolonged opening of the channels results in calcium currents of increased magnitude and duration. Tail currents can be observed upon repolarization of the cell membrane after activation of ion channels by a depolarizing voltage command. The opened channels require a finite time to close or "deactivate" upon repolarization, and the current that flows through the channels during this period is referred to as a tail current. Because Bay K 8644 prolongs opening events in calcium channels, it tends to prolong these tail currents and make them more pronounced.

In practicing these assays, stably or transiently transfected cells or injected cells that express voltage-dependent human calcium channels containing one or more of the subunits of a human calcium channel desirably may be used in assays to identify agents, such as calcium channel agonists and antagonists, that modulate calcium channel activity. Functionally testing the activity of test compounds, including compounds having unknown activity, for calcium channel agonist or antagonist activity to determine if the test compound potentiates, inhibits or otherwise alters the flow of calcium ions or other ions through a human calcium channel can be accomplished by (a) maintaining a eukaryotic cell which is transfected or injected to express a heterologous functional calcium channel capable of regulating the flow of calcium channel-selective ions into the cell in a medium containing calcium channel-selective ions (i) in the presence of and (ii) in the absence of a test compound; (b) maintaining the cell under conditions such that the heterologous calcium channels are substantially closed and endogenous calcium channels of the cell are substantially inhibited (c) depolarizing the membrane of the cell maintained in step (b) to an extent and for an amount of time sufficient to cause (preferably, substantially only) the heterologous calcium channels to become permeable to the calcium channel-selective ions; and (d) comparing the amount and duration of current flow into the cell in the presence of the test compound to that of the current flow into the cell, or a substantially similar cell, in the absence of the test compound.

The assays thus use cells, provided herein, that express heterologous functional calcium channels and measure functionally, such as electrophysiologically, the ability of a test compound to potentiate, antagonize or otherwise modulate the magnitude and duration of the flow of calcium channel-selective ions, such as $Ca^{++}$ or $Ba^{++}$, through the heterologous functional channel. The amount of current which flows through the recombinant calcium channels of a cell may be determined directly, such as electrophysiologically, or by monitoring an independent reaction which occurs intracellularly and which is directly influenced in a calcium (or other) ion dependent manner.

Any method for assessing the activity of a calcium channel may be used in conjunction with the cells and assays provided herein. For example, in one embodiment of the method for testing a compound for its ability to modulate calcium channel activity, the amount of current is measured by its modulation of a reaction which is sensitive to calcium channel-selective ions and uses a eukaryotic cell which expresses a heterologous calcium channel and also contains a transcriptional control element operatively linked for expression to a structural gene that encodes an indicator protein. The transcriptional control element used for transcription of the indicator gene is responsive in the cell to a calcium channel-selective ion, such as $Ca^{2+}$ and $Ba^{2+}$. The details of such transcriptional based assays are described in commonly owned PCT International Patent Application No. PCT/US91/5625, filed Aug. 7, 1991, which claims priority to copending commonly owned allowed U.S. application Ser. No. 07/563,751, filed Aug. 7, 1990; see also, commonly owned published PCT International Patent Application PCT US92/11090, which corresponds to co-pending U.S. applications Ser. Nos. 08/229,150 and 08/244,985. The contents of these applications are herein incorporated by reference thereto.

Assays for Diagnosis of LES

LES is an autoimmune disease characterized by an insufficient release of acetylcholine from motor nerve terminals which normally are responsive to nerve impulses. Immunoglobulins (IgG) from LES patients block individual voltage-dependent calcium channels and thus inhibit calcium channel activity [Kim and Neher, *Science* 239:405–408 (1988)]. A diagnostic assay for Lambert Eaton Syndrome (LES) is provided herein. The diagnostic assay for LES relies on the immunological reactivity of LES IgG with the human calcium channels or particular subunits alone or in combination or expressed on the surface of recombinant cells. For example, such an assay may be based on immunoprecipitation of LES IgG by the human calcium channel subunits and cells that express such subunits provided herein.

Clinical Applications

In relation to therapeutic treatment of various disease states, the availability of DNA encoding human calcium channel subunits permits identification of any alterations in such genes (e.g., mutations) which may correlate with the occurrence of certain disease states. In addition, the creation of animal models of such disease states becomes possible, by specifically introducing such mutations into synthetic DNA fragments which can then be introduced into laboratory animals or in vitro assay systems to determine the effects thereof.

Also, genetic screening can be carried out using the nucleotide sequences as probes. Thus, nucleic acid samples from subjects having pathological conditions suspected of involving alteration/modification of any one or more of the calcium channel subunits can be screened with appropriate probes to determine if any abnormalities exist with respect to any of the endogenous calcium channels. Similarly, subjects having a family history of disease states related to calcium channel dysfunction can be screened to determine if they are also predisposed to such disease states.

EXAMPLES

The following examples are included for illustrative purposes only and are not intended to limit the scope of the invention.

Example I

Preparation of Libraries Used for Isolation of DNA Encoding Human Neuronal Votage-Dependent Calcium Channel Subunits A. RNA Isolation 1. IMR32 Cells IMR32 cells were obtained from the American Type Culture Collection (ATCC Accession No. CCL127, Rockville, Md.) and grown in DMEM, 10% fetal bovine serum, 1% penicillin/streptomycin (GIBCO, Grand Island, N.Y.) plus 1.0 mM dibutyryl cAMP (dbcAMP) for ten days. Total RNA was isolated from the cells according to the procedure described by H. C. Birnboim [(1988) *Nucleic Acids Research* 16:1487–1497]. Poly($A^+$) RNA was selected according to standard procedures [see, e.g., Sambrook et al. (1989) *Molecular Cloning, A Laboratory Manual*, Cold Spring Harbor Laboratory Press; pg. 7.26–7.29].

2. Human Thalamus Tissue

Human thalamus tissue (2.34 g), obtained from the National Neurological Research Bank, Los Angeles, Calif., that had been stored frozen at −70° C. was pulverized using a mortar and pestle in the presence of liquid nitrogen and the cells were lysed in 12 ml of lysis buffer (5 M guanidinium isothiocyanate, 50 mM TRIS, pH 7.4, 10 mM EDTA, 5% β-mercaptoethanol). Lysis buffer was added to the lysate to yield a final volume of 17 ml. N-laurylsarcosine and CsCl were added to the mixture to yield final concentrations of 4% and 0.01 g/ml, respectively, in a final volume of 18 ml.

The sample was centrifuged at 9,000 rpm in a Sorvall SS34 rotor for 10 min at room temperature to remove the insoluble material as a pellet. The supernatant was divided into two equal portions and each was layered onto a 2-ml cushion of a solution of 5.7 M CsCl, 0.1 M EDTA contained in separate centrifuge tubes to yield approximately 9 ml per tube. The samples were centrifuged in an SW41 rotor at 37,000 rpm for 24 h at 20° C.

After centrifugation, each RNA pellet was resuspended in 3 ml ETS (10 mM TRIS, pH 7.4, 10 mM EDTA, 0.2% SDS) and combined into a single tube. The RNA was precipitated with 0.25 M NaCl and two volumes of 95% ethanol.

The precipitate was collected by centrifugation and resuspended in 4 ml PK buffer (0.05 M TRIS, pH 8.4, 0.14 M NaCl, 0.01 M EDTA, 1% SDS). Proteinase K was added to the sample to a final concentration of 200 μg/ml. The sample was incubated at 22° C. for 1 h, followed by extraction with an equal volume of phenol:chloroform:isoamylalcohol (50:48:2) two times, followed by one extraction with an equal volume of chloroform: isoamylalcohol (24:1). The RNA was precipitated with ethanol and NaCl. The precipitate was resuspended in 400 μl of ETS buffer. The yield of total RNA was approximately 1.0 mg. Poly $A^+$ RNA (30 μg) was isolated from the total RNA according to standard methods as stated in Example I.A.1.

B. Library Construction

Double-stranded cDNA was synthesized according to standard methods [see, e.g., Sambrook et al. (1989) IN:

*Molecular Cloning, A Laboratory Manual*, Cold Spring Harbor Laboratory Press, Chapter 8]. Each library was prepared in substantially the same manner except for differences in: 1) the oligonucleotide used to prime the first strand cDNA synthesis, 2) the adapters that were attached to the double-stranded cDNA, 3) the method used to remove the free or unused adapters, and 4) the size of the fractionated cDNA ligated into the λ phage vector.

1. IMR32 cDNA Library #1

Single-stranded cDNA was synthesized using IMR32 poly(A⁺) RNA (Example I.A.1.) as a template and was primed using oligo (dT)$_{12-18}$ (Collaborative Research Inc., Bedford, Mass.). The single-stranded cDNA was converted to double-stranded cDNA and the yield was approximately 2 μg. EcoI adapters:

5'-AATTCGGTACGTACACTCGAGC-3'=22-mer (SEQ ID No.15)

3'-GCCATGCATGTGAGCTCG-5'=18-mer (SEQ ID No.16)

also containing SnaBI and XhoI restriction sites were then added to the double-stranded cDNA according to the following procedure.

a. Phosphorylation of 18-Mer

The 18-mer was phosphorylated using standard methods [see, e.g., Sambrook et al. (1989) IN: *Molecular Cloning, A Laboratory Manual*, Cold Spring Harbor Laboratory Press, Chapter 8] by combining in a 10 μl total volume the 18-mer (225 pmoles) with [³²P]γ-ATP (7000 Ci/mmole; 1.0 μl) and kinase (2 U) and incubating at 37° C. for 15 minutes. After incubation, 1 μl 10 mM ATP and an additional 2 U of kinase were added and incubated at 37° C. for 15 minutes. Kinase was then inactivated by boiling for 10 minutes.

b. Hybridization of 22-Mer

The 22-mer was hybridized to the phosphorylated 18-mer by addition of 225 pmoles of the 22-mer (plus water to bring volume to 15 μl), and incubation at 65° C. for 5 minutes. The reaction was then allowed to slow cool to room temperature.

The adapters were thus present at a concentration of 15 pmoles/μl, and were ready for cDNA-adapter ligation.

c. Ligation of Adapters to cDNA

After the EcoRI, SnaBI, XhoI adapters were ligated to the double-stranded cDNA using a standard protocol [see, e.g., Sambrook et al. (1989) IN: *Molecular Cloning, A Laboratory Manual*, Cold Spring Harbor Laboratory Press, Chapter 8], the ligase was inactivated by heating the mixture to 72° C. for 15 minutes. The following reagents were added to the cDNA ligation reaction and heated at 37° C. for 30 minutes: cDNA ligation reaction (20 μl), water (24 μl), 10× kinase buffer (3 μl), 10 mM ATP (1 μl) and kinase (2 μl of 2 U/μl). The reaction was stopped by the addition of 2 μl 0.5M EDTA, followed by one phenol/chloroform extraction and one chloroform extraction.

d. Size Selection and Packaging of cDNA

The double-stranded cDNA with the EcoRI, SnaBI, XhoI adapters ligated was purified away from the free or unligated adapters using a 5 ml Sepharose CL-4B column (Sigma, St. Louis, Mo.). 100 μl fractions were collected and those containing the cDNA, determined by monitoring the radioactivity, were pooled, ethanol precipitated, resuspended in TE buffer and loaded onto a 1% agarose gel. After the electrophoresis, the gel was stained with ethidium bromide and the 1 to 3 kb fraction was cut from the gel. The cDNA embedded in the agarose was eluted using the "Geneluter Electroelution System" (Invitrogen, San Diego, Calif.). The eluted cDNA was collected by ethanol precipitation and resuspended in TE buffer at 0.10 pmol/μl. The cDNA was ligated to 1 μg of EcoRI digested, dephosphorylated λgt11 in a 5 μl reaction volume at a 2- to 4-fold molar excess ratio of cDNA over the λgt11 vector. The ligated λgt11 containing the cDNA insert was packaged into λ phage virions in vitro using the Gigapack (Stratagene, La Jolla, Calif.) kit. The packaged phage were plated on an *E. coli* Y1088 bacterial lawn in preparation for screening.

2. IMR32 cDNA Library #2

This library was prepared as described (Example I.B.1.) with the exception that 3 to 9 kb cDNA fragments were ligated into the λgt11 phage vector rather than the 1 to 3 kb fragments.

3. IMR32 cDNA Library #3

IMR32 cell poly(A⁺) RNA (Example I.A.1.) was used as a template to synthesize single-stranded cDNA. The primers for the first strand cDNA synthesis were random primers (hexadeoxy-nucleotides [pd(N)$_6$] Cat #5020-1, Clontech, Palo Alto, Calif.). The double-stranded cDNA was synthesized, EcoRI, SnaBI, XhoI adapters were added to the cDNA, the unligated adapters were removed, and the double-stranded cDNA with the ligated adapters was fractionated on an agarose gel, as described in Example I.B.1. The cDNA fraction greater than 1.8 kb was eluted from the agarose, ligated into λgt11, packaged, and plated into a bacterial lawn of Y1088 (as described in Example I.B.1.).

4. IMR32 cDNA Library #4

IMR32 cell poly(A⁺) RNA (Example I.A.1.) was used as a template to synthesize single-stranded cDNA. The primers for the first strand cDNA synthesis were oligonucleotides: 89–365a specific for the $\alpha_{1D}$ (VDCC III) type $\alpha_1$-subunit (see Example II.A.) coding sequence (the complementary sequence of nt 2927 to 2956, SEQ ID No. 1), 89–495 specific for the $\alpha_{1C}$ (VDCC II) type $\alpha_1$-subunit (see Example II.B.) coding sequence (the complementary sequence of nt 852 to 873, SEQ ID No. 3), and 90–12 specific for the $\alpha_{1C}$-subunit coding sequence (the complementary sequence of nt 2496 to 2520, SEQ ID No. 3). The cDNA library was then constructed as described (Example I.B.3), except that the cDNA size-fraction greater than 1.5 kb was eluted from the agarose rather than the greater than 1.8 kb fraction.

5. IMR32 cDNA Library #5

The cDNA library was constructed as described (Example I.B.3.) with the exception that the size-fraction greater than 1.2 kb was eluted from the agarose rather than the greater than 1.8 kb fraction.

6. Human Thalamus cDNA Library #6

Human thalamus poly (A⁺) RNA (Example I.A.2.) was used as a template to synthesize single-stranded cDNA. Oligo (dT) was used to prime the first strand synthesis (Example I.B.1.). The double-stranded cDNA was synthesized (Example I.B.1.) and EcoRI, KpnI, NcoI adapters of the following sequence:

5' CCATGGTACCTTCGTTGACG 3'=20-mer (SEQ ID NO. 17)

3' GGTACCATGGAAGCAACTGCTTAA 5'=24-mer (SEQ ID NO. 18)

were ligated to the double-stranded cDNA as described (Example I.B.1.) with the 20-mer replacing the 18-mer and the 24-mer replacing the 22-mer. The unligated adapters were removed by passing the cDNA-adapter mixture through a 1 ml Bio Gel A-50 (Bio-Rad Laboratories, Richmond, Calif.) column. Fractions (30 μl) were collected and 1 μl of each fraction in the first peak of radioactivity was electrophoresed on a 1% agarose gel. After electrophoresis, the gel was dried on a vacuum gel drier and exposed to x-ray film. The fractions containing cDNA fragments greater than 600 bp were pooled, ethanol precipitated, and ligated into λgt11 (Example I.B.1.) . The construction of the cDNA library was completed as described (Example I.B.1.).

C. Hybridization and Washing Conditions

Hybridization of radiolabelled nucleic acids to immobilized DNA for the purpose of screening cDNA libraries, DNA Southern transfers, or northern transfers was routinely performed in standard hybridization conditions [hybridization: 50% deionized formamide, 200 μg/ml sonicated herring sperm DNA (Cat #223646, Boehringer Mannheim Biochemicals, Indianapolis, Ind.), 5×SSPE, 5×Denhardt's, 42° C.; wash :0.2×SSPE, 0.1% SDS, 65° C.] . The recipes for SSPE and Denhardt's and the preparation of deionized formamide are described, for example, in Sambrook et al. (1989) *Molecular Cloning, A Laboratory Manual*, Cold Spring Harbor Laboratory Press, Chapter 8). In some hybridizations, lower stringency conditions were used in that 10% deionized formamide replaced 50% deionized formamide described for the standard hybridization conditions.

The washing conditions for removing the non-specific probe from the filters was either high, medium, or low stringency as described below:

1) high stringency: 0.1×SSPE, 0.1% SDS, 65° C.

2) medium stringency: 0.2×SSPE, 0.1% SDS, 50° C.

3) low stringency: 1.0×SSPE, 0.1% SDS, 50° C.

It is understood that equivalent stringencies may be achieved using alternative buffers, salts and temperatures.

Example II

Isolation of DNA Encoding the Human Neuronal Calcium Channel $\alpha_1$ Subunit

A. Isolation of DNA Encoding the $\alpha_{1D}$ Subunit

1. Reference List of Partial $\alpha_{1D}$ cDNA Clones

Numerous $\alpha_{1D}$-specific cDNA clones were isolated in order to characterize the complete $\alpha_{1D}$ coding sequence plus portions of the 5' and 3' untranslated sequences. SEQ ID No. 1 shows the complete $\alpha_{1D}$ DNA coding sequence, plus 510 nucleotides of $\alpha_{1D}$ 5' untranslated sequence ending in the guanidine nucleotide adjacent to the adenine nucleotide of the proposed initiation of translation as well as 642 nucleotides of 3' untranslated sequence. Also shown in SEQ ID No. 1 is the deduced amino acid sequence. A list of partial cDNA clones used to characterize the $\alpha_{1D}$ sequence and the nucleotide position of each clone relative to the full-length $\alpha_{1D}$ cDNA sequence, which is set forth in SEQ ID No. 1, is shown below. The isolation and characterization of these clones are described below (Example II.A.2.).

IMR32 1.144 nt 1 to 510 of SEQ ID No. 1 5' untranslated sequence,
nt 511 to 2431, SEQ ID No. 1

IMR32* 1.136 nt 1627 to 2988, SEQ ID No. 1
nt 1 to 104 of SEQ ID No. 2 additional exon, IMR32@ 1.80 nt 2083 to 6468, SEQ ID No. 1

IMR32# 1.36 nt 2857 to 4281, SEQ ID No. 1

IMR32 1.163 nt 5200 to 7635, SEQ ID No. 1

* 5' of nt 1627, IMR32 1.136 encodes an intron and an additional exon described in Example II.A.2.d.

@ IMR32 1.80 contains two deletions, nt 2984 to 3131 and nt 5303 to 5349 (SEQ ID No. 1). The 148 nt deletion (nt 2984 to 3131) was corrected by performing a polymerase chain reaction described in Example II.A.3.b.

IMR32 1.36 contains a 132 nt deletion (nt 3081 to 3212).

2. Isolation and Characterization of Individual Clones Listed in Example II.A.1.

a. IMR32 1.36

Two million recombinants of the IMR32 cDNA library #1 (Example I.B.1.) were screened in duplicate at a density of approximately 200,000 plaques per 150 mm plate using a mixture of radiolabelled fragments of the coding region of the rabbit skeletal muscle calcium channel $\alpha_1$ cDNA [for the sequence of the rabbit skeletal muscle calcium channel a subunit cDNA, see, Tanabe et al. (1987). *Nature* 328:313–318]:

| Fragment | Nucleotides |
| --- | --- |
| KpnI - EcoRI | −78 to 1006 |
| EcoRI - XhoI | 1006 to 2653 |
| ApaI - ApaI | 3093 to 4182 |
| BglII - SacI | 4487 to 5310 |

The hybridization was performed using low stringency hybridization conditions (Example I.C.) and the filters were washed under low stringency (Example I.C.). Only one $\alpha_{1D}$-specific recombinant (IMR32 1.36) of the 2×10⁶ screened was identified. IMR32 1.36 was plaque purified by standard methods (J. Sambrook et al. (1989) *Molecular Cloning, A Laboratory Manual*, Cold Spring Harbor Laboratory Press, Chapter 8) subcloned into pGEM3 (Promega, Madison, Wis.) and characterized by DNA sequencing.

b. IMR32 1.80

Approximately 1×10⁶ recombinants of the IMR32 cDNA library #2 (Example I.B.2.) were screened in duplicate at a density of approximately 100,000 plaques per 150 mm plate using the IMR32 1.36 cDNA fragment (Example II.A.1) as a probe. Standard hybridization conditions were used, and the filters were washed under high stringency (Example I.C.). Three positive plaques were identified one of which was IMR32 1.80. IMR32 1.80 was plaque purified by standard methods, restriction mapped, subcloned, and characterized by DNA sequencing.

C. IMR32 1.144

Approximately 1×10⁶ recombinants of the IMR32 cDNA library #3 (Example I.B.3) were screened with the EcoRI-PvuII fragment (nt 2083 to 2518, SEQ ID No. 1) of IMR32 1.80. The hybridization was performed using standard hybridization conditions (Example I.C.) and the filters were washed under high stringency (Example I.C.). Three positive plaques were identified one of which was IMR32 1.144. IMR32 1.144 was plaque purified, restriction mapped, and the cDNA insert was subcloned into pGEM7Z (Promega, Madison, Wis.) and characterized by DNA sequencing. This characterization revealed that IMR32 1.144 has a series of ATG codons encoding seven possible initiating methionines (nt 511 to 531, SEQ ID No. 1). Nucleic acid amplification analysis, and DNA sequencing of cloned nucleic acid amplification analysis products encoding these seven ATG codons confirmed that this sequence is present in the $\alpha_{1D}$ transcript expressed in dbcAMP-induced IMR32 cells.

d. IMR32 1.136

Approximately 1×10⁶ recombinants of the IMR32 cDNA library #4 (Example I.B.4) were screened with the EcoRI-PvuII fragment (nt 2083 to 2518, SEQ ID No. 1) of IMR32 1.80 (Example II.A.1.). The hybridization was performed using standard hybridization conditions (Example I.C.) and the filters were washed under high stringency (Example I.C.). Six positive plaques were identified one of which was IMR32 1.136. IMR32 1.136 was plaque purified, restriction mapped, and the cDNA insert was subcloned into a standard plasmid vector, pSP72 (Promega, Madison, Wis.), and characterized by DNA sequencing. This characterization revealed that IMR32 1.136 encodes an incompletely spliced $\alpha_{1D}$ transcript. The clone contains nucleotides 1627 to 2988 of SEQ ID No. 1 preceded by an approximate 640 bp intron. This intron is then preceded by a 104 nt exon (SEQ ID No. 2) which is an alternative exon encoding the IS6 transmembrane domain [see, e.g., Tanabe et al. (1987) *Nature* 328:313–318 for a description of the IS1 to IVS6 transmembrane terminology] of the $\alpha_{1D}$ subunit and can replace nt 1627 to 1730, SEQ ID No. 1, to produce a completely spliced $\alpha_{1D}$ transcript.

e. IMR32 1.163

Approximately 1×10⁶ recombinants of the IMR32 cDNA library #3 (Example I.B.3.) were screened with the NcoI-XhoI fragment of IMR32 1.80 (Example II.A.1.) containing nt 5811 to 6468 (SEQ ID No. 1). The hybridization was performed using standard hybridization conditions (Example I.C.) and the filters were washed under high stringency (Example I.C.). Three positive plaques were identified one of which was IMR32 1.163. IMR32 1.163 was plaque purified, restriction mapped, and the cDNA insert was subcloned into a standard plasmid vector, pSP72 (Promega, Madison, Wis.), and characterized by DNA sequencing. This characterization revealed that IMR32 1.163 contains the $\alpha_{1D}$ termination codon, nt 6994 to 6996 (SEQ ID No. 1).

3. Construction of a Full-Length $\alpha_{1D}$ cDNA [pVDCCIII (A)]

$\alpha_{1D}$ cDNA clones IMR32 1.144, IMR32 1.136, IMR32 1.80, and IMR32 1.163 (Example II.A.2.) overlap and include the entire $\alpha_{1D}$ coding sequence, nt 511 to 6993 (SEQ ID No. 1), with the exception of a 148 bp deletion, nt 2984 to 3131 (SEQ ID No. 1). Portions of these partial cDNA clones were ligated to generate a full-length $\alpha_{1D}$ cDNA in a eukaryotic expression vector. The resulting vector was called pVDCCIII (A). The construction of PVDCCIII (A) was performed in four steps described in detail below: (1) the construction of pVDCCIII/5' using portions of IMR32 1.144, IMR32 1.136, and IMR32 1.80, (2) the construction of pVDCCIII/5'.3 that corrects the 148 nt deletion in the IMR32 1.80 portion of pVDCCIII/5', (3) the construction of pVDCCIII/3'.1 using portions of IMR32 1.80 and IMR32 1.163, and (4) the ligation of a portion of the pVDCCIII/5'.3 insert, the insert of pVDCCIII/3'.1, and pcDNA1 (Invitrogen, San Diego, Calif.) to form PVDCCIII(A). The vector pcDNA1 is a eukaryotic expression vector containing a cytomegalovirus (CMV) promoter which is a constitutive promoter recognized by mammalian host cell RNA polymerase II.

Each of the DNA fragments used in preparing the full-length construct was purified by electrophoresis through an agarose gel onto DE81 filter paper (Whatman, Clifton, N.J.) and elution from the filter paper using 1.0 M NaCl, 10 mM TRIS, pH 8.0, 1 mM EDTA. The ligations typically were performed in a 10 µl reaction volume with an equal molar ratio of insert fragment and a two-fold molar excess of the total insert relative to the vector. The amount of DNA used was normally about 50 ng to 100 ng.

a. pVDCCIII/5'

To construct pVDCCIII/5', IMR32 1.144 (Example II.A.2.c.) was digested with XhoI and EcoRI and the fragment containing the vector (pGEM7Z), $\alpha_{1D}$ nt 1 to 510 (SEQ ID No. 1), and $\alpha_{1D}$ nt 511 to 1732 (SEQ ID No. 1) was isolated by gel electrophoresis. The EcoRI-ApaI fragment of IMR32 1.136 (Example II.A.2.d.) nucleotides 1733 to 2671 (SEQ ID No. 1) was isolated, and the ApaI-HindIII fragment of IMR32 1.80 (Example II.A.2.b.), nucleotides 2672 to 4492 (SEQ ID No. 1) was isolated. The three DNA clones were ligated to form pVDCCIII/5' containing nt 1 to 510 (5' untranslated sequence; SEQ ID No. 1) and nt 511 to 4492 (SEQ ID No. 1).

b. pVDCCIII/5'.3

Comparison of the IMR32 1.36 and IMR32 1.80 DNA sequences revealed that these two cDNA clones differ through the $\alpha_{1D}$ coding sequence, nucleotides 2984 to 3212. Nucleic acid amplification analysis of IMR32 1.80 and dbcAMP-induced (1.0 mM, 10 days) IMR32 cytoplasmic RNA (isolated according to Ausubel, F. M. et al. (Eds) (1988) *Current Protocols in Molecular Biology*, John Wiley and Sons, New York) revealed that IMR32 1.80 had a 148 nt deletion, nt 2984 to 3131 (SEQ ID No. 1), and that IMR32 1.36 had a 132 nt deletion, nt 3081 to 3212. To perform the nucleic acid amplification analysis, the amplification reaction was primed with $\alpha_{1D}$-specific oligonucleotides 112 (nt 2548 to 2572, SEQ ID No. 1) and 311 (the complementary sequence of nt 3928 to 3957, SEQ ID No. 1). These products were then reamplified using $\alpha_{1D}$-specific oligeonucleotides 310 (nt 2583 to 2608 SEQ ID No. 1) and 312 (the complementary sequence of nt 3883 to 3909). This reamplified product, which contains AccI and BglII restriction sites, was digested with AccI and BglII and the AccI-BglII fragment, nt 2765 to 3890 (SEQ ID No. 1) was cloned into AccI-BglII digested pVDCCIII/5' to replace the AccI-BglII pVDCCIII/5' fragment that had the deletion. This new construct was named pVDCCIII/5'.3. DNA sequence determination of pVDCCIII/5'.3 through the amplified region confirmed the 148 nt deletion in IMR32 1.80.

c. pVDCCIII/3'.1

To construct pVDCCIII/3'.1, the cDNA insert of IMR32 1.163 (Example II.A.2.e.) was subcloned into pBluescript II (Stratagene, La Jolla, Calif.) as an XhoI fragment. The XhoI sites on the cDNA fragment were furnished by the adapters used to construct the cDNA library (Example I.B.3.). The insert was oriented such that the translational orientation of the insert of IMR32 1.163 was opposite to that of the lacZ gene present in the plasmid, as confirmed by analysis of restriction enzyme digests of the resulting plasmid. This was done to preclude the possibility of expression of $\alpha_{1D}$ sequences in DH5α cells transformed with this plasmid due to fusion with the lacZ gene. This plasmid was then digested with HindIII and BglII and the HindIII-BglII fragment (the HindIII site comes from the vector and the BglII site is at nt 6220, SEQ ID No. 1) was eliminated, thus deleting nt 5200 to 6220 (SEQ ID No. 1) of the IMR32 1.163 clone and removing this sequence from the remainder of the plasmid which contained the 3' BglII-XhoI fragment, nt 6221 to 7635 (SEQ ID No. 1). pVDCCIII/3'.1 was then made by splicing together the HindIII-PvuII fragment from IMR32 1.80 (nucleotides 4493–5296, SEQ ID No. 1), the PvuII-BglII fragment of IMR32 1.163 (nucleotides 5294 to 6220, SEQ ID No. 1) and the HindIII-BglII-digested pBluescript plasmid containing the 3' BglII/XhoI IMR32 1.163 fragment (nt 6221 to 7635, SEQ ID No. 1).

d. pVDCCIII(A): the Full-Length $\alpha_{1D}$ Construct

To construct pVDCCIII(A), the DraI-HindIII fragment (5' untranslated sequence nt 330 to 510, SEQ ID No. 1 and coding sequence nt 511 to 4492, SEQ ID No. 1) of PVDCCIII/5'.3 (Example II.A.3.b.) was isolated; the HindIII-XhoI fragment of pVDCCIII/3'.1 (containing nt 4493 to 7635, SEQ ID No. 1, plus the XhoI site of the adapter) (Example II.A.3.c.) was isolated; and the plasmid vector, pcDNA1, was digested with EcoRV and XhoI and isolated on an agarose gel. The three DNA fragments were ligated and MC1061-P3 (Invitrogen, San Diego, Calif.) was transformed. Isolated clones were analyzed by restriction mapping and DNA sequencing and pVDCCIII (A) was identified which had the fragments correctly ligated together: DraI-HindIII, HindIII-XhoI, XhoI-EcoRV with the blunt-end DraI and EcoRV site ligating together to form the circular plasmid.

The amino-terminus of the $\alpha_{1D}$ subunit is encoded by the seven consecutive 5' methionine codons (nt 511 to 531, SEQ ID No. 1). This 5' portion plus nt 532 to 537, encoding two lysine residues, were deleted from PVDCCIII (A) and replaced with an efficient ribosomal binding site (5'-ACCACC-3') to form pVDCCIII.RBS(A). Expression experiments in which transcripts of this construct were injected into *Xenopus laevis* oöcytes did not result in an enhancement in the recombinant voltage-dependent calcium channel expression level relative to the level of expression in oöcytes injected with transcripts of pVDCCIII(A).

B. Isolation of DNA Encoding the $\alpha_{1C}$ Subunit

1. Reference List of Partial $\alpha_{1C}$ cDNA Clones

Numerous $\alpha_{1C}$-specific cDNA clones were isolated in order to characterize the $\alpha_{1C}$ coding sequence, the $\alpha_{1C}$ initiation of translation, and an alternatively spliced region of $\alpha_{1C}$. SEQ ID No. 3 sets forth one $\alpha_{1C}$ coding sequence ($\alpha_{1C\text{-}1}$) and deduced amino acid sequence; SEQ ID No. 36 sets forth another splice variant designated $\alpha_{1C\text{-}2}$. SEQ ID No. 4 and No. 5 encode two possible amino terminal ends of an $\alpha_{1C}$ splice variant. SEQ ID No. 6 encodes an alternative exon for the IV S3 transmembrane domain. Other $\alpha_{1C}$ variants can be constructed by selecting the alternative amino terminal ends in place of the ends in SEQ ID No. 3 or 36 and/or inserting the alternative exon (SEQ ID No. 6) in the appropriate location, such as in SEQ ID NO. 3 in place of nucleotides 3904–3987. In addition, the 75 nucleotide sequence (nucleotides 1391–1465 in SEQ ID No. 3) can be deleted or inserted to produce an alternative $\alpha_{1C}$ splice variant.

Shown below is a list of clones used to characterize the $\alpha_{1C}$ sequence and the nucleotide position of each clone relative to the characterized $\alpha_{1C}$ sequence (SEQ ID No. 3). The isolation and characterization of these cDNA clones are described below (Example II.B.2).

IMR32 1.66 nt 1 to 916, SEQ ID No. 3
   nt 1 to 132, SEQ ID No. 4
IMR32 1.157 nt 1 to 873, SEQ ID No. 3
   nt 1 to 89, SEQ ID No. 5
IMR32 1.67 nt 50 to 1717, SEQ ID No. 3
*IMR32 1.86 nt 1366 to 2583, SEQ ID No. 3
@1.16G nt 758 to 867, SEQ ID No. 3
IMR32 1.37 nt 2804 to 5904, SEQ ID No. 3
CNS 1.30 nt 2199 to 3903, SEQ ID No. 3
   nt 1 to 84 of alternative exon, SEQ ID No. 6
IMR32 1.38 nt 2448 to 4702, SEQ ID No. 3
   nt 1 to 84 of alternative exon, SEQ ID No. 6

* IMR32 1.86 has a 73 nt deletion compared to the rabbit cardiac muscle calcium channel $\alpha_1$ subunit cDNA sequence.
@1.16G is an $\alpha_{1C}$ genomic clone.

2. Isolation and Characterization of Clones Described in Example II.B.1.

a. CNS 1.30

Approximately $1\times10^6$ recombinants of the human thalamus cDNA library No. 6 (Example I.B.6.) were screened with fragments of the rabbit skeletal muscle calcium channel $\alpha_1$ cDNA described in Example II.A.2.a. The hybridization was performed using standard hybridization conditions (Example I.C.) and the filters were washed under low stringency (Example I.C.). Six positive plaques were identified, one of which was CNS 1.30. CNS 1.30 was plaque purified, restriction mapped, subcloned, and characterized by DNA sequencing. CNS 1.30 encodes $\alpha_{1C}$-specific sequence nt 2199 to 3903 (SEQ ID No. 3) followed by nt 1 to 84 of one of two identified alternative $\alpha_{1C}$ exons (SEQ ID No. 6). 3' of SEQ ID No. 6, CNS 1.30 contains an intron and, thus, CNS 1.30 encodes a partially spliced $\alpha_{1C}$ transcript.

b. 1.16G

Approximately $1\times10^6$ recombinants of a XEMBL3-based human genomic DNA library (Cat # HL1006d Clontech Corp., Palo Alto, Calif.) were screened using a rabbit skeletal muscle cDNA fragment (nt –78 to 1006, Example II.A.2.a.). The hybridization was performed using standard hybridization conditions (Example I.C.) and the filters were washed under low stringency (Example I.C.). Fourteen positive plaques were identified, one of which was 1.16G. Clone 1.16G was plaque purified, restriction mapped, subcloned, and portions were characterized by DNA sequencing. DNA sequencing revealed that 1.16G encodes $\alpha_{1C}$-specific sequence as described in Example II.B.1.

c. IMR32 1.66 and IMR32 1.67

Approximately $1\times10^6$ recombinants of IMR32 cDNA library #5 (Example I.B.5.) were screened with a 151 bp KpnI-SacI fragment of 1.16G (Example II.B.2.b.) encoding $\alpha_{1C}$ sequence (nt 758 to 867, SEQ ID No. 3). The hybridization was performed using standard hybridization conditions (Example I.C.). The filters were then washed in 0.5× SSPE at 65° C. Of the positive plaques, IMR32 1.66 and IMR32 1.67 were identified. The hybridizing plaques were purified, restriction mapped, subcloned, and characterized by DNA sequencing. Two of these cDNA clones, IMR32 1.66 and 1.67, encode $\alpha_{1C}$ subunits as described (Example II.B.1.). In addition, IMR32 1.66 encodes a partially spliced $\alpha_{1C}$ transcript marked by a GT splice donor dinucleotide beginning at the nucleotide 3' of nt 916 (SEQ ID No. 3). The intron sequence within 1.66 is 101 nt long. IMR32 1.66 encodes the $\alpha_{1C}$ initiation of translation, nt 1 to 3 (SEQ ID No. 3) and 132 nt of 5' untranslated sequence (SEQ ID No. 4) precede the start codon in IMR32 1.66.

d. IMR32 1.37 and IMR32 1.38

Approximately $2\times10^6$ recombinants of IMR32 cDNA library #1 (Example I.B.1.) were screened with the CNS 1.30 cDNA fragment (Example II.B.2.a.). The hybridization was performed using low stringency hybridization conditions (Example I.C.) and the filters were washed under low stringency (Example I.C.). Four positive plaques were identified, plaque purified, restriction mapped, subcloned, and characterized by DNA sequencing. Two of the clones, IMR32 1.37 and IMR32 1.38 encode $\alpha_{1C}$-specific sequences as described in Example II.B.1.

DNA sequence comparison of IMR32 1.37 and IMR32 1.38 revealed that the $\alpha_{1C}$ transcript includes two exons that encode the IVS3 transmembrane domain. IMR32 1.37 has a single exon, nt 3904 to 3987 (SEQ ID No. 3) and IMR32 1.38 appears to be anomalously spliced to contain both exons juxtaposed, nt 3904 to 3987 (SEQ ID No. 3) followed by nt 1 to 84 (SEQ ID No. 6). The alternative splice of the $\alpha_{1C}$ transcript to contain either of the two exons encoding the IVS3 region was confirmed by comparing the CNS 1.30 sequence to the IMR32 1.37 sequence. CNS 1.30 contains nt 1 to 84 (SEQ ID No. 6) preceded by the identical sequence contained in IMR32 1.37 for nt 2199 to 3903 (SEQ ID No. 3). As described in Example II.B.2.a., an intron follows nt 1 to 84 (SEQ ID No. 6). Two alternative exons have been spliced adjacent to nt 3903 (SEQ ID No. 3) represented by CNS 1.30 and IMR32 1.37.

e. IMR32 1.86

IMR32 cDNA library #1 (Example I.B.1.) was screened in duplicate using oligonucleotide probes 90-9 (nt 1462 to 1491, SEQ ID No. 3) and 90-12 (nt 2496 to 2520, SEQ ID No. 3). These oligonucleotide probes were chosen in order to isolate a clone that encodes the $\alpha_{1C}$ subunit between the 3' end of IMR32 1.67 (nt 1717, SEQ ID No. 3) and the 5' end of CNS 1.30 (nt 2199, SEQ ID No. 3). The hybridization conditions were standard hybridization conditions (Example I.C.) with the exception that the 50% deionized formamide was reduced to 20%. The filters were washed under low stringency (Example I.C.). Three positive plaques were identified one of which was IMR32 1.86. IMR32 1.86 was plaque purified, subcloned, and characterized by restriction mapping and DNA sequencing. IMR32 1.86 encodes $\alpha_{1C}$ sequences as described in Example II.B.1. Characterization by DNA sequencing revealed that IMR32 1.86 contains a 73 nt deletion compared to the DNA encoding rabbit cardiac muscle calcium channel $\alpha_1$ subunit [Mikami et al. (1989) Nature 340:230], nt 2191 to 2263. These missing nucleotides correspond to nt 2176–2248 of SEQ ID No. 3. Because the 5'-end of CNS 1.30 overlaps the 3'-end of IMR32 1.86, some of these missing nucleotides, i.e., nt 2205–2248 of SEQ ID No. 3, are accounted for by CNS 1.30. The remaining missing nucleotides of the 73 nucleotide deletion in IMR32 1.86 (i.e., nt 2176–2204 SEQ ID No. 3) were determined by nucleic acid amplification analysis of dbcAMP-induced IMR32 cell RNA. The 73 nt deletion is a frame-shift mutation and, thus, needs to be corrected. The exact human sequence through this region, (which has been determined by the DNA sequence of CNS 1.30 and nucleic acid amplification analysis of IMR32 cell RNA) can be inserted into IMR32 1.86 by standard methods, e.g., replacement of a restriction fragment or site-directed mutagenesis.

f. IMR32 1.157

One million recombinants of IMR32 cDNA library #4 (Example I.B.4.) were screened with an XhoI-EcoRI fragment of IMR32 1.67 encoding $\alpha_{1C}$ nt 50 to 774 (SEQ ID No. 3). The hybridization was performed using standard hybridization conditions (Example I.C.). The filters were washed under high stringency (Example I.C.). One of the positive plaques identified was IMR32 1.157. This plaque was purified, the insert was restriction mapped and subcloned to a standard plasmid vector pGEM7Z (Promega, Madison, Wis.). The DNA was characterized by sequencing. IMR32 1.157 appears to encodes an alternative 5' portion of the $\alpha_{1C}$ sequence beginning with nt 1 to 89 (SEQ ID No. 5) and followed by nt 1 to 873 (SEQ ID No. 3). Analysis of the 1.66 and 1.157 5' sequence is described below (Example II.B.3.).

3. Characterization of the $\alpha_{1C}$ Initiation of Translation Site

Portions of the sequences of IMR32 1.157 (nt 57 to 89, SEQ ID No. 5; nt 1 to 67, SEQ ID No. 3), IMR32 1.66 (nt 100 to 132, SEQ ID No. 4; nt 1 to 67, SEQ ID No. 3), were compared to the rabbit lung CaCB-receptor cDNA sequence, nt −33 to 67 [Biel et al. (1990) *FEBS Lett.* 269:409]. The human sequences are possible alternative 5' ends of the $\alpha_{1C}$ transcript encoding the region of initiation of translation. IMR32 1.66 closely matches the CaCB receptor cDNA sequence and diverges from the CaCB receptor cDNA sequence in the 5' direction beginning at nt 122 (SEQ ID No. 4). The start codon identified in the CaCB receptor cDNA sequence is the same start codon used to describe the $\alpha_{1C}$ coding sequence, nt 1 to 3 (SEQ ID No. 3).

The sequences of $\alpha_{1C}$ splice variants, designated $\alpha_{1C-1}$ and $\alpha_{1C-2}$ are set forth in SEQ ID NOs. 3 and 36.

C. Isolation of Partial cDNA Clones Encoding the $\alpha_{1B}$ Subunit and Construction of a Full-Length Clone A human basal ganglia cDNA library was screened with the rabbit skeletal muscle $\alpha_1$ subunit cDNA fragments (see Example II.A.2.a for description of fragments) under low stringency conditions. One of the hybridizing clones was used to screen an IMR32 cell cDNA library to obtain additional partial $\alpha_{1B}$ cDNA clones, which were in turn used to further screen an IMR32 cell cDNA library for additional partial cDNA clones. One of the partial IMR32 $\alpha_{1B}$ clones was used to screen a human hippocampus library to obtain a partial $\alpha_{1B}$ clone encoding the 3' end of the $\alpha_{1B}$ coding sequence. The sequence of some of the regions of the partial cDNA clones was compared to the sequence of products of nucleic acid amplification analysis of IMR32 cell RNA to determine the accuracy of the cDNA sequences.

Nucleic acid amplification analysis of IMR32 cell RNA and genomic DNA using oligonucleotide primers corresponding to sequences located 5' and 3' of the STOP codon of the DNA encoding the $\alpha_{1B}$ subunit revealed an alternatively spliced $\alpha_{1B}$-encoding mRNA in IMR32 cells. This second mRNA product is the result of differential splicing of the $\alpha_{1B}$ subunit transcript to include another exon that is not present in the mRNA corresponding to the other 3'$\alpha_{1B}$ cDNA sequence that was initially isolated. To distinguish these splice variants of the $\alpha_{1B}$ subunit, the subunit encoded by a DNA sequence corresponding to the form containing the additional exon is referred to as $\alpha_{1B-1}$ (SEQ ID No. 7), whereas the subunit encoded by a DNA sequence corresponding to the form lacking the additional exon is referred to as $\alpha_{1B-2}$ (SEQ ID No. 8). The sequence of $\alpha_{1B-1}$ diverges from that of $\alpha_{1B-2}$ beginning at nt 6633 (SEQ ID No. 7). Following the sequence of the additional exon in $\alpha_{1B-1}$ (nt 6633–6819; SEQ ID No. 7), the $\alpha_{1B-1}$ and $\alpha_{1B-2}$ sequences are identical (i.e., nt 6820–7362 in SEQ ID No. 7 and nt 6633–7175 in SEQ ID No. 8). SEQ ID No. 7 and No. 8 set forth 143 nt of 5' untranslated sequence (nt 1–143) as well as 202 nt of 3' untranslated sequence (nt 7161–7362, SEQ ID No. 7) of the DNA encoding $\alpha_{1B-1}$ and 321 nt of 3' untranslated sequence (nt 6855–7175, SEQ ID No. 8) of the DNA encoding $\alpha_{1B-2}$.

Nucleic acid amplification analysis of the IS6 region of the $\alpha_{1B}$ transcript revealed what appear to be additional splice variants based on multiple fragment sizes seen on an ethidium bromide-stained agarose gel containing the products of the amplification reaction.

A full-length $\alpha_{1B-1}$ cDNA clone designated pcDNA-$\alpha_{1B-1}$ was prepared in an eight-step process as follows.

STEP 1: The SacI restriction site of pGEM3 (Promega, Madison, Wis.) was destroyed by digestion at the SacI site, producing blunt ends by treatment with T4 DNA polymerase, and religation. The new vector was designated pGEMΔSac.

STEP 2: Fragment 1 (HindIII/KpnI; nt 2337 to 4303 of SEQ ID No. 7) was ligated into HindIII/KpnI digested pGEM3ΔSac to produce pα1.177HK.

STEP 3: Fragment 1 has a 2 nucleotide deletion (nt 3852 and 3853 of SEQ ID No. 7). The deletion was repaired by inserting an amplfied fragment (fragment 2) of IMR32 RNA into pα1.177HK. Thus, fragment 2 (NarI/KpnI; nt 3828 to 4303 of SEQ ID No. 7) was inserted into NarI/KpnI digested pα1.177HK replacing the NarI/KpnI portion of fragment 1 and producing pα1.177HK/PCR.

STEP 4: Fragment 3 (KpnI/KpnI; nt 4303 to 5663 of SEQ ID No. 7) was ligated into KpnI digested pa1.177HK/PCR to produce pα1B5'K.

STEP 5: Fragment 4 (EcoRI/HindIII; EcoRI adaptor plus nt 1 to 2337 of SEQ ID No. 7) and fragment 5 (HindIII/XhoI fragment of pα1B5'K; nt 2337 to 5446 of SEQ ID No. 7) were ligated together into EcoRI/XhoI digested pcDNA1 (Invitrogen, San Diego, Calif.) to produce pα1B5'.

STEP 6: Fragment 6 (EcoRI/EcoRI; EcoRI adapters on both ends plus nt 5749 to 7362 of SEQ ID No. 7) was ligated into EcoRI digested pBluescript II KS (Stratagene, La Jolla, Calif.) with the 5' end of the fragment proximal to the KpnI site in the polylinker to produce pα1.230.

STEP 7: Fragment 7 (KpnI/XhoI; nt 4303 to 5446 of SEQ ID No. 7), and fragment 8 (XhoI/CspI; nt 5446 to 6259 of SEQ ID No. 7) were ligated into KpnI/CspI digested pα1.230 (removes nt 5749 to 6259 of SEQ ID No. 7 that was encoded in pal.230 and maintains nt 6259 to 7362 of SEQ ID No. 7) to produce pα1B3'.

STEP 8: Fragment 9 (SphI/XhoI; nt 4993 to 5446 of SEQ ID No. 7) and fragment 10 (XhoI/XbaI of pα1B3'; nt 5446 to 7319 of SEQ ID No. 7) were ligated into SphI/XbaI digested pα1B5' (removes nt 4993 to 5446 of SEQ ID No. 7 that were encoded in pα1B5' and maintains nt 1 to 4850 of SEQ ID No. 7) to produce pcDNAα$_{1B-1}$.

The resulting construct, pcDNAα$_{1B-1}$, contains, in pCDNA1, a full-length coding region encoding α$_{1B-1}$ (nt 144–7362, SEQ ID No. 7), plus 5' untranslated sequence (nt 1–143, SEQ ID No. 7) and 3' untranslated sequence (nt 7161–7319, SEQ ID No. 7) under the transcriptional control of the CMV promoter.

D. Isolation of DNA Encoding Human Calcium Channel α$_{1A}$ Subunits

1. Isolation of Partial Clones

DNA clones encoding portions of human calcium channel α$_{1A}$ subunits were obtained by hybridization screening of human cerebellum cDNA libraries and nucleic acid amplification of human cerebellum RNA. Clones corresponding to the 3' end of the α$_{1A}$ coding sequence were isolated by screening 1×10$^6$ recombinants of a randomly primed cerebellum cDNA library (size-selected for inserts greater than 2.8 kb in length) under low stringency conditions (6× SSPE, 5× Denhart's solution, 0.2% SDS, 200 μg/ml sonicated herring sperm DNA, 42° C.) with oligonucleotide 704 containing nt 6190–6217 of the rat α$_{1A}$ coding sequence [Starr et al. (1992) Proc. Natl. Acad. Sci. U.S.A. 88:5621–5625]. Washes were performed under low stringency conditions. Several clones that hybridized to the probe (clones α1.251–α1.259 and α1.244) were purified and characterized by restriction enzyme mapping and DNA sequence analysis. At least two of the clones, α1.244 and α1.254, contained a translation termination codon. Although clones α1.244 and α1.254 are different lengths, they both contain a sequence of nucleotides that corresponds to the extreme 3' end of the α$_{1A}$ transcript, i.e., the two clones overlap. These two clones are identical in the region of overlap, except, clone α1.244 contains a sequence of 5 and a sequence of 12 nucleotides that are not present in α1.254.

To obtain additional α$_{1A}$-encoding clones, 1×10$^6$ recombinants of a randomly primed cerebellum cDNA library (size-selected for inserts ranging from 1.0 to 2.8 kb in length) was screened for hybridization to three oligonucleotides: oligonucleotide 701 (containing nucleotides 2288–2315 of the rat α$_{1A}$ coding sequence), oligonucleotide 702 (containing nucleotides 3559–3585 of the rat α$_{1A}$ coding sequence) and oligonucleotide 703 (containing nucleotides 4798–4827 of the rat α$_{1A}$ coding sequence). Hybridization and washes were performed using the same conditions as used for the first screening with oligonucleotide 704, except that washes were conducted at 45° C. Twenty clones (clones α1.269–α1.288) hybridized to the probe. Several clones were plaque-purified and characterized by restriction enzyme mapping and DNA sequence analysis. One clone, α1.279, contained a sequence of about 170 nucleotides that is not present in other clones corresponding to the same region of the coding sequence. This region may be present in other splice variants. None of the clones contained a translation intiation codon.

To obtain clones corresponding to the 5' end of the human α$_{1A}$ coding sequence, another cerebellum cDNA library was prepared using oligonucleotide 720 (containing nucleotides 2485–2510 of SEQ ID No. 22) to specifically prime first-strand cDNA synthesis. The library (8×10$^5$ recombinants) was screened for hybridization to three oligonucleotides: oligonucleotide 701, oligonucleotide 726 (containing nucleotides 2333–2360 of the rat α$_{1A}$ coding sequence) and oligonucleotide 700 (containing nucleotides 767–796 of the rat α$_{1A}$ coding sequence) under low stringency hybridization and washing conditions. Approximately 50 plaques hybridized to the probe. Hybridizing clones α1.381–α1.390 were plaque-purified and characterized by restriction enzyme maping and DNA sequence analysis. At least one of the clones, α1.381, contained a translation initiation codon.

Alignment of the sequences of the purified clones revealed that the sequences overlapped to comprise the entire α$_{1A}$ coding sequence. However, not all the overlapping sequences of partial clones contained convenient enzyme restriction sites for use in ligating partial clones to construct a full-length α$_{1A}$ coding sequence. To obtain DNA fragments containing convenient restriction enzyme sites that could be used in constructing a full-length α$_{1A}$ DNA, cDNA was synthesized from RNA isolated from human cerebellum tissue and subjected to nucleic acid amplification. The oligonucleotides used as primers corresponded to human α$_{1A}$ coding sequence located 5' and 3' of selected restriction enzyme sites. Thus, in the first amplification reaction, oligonucleotides 753 (containing nucleotides 2368–2391 of SEQ ID No. 22) and 728 (containing nucleotides 3179–3202 of SEQ ID No. 22) were used as the primer pair. To provide a sufficient amount of the desired DNA fragment, the product of this amplification was reamplified using oligonucleotides 753 and 754 (containing nucleotides 3112–3135 of SEQ ID No. 22 as the primer pair. The resulting product was 768 bp in length. In the second amplification reaction, oligonucleotides 719 (containing nucleotides 4950–4975 of SEQ ID No. 22 and 752 (containing nucleotides 5647–5670 of SEQ ID No. 22) were used as the primer pair. To provide a sufficient amount of the desired second DNA fragment, the product of this amplification was reamplified using oligonucleotides 756 (containing nucleotides 5112–5135 of SEQ ID No. 22) and 752 as the primer pair. The resulting product was 559 bp in length.

2. Construction of Full-Length $\alpha_{1A}$ Coding Sequences

Portions of clone α1.381, the 768-bp nucleic acid amplification product, clone α1.278, the 559-bp nucleic acid amplification product, and clone α1.244 were ligated at convenient restriction sites to generate a full-length $\alpha_{1A}$ coding sequence referred to as $\alpha_{1A-1}$.

Comparison of the results of sequence analysis of clones α1.244 and α1.254 indicated that the primary transcript of the $\alpha_{1A}$ subunit gene is alternatively spliced to yield at least two variant mRNAs encoding different forms of the $\alpha_{1A}$ subunit. One form, $\alpha_{1A-1}$, is encoded by the sequence shown in SEQ ID No. 22. The sequence encoding a second form, $\alpha_{1A-2}$, differs from the $\alpha_{1A-1}$-encoding sequence at the 3' end in that it lacks a 5-nt sequence found in clone α1.244 (nucleotides 7035–7039 of SEQ ID No. 22). This deletion shifts the reading frame and introduces a translation termination codon resulting in an $\alpha_{1A-2}$ coding sequence that encodes a shorter $\alpha_{1A}$ subunit than that encoded by the $\alpha_{1A-1}$ splice variant. Consequently, a portion of the 3' end of the $\alpha_{1A-1}$ coding sequence is actually 3' untranslated sequence in the $\alpha_{1A-2}$ DNA. The complete sequence of $\alpha_{1A-2}$, which can be constructed by ligating portions of clone α1.381, the 768-bp nucleic acid amplification product, clone α1.278, the 559-bp nucleic acid amplification product and clone α1.254, is set forth in SEQ ID No. 23.

E. Isolation of DNA Encoding the $\alpha_{1E}$ Subunit

DNA encoding $\alpha_{1E}$ subunits of the human calcium channel were isolated from human hippocampus libraries. The selected clones sequenced. DNA sequence analysis of DNA clones encoding the $\alpha_{1E}$ subunit indicated that at least two alternatively spliced forms of the same $\alpha_{1E}$ subunit primary transcript are expressed. One form has the sequence set forth in SEQ ID No. 24 and was designated $\alpha_{1E-1}$ and the other was designated $\alpha_{1E-3}$, which has the sequence obtained by inserting a 57 base pair fragment between nucleotides 2405 and 2406 of SEQ ID No. 24. The resulting sequence is set forth in SEQ ID No. 25.

The subunit designated $\alpha_{1E-1}$ has a calculated molecular weight of 254,836 and the subunit designated $\alpha_{1E-3}$ has a calculated molecular weight of 257,348. $\alpha_{1E-3}$ has a 19 amino acid insertion (encoded by SEQ ID No. 25) relative to $\alpha_{1E-1}$ in the region that appears to be the cytoplasmic loop between transmembrane domains IIS6 and IIIS1.

Example III

Isolation of cDNA Clones Encoding the Human Neuronal Calcium Channel $\beta_1$ Subunit A. Isolation of Partial cDNA Clones Encoding the β Subunit and Construction of a Full-Length Clone Encoding the $\beta_1$ Subunit A human hippocampus cDNA library was screened with the rabbit skeletal muscle calcium channel $\beta_1$ subunit cDNA fragment (nt 441 to 1379) [for isolation and sequence of the rabbit skeletal muscle calcium channel $\beta_1$ subunit cDNA, see U.S. patent application Ser. No. 482,384 or Ruth et al. (1989) *Science* 245:1115] using standard hybridization conditions (Example I.C.). A portion of one of the hybridizing clones was used to rescreen the hippocampus library to obtain additional cDNA clones. The cDNA inserts of hybridizing clones were characterized by restriction mapping and DNA sequencing and compared to the rabbit skeletal muscle calcium channel $\beta_1$ subunit cDNA sequence.

Portions of the partial $\beta_1$ subunit cDNA clones were ligated to generate a full-length clone encoding the entire $\beta_1$ subunit. SEQ ID No. 9 shows the $\beta_1$ subunit coding sequence (nt 1–1434) as well as a portion of the 3' untranslated sequence (nt 1435–1546). The deduced amino acid sequence is also provided in SEQ ID No. 9. In order to perform expression experiments, full-length $\beta_1$ subunit cDNA clones were constructed as follows.

Step 1: DNA fragment 1 (~800 bp of 5' untranslated sequence plus nt 1–277 of SEQ ID No. 9) was ligated to DNA fragment 2 (nt 277–1546 of SEQ ID No. 9 plus 448 bp of intron sequence) and cloned into pGEM7Z. The resulting plasmid, pβ1-1.18, contained a full-length $\beta_1$ subunit clone that included a 448-bp intron.

Step 2: To replace the 5' untranslated sequence of pβ1-1.18 with a ribosome binding site, a double-stranded adapter was synthesized that contains an EcoRI site, sequence encoding a ribosome binding site (5'-ACCACC-3') and nt 1–25 of SEQ ID No. 9. The adapter was ligated to SmaI-digested pβ1-1.18, and the products of the ligation reaction were digested with EcoRI.

Step 3: The EcoRI fragment from step 2 containing the EcoRI adapter, efficient ribosome binding site and nt 1–1546 of SEQ ID No. 9 plus intron sequence was cloned into a plasmid vector and designated pβ1-1.18RBS. The EcoRI fragment of pβ1-1.18RBS was subcloned into EcoRI-digested pcDNA1 with the initiation codon proximal to CMV promoter to form pHBCaCHβ$_{1a}$RBS(A).

Step 4: To generate a full-length clone encoding the $\beta_1$ subunit lacking intron sequence, DNA fragment 3 (nt 69–1146 of SEQ ID No. 9 plus 448 bp of intron sequence followed by nt 1147–1546 of SEQ ID No. 9), was subjected to site-directed mutagenesis to delete the intron sequence, thereby yielding pβ1(–). The EcoRI-XhoI fragment of pβ1-1.18RBS (containing of the ribosome binding site and nt 1–277 of SEQ ID No. 9) was ligated to the XhoI-EcoRI fragment of pβ1(–) (containing of nt 277–1546 of SEQ ID No. 9) and cloned into pCDNA1 with the initiation of translation proximal to the CMV promoter. The resulting expression plasmid was designated pHBCaCHβ$_{1b}$RBS(A).

B. Splice Variant $\beta_{1-3}$

DNA sequence analysis of the DNA clones encoding the $\beta_1$ subunit indicated that in the CNS at least two alternatively spliced forms of the same human $\beta_1$ subunit primary transcript are expressed. One form is represented by the sequence shown in SEQ ID No. 9 and is referred to as $\beta_{1-2}$. The sequences of $\beta_{1-2}$ and the alternative form, $\beta_{1-3}$, diverge at nt 1334 (SEQ ID No. 9). The complete $\beta_{1-3}$ sequence (nt 1–1851), including 3' untranslated sequence (nt 1795–1851), is set forth in SEQ ID No. 10.

Example IV

Isolation of cDNA Clones Encoding the Human Neuronal Calcium Channel $\alpha_2$-Subunit A. Isolation of cDNA Clones The complete human neuronal $\alpha_2$ coding sequence (nt 35–3310) plus a portion of the 5' untranslated sequence (nt 1 to 34) as well as a portion of the 3' untranslated sequence (nt 3311–3600) is set forth in SEQ ID No. 11.

To isolate DNA encoding the human neuronal $\alpha_2$ subunit, human $\alpha_2$ genomic clones first were isolated by probing human genomic Southern blots using a rabbit skeletal muscle calcium channel $\alpha_2$ subunit cDNA fragment [nt 43 to 272, Ellis et al. (1988) Science 240:1661]. Human genomic DNA was digested with EcoRI, electrophoresed, blotted, and probed with the rabbit skeletal muscle probe using standard hybridization conditions (Example I.C.) and low stringency washing conditions (Example I.C.). Two restriction fragments were identified, 3.5 kb and 3.0 kb. These EcoRI restriction fragments were cloned by preparing a $\lambda$gt11 library containing human genomic EcoRI fragments ranging from 2.2 kb to 4.3 kb. The library was screened as described above using the rabbit $\alpha_2$ probe, hybridizing clones were isolated and characterized by DNA sequencing. HGCaCH$\alpha$2.20 contained the 3.5 kb fragment and HGCaCH$\alpha$2.9 contained the 3.0 kb fragment.

Restriction mapping and DNA sequencing revealed that HGCaCH$\alpha$2.20 contains an 82 bp exon (nt 130 to 211 of the human $\alpha_2$ coding sequence, SEQ ID No. 11) on a 650 bp PstI-XbaI restriction fragment and that HGCaCH$\alpha$2.9 contains 105 bp of an exon (nt 212 to 316 of the coding sequence, SEQ ID No. 11) on a 750 bp XbaI-BglII restriction fragment. These restriction fragments were used to screen the human basal ganglia cDNA library (Example II.C.2.a.). HBCaCH$\alpha$2.1 was isolated (nt 29 to 1163, SEQ ID No. 11) and used to screen a human brain stem cDNA library (ATCC Accession No. 37432) obtained from the American Type Culture Collection, 12301 Parklawn Drive, Rockville, Md. 20852. Two clones were isolated, HBCaCH$\alpha$2.5 (nt 1 to 1162, SEQ ID No. 11) and HBCaCH$\alpha$2.8 (nt 714 to 1562, SEQ ID No. 11, followed by 1600 nt of intervening sequence). A 2400 bp fragment of HBCaCH$\alpha$2.8 (beginning at nt 759 of SEQ ID No. 11 and ending at a SmaI site in the intron) was used to rescreen the brain stem library and to isolate HBCaCH$\alpha$2.11 (nt 879 to 3600, SEQ ID No. 11). Clones HBCaCH$\alpha$2.5 and HBCaCH$\alpha$2.11 overlap to encode an entire human brain $\alpha_2$ protein.

B. Construction of pHBCaCH$\alpha_2$A

To construct pHBCaCH$\alpha_2$A containing DNA encoding a full-length human calcium channel $\alpha_2$ subunit, an (EcoRI)-PvuII fragment of HBCaCH$\alpha$2.5 (nt 1 to 1061, SEQ ID No. 11, EcoRI adapter, PvuII partial digest) and a PvuII-PstI fragment of HBCaCH$\alpha$2.11 (nt 1061 to 2424 SEQ ID No. 11; PvuII partial digest) were ligated into EcoRI-PstI-digested pIBI24 (Stratagene, La Jolla, Calif.). Subsequently, an (EcoRI)-PstI fragment (nt 1 to 2424 SEQ ID No. 11) was isolated and ligated to a PstI-(EcoRI) fragment (nt 2424 to 3600 SEQ ID No. 11) of HBCaCH$\alpha$2.11 in EcoRI-digested pIBI24 to produce DNA, HBCaCH$\alpha$2, encoding a full-length human brain $\alpha_2$ subunit. The 3600 bp EcoRI insert of HBCaCH$\alpha$2 (nt 1 to 3600, SEQ ID No. 11) was subcloned into pcDNA1 (pHBCaCH$\alpha$2A) with the methionine initiating codon proximal to the CMV promoter. The 3600 bp EcoRI insert of HBCaCH$\alpha$2 was also subcloned into pSV2dHFR [Subramani et al. (1981). Mol. Cell. Biol. 1:854–864] which contains the SV40 early promoter, mouse dihydrofolate reductase (dhfr) gene, SV40 polyadenylation and splice sites and sequences required for maintenance of the vector in bacteria.

Example V

Differential Processing of the Human $\beta_1$ Transcript and the Human $\alpha_2$ Transcript A. Differential Processing of the $\beta_1$ Transcript Nucleic acid amplification analysis of the human $\beta_1$ transcript present in skeletal muscle, aorta, hippocampus and basal ganglia, and HEK 293 cells revealed differential processing of the region corresponding to nt 615–781 of SEQ ID No. 9 in each of the tissues. Four different sequences that result in five different processed $\beta_1$ transcripts through this region were identified. The $\beta_1$ transcripts from the different tissues contained different combinations of the four sequences, except for one of the $\beta_1$ transcripts expressed in HEK 293 cells ($\beta_{1-5}$) which lacked all four sequences.

None of the $\beta_1$ transcripts contained each of the four sequences; however, for ease of reference, all four sequences are set forth end-to-end as a single long sequence in SEQ ID No. 12. The four sequences that are differentially processed are sequence 1 (nt 14–34 in SEQ ID No. 12), sequence 2 (nt 35–55 in SEQ ID No. 12), sequence 3 (nt 56–190 in SEQ ID No. 12) and sequence 4 (nt 191–271 in SEQ ID No. 12). The forms of the $\beta_1$ transcript that have been identified include: (1) a form that lacks sequence 1 called $\beta_{1-1}$ (expressed in skeletal muscle), (2) a form that lacks sequences 2 and 3 called $\beta_{1-2}$ (expressed in CNS), (3) a form that lacks sequences 1, 2 and 3 called $\beta_{1-4}$ (expressed in aorta and HEK cells) and (4) a form that lacks sequences 1–4 called $\beta_{1-5}$ (expressed in HEK cells). Additionally, the $\beta_{1-4}$ and $\beta_{1-5}$ contain a guanine nucleotide (nt 13 in SEQ ID No. 12) that is absent in the $\beta_{1-1}$ and $\beta_{1-2}$ forms. The sequences of $\beta_1$ splice variants are set forth in SEQ ID Nos. 9, 10 and 33–35.

B. Differential Processing of Transcripts Encoding the $\alpha_2$ Subunit

The complete human neuronal 2 coding sequence (nt 35–3307) plus a portion of the 5' untranslated sequence (nt 1 to 34) as well as a portion of the 3' untranslated sequence (nt 3308–3600) is set forth as SEQ ID No. 11.

Nucleic acid amplification analysis of the human $\alpha_2$ transcript present in skeletal muscle, aorta, and CNS revealed differential processing of the region corresponding to nt 1595–1942 of SEQ ID No. 11 in each of the tissues.

The analysis indicated that the primary transcript of the genomic DNA that includes the nucleotides corresponding to nt 1595–1942 also includes an additional sequence (SEQ ID No. 13: 5'CCTATTGGTGTAGGTATACCAACAAT-TAATTT AAGAAAAAGGAGACCCAATATCCAG 3') inserted between nt 1624 and 1625 of SEQ ID No. 11. Five alternatively spliced variant transcripts that differ in the presence or absence of one to three different portions of the region of the primary transcript that includes the region of nt 1595–1942 of SEQ ID No. 11 plus SEQ ID No. 13 inserted between nt 1624 and 1625 have been identified. The five $\alpha_2$-encoding transcripts from the different tissues include different combinations of the three sequences, except for one of the $\alpha_2$ transcripts expressed in aorta which lacks all three sequences. None of the $\alpha_2$ transcripts contained each of the three sequences. The sequences of the three regions that are differentially processed are sequence 1 (SEQ ID No. 13), sequence 2 ( 5' AACCCCAAATCTCAG 3', which is nt 1625–1639 of SEQ ID No. 11), and sequence 3 ( 5' CAAAAAAGGGCAAAATGAAGG 3', which is nt 1908–1928 of SEQ ID No. 11). The five $\alpha_2$ forms identified are (1) a form that lacks sequence 3 called $\alpha_{2a}$ (expressed in skeletal muscle), (2) a form that lacks sequence 1 called $\alpha_{2b}$ (expressed in CNS), (3) a form that lacks sequences 1 and 2 called $\alpha_{2c}$ expressed in aorta), (4) a form that lacks sequences 1, 2 and 3 called $\alpha_{2d}$ (expressed in aorta) and (5) a form that lacks sequences 1 and 3 called $\alpha_{2e}$ (expressed in aorta).

The sequences of $\alpha_{2a}$–$\alpha_{2e}$ are set forth in SEQ ID NOS. 11($\alpha_{2b}$), 29($\alpha_{2a}$) and 30–32 ($\alpha_{2c}$–$\alpha_{2e}$, respectively).

Example VI

Isolation of DNA Encoding a Calcium Channel $\gamma$ Subunit From a Human Brain cDNA Library A. Isolation of DNA Encoding the $\gamma$ Subunit Approximately $1\times10^6$ recombinants from a $\lambda$gt11-based human hippocampus cDNA library (Clontech catalog

HL1088b, Palo Alto, Calif.) were screened by hybridization to a 484 bp sequence of the rabbit skeletal muscle calcium channel γ subunit cDNA (nucleotides 621–626 of the coding sequence plus 438 nucleotides of 3'-untranslated sequence) contained in vector γJ10 [Jay, S. et al. (1990). *Science* 248:490–492]. Hybridization was performed using moderate stringency conditions (20% deionized formamide, 5× Denhardt's, 6×SSPE, 0.2% SDS, 20 μg/ml herring sperm DNA, 42° C.) and the filters were washed under low stringency (see Example I.C.). A plaque that hybridized to this probe was purified and insert DNA was subcloned into pGEM7Z. This cDNA insert was designated γ1.4.

B. Characterization of γ1.4

γ1.4 was confirmed by DNA hybridization and characterized by DNA sequencing. The 1500 bp SstI fragment of γ1.4 hybridized to the rabbit skeletal muscle calcium channel γ subunit cDNA γJ10 on a Southern blot. SEQ analysis of this fragment revealed that it contains of approximately 500 nt of human DNA sequence and ~1000 nt of λgt11 sequence (included due to apparent destruction of one of the EcoRI cloning sites in λgt11). The human DNA sequence contains of 129 nt of coding sequence followed immediately by a translational STOP codon and 3' untranslated sequence (SEQ ID No. 14).

To isolate the remaining 5' sequence of the human γ subunit cDNA, human CNS cDNA libraries and/or preparations of mRNA from human CNS tissues can first be assayed by nucleic acid amplification analysis methods using oligonucleotide primers based on the γ cDNA-specific sequence of γ1.4. Additional human neuronal γ subunit-encoding DNA can be isolated from cDNA libraries that, based on the results of the nucleic acid amplification analysis assay, contain γ-specific amplifiable cDNA. Alternatively, cDNA libraries can be constructed from mRNA preparations that, based on the results of the nucleic acid amplification analysis assays, contain γ-specific amplifiable transcripts. Such libraries are constructed by standard methods using oligo dT to prime first-strand cDNA synthesis from poly $A^+$ RNA (see Example I.B.). Alternatively, first-strand cDNA can be specified by priming first-strand cDNA synthesis with a γ cDNA-specific oligonucleotide based on the human DNA sequence in γ1.4. A cDNA library can then be constructed based on this first-strand synthesis and screened with the γ-specific portion of γ1.4.

Example VII

Isolation of cDNA Clones Encoding the Human Neuronal Ca Channel $β_2$ Subunit

Isolation of DNA Encoding Human Calcium Channel $β_2$ Subunits

Sequencing of clones isolated as described in Example III revealed a clone encoding a human neuronal calcium channel $β_2$ subunit (designated $β_{2D}$ see, SEQ ID No. 26). An oligonucleotide based on the 5' end of this clone was used to prime a human hippocampus cDNA library. The library was screened with this $β_2$ clone under conditions of low to medium stringency (final wash 0.5×SSPE, 50° C.). Several hybridizing clones were isolated and sequenced. Among these clones were those that encode $β_{2C}$, $β_{2D}$ and $β_{2E}$. For example, the sequence of $β_{2C}$ is set forth in SEQ ID NO. 37, and the sequeence of $β_{2E}$ is set forth in SEQ ID No. 38.

A randomly primed hippocampus library was then screened using a combination of the clone encoding $β_{2D}$ and a portion of the $β_3$ clone deposited under ATCC Accession No. 69048. Multiple hybridizing clones were isolated. Among these were clones designated β101, β102 and β104. β101 appears to encodes the 5' end of a splice variant of $β_2$, designated $β_{2E}$. β102 and β104 encode portions of the 3' end of $β_2$.

It appears that the $β_2$ splice variants include nucleotides 182–2294 of SEQ ID No. 26 and differ only between the start codon and nucleotides that correspond to 212 of SEQ. ID No. 26.

Example VIII

Isolation of cDNA Clones Encoding Human Calcium Channel $Γ_4$ and $β_3$ Subunits A. Isolation of cDNA Clones Encoding a Human $β_4$ Subunit A clone containing a translation initiation codon and approximately 60% of the $β_4$ coding sequence was obtained from a human cerebellum cDNA library (see nucleotides 1–894 of Sequence ID No. 27). To obtain DNA encoding the remaining 3' portion of the $β_4$ coding sequence, a human cerebellum cDNA library was screened for hybridization a nucleic acid amplification product under high stringency hybridization and wash conditions. Hybridizing clones are purified and characterized by restriction enzyme mapping and DNA sequence analysis to identify those that contain sequence corresponding to the 3' end of the $β_4$ subunit coding sequence and a termination codon. Selected clones are ligated to the clone containing the 5' half of the $β_4$ coding sequence at convenient restriction sites to generate a full-length cDNA encoding a $β_4$ subunit. The sequence of a full-length $β_4$ clone is set forth in SEQ ID No. 27; the amino acid sequence is set forth in SEQ ID No. 28.

B. Isolation of cDNA Clones Encoding a Human $β_3$ Subunit

Sequencing of clones isolated as described in Example III also revealed a clone encoding a human neuronal calcium channel $β_3$ subunit. This clone has been deposited as plasmid β1.42 (ATCC Accession No. 69048).

To isolate a full-length cDNA clone encoding a complete $β_3$ subunit, a human hippocampus cDNA library (Stratagene, La Jolla, Calif.) was screened for hybridization to a 5' EcoRI-PstI fragment of the cDNA encoding $β_{1-2}$ using lower stringency hybridization conditions (20% deionized formamide, 200 μg/ml sonicated herring sperm DNA, 5× SSPE, 5× Denhardt's solution, 42° C.) and wash conditions. One of the hybridizing clones contained both translation initiation and termination codons and encodes a complete $β_3$ subunit designated $β_{3-1}$ (Sequence ID No. 19). In vitro transcripts of the cDNA were prepared and injected into Xenopus oocytes along with transcripts of the $α_{1B-1}$ and $α_{2b}$ cDNAs using methods similiar to those described in Example IX.D. Two-electrode voltage clamp recordings of the oocytes revealed significant voltage-dependent inward $Ba^{2+}$ currents.

An additional $β_3$ subunit-encoding clone, designated $β_{3-2}$, was obtained by screening a human cerebellum cDNA library for hybridization to the nucleic acid amplification product referred to in Example VIII.A. under lower stringency (20% deionized formamide, 200 μg/ml sonicated herring sperm DNA, 5× SSPE, 5× Denhardt's solution, 42° C.) hybridization and wash conditions. The 5' ends of this clone (Sequence ID No. 20, $β_{3-2}$) and the first $β_3$ subunit, designated $β_{3-1}$, (Sequence ID No. 19) differ at their 5' ends and are splice variants of the $β_3$ gene.

Example IX

Recombinant Expression of Human Neuronal Calcium Channel Subunit-Encoding cDNA and RNA Transcripts in Mammalian Cells A. Recombinant Expression of the Human Neuronal Calcium Channel $α_2$ Subunit cDNA in DG44 Cells 1. Stable Transfection of DG44 Cells DG44 cells [dhfr⁻ Chinese hamster ovary cells; see, e.g., Urlaub, G. et al.

(1986) *Som. Cell Molec. Genet.* 12:555–566] obtained from Lawrence Chasin at Columbia University were stably transfected by $CaPO_4$ precipitation methods [Wigler et al. (1979) *Proc. Natl. Acad. Sci. USA* 76:1373–1376] with pSV2dhfr vector containing the human neuronal calcium channel $\alpha_2$-subunit cDNA (see Example IV) for polycistronic expression/selection in transfected cells. Transfectants were grown on 10% DMEM medium without hypoxanthine or thymidine in order to select cells that had incorporated the expression vector. Twelve transfectant cell lines were established as indicated by their ability to survive on this medium.

2. Analysis of $\alpha_2$ Subunit cDNA Expression in Transfected DG44 Cells

Total RNA was extracted according to the method of Birnboim [(1988) *Nuc. Acids Res.* 16:1487–1497] from four of the DG44 cell lines that had been stably transfected with pSV2dhfr containing the human neuronal calcium channel $\alpha_2$ subunit cDNA. RNA (~15 μg per lane) was separated on a 1% agarose formaldehyde gel, transferred to nitrocellulose and hybridized to the random-primed human neuronal calcium channel $\alpha_2$ cDNA (hybridization: 50% formamide, 5×SSPE, 5×Denhardt's, 42° C.; wash :0.2×SSPE, 0.1% SDS, 65° C.). Northern blot analysis of total RNA from four of the DG44 cell lines that had been stably transfected with pSV2dhfr containing the human neuronal calcium channel $\alpha_2$ subunit cDNA revealed that one of the four cell lines contained hybridizing mRNA the size expected for the transcript of the $\alpha_2$ subunit cDNA (5000 nt based on the size of the cDNA) when grown in the presence of 10 mM sodium butyrate for two days. Butyrate nonspecifically induces transcription and is often used for inducing the SV40 early promoter [Gorman, C. and Howard, B. (1983) *Nucleic Acids Res.* 11:1631]. This cell line, $44\alpha_2$-9, also produced mRNA species smaller (several species) and larger (6800 nt) than the size expected for the transcript of the $\alpha_2$ cDNA (5000 nt) that hybridized to the $\alpha_2$ cDNA-based probe. The 5000- and 6800-nt transcripts produced by this transfectant should contain the entire $\alpha_2$ subunit coding sequence and therefore should yield a full-length $\alpha_2$ subunit protein. A weakly hybridizing 8000-nucleotide transcript was present in untransfected and transfected DG44 cells. Apparently, DG44 cells transcribe a calcium channel $\alpha_2$ subunit or similar gene at low levels. The level of expression of this endogenous $\alpha_2$ subunit transcript did not appear to be affected by exposing the cells to butyrate before isolation of RNA for northern analysis.

Total protein was extracted from three of the DG44 cell lines that had been stably transfected with pSV2dhfr containing the human neuronal calcium channel $\alpha_2$ subunit cDNA. Approximately $10^7$ cells were sonicated in 300 μl of a solution containing 50 mM HEPES, 1 mM EDTA, 1 mM PMSF. An equal volume of 2× loading dye [Laemmli, U. K. (1970). *Nature* 227:680] was added to the samples and the protein was subjected to electrophoresis on an 8% polyacrylamide gel and then electrotransferred to nitrocellulose. The nitrocellulose was incubated with polyclonal guinea pig antisera (1:200 dilution) directed against the rabbit skeletal muscle calcium channel $\alpha_2$ subunit (obtained from K. Campbell, University of Iowa) followed by incubation with [$^{125}$I]-protein A. The blot was exposed to X-ray film at –70° C. Reduced samples of protein from the transfected cells as well as from untransfected DG44 cells contained immunoreactive protein of the size expected for the $\alpha_2$ subunit of the human neuronal calcium channel (130–150 kDa). The level of this immunoreactive protein was higher in $44\alpha_2$-9 cells that had been grown in the presence of 10 mM sodium butyrate than in $44\alpha_2$-9 cells that were grown in the absence of sodium butyrate. These data correlate well with those obtained in northern analyses of total RNA from $44\alpha_2$-9 and untransfected DG44 cells. Cell line $44\alpha_2$-9 also produced a 110 kD immunoreactive protein that may be either a product of proteolytic degradation of the full-length $\alpha_2$ subunit or a product of translation of one of the shorter (<5000 nt) mRNAs produced in this cell line that hybridized to the $\alpha_2$ subunit cDNA probe.

B. Expression of DNA Encoding Human Neuronal Calcium Channel $\alpha_1$, $\alpha_2$ and $\beta_1$ Subunits in HEK Cells Human embryonic kidney cells (HEK 293 cells) were transiently and stably transfected with human neuronal DNA encoding calcium channel subunits. Individual transfectants were analyzed electrophysiologically for the presence of voltage-activated barium currents and functional recombinant voltage-dependent calcium channels were.

1. Transfection of HEK 293 Cells

Separate expression vectors containing DNA encoding human neuronal calcium channel $\alpha_{1D}$, $\alpha_2$ and $\beta_1$ subunits, plasmids pVDCCIII(A), pHBCaCH$\alpha_2$A, and pHBCaCH$\beta_{1a}$RBS(A), respectively, were constructed as described in Examples II.A.3, IV.B. and III.B.3., respectively. These three vectors were used to transiently co-transfect HEK 293 cells. For stable transfection of HEK 293 cells, vector pHBCaCH$\beta_{1b}$RBS(A) (Example III.B.3.) was used in place of pHBCaCH$\beta_{1a}$RBS (A) to introduce the DNA encoding the $\beta_1$ subunit into the cells along with pVDCCIII(A) and pHBCaCH$\alpha_2$A.

a. Transient Transfection

Expression vectors pVDCCIII(A), pHBCaCH$\alpha_2$A and pHBCaCH$\beta_{1a}$RBS(A) were used in two sets of transient transfections of HEK 293 cells (ATCC Accession No. CRL1573). In one transfection procedure, HEK 293 cells were transiently cotransfected with the $\alpha_1$ subunit cDNA expression plasmid, the $\alpha_2$ subunit cDNA expression plasmid, the $\beta_1$ subunit cDNA expression plasmid and plasmid pCMVβgal (Clontech Laboratories, Palo Alto, Calif.). Plasmid pCMVβgal contains the lacz gene (encoding *E. coli* β-galactosidase) fused to the cytomegalovirus (CMV) promoter and was included in this transfection as a marker gene for monitoring the efficiency of transfection. In the other transfection procedure, HEK 293 cells were transiently co-transfected with the $\alpha_1$ subunit cDNA expression plasmid pVDCCIII(A) and pCMVβgal. In both transfections, $2-4\times10^6$ HEK 293 cells in a 10-cm tissue culture plate were transiently co-transfected with 5 μg of each of the plasmids included in the experiment according to standard $CaPO_4$ precipitation transfection procedures (Wigler et al. (1979) *Proc. Natl. Acad. Sci. USA* 76:1373–1376). The transfectants were analyzed for β-galactosidase expression by direct staining of the product of a reaction involving β-galactosidase and the X-gal substrate [Jones, J. R. (1986) *EMBO* 5:3133–3142] and by measurement of β-galactosidase activity [Miller, J. H. (1972) Experiments in Molecular Genetics, pp. 352–355, Cold Spring Harbor Press]. To evaluate subunit cDNA expression in these transfectants, the cells were analyzed for subunit transcript production (northern analysis), subunit protein production (immunoblot analysis of cell lysates) and functional calcium channel expression (electrophysiological analysis).

b. Stable transfection

HEK 293 cells were transfected using the calcium phosphate transfection procedure [*Current Protocols in Molecu-* lar Biology, Vol. 1, Wiley Inter-Science, Supplement 14, Unit 9.1.1–9.1.9 (1990)]. Ten-cm plates, each containing one-to-two million HEK 293 cells, were transfected with 1 ml of DNA/calcium phosphate precipitate containing 5 μg PVDCCIII (A), 5 μg pHBCaCHα$_2$A, 5 μg pHBCaCHβ$_{1b}$RBS (A), 5 μg pCMVBgal and 1 μg pSV2neo (as a selectable marker). After 10–20 days of growth in media containing 500 μg G418, colonies had formed and were isolated using cloning cylinders.

2. Analysis of HEK 293 Cells Transiently Transfected With DNA Encoding Human Neuronal Calcium Channel Subunits a. Analysis of β-Galactosidase Expression Transient transfectants were assayed for β-galactosidase expression by β-galactosidase activity assays (Miller, J. H., (1972) Experiments in Molecular Genetics, pp. 352–355, Cold Spring Harbor Press) of cell lysates (prepared as described in Example VII.A.2) and staining of fixed cells (Jones, J. R. (1986) EMBO 5:3133–3142). The results of these assays indicated that approximately 30% of the HEK 293 cells had been transfected.

b. Northern Analysis

PolyA+ RNA was isolated using the Invitrogen Fast Trak Kit (InVitrogen, San Diego, Calif.) from HEK 293 cells transiently transfected with DNA encoding each of the $\alpha_1$, $\alpha_2$ and $\beta_1$ subunits and the lacZ gene or the $\alpha_1$ subunit and the lacZ gene. The RNA was subjected to electrophoresis on an agarose gel and transferred to nitrocellulose. The nitrocellulose was then hybridized with one or more of the following radiolabeled probes: the lacZ gene, human neuronal calcium channel $\alpha_{1D}$ subunit-encoding cDNA, human neuronal calcium channel $\alpha_2$ subunit-encoding cDNA or human neuronal calcium channel $\beta_1$ subunit-encoding cDNA. Two transcripts that hybridized with the $\alpha_1$ subunit-encoding cDNA were detected in HEK 293 cells transfected with the DNA encoding the $\alpha_1$, $\alpha_2$, and $\beta_1$ subunits and the lacZ gene as well as in HEK 293 cells transfected with the $\alpha_1$ subunit cDNA and the lacZ gene. One mRNA species was the size expected for the transcript of the $\alpha_1$ subunit cDNA (8000 nucleotides). The second RNA species was smaller (4000 nucleotides) than the size expected for this transcript. RNA of the size expected for the transcript of the lacZ gene was detected in cells transfected with the $\alpha_1$, $\alpha_2$ and $\beta_1$ subunit-encoding cDNA and the lacZ gene and in cells transfected with the $\alpha_1$ subunit cDNA and the lacZ gene by hybridization to the lacZ gene sequence.

RNA from cells transfected with the $\alpha_1$, $\alpha_2$ and $\beta_1$ subunit-encoding cDNA and the lacZ gene was also hybridized with the $\alpha_2$ and $\beta_1$ subunit cDNA probes. Two mRNA species hybridized to the $\alpha_2$ subunit cDNA probe. One species was the size expected for the transcript of the $\alpha_2$ subunit cDNA (4000 nucleotides). The other species was larger (6000 nucleotides) than the expected size of this transcript. Multiple RNA species in the cells co-transfected with $\alpha_1$, $\alpha_2$ and $\beta_1$ subunit-encoding cDNA and the lacZ gene hybridized to the $\beta_1$ subunit cDNA probe. Multiple β subunit transcripts of varying sizes were produced since the β subunit cDNA expression vector contains two potential polyA$^+$ addition sites.

c. Electrophysiological Analysis

Individual transiently transfected HEK 293 cells were assayed for the presence of voltage-dependent barium currents using the whole-cell variant of the patch clamp technique [Hamill et al. (1981). Pflugers Arch. 391:85–100]. HEK 293 cells transiently transfected with pCMVβgal only were assayed for barium currents as a negative control in these experiments. The cells were placed in a bathing solution that contained barium ions to serve as the current carrier. Choline chloride, instead of NaCl or KCl, was used as the major salt component of the bath solution to eliminate currents through sodium and potassium channels. The bathing solution contained 1 mM MgCl$_2$ and was buffered at pH 7.3 with 10 mM HEPES (pH adjusted with sodium or tetraethylammonium hydroxide). Patch pipettes were filled with a solution containing 135 mM CsCl, 1 mM MgCl$_2$, 10 mM glucose, 10 mM EGTA, 4 mM ATP and 10 mM HEPES (pH adjusted to 7.3 with tetraethylammonium hydroxide). Cesium and tetraethylammonium ions block most types of potassium channels. Pipettes were coated with Sylgard (Dow-Corning, Midland, Mich.) and had resistances of 1–4 megohm. Currents were measured through a 500 megohm headstage resistor with the Axopatch IC (Axon Instruments, Foster City, Calif.) amplifier, interfaced with a Labmaster (Scientific Solutions, Solon, Ohio) data acquisition board in an IBM-compatible PC. PClamp (Axon Instruments) was used to generate voltage commands and acquire data. Data were analyzed with pClamp or Quattro Professional (Borland International, Scotts Valley, Calif.) programs.

To apply drugs, "puffer" pipettes positioned within several micrometers of the cell under study were used to apply solutions by pressure application. The drugs used for pharmacological characterization were dissolved in a solution identical to the bathing solution. Samples of a 10 mM stock solution of Bay K 8644 (RBI, Natick, Mass.), which was prepared in DMSO, were diluted to a final concentration of 1 μM in 15 mM Ba$^{2+}$-containing bath solution before they were applied.

Twenty-one negative control HEK 293 cells (transiently transfected with the lacZ gene expression vector pCMVβgal only) were analyzed by the whole-cell variant of the patch clamp method for recording currents. Only one cell displayed a discernable inward barium current; this current was not affected by the presence of 1 μM Bay K 8644. In addition, application of Bay K 8644 to four cells that did not display Ba$^{2+}$ currents did not result in the appearance of any currents.

Two days after transient transfection of HEK 293 cells with $\alpha_1$, $\alpha_2$ and $\beta_1$ subunit-encoding cDNA and the lacZ gene, individual transfectants were assayed for voltage-dependent barium currents. The currents in nine transfectants were recorded. Because the efficiency of transfection of one cell can vary from the efficiency of transfection of another cell, the degree of expression of heterologous proteins in individual transfectants varies and some cells do not incorporate or express the foreign DNA. Inward barium currents were detected in two of these nine transfectants. In these assays, the holding potential of the membrane was –90 mV. The membrane was depolarized in a series of voltage steps to different test potentials and the current in the presence and absence of 1 μM Bay K 8644 was recorded. The inward barium current was significantly enhanced in magnitude by the addition of Bay K 8644. The largest inward barium current (~160 pA) was recorded when the membrane was depolarized to 0 mV in the presence of 1 μM Bay K 8644. A comparison of the I-V curves, generated by plotting the largest current recorded after each depolarization versus the depolarization voltage, corresponding to recordings conducted in the absence and presence of Bay K 8644 illustrated the enhancement of the voltage-activated current in the presence of Bay K 8644.

Pronounced tail currents were detected in the tracings of currents generated in the presence of Bay K 8644 in HEK 293 cells transfected with $\alpha_1$, $\alpha_2$ and $\beta_1$ subunit-encoding cDNA and the lacZ gene, indicating that the recombinant calcium channels responsible for the voltage-activated barium currents recorded in this transfected appear to be DHP-sensitive.

The second of the two transfected cells that displayed inward barium currents expressed a ~50 pA current when the membrane was depolarized from −90 mV. This current was nearly completely blocked by 200 μM cadmium, an established calcium channel blocker.

Ten cells that were transiently transfected with the DNA encoding the $\alpha_1$ subunit and the lacZ gene were analyzed by whole-cell patch clamp methods two days after transfection. One of these cells displayed a 30 pA inward barium current. This current amplified 2-fold in the presence of 1 μM Bay K 8644. Furthermore, small tail currents were detected in the presence of Bay K 8644. These data indicate that expression of the human neuronal calcium channel $\alpha_{1D}$ subunit-encoding cDNA in HEK 293 yields a functional DHP-sensitive calcium channel.

3. Analysis of HEK 293 Cells Stably Transfected With DNA Encoding Human Neuronal Calcium Channel Subunits Individual stably transfected HEK 293 cells were assayed electrophysiologically for the presence of voltage-dependent barium currents as described for electrophysiological analysis of transiently transfected HEK 293 cells (see Example VII.B.2.c). In an effort to maximize calcium channel activity via cyclic-AMP-dependent kinase-mediated phosphorylation [Pelzer, et al. (1990) Rev. Physiol. Biochem. Pharmacol. 114:107–207], cAMP (Na salt, 250 μM) was added to the pipet solution and forskolin (10 μM) was added to the bath solution in some of the recordings. Qualitatively similar results were obtained whether these compounds were present or not.

Barium currents were recorded from stably transfected cells in the absence and presence of Bay K 8644 (1 μM). When the cell was depolarized to −10 mV from a holding potential of −90 mV in the absence of Bay K 8644, a current of approximately 35 pA with a rapidly deactivating tail current was recorded. During application of Bay K 8644, an identical depolarizing protocol elicited a current of approximately 75 pA, accompanied by an augmented and prolonged tail current. The peak magnitude of currents recorded from this same cell as a function of a series of depolarizing voltages were assessed. The responses in the presence of Bay K 8644 not only increased, but the entire current-voltage relation shifted about −10 mV. Thus, three typical hallmarks of Bay K 8644 action, namely increased current magnitude, prolonged tail currents, and negatively shifted activation voltage, were observed, clearly indicating the expression of a DHP-sensitive calcium channel in these stably transfected cells. No such effects of Bay K 8644 were observed in untransfected HEK 293 cells, either with or without cAMP or forskolin.

C. Use of pCMV-Based Vectors and pcDNA1-Based Vectors for Expression of DNA Encoding Human Neuronal Calcium Channel Subunits 1. Preparation of Constructs Additional expression vectors were constructed using pCMV. The full-length $\alpha_{1D}$ cDNA from PVDCCIII(A) (see Example II.A.3.d), the full-length $\alpha_2$ cDNA, contained on a 3600 bp EcoRI fragment from HBCaCH$\alpha_2$ (see Example IV.B) and a full-length $\beta_1$ subunit cDNA from pHBCaCH$\beta_{1b}$RBS(A) (see Example III.B.3) were separately subcloned into plasmid pCMVβgal. Plasmid pCMVβgal was digested with NotI to remove the lacZ gene. The remaining vector portion of the plasmid, referred to as pCMV, was blunt-ended at the NotI sites. The full-length $\alpha_2$-encoding DNA and $\beta_1$-encoding DNA, contained on separate EcoRI fragments, were isolated, blunt-ended and separately ligated to the blunt-ended vector fragment of pCMV locating the cDNAs between the CMV promoter and SV40 polyadenylation sites in pCMV. To ligate the $\alpha_{1D}$-encoding cDNA with pCMV, the restriction sites in the polylinkers immediately 5' of the CMV promoter and immediately 3' of the SV40 polyadenylation site were removed from pCMV. A polylinker was added at the NotI site. The polylinker had the following sequence of restriction enzyme recognition sites:

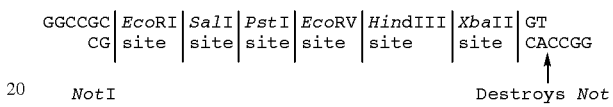

The $\alpha_{1D}$-encoding DNA, isolated as a BamHI/XhoI fragment from pVDCCIII(A), was then ligated to XbaII/SalI-digested pCMV to place it between the CMV promoter and SV40 polyadenylation site.

Plasmid pCMV contains the CMV promoter as does pcDNA1, but differs from pcDNA1 in the location of splice donor/splice acceptor sites relative to the inserted subunit-encoding DNA. After inserting the subunit-encoding DNA into pCMV, the splice donor/splice acceptor sites are located 3' of the CMV promoter and 5' of the subunit-encoding DNA start codon. After inserting the subunit-encoding DNA into pcDNA1, the splice donor/splice acceptor sites are located 3' of the subunit cDNA stop codon.

2. Transfection of HEK 293 Cells

HEK 293 cells were transiently co-transfected with the $\alpha_{1D}$, $\alpha_2$ and $\beta_1$ subunit-encoding DNA in pCMV or with the $\alpha_{1D}\alpha_2$ and β subunit-encoding DNA in pcDNA1 (vectors pVDCCIII(A), pHBCaCH$\alpha_2$A and pHBCaCH$\beta_{1b}$RBS (A), respectively), as described in Example VII.B.1.a. Plasmid pCMVβgal was included in each transfection as a measure of transfection efficiency. The results of β-galactosidase assays of the transfectants (see Example VII.B.2.), indicated that HEK 293 cells were transfected equally efficiently with PCMV- and pcDNA1-based plasmids. The pcDNA1-based plasmids, however, are presently preferred for expression of calcium channel receptors.

D. Expression in *Xenopus Laevis* oöcytes of RNA Encoding Human Neuronal Calcium Channel Subunits Various combinations of the transcripts of DNA encoding the human neuronal $\alpha_{1D}$, $\alpha_2$ and $\beta_1$ subunits prepared in vitro were injected into *Xenopus laevis* oöcytes. Those injected with combinations that included $\alpha_{1D}$ exhibited voltage-activated barium currents.

1. Preparation of Transcripts

Transcripts encoding the human neuronal calcium channel $\alpha_{1D}$, $\alpha_2$ and $\beta_1$ subunits were synthesized according to the instructions of the mCAP mRNA CAPPING KIT (Strategene, La Jolla, Calif. catalog #200350). Plasmids pVDCC III.RBS(A), containing pcDNA1 and the $\alpha_{1D}$ cDNA that begins with a ribosome binding site and the eighth ATG codon of the coding sequence (see Example III.A.3.d), plasmid pHBCaCH$\alpha_1$A containing pcDNA1 and an $\alpha_2$ subunit cDNA (see Example IV), and plasmid pHBCaCH$\beta_{1b}$RBS (A) containing pcDNA1 and the $\beta_1$ DNA lacking intron sequence and containing a ribosome binding site (see Example III), were linearized by restriction digestion. The $\alpha_{1D}$ cDNA- and $\alpha_2$ subunit-encoding plasmids were digested with XhoI, and the $\beta_1$ subunit-encoding plasmid was digested with EcoRV. The DNA insert was transcribed with T7 RNA polymerase.

2. Injection of Oöcytes

Xenopus laevis oöcytes were isolated and defolliculated by collagenase treatment and maintained in 100 mM NaCl, 2 mM KCl, 1.8 mM CaCl$_2$, 1 mM MgCl$_2$, 5 mM HEPES, pH 7.6, 20 μg/ml ampicillin and 25 μg/ml streptomycin at 19–25° C. for 2 to 5 days after injection and prior to recording. For each transcript that was injected into the oöcyte, 6 ng of the specific mRNA was injected per cell in a total volume of 50 nl.

3. Intracellular Voltage Recordings

Injected oöcytes were examined for voltage-dependent barium currents using two-electrode voltage clamp methods [Dascal, N. (1987) CRC Crit. Rev. Biochem. 22:317]. The pClamp (Axon Instruments) software package was used in conjunction with a Labmaster 125 kHz data acquisition interface to generate voltage commands and to acquire and analyze data. Quattro Professional was also used in this analysis. Current signals were digitized at 1–5 kHz, and filtered appropriately. The bath solution contained of the following: 40 mM BaCl$_2$, 36 mM tetraethylammonium chloride (TEA-Cl), 2 mM KCl, 5 mM 4-aminopyridine, 0.15 mM niflumic acid, 5 mM HEPES, pH 7.6.

a. Electrophysiological Analysis of Oöcytes Injected With Transcripts Encoding the Human Neuronal Calcium Channel $\alpha_1$, $\alpha_2$ and $\beta_1$-subunits Uninjected oöcytes were examined by two-electrode voltage clamp methods and a very small (25 nA) endogenous inward Ba$^{2+}$ current was detected in only one of seven analyzed cells.

Oöcytes coinjected with $\alpha_{1D}$, $\alpha_2$ and $\beta_1$ subunit transcripts expressed sustained inward barium currents upon depolarization of the membrane from a holding potential of −90 mV or −50 mV (154±129 nA, n=21) . These currents typically showed little inactivation when test pulses ranging from 140 to 700 msec. were administered. Depolarization to a series of voltages revealed currents that first appeared at approximately −30 mV and peaked at approximately 0 mV.

Application of the DHP Bay K 8644 increased the magnitude of the currents, prolonged the tail currents present upon repolarization of the cell and induced a hyperpolarizing shift in current activation. Bay K 8644 was prepared fresh from a stock solution in DMSO and introduced as a 10x concentrate directly into the 60 μl bath while the perfusion pump was turned off. The DMSO concentration of the final diluted drug solutions in contact with the cell never exceeded 0.1%. Control experiments showed that 0.1% DMSO had no effect on membrane currents.

Application of the DHP antagonist nifedipine (stock solution prepared in DMSO and applied to the cell as described for application of Bay K 8644) blocked a substantial fraction (91±6%, n=7) of the inward barium current in oöcytes coinjected with transcripts of the $\alpha_{1D}$, $\alpha_2$ and $\beta_1$ subunits. A residual inactivating component of the inward barium current typically remained after nifedipine application. The inward barium current was blocked completely by 50 μM Cd$^{2+}$, but only approximately 15% by 100 μM Ni$^{2+}$.

The effect of ωCgTX on the inward barium currents in oöcytes co-injected with transcripts of the $\alpha_{1D}$, $\alpha_2$, and $\beta_1$ subunits was investigated. ωCgTX (Bachem, Inc., Torrance Calif.) was prepared in the 15 mM BaCl$_2$ bath solution plus 0.1% cytochrome C (Sigma) to serve as a carrier protein. Control experiments showed that cytochrome C had no effect on currents. A series of voltage pulses from a −90 mV holding potential to 0 mV were recorded at 20 msec. intervals. To reduce the inhibition of ωCgTX binding by divalent cations, recordings were made in 15 mM BaCl$_2$, 73.5 mM tetraethylammonium chloride, and the remaining ingredients identical to the 40 mM Ba$^{2+}$ recording solution. Bay K 8644 was applied to the cell prior to addition to ωCgTX in order to determine the effect of ωCgTX on the DHP-sensitive current component that was distinguished by the prolonged tail currents. The inward barium current was blocked weakly (54±29%, n=7) and reversibly by relatively high concentrations (10–15 μM) of ωCgTX. The test currents and the accompanying tail currents were blocked progressively within two to three minutes after application of ωCgTX, but both recovered partially as the ωCgTX was flushed from the bath.

b. Analysis of Oöcytes Injected With Only a Transcripts Encoding the Human Neuronal Calcium Channel $\alpha_{1D}$ or Transcripts Encoding an $\alpha_{1D}$ and Other Subunits The contribution of the $\alpha_2$ and $\beta_1$ subunits to the inward barium current in oöcytes injected with transcripts encoding the $\alpha_{1D}$, $\alpha_2$ and $\beta_1$ subunits was assessed by expression of the $\alpha_{1D}$ subunit alone or in combination with either the $\beta_1$ subunit or the 2 subunit. In oöcytes injected with only the transcript of a $\alpha_{1D}$ cDNA, no Ba$^{2+}$ currents were detected (n=3). In oöcytes injected with transcripts of $\alpha_{1D}$ and $\beta_1$ cDNAs, small (108±39 nA) Ba$^{2+}$ currents were detected upon depolarization of the membrane from a holding potential of −90 mV that resembled the currents observed in cells injected with transcripts of $\alpha_{1D}$, $\alpha_2$ and $\beta_1$ cDNAs, although the magnitude of the current was less. In two of the four oöcytes injected with transcripts of the $\alpha_{1D}$-encoding and $\beta_1$-encoding DNA, the Ba$^{2+}$ currents exhibited a sensitivity to Bay K 8644 that was similar to the Bay K 8644 sensitivity of Ba$^{2+}$ currents expressed in oöcytes injected with transcripts encoding the $\alpha_{1D}$ $\alpha_1$-, $\alpha_{2-}$ and $\beta_1$ subunits.

Three of five oöcytes injected with transcripts encoding the $\alpha_{1D}$ and $\alpha_2$ subunits exhibited very small Ba$^{2+}$ currents (15–30 nA) upon depolarization of the membrane from a holding potential of −90 mV. These barium currents showed little or no response to Bay K 8644.

c. Analysis of Oöcytes Injected With Transcripts Encoding the Human Neuronal Calcium Channel $\alpha_2$ and/or $\beta_1$ Subunit To evaluate the contribution of the $\alpha_{1D}$ $\alpha_1$-subunit to the inward barium currents detected in oöcytes co-injected with transcripts encoding the $\alpha_1$D, $\alpha_2$ and $\beta_1$ subunits, oöcytes injected with transcripts encoding the human neuronal calcium channel $\alpha_2$ and/or $\beta_1$ subunits were assayed for barium currents. Oöcytes injected with transcripts encoding the $\alpha_2$ subunit displayed no detectable inward barium currents (n=5). Oöcytes injected with transcripts encoding a $\beta_1$ subunit displayed measurable (54±23 nA, n=5) inward barium currents upon depolarization and oöcytes injected with transcripts encoding the $\alpha_2$ and $\beta_1$ subunits displayed inward barium currents that were approximately 50% larger (80±61 nA, n=18) than those detected in oöcytes injected with transcripts of the $\beta_1$-encoding DNA only.

The inward barium currents in oöcytes injected with transcripts encoding the $\beta_1$ subunit or $\alpha_2$ and $\beta_1$ subunits typically were first observed when the membrane was depolarized to −30 mV from a holding potential of −90 mV and peaked when the membrane was depolarized to 10 to 20 mV. Macroscopically, the currents in oocytes injected with transcripts encoding the $\alpha_2$ and $\beta_1$ subunits or with transcripts encoding the $\beta_1$ subunit were indistinguishable. In contrast to the currents in oocytes co-injected with transcripts of $\alpha_{1D}$, $\alpha_2$ and $\beta_1$ subunit cDNAs, these currents showed a significant inactivation during the test pulse and a strong sensitivity to the holding potential. The inward barium currents in oocytes co-injected with transcripts encoding the $\alpha_2$ and $\beta_1$ subunits usually inactivated to 10–60% of the peak magnitude during a 140-msec pulse and were significantly more sensitive to holding potential than those in oocytes co-injected with transcripts encoding the $\alpha_{1D}$, $\alpha_2$ and $\beta_1$ subunits. Changing the holding potential of the membranes of oocytes co-injected with transcripts encoding the $\alpha_2$ and $\beta_1$ subunits from −90 to −50 mV resulted in an approximately 81% (n=11) reduction in the magnitude of the inward barium current of these cells. In contrast, the inward barium current measured in oocytes co-injected with transcripts encoding the $\alpha_{1D}$, $\alpha_2$ and $\beta_1$ subunits were reduced approximately 24% (n=11) when the holding potential was changed from −90 to −50 mV.

The inward barium currents detected in oocytes injected with transcripts encoding the $\alpha_2$ and $\beta_1$ subunits were pharmacologically distinct from those observed in oocytes co-injected with transcripts encoding the $\alpha_{1D}$, $\alpha_2$ and $\beta_1$ subunits. Oocytes injected with transcripts encoding the $\alpha_2$ and $\beta_1$ subunits displayed inward barium currents that were insensitive to Bay K 8644 (n=11). Nifedipine sensitivity was difficult to measure because of the holding potential sensitivity of nifedipine and the current observed in oocytes injected with transcripts encoding the $\alpha_2$ and $\beta_1$ subunits. Nevertheless, two oocytes that were co-injected with transcripts encoding the $\alpha_2$ and $\beta_1$ subunits displayed measurable (25 to 45 nA) inward barium currents when depolarized from a holding potential of −50 mV. These currents were insensitive to nifedipine (5 to 10 $\mu$M). The inward barium currents in oocytes injected with transcripts encoding the $\alpha_2$ and $\beta_1$ subunits showed the same sensitivity to heavy metals as the currents detected in oocytes injected with transcripts encoding the $\alpha_{1D}$, $\alpha_2$ and $\beta_1$ subunits.

The inward barium current detected in oocytes injected with transcripts encoding the human neuronal $\alpha_2$ and $\beta_1$ subunits has pharmacological and biophysical properties that resemble calcium currents in uninjected Xenopus oocytes. Because the amino acids of this human neuronal calcium channel $\beta_1$ subunit lack hydrophobic segments capable of forming transmembrane domains, it is unlikely that recombinant $\beta_1$ subunits alone can form an ion channel. It is more probable that a homologous endogenous $\alpha_1$ subunit exists in oocytes and that the activity mediated by such an $\alpha_1$ subunit is enhanced by expression of a human neuronal $\beta_1$ subunit.

E. Expression of DNA Encoding Human Neuronal Calcium Channel $\alpha_{1B}$, $\alpha_{2B}$ and $\beta_{1-2}$ Subunits in HEK Cells 1. Transfection of HEK Cells The transient expression of the human neuronal $\alpha_{1B-1}$, $\alpha_{2b}$ and $\beta_{1-2}$ subunits was studied in HEK293 cells. The HEK293 cells were grown as a monolayer culture in Dulbecco's modified Eagle's medium (Gibco) containing 5% defined-supplemented bovine calf serum (Hyclone) plus penicillin G (100 U/ml) and steptomycin sulfate (100 $\mu$g/ml) . HEK293 cell transfections were mediated by calcium phosphate as described above. Transfected cells were examined for inward $Ba^{2+}$ currents ($I_{Ba}$) mediated by voltage-dependent $Ca^{2+}$ channels.

Cells were transfected ($2\times10^6$ per polylysine-coated plate. Standard transfections (10-cm dish) contained 8 $\mu$g of pcDNA$\alpha_{1B-1}$, 5 $\mu$g of pHBCaCH$\alpha_2$A, 2 $\mu$g pHBCaCH$\beta_{1b}$RBS(A) (see, Examples II.A.3, IV.B. and III) and 2 $\mu$g of CMV$\beta$ (Clontech) $\beta$-glactosidase expression plasmid, and pUC18 to maintain a constant mass of 20 $\mu$g/ml. Cells were analyzed 48 to 72 hours after transfection. Transfection efficiencies (±10), which were determined by in situ histochemical staining for $\beta$-galactosidase activity (Sanes et al. (1986) *EMBO J.*, 5:3133), generally were greater than 50%.

2. Electrophysiological Analysis of Transfectant Currents a. Materials and Methods Properties of recombinantly expressed $Ca^{2+}$ channels were studied by whole cell patch-clamp techniques. Recordings were performed on transfected HEK293 cells 2 to 3 days after transfection. Cells were plated at 100,000 to 300,000 cells per polylysine-coated, 35-mm tissue culture dishes (Falcon, Oxnard, Calif.) 24 hours before recordings. Cells were perfused with 15 mM $BaCl_2$, 125 mM choline chloride, 1 mM $MgCl_2$, and 10 mM Hepes (pH=7.3) adjusted with tetraethylammonium hydroxide (bath solution). Pipettes were filled with 135 mM CsCl, 10 mM EGTA, 10 mM Hepes, 4 mM Mg-adenosine triphosphate (pH=7.5) adjusted with tetraethylammonium hydroxide. Sylgard (Dow-Corning, Midland, Mich.) -coated, fire-polished, and filled pipettes had resistances of 1 to 2 megohm before gigohm seals were established to cells.

Bay K 8644 and nifedipine (Research Biochemicals, Natick, Mass.) were prepared from stock solutions (in dimethyl sulfoxide) and diluted into the bath solution. The dimethyl sulfoxide concentration in the final drug solutions in contact with the cells never exceeded 0.1%. Control experiments showed that 0.1% dimethyl sulfoxide had no efect on membrane currents. $\omega$CgTX (Bachem, Inc., Torrance Calif.) was prepared in the 15 mM $BaCl_2$ bath solution plus 0.1% cytochrome C (Sigma, St. Louis Mo.) to serve as a carrier protein. Control experiments showed that cytochrome C had no effect on currents. These drugs were dissolved in bath solution, and continuously applied by means of puffer pipettes as required for a given experiment. Recordings were performed at room temperature (22° to 25° C.). Series resistance compensation (70 to 85%) was employed to minimize voltage error that resulted from pipette access resistance, typically 2 to 3.5 megohm. Current signals were filtered (−3 dB, 4-pole Bessel) at a frequency of ¼ to ⅕ the sampling rate, which ranged from 0.5 to 3 kHz. Voltage commands were generated and data were acquired with CLAMPEX (pClamp, Axon Instruments, Foster City, Calif.) . All reported data are corrected for linear leak and capacitive components. Exponential fitting of currents was performed with CLAMPFIT (Axon Instruments, Foster City, Calif.).

b. Results

Transfectants were examined for inward $Ba^{2+}$ currents ($I_{Ba}$). Cells cotransfected with DNA encoding $\alpha_{1B-1}$, $\alpha_{2b}$ and $\beta_{1-2}$ subunits expressed high-voltage-activated $Ca^{2+}$ channels. $I_{Ba}$ first appeared when the membrane was depolarized from a holding potential of −90 mV to −20 mV and peaked in magnitude at 10 mV. Thirty-nine of 95 cells (12 independent transfections) had $I_{Ba}$ that ranged from 30 to 2700 pA, with a mean of 433 pA. The mean current density was 26 pA/pF, and the highest density was 150 pA/pF. The $I_{Ba}$ typically increased by 2- to 20-fold during the first 5 minutes of recording. Repeated depolarizations during long records often revealed rundown of $I_{Ba}$ usually not exceeding 20% within 10 min. $I_{Ba}$ typically activated within 10 ms and inactivated with both a fast time constant ranging from 46 to 105 ms and a slow time constant ranging from 291 to 453 ms (n=3). Inactivation showed a complex voltage dependence, such that $I_{Ba}$ elicited at $\geq$20 mV inactivated more slowly than $I_{Ba}$ elicited at lower test voltages, possibly a result of an increase in the magnitude of slow compared to fast inactivation components at higher test voltages.

Recombinant $\alpha_{1B-1}\alpha_{2b}\beta_{1-2}$ channels were sensitive to holding potential. Steady-state inactivation of $I_{Ba}$, measured after a 30- to 60-s conditioning at various holding potentials, was approximately 50% at holding potential between −60 and −70 mV and approximately 90% at −40 mV. Recovery of $I_{Ba}$ from inactivation was usually incomplete, measuring 55 to 75% of the original magnitude within 1 min. after the holding potential was returned to more negative potentials, possibly indicating some rundown or a slow recovery rate.

Recombinant $\alpha_{1B-1}\alpha_{2b}\beta_{1-2}$ channels were also blocked irreversibly by ω-CgTx concentrations ranging from 0.5 to 10 μM during the time scale of the experiments. Application of 5 μM toxin (n=7) blocked the activity completely within 2 min., and no recovery of $I_{Ba}$ was observed after washing ω-CgTx from the bath for up to 15 min. $d^{2+}$ blockage (50 μM) was rapid, complete, and reversible; the DHPs Bay K 8644 (1 μM; n=4) or nifedipine (5 μM; n=3) had no discernable effect.

Cells cotransfected with DNA encoding $\alpha_{1B-1}$, $\alpha_{2b}$, and $\beta_{1-2}$ subunits predominantly displayed a single class of saturable, high-affinity ω-CgTx binding sites. The determined dissociation constant ($K_d$) value was 54.6±14.5 pM (n=4). Cells transfected with the vector containing only β-galactosidase-encoding DNA or $\alpha_{2b}\beta$-encoding DNA showed no specific binding. The binding capacity ($B_{max}$) of the $\alpha_{1B-1}\alpha_{2b}\beta$-transfected cells was 28,710±11,950 sites per cell (n=4).

These results demonstrate that $\alpha_{1B-1}\alpha_{2b}\beta_{1-2}$-transfected cells express high-voltage-activated, inactivating $Ca^{2+}$ channel activity that is irreversibly blocked by ω-CgTx, insensitive to DHPs, and sensitive to holding potential. The activation and inactivation kinetics and voltage sensitivity of the channel formed in these cells are generally consistent with previous characterizations of neuronal N-type $Ca^{2+}$ channels.

F. Expression of DNA Encoding Human Neuronal Calcium Channel $\alpha_{1B-1}$, $\alpha_{1B-2}$, $\alpha_{2B}$, $\beta_{1-2}$ and $\beta_{1-3}$ subunits in HEX Cells Significant $Ba^{2+}$ currents were not detected in untransfected HEK293 cells. Furthermore, untransfected HEK293 cells do not express detectable ω-CgTx GVIA binding sites.

In order to approximate the expression of a homogeneous population of trimeric $\alpha_{1B}$, $\alpha_{2b}$ and $\beta_1$ protein complexes in transfected HEK293 cells, the $\alpha_{1B}$, $\alpha_{2b}$ and $\beta_1$ expression levels were altered. The efficiency of expression and assembly of channel complexes at the cell surface were optimized by adjusting the molar ratio of $\alpha_{1B}$, $\alpha_{2b}$ and $\beta_1$ expression plasmids used in the transfections. The transfectants were analyzed for mRNA levels, ω-CgTx GVIA binding and $Ca^{2+}$ channel current density in order to determine near optimal channel expression in the absence of immunological reagents for evaluating protein expression. Higher molar ratios of $\alpha_{2b}$ appeared to increase calcium channel activity.

1. Transfections

HEK293 cells were maintained in DMEM (Gibco #320-1965AJ), 5.5% Defined/Supplemented bovine calf serum (Hyclone #A-2151-L), 100 U/ml penicillin G and 100 μg/ml streptomycin. $Ca^{2+}$-phosphate based transient transfections were performed and analyzed as described above. Cells were co-transfected with either 8 μg pcDNA1α$_{1B-1}$ (described in Example II.C), 5 μg pHBCaCHα$_2$A (see, Example IV.B.), 2 μg pHBCaCHβ$_{1b}$RBS (A) ($\beta_{1-2}$ expression plasmid; see Examples III.A. and IX.E.), and 2 μg pCMVβ-gal [Clontech, Palo Alto, Calif.] (2:1.8:1 molar ratio of $Ca^{2+}$ channel subunit expression plasmids) or with 3 μg pcDNA1α$_{1B-1}$ or pcDNA1α$_{1B-2}$, 11.25 μg pHBCaCHα$_2$A, 0.75 or 1.0 μg pHBCaCHβ$_{1b}$RBS(A) or pcDNA1β$_{1-3}$ and 2 μg pCMVβ-gal (2:10.9:1 molar ratio of $Ca^{2+}$ channel subunit expression plasmids). Plasmid pCMVβ-gal, a β-galactosidase expression plasmid, was included in the transfections as a marker to permit transfection efficiency estimates by histochemical staining. When less than three subunits were expressed, pCMVPL2, a pCMV promoter-containing vector that lacks a cDNA insert, was substituted to maintain equal moles of pCMV-based DNA in the transfection. pUC18 DNA was used to maintain the total mass of DNA in the transfection at 20 μg/plate.

RNA from the transfected cells was analyzed by Northern blot analysis for calcium channel subunit mRNA expression using random primed $^{32}$P-labeled subunit specific probes. HEK293 cells co-transfected with $\alpha_{1B-1}$, $\alpha_{2b}$ and $\beta_{1-2}$ expression plasmids (8, 5 and 2 μg, respectively; molar ratio=2:1.8:1) did not express equivalent levels of each $Ca^{2+}$ channel subunit mRNA. Relatively high levels of $\alpha_{1B-1}$ and $\beta_{1-2}$ mRNAs were expressed, but significantly lower levels of $\alpha_{2b}$ mRNA were expressed. Based on autoradiograph exposures required to produce equivalent signals for all three mRNAs, $\alpha_{2b}$ transcript levels were estimated to be 5 to 10 times lower than $\alpha_{1B-1}$ and $\beta_{1-2}$ transcript levels. Untransfected HEK293 cells did not express detectable levels of $\alpha_{1B-1}$, $\alpha_{2b}$, or $\beta_{1-2}$ mRNAs.

To achieve equivalent $Ca^{2+}$ channel subunit mRNA expression levels, a series of transfections was performed with various amounts of $\alpha_{1B-1}$, $\alpha_{2b}$ and $\beta_{1-2}$ expression plasmids. Because the $\alpha_{1B-1}$ and $\beta_{1-2}$ mRNAs were expressed at very high levels compared to $\alpha_{2b}$ mRNA, the mass of $\alpha_{1B-1}$ and $\beta_{1-2}$ plasmids was lowered and the mass of $\alpha_{2b}$ plasmid was increased in the transfection experiments. Co-transfection with 3, 11.25 and 0.75 μg of $\alpha_{1B-1}$, $\alpha_{2b}$ and $\beta_{1-2}$ expression plasmids, respectively (molar ratio=2:10.9:1), approached equivalent expression levels of each $Ca^{2+}$ channel subunit mRNA. The relative molar quantity of $\alpha_{2b}$ expression plasmid to $\alpha_{1B-1}$ and $\beta_{1-2}$ expression plasmids was increased 6-fold. The mass of $\alpha_{1B-1}$ and $\beta_{1-2}$ plasmids in the transfection was decreased 2.67-fold and the mass of $\alpha_{2b}$ plasmid was increased 2.25-fold. The 6-fold molar increase of $\alpha_{2b}$ relative to $\alpha_{1B-1}$ and $\beta_{1-2}$ required to achieve near equal abundance mRNA levels is consistent with the previous 5- to 10-fold lower estimate of relative $\alpha_{2b}$ mRNA abundance. ω-CgTx GVIA binding to cells transfected with various amounts of expression plasmids indicated that the 3, 11.25 and 0.75 μg of $\alpha_{1B-1}$, $\alpha_{2b}$ and $\beta_{1-2}$ plasmids, respectively, improved the level of cell surface expression of channel complexes. Further increases in the mass of $\alpha_{2b}$ and $\beta_{1-2}$ expression plasmids while $\alpha_{1B-1}$ was held constant, and alterations in the mass of the $\alpha_{1B-1}$ expression plasmid while $\alpha_{2b}$ and $\beta_{1-2}$ were held constant, indicated that the cell surface expression of ω-CgTx GVIA binding sites per cell was nearly optimal. All subsequent transfections were performed with 3, 11.25 and 0.75 μg or 1.0 μg of $\alpha_{1B-1}$ or $\alpha_{1B-2}$, $\alpha_{2b}$ and $\beta_{1-2}$ or $\beta_{1-3}$ expression plasmids, respectively.

2. $^{125}$I-ω-CgTx GVIA Binding to Transfected Cells

Statistical analysis of the $K_d$ and $B_{max}$ values was performed using one-way analysis of variance (ANOVA) followed by the Tukey-Kramer test for multiple pairwise comparisons ($p \leq 0.05$).

Combinations of human voltage-dependent $Ca^{2+}$ channel subunits, $\alpha_{1B-1}$, $\alpha_{1B-2}$, $\alpha_{2b}$, $\beta_{1-2}$ and $\beta_{1-3}$, were analyzed for saturation binding of $^{125}$I-$\omega$-CgTx GVIA. About 200,000 cells were used per assay, except for the $\alpha_{1B-1}$, $\alpha_{1B-1}\alpha_{2b}$ and $\alpha_{1B-2}\alpha_{2b}$ combinations which were assayed with $1\times10^6$ cells per tube The transfected cells displayed a single-class of saturable, high-affinity binding sites. The values for the dissociation constants ($K_d$) and binding capacities ($B_{max}$) were determined for the different combinations. The results are summarized as follows:

| Subunit Combination | $K_d$ (pM) | $B_{max}$ (sites/cell) |
| --- | --- | --- |
| $\alpha_{1B-1}\alpha_{2b}\beta_{1-2}$ | 54.9 ± 11.1 (n = 4) | 45,324 ± 15,606 |
| $\alpha_{1B-1}\alpha_{2b}\beta_{1-3}$ | 53.2 ± 3.6 (n = 3) | 91,004 ± 37,654 |
| $\alpha_{1B-1}\beta_{1-2}$ | 17.9 ± 1.9 (n = 3) | 5,756 ± 2,163 |
| $\alpha_{1B-1}\beta_{1-3}$ | 17.9 ± 1.6 (n = 3) | 8,729 ± 2,980 |
| $\alpha_{1B-1}\alpha_{2b}$ | 84.6 ± 15.3 (n = 3) | 2,256 ± 356 |
| $\alpha_{1B-1}$ | 31.7 ± 4.2 (n = 3) | 757 ± 128 |
| $\alpha_{1B-2}\alpha_{2b}\beta_{1-2}$ | 53.0 ± 4.8 (n = 3) | 19,371 ± 3,798 |
| $\alpha_{1B-2}\alpha_{2b}\beta_{1-3}$ | 44.3 ± 8.1 (n = 3) | 37,652 ± 8,129 |
| $\alpha_{1B-2}\beta_{1-2}$ | 16.4 ± 1.2 (n = 3) | 2,126 ± 412 |
| $\alpha_{1B-2}\beta_{1-3}$ | 22.2 ± 5.8 (n = 3) | 2,944 ± 1,168 |
| $\alpha_{1B-2}\alpha_{2b}$ | N.D.* (n = 3) | N.D. |
| $\alpha_{1B-2}$ | N.D. | N.D. |

*N.D. = not detectable

Cells transfected with subunit combinations lacking either the $\alpha_{1B-1}$ or the $\alpha_{1B-2}$ subunit did not exhibit any detectable $^{125}$I-$\omega$-CgTx GVIA binding (s 600 sites/cell). $^{125}$I-$\omega$-CgTx GVIA binding to HEK293 cells transfected with $\alpha_{1B-2}$ alone or $\alpha_{1B-2}\alpha_{2b}$ was too low for reliable Scatchard analysis of the data. Comparison of the $K_d$ and $B_{max}$ values revealed several relationships between specific combinations of subunits and the binding affinities and capacities of the transfected cells. In cells transfected with all three subunits, ($\alpha_{1B-1}\alpha_{2b}\beta_{1-2}$-, $\alpha_{1B-1}\alpha_{2b}\beta_{1-3}$-, $\alpha_{1B-2}\alpha_{2b}\beta_{1-2}$-, or $\alpha_{1B-2}\alpha_{2b}\beta_{1-3}$-transfectants) the $K_d$ values were indistinguishable (p>0.05), ranging from 44.3±8.1 pM to 54.9±11.1 pM. In cells transfected with two-subunit combinations lacking the $\alpha_{2b}$ subunit ($\alpha_{1B-1}\beta_{1-2}$, $\alpha_{1B-1}\beta_{1-3}$, $\alpha_{1B-2}\beta_{1-2}$ or $\alpha_{1B-2}\beta_{1-3}$) the $K_d$ values were significantly lower than the three-subunit combinations (p<0.01), ranging from 16.4±1.2 to 22.2±5.8 pM. Cells transfected with only the $\alpha_{1B-1}$ subunit had a $K_d$ value of 31.7±4.2 pM, a value that was not different from the two-subunit combinations lacking $\alpha_{2b}$ (p<0.05). As with the comparison between the four $\alpha_{1B}\alpha_{2b}\beta_1$ versus $\alpha_{1B}\beta_1$ combinations, when the $\alpha_{1B-1}$ was co-expressed with $\alpha_{2b}$, the $K_d$ increased significantly (p<0.05) from 31.7±4.2 to 84.6±5.3 pM. These data demonstrate that co-expression of the $\alpha_{2b}$ subunit with $\alpha_{1B-1}$, $\alpha_{1B-1}\beta_{1-2}$, $\alpha_{1B-1}\beta_{1-3}$, $\alpha_{1B-2}\beta_{1-3}$ subunit combinations results in lower binding affinity of the cell surface receptors for $^{125}$I-$\omega$-CgTx GVIA. The Bmax values of cells transfected with various subunit combinations also differed considerably. Cells transfected with the $\alpha_{1B-1}$ subunit alone expressed a low but detectable number of binding sites (approximately 750 binding sites/cell). When the $\alpha_{1B-1}$ subunit was co-expressed with the $\alpha_{2b}$ subunit, the binding capacity increased approximately three-fold while co-expression of a $\beta_{1-2}$ or $\beta_{1-3}$ subunit with $\alpha_{1B-1}$ resulted in 8- to 10-fold higher expression of surface binding. Cells transfected with all three subunits expressed the highest number of cell surface receptors. The binding capacities of cells transfected with $\alpha_{1B-1}\alpha_{2b}\beta_{1-3}$ or $\alpha_{1B-2}\alpha_{2b}\beta_{1-3}$ combinations were approximately two-fold higher than the corresponding combinations containing the $\beta_{1-2}$ subunit. Likewise, cells transfected with $\alpha_{1B-1}\alpha_{2b}\beta_{1-2}$ or $\alpha_{1B-1}\alpha_{2b}\beta_{1-3}$ combinations expressed approximately 2.5-fold more binding sites per cell than the corresponding combinations containing $\alpha_{1B-2}$. In all cases, co-expression of the $\alpha_{2b}$ subunit with $\alpha_{1B}$ and $\beta_1$ increased the surface receptor density compared to cells transfected with only the corresponding $\alpha_{1B}$ and $\beta_1$ combinations; approximately 8-fold for $\alpha_{1B-1}\alpha_{2b}\beta_{1-2}$, 10-fold for $\alpha_{1B-1}\alpha_{2b}\beta_{1-3}$, 9-fold for $\alpha_{1B-2}\alpha_{2b}\beta_{1-2}$, and 13-fold for $\alpha_{1B-2}\alpha_{2b}\beta_{1-3}$. Thus, comparison of the $B_{max}$ values suggests that the toxin-binding subunit, $\alpha_{1B-1}$ or $\alpha_{1B-2}$, is more efficiently expressed and assembled on the cell surface when co-expressed with either the $\alpha_{2b}$ or the $\beta_{1-2}$ or $\beta_{1-3}$ subunit, and most efficiently expressed when $\alpha_{2b}$ and $\beta_1$ subunits are present.

3. Electrophysiology

Functional expression of $\alpha_{1B-1}\alpha_{2b}\beta_{1-2}$ and $\alpha_{1B-1}\beta_{1-2}$ subunit combinations was evaluated using the whole-cell recording technique. Transfected cells that had no contacts with surrounding cells and simple morphology were used approximately 48 hours after transfection for recording. The pipette solution was (in mM) 135 CsCl, 10 EGTA, 1 $MgCl_2$, 10 HEPES, and 4 mM Mg-ATP (pH 7.3, adjusted with TEA-OH). The external solution was (in mM) 15 $BaCl_2$, 125 Choline Cl, 1 $MgCl_2$, and 10 HEPES (pH 7.3, adjusted with TEA-OH). $\omega$-CgTx GVIA (Bachem) was prepared in the external solution with 0.1% cytochrome C (Sigma) to serve as a carrier. Control experiments showed that cytochrome C had no effect on the $Ba^{2+}$ current.

The macroscopic electrophysiological properties of $Ba^{2+}$ currents in cells transfected with various amounts of the $\alpha_{2b}$ expression plasmid with the relative amounts of $\alpha_{1B-1}$ and $\beta_{1-2}$ plasmids held constant were examined. The amplitudes and densities of the $Ba^{2+}$ currents (15 mM $BaCl_2$) recorded from whole cells of these transfectants differed dramatically. The average currents from 7 to 11 cells of three types of transfections (no $\alpha_{2b}$; 2:1.8:1 [$\alpha_{1B-1}$:$\alpha_{2b}$:$\beta_{1-2}$] molar ratio; and 2:10.9:1 [$\alpha_{1B-1}$:$\alpha_{2b}$:$\beta_{1-2}$] molar ratio) were determined. The smallest currents (range: 10 to 205 pA) were recorded when $\alpha_{2b}$ was not included in the transfection, and the largest currents (range: 50 to 8300 pA) were recorded with the 2:10.9:1 ratio of $\alpha_{1B-1}\alpha_{2b}\beta_{1-2}$ plasmids, the ratio that resulted in near equivalent mRNA levels for each subunit transcript. When the amount of $\alpha_{2b}$ plasmid was adjusted to yield approximately an equal abundance of subunit mRNAs, the average peak $Ba^{2+}$ current increased from 433 pA to 1,824 pA (4.2-fold) with a corresponding increase in average current density from 26 pA/pF to 127 pA/pF (4.9-fold). This increase is in the presence of a 2.7-fold decrease in the mass of $\alpha_{1B-1}$ and $\beta_{1-2}$ expression plasmids in the transfections. In all transfections, the magnitudes of the $Ba^{2+}$ currents did not follow a normal distribution.

To compare the subunit combinations and determine the effects of $\alpha_{2b}$, the current-voltage properties of cells transfected with $\alpha_{1B-1}\beta_{1-2}$ or with $\alpha_{1B-1}\alpha_{2b}\beta_{1-2}$ in either the 2:1.8:1 ($\alpha_{1B-1}$:$\alpha_{2b}$:$\beta_{1-2}$) molar ratio or the 2:10.9:1 ($\alpha_{1B-1}$:$\alpha_{2b}$:$\beta_{1-2}$) molar ratio transfectants were examined. The extreme examples of no $\alpha_{2b}$ and 11.25 μg $\alpha_{2b}$ (2:10.9:1 molar ratio) showed no significant differences in the current voltage plot at test potentials between 0 mV and +40 mV (p<0.05). The slight differences observed at either side of the peak region of the current voltage plot were likely due to normalization. The very small currents observed in the $\alpha_{1B-1}\beta_{1-2}$ transfected cells have a substantially higher component of residual leak relative to the barium current that is activated by the test pulse. When the current voltage plots are normalized, this leak is a much greater component than in the $\alpha_{1B-1}\alpha_{2b}\beta_{1-2}$ transfected cells and as a result, the current-voltage plot appears broader. This is the most likely explanation of the apparent differences in the current voltage plots, especially given the fact that the current-voltage plot for the $\alpha_{1B-1}\beta_{1-2}$ transfected cells diverge on both sides of the peak. Typically, when the voltage-dependence activation is shifted, the entire current-voltage plot is shifted, which was not observed. To qualitatively compare the kinetics of each, the average responses of test pulses from −90 mV to 10 mV were normalized and plotted. No significant differences in activation or inactivation kinetics of whole-cell $Ba^{2+}$ currents were observed with any combination.

G. Expression of DNA Encoding Human Neuronal Calcium Channel $\alpha_{1E-3}\alpha_{2B}\beta_{1-3}$ and $\alpha_{1E-1}\alpha_{2B}\beta_{1-3}$ subunits in HEK Cells Functional expression of the $\alpha_{1E-1}\alpha_{2B}\beta_{1-3}$ and $\alpha_{1E-3}\alpha_{2B}\beta_{1-3}$, as well as $\alpha_{1E-3}$ was evaluated using the whole cell recording technique.

1. Methods

Recordings were performed on transiently transfected HER 293 cells two days following the transfection, from cells that had no contacts with surrounding cells and which had simple morphology.

The internal solution used to fill pipettes for recording the barium current from the transfected recombinant calcium channels was (in mM) 135 CsCl, 10 EGTA, 1 $MgCl_2$, 10 HEPES, and 4 mM Mg-ATP (pH 7.4–7.5, adjusted with TEA-OH). The external solution for recording the barium current was (in mM) 15 $BaCl_2$, 150 Choline Cl, 1 $MgCl_2$, and 10 HEPES and 5 TEA-OH (pH 7.3, adjusted with TEA-OH). In experiments in which $Ca^{2+}$ was replaced for $Ba^{2+}$, a Laminar flow chamber was used in order to completely exchange the extracellular solution and prevent any mixing of $Ba^{2+}$ and $Ca^{2+}$. ω-CgTx GVIA was prepared in the external solution with 0.1 cytochrome C to serve as a carrier, the toxin was applied by pressurized puffer pipette. Series resistance was compensated 70–85% and currents were analyzed only if the voltage error from series resistance was less than 5 mV. Leak resistance and capacitance was corrected by subtracting the scaled current observed with the P/-4 protocol as implemented by pClamp (Axon Instruments).

2. Electrophysiology Results

Cells transfected with $\alpha_{1E-1}\alpha_{2b}\beta_{1-3}$ or $\alpha_{1E-3}\alpha_{2b}\beta_{1-3}$ showed strong barium currents with whole cell patch clamp recordings. Cells expressing $\alpha_{1E-3}\alpha_{2B}\beta_{1-3}$ had larger peak currents than those expressing $\alpha_{1B-1}\alpha_{2b}\beta_{1-3}$. In addition, the kinetics of activation and inactivation are clearly substantially faster in the cells expressing $\alpha_{1E}$ calcium channels.

HEK 293 cells expressing $\alpha_{1E-3}$ alone have a significant degree of functional calcium channels, with properties similar to those expressing $\alpha_{1E}\alpha_{2b}\beta_{1-3}$ but with substantially smaller peak barium currents. Thus, with $\alpha_{1E}$, the $\alpha_2$ and $\beta_1$ subunits are not required for functional expression of $\alpha_{1E}$ mediated calcium channels, but do substantially increase the number of functional calcium channels.

Examination of the current voltage properties of $\alpha_{1E}\alpha_{2b}\beta_{1-3}$ expressing cells indicates that $\alpha_{1E-3}\alpha_{2b}\beta_{1-3}$ is a high-voltage activated calcium channel and the peak current is reached at a potential only slightly less positive than other neuronal calcium channels also expressing $\alpha_{2b}$ and $\beta_1$, and $\alpha_{1B}$ and $\alpha_{1D}$. Current voltage properties of $\alpha_{1E-1}\alpha_{2b}\beta_{1-3}$ and $\alpha_{1E-3}\alpha_{2b}\beta_{1-3}$ are statistically different from those of $\alpha_{1B-1}\alpha_{2b}\beta_{1-3}$. Current voltage curves for $\alpha_{1E-1}\alpha_{2b}\beta_{1-3}$ and $\alpha_{1E-3}\alpha_{2b}\beta_{1-3}$ peak at approximately +5mV, as does the current voltage curve for $\alpha_{1E-3}$ alone.

The kinetics and voltage dependence of inactivation using both prepulse (200 ms) and steady-state inactivation was examined. $\alpha_{1E}$ mediated calcium channels are rapidly inactivated relative to previously cloned calcium channels and other high voltage-activated calcium channels. $\alpha_{1E-3}\alpha_{2b}\beta_{1-3}$ mediated calcium channels are inactivated rapidly and are thus sensitive to relatively brief (200 ms) prepulses as well as long prepulses (>20s steady state inactivation), but recover rapidly from steady state inactivation. The kinetics of the rapid inactivation has two components, one with a time constant of approximately 25 ms and the other approximately 400 ms.

To determine whether $\alpha_{1E}$ mediated calcium channels have properties of low voltage activated calcium channels, the details of tail currents activated by a test pulse ranging −60 to +90 mV were measured at −60 mV. Tail currents recorded at −60 mV could be well fit by a single exponential of 150 to 300 μs; at least an order of magnitude faster than those typically observed with low voltage-activated calcium channels.

HEK 293 cells expressing $\alpha_{1E-3}\alpha_{2b}\beta_{1-3}$ flux more current with $Ba^{2+}$ as the charge carrier and currents carried by $Ba^{2+}$ and $Ca^{2+}$ have different current-voltage properties. Furthermore, the time course of inactivation is slower and the amount of prepulse inactivation less with $Ca^{2+}$ as the charge carrier.

While the invention has been described with some specificity, modifications apparent to those with ordinary skill in the art may be made without departing from the scope of the invention. Since such modifications will be apparent to those of skill in the art, it is intended that this invention be limited only by the scope of the appended claims.

---

What is claimed is:

1. An isolated DNA molecule comprising a sequence of nucleotides that encodes a $\beta_4$ subunit of a human calcium channel, wherein the $\beta_4$ subunit comprises the sequence of amino acids set forth is SEQ ID NO. 28.

2. A eukaryotic cell, comprising heterologous DNA that encodes an $\alpha_1$ subunit of a calcium channel and the heterologous DNA of claim 1 that encodes a $\beta_4$ subunit of a human calcium channel.

3. The eukaryotic cell of claim 2 selected from the group consisting of a HEK 293 cell, a Chinese hamster ovary cell, an African green monkey cell, and a mouse L cell.

4. A method to isolate DNA encoding all or part of a $\beta_4$ subunit of a human calcium channel, comprising:
hybridizing a nucleic acid molecule of claim 1 to a human neuronal cDNA library under high stringency hybridization and wash conditions; and
identifying and isolating hybridizing clones, whereby a nucleic acid molecule that encodes all or part of a human $\beta_4$ subunit is isolated.

5. An isolated DNA molecule, comprising the sequence of nucleotides set forth in SEQ ID No. 27.

6. An isolated DNA molecule, comprising a sequence of nucleotides that encodes a $\beta_4$ subunit of a human calcium channel, wherein:
the $\beta_4$ subunit comprises the sequence of amino acids set forth in SEQ ID No. 28; and
the DNA molecule is complementary to DNA present in a human DNA library.

7. A eukaryotic cell, comprising heterologous DNA that encodes an $\alpha_1$ subunit of a calcium channel and the heterologous DNA of claim 6 that encodes a $\beta_4$ subunit of a human calcium channel.

8. The eukaryotic cell of claim 7 selected from the group consisting of a HEK 293 cell, a Chinese hamster ovary cell, an African green monkey cell, and a mouse L cell.

9. A eukaryotic cell with a functional, heterologous calcium channel, produced by a process comprising:
introducing into the cell nucleic acid that encodes an $\alpha_1$ subunit of a human calcium channel and introducing into the cell nucleic acid that encodes a $\beta_4$ subunit of a human calcium channel, wherein:

the $\beta_4$-encoding nucleic acid is the nucleic acid molecule of claim 6;

the heterologous calcium channel contains the encoded $\beta_4$ subunit; and the only heterologous ion channels are calcium channels.

10. The eukaryotic cell of claim 9 selected from the group consisting of a HEK 293 cell, a Chinese hamster ovary cell, an African green monkey cell, a mouse L cell and an amphibian oöcyte.

11. An isolated nucleic acid molecule, comprising a sequence of nucleotides that encodes a $\beta_4$-subunit of a human calcium channel, wherein the $\beta_4$ subunit comprises the sequence of amino acids set forth in SEQ ID No. 28 and the nucleic acid is RNA.

12. An isolated eukaryotic cell, comprising the nucleic acid molecule of claim 11, wherein the cell is a mammalian cell, a yeast cell or an amphibian oöcyte.

13. A eukaryotic cell with a functional, heterologous calcium channel, produced by a process comprising:

introducing into the cell nucleic acid that encodes an $\alpha_1$ subunit of a human calcium channel and introducing into the cell nucleic acid that encodes a $\beta_4$ subunit of a human calcium channel, wherein:

the $\beta_4$ subunit of a human calcium channel comprises the sequence of amino acids set forth in SEQ ID NO. 28;

the heterologous calcium channel contains the encoded $\beta_4$ subunit; and the only heterologous ion channels are calcium channels.

14. The eukaryotic cell of claim 13 selected from the group consisting of a HEK 293 cell, a Chinese hamster ovary cell, an African green monkey cell, a mouse L cell and an amphibian oöcyte.

* * * * *